United States Patent
Wuestefeld et al.

(10) Patent No.: US 12,421,515 B2
(45) Date of Patent: Sep. 23, 2025

(54) METHOD OF STIMULATING PROLIFERATION OF A CELL

(71) Applicant: Agency for Science, Technology and Research, Singapore (SG)

(72) Inventors: Torsten Wuestefeld, Singapore (SG); Viktoriia Iakovleva, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 278 days.

(21) Appl. No.: 17/731,259

(22) Filed: Apr. 27, 2022

(65) Prior Publication Data

US 2022/0364089 A1 Nov. 17, 2022

Related U.S. Application Data

(63) Continuation of application No. PCT/SG2021/050443, filed on Jul. 30, 2021.

(51) Int. Cl.
*C12N 15/113* (2010.01)
*A61P 1/16* (2006.01)

(52) U.S. Cl.
CPC .............. *C12N 15/113* (2013.01); *A61P 1/16* (2018.01); *C12N 2310/14* (2013.01); *C12N 2310/351* (2013.01); *C12N 2310/531* (2013.01); *C12N 2320/30* (2013.01)

(58) Field of Classification Search
CPC .............. C12N 15/113; C12N 2310/14; C12N 2310/351; C12N 2310/11; A61P 1/16; A61K 31/7125; A61K 31/713; A61K 31/712
USPC ...................... 435/6.1, 91.1, 91.31, 455, 458; 514/44 A; 536/23.1, 24.5
See application file for complete search history.

(56) References Cited

U.S. PATENT DOCUMENTS

| | | | | |
|---|---|---|---|---|
| 5,932,442 | A | * 8/1999 | Lal | C12N 9/93 435/320.1 |
| 2008/0113351 | A1 | * 5/2008 | Naito | A61P 5/26 536/23.1 |
| 2019/0255143 | A1 | 8/2019 | Tabas | |
| 2019/0300872 | A1 | * 10/2019 | Woolf | C12N 15/09 |

FOREIGN PATENT DOCUMENTS

| | | | |
|---|---|---|---|
| CN | 111154760 A | 5/2020 | |
| EP | 1074617 A2 * | 2/2001 | ............. C07K 14/47 |
| WO | 2019/149738 A1 | 8/2019 | |

OTHER PUBLICATIONS

Roberts et al (Nature Rev., Drug Discovery, vol. 19, pp. 673-694 (2020)) (Year: 2020).*
Osborn et al (Nucleic Acid Therapeutics, vol. 28, No. 3, pp. 128-136 (2018)) (Year: 2018).*
Damase et al (Frontiers in Bioengineering and Biotechnology, vol. 9, Article 628137, pp. 1-24 (2021)) (Year: 2021).*
Bost et al (ACS Nano, vol. 15, pp. 13993-14021 (2021)) (Year: 2021).*
Fan W. et al., RUVBL 1-ITFG1 interaction is required for collective invasion in breast cancer. Biochim Biophys Acta Gen Subj, Mar. 21, 2017, vol. 1861, No. 7, pp. 1788-1800.
Fiscella M. et al., TIP, a T-cell factor identified using high-throughput screening increases survival in a graft-versus-host disease model. Nat Biotechnol, Feb. 24, 2003, vol. 21, No. 3, pp. 302-307.
Vollmann E.H. et al., Identification of Novel Fibrosis Modifiers by In Vivo siRNA Silencing. Mol Ther Nucleic Acids, Apr. 20, 2017, vol. 7, pp. 314-323.
Zhao Z. et al., siRNA- and mi RNA-based therapeutics for liver fibrosis. Transl Res, Aug. 13, 2019, vol. 214, pp. 17-29.
Iakovleva V. et al., OS-1290 Integrin Alpha FG-GAP Repeat Containing 1 (ITFG1) knockdown enhances liver regeneration and attenuates chronic liver damage related liver fibrosis. J Hepatol, Jun. 26, 2021, vol. 75, Suppl 2, p. S233.
PCT/SG2021/050443; International Search Report and Written Opinion; dated Nov. 1, 2021; 17 pages.
U.S. Appl. No. 17/823,839, "Non-Final Office Action", Jan. 23, 2024, 15 pages.
Bost, et al., "Delivery of Oligonucleotide Therapeutics: Chemical Modifications, Lipid Nanoparticles, and Extracellular Vesicles", ACS Nano, vol. 15, No. 9, 2021, pp. 13993-14021.
Damase, et al., "The Limitless Future of RNA Therapeutics", Frontiers in Bioengineering and Biotechnology, vol. 9, Article 628137, Mar. 18, 2021, pp. 1-24.
Osborn, et al., "Improving siRNA Delivery In Vivo Through Lipid Conjugation", Nucleic Acid Therapeutics, vol. 28, No. 3, 2018, pp. 128-136.
Roberts, et al., "Advances in Oligonucleotide Drug Delivery", Nature Reviews Drug Discovery, vol. 19, Oct. 2020, pp. 673-694.
International Search Report received in Chinese Patent Application No. 2021800586834, dated Dec. 30, 2024.

\* cited by examiner

*Primary Examiner* — Jane J Zara
(74) *Attorney, Agent, or Firm* — Kilpatrick Townsend & Stockton LLP

(57) ABSTRACT

Methods of treating and preventing diseases associated with fibrosis are disclosed, as well as agents for use in such methods. The methods comprise inhibiting at least one of ITFG1, MFAP4, GRHPR, ABCC4, PAK3, TRNP1, APLN, KIF20A, and/or LTB. In one embodiment, the disease is a liver disease or condition. Also disclosed are methods of promoting regeneration of cells, such as hepatocytes.

16 Claims, 89 Drawing Sheets
Specification includes a Sequence Listing.

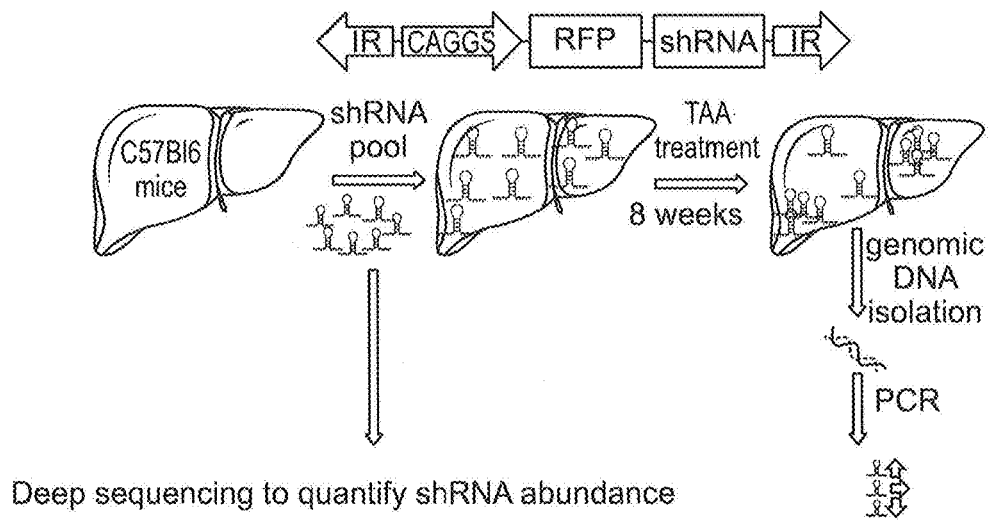
FIG. 1A
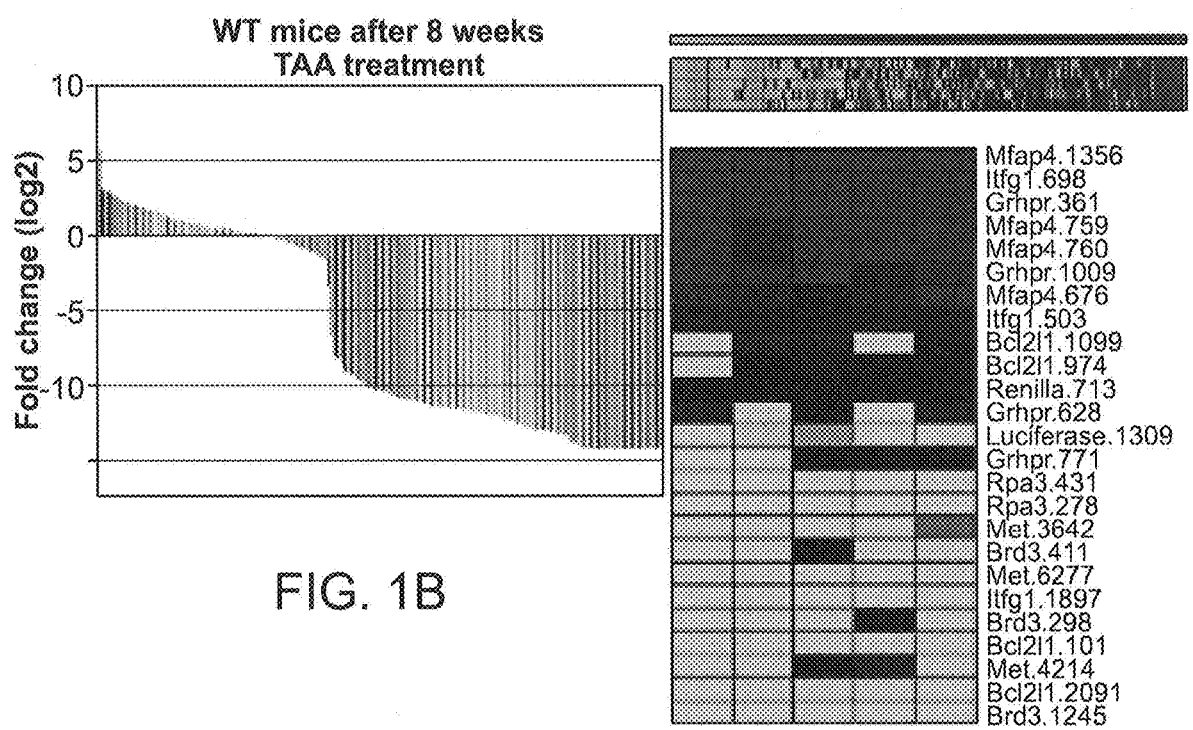
FIG. 1B
FIG. 1C

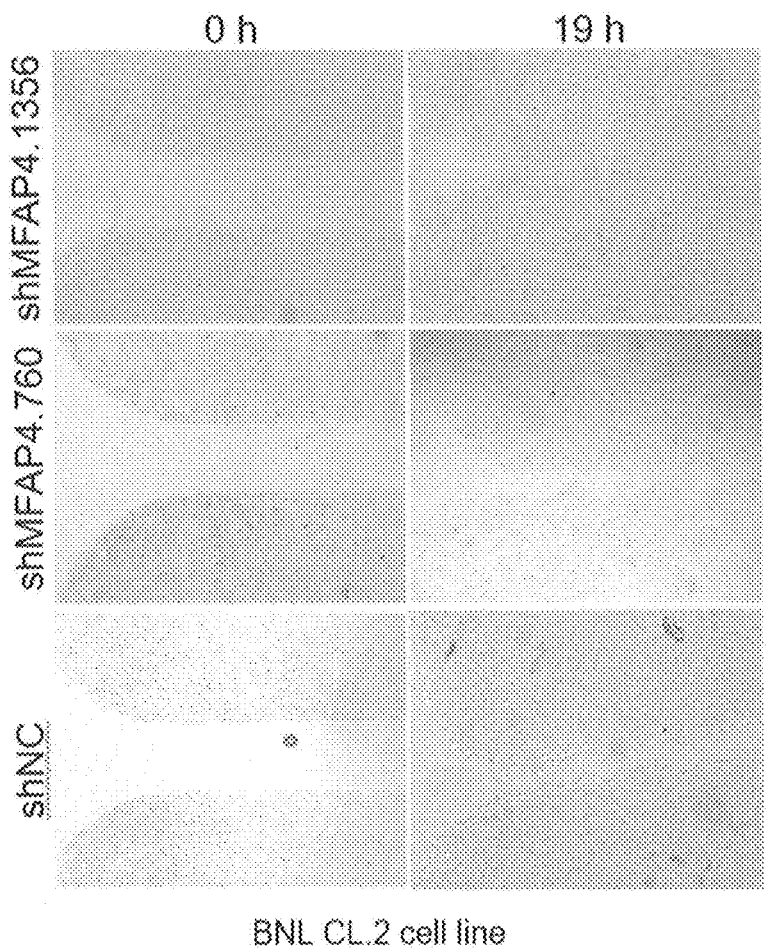
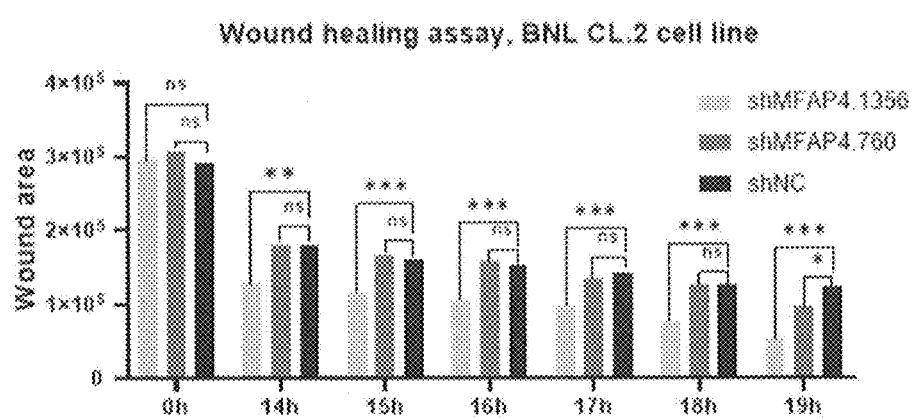
FIG. 2C

FIG. 2E

| shRNA | Doubling time (h) |
|---|---|
| shMfap4.1356 | 35.7 |
| shNC | 45.5 |
| Published data | 45.6 |

FIG. 2F

| shRNA | G0/G1 phase | S phase | G2 phase |
|---|---|---|---|
| shMFAP4.1356 | 39.3 | 15.0 | 45.6 |
| shMFAP4.760 | 51.8 | 10.2 | 37.9 |
| shNC | 56.6 | 10.7 | 32.6 |

FIG. 2G
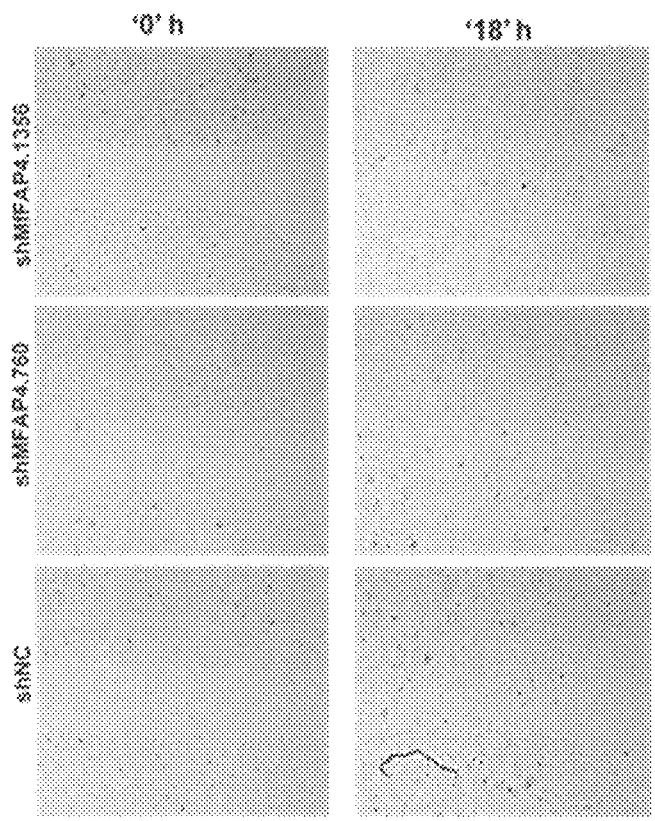
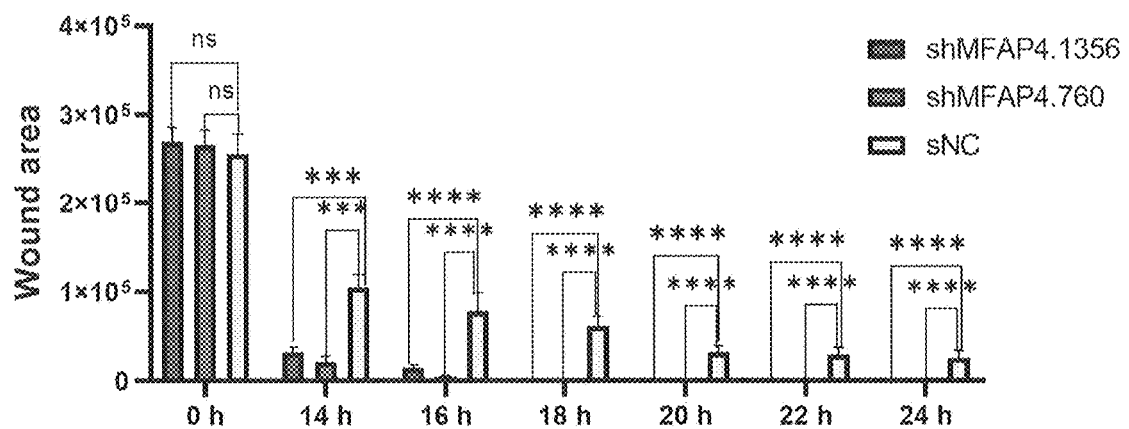

*Dilution of constructs 1.25 ug plasmid: 0.25 ug SB13*

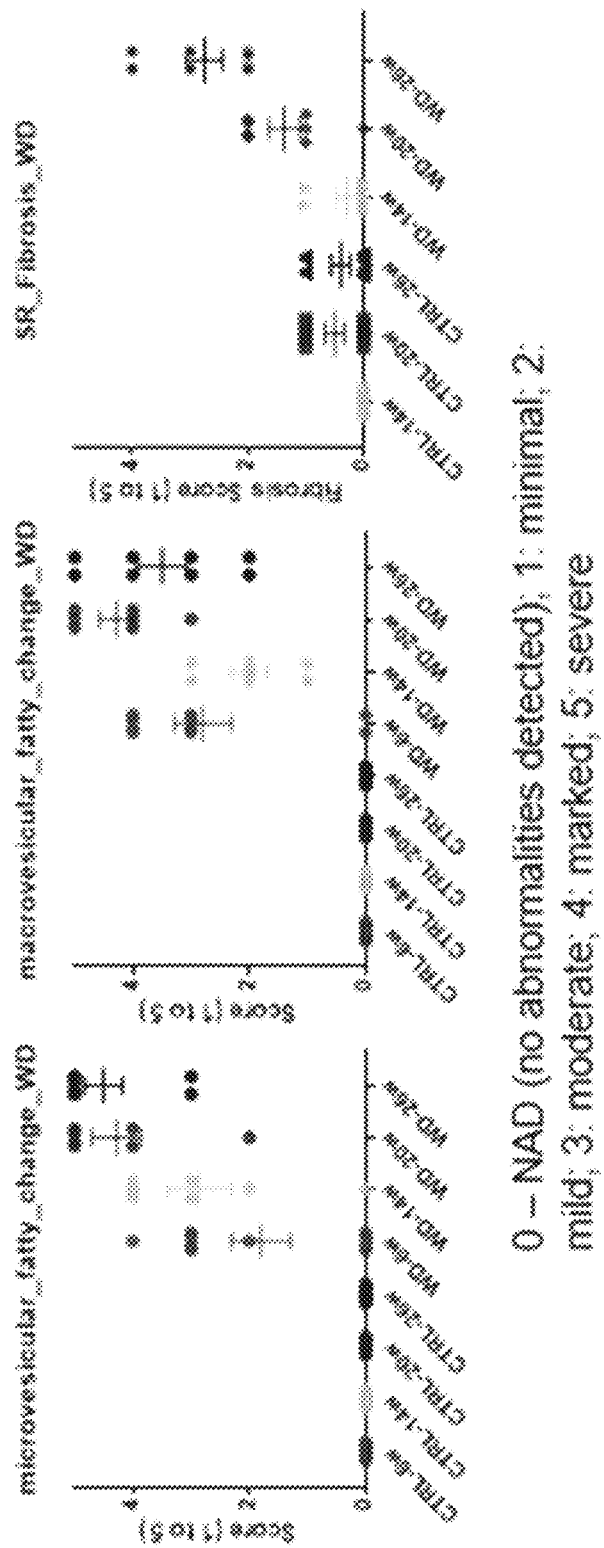

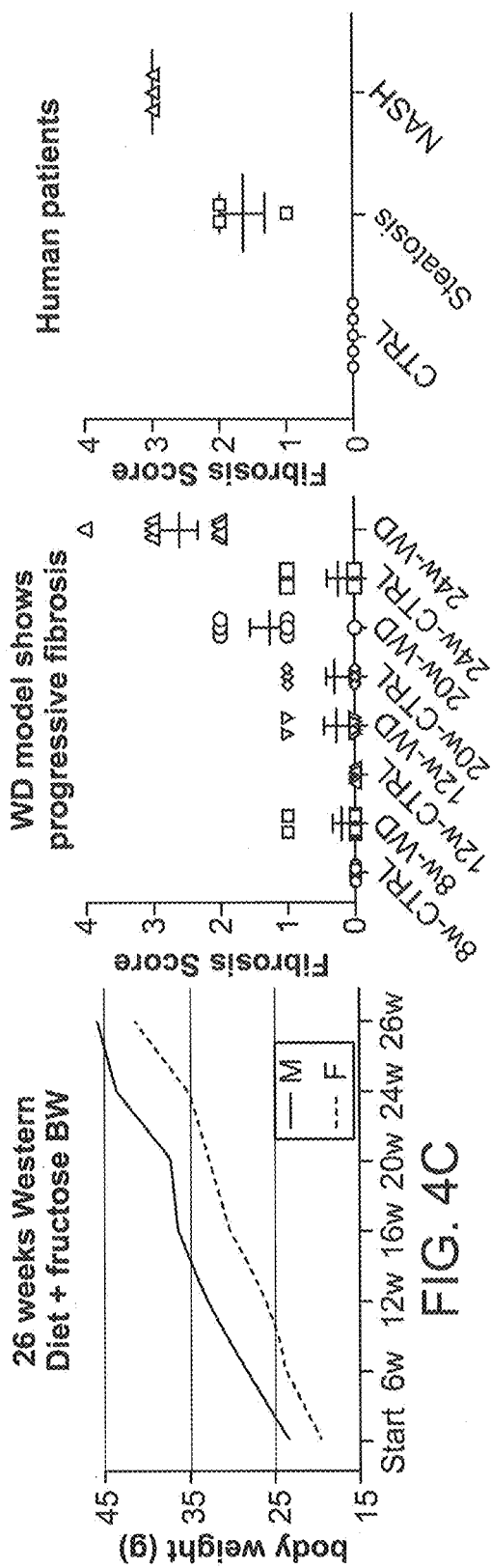
FIG. 4C
FIG. 4D
FIG. 4E
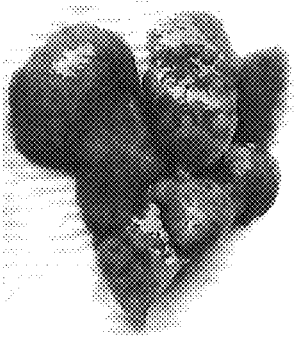
FIG. 4F
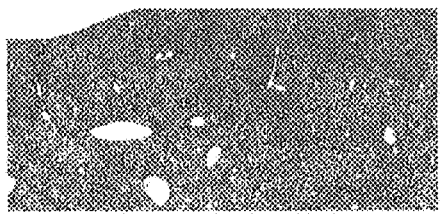
FIG. 4G
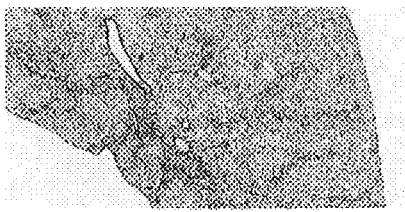
FIG. 4H FIG. 8A
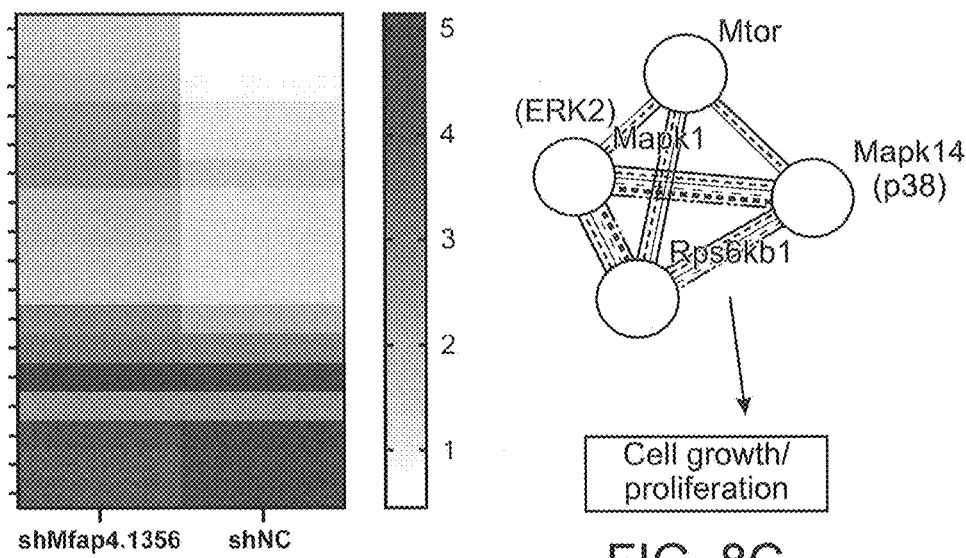
FIG. 8B
FIG. 8C
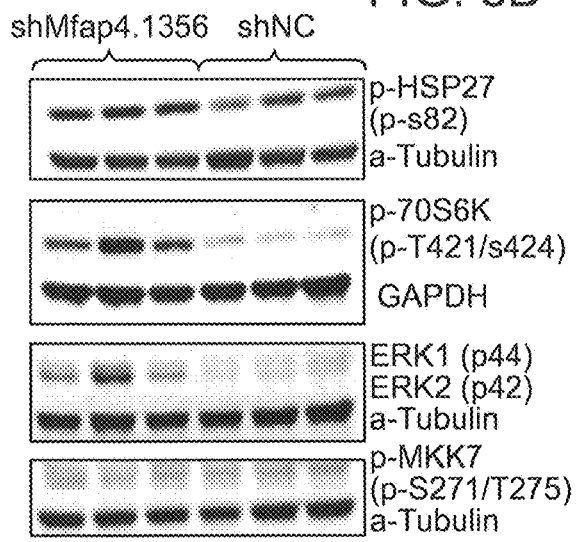
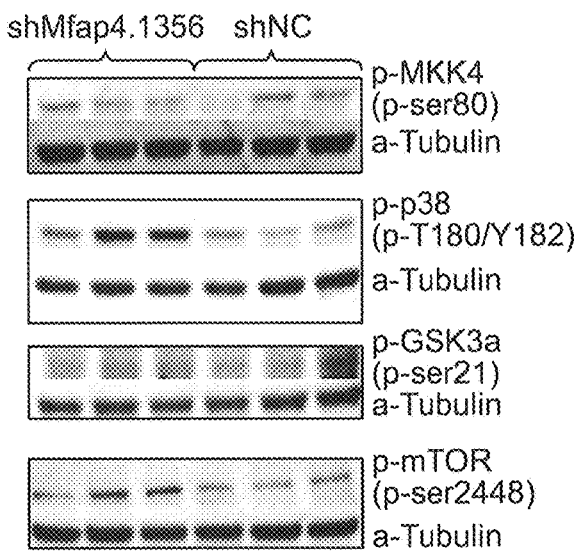
FIG. 8D

- Specific Mfap4 staining in human liver.
- Staining is stronger in cirrhotic liver.
- Interestingly we see also nuclear staining.

GFP imaging

Immortalized human hepatocytes SV40

FIG. 11A
FIG. 11B
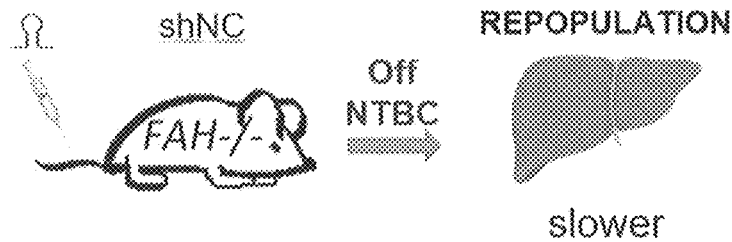
FIG. 11C
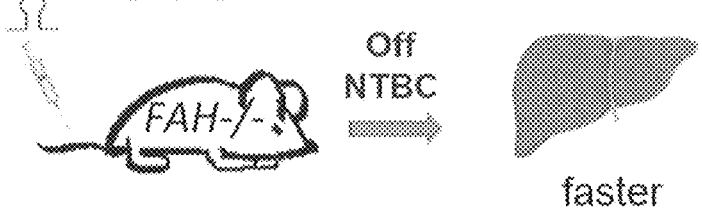
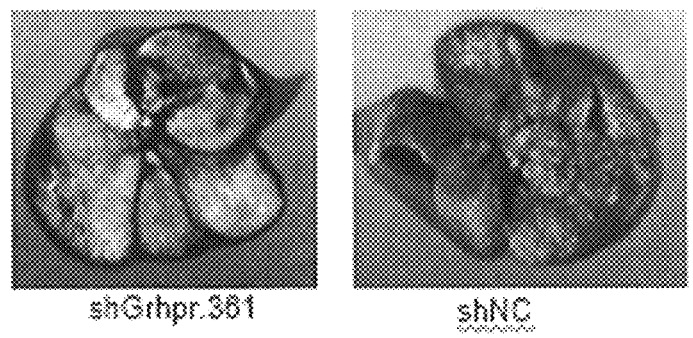
FIG. 11D
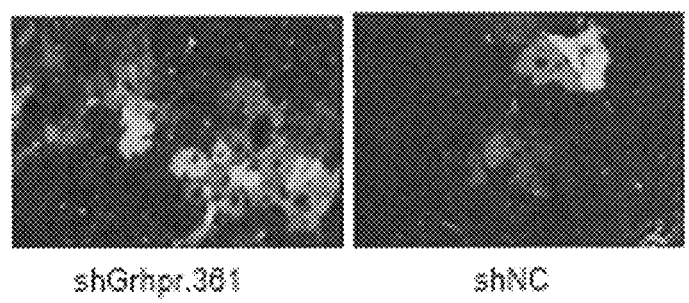

FIG. 11E
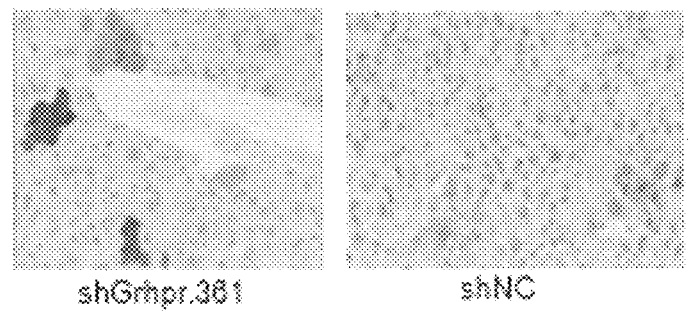
FIG. 11F
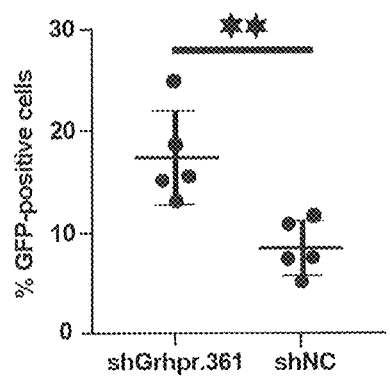
FIG. 11G  Survival curve at dilution of constructs 1:30
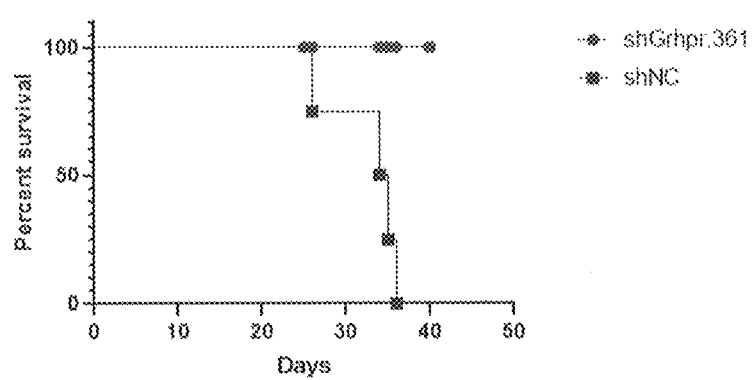

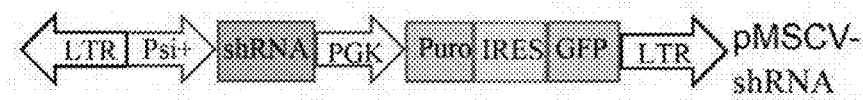
FIG.16A
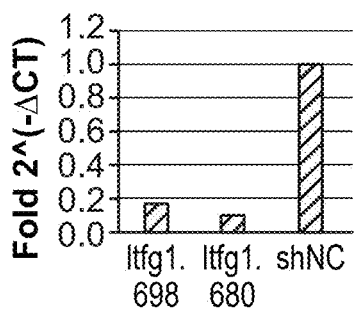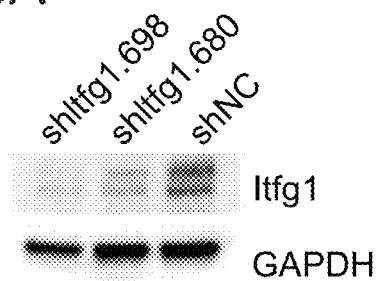
FIG.16B
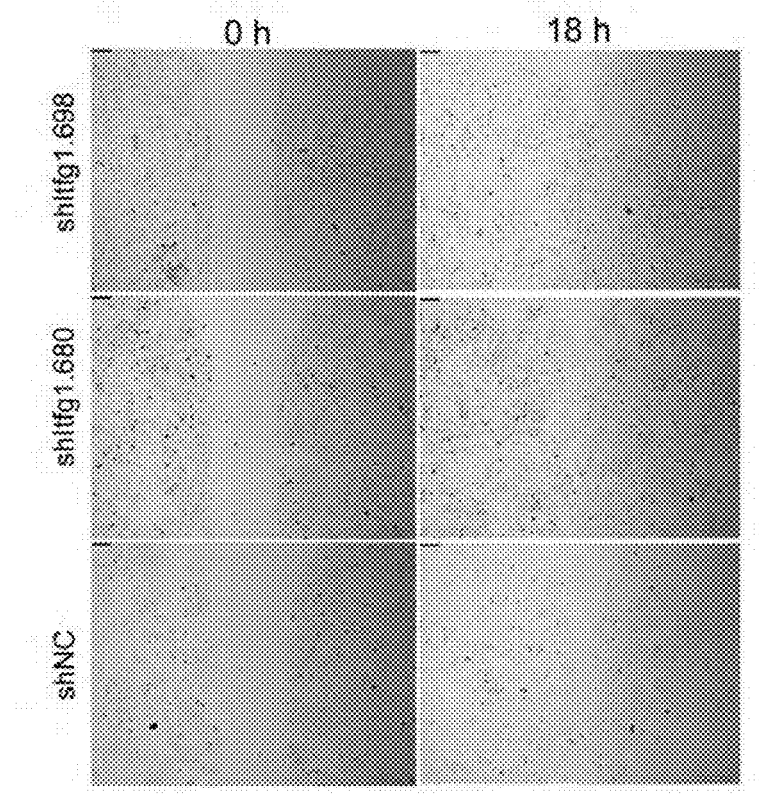
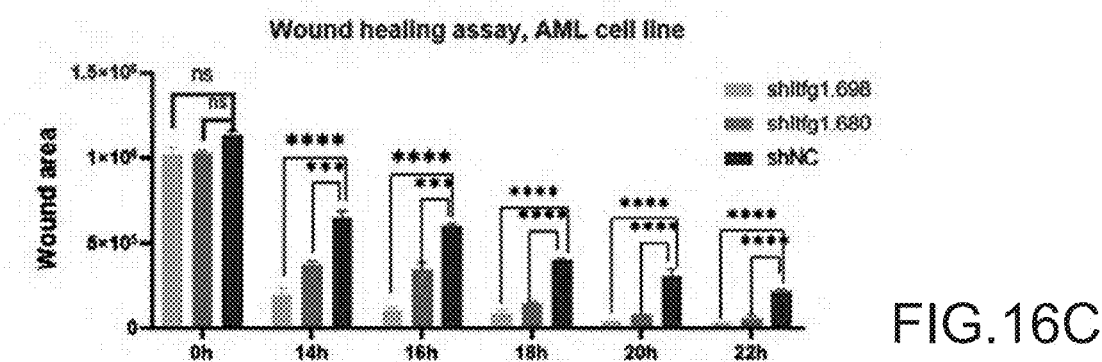
FIG.16C

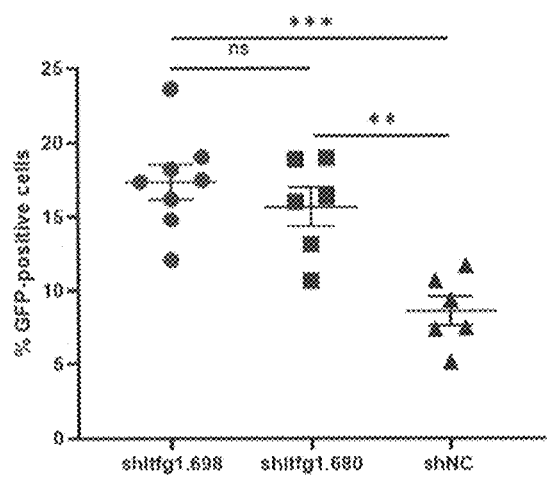
FIG. 16G FAH-/- repopulation, 18 days, 1:20 dilution
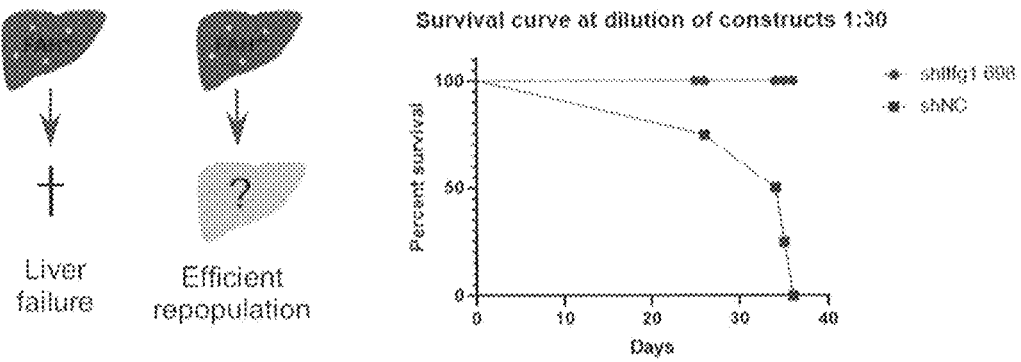
FIG. 16H shltfg.698    shNC

*GFP imager*

Fah-/- repopulated mouse liver 6 month after Western Diet

ITFG1 - ENSG00000129636 - DESeq2 Results

| Analysis | Condition | Reference | Type | log2FC | Padj |
|---|---|---|---|---|---|
| diseaseStage | Simple_Steatosis_NAFLD | Healthy | upReg | 0.14418 | 0.36633 |
| diseaseStage | Incomplete_NAFLD | Healthy | upReg | 0.02061 | 0.93103 |
| diseaseStage | NASH_Early_Fibrosis | Healthy | upReg | 0.0405 | 0.80014 |
| diseaseStage | NASH_Advanced_Fibrosis | Healthy | downReg | -0.04966 | 0.74318 |
| diseaseStage | Cirrhosis | Healthy | upReg | 0.00485 | 0.98494 |
| steatosisGroup | Steatosis1 | Steatosis0 | upReg | 0.05017 | 0.69477 |
| steatosisGroup | Steatosis2 | Steatosis0 | upReg | 0.16766 | 0.25128 |
| steatosisGroup | Steatosis3 | Steatosis0 | upReg | 0.09268 | 0.58054 |
| ballooningGroup | Ballooning1 | Ballooning0 | upReg | 0.10344 | 0.42485 |
| ballooningGroup | Ballooning2 | Ballooning0 | downReg | -0.04851 | 0.70435 |
| inflammationGroup | inflammation1 | inflammation0 | upReg | -0.06393 | 0.58538 |
| inflammationGroup | inflammation2 | inflammation0 | downReg | -0.05675 | 0.76298 |
| inflammationGroup | inflammation3 | inflammation0 | downReg | -0.26781 | 0.1435 |
| fibrosisGroup | Fibrosis1 | Fibrosis0 | downReg | -0.10001 | 0.44571 |
| fibrosisGroup | Fibrosis2 | Fibrosis0 | downReg | -0.11816 | 0.44046 |
| fibrosisGroup | Fibrosis3 | Fibrosis0 | downReg | -0.1251 | 0.40393 |
| fibrosisGroup | Fibrosis4 | Fibrosis0 | downReg | -0.11509 | 0.34234 |

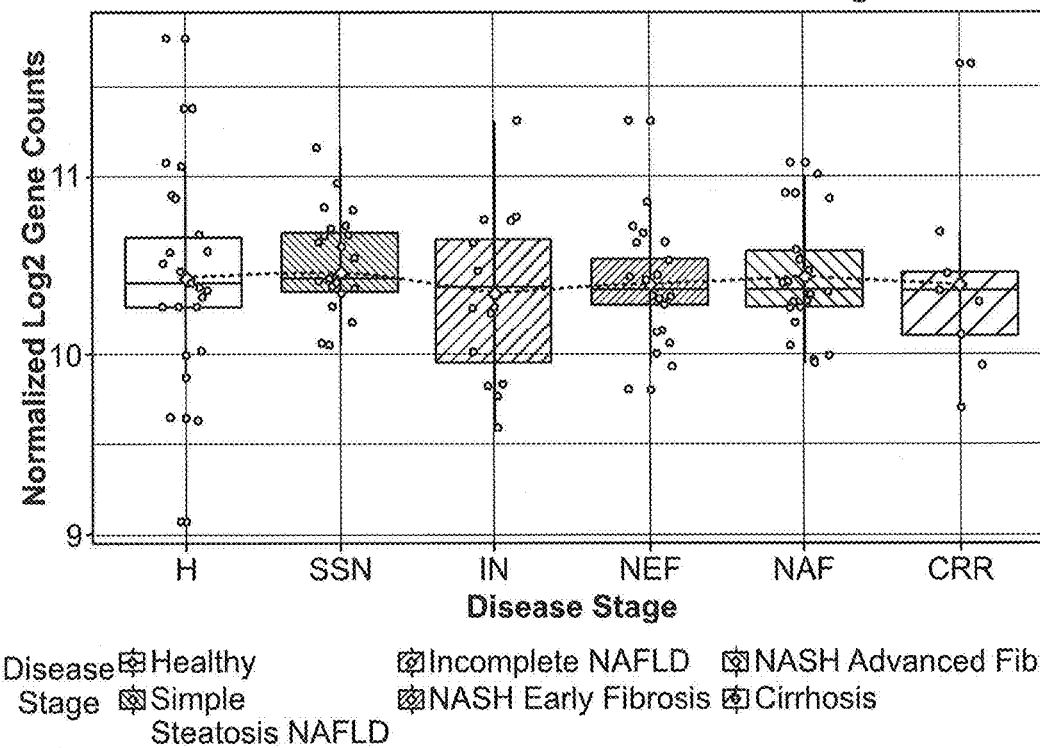

FIG. 18B pMSCV-shRNA

HepG2 cell line

Further validation
ABCC4
Pak3
Apln
Kif20a
TRNP1
LTB

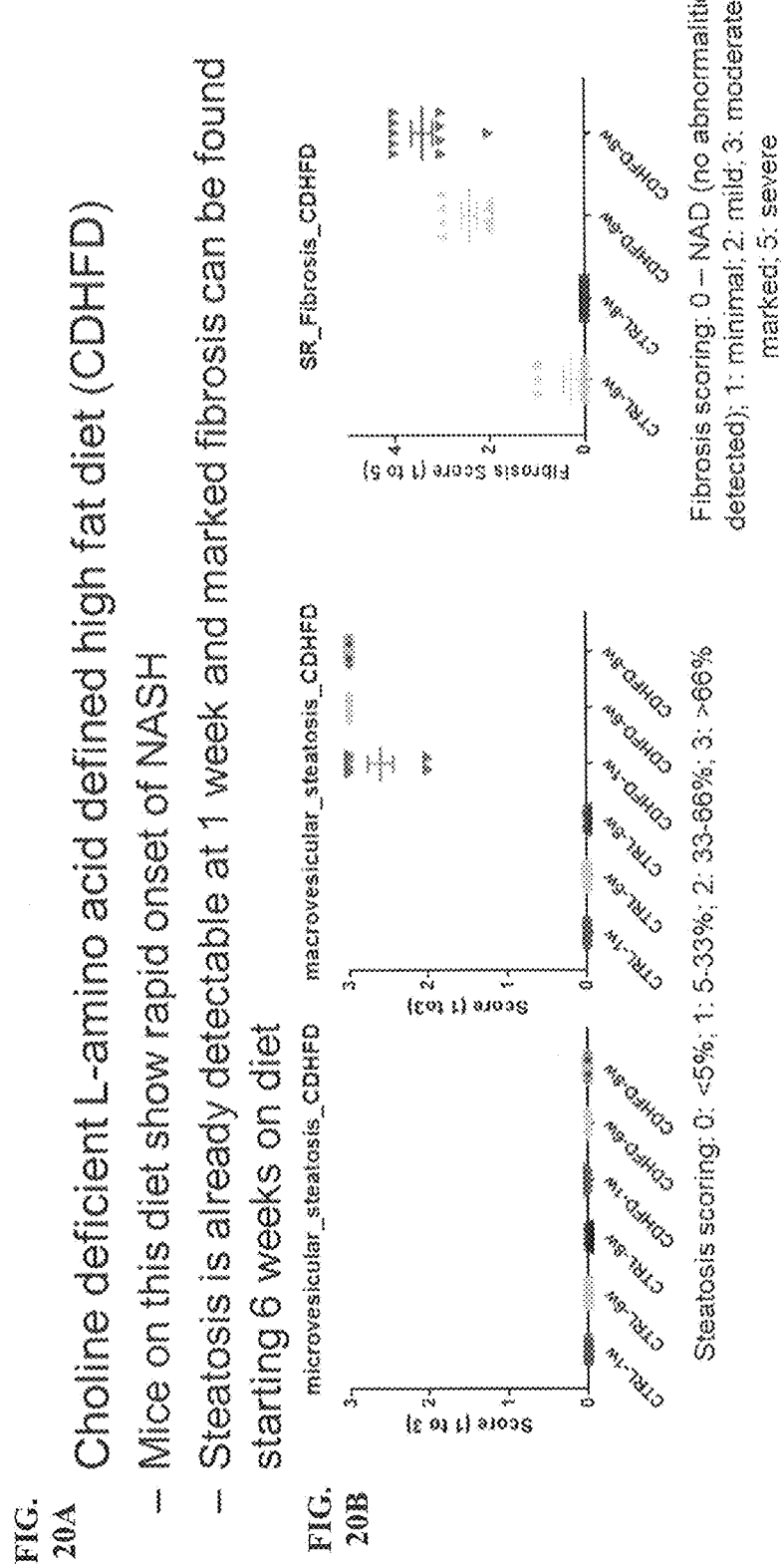

PAK3 - ENSG00000077264 - DESeq2 Results

| Analysis | Condition | Reference | Type | log2FC | Padj |
|---|---|---|---|---|---|
| diseaseStage | Simple_Steatosis_NAFLD | Healthy | downReg | -0.16368 | 0.84552 |
| diseaseStage | Incomplete_NAFLD | Healthy | downReg | -0.12792 | 0.88807 |
| diseaseStage | NASH_Early_Fibrosis | Healthy | downReg | 0.14496 | 0.82063 |
| diseaseStage | NASH_Advanced_Fibrosis | Healthy | upReg | 0.85831 | 0.05391 |
| diseaseStage | Cirrhosis | Healthy | upReg | 1.46315 | 0.01412 |
| steatosisGroup | Steatosis1 | Steatosis0 | downReg | -0.43411 | 0.33816 |
| steatosisGroup | Steatosis2 | Steatosis0 | downReg | -0.23978 | 0.76018 |
| steatosisGroup | Steatosis3 | Steatosis0 | downReg | -0.22464 | 0.76815 |
| ballooningGroup | Ballooning1 | Ballooning0 | downReg | -0.03067 | 0.97259 |
| ballooningGroup | Ballooning2 | Ballooning0 | upReg | 0.46121 | 0.29955 |
| inflammationGroup | inflammation1 | inflammation0 | upReg | 0.33696 | 0.47722 |
| inflammationGroup | inflammation2 | inflammation0 | downReg | -0.07474 | 0.93477 |
| inflammationGroup | inflammation3 | inflammation0 | upReg | 0.21098 | 0.85307 |
| fibrosisGroup | Fibrosis1 | Fibrosis0 | upReg | 0.03773 | 0.95866 |
| fibrosisGroup | Fibrosis2 | Fibrosis0 | upReg | 0.39784 | 0.51875 |
| fibrosisGroup | Fibrosis3 | Fibrosis0 | upReg | 0.46919 | 0.43218 |
| fibrosisGroup | Fibrosis4 | Fibrosis0 | upReg | 1.29834 | 0.00075 |

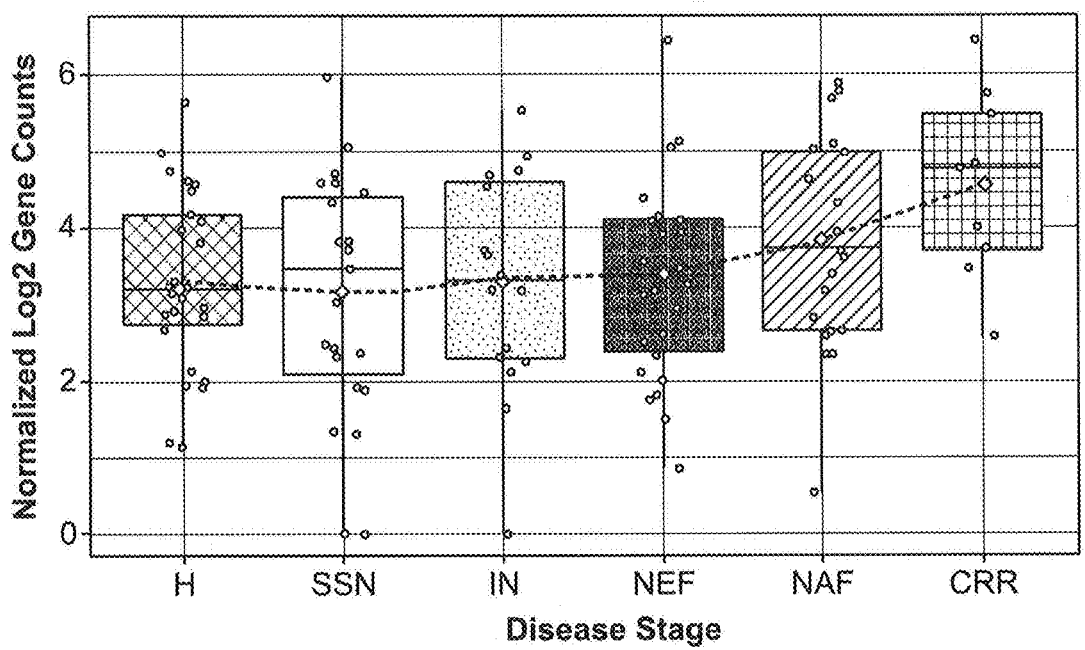

FIG. 22C

TRNP1 - ENSG00000253368 - DESeq2 Results

| Analysis | Condition | Reference | Type | log2FC | Padj |
|---|---|---|---|---|---|
| diseaseStage | Simple_Steatosis_NAFLD | Healthy | downReg | -0.16368 | 0.84552 |
| diseaseStage | Incomplete_NAFLD | Healthy | downReg | -0.12792 | 0.88807 |
| diseaseStage | NASH_Early_Fibrosis | Healthy | downReg | 0.14496 | 0.82063 |
| diseaseStage | NASH_Advanced_Fibrosis | Healthy | downReg | 0.85831 | 0.05391 |
| diseaseStage | Cirrhosis | Healthy | upReg | 1.46315 | 0.01412 |
| steatosisGroup | Steatosis1 | Steatosis0 | downReg | -0.43411 | 0.33816 |
| steatosisGroup | Steatosis2 | Steatosis0 | downReg | -0.23978 | 0.76018 |
| steatosisGroup | Steatosis3 | Steatosis0 | downReg | -0.22464 | 0.76815 |
| ballooningGroup | Ballooning1 | Ballooning0 | downReg | -0.03067 | 0.97259 |
| ballooningGroup | Ballooning2 | Ballooning0 | downReg | 0.46121 | 0.29955 |
| inflammationGroup | inflammation1 | inflammation0 | downReg | 0.33696 | 0.47722 |
| inflammationGroup | inflammation2 | inflammation0 | downReg | -0.07474 | 0.93477 |
| inflammationGroup | inflammation3 | inflammation0 | downReg | 0.21098 | 0.85307 |
| fibrosisGroup | Fibrosis1 | Fibrosis0 | downReg | 0.03773 | 0.95866 |
| fibrosisGroup | Fibrosis2 | Fibrosis0 | downReg | 0.39784 | 0.51875 |
| fibrosisGroup | Fibrosis3 | Fibrosis0 | downReg | 0.46919 | 0.43218 |
| fibrosisGroup | Fibrosis4 | Fibrosis0 | upReg | 1.29834 | 0.00075 |

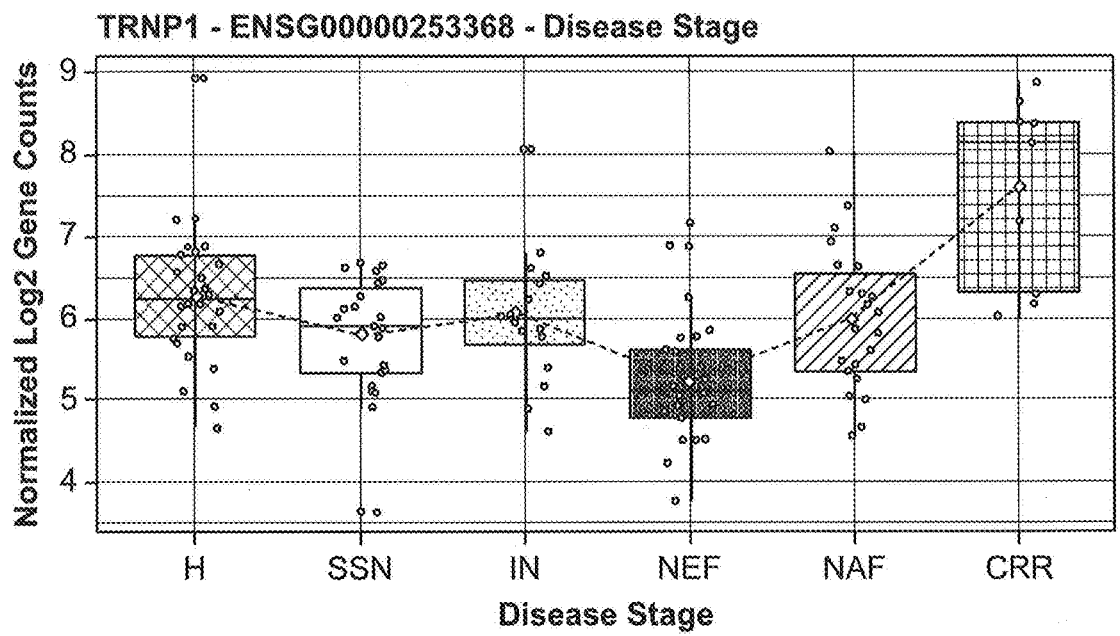

FIG. 23C

APLN - ENSG00000171388 - DESeq2 Results

| Analysis | Condition | Reference | Type | log2FC | Padj |
|---|---|---|---|---|---|
| diseaseStage | Simple_Steatosis_NAFLD | Healthy | downReg | -0.42061 | 0.51014 |
| diseaseStage | Incomplete_NAFLD | Healthy | upReg | 0.10152 | 0.90618 |
| diseaseStage | NASH_Early_Fibrosis | Healthy | downReg | -0.19591 | 0.73029 |
| diseaseStage | NASH_Advanced_Fibrosis | Healthy | downReg | -0.12857 | 0.82464 |
| diseaseStage | Cirrhosis | Healthy | upReg | 2.30945 | 6.398e-06 |
| steatosisGroup | Steatosis1 | Steatosis0 | downReg | -0.61394 | 0.14837 |
| steatosisGroup | Steatosis2 | Steatosis0 | downReg | -0.34948 | 0.63534 |
| steatosisGroup | Steatosis3 | Steatosis0 | downReg | -0.65674 | 0.29672 |
| ballooningGroup | Ballooning1 | Ballooning0 | upReg | 0.251 | 0.7052 |
| ballooningGroup | Ballooning2 | Ballooning0 | upReg | 0.03859 | 0.95326 |
| inflammationGroup | inflammation1 | inflammation0 | downReg | -0.50195 | 0.24597 |
| inflammationGroup | inflammation2 | inflammation0 | downReg | -1.32571 | 0.01819 |
| inflammationGroup | inflammation3 | inflammation0 | downReg | -1.2991 | 0.08982 |
| fibrosisGroup | Fibrosis1 | Fibrosis0 | downReg | -0.17699 | 0.76801 |
| fibrosisGroup | Fibrosis2 | Fibrosis0 | upReg | 0.31572 | 0.61136 |
| fibrosisGroup | Fibrosis3 | Fibrosis0 | downReg | -0.28593 | 0.6619 |
| fibrosisGroup | Fibrosis4 | Fibrosis0 | upReg | 1.63457 | 6.599e-06 |

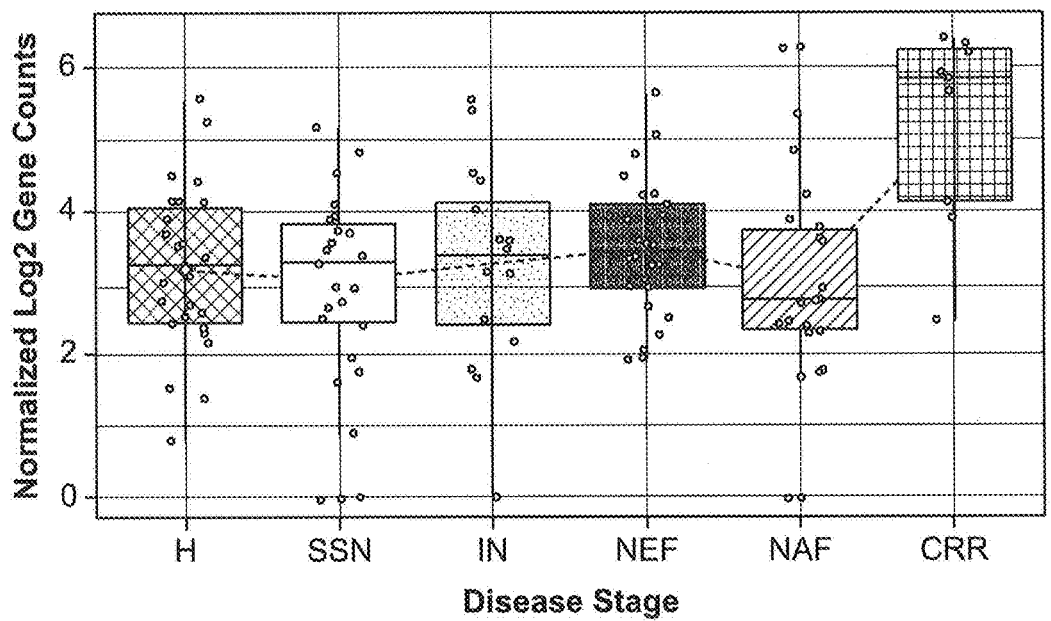

FIG. 24C

LTB - ENSG00000227507 - DESeq2 Results

| Analysis | Condition | Reference | Type | log2FC | Padj |
|---|---|---|---|---|---|
| diseaseStage | Simple_Steatosis_NAFLD | Healthy | upReg | 0.77672 | 0.05295 |
| diseaseStage | Incomplete_NAFLD | Healthy | upReg | 0.96838 | 0.01388 |
| diseaseStage | NASH_Early_Fibrosis | Healthy | upReg | 1.10855 | 0.00034 |
| diseaseStage | NASH_Advanced_Fibrosis | Healthy | upReg | 1.5525 | 1.236e-07 |
| diseaseStage | Cirrhosis | Healthy | upReg | 1.23855 | 0.00428 |
| steatosisGroup | Steatosis1 | Steatosis0 | upReg | 0.76774 | 0.00467 |
| steatosisGroup | Steatosis2 | Steatosis0 | upReg | 0.76214 | 0.05904 |
| steatosisGroup | Steatosis3 | Steatosis0 | upReg | 1.17745 | 0.00129 |
| ballooningGroup | Ballooning1 | Ballooning0 | upReg | 0.47569 | 0.16194 |
| ballooningGroup | Ballooning2 | Ballooning0 | upReg | 0.9027 | 0.00063 |
| inflammationGroup | inflammation1 | inflammation0 | upReg | 0.48322 | 0.10561 |
| inflammationGroup | inflammation2 | inflammation0 | upReg | 0.44956 | 0.32318 |
| inflammationGroup | inflammation3 | inflammation0 | upReg | 1.26002 | 0.00969 |
| fibrosisGroup | Fibrosis1 | Fibrosis0 | upReg | 0.46428 | 0.19242 |
| fibrosisGroup | Fibrosis2 | Fibrosis0 | upReg | 0.63739 | 0.11172 |
| fibrosisGroup | Fibrosis3 | Fibrosis0 | upReg | 1.13633 | 0.00115 |
| fibrosisGroup | Fibrosis4 | Fibrosis0 | upReg | 0.89188 | 0.00264 |

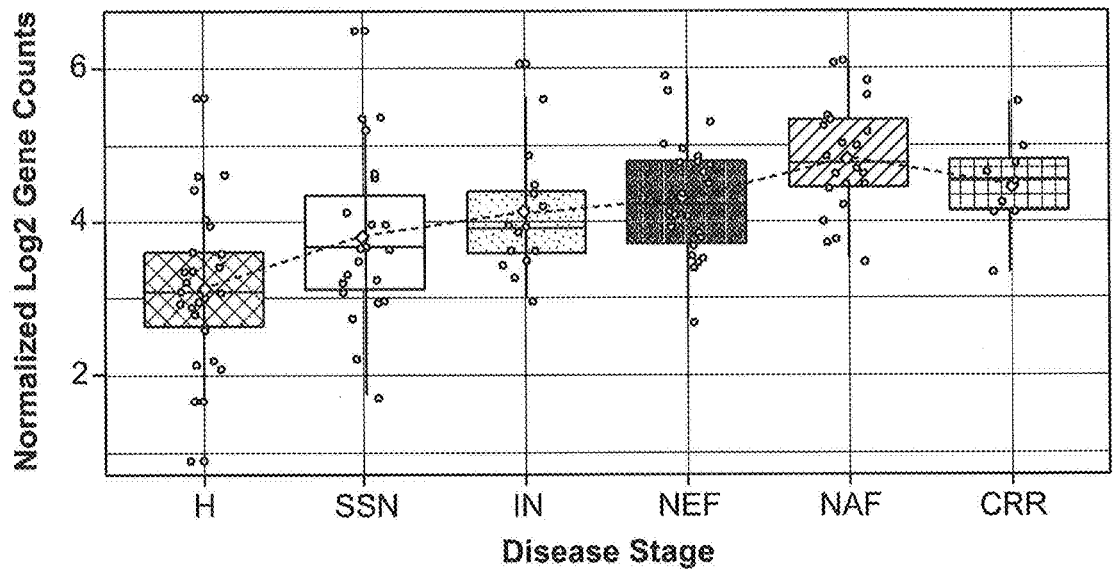

FIG. 26C

Bright field

GFP imager

6 µM each

11 µM each

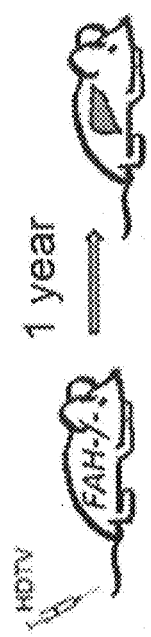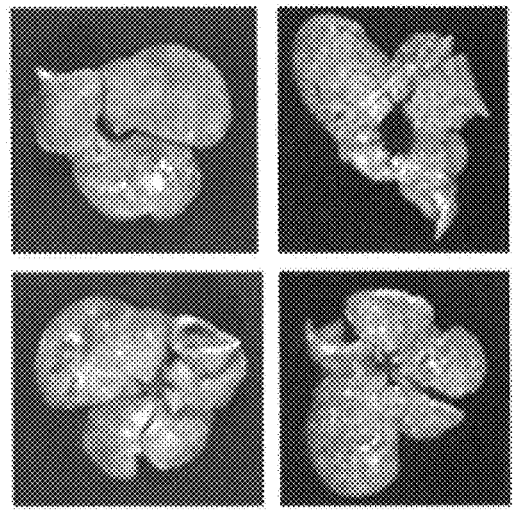
FIG. 30A
FIG. 30B Bright field
FIG. 30C GFP imager pMSCV-shRNA HepG2 cell line

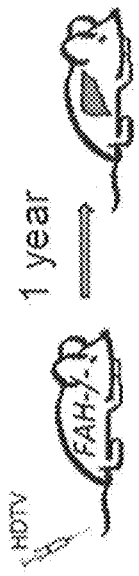
FIG. 34A
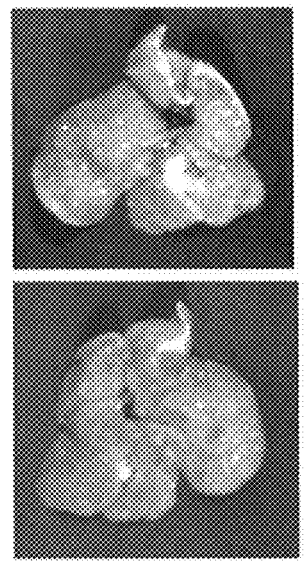
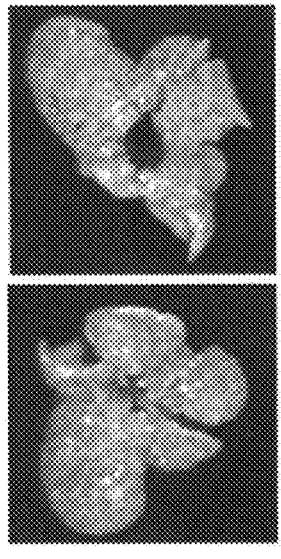
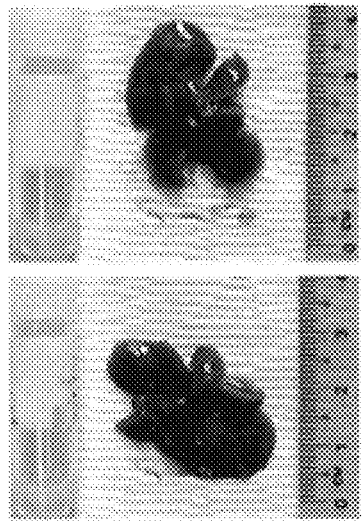
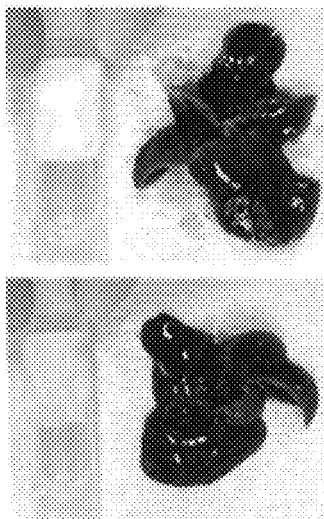
FIG. 34B
FIG. 34C Bright field x50 magnification Based on AMPL Pathology Evaluation (A*STAR)

Based on HistoIndex Pathology Evaluation

Mfap4 or Itfg1 knockdown enhances proliferation and regeneration beyond liver

METHOD OF STIMULATING PROLIFERATION OF A CELL

This application is a continuation of International Application No. PCT/SG2021/050443, filed on 30 Jul. 2021, which claims priority from SG 10202007297P filed 30 Jul. 2020, the contents and elements of which are herein incorporated by reference for all purposes.

REFERENCE TO A "SEQUENCE LISTING" SUBMITTED AS ASCII TEXT FILES VIA EFS-WEB

The Sequence Listing written in file 109046-1326735-SeqListing.txt created on Apr. 27, 2022, 1,592,517 bytes, machine format IBM-PC, MS-Windows operating system, in accordance with 37 C.F.R. §§ 1.821 to 1.825, is hereby incorporated by reference in its entirety for all purposes.

FIELD OF THE INVENTION

The present disclosure relates generally to the field of regenerative therapy. In particular, the specification teaches a method of stimulating or increasing proliferation and/or regeneration of a cell in a subject, comprising administering to the subject an inhibitor of a gene or corresponding gene product associated with organ regeneration to stimulate or increase proliferation of the cell in the subject.

BACKGROUND

The rising incidence of acute and chronic liver failure, which causes more than 1.3 million deaths per year worldwide (World Health Organization, 2018), represents a major global health concern. The main underlying causes of end-stage liver disease are hepatitis virus infections (especially hepatitis B and C), drug- and alcohol-induced liver damage, and non-alcoholic fatty liver disease (NAFLD; associated with obesity and progressing to non-alcoholic steatohepatitis (NASH)). Asia has an especially high burden of hepatitis virus infections (WHO), and an increased incidence of NAFLD. Despite advances in the prevention and treatment of viral hepatitis (hepatitis B vaccination and hepatitis C combination therapies) the number of people with end-stage liver disease is expected to rise, mainly fueled by the obesity epidemic and aging societies.

Currently, the only curative treatment for end-stage liver disease is liver transplantation. However, donor organs are limited, and end-stage liver disease patients may also experience complications that render them unfit for major surgery. Therefore, alternative strategies to hold off or reverse end-stage liver disease are being pursued. These include cell transplantation, artificial liver devices, and enhancing the organ's endogenous regenerative capacity.

The liver is the only visceral organ that possesses the remarkable capacity to regenerate. It is known that as little as 25% of the original liver mass can regenerate back to its full size. Adult hepatocytes are long-lived and normally do not undergo cell division (Go). However, upon liver damage, they have the ability to enter the cell cycle and proliferate. Once cell proliferation is completed, the newly divided cells undergo restructuring, and other regeneration-related processes such as angiogenesis and reformation of extracellular matrix to complete the regeneration process.

Despite this amazing ability, the regenerative capacity of the liver seems limited, especially under chronic damaging conditions. The ability of the liver to regenerate is central to liver homeostasis. Because the liver is the main site of drug detoxification, it is exposed to many chemicals in the body which may potentially induce cell death and injury. Furthermore, through the enterohepatic circulation, it is exposed to microbiota related metabolites. The liver can regenerate damaged tissue rapidly thereby preventing functional failure. Liver regeneration is also critical for patients with partial removal of the liver due to tumor resection or living-donor transplantation.

In the last three decades, scientists have gained a better understanding of the process of liver regeneration. For example, the cytokines IL6 and TNFα prime the hepatocyte to enter the cell cycle and mitogens such as HGF and EGF are important for driving proliferation. However, the process of promoting the regenerative process is not well understood. Importantly, not only liver intrinsic signals are involved in the regenerative response but also signals from distant organs.

Many different processes are involved to modify the regenerative response, including nutrients, oxygen level and others. Importantly, the complex liver architecture and especially the interaction with other organs cannot be perfectly simulated in vitro and therefore in vivo experiments are essential. The disadvantage of in vivo models is in their limited potential for high throughput drug discovery pipelines, especially compound screens.

Accordingly, there is a need to overcome, or at least to alleviate, one or more of the above-mentioned problems.

SUMMARY OF THE INVENTION

The present invention concerns the treatment and/or prevention of disease through inhibition of genes and/or proteins identified to be upregulated in profibrotic processes. Inhibition of such genes/proteins has protective and regenerative effects.

The present disclosure provides a method of treating or preventing a disease associated with fibrosis, comprising inhibiting at least one of ITFG1, MFAP4, GRHPR, ABCC4, PAK3, TRNP1, APLN, KIF20A, and/or LTB.

Also provided is a method of treating or preventing a disease associated with fibrosis, comprising administering a therapeutically or prophylactically effective amount of an inhibitor of at least one of ITFG1, MFAP4, GRHPR, ABCC4, PAK3, TRNP1, APLN, KIF20A, and/or LTB to a subject.

Also provided is an inhibitor of at least one of ITFG1, MFAP4, GRHPR, ABCC4, PAK3, TRNP1, APLN, KIF20A, and/or LTB for use in a method of treating or preventing a disease associated with fibrosis.

Also provided is the use of an inhibitor of at least one of ITFG1, MFAP4, GRHPR, ABCC4, PAK3, TRNP1, APLN, KIF20A, and/or LTB in the manufacture of a medicament for use in a method of treating or preventing a disease associated with fibrosis.

In some embodiments, the disease is a liver disease or condition.

In some embodiments, the disease or condition is selected from: acute liver disease, chronic liver disease, metabolic liver disease, steatosis, liver fibrosis, primary sclerosing cholangitis (PSC), cirrhosis, mild liver fibrosis, advanced liver fibrosis, non-alcoholic fatty liver disease (NAFLD), non-alcoholic steatohepatitis (NASH), alcoholic fatty liver disease (ALFD), alcohol-related liver disease (ARLD), hepatic ischemia reperfusion injury, primary biliary cirrhosis (PBC), hepatitis, liver damage, liver injury, liver failure, metabolic syndrome, obesity, diabetes mellitus, end-stage liver disease, inflammation of the liver, lobular inflammation, and/or hepatocellular carcinoma (HCC).

In some embodiments, the inhibitor is selected from a nucleic acid, peptide, antibody, antigen-binding molecule or small molecule inhibitor. In some embodiments, the inhibitor is capable of binding to a polypeptide according to any one or more of SEQ ID NO: 7156 to 7178, or to a mRNA according to any one of SEQ ID NO: 7179 to 7195.

In some embodiments, the inhibitor is an inhibitory nucleic acid comprising or encoding antisense nucleic acid having at least 75% sequence identity to any one of SEQ ID NOs: 7179 to 7195, or a portion thereof, or having at least 75% sequence identity to the reverse complement of any one of SEQ ID NOs: 7179 to 7195, or a portion thereof.

In some embodiments, the inhibitor is an inhibitory nucleic acid comprising or encoding antisense nucleic acid comprising or consisting of a nucleotide sequence having at least 75% sequence identity to any one of SEQ ID NO: 1 to 7155, and/or having at least 75% sequence identity to the reverse complement of any one of SEQ ID NOs: 1 to 7155.

In some embodiments, the inhibitor is an inhibitory nucleic acid comprising or encoding antisense nucleic acid comprising or consisting of a nucleotide sequence having at least 75% sequence identity to any one of SEQ ID NO: 6, 7, 457 to 1482, 7095, 7096, 7109 to 7114, 7130 to 7140, 7144, 7145, 7149, 7150, 7154, and/or 7155, and/or having at least 75% sequence identity to the reverse complement of any one of SEQ ID NO: 6, 7, 457 to 1482, 7095, 7096, 7109 to 7114, 7130 to 7140, 7144, 7145, 7149, 7150, 7154, and/or 7155, and optionally wherein the antisense nucleic acid is capable of reducing gene and/or protein expression of ITFG1.

In some embodiments, the inhibitor is an inhibitory nucleic acid comprising or encoding antisense nucleic acid comprising or consisting of a nucleotide sequence having at least 75% sequence identity to any one of SEQ ID NO: 1, 2, 14 to 347, 7092, 7093, 7097 to 7102, 7115 to 7120, 7141, 7142, 7146, 7147, 7151, and/or 7152, and/or having at least 75% sequence identity to the reverse complement of any one of SEQ ID NO: 1, 2, 14 to 347, 7092, 7093, 7097 to 7102, 7115 to 7120, 7141, 7142, 7146, 7147, 7151, and/or 7152, and optionally wherein the antisense nucleic acid is capable of reducing gene and/or protein expression of MFAP4.

In some embodiments, the inhibitor is an inhibitory nucleic acid comprising or encoding antisense nucleic acid comprising or consisting of a nucleotide sequence having at least 75% sequence identity to any one of SEQ ID NO: 3 to 5, 348 to 456, 7094, 7103 to 7108, 7121 to 7129, 7143, 7148, and/or 7153, and/or having at least 75% sequence identity to the reverse complement of any one of SEQ ID NO: 3 to 5, 348 to 456, 7094, 7103 to 7108, 7121 to 7129, 7143, 7148, and/or 7153, and optionally wherein the antisense nucleic acid is capable of reducing gene and/or protein expression of GRHPR.

In some embodiments, the inhibitor is an inhibitory nucleic acid comprising or encoding antisense nucleic acid comprising or consisting of a nucleotide sequence having at least 75% sequence identity to any one of SEQ ID NO: 1483 to 2208, and/or having at least 75% sequence identity to the reverse complement of any one of SEQ ID NO: 1483 to 2208, and optionally wherein the antisense nucleic acid is capable of reducing gene and/or protein expression of ABCC4.

In some embodiments, the inhibitor is an inhibitory nucleic acid comprising or encoding antisense nucleic acid comprising or consisting of a nucleotide sequence having at least 75% sequence identity to any one of SEQ ID NO: 2209 to 5060, and/or having at least 75% sequence identity to the reverse complement of any one of SEQ ID NO: 2209 to 5060, and optionally wherein the antisense nucleic acid is capable of reducing gene and/or protein expression of PAK3.

In some embodiments, the inhibitor is an inhibitory nucleic acid comprising or encoding antisense nucleic acid comprising or consisting of a nucleotide sequence having at least 75% sequence identity to any one of SEQ ID NO: 5061 to 5389, and/or having at least 75% sequence identity to the reverse complement of any one of SEQ ID NO: 5061 to 5389, and optionally wherein the antisense nucleic acid is capable of reducing gene and/or protein expression of TRNP1.

In some embodiments, the inhibitor is an inhibitory nucleic acid comprising or encoding antisense nucleic acid comprising or consisting of a nucleotide sequence having at least 75% sequence identity to any one of SEQ ID NO: 5390 to 5966, and/or having at least 75% sequence identity to the reverse complement of any one of SEQ ID NO: 5390 to 5966, and optionally wherein the antisense nucleic acid is capable of reducing gene and/or protein expression of APLN.

In some embodiments, the inhibitor is an inhibitory nucleic acid comprising or encoding antisense nucleic acid comprising or consisting of a nucleotide sequence having at least 75% sequence identity to any one of SEQ ID NO: 5967 to 6974, and/or having at least 75% sequence identity to the reverse complement of any one of SEQ ID NO: 5967 to 6974, and optionally wherein the antisense nucleic acid is capable of reducing gene and/or protein expression of KIF20A.

In some embodiments, the inhibitor is an inhibitory nucleic acid comprising or encoding antisense nucleic acid comprising or consisting of a nucleotide sequence having at least 75% sequence identity to any one of SEQ ID NO: 6975 to 7091, and/or having at least 75% sequence identity to the reverse complement of any one of SEQ ID NO: 6975 to 7091, and optionally wherein the antisense nucleic acid is capable of reducing gene and/or protein expression of LTB.

In some embodiments, the inhibitory nucleic acid comprises: (i) nucleic acid comprising the nucleotide sequence of one of SEQ ID NO: 1 to 7096 or 7146 to 7150, or a nucleotide sequence having at least 75% sequence identity to one of SEQ ID NO: 1 to 7096 or 7146 to 7150; and (ii) nucleic acid comprising a nucleotide sequence having the reverse complement of the nucleotide sequence of (i), or having at least 75% sequence identity to the reverse complement of the nucleotide sequence of (i).

In some embodiments, the inhibitory nucleic acid comprises one or more modified nucleotides selected from: 2'-O-methyluridine-3-phosphate, 2'-O-methyladenosine-3'-phosphate, 2'-O-methylguanosine-3'-phosphate, 2'-O-methylcytidine-3'-phosphate, 2'-O-methyluridine-3-phosphorothioate, 2'-O-methyladenosine-3'-phosphorothioate, 2'-O-methylguanosine-3'-phosphorothioate, 2'-O-methylcytidine-3'-phosphorothioate, 2'-fluorouridine-3-phosphate, 2'-fluoroadenosine-3-phosphate, 2'-fluoroguanosine-3'-phosphate, 2'-fluorocytidine-3'-phosphate, 2'-fluorocytidine-3'-phosphorothioate, 2'-fluoroguanosine-3'-phosphorothioate, 2'-fluoroadenosine-3'-phosphorothioate, and 2'-fluorouridine-3-phosphorothioate. In some embodiments, the inhibitory nucleic acid comprises: (i) nucleic acid comprising the nucleotide sequence (including the modifications thereto) shown in one of SEQ ID NO: 7146 to 7150; and (ii) nucleic acid comprising the nucleotide sequence (including the modifications thereto) shown in one of SEQ ID NO: 7151 to 7155.

In some embodiments, the inhibitor comprises a moiety facilitating uptake of the inhibitory nucleic acid by hepatocytes. In some embodiments, the nucleic acid inhibitor is an antisense nucleic acid, siRNA, or shRNA.

In some embodiments, the method comprises administering the inhibitor to a subject in which expression and/or activity of one or more of MFAP4, GRHPR, ITFG1, ABCC4, PAK3, TRNP1, APLN, KIF20A, and/or LTB is upregulated.

Also provided is an inhibitory nucleic acid for reducing gene and/or protein expression of ITFG1, wherein the nucleic acid comprises or encodes antisense nucleic acid having at least 75% sequence identity to SEQ ID NO: 7182, or a portion thereof, or having at least 75% sequence identity to the reverse complement of SEQ ID NO: 7182, or a portion thereof.

In some embodiments, the inhibitory nucleic acid comprises or encodes antisense nucleic acid comprising or consisting of a nucleotide sequence having at least 75% sequence identity to any one of SEQ ID NO: 6, 7, 457 to 1482, 7095, 7096, 7109 to 7114, 7130 to 7140, 7144, 7145, 7149, 7150, 7154, and/or 7155, and/or having at least 75% sequence identity to the reverse complement of any one of SEQ ID NO: 6, 7, 457 to 1482, 7095, 7096, 7109 to 7114, 7130 to 7140, 7144, 7145, 7149, 7150, 7154, and/or 7155.

Provided is an inhibitory nucleic acid for reducing gene and/or protein expression of MFAP4, wherein the nucleic acid comprises or encodes antisense nucleic acid having at least 75% sequence identity to SEQ ID NO: 7179 or 7180, or a portion thereof, or having at least 75% sequence identity to the reverse complement of SEQ ID NO: 7179 or 7180, or a portion thereof.

In some embodiments, the inhibitory nucleic acid comprises or encodes antisense nucleic acid comprising or consisting of a nucleotide sequence having at least 75% sequence identity to any one of SEQ ID NO: 1, 2, 14 to 347, 7092, 7093, 7097 to 7102, 7115 to 7120, 7141, 7142, 7146, 7147, 7151, and/or 7152, and/or having at least 75% sequence identity to the reverse complement of any one of SEQ ID NO: 1, 2, 14 to 347, 7092, 7093, 7097 to 7102, 7115 to 7120, 7141, 7142, 7146, 7147, 7151, and/or 7152.

Provided is an inhibitory nucleic acid for reducing gene and/or protein expression of GRHPR, wherein the nucleic acid comprises or encodes antisense nucleic acid having at least 75% sequence identity to SEQ ID NO: 7181, or a portion thereof, or having at least 75% sequence identity to the reverse complement of SEQ ID NO: 7181, or a portion thereof.

In some embodiments, the inhibitory nucleic acid comprises or encodes antisense nucleic acid comprising or consisting of a nucleotide sequence having at least 75% sequence identity to any one of SEQ ID NO: 3 to 5, 348 to 456, 7094, 7103 to 7108, 7121 to 7129, 7143, 7148, and/or 7153, and/or having at least 75% sequence identity to the reverse complement of any one of SEQ ID NO: 3 to 5, 348 to 456, 7094, 7103 to 7108, 7121 to 7129, 7143, 7148, and/or 7153.

Provided is an inhibitory nucleic acid for reducing gene and/or protein expression of ABCC4, wherein the nucleic acid comprises or encodes antisense nucleic acid having at least 75% sequence identity to any one of SEQ ID NO: 7183 to 7186, or a portion thereof, or having at least 75% sequence identity to the reverse complement of any one of SEQ ID NO: 7183 to 7186, or a portion thereof.

In some embodiments, the inhibitory nucleic acid comprises or encodes antisense nucleic acid comprising or consisting of a nucleotide sequence having at least 75% sequence identity to any one of SEQ ID NO: 1483 to 2208, and/or having at least 75% sequence identity to the reverse complement of any one of SEQ ID NO: 1483 to 2208.

Provided is an inhibitory nucleic acid for reducing gene and/or protein expression of PAK3, wherein the nucleic acid comprises or encodes antisense nucleic acid having at least 75% sequence identity to any one of SEQ ID NO: 7187 to 7190, or a portion thereof, or having at least 75% sequence identity to the reverse complement of any one of SEQ ID NO: 7187 to 7190, or a portion thereof.

In some embodiments, the inhibitory nucleic acid comprises or encodes antisense nucleic acid comprising or consisting of a nucleotide sequence having at least 75% sequence identity to any one of SEQ ID NO: 2209 to 5060, and/or having at least 75% sequence identity to the reverse complement of any one of SEQ ID NO: 2209 to 5060.

Provided is an inhibitory nucleic acid for reducing gene and/or protein expression of TRNP1, wherein the nucleic acid comprises or encodes antisense nucleic acid having at least 75% sequence identity to SEQ ID NO: 7191, or a portion thereof, or having at least 75% sequence identity to the reverse complement of SEQ ID NO: 7191, or a portion thereof.

In some embodiments, the inhibitory nucleic acid comprises or encodes antisense nucleic acid comprising or consisting of a nucleotide sequence having at least 75% sequence identity to any one of SEQ ID NO: 5061 to 5389, and/or having at least 75% sequence identity to the reverse complement of any one of SEQ ID NO: 5061 to 5389.

Provided is an inhibitory nucleic acid for reducing gene and/or protein expression of APLN, wherein the nucleic acid comprises or encodes antisense nucleic acid having at least 75% sequence identity to SEQ ID NO: 7192, or a portion thereof, or having at least 75% sequence identity to the reverse complement of SEQ ID NO: 7192, or a portion thereof.

In some embodiments, the inhibitory nucleic acid comprises or encodes antisense nucleic acid comprising or consisting of a nucleotide sequence having at least 75% sequence identity to any one of SEQ ID NO: 5390 to 5966, and/or having at least 75% sequence identity to the reverse complement of any one of SEQ ID NO: 5390 to 5966.

Provided is an inhibitory nucleic acid for reducing gene and/or protein expression of KIF20A, wherein the nucleic acid comprises or encodes antisense nucleic acid having at least 75% sequence identity to SEQ ID NO: 7193, or a portion thereof, or having at least 75% sequence identity to the reverse complement of SEQ ID NO: 7193, or a portion thereof.

In some embodiments, the inhibitory nucleic acid comprises or encodes antisense nucleic acid comprising or consisting of a nucleotide sequence having at least 75% sequence identity to any one of SEQ ID NO: 5967 to 6974, and/or having at least 75% sequence identity to the reverse complement of any one of SEQ ID NO: 5967 to 6974.

Provided is an inhibitory nucleic acid for reducing gene and/or protein expression of LTB, wherein the nucleic acid comprises or encodes antisense nucleic acid having at least 75% sequence identity to SEQ ID NO: 7194 or 7195, or a portion thereof, or having at least 75% sequence identity to the reverse complement of SEQ ID NO: 7194 or 7195, or a portion thereof.

In some embodiments, the inhibitory nucleic acid comprises or encodes antisense nucleic acid comprising or consisting of a nucleotide sequence having at least 75% sequence identity to any one of SEQ ID NO: 6975 to 7091, and/or having at least 75% sequence identity to the reverse complement of any one of SEQ ID NO: 6975 to 7091.

Also provided is an inhibitory nucleic acid comprising (i) nucleic acid comprising the nucleotide sequence shown in one of SEQ ID NO: 7092 to 7096; and (ii) nucleic acid comprising the nucleotide sequence shown in one of SEQ ID NO: 7141 to 7145.

In some embodiments, the inhibitory nucleic acid comprises one or more modified nucleotides selected from: 2'-O-methyluridine-3-phosphate, 2'-O-methyladenosine-3'-phosphate, 2'-O-methylguanosine-3'-phosphate, 2'-O-methylcytidine-3'-phosphate, 2'-O-methyluridine-3'-phosphorothioate, 2'-O-methyladenosine-3'-phosphorothioate, 2'-O-methylguanosine-3'-phosphorothioate, 2'-O-methylcytidine-3'-phosphorothioate, 2'-fluorouridine-3-phosphate, 2'-fluoroadenosine-3-phosphate, 2'-fluoroguanosine-3'-phosphate, 2'-fluorocytidine-3'-phosphate, 2'-fluorocytidine-3'-phosphorothioate, 2'-fluoroguanosine-3'-phosphorothioate, 2'-fluoroadenosine-3'-phosphorothioate, and 2'-fluorouridine-3'-phosphorothioate.

Also provided is inhibitory nucleic acid comprising (i) nucleic acid comprising the nucleotide sequence (including the modifications thereto) shown in one of SEQ ID NO: 7146 to 7150; and (ii) nucleic acid comprising the nucleotide sequence (including the modifications thereto) shown in one of SEQ ID NO: 7151 to 7155.

In some embodiments, the inhibitory nucleic acid further comprises a moiety facilitating uptake of the inhibitory nucleic acid by hepatocytes. In some embodiments, the inhibitory nucleic acid is an antisense nucleic acid, siRNA or shRNA.

The present disclosure also provides a nucleic acid, optionally isolated, encoding an inhibitory nucleic acid according to the present disclosure.

The present disclosure also provides an expression vector, comprising a nucleic acid according to the present disclosure.

The present disclosure also provides a composition comprising an inhibitory nucleic acid, a nucleic acid, or an expression vector according to the present disclosure, and a pharmaceutically acceptable carrier, diluent, excipient or adjuvant.

The present disclosure also provides a cell comprising an inhibitory nucleic acid, a nucleic acid, or an expression vector according to the present disclosure.

The present disclosure also provides a method of treating or preventing a disease according to the present disclosure, comprising administering a therapeutically or prophylactically effective amount of an inhibitor, an inhibitory nucleic acid, a nucleic acid, an expression vector, a composition, or a cell according to the present disclosure to a subject.

The present disclosure also provides an inhibitor, an inhibitory nucleic acid, a nucleic acid, an expression vector, a composition, or a cell according to the present disclosure for use in therapy. In some embodiments, the inhibitor, inhibitory nucleic acid, nucleic acid, expression vector, composition, or cell is provided for use in a method of treating or preventing a disease, e.g. a disease according to the present disclosure.

The present disclosure also provides the use of an inhibitor, an inhibitory nucleic acid, a nucleic acid, an expression vector, a composition, or a cell according to the present disclosure in the manufacture of a medicament for use in a method of treating or preventing a disease, e.g. a disease according to the present disclosure.

Also disclosed is an in vitro or in vivo method for reducing gene and/or protein expression of one or more of ITFG1, MFAP4, GRHPR, ABCC4, PAK3, TRNP1, APLN, KIF20A, and/or LTB in a cell, comprising introducing an inhibitory nucleic acid, a nucleic acid, or an expression vector according to the present disclosure into a cell.

Also disclosed is a method of regenerating liver tissue in vitro or in vivo, the method comprising inhibiting at least one of ITFG1, MFAP4, GRHPR, ABCC4, PAK3, TRNP1, APLN, KIF20A, and/or LTB in a cell of the tissue.

Also disclosed is a method of proliferating/expanding a hepatocyte in vitro or in vivo, the method comprising inhibiting at least one of ITFG1, MFAP4, GRHPR, ABCC4, PAK3, TRNP1, APLN, KIF20A, and/or LTB in the hepatocyte.

In some embodiments, a method disclosed herein comprises introducing an inhibitory nucleic acid, a nucleic acid, or an expression vector according to the present disclosure into a cell, e.g. a cell of the tissue or a hepatocyte.

Disclosed herein is a method of stimulating or increasing proliferation and/or regeneration of a cell in a subject, the method comprising administering to the subject an inhibitor of a gene or corresponding gene product associated with organ regeneration for a sufficient time and under conditions to stimulate or increase proliferation and/or regeneration of the cell in the subject.

Disclosed herein is a method of enhancing cell function in a subject, the method comprising administering to the subject an inhibitor of a gene or corresponding gene product associated with organ regeneration for a sufficient time and under conditions to enhance cell function in the subject.

Disclosed herein is a method of enhancing cell viability in a subject, the method comprising administering to the subject an inhibitor of a gene or corresponding gene product associated with organ regeneration for a sufficient time and under conditions to enhance cell viability in the subject.

Disclosed herein is a method of treating a liver condition or disease in a subject, the method comprising administering to the subject an inhibitor of a gene or corresponding gene product associated with organ regeneration for a sufficient time and under conditions to treat the liver condition or disease in the subject.

Disclosed herein is a method of protecting a subject from liver damage, the method comprising administering to the subject an inhibitor of a gene or corresponding gene product associated with organ regeneration for a sufficient time and under conditions to protect the subject from liver damage.

Disclosed herein is a method of detecting a liver condition or disease in a subject, the method comprising detecting in a sample the level of one or more biomarkers associated with organ regeneration, wherein a change in the level of the one or more biomarkers as compared to a reference indicates that the subject is suffering from a liver condition or disease.

Disclosed herein is an inhibitor of a gene or corresponding gene product associated with organ regeneration for use in preventing or treating a liver condition or disease in the subject.

Disclosed herein is the use of an inhibitor of a gene or corresponding gene product associated with organ regeneration in the manufacture of a medicament for preventing or treating a liver condition or disease in the subject.

The methods disclosed herein may employ any suitable inhibitor. In some embodiments, the inhibitor is an inhibitor according to the present disclosure.

Disclosed herein is a nucleic acid inhibitor consisting, comprising or encoding an RNAi agent having at least 70%, 80%, 90% or 95% sequence identity to an RNA sequence listed in any of Tables 1-14 or an RNAi agent that hybridizes to the complement of an RNA sequence listed in any of Tables 1-14 under stringency conditions.

Disclosed herein is a method of screening for an inhibitor of a gene or corresponding gene product associated with organ regeneration by: a) contacting the gene or corresponding gene product with a chemical compound library, and b) identifying a chemical compound within the library that is binds to the gene or corresponding gene product to inhibit the expression or function of the gene or corresponding gene product.

The invention includes the combination of the aspects and preferred features described except where such a combination is clearly impermissible or expressly avoided.

DETAILED DESCRIPTION

The present invention relates to the identification of proteins that are involved in the development of liver disease and/or are detrimental to liver regeneration after injury, and targeting such proteins to treat liver diseases.

Without being bound by theory, the inventors have used an unbiased in vivo functional genetic screen to identify new therapeutic targets that are upregulated in liver diseases and conditions associated with fibrosis. Enrichment of target shRNAs indicates that the knockdown/inhibition of these targets gives a survival advantage to hepatocytes under a chronic liver damaging condition. As enrichment indicates a relative expansion to the control, knockdown or inhibition of the identified genes supports hepatocyte expansion, proliferation and robustness. This is therapeutically beneficial for liver disease interception, accelerating liver regeneration, protecting against liver damage, promoting cell proliferation, stopping and reversing liver fibrosis, and increasing survival.

Targets

The present disclosure relates to inhibition of gene and/or protein expression of one or more of MFAP4, GRHPR, ITFG1, ABCC4, PAK3, TRNP1, APLN, KIF20A, and/or LTB. Any one or combination of these genes (i.e. any one, two, three, four, five, six, seven, eight or all nine) may be inhibited in the methods provided herein. Any one or combination of these genes may be referred to herein as a target gene(s), target mRNA(s), or target protein(s). One or more of MFAP4, GRHPR, ITFG1, ABCC4, PAK3, TRNP1, APLN, KIF20A, and/or LTB may be described herein as a "gene or corresponding gene product associated with organ regeneration".

MFAP4, GRHPR and ITFG1 are found in recurrent amplifications in hepatocellular carcinoma (Nat Med. 2014 October; 20(10): 1138-1146). ABCC4, PAK3, TRNP1, APLN, KIF20A and LTB were all found by the present inventors to be dysregulated in a local patient cohort with non-alcoholic fatty liver disease (NAFLD). Microfibril-associated glycoprotein 4 (MFAP4) is an extracellular matrix protein belonging to the fibrinogen-related domain (FReD) superfamily. Human MFAP4 is identified by UniProtKB P55083.

MFAP4 structure and function is described in e.g. Pilecki B., et al., J. Biol. Chem. 291:1103-1114 (2016), which is hereby incorporated by reference in its entirety.

MFAP4 is an extracellular glycoprotein found in elastic fibres and is required for proper elastic fibre organisation. It specifically binds tropoelastin and fibrillin-1 and -2, as well as the elastin cross-linking amino acid desmosine, and it co-localizes with fibrillin-1-positive fibres in vivo. Human MFAP4 has been localized to elastic fibres in a variety of elastic tissues, including aorta, skin, and lung.

MFAP4 is closely associated with remodelling-related diseases, including liver fibrosis, atherosclerosis, arterial injury stimulated remodelling, and asthma (Wang H B et al., J Am Heart Assoc. 2020; 9(17):e015307). Pan Z et al., FASEB J. 2020, 34(11):14250-14263 reported that MFAP4 deficiency alleviates renal fibrosis by inhibiting the activation of NF-κB and TGF-β/Smad signalling pathways and downregulating the expression of fibrosis-related proteins. MFAP4 is produced by activated myofibroblasts and may be a predictive biomarker for severity of hepatic fibrosis (Madsen B S et al., Liver Int. 2020; 40(7): 1701-1712; Seekmose S G, et al., PLoS One. 2015; 10(10):e0140418). Example 2 of the present application shows that genes known to be involved in liver regeneration, e.g. Ptgs2, Areg, Dhrs9, Hmox1 and Nqo1, are upregulated after Mfap4 knockdown.

Alternative splicing of the mRNA transcribed from the human MFAP4 gene yields two isoforms: isoform 1 (UniProtKB: P55083-1, v2; SEQ ID NO: 7156), and isoform 2 (UniProtKB: P55083-2; SEQ ID NO: 7157) in which the amino acid sequence corresponding to positions 1 to 2 of SEQ ID NO: 7156 are replaced with the sequence 'MGELSPLQRPLATEGTMKAQGVLLKL'.

The 255-amino acid sequence of human MFP4 isoform 1 comprises an N-terminal signal peptide at positions 1-21 of SEQ ID NO: 7156 and the mature protein region at positions 22-255 of SEQ ID NO: 7156. Positions 26-28 of SEQ ID NO: 7156 constitute the cell attachment site and positions 32-255 of SEQ ID NO: 7156 constitute the fibrinogen C-terminal domain.

In this specification, reference to 'MFAP4' encompasses: human MFAP4, isoforms of human MFAP4, homologues of human MFAP4 (i.e. encoded by the genome of a non-human animal), and variants thereof. In some embodiments, MFAP4 according to the present disclosure comprises or consists of an amino acid sequence having at 70% or greater amino acid sequence identity, preferably one of 75%, 80%, 85%, 90%, 91%, 92%, 93%, 94%, 95%, 96%, 97%, 98%, 99% or 100% amino acid sequence identity to the amino acid sequence of SEQ ID NO: 7156.

Glyoxylate reductase/hydroxypyruvate reductase (GRHPR) is an NADPH/NADH dependent enzyme with hydroxy-pyruvate reductase, glyoxylate reductase and D-glycerate dehydrogenase enzymatic activities. It reduces toxic intermediate glyoxylate to easily-excreted glycolate and reduces hydroxypyruvate into D-glycerate for use in glucose synthesis. Deficiency of GRHPR is the underlying cause of primary hyperoxaluria type 2 (PH2) and leads to increased urinary oxalate levels, formation of kidney stones and renal failure (Cregeen D P et al., Hum Mol Genet. 1999; 8(11):2063-9). Human GRHPR is identified by UniProtKB Q9UBQ7.

GRHPR structure and function is described in e.g. Rumsby G. and Cregeen D. P. Biochim. Biophys. Acta 1446: 383-388 (1999), and Booth et al., J Mol Biol, 2006; 360(1): 178-89, which are hereby incorporated by reference in their entirety.

Alternative splicing of the mRNA transcribed from the human GRHPR gene yields two isoforms: isoform 1 (UniProtKB: Q9UBQ7-1, v1; SEQ ID NO: 7158), and isoform 2 (UniProtKB: Q9UBQ7-2; SEQ ID NO: 7159) in which the amino acid sequence corresponding to positions 1 to 21 of SEQ ID NO: 7158 are replaced with the sequence 'MLGGVPTLCGTGNETWTLLAL', positions 22-164 of SEQ ID NO: 7158 are missing, and positions 246-328 of SEQ ID NO: 7158 are replaced with the sequence 'YPRATLPSKPGEEPSPLLPSGDFLPRGLLVRPQAEL-AGFHKPNNQLRNSWEYTRPPYREEEPSEWAWP VCFSAVAPTRRGLAHSSVASGSVPREPLQAHY-
PPPQRAGLEDLKGPLEAASHTAE-
PGFVWLWFSDTLNL MLLGGQTLKLTWS'.

The 328-amino acid sequence of human GRHPR isoform 1 comprises NADP binding sites at positions 217, 243, 162-164, 185-188 and 295 of SEQ ID NO: 7158, and substrate (glyoxylate/hydroxypyruvate) binding sites at positions 83-84, 245, 269, and 293-296 of SEQ ID NO: 7158.

In this specification, reference to 'GRHPR' encompasses: human GRHPR, isoforms of human GRHPR, homologues of human GRHPR (i.e. encoded by the genome of a non-human animal), and variants thereof. In some embodiments, GRHPR according to the present disclosure comprises or consists of an amino acid sequence having at 70% or greater amino acid sequence identity, preferably one of 75%, 80%, 85%, 90%, 91%, 92%, 93%, 94%, 95%, 96%, 97%, 98%, 99% or 100% amino acid sequence identity to the amino acid sequence of SEQ ID NO: 7158.

T-cell immunomodulatory protein (ITFG1; also known as Protein TIP, Integrin-alpha FG-GAP repeat-containing protein 1, or Linkin/LNKN-1) is a modulator of T cell function. Human ITFG1 is identified by UniProtKB Q8TB96.

ITFG1 structure and function is described in e.g. Fiscella M., et al., Nat. Biotechnol. 21:302-307 (2003), which is hereby incorporated by reference in its entirety. Treatment of primary human and murine T cells with ITFG1 in vitro resulted in the secretion of IFN-gamma, TNF-alpha, and IL-10, whereas in vivo ITFG1 reportedly has a protective effect in a mouse acute graft-versus-host disease (GVHD) model. The interaction between ITFG1 and the ATPase RUVBL1 is reported to be required for breast cancer cell invasion and progression (Fan W. et al., Biochim Biophys Acta Gen Subj. 2017; 1861(7):1788-1800).

The 612-amino acid sequence of human ITFG1 is shown in SEQ ID NO: 7160 (UniprotKB: Q8TB96-1, v1). This sequence comprises: an N-terminal signal peptide at positions 1-33 of SEQ ID NO: 7160, an FG-GAP repeat at positions 258-293 of SEQ ID NO: 7160, and a transmembrane domain at positions 567-587 of SEQ ID NO: 7160.

In this specification, reference to 'ITFG1' encompasses: human ITFG1, isoforms of human ITFG1, homologues of human ITFG1 (i.e. encoded by the genome of a non-human animal), and variants thereof. In some embodiments, ITFG1 according to the present disclosure comprises or consists of an amino acid sequence having at 70% or greater amino acid sequence identity, preferably one of 75%, 80%, 85%, 90%, 91%, 92%, 93%, 94%, 95%, 96%, 97%, 98%, 99% or 100% amino acid sequence identity to the amino acid sequence of SEQ ID NO: 7160.

ATP-binding cassette sub-family C member 4 (ABCC4; also known as multidrug resistance protein 4 (MRP4)) is an ATP-dependent transporter of the ATP-binding cassette (ABC) family that actively extrudes physiological compounds and xenobiotics from cells. It transports a range of endogenous molecules that have a key role in cellular communication and signalling, including cyclic nucleotides such as cyclic AMP (cAMP) and cyclic GMP (cGMP), bile acids, steroid conjugates, urate, and prostaglandins. It is expressed in several tissues, including hepatocytes, with highest expression in the kidney and choroid plexus (Maher J M, et al., Drug Metab. Dispos., 33 (2005), pp. 947-955). Human ABCC4 is identified by UniProtKB 015439.

ABCC4 structure and function is described in e.g. Russel et al., Trends Pharmacol Sci. 2008, 29(4):200-7, which is hereby incorporated by reference in its entirety. ABCC4 is an inducible gene in the liver following toxic acetaminophen exposure in both humans and rodents. In mice, ABCC4 deficiency is linked to increased risk of liver injury, altered gut epithelial function and altered drug disposition, although protein expression is reportedly increased in human livers with steatosis, alcoholic cirrhosis, and diabetic cirrhosis (More V R et al., Drug Metab Dispos. 2013; 41(5): 1148-1155).

Alternative splicing of the mRNA transcribed from the human ABCC4 gene yields four isoforms: isoform 1 (UniProtKB: 015439-1, v3; SEQ ID NO: 7161), isoform 2 (015439-2, SEQ ID NO: 7162) in which the amino acid sequence corresponding to positions 679-725 of SEQ ID NO: 7161 are missing, isoform 3 (015439-3, SEQ ID NO: 7163) in which the amino acid sequence corresponding to positions 846-859 of SEQ ID NO: 7161 are replaced with the sequence 'RWDLAVLSWLVSNS' and positions 860-1325 of SEQ ID NO: 7161 are missing, and isoform 4 (015439-4, SEQ ID NO: 7164) in which the amino acid sequence corresponding to positions 103-177 of SEQ ID NO: 7161 are missing, the amino acid sequence corresponding to positions 846-859 of SEQ ID NO: 7161 are replaced with the sequence 'RWDLAVLSWLVSNS', and the amino acid sequence corresponding to positions 860-1325 of SEQ ID NO: 7161 are missing.

The 1325-amino acid sequence of human ABCC4 isoform 1 comprises: an ABC transmembrane type-1 1 domain at positions 92-377, an ABC transporter 1 domain at positions 410-633, an ABC transmembrane type-1 2 domain at positions 714-1005, an ABC transporter 2 domain at positions 1041-1274, and ATP binding regions at positions 445-452 and 1075-1082 of SEQ ID NO: 7161.

In this specification, reference to 'ABCC4' encompasses: human ABCC4, isoforms of human ABCC4, homologues of human ABCC4 (i.e. encoded by the genome of a non-human animal), and variants thereof. In some embodiments, ABCC4 according to the present disclosure comprises or consists of an amino acid sequence having at 70% or greater amino acid sequence identity, preferably one of 75%, 80%, 85%, 90%, 91%, 92%, 93%, 94%, 95%, 96%, 97%, 98%, 99% or 100% amino acid sequence identity to the amino acid sequence of SEQ ID NO: 7161.

p21-activated kinase 3 (PAK3; also known as Serine/threonine-protein kinase PAK 3, Beta-PAK or Oligophrenin-3) is a serine/threonine protein kinase that plays a role in a variety of different signalling pathways including cytoskeleton regulation, cell migration, or cell cycle regulation. Activation by the binding of active CDC42 and RAC1 results in a conformational change and a subsequent autophosphorylation on several serine and/or threonine residues. It phosphorylates MAPK4 and MAPK6 and activates the downstream target MAPKAPK5, a regulator of F-actin polymerization and cell migration. PAK3 is also a core mediator of integrin beta-1 signalling (a critical mediator of HSC activation and progression of fibrotic disease). Human PAK3 is identified by UniProtKB O75914.

PAK3 structure and function is described in e.g. Deleris P., et al., J. Biol. Chem. 286:6470-6478 (2011) and Chong C. et al., J. Biol. Chem. 276:17347-17353 (2001), which are both hereby incorporated by reference in their entirety.

Alternative splicing of the mRNA transcribed from the human PAK3 gene yields four isoforms: isoform 1 (UniProtKB: O75914-1, v2; SEQ ID NO: 7165), isoform 2 (O75914-2, SEQ ID NO: 7166) in which the amino acid sequence corresponding to positions 93-107 of SEQ ID NO: 7165 are missing, isoform 3 (O75914-3, SEQ ID NO: 7167) in which the amino acid at position 92 of SEQ ID NO: 7165 is replaced with the sequence 'TNSPFQTSRPVT- VASSQSEGKM', and isoform 4 (O75914-4, SEQ ID NO: 7168) in which the amino acid sequence corresponding to positions 92-107 of SEQ ID NO: 7165 are replaced with the sequence 'TNSPFQTSRPVTVASSQSEGKM'.

The 559-amino acid sequence of human PAK3 isoform 1 comprises: a CRIB domain at positions 70-83 and a protein kinase domain at positions 283-534 of SEQ ID NO: 7165.

In this specification, reference to 'PAK3' encompasses: human PAK3, isoforms of human PAK3, homologues of human PAK3 (i.e. encoded by the genome of a non-human animal), and variants thereof. In some embodiments, PAK3 according to the present disclosure comprises or consists of an amino acid sequence having at 70% or greater amino acid sequence identity, preferably one of 75%, 80%, 85%, 90%, 91%, 92%, 93%, 94%, 95%, 96%, 97%, 98%, 99% or 100% amino acid sequence identity to the amino acid sequence of SEQ ID NO: 7165.

TMF-regulated nuclear protein 1 (TRNP1) is a DNA-binding factor that regulates the expression of a subset of genes and plays a key role in tangential, radial, and lateral expansion of the brain neocortex. Human TRNP1 is identified by UniProtKB Q6NT89.

TRNP1 structure and function is described in e.g. Stahl R. et al., Cell 153:535-549 (2013), which is hereby incorporated by reference in its entirety.

The 227-amino acid sequence of human TRNP1 is shown in SEQ ID NO: 7169 (UniprotKB: Q6NT89-1, v2).

In this specification, reference to 'TRNP1' encompasses: human TRNP1, isoforms of human TRNP1, homologues of human TRNP1 (i.e. encoded by the genome of a non-human animal), and variants thereof. In some embodiments, TRNP1 according to the present disclosure comprises or consists of an amino acid sequence having at 70% or greater amino acid sequence identity, preferably one of 75%, 80%, 85%, 90%, 91%, 92%, 93%, 94%, 95%, 96%, 97%, 98%, 99% or 100% amino acid sequence identity to the amino acid sequence of SEQ ID NO: 7169.

Apelin (APLN) is a peptide ligand for the G-protein coupled apelin receptor (APLNR). The APLN system plays important and various roles in the physiology and pathophysiology of many organs, including regulation of blood pressure, cardiac contractility, angiogenesis, metabolic balance, and cell proliferation, apoptosis or inflammation. Apelin is expressed in the heart, endothelium, vascular smooth muscle cells (VSMCs), brain, kidney, testis, ovary, liver and adipose tissue, with the highest expression levels in the lung and the mammary gland. Human APLN is identified by UniProtKB Q9ULZ1.

APLN structure and function is described in e.g. Tatemoto K. et al., Biochem. Biophys. Res. Commun. 251:471-476 (1998), and Lee D. K. et al., J. Neurochem. 74:34-41 (2000), which are both hereby incorporated by reference in their entirety.

The 77-amino acid sequence of human APLN is shown in SEQ ID NO: 7170 (UniprotKB: Q9ULZ1-1, v1). SEQ ID NO: 7170 encompasses a signal peptide at positions 1-22 and a propeptide at positions 23-41. SEQ ID NO: 7170 is cleaved into one or more active peptides by proteolytic processing: Apelin-36 (SEQ ID NO: 7171) at positions 42-77 of SEQ ID NO: 7170, Apelin-31 (SEQ ID NO: 7172) at positions 47-77 of SEQ ID NO: 7170, Apelin-28 (SEQ ID NO: 7173) at positions 50-77 of SEQ ID NO: 7170, or Apelin-13 (SEQ ID NO: 7174) at positions 65-77 of SEQ ID NO: 7170.

In this specification, reference to 'APLN' encompasses: human APLN, isoforms of human APLN, homologues of human APLN (i.e. encoded by the genome of a non-human animal), proteolytic peptides derived from human APLN, and variants thereof. In some embodiments, APLN according to the present disclosure comprises or consists of an amino acid sequence having at 70% or greater amino acid sequence identity, preferably one of 75%, 80%, 85%, 90%, 91%, 92%, 93%, 94%, 95%, 96%, 97%, 98%, 99% or 100% amino acid sequence identity to the amino acid sequence of SEQ ID NO: 7170.

Kinesin-like protein KIF20A (also known as GG10_2, Mitotic kinesin-like protein 2 (MKlp2), Rab6-interacting kinesin-like protein (RAB6KIFL), Rabkinesin-6) is a mitotic kinesin required for chromosome passenger complex (CPC)-mediated cytokinesis. KIF20A is a target for polo-like kinase 1 (Plk1), and phosphorylated KIF20A binds to the polo box domain of Plk1. Phosphorylation of KIF20A by Plk1 is necessary for the spatial restriction of Plk1 to the central spindle during anaphase and telophase, and the complex of these two proteins is required for cytokinesis. Human KIF20A is identified by UniProtKB O95235.

KIF20A structure and function is described in e.g. Neef R. et al., J Cell Biol. 2003; 162(5): 863-75, which is hereby incorporated by reference in its entirety.

Alternative splicing of the mRNA transcribed from the human KIF20A gene yields two isoforms: isoform 1 (UniProtKB: O95235-1, v1; SEQ ID NO: 7175), and isoform 2 (UniProtKB: O95235-2; SEQ ID NO: 7176) in which the amino acid sequence corresponding to positions 65-82 of SEQ ID NO: 7175 are missing.

The 890-amino acid sequence of human KIF20A isoform 1 comprises: a kinesin motor domain at positions 64-507 and a coiled coil domain at positions 611-762 of SEQ ID NO: 7175.

In this specification, reference to 'KIF20A' encompasses: human KIF20A, isoforms of human KIF20A, homologues of human KIF20A (i.e. encoded by the genome of a non-human animal), and variants thereof.

In some embodiments, KIF20A according to the present disclosure comprises or consists of an amino acid sequence having at 70% or greater amino acid sequence identity, preferably one of 75%, 80%, 85%, 90%, 91%, 92%, 93%, 94%, 95%, 96%, 97%, 98%, 99% or 100% amino acid sequence identity to the amino acid sequence of SEQ ID NO: 7175.

Lymphotoxin-beta (LTB, also known as Tumor necrosis factor C (TNF-C), Tumor necrosis factor ligand superfamily member 3) is a pro-inflammatory cytokine belonging to the TNF family that binds to receptors LTBR/TNFRSF3. It participates in the regulation of immune and inflammatory responses and, along with other LT-related cytokines such as LT-alpha, TNFα and LIGHT (TNFSF14) and their receptors, plays a role in the development and homeostasis of secondary lymphoid organs. Human LTB is identified by UniProtKB Q06643.

LTB structure and function is described in e.g. Sudhamsu J., et al., Proc Natl Acad Sci USA 110:19896-19901 (2013); Browning J. L., et al., Cell 72:847-856 (1993), Neville M. J. & Campbell R. D. J. Immunol. 162:4745-4754 (1999); Crowe P. D. et al., Science. 1994; 264(5159):707-10; and Bjordahl R. L. et al., Curr Opin Immunol. 2013, 25(2): 222-229, which are all hereby incorporated by reference in their entirety.

Alternative splicing of the mRNA transcribed from the human LTB gene yields two isoforms: isoform 1 (UniProtKB: Q06643-1, v1; SEQ ID NO: 7177), and isoform 2 (UniProtKB: Q06643-2; SEQ ID NO: 7178) in which the amino acid sequence corresponding to positions 53-77 of SEQ ID NO: 7177 are replaced with the sequence 'GLG- FRSCQRRSQKQISAPGSQLPTS' and positions 78-244 of SEQ ID NO: 7177 are missing.

The 244-amino acid sequence of human LTB isoform 1 comprises: a cytoplasmic domain at positions 1-18, a transmembrane domain at positions 19-48, and an extracellular domain at positions 49-244 of SEQ ID NO: 7177.

In this specification, reference to 'LTB' encompasses: human LTB, isoforms of human LTB, homologues of human LTB (i.e. encoded by the genome of a non-human animal), and variants thereof. In some embodiments, LTB according to the present disclosure comprises or consists of an amino acid sequence having at 70% or greater amino acid sequence identity, preferably one of 75%, 80%, 85%, 90%, 91%, 92%, 93%, 94%, 95%, 96%, 97%, 98%, 99% or 100% amino acid sequence identity to the amino acid sequence of SEQ ID NO: 7177.

As used herein, a "fragment", "variant" or "homologue" of a protein may optionally be characterised as having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of the reference protein (e.g. a reference isoform). In some embodiments, fragments, variants, isoforms and homologues of a reference protein may be characterised by ability to perform a function performed by the reference protein.

A "fragment" generally refers to a fraction of the reference protein. A "variant" generally refers to a protein having an amino acid sequence comprising one or more amino acid substitutions, insertions, deletions or other modifications relative to the amino acid sequence of the reference protein, but retaining a considerable degree of sequence identity (e.g. at least 60%) to the amino acid sequence of the reference protein. An "isoform" generally refers to a variant of the reference protein expressed by the same species as the species of the reference protein. A "homologue" generally refers to a variant of the reference protein produced by a different species as compared to the species of the reference protein. Homologues include orthologues.

A "fragment" may be of any length (by number of amino acids), although may optionally be at least 20% of the length of the reference protein (that is, the protein from which the fragment is derived) and may have a maximum length of one of 50%, 75%, 80%, 85%, 90%, 91%, 92%, 93%, 94%, 95%, 96%, 97%, 98%, or 99% of the length of the reference protein.

In some embodiments, the target gene/protein (i.e. MFAP4, GRHPR, ITFG1, ABCC4, PAK3, TRNP1, APLN, KIF20A, and/or LTB) is a target gene/protein from a mammal (any species in the class Mammalia, e.g. a primate (rhesus, cynomolgous, non-human primate or human) and/or a rodent (e.g. rat or mouse).

Isoforms, fragments, variants or homologues of MFAP4, GRHPR, ITFG1, ABCC4, PAK3, TRNP1, APLN, KIF20A, and/or LTB may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature MFAP4, GRHPR, ITFG1, ABCC4, PAK3, TRNP1, APLN, KIF20A, and/or LTB isoform from a given species, e.g. human.

A homologue of a human gene described herein may be from any animal. In some embodiments, a homologue of a human gene described herein may be from a mammal. In some embodiments, the mammal may be a non-human mammal, e.g. a primate (e.g. a non-human primate, e.g. an animal of the genus *Macaca* (e.g. *Macaca fascicularis*, *Macaca mulatta*), e.g. a non-human hominid (e.g. *Pan troglodytes*)). In some embodiments, the mammal may be a rabbit, guinea pig, rat, mouse or animal of the order Rodentia, cat, dog, pig, sheep, goat, an animal of the order Bos (e.g. cattle), an animal of the family Equidae (e.g. horse) or donkey.

Homologues of a human protein described herein may optionally be characterised as having 70% or greater amino acid sequence identity, preferably one of 75%, 80%, 85%, 90%, 91%, 92%, 93%, 94%, 95%, 96%, 97%, 98%, 99% or 100% amino acid sequence identity to the amino acid sequence of SEQ ID NOs: 7156 to 7178. Variants of a human protein described herein may optionally be characterised as having 70% or greater amino acid sequence identity, preferably one of 75%, 80%, 85%, 90%, 91%, 92%, 93%, 94%, 95%, 96%, 97%, 98%, 99% or greater amino acid sequence identity to the amino acid sequence of SEQ ID NOs: 7156 to 7178.

Isoforms, fragments, variants or homologues may optionally be functional isoforms, fragments, variants or homologues, e.g. having a functional property/activity of the reference MFAP4, GRHPR, ITFG1, ABCC4, PAK3, TRNP1, APLN, KIF20A, and/or LTB, as determined by analysis by a suitable assay for the functional property/activity.

Inhibition of Targets

The present invention is concerned with inhibition of MFAP4, GRHPR, ITFG1, ABCC4, PAK3, TRNP1, APLN, KIF20A, and/or LTB (i.e. a target gene/protein described herein). That is, the invention is concerned with inhibition of the expression and/or activity of MFAP4, GRHPR, ITFG1, ABCC4, PAK3, TRNP1, APLN, KIF20A, and/or LTB and the downstream functional consequences thereof.

Inhibition of MFAP4, GRHPR, ITFG1, ABCC4, PAK3, TRNP1, APLN, KIF20A, and/or LTB encompasses decreased/reduced expression (gene and/or protein expression) of any one or more of MFAP4, GRHPR, ITFG1, ABCC4, PAK3, TRNP1, APLN, KIF20A, and/or LTB, and/or decreased/reduced activity of any one or more of MFAP4, GRHPR, ITFG1, ABCC4, PAK3, TRNP1, APLN, KIF20A, and/or LTB, relative to the level of expression/activity observed in the absence of inhibition. "Inhibition" may herein also be referred to as "antagonism". Any one, two, three, four, five, six, seven, eight or nine of the genes/proteins may be inhibited in the methods according to the present disclosure.

In some embodiments, inhibition of MFAP4, GRHPR, ITFG1, ABCC4, PAK3, TRNP1, APLN, KIF20A, and/or LTB may be characterised by one or more of the following (relative to the uninhibited state):
  Reduce expression (e.g. gene and/or protein expression) of MFAP4, GRHPR, ITFG1, ABCC4, PAK3, TRNP1, APLN, KIF20A, and/or LTB;
  Reduce the level of RNA encoding MFAP4, GRHPR, ITFG1, ABCC4, PAK3, TRNP1, APLN, KIF20A, and/or LTB;
  Reduce/prevent transcription of nucleic acid encoding MFAP4, GRHPR, ITFG1, ABCC4, PAK3, TRNP1, APLN, KIF20A, and/or LTB;
  Increase degradation of RNA (e.g. mRNA) encoding MFAP4, GRHPR, ITFG1, ABCC4, PAK3, TRNP1, APLN, KIF20A, and/or LTB;
  Reduce the level of MFAP4, GRHPR, ITFG1, ABCC4, PAK3, TRNP1, APLN, KIF20A, and/or LTB protein;
  Reduce/prevent post-transcriptional processing (e.g. splicing, translation, post-translational processing) of RNA encoding MFAP4, GRHPR, ITFG1, ABCC4, PAK3, TRNP1, APLN, KIF20A, and/or LTB;

Promote/increase degradation of MFAP4, GRHPR, ITFG1, ABCC4, PAK3, TRNP1, APLN, KIF20A, and/or LTB protein;

Reduce/prevent the level of a MFAP4, GRHPR, ITFG1, ABCC4, PAK3, TRNP1, APLN, KIF20A, and/or LTB function; and/or Reduce/prevent interaction between MFAP4, GRHPR, ITFG1, ABCC4, PAK3, TRNP1, APLN, KIF20A, and/or LTB and an interaction partner for MFAP4, GRHPR, ITFG1, ABCC4, PAK3, TRNP1, APLN, KIF20A, and/or LTB.

Gene expression can be determined by means well known to the skilled person. The level of RNA encoding one or more of the target proteins can be determined e.g. by techniques such as RT-qPCR, northern blot, etc. By way of illustration, qRT-PCR may be used to determine the level of RNA encoding a target protein.

A reduction in the level of RNA encoding a target protein may e.g. be the result of reduced transcription of nucleic acid encoding the target protein, or increased degradation of RNA encoding the target protein.

Reduced transcription of nucleic acid encoding a target protein may be a consequence of inhibition of assembly and/or activity of factors required for transcription of the DNA encoding the target protein. Increased degradation of RNA encoding a target protein may be a consequence of increased enzymatic degradation of RNA encoding the target protein, e.g. as a consequence of RNA interference (RNAi), and/or reduced stability of RNA encoding the target protein.

Protein expression can be determined by means well known to the skilled person. The level of protein encoding a target protein can be determined e.g. by antibody-based methods including western blot, immunohisto/cytochemistry, flow cytometry, ELISA, ELISPOT, or by reporter-based methods.

A reduction in the level of a target protein may e.g. be the result of reduced level of RNA encoding the target protein, reduced post-transcriptional processing of RNA encoding the target protein, or increased degradation of the target protein.

Reduced post-transcriptional processing of a target protein may be e.g. reduced splicing of pre-mRNA encoding the target protein to mature mRNA encoding the target protein, reduced translation of mRNA encoding the target protein, or reduced post-translational processing of the target protein.

Reduced splicing of pre-mRNA encoding the target protein to mature mRNA encoding the target protein may be a consequence of inhibition of assembly and/or activity of factors required for splicing. Reduced translation of mRNA encoding the target protein may be a consequence of inhibition of assembly and/or activity of factors required for translation. Reduced post-translational processing (e.g. enzymatic processing, folding) of the target protein may be a consequence of inhibition of assembly and/or activity of factors required for post-translational processing of the target protein. Increased degradation of the target protein may be a consequence of increased enzymatic (e.g. protease-mediated) degradation of the target protein.

In some embodiments, inhibition of a target gene/protein may be characterised by a reduced level of a function of the target protein. A function of the target protein may be any functional property of the target protein.

An interaction partner may be any nucleic acid or protein which interacts with, or jointly contributes to a shared function with, any one or more of MFAP4, GRHPR, ITFG1, ABCC4, PAK3, TRNP1, APLN, KIF20A, and/or LTB.

In some embodiments, an interaction partner for MFAP4 is integrin αvβ3, tropoelastin, fibrillin-1, fibrillin-2, desmosine, LOX, MFAP2, FBLN1, FBLN2, MFAP5, EFEMP2, EFEMP1, SFTPD, or elastin.

In some embodiments, an interaction partner for GRHPR is glyoxylate, hydroxypyruvate, D-glycerate, AGXT, HYI, GLYCTK, PGP, GLO1, HAO1, HAO2, DAO, NADPH or NADH.

In some embodiments, an interaction partner for ITFG1 is RUVBL1, RUVBL2, alpha-tubulin, TIPIN, ATP9A, ASCC2, RFX7, or TM7SF3.

In some embodiments, an interaction partner for ABCC4 is ATP, ABCG4, SNX27, ABCA3, ABCE1, MRPS7, SLC22A8, SLCO1B1, NR1H4 or SLC22A6.

In some embodiments, an interaction partner for PAK3 is PAK1, CDC42, NCK1, MAPK14, RAC1, PXN, GIT1, GIT2, ARHGEF7 or ARHGEF6.

In some embodiments, an interaction partner for TRNP1 is TMF1, FAM18A, CNIH3, SMARCC2, FAM19A3, TBC1D3A, TBC13D, ARHGAP11B, or GPR56.

In some embodiments, an interaction partner for APLN is APLNR, AGTR1, AGT, CXCR4, CCR5, KNG1, NPY, PDYN, NMU, or POMC.

In some embodiments, an interaction partner for KIF20A is MAD2L1, AURKB, RACGAP1, KIF11, PLK1, CDCA8, KIF4A, CENPE, PRC1, or INCENP.

In some embodiments, an interaction partner for LTB is LTBR, LTA, TNF, TNFSF14, TNFRSF1B, TNFSF13B, TNFRSF11A, CD40LG, MAP3K14, TNFSF11.

Functional properties of MFAP4, GRHPR, ITFG1, ABCC4, PAK3, TRNP1, APLN, KIF20A, and/or LTB can be analysed using appropriate assays, e.g. in vitro assays.

In some embodiments, MFAP4 inhibition increases expression and/or activation of one or more of Ptgs2, Areg, Dhrs9, Hmox1, Nqo1, P70S6k, p38, mTOR, and/or ERK2. In some embodiments, an inhibitor of MFAP4 activates mTOR, p70S6K, ERK and p38 signalling pathways.

Inhibition of interaction between a target protein and an interaction partner for the target protein can be identified e.g. by detection of a reduction in the level of interaction between the target protein and the interaction partner, relative to a control, uninhibited condition. The ability of proteins to interact can be analysed by methods well known to the skilled person, such as co-immunoprecipitation, and resonance energy transfer (RET) assays.

Inhibition of target protein function can also be evaluated by analysis of one or more correlates of target protein function. That is, target protein function can be evaluated by analysis of downstream functional consequences of target protein function. For example, inhibition of target protein function can be identified by detection of reduced expression (gene and/or protein expression) and/or activity of one or more proteins whose expression is directly/indirectly upregulated as a consequence of target protein function. Inhibition of target protein function can also be identified by detection of increased expression (gene and/or protein expression) and/or activity of one or more proteins whose expression is directly/indirectly downregulated as a consequence of target protein function.

Inhibitors

Provided herein are inhibitors that target one or more genes/proteins from the group selected from: MFAP4, GRHPR, ITFG1, ABCC4, PAK3, TRNP1, APLN, KIF20A, and LTB.

An "inhibitor of MFAP4, GRHPR, ITFG1, ABCC4, PAK3, TRNP1, APLN, KIF20A, and/or LTB" refers to any agent capable of inhibiting any one or more of MFAP4, GRHPR, ITFG1, ABCC4, PAK3, TRNP1, APLN, KIF20A, and/or LTB expression and/or function. Such agents may be effectors of (i.e. may directly or indirectly cause) inhibition of any one or more of MFAP4, GRHPR, ITFG1, ABCC4, PAK3, TRNP1, APLN, KIF20A, and/or LTB as described hereinabove.

Agents capable of inhibiting any one or more of MFAP4, GRHPR, ITFG1, ABCC4, PAK3, TRNP1, APLN, KIF20A, and/or LTB may be referred to herein as MFAP4, GRHPR, ITFG1, ABCC4, PAK3, TRNP1, APLN, KIF20A, and/or LTB inhibitors. MFAP4, GRHPR, ITFG1, ABCC4, PAK3, TRNP1, APLN, KIF20A, and/or LTB inhibitors may also be referred to herein as antagonists of MFAP4, GRHPR, ITFG1, ABCC4, PAK3, TRNP1, APLN, KIF20A, and/or LTB, or MFAP4, GRHPR, ITFG1, ABCC4, PAK3, TRNP1, APLN, KIF20A, and/or LTB antagonists.

"An inhibitor" of MFAP4, GRHPR, ITFG1, ABCC4, PAK3, TRNP1, APLN, KIF20A, and/or LTB may refer to any agent capable of inhibiting any one of MFAP4, GRHPR, ITFG1, ABCC4, PAK3, TRNP1, APLN, KIF20A, or LTB. In addition, "An inhibitor of MFAP4, GRHPR, ITFG1, ABCC4, PAK3, TRNP1, APLN, KIF20A, and/or LTB" may refer to two or more agents capable of inhibiting two, three, four, five, six, seven, eight, or nine target genes/proteins selected from the group consisting of MFAP4, GRHPR, ITFG1, ABCC4, PAK3, TRNP1, APLN, KIF20A, and LTB. Multiple inhibitors may be used in the methods of the present disclosure to target two or more of the target genes/proteins.

In some embodiments, an inhibitor of MFAP4, GRHPR, ITFG1, ABCC4, PAK3, TRNP1, APLN, KIF20A, and/or LTB (i.e. a target protein) may:

Reduce/prevent expression (e.g. gene and/or protein expression) of MFAP4, GRHPR, ITFG1, ABCC4, PAK3, TRNP1, APLN, KIF20A, and/or LTB;

Reduce the level of RNA encoding MFAP4, GRHPR, ITFG1, ABCC4, PAK3, TRNP1, APLN, KIF20A, and/or LTB;

Reduce/prevent transcription of nucleic acid encoding MFAP4, GRHPR, ITFG1, ABCC4, PAK3, TRNP1, APLN, KIF20A, and/or LTB;

Increase degradation of RNA (e.g. mRNA) encoding MFAP4, GRHPR, ITFG1, ABCC4, PAK3, TRNP1, APLN, KIF20A, and/or LTB;

Reduce the level of MFAP4, GRHPR, ITFG1, ABCC4, PAK3, TRNP1, APLN, KIF20A, and/or LTB protein;

Reduce/prevent post-transcriptional processing (e.g. splicing, translation, post-translational processing) of RNA encoding MFAP4, GRHPR, ITFG1, ABCC4, PAK3, TRNP1, APLN, KIF20A, and/or LTB;

Promote/increase degradation of MFAP4, GRHPR, ITFG1, ABCC4, PAK3, TRNP1, APLN, KIF20A, and/or LTB protein;

Reduce/prevent the level of a MFAP4, GRHPR, ITFG1, ABCC4, PAK3, TRNP1, APLN, KIF20A, and/or LTB function; and/or Reduce/prevent interaction between MFAP4, GRHPR, ITFG1, ABCC4, PAK3, TRNP1, APLN, KIF20A, and/or LTB and an interaction partner for MFAP4, GRHPR, ITFG1, ABCC4, PAK3, TRNP1, APLN, KIF20A, and/or LTB.

It will be appreciated that a given inhibitor may display more than one of the properties recited in the preceding paragraph. A given inhibitor may be evaluated for the properties recited in the preceding paragraph using suitable assays. The assays may be e.g. in vitro assays, optionally cell-based assays or cell-free assays. The assays may be e.g. in vivo assays, i.e. performed in non-human animals.

Where assays are cell-based assays, they may comprise treating cells with an inhibitor (e.g. a nucleic acid) in order to determine whether the inhibitor displays one or more of the recited properties. Assays may employ species labelled with detectable entities in order to facilitate their detection. Assays may comprise evaluating the recited properties following treatment of cells separately with a range of quantities/concentrations of a given inhibitor (e.g. a dilution series). It will be appreciated that the cells are preferably cells that express the target protein to be inhibited, e.g. liver cells (e.g. HepG2 cells or HuH7 cells).

Analysis of the results of such assays may comprise determining the concentration at which 50% of the maximal level of the relevant activity is attained. The concentration of nucleic acid at which 50% of the maximal level of the relevant activity is attained may be referred to as the 'half-maximal effective concentration' of the inhibitor in relation to the relevant activity, which may also be referred to as the '$EC_{50}$'. By way of illustration, the $EC_{50}$ of a given inhibitor (e.g. inhibitory nucleic acid) for increasing degradation of RNA encoding a target protein may be the concentration at which 50% of the maximal level of degradation of RNA encoding a target protein is achieved.

Depending on the property, the $EC_{50}$ may also be referred to as the 'half-maximal inhibitory concentration' or '$IC_{50}$', this being the concentration of inhibitor at which 50% of the maximal level of inhibition of a given property is observed. By way of illustration, the $IC_{50}$ of a given inhibitor (e.g. inhibitory nucleic acid) for reducing expression of a gene encoding a target protein may be the concentration at which 50% of the maximal level of inhibition of expression of the gene is achieved.

Agents capable of reducing/preventing gene expression of any one or more MFAP4, GRHPR, ITFG1, ABCC4, PAK3, TRNP1, APLN, KIF20A, and/or LTB (e.g. reducing the level of RNA encoding MFAP4, GRHPR, ITFG1, ABCC4, PAK3, TRNP1, APLN, KIF20A, and/or LTB; reducing/preventing transcription of nucleic acid encoding MFAP4, GRHPR, ITFG1, ABCC4, PAK3, TRNP1, APLN, KIF20A, and/or LTB; and/or increasing degradation of RNA encoding MFAP4, GRHPR, ITFG1, ABCC4, PAK3, TRNP1, APLN, KIF20A, and/or LTB) may be identified using assays comprising detecting the level of RNA encoding the target protein, e.g. by RT-qPCR (a technique well known to the skilled person). The methods may employ primers and/or probes for the detection and/or quantification of RNA encoding MFAP4, GRHPR, ITFG1, ABCC4, PAK3, TRNP1, APLN, KIF20A, and/or LTB.

Such assays may comprise introducing (e.g. by transfection) into cells that express the target protein in in vitro culture (i) a putative inhibitor (e.g. an inhibitory nucleic acid), or (ii) a control agent (e.g. a control nucleic acid, such as a nucleic acid known not to influence the level of RNA encoding the target protein), and subsequently (e.g. after an appropriate period of time, i.e. a period of time sufficient for a reduction in the level of gene expression of the target protein/transcription of nucleic acid encoding the target protein/level of RNA encoding the target protein or an increase in the level of degradation of RNA encoding the target protein to be observed) measuring the level of RNA encoding the target protein in cells according to (i) and (ii), and (iii) comparing the level of RNA encoding the target protein detected to determine whether the putative inhibitor reduces/prevents gene expression of the target protein, reduces/prevents transcription of nucleic acid encoding the target protein, reduces the level of RNA encoding the target protein, and/or increases degradation of RNA encoding the target protein.

Agents capable of reducing protein expression of any one or more MFAP4, GRHPR, ITFG1, ABCC4, PAK3, TRNP1, APLN, KIF20A, and/or LTB (e.g. reducing the level of MFAP4, GRHPR, ITFG1, ABCC4, PAK3, TRNP1, APLN, KIF20A, and/or LTB protein, increasing degradation of MFAP4, GRHPR, ITFG1, ABCC4, PAK3, TRNP1, APLN, KIF20A, and/or LTB protein) may be identified using assays comprising detecting the level of the target protein, e.g. using antibody/reporter-based methods (western blot, ELISA, immunohisto/cytochemistry, etc.). Such assays may comprise treating cells/tissue with the agent, and subsequently comparing the level of the target protein in such cells/tissue to the level of the target protein in cells/tissue of an appropriate control condition (e.g. untreated/vehicle-treated cells/tissue).

The methods may employ antibodies specific for the target protein. Such assays may comprise introducing (e.g. by transfection) into cells that express a target protein in in vitro culture (i) a putative inhibitor (e.g. an inhibitory nucleic acid), or (ii) a control agent (e.g. a nucleic acid known not to influence the level of the target protein), and subsequently (e.g. after an appropriate period of time, i.e. a period of time sufficient for a reduction in the level of the target protein to be observed) measuring the level of the target protein in cells according to (i) and (ii), and (iii) comparing the level of the target protein detected to determine whether the putative inhibitor reduces the level of the target protein and/or reduces/prevents translation of mRNA encoding the target protein.

Agents capable of reducing the level of a function of any one or more MFAP4, GRHPR, ITFG1, ABCC4, PAK3, TRNP1, APLN, KIF20A, and/or LTB (e.g. a function of a target protein as described herein) may be identified using assays comprising detecting the level of the relevant function. Such assays may comprise introducing (e.g. by transfection) into cells that express the target protein in in vitro culture (i) a putative inhibitor (e.g. an inhibitory nucleic acid), or (ii) a control agent (e.g. a nucleic acid known not to influence target protein function), and subsequently (e.g. after an appropriate period of time, i.e. a period of time sufficient for a reduction in the level of a function of the target protein to be observed) measuring the level of a function of the target protein in cells according to (i) and (ii), and (iii) comparing the level of the function of the target protein detected to determine whether the putative inhibitor reduces the level of a function of the target protein.

Reference herein to 'a function of the target protein' may refer to any functional property of, and/or activity mediated by, MFAP4, GRHPR, ITFG1, ABCC4, PAK3, TRNP1, APLN, KIF20A, and/or LTB protein.

Agents capable of reducing/preventing normal splicing of pre-mRNA encoding any one or more of MFAP4, GRHPR, ITFG1, ABCC4, PAK3, TRNP1, APLN, KIF20A, and/or LTB may be identified using assays comprising detecting and/or quantifying the level of RNA (e.g. mature mRNA) encoding one or more isoforms of MFAP4, GRHPR, ITFG1, ABCC4, PAK3, TRNP1, APLN, KIF20A, and/or LTB. Such assays may comprise quantifying RNA (e.g. mature mRNA) encoding one or more isoforms of MFAP4, GRHPR, ITFG1, ABCC4, PAK3, TRNP1, APLN, KIF20A, and/or LTB by RT-qPCR. The methods may employ primers and/or probes for the detection and/or quantification of mature mRNA produced by canonical splicing of pre-mRNA transcribed from a gene encoding MFAP4, GRHPR, ITFG1, ABCC4, PAK3, TRNP1, APLN, KIF20A, and/or LTB, and/or primers and/or probes for the detection and/or quantification of mature mRNA produced by alternative splicing of pre-mRNA transcribed from a gene encoding MFAP4, GRHPR, ITFG1, ABCC4, PAK3, TRNP1, APLN, KIF20A, and/or LTB.

Mature mRNA produced by canonical splicing of pre-mRNA transcribed from a gene encoding MFAP4, GRHPR, ITFG1, ABCC4, PAK3, TRNP1, APLN, KIF20A, and/or LTB may be mature mRNA encoding the major isoform produced by expression of the gene encoding MFAP4, GRHPR, ITFG1, ABCC4, PAK3, TRNP1, APLN, KIF20A, and/or LTB. The major isoform may be the most commonly produced/detected isoform. For example, mature mRNA produced by canonical splicing of pre-mRNA transcribed from human MFAP4 may be mature mRNA encoding human MFAP4 isoform 1 (i.e. having the amino acid sequence shown in SEQ ID NO: 7156). Mature mRNA produced by alternative splicing of pre-mRNA transcribed from a gene encoding MFAP4, GRHPR, ITFG1, ABCC4, PAK3, TRNP1, APLN, KIF20A, and/or LTB may be mature mRNA encoding an isoform other than the major isoform produced by expression of said gene. For example, mature mRNA produced by alternative splicing of pre-mRNA transcribed from human MFAP4 may be mature mRNA encoding an isoform of human MFAP4 other than isoform 1 (i.e. having an amino acid sequence non-identical to SEQ ID NO: 7156); e.g. mature mRNA encoding human MFAP4 isoform 2 (i.e. having an amino acid sequence shown in SEQ ID NO: 7157).

Such assays may comprise introducing (e.g. by transfection) into cells that express MFAP4, GRHPR, ITFG1, ABCC4, PAK3, TRNP1, APLN, KIF20A, and/or LTB in in vitro culture (i) a putative inhibitor (e.g. an inhibitory nucleic acid), or (ii) a control agent (e.g. a nucleic acid known not to influence splicing of pre-mRNA encoding the target gene), and subsequently (e.g. after an appropriate period of time, i.e. a period of time sufficient for an effect on splicing of pre-mRNA encoding the target gene to be observed) measuring the level of mature mRNA encoding one or more isoforms of the target gene in cells according to (i) and (ii), and (iii) comparing the level of mature mRNA encoding the isoform(s) to determine whether the putative inhibitor reduces/prevents normal splicing of pre-mRNA encoding the target gene.

Agents capable of reducing interaction between a target protein described herein and an interaction partner for said target protein may be identified using assays comprising detecting the level of interaction between the target protein and its interaction partner, e.g. using antibody/reporter-based methods. The level of interaction between the target protein and its interaction partner can be analysed e.g. using resonance energy transfer techniques (e.g. FRET, BRET), or methods analysing a correlate of interaction between the target protein and its interaction partner. Assays may comprise treating cells/tissue with the agent, and subsequently comparing the level of interaction between the target protein and its interaction partner in such cells/tissue to the level of interaction between the target protein and its interaction partner in cells/tissue of an appropriate control condition (e.g. untreated/vehicle-treated cells/tissue). The level of interaction between the target protein and its interaction partner can also be analysed e.g. using techniques such as ELISA, surface plasmon resonance or biolayer interferometry analysis. Assays may comprise comparing the level of interaction between the target protein and its interaction partner in the presence of the agent to the level of interaction between the target protein and its interaction partner in an appropriate control condition (e.g. the absence of the agent).

In some embodiments, an inhibitor according to the present disclosure may be capable of reducing expression of a gene encoding any one or more of MFAP4, GRHPR, ITFG1, ABCC4, PAK3, TRNP1, APLN, KIF20A, and/or LTB to less than 1 times, e.g. one of ≤0.99 times, ≤0.95 times, ≤0.9 times, ≤0.85 times, ≤0.8 times, 50.75 times, 50.7 times, 50.65 times, 50.6 times, 50.55 times, 50.5 times, 50.45 times, 50.4 times, 50.35 times, 50.3 times, 50.25 times, 50.2 times, 50.15 times, 50.1 times, 50.05 times, or ≤0.01 times the level of expression observed in the absence of the inhibitor, or in the presence of the same quantity of a control agent known not to inhibit expression of the relevant gene, in a given assay. In some embodiments, an inhibitor according to the present disclosure may be capable of reducing expression of a gene encoding any one or more of MFAP4, GRHPR, ITFG1, ABCC4, PAK3, TRNP1, APLN, KIF20A, and/or LTB to less than 100%, e.g. one of ≤99%, ≤95%, ≤90%, ≤85%, ≤80%, ≤75%, ≤70%, ≤65%, ≤60%, ≤55%, ≤50%, ≤45%, 540%, 535%, 530%, 525%, 520%, 515%, 510%, 55%, or ≤1% of the level of expression observed in the absence of the inhibitor, or in the presence of the same quantity of a control agent known not to inhibit expression of the relevant gene, in a given assay.

In some embodiments, an inhibitor according to the present disclosure may be capable of reducing the level of RNA encoding any one or more of MFAP4, GRHPR, ITFG1, ABCC4, PAK3, TRNP1, APLN, KIF20A, and/or LTB to less than 1 times, e.g. one of 50.99 times, 50.95 times, 50.9 times, 50.85 times, 50.8 times, 50.75 times, 50.7 times, 50.65 times, 50.6 times, 50.55 times, 50.5 times, 50.45 times, 50.4 times, 50.35 times, 50.3 times, 50.25 times, 50.2 times, 50.15 times, 50.1 times, 50.05 times, or ≤0.01 times the level observed in the absence of the inhibitor, or in the presence of the same quantity of a control agent known not to reduce the level of RNA encoding MFAP4, GRHPR, ITFG1, ABCC4, PAK3, TRNP1, APLN, KIF20A, and/or LTB, in a given assay. In some embodiments, an inhibitor according to the present disclosure may be capable of reducing the level of RNA encoding any one or more of MFAP4, GRHPR, ITFG1, ABCC4, PAK3, TRNP1, APLN, KIF20A, and/or LTB to less than 100%, e.g. one of 599%, 595%, 590%, 585%, ≤80%, ≤75%, ≤70%, ≤65%, ≤60%, ≤55%, ≤50%, ≤45%, ≤40%, ≤35%, ≤30%, ≤25%, ≤20%, ≤15%, ≤10%, 55%, or ≤1% of the level observed in the absence of the inhibitor, or in the presence of the same quantity of a control agent known not to reduce the level of RNA encoding MFAP4, GRHPR, ITFG1, ABCC4, PAK3, TRNP1, APLN, KIF20A, and/or LTB, in a given assay.

In some embodiments, an inhibitor according to the present disclosure may be capable of reducing the level of transcription of nucleic acid encoding any one or more of MFAP4, GRHPR, ITFG1, ABCC4, PAK3, TRNP1, APLN, KIF20A, and/or LTB to less than 1 times, e.g. one of ≤0.99 times, 50.95 times, 50.9 times, 50.85 times, 50.8 times, 50.75 times, 50.7 times, 50.65 times, 50.6 times, 50.55 times, 50.5 times, 50.45 times, 50.4 times, 50.35 times, 50.3 times, 50.25 times, 50.2 times, 50.15 times, 50.1 times, 50.05 times, or ≤0.01 times the level observed in the absence of the inhibitor, or in the presence of the same quantity of a control agent known not to reduce transcription of nucleic acid encoding MFAP4, GRHPR, ITFG1, ABCC4, PAK3, TRNP1, APLN, KIF20A, and/or LTB, in a given assay. In some embodiments, an inhibitor according to the present disclosure may be capable of reducing the level of transcription of nucleic acid encoding any one or more of MFAP4, GRHPR, ITFG1, ABCC4, PAK3, TRNP1, APLN, KIF20A, and/or LTB to less than 100%, e.g. one of ≤99%, ≤95%, ≤90%, ≤85%, ≤80%, ≤75%, ≤70%, ≤65%, ≤60%, ≤55%, ≤50%, 545%, 540%, 535%, 530%, 525%, 520%, 515%, 510%, 55%, or ≤1% of the level observed in the absence of the inhibitor, or in the presence of the same quantity of a control agent known not to reduce transcription of nucleic acid encoding MFAP4, GRHPR, ITFG1, ABCC4, PAK3, TRNP1, APLN, KIF20A, and/or LTB, in a given assay.

In some embodiments, an inhibitor according to the present disclosure may be capable of reducing the level of any one or more of MFAP4, GRHPR, ITFG1, ABCC4, PAK3, TRNP1, APLN, KIF20A, and/or LTB protein to less than 1 times, e.g. one of ≤0.99 times, 50.95 times, 50.9 times, 50.85 times, 50.8 times, 50.75 times, 50.7 times, 50.65 times, 50.6 times, 50.55 times, 50.5 times, 50.45 times, 50.4 times, 50.35 times, 50.3 times, 50.25 times, 50.2 times, 50.15 times, 50.1 times, 50.05 times, or ≤0.01 times the level observed in the absence of the inhibitor, or in the presence of the same quantity of a control agent known not to reduce the level of MFAP4, GRHPR, ITFG1, ABCC4, PAK3, TRNP1, APLN, KIF20A, and/or LTB protein, in a given assay. In some embodiments, an inhibitor according to the present disclosure may be capable of reducing the level of any one or more of MFAP4, GRHPR, ITFG1, ABCC4, PAK3, TRNP1, APLN, KIF20A, and/or LTB protein to less than 100%, e.g. one of ≤99%, ≤95%, ≤90%, ≤85%, ≤80%, ≤75%, ≤70%, ≤65%, ≤60%, ≤55%, ≤50%, ≤45%, ≤40%, ≤35%, ≤30%, ≤25%, ≤20%, ≤15%, ≤10%, ≤5%, or ≤1% of the level observed in the absence of the inhibitor, or in the presence of the same quantity of a control agent known not to reduce the level of MFAP4, GRHPR, ITFG1, ABCC4, PAK3, TRNP1, APLN, KIF20A, and/or LTB protein, in a given assay.

In some embodiments, an inhibitor according to the present disclosure may be capable of reducing the level of a function of any one or more of MFAP4, GRHPR, ITFG1, ABCC4, PAK3, TRNP1, APLN, KIF20A, and/or LTB to less than 1 times, e.g. one of 50.99 times, 50.95 times, 50.9 times, 50.85 times, 50.8 times, 50.75 times, 50.7 times, 50.65 times, 50.6 times, 50.55 times, 50.5 times, 50.45 times, 50.4 times, 50.35 times, 50.3 times, 50.25 times, 50.2 times, 50.15 times, 50.1 times, 50.05 times, or ≤0.01 times the level observed in the absence of the inhibitor, or in the presence of the same quantity of a control agent known not to reduce the level of the function of MFAP4, GRHPR, ITFG1, ABCC4, PAK3, TRNP1, APLN, KIF20A, and/or LTB, in a given assay. In some embodiments, an inhibitor according to the present disclosure may be capable of reducing the level of a function of any one or more of MFAP4, GRHPR, ITFG1, ABCC4, PAK3, TRNP1, APLN, KIF20A, and/or LTB to less than 100%, e.g. one of 599%, 595%, 590%, 585%, ≤80%, ≤75%, ≤70%, ≤65%, ≤60%, ≤55%, ≤50%, ≤45%, ≤40%, ≤35%, ≤30%, ≤25%, ≤20%, ≤15%, ≤10%, 55%, or ≤1% of the level observed in the absence of the inhibitor, or in the presence of the same quantity of a control agent known not to reduce the level of the function of MFAP4, GRHPR, ITFG1, ABCC4, PAK3, TRNP1, APLN, KIF20A, and/or LTB, in a given assay.

In some embodiments, an inhibitor according to the present disclosure may be capable of reducing the level of binding of any one or more of MFAP4, GRHPR, ITFG1, ABCC4, PAK3, TRNP1, APLN, KIF20A, and/or LTB to an interaction partner to less than 1 times, e.g. one of 50.99 times, 50.95 times, 50.9 times, 50.85 times, 50.8 times, 50.75 times, 50.7 times, 50.65 times, 50.6 times, 50.55 times, 50.5 times, 50.45 times, 50.4 times, 50.35 times, 50.3 times, 50.25 times, 50.2 times, 50.15 times, 50.1 times, 50.05 times, or ≤0.01 times the level observed in the absence of the inhibitor, or in the presence of the same quantity of a control agent known not to reduce the level of binding, in a given assay. In some embodiments, an inhibitor according to the present disclosure may be capable of reducing the level of binding of any one or more of MFAP4, GRHPR, ITFG1, ABCC4, PAK3, TRNP1, APLN, KIF20A, and/or LTB to an interaction partner to less than 100%, e.g. one of ≤99%, ≤95%, ≤90%, ≤85%, ≤80%, ≤75%, ≤70%, ≤65%, ≤60%, ≤55%, ≤50%, 545%, 540%, 535%, 530%, 525%, 520%, 515%, 510%, 55%, or ≤1% of the level observed in the absence of the inhibitor, or in the presence of the same quantity of a control agent known not to reduce the level of the relevant binding, in a given assay.

In some embodiments, an inhibitor according to the present disclosure may be capable of reducing normal splicing of pre-mRNA encoding any one or more of MFAP4, GRHPR, ITFG1, ABCC4, PAK3, TRNP1, APLN, KIF20A, and/or LTB to less than 1 times, e.g. one of 50.99 times, 50.95 times, 50.9 times, 50.85 times, 50.8 times, 50.75 times, 50.7 times, 50.65 times, 50.6 times, 50.55 times, 50.5 times, 50.45 times, 50.4 times, 50.35 times, 50.3 times, 50.25 times, 50.2 times, 50.15 times, 50.1 times, 50.05 times, or ≤0.01 times the level observed in the absence of the inhibitor, or in the presence of the same quantity of a control agent known not to reduce normal splicing of pre-mRNA encoding the relevant target protein(s), in a given assay. In some embodiments, an inhibitor according to the present disclosure may be capable of reducing the level of normal splicing of pre-mRNA encoding any one or more of MFAP4, GRHPR, ITFG1, ABCC4, PAK3, TRNP1, APLN, KIF20A, and/or LTB to less than 100%, e.g. one of 599%, 595%, 590%, 585%, ≤80%, ≤75%, ≤70%, ≤65%, ≤60%, ≤55%, ≤50%, ≤45%, ≤40%, ≤35%, ≤30%, ≤25%, ≤20%, ≤15%, ≤10%, 55%, or ≤1% of the level observed in the absence of the inhibitor, or in the presence of the same quantity of a control agent known not to reduce normal splicing of pre-mRNA encoding the relevant target protein(s), in a given assay.

In some embodiments, an inhibitor according to the present disclosure may be capable of reducing translation of mRNA encoding any one or more of MFAP4, GRHPR, ITFG1, ABCC4, PAK3, TRNP1, APLN, KIF20A, and/or LTB to less than 1 times, e.g. one of ≤0.99 times, ≤0.95 times, ≤0.9 times, ≤0.85 times, ≤0.8 times, 50.75 times, 50.7 times, 50.65 times, 50.6 times, 50.55 times, 50.5 times, 50.45 times, 50.4 times, 50.35 times, 50.3 times, 50.25 times, 50.2 times, 50.15 times, 50.1 times, 50.05 times, or ≤0.01 times the level observed in the absence of the inhibitor, or in the presence of the same quantity of a control agent known not to reduce translation of mRNA encoding the relevant target protein(s), in a given assay. In some embodiments, an inhibitor according to the present disclosure may be capable of reducing translation of mRNA encoding any one or more of MFAP4, GRHPR, ITFG1, ABCC4, PAK3, TRNP1, APLN, KIF20A, and/or LTB to less than 100%, e.g. one of 599%, 595%, 590%, 585%, 580%, 575%, 570%, 565%, 560%, ≤55%, ≤50%, ≤45%, ≤40%, ≤35%, ≤30%, ≤25%, ≤20%, ≤15%, ≤10%, ≤5%, or ≤1% of the level observed in the absence of the inhibitor, or in the presence of the same quantity of a control agent known not to reduce translation of mRNA encoding the relevant target protein(s), in a given assay.

Preferred levels of reduction in accordance with the preceding eight paragraphs are reduction to less than 0.5 times/550%, e.g. one of less than 0.4 times/540%, less than 0.3 times/530%, less than 0.2 times/≤20%, less than 0.15 times/≤15%, or less than 0.1 times/≤10%.

In some embodiments, an inhibitor according to the present disclosure may be capable of increasing degradation of RNA encoding any one or more of MFAP4, GRHPR, ITFG1, ABCC4, PAK3, TRNP1, APLN, KIF20A, and/or LTB to more than 1 times, e.g. one of ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level observed in the absence of the inhibitor, or in the presence of the same quantity of a control agent known not to increase degradation of RNA encoding the relevant target protein(s), in a given assay.

In some embodiments, an inhibitor according to the present disclosure prevents or silences expression of a gene encoding any one or more of MFAP4, GRHPR, ITFG1, ABCC4, PAK3, TRNP1, APLN, KIF20A, and/or LTB. In some embodiments, an inhibitor according to the present disclosure prevents or silences expression of any one or more of MFAP4, GRHPR, ITFG1, ABCC4, PAK3, TRNP1, APLN, KIF20A, and/or LTB at the protein level. As used herein, expression of a given gene/protein may be considered to be 'prevented' or 'silenced' where the level of expression is reduced to less than 0.1 times/≤10% of the level observed in the absence of the inhibitor, or in the presence of the same quantity of a control agent known not to be an inhibitor of expression of the relevant gene(s)/protein(s).

In preferred embodiments, an inhibitor (e.g. an inhibitory nucleic acid, such as an siRNA or shRNA) according to the present disclosure inhibits greater than 50%, e.g. one of 260%, ≥61%, ≥62%, ≥63%, ≥64%, ≥65%, ≥66%, ≥67%, ≥68%, ≥69%, ≥70%, ≥71%, ≥72%, ≥73%, ≥74%, ≥75%, ≥76%, ≥77%, ≥78%, ≥79%, ≥80%, ≥81%, ≥82%, ≥83%, ≥84%, ≥85%, ≥86%, ≥87%, ≥88%, ≥89%, ≥90%, ≥91%, ≥92%, ≥93%, ≥94%, ≥95%, ≥96%, ≥97%, ≥98%, ≥99% or 100% of the gene and/or protein expression of any one or more of MFAP4, GRHPR, ITFG1, ABCC4, PAK3, TRNP1, APLN, KIF20A, and/or LTB observed in the absence of the inhibitor, or in the presence of the same quantity of a control agent known not to inhibit gene and/or protein expression of the relevant gene(s)/protein(s), in a given assay.

In preferred embodiments, an inhibitor (e.g. an inhibitory nucleic acid, such as an siRNA or shRNA) according to the present disclosure inhibits greater than 50%, e.g. one of 260%, ≥61%, ≥62%, ≥63%, ≥64%, 65%, ≥66%, ≥67%, ≥68%, ≥69%, ≥70%, ≥71%, ≥72%, ≥73%, ≥74%, ≥75%, ≥76%, ≥77%, ≥78%, ≥79%, 80%, ≥81%, ≥82%, ≥83%, ≥84%, ≥85%, ≥86%, ≥87%, ≥88%, ≥89%, ≥90%, ≥91%, ≥92%, ≥93%, ≥94%, ≥95%, ≥96%, ≥97%, ≥98%, ≥99% or 100% of the gene expression of any one or more of MFAP4, GRHPR, ITFG1, ABCC4, PAK3, TRNP1, APLN, KIF20A, and/or LTB (e.g. as determined by qRT-PCR) observed in the absence of the inhibitor, or in the presence of the same quantity of a control agent known not to inhibit gene and/or protein expression of the relevant gene(s)/protein(s), in a given assay.

In preferred embodiments, an inhibitor (e.g. an inhibitory nucleic acid, such as an siRNA or shRNA) according to the present disclosure inhibits greater than 50%, e.g. one of 260%, ≥61%, ≥62%, ≥63%, ≥64%, ≥65%, ≥66%, ≥67%, ≥68%, ≥69%, ≥70%, ≥71%, ≥72%, ≥73%, ≥74%, ≥75%, ≥76%, ≥77%, ≥78%, ≥79%, ≥80%, ≥81%, ≥82%, ≥83%, ≥84%, ≥85%, ≥86%, ≥87%, ≥88%, ≥89%, ≥90%, ≥91%, ≥92%, ≥93%, ≥94%, 295%, 296%, 297%, 298%, 299% or 100% of the protein expression of any one or more of MFAP4, GRHPR, ITFG1, ABCC4, PAK3, TRNP1, APLN, KIF20A, and/or LTB (e.g. as determined by ELISA) observed in the absence of the inhibitor, or in the presence of the same quantity of a control agent known not to inhibit gene and/or protein expression of the relevant gene(s)/protein(s), in a given assay.

In some embodiments, an inhibitor (e.g. an inhibitory nucleic acid, such as an siRNA or shRNA) according to the present disclosure may inhibit gene and/or protein expression of any one or more of MFAP4, GRHPR, ITFG1, ABCC4, PAK3, TRNP1, APLN, KIF20A, and/or LTB with an $IC_{50}$ of ≤1 µM, e.g. one of ≤500 nM, ≤100 nM, 575 nM, ≤50 nM, 540 nM, ≤30 nM, 520 nM, ≤15 nM, 512.5 nM, 510 nM, ≤9 nM, 58 nM, ≤7 nM, 56 nM, ≤5 nM, ≤4 nM, ≤3 nM, 52 nM, ≤1 nM, ≤900 pM, ≤800 pM, ≤700 pM, ≤600 pM, ≤500 pM, ≤400 pM, ≤300 pM, ≤200 pM, ≤100 pM, ≤50 pM, ≤40 pM, ≤30 pM, ≤20 pM, ≤10 pM or ≤1 pM.

In some embodiments an inhibitor according to the present disclosure may inhibit gene expression of any one or more of MFAP4, GRHPR, ITFG1, ABCC4, PAK3, TRNP1, APLN, KIF20A, and/or LTB (e.g. as determined by qRT-PCR) with an $IC_{50}$ of ≤1 nM, 5900 pM, ≤800 pM, ≤700 pM, ≤600 pM, ≤500 pM, ≤400 pM, 5300 pM, ≤200 pM, ≤100 pM, ≤50 pM, ≤40 pM, ≤30 pM, ≤20 pM, ≤10 pM or ≤1 pM.

In some embodiments an inhibitor according to the present disclosure may inhibit protein expression of any one or more of MFAP4, GRHPR, ITFG1, ABCC4, PAK3, TRNP1, APLN, KIF20A, and/or LTB (e.g. as determined by ELISA) with an $IC_{50}$ of ≤1 nM, 5900 pM, ≤800 pM, ≤700 pM, ≤600 pM, ≤500 pM, ≤400 pM, 5300 pM, ≤200 pM, ≤100 pM, ≤50 pM, ≤40 pM, ≤30 pM, ≤20 pM, ≤10 pM or ≤1 pM.

Types of Inhibitors

Inhibitors according to the present disclosure may be any kind of agent possessing the appropriate inhibitory activity.

The term "inhibitor" as used herein refers to an agent that decreases or inhibits at least one function or biological activity of a target molecule, such as those described herein.

An inhibitor according to the present disclosure may be a molecule that is capable of binding to any one or more of MFAP4, GRHPR, ITFG1, ABCC4, PAK3, TRNP1, APLN, KIF20A, and/or LTB mRNA or protein, a molecule that is capable of binding to an interacting partner of one or more of MFAP4, GRHPR, ITFG1, ABCC4, PAK3, TRNP1, APLN, KIF20A, and/or LTB, or a molecule capable of reducing expression of one or more of MFAP4, GRHPR, ITFG1, ABCC4, PAK3, TRNP1, APLN, KIF20A, and/or LTB.

In some embodiments an inhibitor is capable of binding to a polypeptide according to any one or more of SEQ ID NO: 7156 to 7178, or a mRNA according to any one of SEQ ID NO: 7179 to 7195.

In some embodiments an inhibitor targets, e.g. is capable of binding to, a functional domain or region of any one or more of SEQ ID NO: 7156 to 7178. In some embodiments an inhibitor targets a region comprising positions 22-255, 26-28 or 32-255 of SEQ ID NO: 7156. In some embodiments an inhibitor targets a region comprising one or more of positions 83-84, 162-164, 185-188, 217, 243, 245, 269, and 293-296 of SEQ ID NO: 7158. In some embodiments an inhibitor targets a region comprising positions 258-293 of SEQ ID NO: 7160. In some embodiments an inhibitor targets a region comprising positions 92-377, 410-633, 714-1005, 1041-1274, 445-452, or 1075-1082 of SEQ ID NO: 7161. In some embodiments an inhibitor targets a region comprising positions 70-83 or 283-534 of SEQ ID NO: 7165. In some embodiments an inhibitor targets a region comprising positions 64-507 or 611-762 of SEQ ID NO: 7175. In some embodiments an inhibitor targets a region comprising positions 1-18, 19-48, or 49-244 of SEQ ID NO: 7177.

In some embodiments an inhibitor is capable of binding to an interacting partner of one or more of MFAP4, GRHPR, ITFG1, ABCC4, PAK3, TRNP1, APLN, KIF20A, and/or LTB, such as those described hereinabove.

Such binding molecules can be identified using any suitable assay for detecting binding of a molecule to the relevant factor (i.e. a target gene/protein described herein, or an interaction partner for said protein(s)). Such assays may comprise detecting the formation of a complex between the relevant factor and the molecule.

In some embodiments, the inhibitor is a nucleic acid, peptide, antibody, antigen-binding molecule or small molecule inhibitor.

Small molecule inhibitors that bind to the target mRNA/proteins described herein, or their binding partners, can be identified by screening of small molecule libraries. As used herein, a "small molecule" refers to a low molecular weight (<1000 daltons, typically between ~300-700 daltons) organic compound. Small molecule inhibitors that bind to the target mRNA/proteins described herein can be identified e.g. using a method described in Horswill A R et al., PNAS, 2004,101 (44) 15591-15596, which is hereby incorporated by reference in its entirety.

An inhibitor of GRHPR may be 4-hydroxy-2-oxoglutarate.

An inhibitor of ABCC4 may be Methotrexate, Mercaptopurine, Zidovudine, Dipyridamole, Probenecid, Sulfinpyrazone, Fluorouraci, Rucaparib, Adefovir dipivoxil, Cefazolin, Tyrphostin AG1478, Dantrolene, Glafenine, Nalidixic Acid or Prazosin.

An inhibitor of PAK3 may be FRAX597.

An inhibitor of APLN may be ML221, an apelin receptor (APJ) antagonist.

An inhibitor of KIF20A may be BKS0349 or Paprotrain.

Inhibitors provided herein include peptides/polypeptides, e.g. peptide aptamers, thioredoxins, monobodies, anticalin, Kunitz domains, avimers, knottins, fynomers, atrimers, DARPins, affibodies, nanobodies (i.e. single-domain antibodies (sdAbs)) affilins, armadillo repeat proteins (ArmRPs), OBodies and fibronectin—reviewed e.g. in Reverdatto et al., Curr Top Med Chem. 2015; 15(12): 1082-1101, which is hereby incorporated by reference in its entirety (see also e.g. Boersma et al., J Biol Chem (2011) 286:41273-85 and Emanuel et al., Mabs (2011) 3:38-48). Inhibitors include peptides/polypeptides that can be identified by screening of libraries of the relevant peptides/polypeptides. The peptide/polypeptide inhibitors may be referred to as inhibitory peptides/polypeptides.

Inhibitory peptides/polypeptides may also include e.g. peptide/polypeptide interaction partners for the target gene/mRNA/protein of interest (i.e. MFAP4, GRHPR, ITFG1, ABCC4, PAK3, TRNP1, APLN, KIF20A, and/or LTB).

Peptide/polypeptide interaction partners may be based on an interaction partner for the target gene/mRNA/protein of interest, and may e.g. comprise a fragment of an interaction partner said target(s). Peptide/polypeptide interaction partners may be based on one or more of MFAP4, GRHPR, ITFG1, ABCC4, PAK3, TRNP1, APLN, KIF20A, and/or LTB, and may e.g. comprise a fragment of MFAP4, GRHPR, ITFG1, ABCC4, PAK3, TRNP1, APLN, KIF20A, and/or LTB that binds to an interaction partner for said mRNA/protein. Such agents may behave as 'decoy' molecules, and preferably display competitive inhibition of interaction between MFAP4, GRHPR, ITFG1, ABCC4, PAK3, TRNP1, APLN, KIF20A, and/or LTB and a corresponding interaction partner for MFAP4, GRHPR, ITFG1, ABCC4, PAK3, TRNP1, APLN, KIF20A, and/or LTB.

An inhibitor of MFAP4 may, for example, be a peptide/polypeptide that is capable of blocking the interaction between MFAP4 and an integrin receptor, integrin αvβ3, tropoelastin, fibrillin-1, fibrillin-2, desmosine, LOX, MFAP2, FBLN1, FBLN2, MFAP5, EFEMP2, EFEMP1, SFTPD, or elastin.

An inhibitor of GRHPR may, for example, be a peptide/polypeptide that is capable of blocking the interaction between GRHPR and glyoxylate, hydroxypyruvate, D-glycerate, AGXT, HYI, GLYCTK, PGP, GLO1, HAO1, HAO2, DAO, NADPH or NADH.

An inhibitor of ITFG1 may, for example, be a peptide/polypeptide that is capable of blocking the interaction between ITFG1 and RUVBL1, RUVBL2, alpha-tubulin, TIPIN, ATP9A, ASCC2, RFX7, or TM7SF3.

An inhibitor of ABCC4 may, for example, be a peptide/polypeptide that is capable of blocking the interaction between ABCC4 and ATP, ABCG4, SNX27, ABCA3, ABCE1, MRPS7, SLC22A8, SLCO1B1, NR1H4 or SLC22A6.

An inhibitor of PAK3 may, for example, be a peptide/polypeptide that is capable of blocking the interaction between PAK3 and PAK1, CDC42, NCK1, MAPK14, RAC1, PXN, GIT1, GIT2, ARHGEF7 or ARHGEF6.

An inhibitor of TRNP1 may, for example, be a peptide/polypeptide that is capable of blocking the interaction between TRNP1 and TMF1, FAM18A, CNIH3, SMARCC2, FAM19A3, TBC1D3A, TBC1D3D, ARHGAP11B, or GPR56.

An inhibitor of APLN may, for example, be a peptide/polypeptide that is capable of blocking the interaction between APLN and APLNR, AGTR1, AGT, CXCR4, CCR5, KNG1, NPY, PDYN, NMU, or POMC.

An inhibitor of KIF20A may, for example, be a peptide/polypeptide that is capable of blocking the interaction between KIF20A and MAD2L1, AURKB, RACGAP1, KIF11, PLK1, CDCA8, KIF4A, CENPE, PRC1, or INCENP.

An inhibitor of LTB may, for example, be a peptide/polypeptide that is capable of blocking the interaction between LTB and LTBR, LTA, TNF, TNFSF14, TNFRSF1B, TNFSF13B, TNFRSF11A, CD40LG, MAP3K14, TNFSF11.

In some embodiments, an inhibitory peptide/polypeptide may comprise or consist of an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of an interaction partner for one or more of MFAP4, GRHPR, ITFG1, ABCC4, PAK3, TRNP1, APLN, KIF20A, and/or LTB, or the amino acid sequence of a fragment thereof.

In some embodiments, an inhibitory peptide/polypeptide may comprise or consist of an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of one or more of MFAP4, GRHPR, ITFG1, ABCC4, PAK3, TRNP1, APLN, KIF20A, and/or LTB, or the amino acid sequence of a fragment thereof. In such embodiments it will be appreciated that the inhibitory peptide/polypeptide will lack normal activity and/or have reduced activity compared to the wildtype version of the protein. For example, in some embodiments an inhibitory peptide/polypeptide may be a variant (e.g. mutant) version of MFAP4, GRHPR, ITFG1, ABCC4, PAK3, TRNP1, APLN, KIF20A, and/or LTB having reduced function relative to wildtype MFAP4, GRHPR, ITFG1, ABCC4, PAK3, TRNP1, APLN, KIF20A, and/or LTB.

Inhibitory peptides/polypeptides include aptamers. Nucleic acid aptamers are reviewed e.g. in Zhou and Rossi Nat Rev Drug Discov. 2017 16(3):181-202, and may be identified and/or produced by the method of Systematic Evolution of Ligands by EXponential enrichment (SELEX), or by developing SOMAmers (slow off-rate modified aptamers) (Gold L et al. (2010) PLoS ONE 5(12):e15004). Aptamers and SELEX are described in Tuerk and Gold, Science (1990) 249(4968):505-10, and in WO 91/19813. Nucleic acid aptamers may comprise DNA and/or RNA, and may be single stranded or double stranded. They may comprise chemically modified nucleic acids, for example in which the sugar and/or phosphate and/or base is chemically modified. Such modifications may improve the stability of the aptamer or make the aptamer more resistant to degradation and may include modification at the 2' position of ribose. Nucleic acid aptamers may be chemically synthesised, e.g. on a solid support. Solid phase synthesis may use phosphoramidite chemistry. Briefly, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle may then be repeated to assemble the aptamer (e.g., see Sinha, N. D.; Biernat, J.; McManus, J.; Köster, H. Nucleic Acids Res. 1984, 12, 4539; and Beaucage, S. L.; Lyer, R. P. (1992). Tetrahedron 48 (12): 2223). Peptide aptamers and methods for their generation and identification are reviewed in Reverdatto et al., Curr Top Med Chem. (2015) 15(12):1082-101, which is hereby incorporated by reference in its entirety.

Inhibitory peptides/polypeptides also include antibodies (immunoglobulins) such as monoclonal antibodies, polyclonal antibodies, monospecific antibodies, multispecific antibodies (e.g., bispecific antibodies), and fragments and derivatives thereof (e.g. Fv, scFv, Fab, scFab, F(ab')$_2$, Fab$_2$, diabodies, triabodies, scFv-Fc, minibodies, single domain antibodies (e.g. VhH), etc.).

In some embodiments, an inhibitor described herein is an antibody that is capable of binding to one or more of MFAP4, GRHPR, ITFG1, ABCC4, PAK3, TRNP1, APLN, KIF20A, and/or LTB.

An inhibitor of MFAP4 may be an antibody with catalog number PA5-42013 (ThermoFisher) or ab169757 (abcam). An inhibitor of GRHPR may be an antibody with catalog number PA5-54652 (ThermoFisher) or ab155604 (abcam). An inhibitor of ITFG1 may be an antibody with catalog number PA5-54067 (ThermoFisher) or TA339563 (ORIGENE). An inhibitor of ABCC4 may be an antibody with catalog number PA5-82019 (ThermoFisher) or ab15602 (abcam). An inhibitor of PAK3 may be an antibody with catalog number PA5-79781 (ThermoFisher) or ab40808 (abcam). An inhibitor of TRNP1 may be an antibody with catalog number PA5-71277 (ThermoFisher) or ab174303 (abcam). An inhibitor of APLN may be an APLN-blocking antibody. An inhibitor of APLN may be an antibody with catalog number PA5-114860 (ThermoFisher) or ab125213 (abcam). An inhibitor of KIF20A may be an antibody with catalog number PA5-38648 (ThermoFisher). An inhibitor of LTB may be an antibody (e.g. a recombinant Mouse Anti-LTA and LTB Antibody (CBL543)).

Inhibitors/inhibitory molecules that bind to any one of MFAP4, GRHPR, ITFG1, ABCC4, PAK3, TRNP1, APLN, KIF20A, and/or LTB, or that bind to an interacting partner thereof, may display specific binding to the relevant factor (i.e. the relevant mRNA/protein, or the interaction partner for said mRNA/protein). As used herein, "specific binding" refers to binding which is selective, and which can be discriminated from non-specific binding to non-target molecules.

An inhibitor or binding molecule that specifically binds to any one of MFAP4, GRHPR, ITFG1, ABCC4, PAK3, TRNP1, APLN, KIF20A, and/or LTB preferably binds to any one of MFAP4, GRHPR, ITFG1, ABCC4, PAK3, TRNP1, APLN, KIF20A, and/or LTB with greater affinity, and/or with greater duration than it binds to other, non-target molecules. Such binding molecules may be described as being "specific for" any one of MFAP4, GRHPR, ITFG1, ABCC4, PAK3, TRNP1, APLN, KIF20A, and/or LTB. An inhibitor or binding molecule that specifically binds to an interaction partner for any one of MFAP4, GRHPR, ITFG1, ABCC4, PAK3, TRNP1, APLN, KIF20A, and/or LTB preferably binds to the interaction partner for any one of MFAP4, GRHPR, ITFG1, ABCC4, PAK3, TRNP1, APLN, KIF20A, and/or LTB with greater affinity, and/or with greater duration than it binds to other, non-target molecules; such binding molecules may be described as being "specific for" the interaction partner for any one of MFAP4, GRHPR, ITFG1, ABCC4, PAK3, TRNP1, APLN, KIF20A, and/or LTB.

In some embodiments an inhibitor/binding molecule described herein inhibits the ability of any one of MFAP4, GRHPR, ITFG1, ABCC4, PAK3, TRNP1, APLN, KIF20A, and/or LTB to bind to a corresponding interaction partner (i.e. an interaction partner for MFAP4, GRHPR, ITFG1, ABCC4, PAK3, TRNP1, APLN, KIF20A, or LTB, respectively). In some embodiments the inhibitor/binding molecule behaves as a competitive inhibitor of interaction between any one of MFAP4, GRHPR, ITFG1, ABCC4, PAK3, TRNP1, APLN, KIF20A, and/or LTB and a corresponding interaction partner. The binding molecule may occupy, or otherwise reduce access to, a region of the protein required for binding to a corresponding interaction partner, or may occupy, or otherwise reduce access to, a region of an interaction partner required for binding to the corresponding protein.

The ability of an inhibitor, e.g. a binding molecule, to inhibit interaction between a protein of interest and a corresponding interaction partner can be evaluated e.g. by analysis of interaction in the presence of, or following incubation of one or both of the interaction partners with, the inhibitor. An example of a suitable assay to determine whether a given binding agent is capable of inhibiting interaction between a protein of interest and a corresponding interaction partner is a competition ELISA.

An inhibitor described herein may be a molecule capable of reducing expression of any one of MFAP4, GRHPR, ITFG1, ABCC4, PAK3, TRNP1, APLN, KIF20A, and/or LTB. A "molecule capable of reducing expression of any one of MFAP4, GRHPR, ITFG1, ABCC4, PAK3, TRNP1, APLN, KIF20A, and/or LTB" refers to a molecule which is capable of reducing gene, mRNA and/or protein expression of any one of MFAP4, GRHPR, ITFG1, ABCC4, PAK3, TRNP1, APLN, KIF20A, and/or LTB. In some embodiments the molecule reduces or prevents the expression of a polypeptide according to SEQ ID NO: 7156 to 7178. In some embodiments the molecule reduces or prevents the expression of a polypeptide from a sequence according to SEQ ID NO: 7179 to 7195.

Repression of expression of MFAP4, GRHPR, ITFG1, ABCC4, PAK3, TRNP1, APLN, KIF20A, or LTB or an isoform thereof will preferably result in a decrease in the quantity of MFAP4, GRHPR, ITFG1, ABCC4, PAK3, TRNP1, APLN, KIF20A, or LTB expressed by a cell/tissue/organ/organ system/subject. For example, in a given cell the repression of MFAP4, GRHPR, ITFG1, ABCC4, PAK3, TRNP1, APLN, KIF20A, or LTB by administration of a suitable nucleic acid will result in a decrease in the level of expression relative to an untreated cell. Repression may be partial. Preferred degrees of repression are at least 50%, more preferably one of at least 60%, 70%, 80%, 85% or 90%. A level of repression between 90% and 100% is considered a 'silencing' of expression or function. Gene and protein expression may be determined as described herein or by methods in the art that are well known to a skilled person.

In some embodiments, inhibition of MFAP4, GRHPR, ITFG1, ABCC4, PAK3, TRNP1, APLN, KIF20A, and/or LTB may comprise modification of a cell(s) to reduce or prevent expression of one or more of MFAP4, GRHPR, ITFG1, ABCC4, PAK3, TRNP1, APLN, KIF20A, and/or LTB. In some embodiments inhibition of MFAP4, GRHPR, ITFG1, ABCC4, PAK3, TRNP1, APLN, KIF20A, and/or LTB comprises modifying nucleic acid encoding one or more of MFAP4, GRHPR, ITFG1, ABCC4, PAK3, TRNP1, APLN, KIF20A, and/or LTB. The modification causes the cell to have a reduced level of gene and/or protein expression of MFAP4, GRHPR, ITFG1, ABCC4, PAK3, TRNP1, APLN, KIF20A, and/or LTB as compared to an unmodified cell.

In some embodiments inhibition of MFAP4, GRHPR, ITFG1, ABCC4, PAK3, TRNP1, APLN, KIF20A, and/or LTB may comprise modifying a gene encoding MFAP4, GRHPR, ITFG1, ABCC4, PAK3, TRNP1, APLN, KIF20A, and/or LTB.

In some embodiments inhibition of MFAP4, GRHPR, ITFG1, ABCC4, PAK3, TRNP1, APLN, KIF20A, and/or LTB comprises introducing an insertion, substitution or deletion into a nucleic acid sequence encoding MFAP4, GRHPR, ITFG1, ABCC4, PAK3, TRNP1, APLN, KIF20A, and/or LTB.

In some embodiments inhibition of MFAP4, GRHPR, ITFG1, ABCC4, PAK3, TRNP1, APLN, KIF20A, and/or LTB comprises introducing a modification which reduces or prevents the expression of a polypeptide according to any one of SEQ ID NO: 7156 to 7178 from the modified nucleic acid sequence. In some embodiments inhibition of MFAP4, GRHPR, ITFG1, ABCC4, PAK3, TRNP1, APLN, KIF20A, and/or LTB comprises modifying a cell to comprise an allele of MFAP4, GRHPR, ITFG1, ABCC4, PAK3, TRNP1, APLN, KIF20A, and/or LTB which does not encode an amino acid sequence according to any one of SEQ ID NO: 7156 to 7178. In some embodiments inhibition of MFAP4, GRHPR, ITFG1, ABCC4, PAK3, TRNP1, APLN, KIF20A, and/or LTB comprises modifying a cell to lack nucleic acid encoding a polypeptide according to any one of SEQ ID NO: 7156 to 7178.

In some embodiments inhibition of MFAP4, GRHPR, ITFG1, ABCC4, PAK3, TRNP1, APLN, KIF20A, and/or LTB comprises modifying the relevant gene(s) to introduce a premature stop codon in the sequence transcribed from said gene(s). In some embodiments inhibition of MFAP4, GRHPR, ITFG1, ABCC4, PAK3, TRNP1, APLN, KIF20A, and/or LTB comprises modifying the relevant gene(s) to encode a truncated and/or non-functional polypeptide(s). In some embodiments inhibition of MFAP4, GRHPR, ITFG1, ABCC4, PAK3, TRNP1, APLN, KIF20A, and/or LTB comprises modifying the relevant gene(s) to encode polypeptide(s) which is/are misfolded and/or degraded.

Methods for modifying nucleic acids encoding proteins of interest and agents for achieving the same are well known in the art, and include e.g. including modification of the target nucleic acid by homologous recombination, and target nucleic acid editing using site-specific nucleases (SSNs).

Suitable methods may employ targeting by homologous recombination, which is reviewed, for example, in Mortensen Curr Protoc Neurosci. (2007) Chapter 4:Unit 4.29 and Vasquez et al., PNAS 2001, 98(15): 8403-8410, both of which are hereby incorporated by reference in their entirety. Targeting by homologous recombination involves the exchange of nucleic acid sequence through crossover events guided by homologous sequences.

In some embodiments the methods employ target nucleic acid editing using SSNs. Gene editing using SSNs is reviewed e.g. in Eid and Mahfouz, Exp Mol Med. 2016 October; 48(10): e265, which is hereby incorporated by reference in its entirety. Enzymes capable of creating site-specific double strand breaks (DSBs) can be engineered to introduce DSBs to target nucleic acid sequence(s) of interest. DSBs may be repaired by either error-prone non-homologous end-joining (NHEJ), in which the two ends of the break are rejoined, often with insertion or deletion of nucleotides. Alternatively DSBs may be repaired by highly homology-directed repair (HDR), in which a DNA template with ends homologous to the break site is supplied and introduced at the site of the DSB.

SSNs capable of being engineered to generate target nucleic acid sequence-specific DSBs include zinc-finger nucleases (ZFNs), transcription activator-like effector nucleases (TALENs) and clustered regularly interspaced palindromic repeats/CRISPR-associated-9 (CRISPR/Cas9) systems.

ZFN systems are reviewed e.g. in Umov et al., Nat Rev Genet. (2010) 11(9):636-46, which is hereby incorporated by reference in its entirety. ZFNs comprise a programmable Zinc Finger DNA-binding domain and a DNA-cleaving domain (e.g. a FokI endonuclease domain). The DNA-binding domain may be identified by screening a Zinc Finger array capable of binding to the target nucleic acid sequence.

TALEN systems are reviewed e.g. in Mahfouz et al., Plant Biotechnol J. (2014) 12(8):1006-14, which is hereby incorporated by reference in its entirety. TALENs comprise a programmable DNA-binding TALE domain and a DNA-cleaving domain (e.g. a FokI endonuclease domain). TALEs comprise repeat domains consisting of repeats of 33-39 amino acids, which are identical except for two residues at positions 12 and 13 of each repeat which are repeat variable di-residues (RVDs). Each RVD determines binding of the repeat to a nucleotide in the target DNA sequence according to the following relationship: 'HD' binds to C, 'NI' binds to A, 'NG' binds to T and 'NN' or 'NK' binds to G (Moscou and Bogdanove, Science (2009) 326(5959):1501.).

CRISPR/Cas9 and related systems e.g. CRISPR/Cpf1, CRISPR/C2c1, CRISPR/C2c2 and CRISPR/C2c3 are reviewed e.g. in Nakade et al., Bioengineered (2017) 8(3): 265-273, which is hereby incorporated by reference in its entirety. These systems comprise an endonuclease (e.g. Cas9, Cpf1 etc.) and the single-guide RNA (sgRNA) molecule. The sgRNA can be engineered to target endonuclease activity to nucleic acid sequences of interest.

In some embodiments, inhibition of one or more of MFAP4, GRHPR, ITFG1, ABCC4, PAK3, TRNP1, APLN, KIF20A, and/or LTB employs a site-specific nuclease (SSN) system targeting the relevant nucleic acid sequence(s). Accordingly in some embodiments the inhibitor comprises or consists of an SSN system targeting nucleic acid(s) encoding one or more of MFAP4, GRHPR, ITFG1, ABCC4, PAK3, TRNP1, APLN, KIF20A, and/or LTB. In some embodiments inhibition of MFAP4, GRHPR, ITFG1, ABCC4, PAK3, TRNP1, APLN, KIF20A, and/or LTB employs nucleic acid(s) encoding a SSN system targeting the relevant nucleic acid sequence(s).

In some embodiments, the SSN system targets a region of the nucleic acid encoding a domain of a MFAP4, GRHPR, ITFG1, ABCC4, PAK3, TRNP1, APLN, KIF20A, and/or LTB protein required for protein function, e.g. a domain as described herein.

In some embodiments the SSN system is a ZFN system, a TALEN system, CRISPR/Cas9 system, a CRISPR/Cpf1 system, a CRISPR/C2c1 system, a CRISPR/C2c2 system or a CRISPR/C2c3 system. In some embodiments the SSN system is a CRISPR/Cas9 system. In such embodiments, the inhibition may employ nucleic acid(s) encoding a CRISPR RNA (crRNA) targeting nucleic acid encoding one or more of MFAP4, GRHPR, ITFG1, ABCC4, PAK3, TRNP1, APLN, KIF20A, and/or LTB, and a trans-activating crRNA (tracrRNA) for processing the crRNA to its mature form.

Nucleic Acid Inhibitors

In some embodiments, the inhibitor is a nucleic acid inhibitor. A nucleic acid inhibitor may also be described herein as an inhibitory nucleic acid.

Nucleic acid inhibitors according to the present disclosure may comprise or consist of DNA and/or RNA. Nucleic acid inhibitors may be single-stranded (e.g. in the case of antisense oligonucleotides (e.g. gapmers)). Nucleic acid inhibitors may be double-stranded or may comprise double-stranded region(s) (e.g. in the case of siRNA, shRNA, etc.). Inhibitory nucleic acids may comprise both double-stranded and single-stranded regions (e.g. in the case of shRNA and pre-miRNA molecules, which are double-stranded in the stem region of the hairpin structure, and single-stranded in the loop region of the hairpin structure).

In some embodiments, a nucleic acid inhibitor according to the present disclosure may be an antisense nucleic acid as described herein. In some embodiments, a nucleic acid inhibitor may comprise an antisense nucleic acid as described herein. In some embodiments, a nucleic acid inhibitor may encode an antisense nucleic acid as described herein.

As used herein, an 'antisense nucleic acid' refers to a nucleic acid (e.g. DNA or RNA) that is complementary to at least a portion of a target nucleotide sequence (e.g. of RNA encoding a target gene described herein). Antisense nucleic acids according to the present disclosure are preferably single-stranded nucleic acids, and bind via complementary Watson-Crick base-pairing to a target nucleotide sequence. Complementary base-pairing may involve hydrogen bonding between complementary base pairs. Antisense nucleic acids may be provided as single-stranded molecules, as for example in the case of antisense oligonucleotides, or may be comprised in double-stranded molecular species, as for example in the case of siRNA, shRNA and pre-miRNA molecules.

Complementary base-pairing between the antisense nucleic acid and its target nucleotide sequence may be complete. In such embodiments the antisense nucleic acid comprises, or consists of, the reverse complement of its target nucleotide sequence, and complementary base-pairing occurs between each nucleotide of the target nucleotide sequence and complementary nucleotides in the antisense nucleic acid. Alternatively, complementary base-pairing between the antisense nucleic acid and its target nucleotide sequence may be incomplete/partial. In such embodiments complementary base-pairing occurs between some, but not all, nucleotides of the target nucleotide sequence and complementary nucleotides in the antisense nucleic acid.

Such binding between nucleic acids through complementary base pairing may be referred to as 'hybridisation'. Through binding to its target nucleotide sequence, an antisense nucleic acid may form a nucleic acid complex comprising (i) the antisense nucleic acid and (ii) a target nucleic acid comprising the target nucleotide sequence.

The nucleotide sequence of an antisense nucleic acid is sufficiently complementary to its target nucleotide sequence such that it binds or hybridises to the target nucleotide sequence. It will be appreciated that an antisense nucleic acid preferably has a high degree of sequence identity to the reverse complement of its target nucleotide sequence. In some embodiments, the antisense nucleic acid comprises or consists of a nucleotide sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to the reverse complement of its target nucleotide sequence.

In some embodiments, an antisense nucleic acid according to the present disclosure comprises: a nucleotide sequence which is the reverse complement of its target nucleotide sequence, or a nucleotide sequence comprising 1 to 10 (e.g. one of 1, 2, 3, 4, 5, 6, 7, 8, 9 or 10) substitutions relative to the reverse complement of its target nucleotide sequence.

In some embodiments, the target nucleotide sequence for an antisense nucleic acid according to the present disclosure comprises, or consists of, 5 to 100 nucleotides, e.g. one of 10 to 80, 12 to 50, or 15 to 30 nucleotides (e.g. 20 to 27, e.g. ~21 to 23). In some embodiments, the target nucleotide sequence for an antisense nucleic acid according to the present disclosure comprises or consists of DNA and/or RNA. In some embodiments, the target nucleotide sequence for an antisense nucleic acid according to the present disclosure comprises or consists of RNA.

In some embodiments, the antisense nucleic acid reduces/prevents transcription of nucleic acid comprising its target nucleotide sequence. In some embodiments, the antisense nucleic acid reduces/prevents association of factors required for normal transcription (e.g. enhancers, RNA polymerase) with nucleic acid comprising its target nucleotide sequence.

In some embodiments, the antisense nucleic acid increases/potentiates degradation of nucleic acid comprising its target nucleotide sequence, e.g. through RNA interference. In some embodiments, the antisense nucleic acid reduces/prevents translation of nucleic acid comprising its target nucleotide sequence, e.g. through RNA interference or antisense degradation via RNase H.

RNA interference is described e.g. in Agrawal et al., Microbiol. Mol. Bio. Rev. (2003) 67(4): 657-685 and Hu et al., Sig. Transduc. Tar. Ther. (2020) 5(101), both of which are hereby incorporated by reference in their entirety. Briefly, double-stranded RNA molecules are recognised by the argonaute component of the RNA-induced silencing complex (RISC). The double-stranded RNAs are separated into single strands and integrated into an active RISC, by the RISC-Loading Complex (RLC). The RISC-integrated strands bind to their target RNA through complementary base pairing, and depending on the identity of the RISC-integrated RNA and degree of complementarity to the target RNA, the RISC then either cleaves the target RNA resulting in its degradation, or otherwise blocks access of ribosomes thereby preventing its translation. RNAi based therapeutics have been approved for a number of indications (Kim, Chonnam Med J. (2020) 56(2): 87-93).

In some embodiments, the antisense nucleic acid reduces/prevents normal post-transcriptional processing (e.g. splicing and/or translation) of nucleic acid comprising its target nucleotide sequence. In some embodiments, the antisense nucleic acid reduces or alters splicing of pre-mRNA comprising its target nucleotide sequence to mature mRNA. In some embodiments, the antisense nucleic acid reduces translation of mRNA comprising its target nucleotide sequence to protein.

In some embodiments, the antisense nucleic acid reduces/prevents association of factors required for normal post-transcriptional processing (e.g. components of the spliceosome) with nucleic acid comprising its target nucleotide sequence. In such instances, the antisense nucleic may be referred to as a 'splice-switching' nucleic acid.

Splice-switching nucleic acids are reviewed e.g. in Haves and Hastings, Nucleic Acids Res. (2016) 44(14): 6549-6563, which is hereby incorporated by reference in its entirety. Splice-switching nucleic acids include e.g. splice-switching oligonucleotides (SSOs). They disrupt the normal splicing of target RNA transcripts by blocking the RNA:RNA base-pairing and/or protein:RNA binding interactions that occur between components of the splicing machinery and pre-mRNA. Splice-switching nucleic acids may be employed to alter the number/proportion of mature mRNA transcripts encoding a protein described herein. Splice-switching nucleic acids may be designed to target a specific region of the target transcript, e.g. to effect skipping of exon(s) of interest, e.g. exons encoding domains/regions of interest. SSOs often comprise alterations to oligonucleotide sugar-phosphate backbones in order to reduce/prevent RNAse H degradation, such as e.g. phosphorothioate linkages, phosphorodiamidate linkages such as phosphorodiamidate morpholino (PMOs), and may comprise e.g. peptide nucleic acids (PNAs), locked nucleic acids (LNAs), methoxyethyl nucleotide modifications, e.g. 2'O-methyl (2'OMe) and 2'-O-methoxyethyl (MOE) ribose modifications and/or 5'-methylcytosine modifications.

In some embodiments, the antisense nucleic acid inhibits/reduces translation of nucleic acid comprising its target nucleotide sequence. In some embodiments, the antisense nucleic acid reduces/prevents association of factors required for translation (e.g. ribosomes) with nucleic acid comprising its target nucleotide sequence.

As used herein, "target sequence" refers to a contiguous portion of the nucleotide sequence of an mRNA molecule formed during the transcription of a gene (e.g. a gene associated with organ regeneration), including mRNA that is a product of RNA processing of a primary transcription product.

It will be appreciated that the target nucleotide sequence to which an antisense nucleic acid binds is a nucleotide sequence encoding a protein which it is desired to inhibit expression of. Accordingly, in aspects and embodiments of the present disclosure, the target nucleotide sequence for an antisense nucleic acid is a nucleotide sequence of a gene encoding any one or more of MFAP4, GRHPR, ITFG1, ABCC4, PAK3, TRNP1, APLN, KIF20A, and/or LTB.

In some embodiments, the target nucleotide sequence is a nucleotide sequence of RNA encoded by a gene encoding any one of MFAP4, GRHPR, ITFG1, ABCC4, PAK3, TRNP1, APLN, KIF20A, or LTB. In some embodiments, the target nucleotide sequence is a nucleotide sequence of RNA encoding any one of MFAP4, GRHPR, ITFG1, ABCC4, PAK3, TRNP1, APLN, KIF20A, or LTB. In some embodiments, the target nucleotide sequence comprises one or more nucleotides of an exon of RNA encoding any one of MFAP4, GRHPR, ITFG1, ABCC4, PAK3, TRNP1, APLN, KIF20A, or LTB. In some embodiments, the target nucleotide sequence is a nucleotide sequence of an exon of RNA encoding any one of MFAP4, GRHPR, ITFG1, ABCC4, PAK3, TRNP1, APLN, KIF20A, or LTB.

In some embodiments, the target nucleotide sequence is a nucleotide sequence provided in Table 14.

In some embodiments, the target nucleotide sequence is a nucleotide sequence of NM_001198695.2 (GI: 1677501926, version 2), which is the NCBI Reference Sequence for human MFAP4 transcript variant 1 mRNA (SEQ ID NO: 7179), or a portion thereof. In some embodiments, the target nucleotide sequence is a nucleotide sequence of NM_002404.3 (GI: 1677501522, version 3), which is the NCBI Reference Sequence for human MFAP4 transcript variant 2 mRNA (SEQ ID NO: 7180), or a portion thereof.

In some embodiments, the target nucleotide sequence is a nucleotide sequence of NM_012203.2 (GI: 1519473711, version 2) which is the NCBI Reference Sequence for human GRHPR transcript variant 1 mRNA (SEQ ID NO: 7181), or a portion thereof.

In some embodiments, the target nucleotide sequence is a nucleotide sequence of NM_030790.5 (GI: 1653961895, version 5) which is the NCBI Reference Sequence for human ITFG1 transcript variant 1 mRNA (SEQ ID NO: 7182), or a portion thereof.

In some embodiments, the target nucleotide sequence is a nucleotide sequence of NM_005845.5 (GI: 1813751621, version 5) which is the NCBI Reference Sequence for human ABCC4 transcript variant 1 mRNA (SEQ ID NO: 7183), or a portion thereof. In some embodiments, the target nucleotide sequence is a nucleotide sequence of NM_001105515.3 (GI: 1677498821, version 3) which is the NCBI Reference Sequence for human ABCC4 transcript variant 2 mRNA (SEQ ID NO: 7184), or a portion thereof. In some embodiments, the target nucleotide sequence is a nucleotide sequence of NM_001301829.2 (GI: 1677530022, version 2) which is the NCBI Reference Sequence for human ABCC4 transcript variant 3 mRNA (SEQ ID NO: 7185), or a portion thereof. In some embodiments, the target nucleotide sequence is a nucleotide sequence of NM_001301830.2 (GI: 1677498275, version 2) which is the NCBI Reference Sequence for human ABCC4 transcript variant 4 mRNA (SEQ ID NO: 7186), or a portion thereof.

In some embodiments, the target nucleotide sequence is a nucleotide sequence of NM_001128166.3 (GI: 1889680926, version 3) which is the NCBI Reference Sequence for human PAK3 transcript variant 1 mRNA (SEQ ID NO: 7187), or a portion thereof. In some embodiments, the target nucleotide sequence is a nucleotide sequence of NM_002578.5 (GI: 1519316149, version 5) which is the NCBI Reference Sequence for human PAK3 transcript variant 2 mRNA (SEQ ID NO: 7188), or a portion thereof. In some embodiments, the target nucleotide sequence is a nucleotide sequence of NM_001128167.3 (GI: 1890283404, version 3) which is the NCBI Reference Sequence for human PAK3 transcript variant 3 mRNA (SEQ ID NO: 7189), or a portion thereof. In some embodiments, the target nucleotide sequence is a nucleotide sequence of NM_001128168.3 (GI: 1676441496, version 3) which is the NCBI Reference Sequence for human PAK3 transcript variant 4 mRNA (SEQ ID NO: 7190), or a portion thereof.

In some embodiments, the target nucleotide sequence is a nucleotide sequence of NM_001013642.3 (GI: 1519242294, version 3) which is the NCBI Reference Sequence for human TRNP1 mRNA (SEQ ID NO: 7191), or a portion thereof.

In some embodiments, the target nucleotide sequence is a nucleotide sequence of NM_017413.5 (GI: 1519315208, version 5) which is the NCBI Reference Sequence for human APLN mRNA (SEQ ID NO: 7192), or a portion thereof.

In some embodiments, the target nucleotide sequence is a nucleotide sequence of NM_005733.3 (GI: 1519313609, version 3) which is the NCBI Reference Sequence for human KIF20A transcript variant 1 mRNA (SEQ ID NO: 7193), or a portion thereof.

In some embodiments, the target nucleotide sequence is a nucleotide sequence of NM_002341.2 (GI: 1720810086, version 2) which is the NCBI Reference Sequence for human LTB transcript variant 1 mRNA (SEQ ID NO: 7194), or a portion thereof. In some embodiments, the target nucleotide sequence is a nucleotide sequence of NM_009588.1 (GI: 6996015, version 1) which is the NCBI Reference Sequence for human LTB transcript variant 2 mRNA (SEQ ID NO: 7195), or a portion thereof.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to the reverse complement of any one of SEQ ID NOs: 7179 to 7195, or a portion thereof, e.g. calculated over the length of the antisense nucleic acid or over the length of the portion of the reference sequence.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one of SEQ ID NOs: 7179 to 7195, or a portion thereof, e.g. calculated over the length of the antisense nucleic acid or over the length of the portion of the reference sequence.

In some embodiments the antisense nucleic acid and/or the portion of the reference sequence is 5 to 50, 5 to 40, 8 to 30, 8 to 25, 10 to 25, 15 to 25, or 19 to 22 nucleotides in length. Antisense nucleic acids described herein may comprise thymine or uracil residues. Where antisense nucleic acids described herein are defined by reference to sequence identity with a reference sequence, the nucleic acids may comprise uracil residues in place of any thymine residues in the reference sequence, or vice versa.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to a sequence, or to the reverse complement of a sequence, in any one or more of Tables 1, 2, 3, 4, 5, 6, 7, 8, 9, 10, 11, 12 and/or 13, e.g. calculated over the length of the antisense nucleic acid or over the length of the reference sequence from a Table.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 1 to 7155, or to the reverse complement of any one or more of SEQ ID NOs: 1 to 7155, e.g. calculated over the length of the antisense nucleic acid or the length of the reference sequence.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 14 to 7114 or 7141 to 7155, or to the reverse complement of any one or more of SEQ ID NOs: 14 to 7114 or 7141 to 7155, e.g. calculated over the length of the antisense nucleic acid or the length of the reference sequence.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one of SEQ ID NOs: 1 to 13, or to the reverse complement of any one of SEQ ID NOs: 1 to 13, e.g. calculated over the length of the antisense nucleic acid or over the length of the reference sequence.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one of SEQ ID NOs: 7115 to 7140, or to the reverse complement of any one of SEQ ID NOs: 7115 to 7140, e.g. calculated over the length of the antisense nucleic acid or over the length of the reference sequence.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 14 to 347, and/or to the reverse complement of any one or more of SEQ ID NOs: 14 to 347, e.g. calculated over the length of the antisense nucleic acid or over the length of the reference sequence. The antisense nucleic acid may be capable of reducing gene and/or protein expression of MFAP4, e.g. human MFAP4.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NOs: 1, 2, 15, 19 or 25, and/or to the reverse complement of SEQ ID NOs: 1, 2, 15, 19, or 25, e.g. calculated over the length of the antisense nucleic acid or over the length of the reference sequence. The antisense nucleic acid may be capable of reducing gene and/or protein expression of MFAP4, e.g. human MFAP4.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NOs: 7092, 7093, 7141, 7142, 7146, 7147, 7151, 7152 and/or 7097 to 7102, and/or to the reverse complement of SEQ ID NOs: 7092, 7093, 7141, 7142, 7146, 7147, 7151, 7152 and/or 7097 to 7102, e.g. calculated over the length of the antisense nucleic acid or over the length of the reference sequence. The antisense nucleic acid may be capable of reducing gene and/or protein expression of MFAP4, e.g. human MFAP4.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NOs: 7097 or 7100, and/or to the reverse complement of SEQ ID NOs: 7097 or 7100, e.g. calculated over the length of the antisense nucleic acid or over the length of the reference sequence. The antisense nucleic acid may be capable of reducing gene and/or protein expression of MFAP4, e.g. human MFAP4.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 7115 to 7120, and/or to the reverse complement of any one or more of SEQ ID NOs: 7115 to 7120, e.g. calculated over the length of the antisense nucleic acid or over the length of the reference sequence. The antisense nucleic acid may be capable of reducing gene and/or protein expression of MFAP4, e.g. mouse MFAP4.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 348 to 456, and/or to the reverse complement of any one or more of SEQ ID NOs: 348 to 456, e.g. calculated over the length of the antisense nucleic acid or over the length of the reference sequence. The antisense nucleic acid may be capable of reducing gene and/or protein expression of GRHPR, e.g. human GRHPR.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 3, 4, 5, 349, 350 and/or 351, and/or to the reverse complement of any one or more of SEQ ID NOs: 3, 4, 5, 349, 350, and/or 351, e.g. calculated over the length of the antisense nucleic acid or over the length of the reference sequence. The antisense nucleic acid may be capable of reducing gene and/or protein expression of GRHPR, e.g. human GRHPR.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 7094, 7143, 7148, 7153 and/or 7103 to 7108, and/or to the reverse complement of any one or more of SEQ ID NOs: 7094, 7143, 7148, 7153 and/or 7103 to 7108, e.g. calculated over the length of the antisense nucleic acid or over the length of the reference sequence. The antisense nucleic acid may be capable of reducing gene and/or protein expression of GRHPR, e.g. human GRHPR.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 7121 to 7129, and/or to the reverse complement of any one or more of SEQ ID NOs: 7121 to 7129, e.g. calculated over the length of the antisense nucleic acid or over the length of the reference sequence. The antisense nucleic acid may be capable of reducing gene and/or protein expression of GRHPR, e.g. mouse GRHPR.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 457 to 1482, and/or to the reverse complement of any one or more of SEQ ID NOs: 457 to 1482, e.g. calculated over the length of the antisense nucleic acid or over the length of the reference sequence. The antisense nucleic acid may be capable of reducing gene and/or protein expression of ITFG1, e.g. human ITFG1.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 6, 7, 457, 465, 468, 470, and/or 473, and/or to the reverse complement of any one or more of SEQ ID NOs: 6, 7, 457, 465, 468, 470, and/or 473, e.g. calculated over the length of the antisense nucleic acid or over the length of the reference sequence. The antisense nucleic acid may be capable of reducing gene and/or protein expression of ITFG1, e.g. human ITFG1.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 7095, 7096, 7144, 7145, 7149, 7150, 7154, 7155, and/or 7109 to 7114, and/or to the reverse complement of any one or more of SEQ ID NOs: 7095, 7096, 7144, 7145, 7149, 7150, 7154, 7155, and/or 7109 to 7114, e.g. calculated over the length of the antisense nucleic acid or over the length of the reference sequence. The antisense nucleic acid may be capable of reducing gene and/or protein expression of ITFG1, e.g. human ITFG1.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 7130 to 7140, and/or to the reverse complement of any one or more of SEQ ID NOs: 7130 to 7140, e.g. calculated over the length of the antisense nucleic acid or over the length of the reference sequence. The antisense nucleic acid may be capable of reducing gene and/or protein expression of ITFG1, e.g. mouse ITFG1.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 1483 to 2208, and/or to the reverse complement of any one or more of SEQ ID NOs: 1483 to 2208, e.g. calculated over the length of the antisense nucleic acid or over the length of the reference sequence. The antisense nucleic acid may be capable of reducing gene and/or protein expression of ABCC4, e.g. human ABCC4.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 1483, 1485, 1486, 1488, 1489 and/or 1490, and/or to the reverse complement of any one or more of SEQ ID NOs: 1483, 1485, 1486, 1488, 1489 and/or 1490, e.g. calculated over the length of the antisense nucleic acid or over the length of the reference sequence. The antisense nucleic acid may be capable of reducing gene and/or protein expression of ABCC4, e.g. human ABCC4.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 2209 to 5060, and/or to the reverse complement of any one or more of SEQ ID NOs: 2209 to 5060, e.g. calculated over the length of the antisense nucleic acid or over the length of the reference sequence. The antisense nucleic acid may be capable of reducing gene and/or protein expression of PAK3, e.g. human PAK3.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 2209, 2225 and/or 2234, and/or to the reverse complement of any one or more of SEQ ID NOs: 2209, 2225 and/or 2234 e.g. calculated over the length of the antisense nucleic acid or over the length of the reference sequence. The antisense nucleic acid may be capable of reducing gene and/or protein expression of PAK3, e.g. human PAK3.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 5061 to 5389, and/or to the reverse complement of any one or more of SEQ ID NOs: 5061 to 5389, e.g. calculated over the length of the antisense nucleic acid or over the length of the reference sequence. The antisense nucleic acid may be capable of reducing gene and/or protein expression of TRNP1, e.g. human TRNP1.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 5061 and/or 5062, and/or to the reverse complement of any one or more of SEQ ID NOs: 5061 and/or 5062 e.g. calculated over the length of the antisense nucleic acid or over the length of the reference sequence. The antisense nucleic acid may be capable of reducing gene and/or protein expression of TRNP1, e.g. human TRNP1.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 5390 to 5966, and/or to the reverse complement of any one or more of SEQ ID NOs: 5390 to 5966, e.g. calculated over the length of the antisense nucleic acid or over the length of the reference sequence. The antisense nucleic acid may be capable of reducing gene and/or protein expression of APLN, e.g. human APLN.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 5390, 5391, 5392 and/or 5393, and/or to the reverse complement of any one or more of SEQ ID NOs: 5390, 5391, 5392 and/or 5393, e.g. calculated over the length of the antisense nucleic acid or over the length of the reference sequence. The antisense nucleic acid may be capable of reducing gene and/or protein expression of APLN, e.g. human APLN.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 5967 to 6974, and/or to the reverse complement of any one or more of SEQ ID NOs: 5967 to 6974, e.g. calculated over the length of the antisense nucleic acid or over the length of the reference sequence. The antisense nucleic acid may be capable of reducing gene and/or protein expression of KIF20A, e.g. human KIF20A.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 5967, 5970 and/or 5971, and/or to the reverse complement of any one or more of SEQ ID NOs: 5967, 5970 and/or 5971, e.g. calculated over the length of the antisense nucleic acid or over the length of the reference sequence. The antisense nucleic acid may be capable of reducing gene and/or protein expression of KIF20A, e.g. human KIF20A.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 6975 to 7091, and/or to the reverse complement of any one or more of SEQ ID NOs: 6975 to 7091, e.g. calculated over the length of the antisense nucleic acid or over the length of the reference sequence. The antisense nucleic acid may be capable of reducing gene and/or protein expression of LTB, e.g. human LTB.

In some embodiments, the antisense nucleic acid comprises or consists of a sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to any one or more of SEQ ID NOs: 6977, 6978 and/or 6993, and/or to the reverse complement of any one or more of SEQ ID NOs: 6977, 6978 and/or 6993, e.g. calculated over the length of the antisense nucleic acid or over the length of the reference sequence. The antisense nucleic acid may be capable of reducing gene and/or protein expression of LTB, e.g. human LTB.

The antisense nucleic acid may comprise or consist of a sequence that hybridises to a sequence listed in any of Tables 1 to 14, or a sequence that hybridises to the complement of a sequence listed in any of Tables 1 to 14.

In some embodiments, a nucleic acid inhibitor is an antisense oligonucleotide (ASO). ASOs are single-stranded nucleic acid molecules comprising or consisting of an antisense nucleic acid to a target nucleotide sequence. An antisense oligonucleotide according to the present disclosure may comprise or consist of an antisense nucleic acid as described herein.

ASOs can modify expression of RNA molecules comprising their target nucleotide sequence by altering splicing, or by recruiting RNase H to degrade RNA comprising the target nucleotide sequence. RNase H recognises nucleic acid complex molecules formed when the ASO binds to RNA comprising its target nucleotide sequence. ASOs according to the present disclosure may comprise or consist of an antisense nucleic acid according to the present disclosure. ASOs may comprise 10 to 40 (e.g. 17 to 30, 20 to 27, 21 to 23) nucleotides in length. Many ASOs are designed as chimeras, comprising a mix of bases with different chemistries, or as gapmers, comprising a central DNA portion surrounded by 'wings' of modified nucleotides. ASOs are described in e.g. Scoles et al., Neurol Genet. 2019 April; 5(2): e323. ASOs sometimes comprise alterations to the sugar-phosphate backbone in order to increase their stability and/or reduce/prevent RNAse H degradation, such as e.g. phosphorothioate linkages, phosphorodiamidate linkages such as phosphorodiamidate morpholino (PMOs), and may comprise e.g. peptide nucleic acids (PNAs), locked nucleic acids (LNAs), methoxyethyl nucleotide modifications, e.g. 2'O-methyl (2'OMe) and 2'-O-methoxyethyl (MOE) ribose modifications and/or 5'-methylcytosine modifications.

In some embodiments, a nucleic acid inhibitor is selected from: an siRNA, dsiRNA, miRNA, shRNA, pri-miRNA, pre-miRNA, saRNA, snoRNA, or antisense oligonucleotide (e.g. a gapmer), or a nucleic acid encoding the same. In some embodiments, a nucleic acid inhibitor is selected from: an siRNA, dsiRNA, miRNA, shRNA. In some embodiments, a nucleic acid inhibitor is an siRNA. In some embodiments, a nucleic acid inhibitor is an shRNA.

The nucleic acid inhibitor may be an RNAi agent (e.g. siRNA, shRNA or miRNA-based shRNA or gRNA for CRISR/CAS9 knockout) or a nucleic acid encoding an RNAi agent that reduces expression of a gene/mRNA, e.g. one or more of MFAP4, GRHPR, ITFG1, ABCC4, PAK3, TRNP1, APLN, KIF20A, and/or LTB.

In some embodiments, an inhibitory nucleic acid may comprise an antisense nucleic acid described herein, e.g. as part of a larger nucleic acid species. For example, in some embodiments, an inhibitory nucleic acid may be an siRNA, dsiRNA, miRNA, shRNA, pri-miRNA, pre-miRNA, saRNA or snoRNA comprising an antisense nucleic acid described herein.

In some embodiments, an inhibitory nucleic acid is a small interfering RNA (siRNA). As used herein, 'siRNA' refers to a double-stranded RNA molecule having a length between 17 to 30 (e.g. 20 to 27, e.g. ~21 to 23) base pairs, which is capable of engaging the RNA interference (RNAi) pathway for the targeted degradation of target RNA. Double-stranded siRNA molecules may be formed as a nucleic acid complex of RNA strands having a high degree of complementarity. The strand of the double-stranded siRNA molecule having complementarity to a target nucleotide sequence (i.e. the antisense nucleic acid) may be referred to as the 'guide' strand, and the other strand may be referred to as the 'passenger' strand. The structure and function of siRNAs is described e.g. in Kim and Rossi, Biotechniques. 2008 April; 44(5): 613-616.

The RNAi agent may contain one or more overhang regions and/or capping groups at the 3'-end, 5'-end, or both ends of one or both strands e.g. comprising one or two or three nucleotides (e.g. a 'UU'3' overhang, a 'TT' 3' overhang, or a 'CCA' 5' overhang). The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In some embodiments, a passenger strand of an siRNA according to the present disclosure may comprise a 'CCA' modification at the 5' end, i.e. the addition of nucleotides 'CCA'. In some embodiments, a passenger strand of an siRNA according to the present disclosure may comprise a 'TT' modification at the 3' end, e.g. replacing the 3' two nucleotides.

In some embodiments, the guide strand of an siRNA according to the present disclosure may comprise or consist of an antisense nucleic acid according to an embodiment of an antisense nucleic acid described herein.

In some embodiments an siRNA according to the present disclosure (e.g. in Tables 1-11) may be contained within a longer shRNA sequence (e.g. in Tables 12 and 13) that undergoes processing to form the siRNA.

The term "RNAi agent" or "RNAi" as used interchangeably herein, refer to an agent that contains RNA as that term is defined herein, and which mediates the targeted cleavage of an RNA transcript via an RNA-induced silencing complex (RISC) pathway. RNAi agent directs the sequence-specific degradation of mRNA through a process known as RNA interference (RNAi). The RNAi agent modulates, e.g., inhibits, the expression of a gene associated with organ regeneration in a cell, e.g., a cell within a subject, such as a mammalian subject. The term "RNAi agent" includes both shRNAs (e.g. in Table 12 or 13), or precursor RNAs that are processed by RISC into siRNAs (e.g. in Tables 1 to 11), as well as the siRNAs themselves that inhibits the expression of an endogenous gene.

The invention provides for double-stranded RNAi agents capable of inhibiting the expression of a target gene in vivo. The RNAi agent may comprise a sense strand and an antisense strand. Each strand of the RNAi agent may range from 12-30 nucleotides in length. For example, each strand may be between 14-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"). The duplex region of an RNAi agent may be 12-30 nucleotide pairs in length. For example, the duplex region can be between 14-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length.

In some embodiments, an inhibitory nucleic acid is a dicer small interfering RNA (dsiRNA). As used herein, 'dsiRNA' refers to a double-stranded RNA molecule having a length of ~27 base pairs, which is processed by Dicer to siRNA for RNAi-mediated degradation of target RNA. DsiRNAs are described e.g. in Raja et al., Asian J Pharm Sci. (2019) 14(5): 497-510, which is hereby incorporated by reference in their entirety. DsiRNAs are optimised for Dicer processing and may have increased potency compared with 21-mer siRNAs (see e.g. Kim et al., Nat Biotechnol. (2005) 23(2):222-226), which may be related to the link between Dicer-mediated nuclease activity and RISC loading.

In some embodiments, an inhibitory nucleic acid is a micro RNA (miRNA), or a precursor thereof (e.g. a pri-miRNA or a pre-miRNA). miRNA molecules have a similar structure to siRNA molecules, but are encoded endogenously, and derived from processing of short hairpin RNA molecules. They are initially expressed as long primary transcripts (pri-miRNAs), which are processed within the nucleus into 60 to 70 nucleotide hairpins (pre-miRNAs), which are further processed in the cytoplasm into smaller species that interact with RISC and target mRNA. miRNAs comprise 'seed sequences' that are essential for binding to target mRNA. Seed sequences usually comprise six nucleotides and are situated at positions 2 to 7 at the miRNA 5' end.

In some embodiments, an inhibitory nucleic acid is a short hairpin RNA (shRNA), e.g. as provided in Tables 12 and 13 (showing sense-loop-antisense sequences). shRNA molecules comprise sequences of nucleotides having a high degree of complementarity that associate with one another through complementary base pairing to form the stem region of the hairpin. The sequences of nucleotides having a high degree of complementarity may be linked by one or more nucleotides that form the loop region of the hairpin. shRNA molecules may be processed (e.g. via catalytic cleavage by DICER) to form siRNA or miRNA molecules. shRNA molecules may have a length of between 35 to 100 (e.g. 40 to 70) nucleotides. The stem region of the hairpin may have a length between 17 to 30 (e.g. 20 to 27, e.g. ~21-23) base pairs. The stem region may comprise G-U pairings to stabilise the hairpin structure. An shRNA sequence described herein may comprise sequences that will be subsequently processed into shorter siRNA strand(s), such as the guide/passenger strands presented in Tables 1-11.

siRNA, dsiRNA, miRNAs and shRNAs for the targeted inhibition of gene and/or protein expression of one or more of MFAP4, GRHPR, ITFG1, ABCC4, PAK3, TRNP1, APLN, KIF20A, or LTB may be identified/designed in accordance with principles and/or using tools well known to the skilled person. Parameters and tools for designing siRNA and shRNA molecules are described e.g. in Fakhr et al., Cancer Gene Therapy (2016) 23:73-82 (hereby incorporated by reference in its entirety). Software that may be used by the skilled person for the design of such molecules is summarised in Table 1 of Fakhr et al., Cancer Gene Therapy (2016) 23:73-82, and includes e.g. siRNA Wizard (InvivoGen). Details for making such molecules can be found in the websites of commercial vendors such as Ambion, Dharmacon, GenScript, Invitrogen and Oligo-Engine.

In some embodiments, an inhibitory nucleic acid according to the present disclosure comprises: (i) nucleic acid comprising the nucleotide sequence of any one or more of SEQ ID NOs: 1 to 7091, or a nucleotide sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to one of SEQ ID NOs: 1 to 7091; and (ii) nucleic acid comprising a nucleotide sequence having the reverse complement of the nucleotide sequence of (i), or having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to the reverse complement of the nucleotide sequence of (i). SEQ ID NOs 1 to 7091 are displayed in Tables 1 to 10 provided herein. The nucleic acid according to the present disclosure may be capable of reducing gene and/or protein expression of any one of MFAP4, GRHPR, ITFG1, ABCC4, PAK3, TRNP1, APLN, KIF20A, or LTB, according to the heading of the Table in which the SEQ ID NO is presented. For example, a SEQ ID NO presented in Table 2 may be capable of reducing gene and/or protein expression of MFAP4.

In some embodiments, an inhibitory nucleic acid according to the present disclosure comprises: (i) nucleic acid comprising the nucleotide sequence of any one or more of SEQ ID NOs: 7092 to 7096, or a nucleotide sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to one of SEQ ID NOs: 7092 to 7096; and (ii) nucleic acid comprising a nucleotide sequence having the reverse complement of the nucleotide sequence of (i), or having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to the reverse complement of the nucleotide sequence of (i).

In some embodiments, an inhibitory nucleic acid according to the present disclosure comprises: (i) nucleic acid comprising the nucleotide sequence of SEQ ID NO: 7092, or a nucleotide sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7092; and (ii) nucleic acid comprising a nucleotide sequence of SEQ ID NO: 7141, or having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7141.

In some embodiments, an inhibitory nucleic acid according to the present disclosure comprises: (i) nucleic acid comprising the nucleotide sequence of SEQ ID NO: 7093, or a nucleotide sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7093; and (ii) nucleic acid comprising a nucleotide sequence of SEQ ID NO: 7142, or having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7142.

In some embodiments, an inhibitory nucleic acid according to the present disclosure comprises: (i) nucleic acid comprising the nucleotide sequence of SEQ ID NO: 7094, or a nucleotide sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7094; and (ii) nucleic acid comprising a nucleotide sequence of SEQ ID NO: 7143, or having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7143.

In some embodiments, an inhibitory nucleic acid according to the present disclosure comprises: (i) nucleic acid comprising the nucleotide sequence of SEQ ID NO: 7095, or a nucleotide sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7095; and (ii) nucleic acid comprising a nucleotide sequence of SEQ ID NO: 7144, or having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7144.

In some embodiments, an inhibitory nucleic acid according to the present disclosure comprises: (i) nucleic acid comprising the nucleotide sequence of SEQ ID NO: 7096, or a nucleotide sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7096; and (ii) nucleic acid comprising a nucleotide sequence of SEQ ID NO: 7145, or having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7145.

In some embodiments in accordance with the preceding seven paragraphs, the nucleotide sequence of (i) and the nucleotide sequence of (ii) may be provided on different nucleic acids (i.e. separate oligonucleotides). As such, the nucleic acid of (i) and (ii) may be different nucleic acids. In such embodiments, the inhibitory nucleic acid may comprise or consist of a nucleic acid duplex formed by complementary base pairing between the different nucleic acids comprising the nucleotide sequences of (i) and (ii).

Alternatively, in some embodiments the nucleotide sequence of (i) and the nucleotide sequence of (ii) may be provided on the same nucleic acid (i.e. a single oligonucleotide). That is, the nucleic acid of (i) and (ii) may be the same nucleic acid. In such embodiments, the nucleotide sequence of (i) and the nucleotide sequence of (ii) may be connected by one or more linker nucleotides. The inhibitory nucleic acid may comprise a nucleic acid duplex region formed by complementary base pairing between the nucleotide sequences of (i) and (ii), and the linker regions may form a single-stranded loop region.

Disclosed herein is a nucleic acid inhibitor consisting, comprising or encoding an RNAi agent having at least 70%, 80%, 90% or 95% sequence identity to an RNA sequence listed in any of Tables 1 to 13 (or any combination of Tables thereof) or an RNAi agent that hybridizes to the complement of an RNA sequence listed in any of Tables 1 to 13 (or any combination of Tables thereof) under stringency conditions.

Disclosed herein is a nucleic acid inhibitor consisting, comprising or encoding an RNAi agent having at least 70%, 80%, 90% or 95% sequence identity to an RNA sequence listed in any of Tables 2-12 (or any combination of Tables thereof) or an RNAi agent that hybridizes to the complement of an RNA sequence listed in any of Tables 2-12 (or any combination of Tables thereof) under stringency conditions.

Disclosed herein is a nucleic acid inhibitor consisting, comprising or encoding an RNAi agent having at least 70%, 80%, 90% or 95% sequence identity to an RNA sequence listed in Table 1 or 13, or an RNAi agent that hybridizes to the complement of an RNA sequence listed in Table 1 or 13 under stringency conditions.

The terms "nucleic acid" and "polynucleotide', used interchangeably herein, refer to polymeric forms of nucleotides of any length, either ribonucleotides or deoxyribonucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These terms further include, but are not limited to, mRNA or cDNA that comprise intronic sequences. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. The term "polynucleotide" also encompasses peptidic nucleic acids, PNA and LNA. Polynucleotides may further comprise genomic DNA, cDNA, or DNA-RNA hybrids.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

"Stringency conditions" refers to conditions under which a nucleic acid may hybridize to its target polynucleotide sequence, but not other sequences. Stringent conditions are sequence-dependent (e.g., longer sequences hybridize specifically at higher temperatures). Generally, stringent conditions are selected to be about 5° C. lower than the thermal melting point (Tm) for the specific sequence at a defined ionic strength and pH. The Tm is the temperature (under defined ionic strength, pH, and polynucleotide concentration) at which 50% of the probes complementary to the target sequence hybridize to the target sequence at equilibrium. Typically, stringent conditions will be those in which the salt concentration is at least about 0.01 to about 1.0 M sodium ion concentration (or other salts) at about pH 7.0 to about pH 8.3 and the temperature is at least about 30° C. for short probes (e.g., 10 to 50 nucleotides).

As used herein, the term "complement" when used in reference to a nucleic acid sequence refers to the complementary sequence of the nucleic acid sequence as dictated by base-pairing, but in reverse orientation so as to result in complementarity upon fold-over into a hairpin structure. The term encompasses partial complementarity where only some of the bases are matched according to base pairing rules as well as total complementarity between the two nucleic acid sequences.

Modifications

Nucleic acid inhibitors/inhibitory nucleic acids according to the present disclosure may comprise chemically modified nucleotide acids, e.g. in which the phosphonate and/or ribose and/or base is/are chemically modified. Such modifications may influence the activity, specificity and/or stability of nucleic acid. One or more (e.g. one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or all) nucleotides of a nucleic acid inhibitor may comprise such chemical modification.

Modifications contemplated in accordance with nucleic acid inhibitors according to the present disclosure include those described in Hu et al., Sig. Transduc. Tar. Ther. (2020) 5(101) (incorporated by reference hereinabove), in particular those shown in FIG. 2 of Hu et al., Sig. Transduc. Tar. Ther. (2020) 5(101). Further modifications contemplated in accordance with nucleic acid inhibitors according to the present disclosure include those described in Selvam et al., Chem Biol Drug Des. (2017) 90(5): 665-678, which is hereby incorporated by reference in its entirety).

In some embodiments, an inhibitory nucleic acid according to the present disclosure comprises one or more nucleotides comprising a phosphonate modification. In some embodiments, the phosphonate modification(s) may be selected from: phosphorothioate (e.g. Rp isomer, Sp isomer), phosphorodithioate, methylphosphonate, methoxypropylphosphonate, 5'-(E)-vinylphosphonate, 5'-methylphosphonate, (S)-5'-C-methyl with phosphate, 5'-phosphorothioate, and peptide nucleic acid. In some embodiments, aa nucleic acid inhibitor comprises one or more nucleotides comprising phosphorothioate modification.

In some embodiments, an inhibitory nucleic acid according to the present disclosure comprises one or more nucleotides comprising a ribose modification. In some embodiments, the ribose modification(s) may be selected from: 2'-O-methyl, 2'-O-methoxyethyl, 2'-fluoro, 2'-deoxy-2'- fluoro, 2'-methoxyethyl, 2'-O-alkyl, 2'-O-allyl, 2'-C-allyl, 2'-deoxy, 2'-hydroxyl, 2'-arabino-fluoro, 2'-O-benzyl, 2'-O-methyl-4-pyridine, locked nucleic acid, (S)-cEt-BNA, tricyclo-DNA, PMO, unlocked nucleic acid, hexitol nucleic acid and glycol nucleic acid. In some embodiments, an inhibitory nucleic acid comprises one or more nucleotides comprising 2'-O-methyl modification. In some embodiments, an inhibitory nucleic acid comprises one or more nucleotides comprising 2'-fluoro modification.

In some embodiments, an inhibitory nucleic acid according to the present disclosure comprises one or more nucleotides comprising a base modification. In some embodiments, the base modification(s) may be selected from: pseudouridine, 2'-thiouridine, N6'-methyladenosine, 5'-methylcytidine, 5'-fluoro-2'-deoxyuridine, N-ethylpiperidine 7-EAA triazole-modified adenine, N-ethylpiperidine 6'-triazole-modified adenine, 6'-phenylpyrrolo-cytosine, 2',4'-difluorotoluyl ribonucleoside and 5'-nitroindole.

In some embodiments, an inhibitory nucleic acid according to the present disclosure comprises: one or more nucleotides comprising phosphorothioate modification, one or more nucleotides comprising 2'-O-methyl modification, and one or more nucleotides comprising 2'-fluoro modification.

In some embodiments, an inhibitory nucleic acid according to the present disclosure comprises one or more modified nucleotides selected from: 2'-O-methyluridine-3-phosphate, 2'-O-methyladenosine-3'-phosphate, 2'-O-methylguanosine-3'-phosphate, 2'-O-methylcytidine-3-phosphate, 2'-O-methyluridine-3'-phosphorothioate, 2'-O-methyladenosine-3'-phosphorothioate, 2'-O-methylguanosine-3'-phosphorothioate, 2'-O-methylcytidine-3'-phosphorothioate, 2'-fluorouridine-3-phosphate, 2'-fluoroadenosine-3'-phosphate, 2'-fluoroguanosine-3'-phosphate, 2'-fluorocytidine-3'-phosphate, 2'-fluorocytidine-3'-phosphorothioate, 2'-fluoroguanosine-3'-phosphorothioate, 2'-fluoroadenosine-3'-phosphorothioate, and 2'-fluorouridine-3'-phosphorothioate.

In some embodiments, an inhibitory nucleic acid according to the present disclosure comprises a nucleotide sequence comprising 3 to 10 (e.g. one of 3, 4, 5, 6, 7, 8, 9 or 10) nucleotides comprising 2'-fluoro modification. In some embodiments, an inhibitory nucleic acid according to the present disclosure comprises 4 to 15 (e.g. one of 4, 5, 6, 7, 8, 9, 10, 11, 12, 13, 14 or 15) nucleotides comprising 2'-fluoro modification. In some embodiments, an inhibitory nucleic acid according to the present disclosure comprises a nucleotide sequence comprising 2 to 6 (e.g. one of 2, 3, 4, 5 or 6) nucleotides comprising phosphorothioate modification. In some embodiments, an inhibitory nucleic acid according to the present disclosure comprises 5 to 20 (e.g. one of 5, 6, 7, 8, 9, 10, 11, 12, 13, 14, 15, 16, 17, 18, 19 or 20) nucleotides comprising 2'-O-methyl modification. In some embodiments, an inhibitory nucleic acid according to the present disclosure comprises a nucleotide sequence comprising 2 to 6 (e.g. one of 2, 3, 4, 5 or 6) nucleotides comprising 2'-O-methyl and phosphorothioate modification. In some embodiments, an inhibitory nucleic acid according to the present disclosure comprises a nucleotide sequence comprising 1 to 4 (e.g. one of 1, 2, 3 or 4) nucleotides comprising 2'-fluoro and phosphorothioate modification.

In embodiments wherein nucleic acid inhibitors/inhibitory nucleic acids comprise nucleotides comprising chemical modification as described herein, the nucleotide sequence is nevertheless evaluated for the purposes of sequence comparison in accordance with the present disclosure as if the equivalent unmodified nucleotide were instead present.

Nucleic acids comprising nucleotide(s) comprising a modified phosphonate group are evaluated for the purposes of nucleotide sequence comparison as if nucleotide(s) comprising a modified phosphonate group instead comprise the equivalent unmodified phosphonate group. Nucleic acids comprising nucleotide(s) comprising a modified ribose group are evaluated for the purposes of nucleotide sequence comparison as if nucleotide(s) comprising a modified ribose group instead comprise the equivalent unmodified ribose group. Nucleic acids comprising nucleotide(s) comprising a modified base group are evaluated for the purposes of nucleotide sequence comparison as if nucleotide(s) comprising a modified base group instead comprise the equivalent unmodified base group.

By way of illustration, nucleic acids comprising nucleotides comprising pseudouridine, 2-thiouridine and/or 5'-fluoro-2'-deoxyuridine are evaluated for the purposes of nucleotide sequence comparison as if nucleotides comprising uridine were instead present at their respective positions. By way of illustration, nucleic acids comprising nucleotides comprising N6'-methyladenosine, N-ethylpiperidine 7'-EAA triazole-modified adenine and/or N-ethylpiperidine 6'-triazole-modified adenine are evaluated for the purposes of nucleotide sequence comparison as if nucleotides comprising adenine were instead present at their respective positions. By way of illustration, nucleic acids comprising nucleotides comprising 5'-methylcytidine and/or 6'-phenylpyrrolo-cytosine are evaluated for the purposes of nucleotide sequence comparison as if nucleotides comprising cytosine were instead present at their respective positions.

In some embodiments, an inhibitory nucleic acid according to the present disclosure comprises nucleic acid comprising the nucleotide sequence (including the modifications thereto) shown in Table 11.

In some embodiments, an inhibitory nucleic acid comprises nucleic acid comprising the nucleotide sequence (including the modifications thereto) shown in any one or more of SEQ ID NOs: 7146 to 7155 of Table 11. The following six paragraphs refer to SEQ ID NOs presented in Table 11.

In some embodiments, an inhibitory nucleic acid according to the present disclosure comprises: (i) nucleic acid comprising the nucleotide sequence (including the modifications thereto) of any one of SEQ ID NOs: 7146 to 7150, or a nucleotide sequence (including the modifications thereto) having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to one of SEQ ID NOs: 7146 to 7150; and (ii) nucleic acid comprising the nucleotide sequence (including the modifications thereto) of any one of SEQ ID NOs: 7151 to 7155, or a nucleotide sequence (including the modifications thereto) having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to one of SEQ ID NOs: 7151 to 7155.

In some embodiments, an inhibitory nucleic acid according to the present disclosure comprises: (i) nucleic acid comprising the nucleotide sequence (including the modifications thereto) of SEQ ID NO: 7146, or a nucleotide sequence (including the modifications thereto) having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7146; and (ii) nucleic acid comprising the nucleotide sequence (including the modifications thereto) of SEQ ID NO: 7151, or a nucleotide sequence (including the modifications thereto) having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7151.

In some embodiments, an inhibitory nucleic acid according to the present disclosure comprises: (i) nucleic acid comprising the nucleotide sequence (including the modifications thereto) of SEQ ID NO: 7147, or a nucleotide sequence (including the modifications thereto) having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7147; and (ii) nucleic acid comprising the nucleotide sequence (including the modifications thereto) of SEQ ID NO: 7152, or a nucleotide sequence (including the modifications thereto) having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7152.

In some embodiments, an inhibitory nucleic acid according to the present disclosure comprises: (i) nucleic acid comprising the nucleotide sequence (including the modifications thereto) of SEQ ID NO: 7148, or a nucleotide sequence (including the modifications thereto) having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7148; and (ii) nucleic acid comprising the nucleotide sequence (including the modifications thereto) of SEQ ID NO: 7153, or a nucleotide sequence (including the modifications thereto) having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7153.

In some embodiments, an inhibitory nucleic acid according to the present disclosure comprises: (i) nucleic acid comprising the nucleotide sequence (including the modifications thereto) of SEQ ID NO: 7149, or a nucleotide sequence (including the modifications thereto) having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7149; and (ii) nucleic acid comprising the nucleotide sequence (including the modifications thereto) of SEQ ID NO: 7154, or a nucleotide sequence (including the modifications thereto) having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7154.

In some embodiments, an inhibitory nucleic acid according to the present disclosure comprises: (i) nucleic acid comprising the nucleotide sequence (including the modifications thereto) of SEQ ID NO: 7150, or a nucleotide sequence (including the modifications thereto) having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7150; and (ii) nucleic acid comprising the nucleotide sequence (including the modifications thereto) of SEQ ID NO: 7155, or a nucleotide sequence (including the modifications thereto) having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to SEQ ID NO: 7155.

In general, the majority of nucleotides of each strand of a dsRNA molecule are ribonucleotides, but as described in detail herein, each or both strands can also include one or more non-ribonucleotides, e.g., a deoxyribonucleotide and/or a modified nucleotide. In addition, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims.

In one embodiment, each residue of the sense strand and antisense strand is independently modified with LNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification.

Inhibitory nucleic acids according to the present disclosure may be produced in accordance with techniques well known to the skilled person.

For example, inhibitory nucleic acids may be produced recombinantly by transcription of a nucleic acid sequence encoding the inhibitory nucleic acid. A nucleic acid encoding an inhibitory nucleic acid according to the present disclosure may e.g. be contained within an expression vector for expression of the inhibitory nucleic acid.

Transcription may be performed in cell-free transcription reactions using recombinant enzymes (e.g. RNA polymerase) for transcription of the inhibitory nucleic acids. Alternatively, production of an inhibitory nucleic acid according to the present disclosure may be performed in a cell comprising nucleic acid encoding the inhibitory nucleic acid, and may employ cellular enzymes (e.g. RNA polymerase) for transcription. Production of an inhibitory nucleic acid according to the present disclosure by expression within a cell may comprise transcription from a vector. Introduction of nucleic acid/vectors for the purposes of production of inhibitory nucleic acids according to the present disclosure may be performed in any of the ways known in the art (e.g. transfection, transduction, electroporation, etc.). Expression of an inhibitory nucleic acid can be regulated using a cell-specific promoter (e.g. a liver cell-specific promoter).

For example, an shRNA molecule according to the present disclosure may be produced within a cell by transcription from a vector encoding the shRNA. shRNAs may be produced within a cell by transfecting the cell with a vector encoding the shRNA sequence under control of an RNA polymerase promoter.

An siRNA molecule according to the present disclosure may be produced within a cell by transcription from a vector encoding shRNA encoding/comprising the siRNA, and subsequent processing of the shRNA molecule by cellular DICER to form the siRNA molecule. An shRNA molecule according to the present disclosure, e.g. a sequence in Table 12 or 13, may be embedded into and expressed using a miR-30-based system, e.g. as described in Fellmann C et al., Cell Rep. 2013; 5(6):1704-13, and Rio D C et al., Cold Spring Harb Protoc; 2013; doi:10.1101/pdb.prot075853, which are hereby incorporated by reference in their entirety.

Inhibitory nucleic acids may also be synthesised using standard solid or solution phase synthesis techniques which are well known in the art. Solid phase synthesis may use phosphoramidite chemistry. Briefly, a solid supported nucleotide may be detrytilated, then coupled with a suitably activated nucleoside phosphoramidite to form a phosphite triester linkage. Capping may then occur, followed by oxidation of the phosphite triester with an oxidant, typically iodine. The cycle may then be repeated to yield a polynucleotide.

The present disclosure provides nucleic acid comprising or encoding an inhibitory nucleic acid according to the present disclosure. In some embodiments, nucleic acid comprising or encoding an inhibitory nucleic acid comprises, or consists of, DNA and/or RNA.

The present disclosure also provides a vector comprising the nucleic acid comprising or encoding an inhibitory nucleic acid according to the present disclosure.

Nucleic acids and vectors according to the present disclosure may be provided in purified or isolated form, i.e. from other nucleic acid, or naturally-occurring biological material.

The nucleotide sequence of a nucleic acid comprising or encoding an inhibitory nucleic acid according to the present disclosure may be contained in a vector, e.g. an expression vector. A 'vector' as used herein is a nucleic acid molecule used as a vehicle to transfer exogenous nucleic acid into a cell. The vector may be a vector for expression of the nucleic acid in the cell. Such vectors may include a promoter sequence operably linked to the nucleotide sequence encoding the sequence to be expressed. A vector may also include a termination codon and expression enhancers. Any suitable vectors, promoters, enhancers and termination codons known in the art may be used to express nucleic acid from a vector according to the present disclosure.

The term 'operably linked' may include the situation where a selected nucleic acid sequence and regulatory nucleic acid sequence (e.g. promoter and/or enhancer) are covalently linked in such a way as to place the expression of nucleic acid sequence under the influence or control of the regulatory sequence (thereby forming an expression cassette). Thus, a regulatory sequence is operably linked to the selected nucleic acid sequence if the regulatory sequence is capable of affecting transcription of the nucleic acid sequence.

Suitable vectors include plasmids, binary vectors, DNA vectors, mRNA vectors, viral vectors (e.g. gammaretroviral vectors (e.g. murine Leukemia virus (MLV)-derived vectors), lentiviral vectors, adenovirus vectors, adeno-associated virus vectors, vaccinia virus vectors and herpesvirus vectors), transposon-based vectors, and artificial chromosomes (e.g. yeast artificial chromosomes).

In some embodiments, the vector may be a eukaryotic vector, e.g. a vector comprising the elements necessary for expression of nucleic acid from the vector in a eukaryotic cell. In some embodiments, the vector may be a mammalian vector, e.g. comprising a cytomegalovirus (CMV) or SV40 promoter to drive expression. In some embodiments, the vector comprises a cell- or tissue-specific promoter. In some embodiments, the vector comprises a liver cell-specific promoter.

The present disclosure also provides a plurality of inhibitory nucleic acids according to the present disclosure. The present disclosure also provides nucleic acids and vectors comprising or encoding a plurality of inhibitory nucleic acids according to the present disclosure.

Individual inhibitory nucleic acids of a plurality of inhibitory nucleic acids according to the present disclosure may be identical or non-identical. Similarly, in embodiments wherein a nucleic acid/vector comprising or encoding an inhibitory nucleic acid according to the present disclosure comprises/encodes more than one inhibitory nucleic acid according to the present disclosure, the inhibitory nucleic acids comprised/encoded by the nucleic acid/vector may be identical or non-identical.

In some embodiments, nucleic acids/vectors may encode one of 1, 2, 3, 4, 5, 6, 7, 8, 9, 10, 11, 12, 13, 14, 15, 16, 17, 18, 19 or 20 inhibitory nucleic acids according to the present disclosure. In some embodiments, nucleic acids/vectors may encode multiple (e.g. 2, 3, 4, 5, 6, 7, 8, 9, 10, etc.) copies of a given inhibitory nucleic acid according to the present disclosure.

In some embodiments, a plurality of inhibitory nucleic acids according to the present disclosure may be a plurality of non-identical inhibitory nucleic acids. In some embodiments, a plurality of inhibitory nucleic acids may comprise one of 1, 2, 3, 4, 5, 6, 7, 8, 9, 10, 11, 12, 13, 14, 15, 16, 17, 18, 19 or 20 non-identical inhibitory nucleic acids. In some embodiments, nucleic acids/vectors may comprise/encode a plurality of non-identical inhibitory nucleic acids according to the present disclosure.

The following two paragraphs further define pluralities of non-identical inhibitory nucleic acids in accordance with embodiments of pluralities of inhibitory nucleic acids according to the present disclosure, and also in accordance with embodiments of nucleic acids/vectors comprising/encoding a plurality of non-identical inhibitory nucleic acids according to the present disclosure.

In some embodiments, the non-identical inhibitory nucleic acids comprise or encode non-identical antisense nucleic acids. In such embodiments, the non-identical antisense nucleic acids may each independently conform to any embodiment of an antisense nucleic acid as described hereinabove.

In some embodiments, the non-identical inhibitory nucleic acids may comprise or encode antisense nucleic acids targeting non-identical target nucleotide sequences. In such embodiments, the non-identical target nucleotide sequences may each independently conform to any embodiment of a target nucleotide sequence for an antisense nucleic acid as described hereinabove.

The present disclosure also provides a cell comprising or expressing (i) an inhibitory nucleic acid according to the present disclosure, (ii) nucleic acid comprising or encoding an inhibitory nucleic acid according to the present disclosure, and/or (iii) a vector comprising nucleic acid comprising or encoding an inhibitory nucleic acid according to the present disclosure.

The cell may be a eukaryotic cell, e.g. a mammalian cell. The mammal may be a primate (rhesus, cynomolgous, non-human primate or human) or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate). In preferred embodiments, the cell may be a human cell. In some embodiments, the cell may be a liver cell.

The present disclosure also provides a method for producing a cell comprising a nucleic acid or vector according to the present disclosure, comprising introducing a nucleic acid or vector according to the present disclosure into a cell. In some embodiments, introducing a nucleic acid or vector according to the present disclosure into a cell comprises transformation, transfection, electroporation or transduction (e.g. retroviral transduction).

The present disclosure also provides a method for producing an inhibitory nucleic acid according to the present disclosure or a nucleic acid comprising or encoding an inhibitory nucleic acid according to the present disclosure, comprising culturing a cell comprising nucleic acid comprising or encoding an inhibitory nucleic acid according to the present disclosure or a vector according to the present disclosure under conditions suitable for expression of the nucleic acid or vector by the cell. In some embodiments, the methods are performed in vitro.

The present disclosure also provides compositions comprising nucleic acids (including inhibitory nucleic acids, nucleic acids comprising/encoding an inhibitory nucleic acid, expression vectors comprising/encoding such nucleic acids) or cells according to the present disclosure.

In therapeutic and prophylactic applications, the inhibitors and compositions of the present disclosure are preferably formulated as a medicament or pharmaceutical composition (suitable for clinical use). Such compositions may comprise the inhibitor or cell together with one or more other pharmaceutically-acceptable ingredients well known to those skilled in the art. Such ingredients include, but are not limited to, pharmaceutically-acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents.

Provided herein is a pharmaceutical composition comprising an inhibitor as defined herein and a pharmaceutically acceptable carrier.

Compositions according to the present disclosure may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The compositions may be prepared for topical, parenteral, systemic, intracavitary, intravenous, intra-arterial, intramuscular, intrathecal, intraocular, intravitreal, intraconjunctival, subretinal, suprachoroidal, subcutaneous, intradermal, intrathecal, oral, nasal or transdermal routes of administration which may include injection or infusion. Suitable formulations may comprise the selected agent in a sterile or isotonic medium. The formulation and mode of administration may be selected according to the agent to be administered, and disease to be treated/prevented.

The pharmaceutical compositions of the present invention may be administered in a number of ways depending upon whether local or systemic treatment is desired and upon the area to be treated. Administration may be topical (including intranasal or intrapulmonary), oral or parenteral. Parenteral administration includes intravenous, subcutaneous, intraperitoneal or intramuscular injection.

The compositions of the present disclosure may be formulated in fluid, including gel, form. Fluid formulations may be formulated for administration by injection or infusion (e.g. via catheter) to a selected organ or region of the human or animal body. A further aspect of the present disclosure relates to a method of formulating or producing a medicament or pharmaceutical composition according to the present disclosure, the method comprising formulating a pharmaceutical composition or medicament by mixing an agent with a pharmaceutically acceptable carrier, adjuvant, excipient or diluent.

Delivery of Inhibitors

Inhibitors (including e.g. small molecules, antibodies and nucleic acids (including inhibitory nucleic acids, expression vectors)), cells and compositions according to the present disclosure may be modified and/or be formulated to facilitate delivery to, and/or uptake by, a cell/tissue of interest, e.g. a liver cell (hepatocyte) or hepatic tissue.

Strategies for targeted delivery of such species are reviewed e.g. in Li et al., Int. J. Mol. Sci. (2015) 16: 19518-19536 and Fu et al., Bioconjug Chem. (2014) 25(9): 1602-1608, which are hereby incorporated by reference in their entirety. In particular, nucleic acids according to the present disclosure may employ a delivery platform described in Hu et al., Sig. Transduc. Tar. Ther. (2020) 5(101) (incorporated by reference hereinabove), or Tatiparti et al. 'siRNA Delivery Strategies: A Comprehensive Review of Recent Developments.' Ed. Thomas Nann. Nanomaterials 7.4 (2017): 77, and Lehto T et al., Adv Drug Deliv Rev. 2016, 106(Pt A):172-182, which are hereby incorporated by reference in their entirety.

In some embodiments, articles of the present disclosure may be encapsulated in a nanoparticle or a liposome. In some embodiments, articles of the present disclosure may be (covalently or non-covalently) associated with a cell-penetrating peptide (e.g. a protein transduction domain, trojan peptide, arginine-rich peptide, vectocell peptide), a cationic polymer, a cationic lipid or a viral carrier.

Nanoparticles may be organic, e.g. micelles, liposomes, proteins, solid-lipid particles, solid polymer particles, dendrimers, and polymer therapeutics. Nanoparticles may be inorganic, e.g. such as nanotubes or metal particles, optionally with organic molecules added. In some embodiments, a nanoparticle is a nanoparticle described in Chen et al., Mol Ther Methods Clin Dev. (2016) 3:16023, which is hereby incorporated by reference in its entirety. In some embodiments, a nanoparticle is a PLGA, polypeptide, poly(β-amino ester), DOPE, β-cyclodextrin-containing polycation, linear PEI, PAMAM dendrimer, branched PEI, chitosan or polyphosphoester nanoparticle.

The delivery of a nucleic acid inhibitor, e.g. an RNAi agent, to a cell e.g., a cell within a subject, such as a human subject can be achieved in a number of different ways. For example, delivery may be performed by contacting a cell with a nucleic acid of the invention either in vitro or in vivo. In vivo delivery may also be performed directly by administering a composition comprising a nucleic acid inhibitor, e.g., a siRNA, shRNA, dsRNA, to a subject. Alternatively, in vivo delivery may be performed indirectly by administering one or more vectors (e.g. one or more DNA vectors) that encode and direct the expression of the nucleic acid inhibitor. In one embodiment, the nucleic acid inhibitor is delivered using a viral-based or transposon-based nucleic acid construct. In one embodiment, the nucleic acid inhibitor is encapsulated in a liposome.

In some embodiments, an inhibitor according to the present disclosure (e.g. a small molecule, a peptide, an antibody, an inhibitory nucleic acid, a nucleic acid comprising/encoding an inhibitory nucleic acid, or an expression vector) comprises modification to incorporate one or more moieties facilitating delivery to, and/or uptake by, a cell type or tissue of interest. In some embodiments, an inhibitor according to the present disclosure is linked (e.g. chemically conjugated to) one or more moieties facilitating delivery to, and/or uptake by, a cell type or tissue of interest.

Modification to, and formulation of, inhibitors to facilitate targeted delivery to cell types and/or tissues of interest is described e.g. in Lorenzer et al., J Control Release (2015) 203:1-15, which is hereby incorporated by reference in its entirety. The moiety facilitating delivery to, and/or uptake by, a cell type or tissue of interest may bind selectively to the target cell type/tissue of interest. The moiety may facilitate traversal of the cell membrane of the target cell type and/or of cells of the tissue of interest. The moiety may bind to a molecule expressed at the cell surface of the target cell type/tissue of interest. The moiety may facilitate internalisation of the nucleic acid by the target cell type/tissue of interest (e.g. by endocytosis).

Moieties facilitating delivery to, and/or uptake by, cell types or tissues of interest are described e.g. in Benizri et al., Bioconjug Chem. (2019) 30(2): 366-383, which is hereby incorporated by reference in its entirety. Such moieties include e.g. N-acetylgalactosamine (GalNAc), α-tocopherol, cell-penetrating peptide, nucleic acid aptamer, antibody and antigen-binding fragments/derivatives thereof, cholesterol, squalene, polyethylene glycol (PEG), fatty acid (e.g. palmitic acid) and nucleolipid moieties.

In some embodiments, the moiety may e.g. be a peptide/polypeptide (e.g. an antibody, fragment or derivative thereof, peptide aptamer or cell-penetrating peptide) or nucleic acid (e.g. a nucleic acid aptamer) which binds to the target cell type/tissue of interest, e.g. via interaction with a molecule expressed at the cell surface of the target cell type/tissue of interest.

In some embodiments, a nucleic acid according to the present disclosure comprises a moiety facilitating delivery to, and/or uptake by, a liver cell (e.g. a hepatocyte) and/or hepatic tissue. In such embodiments, the moiety may facilitate traversal of the hepatocyte cell membrane. The moiety may bind to a molecule expressed at the cell surface of hepatocytes. In some embodiments, a molecule expressed at the cell surface of hepatocytes is an asialoglycoprotein receptor, e.g. ASGR1 or ASGR2. The moiety may facilitate internalisation of a nucleic acid by hepatocytes (e.g. by endocytosis).

In some embodiments, the moiety may e.g. be a peptide/polypeptide (e.g. an antibody, fragment or derivative thereof, peptide aptamer or cell-penetrating peptide) or nucleic acid (e.g. a nucleic acid aptamer) which binds to a hepatocyte and/or hepatic tissue, e.g. via interaction with a molecule expressed at the cell surface of a hepatocyte (e.g. an asialoglycoprotein receptor, e.g. ASGR1 or ASGR2).

In some embodiments, the moiety is, or comprises, GalNAc. In some embodiments, an inhibitor, e.g. a nucleic acid, is conjugated to GalNAc. GalNAc interacts with asialoglycoprotein receptors expressed by hepatocytes. Nucleic acids conjugated to GalNAc are efficiently internalised by hepatic cells via receptor-mediated endocytosis following binding of GalNAc to ASGPR (see e.g. Nair et al., J. Am. Chem. Soc. (2014) 136(49): 16958-16961). In some embodiments, an inhibitor, e.g. a nucleic acid, is conjugated to one or more (e.g. 1, 2, 3, 4 or more) GalNAc moieties. In some embodiments, one or more GalNAc moieties may be covalently associated to the 5' or 3' end of one or more strands of a nucleic acid. In some embodiments, a nucleic acid is conjugated to a triantennary GalNAc carbohydrate moiety (such moieties are described e.g. in Nair et al., supra).

In some embodiments, an inhibitory nucleic acid according to the present disclosure comprises: (i) nucleic acid comprising the nucleotide sequence of one of SEQ ID NOs: 1 to 7155, or a nucleotide sequence having at least 75% sequence identity (e.g. one of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity) to one of SEQ ID NOs: 1 to 7155; and (ii) a triantennary GalNAc carbohydrate moiety.

In some embodiments, the moiety is, or comprises, α-tocopherol (i.e. vitamin E). In some embodiments, a nucleic acid is conjugated to α-tocopherol. Nucleic acid-α-tocopherol conjugates have been employed for targeted delivery of nucleic acids to the liver (see e.g. Nishina et al., Mol Ther. (2008) 16(4):734-740). In some embodiments, a nucleic acid is conjugated to one or more (e.g. 1, 2, 3, 4 or more) α-tocopherol moieties. In some embodiments, one or more α-tocopherol moieties may be covalently associated to the 5' or 3' end of one or more strands of a nucleic acid.

Conjugates of biomolecules may be produced utilising 'click chemistry', as described e.g. in Nwe and Brechbiel Cancer Biother Radiopharm. (2009) 24(3):289-302 and Astakhova et al., Mol Pharm. (2018) 15(8): 2892-2899, both of which are hereby incorporated by reference in their entirety. In some embodiments, conjugation may employ akyne-azide or thio-maleimide approaches. In some embodiments, an inhibitor, e.g. nucleic acid, may be conjugated to a moiety facilitating delivery to, and/or uptake by, a cell type or tissue of interest, e.g. at the 3' and/or 5' end of one or more strands of the nucleic acid.

Inhibitors may be conjugated to one or more moieties facilitating delivery to, and/or uptake by, cell types or tissues of interest via a linker. In some embodiments, a linker may be or comprise a nucleotide sequence. The nucleotide sequence of a linker may comprise one or more modified nucleotides as described herein.

Treatment/Prevention of Disease

The inhibitors, nucleic acids, expression vectors, cells and compositions described herein find use in therapeutic and prophylactic methods.

The present invention provides methods and articles (agents and compositions) for the treatment and/or prevention of diseases through inhibition of MFAP4, GRHPR, ITFG1, ABCC4, PAK3, TRNP1, APLN, KIF20A, and/or LTB. Treatment/prevention of disease is achieved by inhibition of MFAP4, GRHPR, ITFG1, ABCC4, PAK3, TRNP1, APLN, KIF20A, and/or LTB in e.g. a cell, tissue/organ/organ system/subject.

The invention is concerned with the treatment and/or prevention of diseases which are caused and/or exacerbated by an increase in the expression/activity of one or more of MFAP4, GRHPR, ITFG1, ABCC4, PAK3, TRNP1, APLN, KIF20A, and/or LTB (and/or associated downstream factors), or diseases which are caused and/or exacerbated by a decrease in the expression/activity of one or more associated downstream factors that are downregulated by one or more of MFAP4, GRHPR, ITFG1, ABCC4, PAK3, TRNP1, APLN, KIF20A, and/or LTB.

Inhibition of one or more of MFAP4, GRHPR, ITFG1, ABCC4, PAK3, TRNP1, APLN, KIF20A, and/or LTB (genes, mRNA and/or proteins) in any of the methods described herein may be achieved using any suitable inhibitor. In some embodiments, the inhibitor is a nucleic acid, peptide, antibody, antigen-binding molecule or small molecule inhibitor, e.g. as described herein. Multiple inhibitors may be used to target any two or more of the genes/proteins.

In any method provided herein, the inhibitor may be a nucleic acid as described herein, e.g. an inhibitory nucleic acid.

The utility of the present invention extends to the treatment/prevention of any disease that would derive therapeutic/prophylactic benefit from a reduction in the level of one or more of MFAP4, GRHPR, ITFG1, ABCC4, PAK3, TRNP1, APLN, KIF20A, and/or LTB expression and/or activity.

In some embodiments, a disease to be treated/prevented may be characterised by an increase in the expression/activity of one or more of MFAP4, GRHPR, ITFG1, ABCC4, PAK3, TRNP1, APLN, KIF20A, and/or LTB (or a correlate thereof) in an organ/tissue/subject affected by the disease e.g. as compared to normal organ/tissue/subject (i.e. in the absence of the disease).

Treatment/prevention may be of a disease that is associated with an upregulation in the expression/activity of one or more of MFAP4, GRHPR, ITFG1, ABCC4, PAK3, TRNP1, APLN, KIF20A, and/or LTB (or a correlate thereof) in cells/tissue/an organ in which the symptoms of the disease manifest.

The experimental examples demonstrate that expression of MFAP4, GRHPR, ITFG1, ABCC4, PAK3, TRNP1, APLN, KIF20A, and LTB is upregulated in fibroinflammatory disorders, such as liver disease, inflammatory liver disorders, steatosis, non-alcoholic fatty liver disease (NAFLD), non-alcoholic steatohepatitis (NASH), fibrosis, cirrhosis, and hepatocellular carcinoma (HCC).

Thus, the present disclosure establishes inhibition of MFAP4, GRHPR, ITFG1, ABCC4, PAK3, TRNP1, APLN, KIF20A, or LTB as being useful for the treatment/prevention of diseases that are characterised by, e.g., NAFLD, NASH, fibrosis, and/or inflammation, e.g. of the liver or other tissues.

Aspects of the present invention are concerned with the treatment/prevention of a liver disease or condition.

Thus, in one aspect the present invention provides a method of treating or preventing a liver disease or condition, comprising inhibiting at least one of MFAP4, GRHPR, ITFG1, ABCC4, PAK3, TRNP1, APLN, KIF20A, and/or LTB. As described hereinabove, inhibition/inhibiting may refer to inhibition of the expression and/or activity of MFAP4, GRHPR, ITFG1, ABCC4, PAK3, TRNP1, APLN, KIF20A, and/or LTB and the downstream functional consequences thereof, and encompasses decreased/reduced gene and/or protein expression or decreased/reduced activity of any one of said genes/proteins.

Also provided is a method of treating or preventing a liver disease or condition, comprising administering a therapeutically or prophylactically effective amount of an inhibitor of at least one of MFAP4, GRHPR, ITFG1, ABCC4, PAK3, TRNP1, APLN, KIF20A, and/or LTB to a subject. The method may comprise administering two or more (i.e. 2, 3, 4, 5, 6, 7, 8 or 9) inhibitors that target two or more (i.e. 2, 3, 4, 5, 6, 7, 8 or 9) of MFAP4, GRHPR, ITFG1, ABCC4, PAK3, TRNP1, APLN, KIF20A, and/or LTB.

Also provided is an inhibitor of at least one of MFAP4, GRHPR, ITFG1, ABCC4, PAK3, TRNP1, APLN, KIF20A, and/or LTB for use in a method of treating or preventing a liver disease or condition.

Also provided is the use of an inhibitor of at least one of MFAP4, GRHPR, ITFG1, ABCC4, PAK3, TRNP1, APLN, KIF20A, and/or LTB in the manufacture of a medicament for use in a method of treating or preventing a liver disease or condition.

The inhibitor may be any suitable inhibitor of at least one of MFAP4, GRHPR, ITFG1, ABCC4, PAK3, TRNP1, APLN, KIF20A, and/or LTB, such as any agent described herein, e.g. nucleic acid, peptide, antibody, antigen-binding molecule or small molecule inhibitor. In some embodiments the inhibitor is an inhibitory nucleic acid, such as those described herein.

In some embodiments, the liver disease or condition to be treated/prevented is selected from the group consisting of: acute liver disease, chronic liver disease, metabolic liver disease, steatosis, liver fibrosis, primary sclerosing cholangitis (PSC), cirrhosis, mild liver fibrosis, advanced liver fibrosis, non-alcoholic fatty liver disease (NAFLD), non-alcoholic steatohepatitis (NASH), alcoholic fatty liver disease (ALFD), alcohol-related liver disease (ARLD), hepatic ischemia reperfusion injury, primary biliary cirrhosis (PBC), hepatitis, liver damage, liver injury, liver failure, metabolic syndrome, obesity, diabetes mellitus, end-stage liver disease, inflammation of the liver, lobular inflammation, and/or hepatocellular carcinoma (HCC).

In some embodiments, the liver fibrosis is a virus-induced liver fibrosis. In some embodiments, the hepatitis is an alcohol-induced hepatitis. In some embodiments, the liver damage is a drug or virus-induced liver damage.

The experimental examples of the present disclosure identify MFAP4, GRHPR, ITFG1, ABCC4, PAK3, TRNP1, APLN, KIF20A, and LTB as regulators of fibroinflammatory processes, which are moreover conserved between different tissue types.

Aspects of the present invention are concerned with the treatment/prevention of diseases in which profibrotic processes are pathologically implicated. Accordingly, in some embodiments the disease is fibrosis, or a disease characterised by fibrosis.

As used herein, "fibrosis" refers to the formation of excess fibrous connective tissue as a result of the excess deposition of extracellular matrix components, for example collagen. Fibrous connective tissue is characterised by having extracellular matrix (ECM) with a high collagen content. The collagen may be provided in strands or fibers, which may be arranged irregularly or aligned. The ECM of fibrous connective tissue may also include glycosaminoglycans.

As used herein, "excess fibrous connective tissue" refers to an amount of connective tissue at a given location (e.g. a given tissue or organ, or part of a given tissue or organ) which is greater than the amount of connective tissue present at that location in the absence of fibrosis, e.g. under normal, non-pathological conditions. As used herein, "excess deposition of ECM components" refers to a level of deposition of one or more ECM components which is greater than the level of deposition in the absence of fibrosis, e.g. under normal, non-pathological conditions.

The cellular and molecular mechanisms of fibrosis are described in Wynn, J. Pathol. (2008) 214(2): 199-210, and Wynn and Ramalingam, Nature Medicine (2012) 18:1028-1040, which are hereby incorporated by reference in their entirety.

Damage to tissues can result from various stimuli, including infections, autoimmune reactions, toxins, radiation and mechanical injury. Repair typically involves replacement of injured cells by cells of the same type, and replacement of normal parenchymal tissue with connective tissue. Repair processes become pathogenic when they are not controlled properly, resulting in substantial deposition of ECM components in which normal tissue is replaced with permanent scar tissue. In diseases such as idiopathic pulmonary fibrosis, liver cirrhosis, cardiovascular fibrosis, systemic sclerosis and nephritis, extensive tissue remodelling and fibrosis can ultimately lead to organ failure and death.

The main cellular effectors of fibrosis are myofibroblasts, which produce a collagen-rich ECM. In response to tissue injury, damaged cells and leukocytes produce pro-fibrotic factors such as TGFβ, IL-13 and PDGF, which activate fibroblasts to αSMA-expressing myofibroblasts, and recruit myofibroblasts to the site of injury. Myofibroblasts produce a large amount of ECM, and are important mediators in aiding contracture and closure of the wound. However, under conditions of persistent infection or during chronic inflammation there can be overactivation and recruitment of myofibroblasts, and thus over-production of ECM components, resulting in the formation of excess fibrous connective tissue.

Inflammatory reactions play an important part in triggering fibrosis in many different organ systems. Inflammation can lead to excess in deposition of ECM components in the affected tissues. Low-grade but persistent inflammation is also thought to contribute to the progression of fibrosis in cardiovascular disease and hypertension. In many fibrotic disorders, a persistent inflammatory trigger is crucial to upregulation of production of growth factors, proteolytic enzymes, angiogenic factors and fibrogenic cytokines, which stimulate the deposition of connective tissue elements that progressively remodel and destroy normal tissue architecture.

In some embodiments fibrosis may be triggered by pathological conditions, e.g. conditions, infections or disease states that lead to production of pro-fibrotic factors such as TGFβ1. In some embodiments, fibrosis may be caused by physical injury/stimuli, chemical injury/stimuli or environmental injury/stimuli. Physical injury/stimuli may occur during surgery, e.g. iatrogenic causes. Chemical injury/stimuli may include drug induced fibrosis, e.g. following chronic administration of drugs such as bleomycin, cyclophosphamide, amiodarone, procainamide, penicillamine, gold and nitrofurantoin (Daba et al., Saudi Med J 2004 June, 25(6): 700-6). Environmental injury/stimuli may include exposure to asbestos fibres or silica.

Fibrosis can be of any tissue/organ of the body. In some embodiments, fibrosis is of the heart, kidney, liver, lung, skeletal muscle, blood vessels, eye, skin, pancreas, bowel, small intestine, large intestine, colon, brain, or bone marrow. In some embodiments, the fibrosis is of the liver. In some embodiments, the fibrosis is of the heart, lung or kidney. Fibrosis may also occur in multiple tissues/organs at once.

Thus, the present invention provides methods and articles (agents and compositions) for the treatment and/or prevention of diseases characterised by fibrosis through inhibition of MFAP4, GRHPR, ITFG1, ABCC4, PAK3, TRNP1, APLN, KIF20A, and/or LTB.

Thus, in one aspect the present invention provides a method of treating or preventing a disease characterised by fibrosis, comprising inhibiting at least one of MFAP4, GRHPR, ITFG1, ABCC4, PAK3, TRNP1, APLN, KIF20A, and/or LTB.

Also provided is a method of treating or preventing a disease characterised by fibrosis, comprising administering a therapeutically or prophylactically effective amount of an inhibitor of at least one of MFAP4, GRHPR, ITFG1, ABCC4, PAK3, TRNP1, APLN, KIF20A, and/or LTB to a subject. The method may comprise administering two or more (i.e. 2, 3, 4, 5, 6, 7, 8 or 9) inhibitors that target two or more (i.e. 2, 3, 4, 5, 6, 7, 8 or 9) of MFAP4, GRHPR, ITFG1, ABCC4, PAK3, TRNP1, APLN, KIF20A, and/or LTB.

Also provided is an inhibitor of at least one of MFAP4, GRHPR, ITFG1, ABCC4, PAK3, TRNP1, APLN, KIF20A, and/or LTB for use in a method of treating or preventing a disease characterised by fibrosis.

Also provided is the use of an inhibitor of at least one of MFAP4, GRHPR, ITFG1, ABCC4, PAK3, TRNP1, APLN, KIF20A, and/or LTB in the manufacture of a medicament for use in a method of treating or preventing a disease characterised by fibrosis.

A "disease characterised by fibrosis" refers to a disease in which fibrosis and/or profibrotic processes are pathologically implicated. A "disease characterised by fibrosis" may be fibrosis, e.g. of any cell, tissue or organ.

Diseases characterised by fibrosis include but are not limited to: respiratory conditions such as pulmonary fibrosis, cystic fibrosis, idiopathic pulmonary fibrosis, progressive massive fibrosis, scleroderma, obliterative bronchiolitis, Hermansky-Pudlak syndrome, asbestosis, silicosis, chronic pulmonary hypertension, AIDS associated pulmonary hypertension, sarcoidosis, tumor stroma in lung disease, and asthma; chronic liver disease, cirrhosis, non-alcoholic fatty liver disease (NAFLD), non-alcoholic steatohepatitis (NASH), primary biliary cirrhosis (PBC), schistosomal liver disease, cardiovascular conditions such as hypertrophic cardiomyopathy (HCM), dilated cardiomyopathy (DCM), fibrosis of the atrium, atrial fibrillation, fibrosis of the ventricle, ventricular fibrillation, myocardial fibrosis, Brugada syndrome, myocarditis, endomyocardial fibrosis, myocardial infarction, fibrotic vascular disease, hypertensive heart disease, arrhythmogenic right ventricular cardiomyopathy (ARVC), tubulointerstitial and glomerular fibrosis, atherosclerosis, varicose veins, cerebral infarcts; neurological conditions such as gliosis and Alzheimer's disease; muscular dystrophy such as Duchenne muscular dystrophy (DMD) or Becker's muscular dystrophy (BMD); gastrointestinal conditions such as Crohn's disease, microscopic colitis and primary sclerosing cholangitis (PSC); skin conditions such as scleroderma, nephrogenic systemic fibrosis and cutis keloid; arthrofibrosis; Dupuytren's contracture; mediastinal fibrosis; retroperitoneal fibrosis; myelofibrosis; Peyronie's disease; adhesive capsulitis; kidney disease (e.g., renal fibrosis, nephritic syndrome, Alport's syndrome, HIV associated nephropathy, polycystic kidney disease, Fabry's disease, diabetic nephropathy, chronic glomerulonephritis, nephritis associated with systemic lupus); progressive systemic sclerosis (PSS); chronic graft versus host disease; diseases of the eye such as Grave's opthalmopathy, epiretinal fibrosis, retinal fibrosis, subretinal fibrosis (e.g. associated with macular degeneration (e.g. wet age-related macular degeneration (AMD)), diabetic retinopathy, glaucoma, corneal fibrosis, post-surgical fibrosis (e.g. of the posterior capsule following cataract surgery, or of the bleb following trabeculectomy for glaucoma), conjunctival fibrosis, subconjunctival fibrosis; arthritis; fibrotic pre-neoplastic and fibrotic neoplastic disease; and fibrosis induced by chemical or environmental insult (e.g., cancer chemotherapy, pesticides, radiation/cancer radiotherapy).

It will be appreciated that many of the diseases/conditions recited in the preceding paragraph are interrelated. For example, fibrosis of the ventricle may occur post myocardial infarction, and is associated with DCM, HCM and myocarditis.

Fibrosis can lead directly or indirectly to, and/or increase susceptibility to development of, diseases. For example, more than 80% of hepatocellular carcinomas (HCCs) develop in fibrotic or cirrhotic livers (Affo et al. 2016, Annu Rev Pathol.), suggesting an important role for liver fibrosis in the premalignant environment (PME) of the liver.

Accordingly, the present invention also finds use in methods for the treatment and prevention of diseases associated with fibrosis, and/or for which fibrosis is a risk factor. In some embodiments, the disease associated with fibrosis, or for which fibrosis is a risk factor, is a cancer, e.g. cancer of the liver (e.g. hepatocellular carcinoma).

In some embodiments, the fibrosis to be treated/prevented according to the present invention may be of fibrosis that is associated with an upregulation of MFAP4, GRHPR, ITFG1, ABCC4, PAK3, TRNP1, APLN, KIF20A, and/or LTB expression and/or activity, e.g. in cells/tissue/an organ in which the fibrosis occurs or may occur.

The therapy may be effective to inhibit development (delay/prevent) of the fibrosis, or of progression (e.g. worsening) of the fibrosis. In some embodiments therapy may lead to an improvement in the disease, e.g. a reduction in the symptoms of fibrosis. Prevention of fibrosis may refer to prevention of a worsening of the condition or prevention of the development of fibrosis, e.g. preventing an early stage fibrosis (e.g. inflammation, steatosis, NAFLD) developing to a later stage (e.g. fibrosis, cirrhosis, HCC).

Aspects of the present invention are concerned with the treatment/prevention of diseases in which proinflammatory processes are pathologically implicated. Inflammation is reviewed e.g. in Chen et al., Oncotarget. (2018) 9(6): 7204-7218, which is hereby incorporated by reference in its entirety. Inflammation refers to the bodily response to cellular/tissue injury, and is characterised by edema, erythema (redness), heat, pain, and loss of function (stiffness and immobility) resulting from local immune, vascular and inflammatory cell responses to infection or injury. The injury may result from e.g. of physical (e.g. mechanical) or chemical insult, trauma, infection, cancer or overactive/aberrant immune responses (e.g. autoimmune disease). Inflammation forms part of the innate immune response, and plays an important physiological role in wound healing and the control of infection, and contributes to the restoration of tissue homeostasis.

However, many diseases are associated with an overactive inflammatory response (i.e. excessive inflammation and/or aberrantly activated inflammation), and/or chronic (prolonged) inflammation. Herein, excessive and/or chronic inflammation may be referred to as "pathological inflammation". Pathological inflammation may refer to inflammation which is implicated in (i.e. which positively contributes to) the pathology of a disease.

In some embodiments, the disease to be treated/prevented in accordance with the present invention is a disease characterised by chronic inflammation. In some embodiments, the disease to be treated/prevented is a disease characterised by an overactive inflammatory response.

In some embodiments, the treatment/prevention of chronic inflammation or an overactive inflammatory immune response associated with a chronic infection, cancer, autoimmune disease, degenerative disease or allergic disease is contemplated.

Pathological inflammation which is "associated with" a given disease (e.g. a chronic infection, a cancer, an autoimmune disease, a degenerative disease or an allergic disease) may refer to pathological inflammation caused by, initiated by and/or which is a consequence of the disease. Pathological inflammation associated with a given disease may be concurrent with the disease.

Chronic inflammation generally refers to inflammation lasting for prolonged periods of time, e.g. from months to years. Chronic inflammation can result e.g. from failure to properly control/eliminate an infectious agent causing inflammation (i.e. chronic infection), prolonged/repeated exposure to physical/chemical insult, prolonged/repeated exposure to an allergen (allergy), and autoimmune disease.

The chronic inflammation, overactive inflammatory immune response, chronic infection, cancer, autoimmune disease, degenerative disease or allergic disease may affect any tissue/organ of the body, e.g. the heart, kidney, liver, lung, skeletal muscle, blood vessels, eye, skin, pancreas, bowel, small intestine, large intestine, colon, brain, or bone marrow, or multiple tissues/organs at once.

An overactive inflammatory immune response generally refers to an inflammatory immune response that is excessive, and/or which has been activated inappropriately (i.e. an inflammatory immune response which is aberrant). An excessive inflammatory immune response refers to an inflammatory immune response which is greater than the response required for restoration of tissue homeostasis following injury to tissue (e.g. as a result of physical or chemical insult or infection). Aberrant inflammatory immune responses include inflammatory immune responses resulting from autoimmunity and allergy.

Chronic infections include persistent/unresolved infection by any infectious agent, e.g. chronic viral, bacterial, fungal and protozoal infections. Chronic viral infections may be caused e.g. by infection with human immunodeficiency viruses (HIVs), hepatitis B virus (HBV), hepatitis C virus (HCV), Epstein-Barr Virus (EBV), measles virus (MV), cytomegalovirus (CMV), human T-cell leukemia viruses (HTLVs), human herpesviruses (HHVs), herpes simplex viruses (HSVs), Varicella-Zoster virus (VZV), human papovaviruses (e.g. JC virus, BK virus), adenoviruses (AdVs), paroviruses or human papillomaviruses (HPVs). Chronic bacterial infections may be caused e.g. by infection with *Mycobacterium tuberculosis Helicobacter pylori*, *Salmonella Typhi, Treponema pallidum, Pseudomonas aeruginosa, Escherichia coli, Staphylococcus aureus*, Hemophilus *influenza* or *Mycobacterium leprae*. Chronic fungal infections may be caused e.g. by infection with *Candida* spp or *Aspergillus*. Chronic protozoal infections may be caused e.g. by infection with *Plasmodium* spp., *Babesia* spp., Giardia spp., *Leishmania* spp., *Trypanosoma* spp. or *Toxoplasma* spp.

A cancer may be any cancer. As used herein, cancers include any unwanted cell proliferation (or any disease manifesting itself by unwanted cell proliferation), neoplasm or tumor. The cancer may be benign or malignant and may be primary or secondary (metastatic). A neoplasm or tumor may be any abnormal growth or proliferation of cells and may be located in any tissue. The cancer may be of tissues/cells derived from e.g. the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, and/or white blood cells.

An autoimmune disease may be selected from: diabetes mellitus type 1, diabetes mellitus type 2, coeliac disease, Graves' disease, inflammatory bowel disease (e.g. Crohn's disease), multiple sclerosis, psoriasis, rheumatoid arthritis, and systemic lupus erythematosus.

Degenerative diseases are characterised by deterioration of cell/tissue/organ condition or function over time. Proinflammatory and profibrotic processes are implicated in the pathology of many degenerative diseases.

Degenerative disease include e.g. Alzheimer's disease, amyotrophic lateral sclerosis, cancers, Charcot-Marie-Tooth disease, chronic traumatic encephalopathy, cystic fibrosis, degenerative Leigh syndrome, Ehlers-Danlos syndrome, fibrodysplasia ossificans progressiva, Friedreich's ataxia, frontotemporal dementia, cardiovascular diseases (e.g. atherosclerotic cardiovascular disease (e.g. coronary artery disease, aortic stenosis), myocardial infarction, pulmonary arterial hypertension), Huntington's disease, infantile neuroaxonal dystrophy, keratoconus, keratoglobus, leukodystrophies, macular degeneration, Marfan's syndrome, mitochondrial myopathies, mitochondrial DNA depletion syndrome, multiple sclerosis, multiple system atrophy, muscular dystrophies, neuronal ceroid lipofuscinosis, Niemann-Pick disease, osteoarthritis, osteoporosis, Parkinson's disease, pulmonary arterial hypertension, all prion diseases (Creutzfeldt-Jakob disease, fatal familial insomnia etc.), progressive supranuclear palsy, retinitis pigmentosa, rheumatoid arthritis, Sandhoff Disease, spinal muscular atrophy, subacute sclerosing panencephalitis, Tay-Sachs disease and vascular dementia.

An allergic disease may be selected from allergic asthma, allergic rhinitis, food allergy and atopic dermatitis.

In some embodiments the chronic inflammation, overactive inflammatory immune response, chronic infection, cancer, autoimmune disease or allergic disease may be of: an organ of the cardiovascular system, e.g. of the heart or blood vessels; an organ of the gastrointestinal system, e.g. of the liver, bowel, small intestine, large intestine, colon, or pancreas; an organ of the respiratory system, e.g. the lung; the skin; an organ of the nervous system, e.g. the brain; an organ of the urinary system, e.g. the kidneys; or an organ of the musculoskeletal system, e.g. muscle tissue.

Pathological inflammation often leads to fibrosis—see e.g. Mack, Matrix Biol. (2018) 68-69:106-121 and Suthahar et al., Curr Heart Fail Rep. (2017) 14(4): 235-250, both of which are hereby incorporated by reference in their entirety.

The present invention also finds use in methods for the treatment and prevention of diseases associated with pathological inflammation, and/or for which pathological inflammation is a risk factor. In some embodiments, the disease associated with pathological inflammation, or for which pathological inflammation is a risk factor, is fibrosis or a disease characterised by fibrosis.

In some embodiments, the pathological inflammation to be treated/prevented according to the present invention may be of pathological inflammation that is associated with an upregulation of expression and/or activity of one or more of MFAP4, GRHPR, ITFG1, ABCC4, PAK3, TRNP1, APLN, KIF20A, and/or LTB, e.g. in cells/tissue/an organ in which the pathological inflammation occurs or may occur.

The therapy may be effective to inhibit development (delay/prevent) of the pathological inflammation, or of progression (e.g. worsening) of the pathological inflammation. In some embodiments therapy may lead to an improvement in the disease, e.g. a reduction in the symptoms of pathological inflammation. Prevention of pathological inflammation may refer to prevention of a worsening of the condition or prevention of the development of pathological inflammation, e.g. preventing an early stage pathological inflammation developing to a later stage.

Therapeutic/prophylactic intervention in accordance with the present invention may be employed in the context of additional treatment for the relevant disease. That is, expression/activity of one or more of MFAP4, GRHPR, ITFG1, ABCC4, PAK3, TRNP1, APLN, KIF20A, and/or LTB may be inhibited in a subject (e.g. by treatment with a suitable inhibitor such as those described herein) that is also receiving/has received/will receive further therapeutic/prophylactic intervention for the treatment/prevention of the disease.

The experimental examples show that proliferation, expansion and regeneration of liver and lung cells/tissue can be achieved via inhibition of one or more of MFAP4, GRHPR, ITFG1, ABCC4, PAK3, TRNP1, APLN, KIF20A, and/or LTB.

In accordance with various aspects of the present invention, a method of treating and/or preventing a disease according to the present invention may comprise one or more of the following:

Reducing the level of gene/protein expression of one or more of MFAP4, GRHPR, ITFG1, ABCC4, PAK3, TRNP1, APLN, KIF20A, and/or LTB;

Reducing the level of activity of one or more of MFAP4, GRHPR, ITFG1, ABCC4, PAK3, TRNP1, APLN, KIF20A, and/or LTB;

Reducing the level of a correlate of fibrosis (e.g. a collagen, αSMA, periostin, fibronectin, CTGF, vimentin or lumican);

Reducing gene/protein expression of a pro-fibrotic factor (e.g. a collagen, αSMA, periostin, fibronectin, CTGF, vimentin or lumican);

Reducing the number/proportion of myofibroblasts;

Reducing the level of a correlate of pathological inflammation;

Reducing gene/protein expression of a pro-inflammatory factor;

Reducing the number/proportion of myofibroblasts;

Increasing the function of an organ/tissue affected by the disease;

Stimulating/increasing proliferation of a cell affected by the disease;

Stimulating/increasing expansion of a cell affected by the disease;

Stimulating/increasing regeneration of a cell affected by the disease;

Stimulating/increasing proliferation of a myoblast;

Stimulating/increasing expansion of a myoblast;

Stimulating/increasing regeneration of a myoblast;

Increasing the number/proportion of health myoblasts;

Stimulating/increasing regeneration of an organ/tissue affected by the disease;

Stimulating/increasing proliferation and/or expansion of a cell in an organ/tissue affected by the disease;

Stimulating/increasing proliferation and/or expansion of a hepatocyte, e.g. that is affected by the disease or that is in an organ/tissue affected by the disease;

Stimulating/increasing regeneration of liver tissue;

Stimulating/increasing regeneration of lung tissue;

Stimulating/increasing regeneration of the liver;

Stimulating/increasing regeneration of the lung;

Increasing function of an organ/tissue affected by the disease;

Increasing liver function;

Increasing lung function;

Increasing wound healing in an organ/tissue affected by the disease;

Increasing wound healing in liver tissue;

Increasing wound healing in lung tissue;

Protecting an organ/tissue affected by the disease;

Protecting a liver/liver tissue affected by the disease;

Protecting a lung/lung tissue affected by the disease;

Increasing the survival of a subject having the disease;

Reducing the number/proportion of macrophages in an organ/tissue affected by the disease; and/or Reducing the number/proportion of monocytes in an organ/tissue affected by the disease;

Methods for treating a subject are provided herein.

The disclosure teaches a method of treating a condition or disease in a subject, the method comprising administering to the subject an inhibitor of a gene or corresponding gene product associated with organ regeneration for a sufficient time and under conditions to treat the condition or disease in the subject.

Disclosed herein is a method of treating a liver condition or disease in a subject, the method comprising administering to the subject an inhibitor of a gene or corresponding gene product associated with organ regeneration for a sufficient time and under conditions to treat the liver condition or disease in the subject.

A "gene associated with organ regeneration" as used herein may refer to one or more of MFAP4, GRHPR, ITFG1, ABCC4, PAK3, TRNP1, APLN, KIF20A, and/or LTB genes. A "corresponding gene product associated with organ regeneration" as used herein may refer to an mRNA encoded by one or more genes above, or a MFAP4, GRHPR, ITFG1, ABCC4, PAK3, TRNP1, APLN, KIF20A, and/or LTB protein.

In one embodiment, a subject herein is suffering from a liver condition or disease, as described herein. The methods described herein may comprise preventing or treating the liver condition or disease.

In one embodiment, a subject herein is suffering from a lung condition or disease. The lung condition or disease may be a cigarette or viral-induced lung condition or disease. The lung condition or disease may be lung damage or fibrosis. The method may comprise preventing or treating the lung condition or disease.

Disclosed herein is a method of protecting a subject from liver damage or a disease associated with fibrosis, the method comprising administering to the subject an inhibitor of a gene or corresponding gene product associated with organ regeneration for a sufficient time and under conditions to protect the subject from liver damage. The inhibitor may be one described herein. A gene/corresponding gene product associated with organ regeneration may be one or more of MFAP4, GRHPR, ITFG1, ABCC4, PAK3, TRNP1, APLN, KIF20A, and/or LTB.

Disclosed herein is an inhibitor of a gene or corresponding gene product associated with organ regeneration for use in preventing or treating a liver condition or disease in the subject. In one embodiment, the inhibitor is capable of stimulating or increasing proliferation of hepatocytes in the subject.

Disclosed herein is the use of an inhibitor of a gene or corresponding gene product associated with organ regeneration in the manufacture of a medicament for preventing or treating a liver condition or disease in the subject.

Disclosed herein is a method of enhancing cell function in a subject, the method comprising administering to the subject an inhibitor of a gene or corresponding gene product associated with organ regeneration for a sufficient time and under conditions to enhance cell function in the subject. "Enhancing cell function" refers to improving the endogenous activity of a cell, e.g. signalling, proliferation, expansion. Function of a cell may be enhanced starting from a healthy state, or from a diseased/impaired state.

The method may comprise improving the robustness of the cell under diseased condition. The term robustness refers to being able to survive under diseased condition.

Disclosed herein is a method of enhancing cell viability in a subject, the method comprising administering to the subject an inhibitor of a gene or corresponding gene product associated with organ regeneration for a sufficient time and under conditions to enhance cell viability in the subject, e.g. in inhibitor described herein.

The present disclosure teaches a method of stimulating or increasing proliferation and/or regeneration of a cell in a subject, the method comprising administering to the subject an inhibitor of a gene or corresponding gene product associated with organ regeneration for a sufficient time and under conditions to stimulate or increase proliferation of the cell in the subject.

In one embodiment, the method further increases the robustness of the cell under diseased conditions in the subject.

In one embodiment, the gene associated with organ regeneration is identified by knocking down the gene in a hepatocyte of an animal model and detecting proliferation and/or regeneration of the hepatocyte in the animal model.

The gene associated with organ regeneration is selected from the group consisting of Microfibril Associated Protein 4 (Mfap4), Glyoxylate and Hydroxypyruvate Reductase (Grhpr), Integrin Alpha FG-GAP Repeat Containing 1 (Itfg1), ATP binding cassette subfamily C member 4 (ABCC4), p21 (RAC1) activated kinase 3 (PAK3), TMF1 regulated nuclear protein 1 (TRNP1), Apelin (APLN), Kindesin Family Member 20A (KIF20A) and Lymphotoxin beta (LTB).

A "gene product" is a biopolymeric product that is expressed or produced by a gene. A gene product may be, for example, an unspliced RNA, an mRNA, a splice variant mRNA, a polypeptide, a post-translationally modified polypeptide, a splice variant polypeptide etc. Also encompassed by this term is biopolymeric products that are made using an RNA gene product as a template (i.e. cDNA of the RNA). A gene product may be made enzymatically, recombinantly, chemically, or within a cell to which the gene is native. In many embodiments, if the gene product is proteinaceous, it exhibits a biological activity. In many embodiments, if the gene product is a nucleic acid, it can be translated into a proteinaceous gene product that exhibits a biological activity.

Disclosed herein is an in vitro or in vivo method for reducing gene and/or protein expression of one or more of MFAP4, GRHPR, ITFG1, ABCC4, PAK3, TRNP1, APLN, KIF20A, and/or LTB in a cell, comprising introducing an inhibitor described herein into the cell. In some embodiments, the inhibitor is an inhibitory nucleic acid as described herein.

Disclosed herein is a method of regenerating liver tissue in vitro or in vivo, the method comprising inhibiting at least one of MFAP4, GRHPR, ITFG1, ABCC4, PAK3, TRNP1, APLN, KIF20A, and/or LTB in a cell of the tissue, e.g. using an inhibitor described herein.

Disclosed herein is a method for preventing age-dependent decline in the regenerative capacity of a hepatocyte, the method comprising inhibiting at least one of MFAP4, GRHPR, ITFG1, ABCC4, PAK3, TRNP1, APLN, KIF20A, and/or LTB in a cell of the tissue, e.g. using an inhibitor described herein.

The term "treating" as used herein may refer to (1) preventing or delaying the appearance of one or more symptoms of the disorder; (2) inhibiting the development of the disorder or one or more symptoms of the disorder; (3) relieving the disorder, i.e., causing regression of the disorder or at least one or more symptoms of the disorder; and/or (4)

causing a decrease in the severity of one or more symptoms of the disorder. The term "treating" may refer to regeneration of the tissue/organ in question, or preventing a disease/condition from progressing to a later, more severe stage.

The term "administering" refers to contacting, applying, injecting, transfusing or providing an inhibitor as referred to herein to a subject.

The term "subject" as used throughout the specification is to be understood to mean a human or may be a domestic or companion animal. While it is particularly contemplated that the methods of the invention are for treatment of humans, they are also applicable to veterinary treatments, including treatment of companion animals such as dogs and cats, and domestic animals such as horses, cattle and sheep, or zoo animals such as primates, felids, canids, bovids, and ungulates. The "subject" may include a person, a patient or individual, and may be of any age or gender.

The patient may have a disease described herein. A subject may have been diagnosed with a disease requiring treatment, may be suspected of having such a disease, or may be at risk from developing a disease.

In embodiments according to the present invention the subject is preferably a human subject. In embodiments according to the present invention, a subject may be selected for treatment according to the methods based on characterisation for certain markers of a disease described herein.

In some embodiments, any method disclosed herein comprises administering an inhibitor according to the present disclosure into a subject, organ, tissue or cell. The organ, tissue or cell may be in vivo or in vitro. Any method described herein may be performed in vivo or in vitro.

Aspects and embodiments of the present invention concern detection of expression of one or more of MFAP4, GRHPR, ITFG1, ABCC4, PAK3, TRNP1, APLN, KIF20A, and/or LTB (gene and/or protein expression) and/or activity in a cell/tissue/organ of a subject, e.g. as determined by analysis of a cell/tissue/organ of a subject, e.g. in a sample obtained from the subject (such as an in vitro cell/tissue/organ/sample).

Disclosed herein is a method of detecting a liver condition or disease in a subject, the method comprising detecting in a sample the level of one or more biomarkers associated with liver regeneration, wherein a change in the level of the one or more biomarkers as compared to a reference indicates that the subject is suffering from a liver condition or disease. The one or more biomarkers may be one or more of MFAP4, GRHPR, ITFG1, ABCC4, PAK3, TRNP1, APLN, KIF20A, and/or LTB.

Upregulated expression and/or activity of one or more of MFAP4, GRHPR, ITFG1, ABCC4, PAK3, TRNP1, APLN, KIF20A, and/or LTB may identify a subject as a subject to be treated with an inhibitor of at least one of those genes/proteins in accordance with the present invention.

Upregulated expression/activity of one or more of MFAP4, GRHPR, ITFG1, ABCC4, PAK3, TRNP1, APLN, KIF20A, and/or LTB refers to a level of expression/activity that is greater than would be expected for a cell/tissue of a given type. Gene or protein expression and activity can be analysed as described herein.

Upregulation may be determined by measuring the level of expression/activity of one or more of MFAP4, GRHPR, ITFG1, ABCC4, PAK3, TRNP1, APLN, KIF20A, and/or LTB in a cell/tissue. Comparison may be made between the level of expression/activity in a cell or tissue sample from a subject and a reference level of expression/activity, e.g. a value/range of values representing a normal level of expression/activity for the same or corresponding cell/tissue type.

In some embodiments reference levels may be determined by detecting expression/activity of one or more of MFAP4, GRHPR, ITFG1, ABCC4, PAK3, TRNP1, APLN, KIF20A, and/or LTB in a control sample, e.g. in corresponding cells or tissue from a healthy subject or from healthy tissue of the same subject. In some embodiments reference levels may be obtained from a standard curve or data set.

A sample obtained from a subject may be of any kind. A biological sample may be taken from any tissue or bodily fluid, e.g. a blood sample, blood-derived sample, serum sample, lymph sample, semen sample, saliva sample, synovial fluid sample. A blood-derived sample may be a selected fraction of a patient's blood, e.g. a selected cell-containing fraction or a plasma or serum fraction. A sample may comprise a tissue sample or biopsy; or cells isolated from a subject. Samples may be collected by known techniques, such as biopsy or needle aspirate. Samples may be stored and/or processed for subsequent determination of the level of expression/activity of one or more of MFAP4, GRHPR, ITFG1, ABCC4, PAK3, TRNP1, APLN, KIF20A, and/or LTB.

In some preferred embodiments a sample may be a tissue sample, e.g. biopsy, taken from a tissue/organ affected by a disease described herein. A sample may contain cells.

A subject may be selected for therapy/prophylaxis in accordance with the present invention based on determination that the subject has an upregulated level of expression/activity of one or more of MFAP4, GRHPR, ITFG1, ABCC4, PAK3, TRNP1, APLN, KIF20A, and/or LTB. Upregulated expression/activity of said genes/proteins may serve as a marker of a disease suitable for treatment in accordance with the present invention.

Following selection, a subject may be treated to inhibit expression and/or activity of one or more of MFAP4, GRHPR, ITFG1, ABCC4, PAK3, TRNP1, APLN, KIF20A, and/or LTB, e.g. by administration of an inhibitor of at least one of MFAP4, GRHPR, ITFG1, ABCC4, PAK3, TRNP1, APLN, KIF20A, and/or LTB (e.g. that has an upregulated level of expression/activity).

Detection of upregulation of expression/activity of one or more of MFAP4, GRHPR, ITFG1, ABCC4, PAK3, TRNP1, APLN, KIF20A, and/or LTB may also be used in a method of diagnosing a disease described herein, identifying a subject at risk of developing a disease described herein, and in methods of prognosing a subject's response to inhibition of one or more of MFAP4, GRHPR, ITFG1, ABCC4, PAK3, TRNP1, APLN, KIF20A, and/or LTB (e.g. via treatment with an inhibitor targeting one or more of said genes/proteins).

In some embodiments a subject may be suspected of having or suffering from a disease, e.g. based on the presence of other symptoms indicative of the disease in the subject's body or in selected cells/tissues of the subject's body, or be considered at risk of developing the disease, e.g. because of genetic predisposition or exposure to environmental conditions, known to be risk factors for the disease. Determination of upregulation of expression/activity of one or more of MFAP4, GRHPR, ITFG1, ABCC4, PAK3, TRNP1, APLN, KIF20A, and/or LTB may confirm a diagnosis or suspected diagnosis, or may confirm that the subject is at risk of developing the disease. The determination may also diagnose a disease or predisposition as one suitable for treatment with an inhibitor of one or more of MFAP4, GRHPR, ITFG1, ABCC4, PAK3, TRNP1, APLN, KIF20A, and/or LTB.

As such, a method of providing a prognosis for a subject having, or suspected of having a disease may be provided, the method comprising determining whether expression/activity of one or more of MFAP4, GRHPR, ITFG1, ABCC4, PAK3, TRNP1, APLN, KIF20A, and/or LTB is upregulated in a sample obtained from the subject and, based on the determination, providing a prognosis for treatment of the subject with a inhibitor of one or more of MFAP4, GRHPR, ITFG1, ABCC4, PAK3, TRNP1, APLN, KIF20A, and/or LTB.

The method may further comprise the step of selecting the subject for treatment with an inhibitor of one or more of MFAP4, GRHPR, ITFG1, ABCC4, PAK3, TRNP1, APLN, KIF20A, and/or LTB, and/or administering an inhibitor of one or more of MFAP4, GRHPR, ITFG1, ABCC4, PAK3, TRNP1, APLN, KIF20A, and/or LTB to the subject in order to provide a treatment for a disease described herein in the subject or to prevent development or progression of a disease described herein in the subject.

Methods of diagnosis or prognosis may be performed in vitro on a sample obtained from a subject, or following processing of a sample obtained from a subject. Once the sample is collected, the patient is not required to be present for the in vitro method of diagnosis or prognosis to be performed and therefore the method may be one which is not practised on the human or animal body. The sample obtained from a subject may be of any kind, as described herein above.

Other diagnostic or prognostic tests may be used in conjunction with those described here to enhance the accuracy of the diagnosis or prognosis or to confirm a result obtained using the tests described herein.

The terms "therapeutically effective amount" and "effective amount" are used interchangeably and refer to an amount of a compound that is sufficient to effect treatment as defined below, when administered to a patient (e.g., a human) in need of such treatment in one or more doses. The therapeutically effective amount will vary depending upon the patient, the disease being treated, the weight and/or age of the patient, the severity of the disease, the nature of the agent, or the manner of administration as determined by a qualified prescriber or care giver. Examples of the techniques and protocols mentioned above can be found in Remington's Pharmaceutical Sciences, 20th Edition, 2000, pub. Lippincott, Williams & Wilkins.

Multiple doses of the agent may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

In therapeutic applications, inhibitors for use as described herein are preferably formulated as a medicament or pharmaceutical together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents.

As used herein, "pharmaceutically acceptable carrier" includes excipients or agents such as solvents, diluents, dispersion media, coatings, antibacterial and antifungal agents, isotonic and absorption delaying agents and the like that are not deleterious to the disclosed compound or use thereof. The use of such carriers and agents to prepare compositions of pharmaceutically active substances is well known in the art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.). Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulations may be prepared for topical, parenteral, systemic, intravenous, intra-arterial, intramuscular, intrathecal, intraocular, intra-conjunctival, subcutaneous, oral or transdermal routes of administration which may include injection. Injectable formulations may comprise the selected agent in a sterile or isotonic medium. The formulation and mode of administration may be selected according to the agent and disease to be treated/prevented.

Disclosed herein is a method of screening for an inhibitor of a gene or corresponding gene product associated with organ regeneration by: a) contacting the gene or corresponding gene product with a chemical compound library, and b) identifying a chemical compound within the library that is binds to the gene or corresponding gene product to inhibit the expression or function of the gene or corresponding gene product.

Also provided herein are reporter cells lines for screening of small compound inhibitors for a gene or corresponding gene product associated with cell regeneration.

Numbered Paragraphs

1. A method of stimulating or increasing proliferation and/or regeneration of a cell in a subject, the method comprising administering to the subject an inhibitor of a gene or corresponding gene product associated with organ regeneration for a sufficient time and under conditions to stimulate or increase proliferation of the cell in the subject.

2. The method of paragraph 1, wherein the method increases the robustness of the cell under diseased conditions in the subject.

3. The method of paragraph 1, wherein the gene associated with organ regeneration is identified by knocking down the gene in a hepatocyte of an animal model and detecting proliferation and/or regeneration of the hepatocyte in the animal model.

4. The method of paragraph 2, wherein the gene associated with organ regeneration is selected from the group consisting of Microfibril Associated Protein 4 (Mfap4), Glyoxylate and Hydroxypyruvate Reductase (Grhpr), Integrin Alpha FG-GAP Repeat Containing 1 (Itfg1), ATP binding cassette subfamily C member 4 (ABCC4), p21 (RAC1) activated kinase 3 (PAK3), TMF1 regulated nuclear protein 1 (TRNP1), Apelin (APLN), Kindesin Family Member 20A (KIF20A) and Lymphotoxin beta (LTB).

5. The method of paragraph 1, wherein the inhibitor is a nucleic acid, peptide, antibody or small molecule inhibitor.

6. The method of paragraph 5, wherein the inhibitor is a nucleic acid inhibitor comprising or encoding an RNAi agent having at least 70%, 80%, 90% or 95% sequence identity to an RNA sequence listed in any of Tables 1-14 or an RNAi agent that hybridizes to the complement of an RNA sequence listed in any of Tables 1-14 under stringency conditions.

7. The method of paragraph 1, wherein the subject is suffering from a liver condition or disease.

8. The method of paragraph 7, wherein the liver condition or disease is selected from the group consisting of acute liver disease, chronic liver disease, metabolic liver disease, steatosis, liver fibrosis, primary sclerosing cholangitis (PSC), cirrhosis, liver fibrosis, non-alcoholic fatty liver disease (NAFLD), non-alcoholic steatohepatitis (NASH), hepatic ischemia reperfusion injury, primary biliary cirrhosis (PBC), hepatitis and liver damage.

9. The method of paragraph 7, wherein the method comprises preventing or treating the liver condition or disease.

10. A method of enhancing cell function in a subject, the method comprising administering to the subject an inhibitor of a gene or corresponding gene product associated with organ regeneration for a sufficient time and under conditions to enhance cell function in the subject.

11. The method of paragraph 10, wherein the method comprises improving the robustness of the cell under diseased condition.

12. A method of enhancing cell viability in a subject, the method comprising administering to the subject an inhibitor of a gene or corresponding gene product associated with organ regeneration for a sufficient time and under conditions to enhance cell viability in the subject.

13. A method of treating a liver condition or disease in a subject, the method comprising administering to the subject an inhibitor of a gene or corresponding gene product associated with organ regeneration for a sufficient time and under conditions to treat the liver condition or disease in the subject.

14. A method of protecting a subject from liver damage, the method comprising administering to the subject an inhibitor of a gene or corresponding gene product associated with organ regeneration for a sufficient time and under conditions to protect the subject from liver damage.

15. A method of detecting a liver condition or disease in a subject, the method comprising detecting in a sample the level of one or more biomarkers associated with liver regeneration, wherein a change in the level of the one or more biomarkers as compared to a reference indicates that the subject is suffering from a liver condition or disease.

16. An inhibitor of a gene or corresponding gene product associated with organ regeneration for use in preventing or treating a liver condition or disease in the subject.

17. The inhibitor of paragraph 16, wherein the liver condition or disease is selected from the group consisting of acute liver disease, chronic liver disease, metabolic liver disease, steatosis, liver fibrosis, primary sclerosing cholangitis (PSC), cirrhosis, liver fibrosis, non-alcoholic fatty liver disease (NAFLD), non-alcoholic steatohepatitis (NASH), hepatic ischemia reperfusion injury, primary biliary cirrhosis (PBC) hepatitis or liver damage.

18. The inhibitor of paragraph 17, wherein the inhibitor is capable of stimulating or increasing proliferation of hepatocytes in the subject.

19. Use of an inhibitor of a gene or corresponding gene product associated with organ regeneration in the manufacture of a medicament for preventing or treating a liver condition or disease in the subject.

20. The use of paragraph 19, wherein the liver condition or disease is selected from the group consisting of acute liver disease, chronic liver disease, metabolic liver disease, steatosis, liver fibrosis, primary sclerosing cholangitis (PSC), cirrhosis, liver fibrosis, non-alcoholic fatty liver disease (NAFLD), non-alcoholic steatohepatitis (NASH), hepatic ischemia reperfusion injury, primary biliary cirrhosis (PBC) hepatitis or liver damage.

21. The use of paragraph 19, wherein the inhibitor is capable of stimulating or increasing proliferation of hepatocytes in the subject.

22. A nucleic acid inhibitor consisting, comprising or encoding an RNAi agent having at least 70%, 80%, 90% or 95% sequence identity to an RNA sequence listed in any of Tables 1-14 or an RNAi agent that hybridizes to the complement of an RNA sequence listed in any of Tables 1-14 under stringency conditions.

23. A method of screening for an inhibitor of a gene or corresponding gene product associated with organ regeneration by: a) contacting the gene or corresponding gene product with a chemical compound library, and b) identifying a chemical compound within the library that is binds to the gene or corresponding gene product to inhibit the expression or function of the gene or corresponding gene product.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

As used in this application, the singular form "a," "an," and "the" include plural references unless the context clearly dictates otherwise. For example, the term "an agent" includes a plurality of agents, including mixtures thereof. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavor to which this specification relates.

Certain embodiments of the invention will now be described with reference to the following figures and examples which are intended for the purpose of illustration only and are not intended to limit the scope of the generality hereinbefore described. Further aspects and embodiments will be apparent to those skilled in the art. All documents mentioned in this text are incorporated herein by reference.

For standard molecular biology techniques, see Sambrook, J., Russel, D. W. *Molecular Cloning, A Laboratory Manual*. 3 ed. 2001, Cold Spring Harbor, New York: Cold Spring Harbor Laboratory Press, which is hereby incorporated by reference in its entirety.

SUMMARY OF THE FIGURES

Embodiments and experiments illustrating the principles of the invention will now be discussed, by way of non-limiting example only, with reference to the accompanying figures in which:

FIG. 1A, 1B, 1C, 1D. Functional genetic in vivo RNAi screen for modulators of liver regeneration FIG. 1A) Outline of screen. A library of 250 shRNAs targeting 89 genes was delivered to the liver by hydrodynamic-tail vine injection (HDTV) of the transposon based construct (upper panel) in combination with a sleeping beauty 13 (SB13) encoding plasmid (5 independent mice). After stable integration in ~5 to 10% of hepatocytes, thioacetamide (TAA) treatment (3 times per week for 8 weeks) induces chronic liver damage associated with advanced liver fibrosis. Changes in shRNA abundance is detected by deep sequencing. FIG. 1B) Representation of fold change for each shRNA. The majority of shRNAs is depleted but a small number is clearly enriched. FIG. 1C) ROMAampl-library (250shRNAs) distribution. Abundance of potential candidates is shown. Heatmap based representation of enrichment (dark grey) or depletion (light grey) for each animal. Upper panel shows all shRNAs (each raw represents one animal). Lower panel represents a higher magnification for highly significant enriched, depleted and neutral shRNAs (each column represents one animal). FIG. 1D) Functional genetic screen identifies high confidence candidates (zoom in of FIG. 1B) is shown). At least two independent shRNAs were enriched targeting Mfap4, Grhpr, and Itfg1. Furthermore, non-targeting control (shNC) shRNAs (*Renilla*.713 and Luciferase.1309) did not show significant enrichment or depletion and known important liver regeneration genes are depleted, whereas shRNAs targeting the c-Met an essential receptor for liver regeneration are depleted. These results give confidence in the screening approach.

FIG. 2A, 2B, 2C, 2D, 2E, 2F, 2G: In vitro validation of targeting Mfap4 for enhancing regeneration—shRNA mediated knockdown of Mfap4 accelerates proliferation rate in embryonic liver cell line FIG. 2A) Test of knockdown efficiency of top scoring shRNAs targeting Mfap4. Upper panel, retroviral backbone for generating stable cell lines. Lower panel, Western blot showing efficient knockdown of Mfap4 by our shRNAs (control: aTub=α-TUBULIN). FIG. 2B) Schematic outline for stable cell line based assays. FIG. 2C) Wound healing assay in TIB 73 (BNLCL.2) cell line. Stable cell lines were grown to full confluence, then the silicon gasket was removed leaving a defined cell free area. Filling of this "wound" gap was monitored. In the left panels representative images for each group are shown. Three technical replicates were performed. On the right panel the quantification over different time points is shown (Data was analyzed by ImageJ software and 2-way ANOVA test of GraphPad Prism software). Significant difference between shMfap4.1356 (SEQ ID NO: 1), shMfap4.760 (SEQ ID NO: 2) and shNC is shown by '*'). FIG. 2D) EdU incorporation assay. DNA synthesis of TIB 73 cells (BNLCL.2) transfected with shMfap4.1356 (SEQ ID NO: 2) and shNC was assessed by EdU assays. Quantification shows significant difference between experiment and control. Three technical replicates were performed. FIG. 2E) Cell doubling. Doubling time assay results are shown. Cells were seeded at same seeding densities. Doubling time was calculated based on the exponential phase of the growth curve. Three technical replicates were performed. FIG. 2F) Cell cycle analysis by flow cytometry using the Guava Muse Cell Analyzer. Shown is the percentage of cells in the indicated cell cycle phase. Greater amount of cells in G2 phase is indicated in case of experiment (cells with stable Mfap4 knockdown by shMfap4.1356 and shMfap4.760) compared to control NC. FIG. 2G) Wound healing assay using adult liver mouse cell line AML12. Left panel, the same effects were observed as in FIG. 2C). Right panel. quantification of FIG. 2A) shows significantly faster wound closure already at the 14 h timepoint.

FIG. 3B) GFP imager images. GFP imaging of explanted mouse livers shows enhanced clonal expansion (repopulation) of hepatocytes stably expressing shMfap4.1356 (SEQ ID NO: 1) compared to hepatocytes expressing shNC (day 18 after HDTV injection of 25 μg of the indicated plasmid). Representative photographs are shown for each group (n=8 in group with shMfap4.1356, n=6 in group with shMfap4.760, n=6 in group with shNC). Light, white points represent GFP positive macroscopically visible clonal expansions. FIG. 3C) Native GFP on tissue sections. Shown are representative GFP fluorescence photographs of liver sections (200×) of FAH−/− mice 18 days after in vivo delivery of transposon constructs either expressing shMfap4 or a control shRNA corresponding to B). FIG. 3D) Histological analysis (immunostaining against GFP) for GFP-positive cells of mouse livers with stable expression of shMfap4.1356 (SEQ ID NO: 1), shMfap4.760 (SEQ ID NO: 2) and shNC (shown are representative photographs, n=8 in group with shMfap4.1356, n=6 in group with shMfap4.760, n=6 in group with shNC). Day 18 after HDTV injection of 1.25 µg of the indicated plasmid (200× magnification). Increased clonal expansion can be seen for shMfap4. FIG. 3E) Quantification of GFP-positive cells (corresponding to FIG. 3D) shows significant increase in GFP positive hepatocytes in case of Mfap4 knockdown compared to control. Each dot represents one animal. FIG. 3F) Kaplan-Meier survival curve of FAH−/− mice injected with a 1:30 (0.83 µg plasmid and 0.17 mg SB13) dilution of either p/T-FAHIG-shMfap4.1356 (n=5) or p/T-FAHIG-shNC (n=5) and SB13 (p<0.05). NTBC off indicates the time of NTBC drug removal, inducing the selection process (1 day post injection).

FIG. 4A, 4B, 4C, 4D, 4E, 4F, 4G, 4H: "Western Diet" (WD) mouse fatty liver model FIG. 4A) WD+fructose Diet facts. The used diet is rich in fat and carbohydrates. 45% energy comes from fat, predominantly saturated fat, with 0.2% cholesterol. In addition, the animals get 60% fructose/water (wt/vol). FIG. 4B) Pathological evaluation. Histological slides of liver tissue form C56B16 mice exposed for the indicated time to the "Western Diet" or normal chow were evaluated and scored by a certified pathologist. Shown are the scoring results for steatosis and fibrosis. Each point represents an animal. FIG. 4C) Mice on "Western Diet" show a progressive weight gain independent of gender. FIG. 4D) WD model shows progressive fibrosis similar to human patients (see FIG. 4E). FIG. 4E) Progressive increase in fibrosis in human patients based and disease stage, similar to the mouse model (FIGS. 4D & 4B). FIG. 4F). Advanced liver fibrosis can already macroscopically be detected after 24 weeks of WD (representative image). FIG. 4G) After 24 weeks of WD mouse liver show high levels of steatosis (H&E stained liver tissue, representative image). FIG. 4H) Sirius Red staining for collagen fibers indicating advanced fibrosis after 24 weeks of WD exposure.

FIG. 5B) Representative macro-photographs of the livers are shown. Already macroscopically differences between groups were visible. FIG. 5C) Picro Sirius Red staining (staining for fibrotic scar tissue) and Hematoxylin & Eosin staining on sections of indicated repopulated mouse livers (n=5 per experimental group and n=7 per control group; representative sections are shown, 50× magnification). FIG. 5D) The fibrotic score for each animal is shown. The score was given by a certified pathologist, who was blinded regarding the experimental group. Fibrosis score is significantly lower in the experimental group compared to the control group. FIG. 5E) The score of oval cell hyperplasia is shown. The score was given by a certified pathologist, who was blinded regarding the experimental group. The score is significantly lower (=0) in the experimental group compared to the control group. Oval cell hyperplasia is considered a compensatory mechanism, if regeneration through hepatocytes is not sufficient anymore. FIG. 5F) Representative GFP-scanner macro-photographs of the livers are shown. Strong GFP signal on the surface of the livers indicates full repopulation.

FIG. 6B) Representative macro-photographs of the livers are shown. Already macroscopically differences between groups were visible. FIG. 6C) Picro Sirius Red staining (staining for fibrotic scar tissue) and Hematoxylin & Eosin staining on sections of indicated repopulated mouse livers (n=6 per experimental group and n=7 per control group; representative sections are shown, 50× magnification). FIG. 6D) The fibrotic score for each animal is shown. The score was given by a certified pathologist, who was blinded regarding the experimental groups. Fibrosis score is significantly lower in the experimental group compared to the control group.

FIG. 7B) Representative photographs of Ki67 immunofluorescence stained (top row) and DAB Ki67-stained (bottom row) liver sections 48 h post hepatectomy are shown (200× magnification, n=5 per experimental/control group). FIG. 7C) Quantification of Ki67 positive cells of DAB-stained liver sections (corresponding to FIG. 7B)) show increased hepatocyte proliferation after partial hepatectomy in shMfap4-expressing livers compared to shNC livers (individual points represent individual animals, data shows average±SEM, n=5 per group). FIG. 7D) Western blot analyses for cyclin A (nuclear extracts from repopulated mouse livers at the indicated time point) indicate an earlier cell-cycle entry and faster cell-cycle progression of shMfap4-expressing mouse livers (n=2). FIG. 7E) Experimental outline. Immune-competent FAH−/− mice were injected with our constructs, then, mice were kept for full repopulation for 3 months. After that ⅔ of the liver was surgically removed. The remaining regenerating liver was harvested 42 h and 48 h after surgery. FIG. 7F) Representative photographs of DAB Ki67-stained liver sections 42 h (n=5 per experimental group, n=6 per control group) and 48 h (n=5 per experimental group, n=10 per control group) post hepatectomy are shown (200× magnification). FIG. 7G) Quantification of Ki67 positive cells of DAB-stained liver sections (corresponding to FIG. 7B)) show increased hepatocyte proliferation and accelerated liver regeneration after partial hepatectomy in shMfap4-expressing livers compared to shNC livers (individual points represent individual animals, data shows average±SEM). FIG. 7H) Western blot analyses for cyclin E (nuclear extracts from repopulated mouse livers at the indicated time point) indicate an earlier cell-cycle entry and faster cell-cycle progression of shMfap4-expressing mouse livers (n=2). FIG. 7I) GFP-imaging of fully repopulated FAH−/− livers (3 months post-HDTV injections) after ⅔ surgical partial removal of livers corresponding to different time-points of PHx. Strong GFP signal on the surface of the livers indicates full repopulation. FIG. 7J) Representative pictures of DAB GFP staining which show that full repopulation of FAH livers is around 90-95%. Dark brown zones represent repopulated hepatocytes, light brow zones are non-repopulated.

FIG. 8A, 8B, 8C, 8D, 8E, 8F, 8G, 8H, 8I, 8J, 8K: In vivo knockdown of Mfap4 impacts mTOR and p38 signalling FIG. 8A) Schematic outline of experiment. Whole-cell protein extracts from repopulated mouse livers were isolated and analyzed by protein array. FIG. 8B) Heat map shows results for phospho-antibody MAPK pathway protein array. Whole-cell protein extracts from repopulated mouse livers with stable expression of either shMfap4 or shNC were analyzed (shown is the relative spot intensity). FIG. 8C) According to STRING database, all indicated proteins are interacting and are linked to cell growth and proliferation. FIG. 8D) After performing a broad protein array focused Western blot experiments were done. Results of Western blot are shown here. Proteins from fully repopulated livers were isolated. P-P70S6k, β-p38, p-mTOR, p-ERK2 are greater expressed in case of Mfap4 knockdown compare to control and, thus, show stronger activation in case of Mfap4 knockdown compared to control. There are 3 biological replicates in experiment and 3 biological replicates in control. FIG. 8E) Schematic representation for mTOR mediated regulation. The specific mTOR phosphorylation is upstream of p70S6k activation and leads to enforced translation. FIG. 8F) Wound healing under double knockdown conditions. Based on pathway analysis double knockout experiments were commenced. Our stable cell line was expanded, cells were treated with respective siRNAs and the silicon gasket was removed. Wound healing was monitored. Slower growth and migration were observed in case of double-knockdown of Mfap4 and p70S6k and Mfap4 and p38. FIG. 8G) Western blot on proteins from cells in FIG. 8F were isolated. Interestingly p38 knockdown also affects p70S6k. FIG. 8H) Schematic outline of preparation of stable cell line with Mfap4 knockdown for transcriptomic analysis. FIG. 8I) Principal component analysis for AML12-shMfap4.1356, AML12-shMfap4.760, AML12-shNC, (Rb88-RMA050 & Ren_RMA061) and AML12 (AML_RMA052) is shown. We observed cluster separation between experiment and control. FIG. 8J) Heatmap of the following samples is shown. Ptgs2, Areg, Dhrs9, Hmox1, Nqo1 are upregulated in experimental samples compared to control and these genes are known to be involved in liver regeneration according to the literature. FIG. 8K) String Database shows connections between proteins which are upregulated according to FIGS. 8D and 8J.

FIG. 9B) EdU incorporation assay. DNA synthesis of HepG2 cells transfected with hushMfap4 and shNC was assessed by EdU assays. Quantification shows significant difference between experiment and control. FIG. 9C-9E) Transcriptomic analysis of liver samples from ~150 patients shows increased Mfap4 expression in NAFLD patients with cirrhosis and fibrosis 4 score (Table: boxes indicate disease stages with significant change, but less than log 2 2 fold change; grey mark indicates significant upregulation of at least log 2 2 fold; *p<0.05, p<0.01, *p, 0.005). FIG. 9F) Human tissue samples from healthy and cirrhotic liver was stained for Mfap4 protein (Mfap4 specific antibody & DAB staining). On the left side healthy liver tissue was stained without primary antibody as a control. In the middle, the staining of healthy liver indicates hepatocytes are slightly positive for Mfap4. Interestingly we also see some nuclear staining. Right panel shows staining of cirrhotic human liver. Human hepatocytes show strong staining in cytoplasm as well as nuclear staining. On the left side of the cirrhotic liver fibrotic scar tissue can be seen and is highly positive for Mfap4. FIG. 9G) Knockdown test of human MFAP4 siRNA pool. Western blot analysis of protein extracts from immortalized human hepatocytes (Creative Bioarray CSC-19016L) either treated with si huMFAP4 or siNC, α-Tubulin serves as loading control (n=3). FIG. 9H) EdU incorporation assay shows greater number of EdU-positive cells in experiment compared to control. FIG. 9I) EdU incorporation assay (3 technical replicates). Shown is the value of % EdU positive cells±SEM. Immortalized human hepatocytes were either treated with siRNA targeting human MFAP4 or siNC as control (*p<0.05). FIG. 9J) Scheme of retroviral backbone for generating stable cell lines. FIG. 9K) Representative GFP pictures of immortalized Human Hepatocytes (Creative Bioarray CSC-19016L) with stable integration of shRNAs against human Mfap4. FIG. 9L) qPCR analysis showing efficient knockdown of huMfap4 by two shRNAs—hu shMfap4.1812 (SEQ ID NO: 7100) and hu shMfap4.1602 (7097) compared to non-targeting control. FIG. 9M) Western blot showing efficient knockdown of human Mfap4 by two independent shRNAs in immortalized human hepatocytes-SV40. FIG. 9N) Mfap4 knockdown in human immortalized hepatocytes accelerates wound healing. Wound healing assay using immortalized human hepatocytes with stable expression of shhuMFAP4.1602 or shNC respectively. Cells were grown to full confluence, then the silicon gasket was removed leaving a defined cell free area (0 h). Filling of this "wound" gap was monitored (48 h; n=3 for each condition). FIG. 9O) Quantification of L), wound healing area (n=3; *p<0.05, ns=non-significant).

FIG. 10B) Test of knockdown efficiency of top scoring shRNAs targeting Grhpr. Western blot showing efficient knockdown of Grhpr by our shRNAs (Alpha-tubulin, αTub functions as loading control). FIG. 10C) Wound healing assay. Stable cell lines were grown to full confluence, then the silicon gasket was removed leaving a defined cell free area. Filling of this "wound" gap was monitored. Representative images for each group are shown. FIG. 10D) Quantification over different time points of wound healing assay is shown (Data was analyzed by ImageJ software and 2-way ANOVA test of GraphPad Prism software. Significant difference between shGrhpr361 (SEQ ID NO: 3) and shNC is shown by '*').

FIG. 11A, 11B, 11C, 11D, 11E, 11F, 11G: Grhpr knockdown accelerates liver repopulation FIG. 11A) Outline shows the transposon based vector for the expression of the enzyme FAH, the marker GFP and the shRNA of interest. FIG. 11B) FAH knockout mice based liver repopulation assay. Outline shows the rational for the assay. If the knockdown of a certain shRNA is able to enhance regeneration and accelerate hepatocyte proliferation, we should be able to see a faster clonal expansion compared to a control shRNA starting from the stably integrated hepatocytes. FIG. 11C) GFP imager images. GFP imaging of explanted mouse livers shows enhanced clonal expansion (repopulation) of hepatocytes stably expressing shGrhpr.361 (SEQ ID NO: 3) compared to hepatocytes expressing shNC (day 18 after HDTV injection of 25 µg of the indicated plasmid). Representative photographs are shown for each group (n=5). Light, white points represent GFP positive macroscopically visible clonal expansions. FIG. 11D) Native GFP on tissue sections. Shown are representative GFP fluorescence photographs of liver sections (200×) of FAH−/− mice 18 days after in vivo delivery of transposon constructs either expressing shGrhpr or a control shRNA corresponding to C). FIG. 11E) Histological analysis (immunostaining against GFP) for GFP-positive cells of mouse livers with stable expression of shGrhpr.361 (SEQ ID NO: 3) and shNC (shown are representative photographs, n=5 in group with shGrhpr.361, n=5 in group with shNC). Day 18 after HDTV injection of 1.25 µg of the indicated plasmid (200× magnification). Increased clonal expansion can be seen for shMfap4. FIG. 11F) Quantification of GFP-positive cells (corresponding to E)) shows significant increase in GFP positive hepatocytes in case of Mfap4 knockdown compared to control. Each dot represents one animal. FIG. 11G) Survival curve with dilution of constructs (1:30) as 0.83 µg plasmid and 0.17 mg SB13. All experimental mice with shGrhpr constructs (n=5) survived whereas control mice died (n=5).

FIG. 12B) Representative photographs of Ki67 DAB-stained liver sections (200× magnification) at 24 hours' (n=5 per group), 38 hours' (n=6 per group), 48 hours' (n=9 per group) time points after partial hepatectomy. Earlier and increased hepatocyte proliferation after partial hepatectomy in shGrhpr-expressing livers compared to shNC livers can be seen. FIG. 12C) Quantification of Ki67 positive cells of DAB-stained liver sections (corresponding to B)) show earlier and increased hepatocyte proliferation after partial hepatectomy in shGrhpr-expressing livers compared to shNC livers (individual points represent individual animals, data shows average±SEM). FIG. 12D) Schematic representation of peak shifting of mitotic cycle in case of Grhpr knockdown compare to control shNC (corresponding to C)).

FIG. 13B) Representative macro-photographs of the livers are shown. Already macroscopically differences between groups were visible. FIG. 13C) Sirius Red staining (staining for fibrotic scar tissue) and Hematoxylin & Eosin staining on sections of indicated repopulated mouse livers (n=5 per each group, 50× magnification). FIG. 13D) The fibrotic score for each animal is shown. The score was given by a certified pathologist, who was blinded regarding the experimental groups.

FIG. 14B) Representative macro-photographs of the livers are shown. FIG. 14C) Sirius Red staining (staining for fibrotic scar tissue) and Hematoxylin & Eosin staining on sections of indicated repopulated mouse livers (n=6 per experimental group and n=7 per control group; representative sections are shown, 50× magnification). FIG. 14D) The fibrotic score for each animal is shown. The score was given by a certified pathologist, who was blinded regarding the experimental group.

FIG. 16A, 16B, 16C, 16D, 16E, 16F, 16G, 16H: Itfg1 knockdown accelerates wound healing and liver repopulation FIG. 16A) Outline of retroviral backbone for generating stable cell lines. FIG. 16B) Test of knockdown efficiency of top scoring shRNAs targeting Itfg1. qPCR analysis and Western blot analysis show efficient knockdown of Itfg1 by our shRNAs. FIG. 16C) Itfg1 knockdown accelerates wound healing in vitro. Stable cell lines were grown to full confluence, then the silicon gasket was removed leaving a defined cell free area. Filling of this "wound" gap was monitored. Representative images are shown in upper part. Quantification over different time points of wound healing assay is shown (lower part, Data was analyzed by ImageJ software and 2-way ANOVA test of GraphPrizm software. Significant difference between shItfg1.698 (SEQ ID NO: 6), shItfg1.680 (SEQ ID NO: 7) and shNC is shown by '*'). FIG. 16D) Outline shows the transposon-based vector for the expression of the enzyme FAH, the marker GFP and the shRNA of interest (upper panel). Lower panel shows FAH knockout mice based liver repopulation assay. Outline shows the rational for the assay. If the knockdown of a certain shRNA is able to enhance regeneration and accelerate hepatocyte proliferation, we should be able to see a faster clonal expansion compared to a control shRNA starting from the stably integrated hepatocytes. FIG. 16E) GFP imager images. GFP imaging of explanted mouse livers shows enhanced clonal expansion (repopulation) of hepatocytes stably expressing shItfg1 compared to hepatocytes expressing shNC (day 18 after HDTV injection of 1.25 µg of the indicated plasmid; representative photographs are shown; n=8 per experimental group with knockdown by shItfg1.698, n=6 per experimental group with knockdown by shItfg1.680, and n=6 per control group). Light, white points represent GFP positive macroscopically visible clonal expansions. FIG. 16F) Histological analysis (immunostaining against GFP) for GFP-positive cells of mouse livers with stable expression of shItfg1.698, shItfg1.680 and shNC (shown are representative photographs). Day 18 after HDTV injection of 1.25 µg of the indicated plasmid (200× magnification). Increased clonal expansion can be seen for shItfg1. FIG. 16G) Quantification of GFP-positive cells (corresponding to F)) shows significant increase in GFP positive hepatocytes in case of Itfg1 knockdown compared to control. Each dot represents one animal. FIG. 16H) Repopulation survival assay. The right panel shows the outline of the experiments. We further diluted the plasmid amount delivered to the liver. At a certain dilution the amount of hepatocytes with stable integration will be not enough to expand and compensate for the loss of FAH−/− hepatocytes. However, if the knockdown by our candidate accelerates repopulation it might be sufficient to compensate and allow survival. Left panel shows the survival curve after 1:30 dilution. All animals injected with our construct expressing the control shRNA died, whereas all mice injected with our construct expressing shItfg1 survived. There is statistical significance between experiment and control. Statistical significance was calculated using a log rank test (n=5 per group).

FIG. 17B) Representative macrophotographs of the livers are shown. Already macroscopically differences between groups were visible. FIG. 17C) Picro Sirius Red staining (staining for fibrotic scar tissue) and Hematoxylin & Eosin staining on sections of indicated repopulated mouse livers (n=6 for shItfg1.698 and n=7 for control group, 50× magnification). FIG. 17D) The fibrotic score for each animal is shown. The score was given by a certified pathologist, who was blinded regarding the experimental groups. FIG. 17E) Representative macro-photographs of the livers with GFP-imaging system is shown. Livers are all green, hence fully repopulated.

FIG. 18A, 18B, 18C, 18D, 18E, 18F, 18G, 18H, 18I: ITFG1 expression in human liver tissue; knockdown protects against NASH related fibrosis (see also FIG. 35A-35F). FIG. 18A) Macroscopic pictures of mice with repopulated liver exposed to Western Diet. shItfg1 indicates liver was repopulated so that every hepatocyte expresses the shRNA targeting Itfg1, whereas shNC indicates repopulation so that every hepatocyte expresses a non-targeting control shRNA. Already macroscopically, livers with Itfg1 knockdown show reduced fibrosis. FIG. 18B-18D) Transcriptomic analysis of liver samples from ~150 patients show no significant expression change for Itfg1. FIG. 18E) ITFG1 is expressed in healthy liver tissue and in NASH Cirrhosis. FIG. 18F) Expression of ITFG1 in human tissues is shown. Data is taken from The Human Protein Atlas. FIG. 18G) Low expression of ITFG1 is associated with longer survival in case of liver cancer. Data is taken from The Human Protein Atlas. FIG. 18H) Scheme of retroviral backbone for generating stable cell lines. FIG. 18I) shRNAs efficiently targeting human ITFG1 were identified. Knockdown test by Western blot analysis using whole-cell lysates. HepG2 cells stably expressing the shRNA of interest were generate by retroviral infection and selection. GAPDH serves as a loading control.

FIG. 19B) Representation of fold change for each shRNA passing a β-value of 0.1 from male mice exposed to choline-deficient L-amino acid defined high fat diet for 8 weeks. The majority of shRNAs is deplete but a small number is clearly enriched. FIG. 19C) Principal component analysis based on normalized shRNA abundance level. We can see a clear separation based on diet exposure. FIG. 19D) Heatmap based enrichment/depletion for each animal for top-enriched and depleted shRNAs. Based on our analysis we identified 6 high confidence targets.

FIG. 20A, 20B: CDHFD mouse fatty liver model FIG. 20A) Choline deficient L-amino acid defined high fat diet (CDHFD) leads to fast and progressive fatty liver disease in mice. Already after 8 weeks of diet exposure mice show NASH with advanced fibrosis. FIG. 20B) Pathological evaluation. Histological slides of liver tissue form C56B16 mice exposed to the indicated time to the CDHFD or normal chow were evaluated and scored by a certified pathologist. Shown are the scoring results for steatosis and fibrosis. Each point represents an animal.

FIG. 21B) Summary of screening result for the shRNA expression cassette targeting Abcc4. Shown are the average relative reads for each group, the fold change and the log 2 fold change comparing CDHFD mice to NC mice. FIG. 21C-21E) Transcriptomic analysis of liver samples from ~150 patients show significant increase in Abcc4 gene expression at NASH late fibrosis and cirrhosis stage. Furthermore, an increase expression can be detected based on ballooning and fibrosis stage (Table: grey mark indicates significant upregulation of at least log 2 2 fold; *p<0.05, p<0.01, *p,0.005).

FIG. 22A, 22B, 22C, 22D, 22E: Pak3 is a potential therapeutic target for NAFLD FIG. 22A) Shown is the relative read numbers for the shRNA expression cassette targeting Pak3 for each animal (NC=normal chow, CD=CDHFD). FIG. 22B) Summary of screening result for the shRNA expression cassette targeting Pak3. Shown are the average relative reads for each group, the fold change and the log 2 fold change comparing CDHFD mice to NC mice. FIG. 22C-22E) Transcriptomic analysis of liver samples from ~150 patients show significant increase in Pak3 gene expression at NASH cirrhosis stage. Furthermore, an increase expression can be detected based on fibrosis stage (Table: grey mark indicates significant upregulation of at least log 2 2 fold; *p<0.05, p<0.01, *p,0.005).

FIG. 23A, 23B, 23C, 23D, 23E: Trnp1 is a potential therapeutic target for NAFLD FIG. 23A) Shown is the relative read numbers for the shRNA expression cassette targeting Trnp1 for each animal (NC=normal chow, CD=CDHFD). FIG. 23B) Summary of screening result for the shRNA expression cassette targeting Trnp1. Shown are the average relative reads for each group, the fold change and the log 2 fold change comparing CDHFD mice to NC mice. FIG. 23C-23E) Transcriptomic analysis of liver samples from ~150 patients show significant increase in Trnp1 gene expression at NASH cirrhosis stage. Interestingly, with increased steatosis and inflammation expression seems to be downregulated (Table: grey mark indicates significant upregulation of at least log 2 2 fold; boxed grey mark indicates significant downregulation of at least log 2 2 fold; *p<0.05, p<0.01, *p,0.005).

FIG. 24A, 24B, 24C, 24D, 24E: Apln is a potential therapeutic target for NAFLD FIG. 24A) Shown is the relative read numbers for the shRNA expression cassette targeting Apln for each animal (NC=normal chow, CD=CDHFD). FIG. 24B) Summary of screening result for the shRNA expression cassette targeting Apln. Shown are the average relative reads for each group, the fold change and the log 2 fold change comparing CDHFD mice to NC mice. FIG. 24C-24E) Transcriptomic analysis of liver samples from ~150 patients show significant increase in Apln gene expression at NASH cirrhosis stage. Interestingly, with increased inflammation expression seems to be downregulated (Table: grey mark indicates significant upregulation of at least log 2 2 fold; boxed grey mark indicates significant downregulation of at least log 2 2 fold; *p<0.05, p<0.01, *p,0.005).

FIG. 25B) Summary of screening result for the shRNA expression cassette targeting Kif20a. Shown are the average relative reads for each group, the fold change and the log 2 fold change comparing CDHFD mice to NC mice. FIG. 25C-25E) Transcriptomic analysis of liver samples from ~150 patients show a progressive increase in Kif20a gene expression till the NASH advanced fibrosis stage (Table: grey mark indicates significant upregulation of at least log 2 2 fold; *p<0.05, p<0.01, *p,0.005)

FIG. 26A, 26B, 26C, 26D, 26E: Ltb is a potential therapeutic target for NAFLD FIG. 26A) Shown is the relative read numbers for the shRNA expression cassette targeting Ltb for each animal (NC=normal chow, CD=CDHFD). FIG. 26B) Summary of screening result for the shRNA expression cassette targeting Ltb. Shown are the average relative reads for each group, the fold change and the log 2 fold change comparing CDHFD mice to NC mice. FIG. 26C-26E) Transcriptomic analysis of liver samples from ~150 patients show a progressive increase in Ltb gene expression till the NASH advanced fibrosis stage (Table: grey mark indicates significant upregulation of at least log 2 2 fold; *p<0.05, p<0.01, *p,0.005).

FIG. 28B) Bright field. Representative pictures are shown (both surfaces of the liver) (n=5 mice per experimental group, n=5 mice per control group). FIG. 28C) GFP-imaging. Representative pictures are shown (both surfaces of the liver). No GFP-positive tumor is observed. Livers are fully repopulated (strong GFP-positive signal). FIG. 28D) Hematoxylin & Eosin staining. Representative pictures are shown. No malignant disease is observed in both: experimental group and control group. Pathology evaluation is conducted by certified pathologist. The pathologist did not find malignant lesions in the liver. FIG. 28E) GFP (DAB) staining. Representative pictures are shown. Around 95% of hepatocytes are GFP-positive which means livers were fully repopulated.

FIG. 29B) Western blot analysis with concentration 6 µM shows efficient knockdown of Mfap4 by two different conjugates GalNAC-si Mfap4.1356 (SEQ ID NOs: 7092) and GalNAC-si Mfap4. 760 (SEQ ID NOs: 7093) compared to control. FIG. 29C) Western blot analysis with concentration 11 µM shows efficient knockdown of Mfap4 by two different conjugates GalNAC-si Mfap4.1356 and GalNAC-si Mfap4. 760 compared to control.

FIG. 30A, 30B, 30C: Grhpr knockdown for 1 year does not lead to liver cancer FIG. 30A) Schematic representation of the experiment. FAH−/− mice were injected with p/T-FAHIG-shRNA & SB13 expressing constructs via HDTV; then, mice were kept for 1 year to observe any tumor formation or abnormal liver histology. Livers were harvested at 1 year after injections. FIG. 30B) Bright field. Representative pictures are shown (both surfaces of the liver) (n=3 mice per experimental group, n=5 mice per control group). FIG. 30C) GFP-imaging. Representative pictures are shown (both surfaces of the liver). No GFP-positive tumor is observed. Livers are fully repopulated (strong GFP-positive signal).

FIG. 31B) shRNAs efficiently targeting human Grhpr were identified. Knockdown test by qPCR using whole-cell lysates. HepG2 cells were cotransfected with pMSCV vector. FIG. 31C) Knockdown test by Western blot using whole-cell lysates. HepG2 cells with stable expression of indicated shRNAs were generated by retroviral infection and selection. Tubulin serves as a loading control.

FIG. 32B) Western blot analysis with concentration 6 µM shows efficient knockdown of Grhpr by conjugate GalNAC-si Grhpr.361 (SEQ ID NO: 7094) compared to scrambled control. Western blot analysis with concentration 11 µM shows efficient knockdown of Grhpr by conjugate GalNAC-si Grhpr.361 compared to scrambled control.

FIG. 33B) Representative photographs of DAB Ki67-stained liver sections 42 h (n=4 per experimental group, n=6 per control group) and 48 h (n=5 per experimental group, n=10 per control group) post hepatectomy are shown (200× magnification). FIG. 33C) Quantification of Ki67 positive cells of DAB-stained liver sections (corresponding to B) show increased hepatocyte proliferation after partial hepatectomy in shItfg1-expressing livers compared to shNC livers (individual points represent individual animals, data shows average±SEM).

FIG. 34A, 34B, 34C, 34D, 34E, 34F, 34G: Itfg1 knockdown for 1 year does not lead to liver cancer FIG. 34A) Schematic representation of the experiment. FAH−/− mice were injected with p/T-FAHIG-shRNA & SB13 expressing constructs via HDTV; then, mice were kept for 1 year to observe any tumor formation or abnormal liver histology. Livers were harvested at 1 year after injections. FIG. 34B) Bright field. Representative pictures are shown (both surfaces of the liver). No tumor is observed (n=5 mice per experimental group, n=5 mice per control group). FIG. 34C) GFP-imaging. Representative pictures are shown (both surfaces of the liver). No GFP-positive tumor is observed. Livers are fully repopulated (GFP-positive). FIGS. 34D and 34F) Hematoxylin & Eosin staining. Representative pictures are shown. No malignant disease is observed in both: experimental group and control group. Pathology evaluation is conducted by certified pathologist. FIGS. 34E and 34G) GFP (DAB) staining. Representative pictures are shown. Around 95% of hepatocytes are GFP-positive which means livers were fully repopulated.

FIG. 35B) Representative macro-photographs of the livers are shown. Already macroscopically differences between groups were visible. FIG. 35C) Picro Sirius Red staining (staining for fibrotic scar tissue) and Hematoxylin & Eosin staining on sections of indicated repopulated mouse livers (representative images are shown; n=6 for shItfg1.698 and n=7 for control group, 50× magnification). FIG. 35D) The fibrotic score for each animal is shown. The score was given by a certified pathologist, who was blinded regarding the experimental groups. FIG. 35E) Objective, AI-based analysis of steatosis done by HistoIndex. Representative pictures are shown. FIG. 35F) Quantification analysis shows significantly lower steatosis score in experimental group (n=7 mice per group) compared to control group (n=7 mice per group).

FIG. 36B) After performing a broad protein array focused Western blot experiments were done. Results of Western blot are shown here. Proteins from fully repopulated livers were isolated. Especially P-MKK6/P-MKK3 are greater activated in case of Itfg1 knockdown compared to control. There are 3 biological replicates in experiment and 3 biological replicates in control. FIG. 36C) According to STRING database, all indicated proteins are interacting and are linked to cell growth and proliferation.

FIG. 37B) Western blot analysis with concentration 6 μM shows efficient knockdown of Itfg1 by two different conjugates GalNAC-si Itfg1.698 (SEQ ID NO: 7095) and GalNAC-si Itfg1.680 (SEQ ID NO: 7096) compared to control. Western blot analysis with concentration 11 μM shows efficient knockdown of Itfg1 by two different conjugates GalNAC-si Itfg1.698 and GalNAC-si Itfg1.680 compared to control.

FIG. 38B) Knockdown of Mfap4 as well as the knockdown of Itfg1 accelerates wound healing of mouse lung cells (cell line CCL206). FIG. 38C) Knockdown of Mfap4 as well as the knockdown of Itfg1 accelerates wound healing of mouse myoblast cells (Myoblast cell line CRL1772).

EXAMPLES

Example 1 Functional Genetic In Vivo RNAi Screen

An in vivo functional genetic screen was conducted to identify new modulators of liver regeneration as therapeutic targets to increase endogenous regeneration and counteract liver disease. This approach was originally pioneered by taking advantage of FAH−/− mice. From there the screening set up was further modified and improved, so it can be applied to any mouse independent of genetic background and modification (FIG. 1A). A focused shRNA library was delivered, comprising of 250 shRNAs targeting 89 genes, by hydrodynamic tail vine injection to the liver. Through the combination with a plasmid encoding for the sleeping beauty 13 transposase, stable integration was obtained in around 5 to 10% of hepatocytes. Therefore, a chimeric mouse liver in which the shRNA expressing hepatocytes are surrounded by "wt" hepatocytes is generated. To simulate chronic liver damage the inventors treated 3 times per week for 8 weeks mice with thioacetamid (TAA), a chemical inducing liver damage (FIG. 1A). Cycles of liver damage and compensatory regeneration induce a competitive environment. If the knockdown by a certain shRNA gives an advantage to hepatocytes, the cells will expand and an enrichment for the shRNA can be detected. In contrast, if the expression of a shRNA is detrimental, this shRNA should deplete. No change compared to the starting pool indicates no effect in this environment. The abundance of the shRNAs can be determined by Illumina based deep sequencing. For sequencing, the genomic DNA was isolated from the liver, the shRNA expressing cassette was amplified with primers including Illumina adapter sequences and the product was directly sequenced.

Figure 1D:
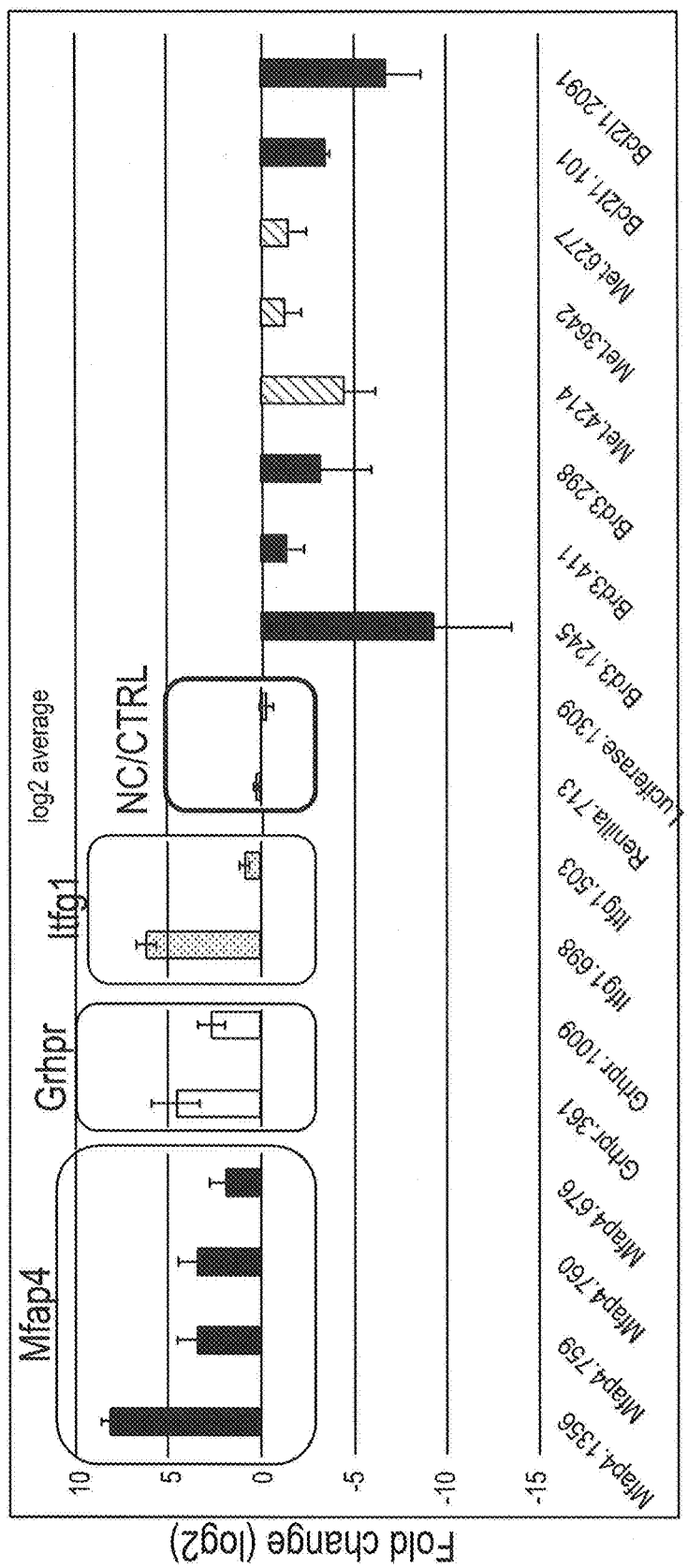

Also, the majority of the shRNAs were depleted in this screen, a subset was consistently enriched in all biological replicates (5 independent mice) (FIG. 1B-1C). Importantly and giving confidence in the screen, two independent non-targeting control shRNAs (also named shNC or shCTRL; one targeting Renilla and one targeting luciferase, both are not expressed in mice) were not enriched or depleted. Furthermore, three independent shRNAs targeting c-Met the receptor for hepatocyte growth factor and essential for liver regeneration were depleted (FIG. 1D). To avoid off-target effects of the shRNAs the inventors focused on targets against which at least two independent shRNAs were enriched (FIG. 1D). Four independent shRNAs were found enriched targeting Mfap4, two independent shRNAs for each targeting Grhpr and Itfg1.

Example 2 Validation of Identified Therapeutic Targets

Mfap4—Microfibril Associated Protein 4

Figure 2A:
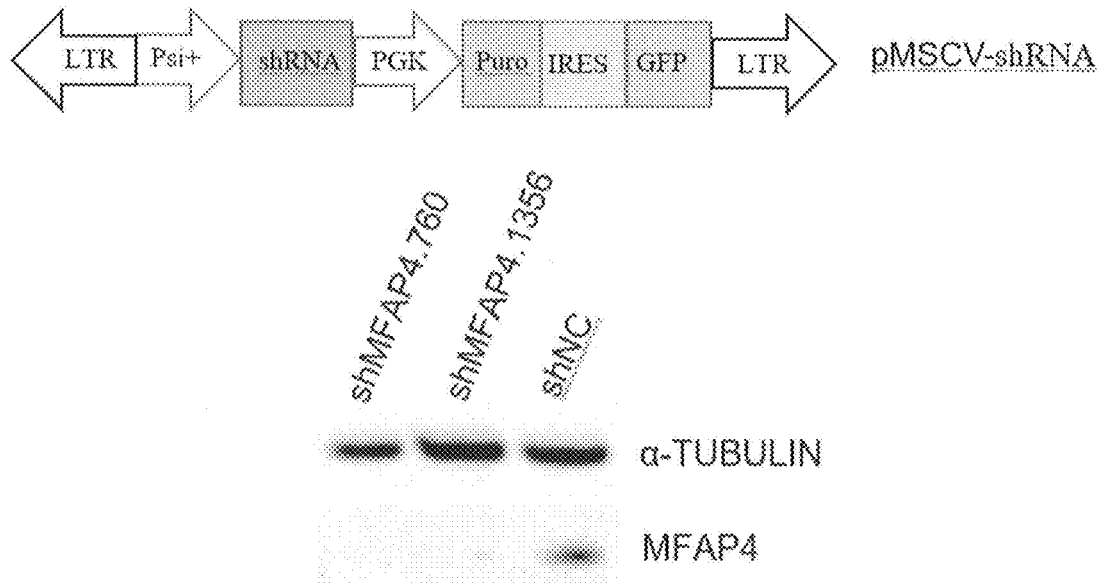
Figure 2B:
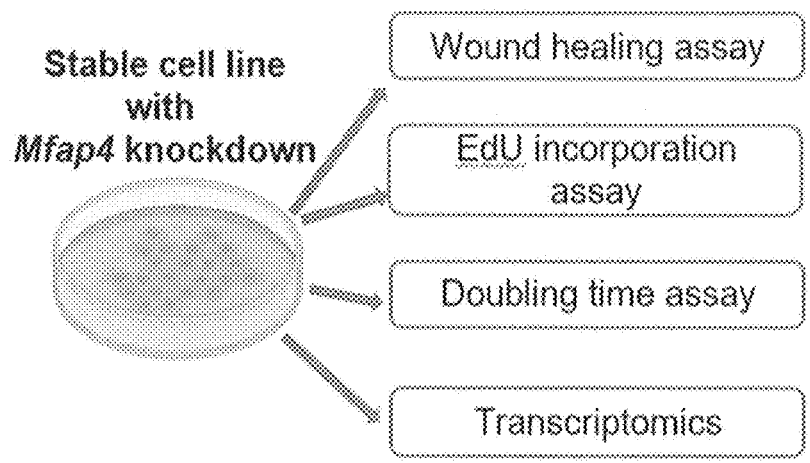
Figure 2D:
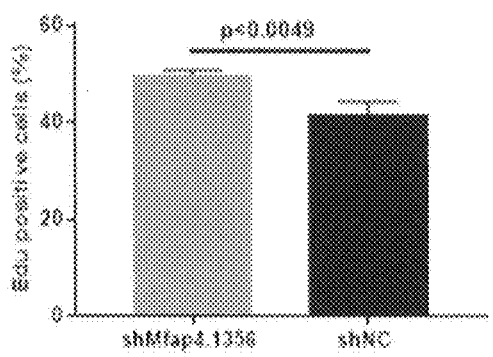

For validation, the knockdown efficiency of the two top-enriched shRNAs targeting Mfap4 in vitro were first tested (FIG. 2A). Both shRNAs show efficient knockdown. For each shRNA stable expressing cell lines (FIG. 2B) were generated as well as for a non-targeting control shRNA and the effect of the shRNAs in a wound healing assay was tested. The knockdown of Mfap4 (two independent shRNAs tested) increased wound closure in TIB 73 (BNLCL.2) cells and AML 12 cells, indicating increased proliferation (FIGS. 2C and 2G). Furthermore, using the stable cell lines the inventors checked for enhanced cell replication by EdU incorporation and determining the cell doubling time (FIG. 2D-2E). Accelerated proliferation was clearly detected. Cell cycle analysis by flow cytometry using the Guava Muse Cell Analyzer showed greater cell amounts (shown is amount of cell in %) in the G2 phase of cell cycle for cells with stable Mfap4 knockdown by shMfap4.1356 (SEQ ID NO: 1) and shMfap4.760 (SEQ ID NO: 2) compared to the non-targeting control (shNC), likewise indicating increased proliferation (FIG. 2F).

Figure 3A:
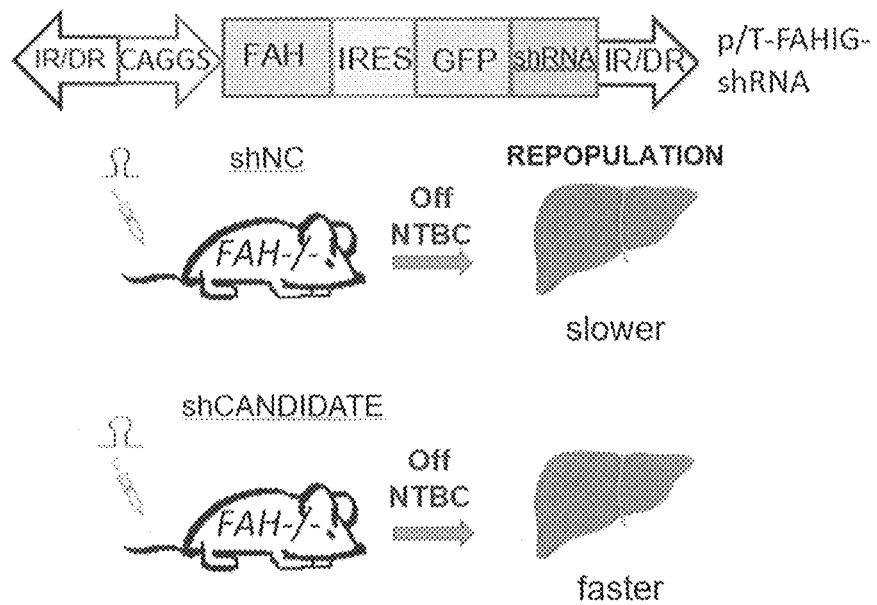
FIG. 3A, 3B, 3C, 3D, 3E, 3F: Mfap4 knockdown accelerates liver repopulation FIG. 3A) FAH knockout mice based liver repopulation assay. Upper panel shows the outline of the transposon based vector for the expression of the enzyme FAH, the marker GFP and the shRNA of interest. Lower panel shows the outline and rational for the assay. If the knockdown of a certain shRNA is able to enhance regeneration and accelerate hepatocyte proliferation, we should be able to see a faster clonal expansion compared to a control shRNA starting from the stably integrated hepatocytes.
Figure 3B:
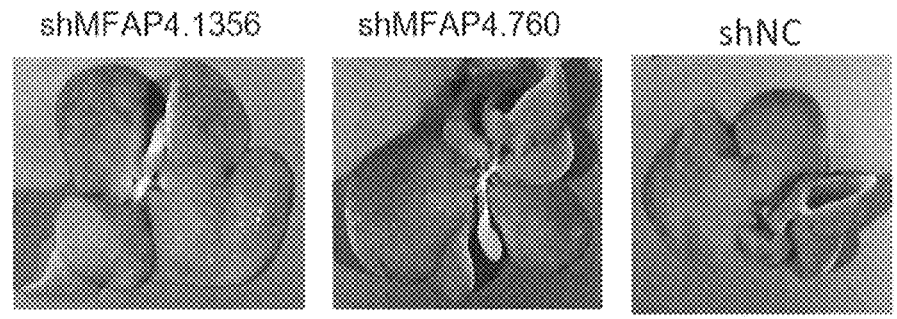
Figure 3C:
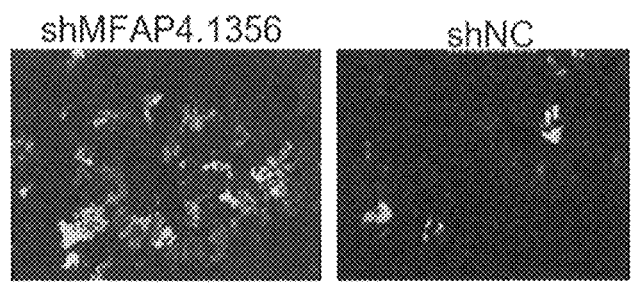
Figure 3D:
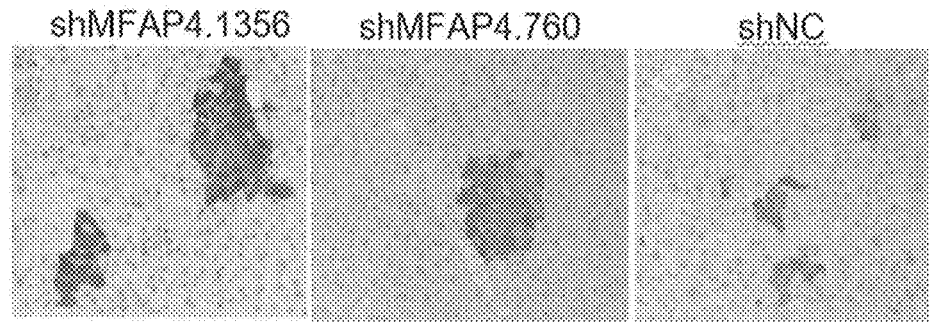
Figure 3E:
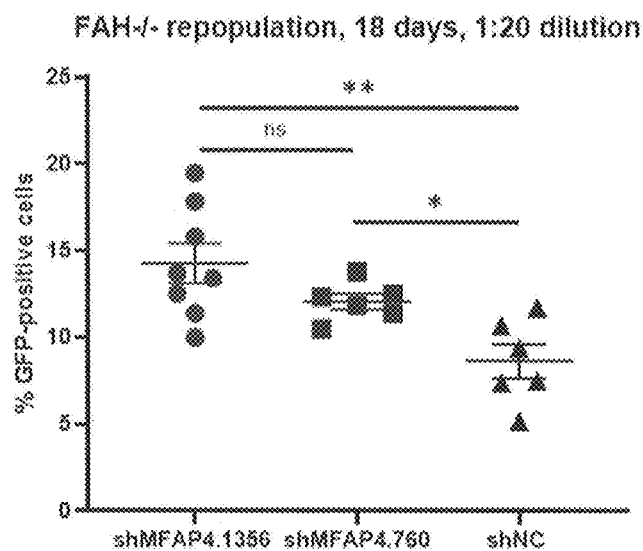
Figure 3F:
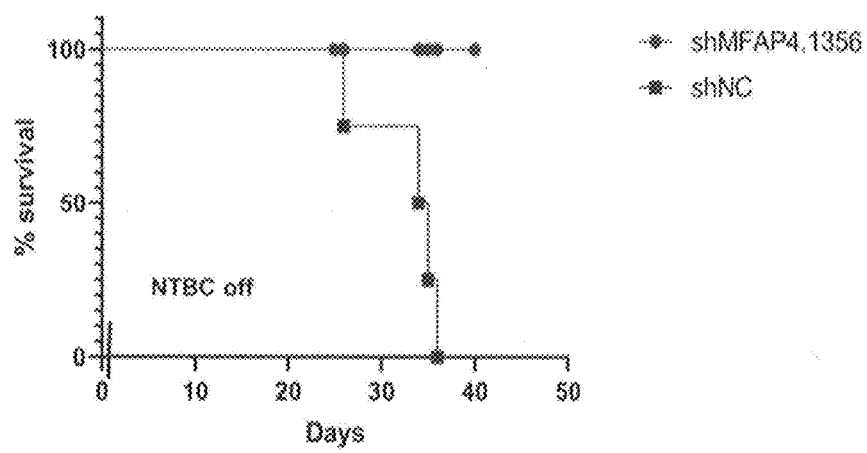

The inventors then took advantage of the FAH (fumarylacetoacetate) knock out mouse. The defect in the tyrosine metabolism leads to the accumulation of toxic side products in hepatocytes resulting in liver failure. Delivering a construct to around 5-10% of hepatocytes for the expression of the missing enzyme FAH and the shRNAs by hydrodynamic tail vine injection, the repopulation efficiency could be tested. If the knockdown by the shRNA targeting Mfap4 enhances regeneration and proliferation, a faster clonal expansion should be seen (FIG. 3A). As expected, knockdown of Mfap4 enhances repopulation detected by GFP-imaging of the whole liver (FIG. 3B), native-GFP fluorescence of cryosections (FIG. 3C) of the liver and antibody based staining for GFP in paraffin sections (FIG. 3D-3E). A further dilution of the amount of injected plasmids could reduce the amount of hepatocytes with stable expression of FAH, GFP and the shRNA of interest, so that the FAH expressing hepatocytes cannot fast enough expand and compensate for FAH−/− hepatocyte loss. However a shRNA dependent acceleration of regeneration might be able to allow survival. At a 1:30 dilution still all shMfap4.1356 (SEQ ID NO: 1) injected mice survive whereas all control shNC injected mice die (FIG. 3F). This further supports the Mfap4 knockdown mediated acceleration, as only in case of Mfap4 the hepatocytes expand fast enough to compensate for hepatocyte loss.

Figure 5A:
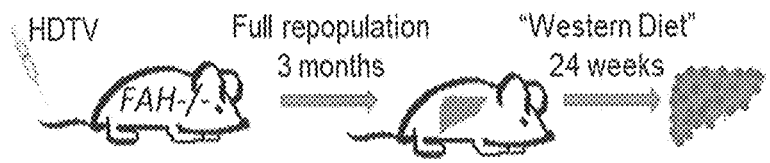
FIG. 5A, 5B, 5C, 5D, 5E, 5F: Mfap4 knockdown attenuates NASH related liver fibrosis FIG. 5A) Experimental outline. FAH−/− mice were injected with our constructs, then, mice were kept for full repopulation for 3 months, so that every hepatocyte in the liver expresses the shRNA construct of interest. After full repopulation was reached mice were exposed to the "Western Diet" (high fat diet and 60% fructose) for 24 weeks. Livers were harvested, processed and analyzed.
Figure 5B:
Figure 5C:
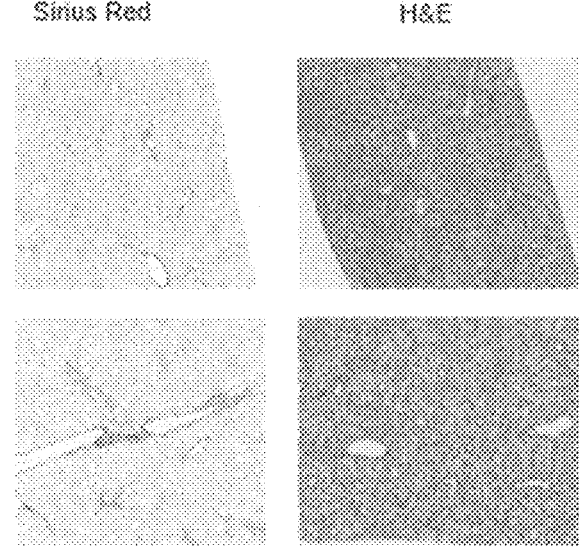
Figure 5D:
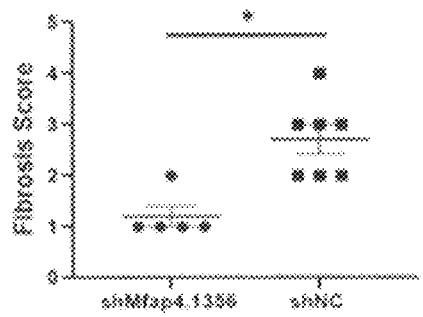
Figure 5E:
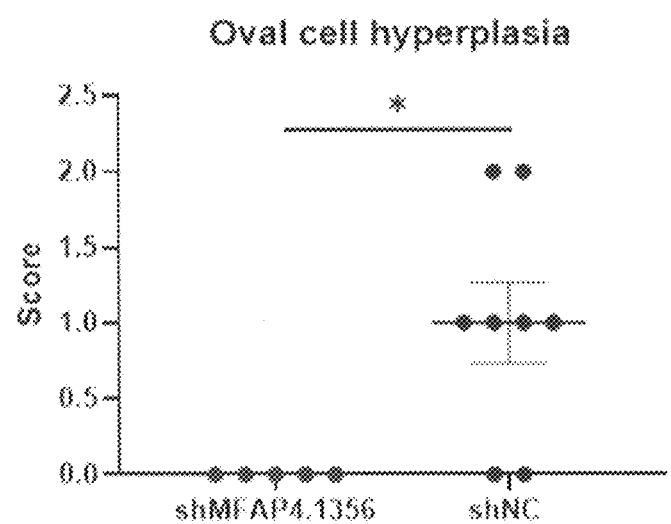
Figure 5F:
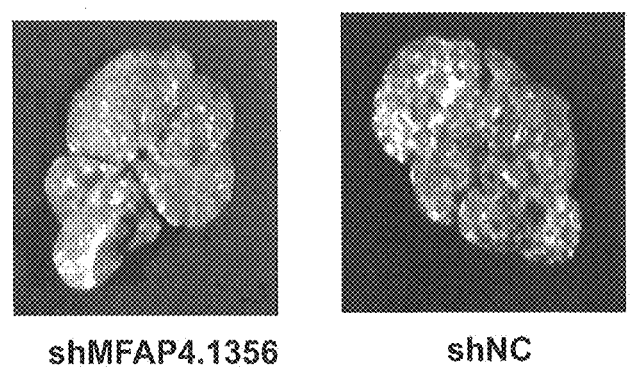
Figure 6A:
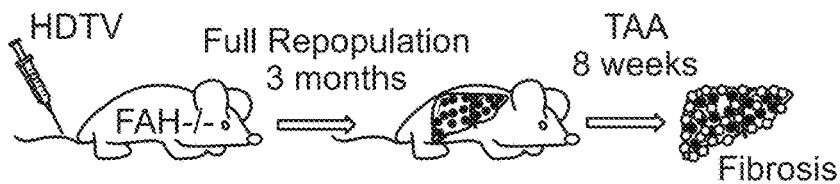
FIG. 6A, 6B, 6C, 6D: Mfap4 knockdown attenuates chronic liver damage related liver fibrosis FIG. 6A) Experimental outline. FAH−/− mice were injected with our constructs, then, mice were kept for full repopulation for 3 months. After that chronic liver damage was induced by repetitive doses of thioacetamide administered intraperitoneal 3 times per week for 8 weeks. Livers were harvested, processed and analyzed.
Figure 6B:
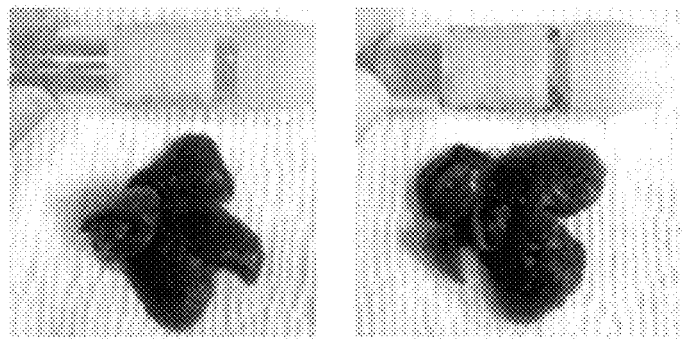
Figure 6C:
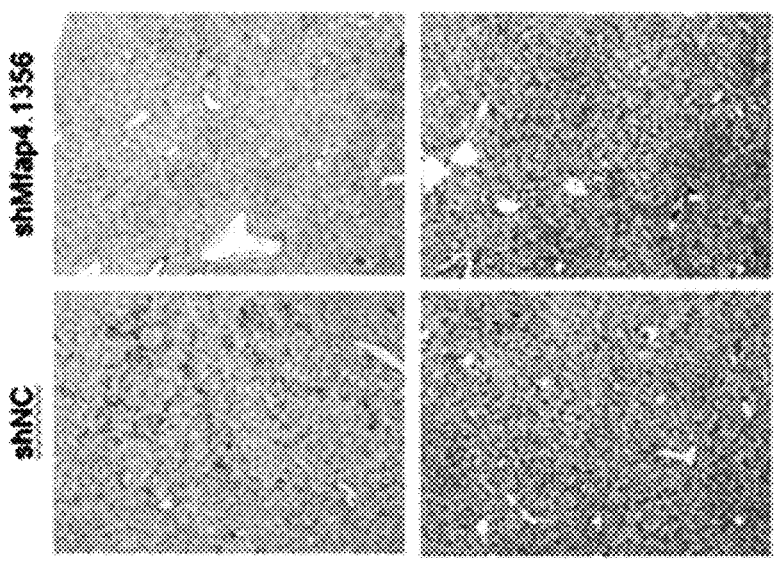
Figure 6D:
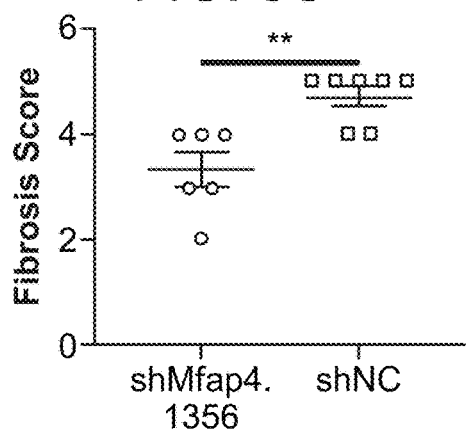
Figure 7A:
FIG. 7A, 7B, 7C, 7D, 7E, 7F, 7G, 7H, 7I, 7J: Mfap4 knockdown accelerates liver regeneration after partial hepatectomy (PH) FIG. 7A) Experimental outline. FRGN were injected with our constructs, then, mice were kept for full repopulation for 3 months. FRGN mice are FAH−/−, Rag2−/−, Il2rg−/− on a NOD background and are immune compromised. After full repopulation of mouse liver, ⅔ of the liver was surgically removed. The remaining regenerating liver was harvested 48 h after surgery.
Figure 7B:
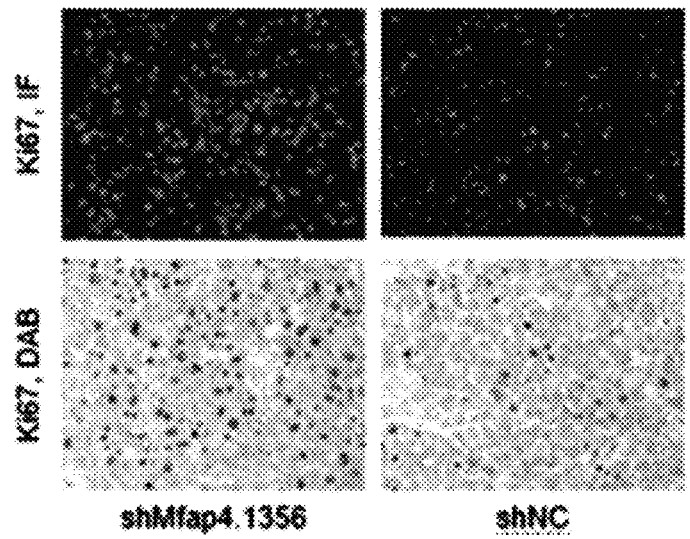
Figure 7C:
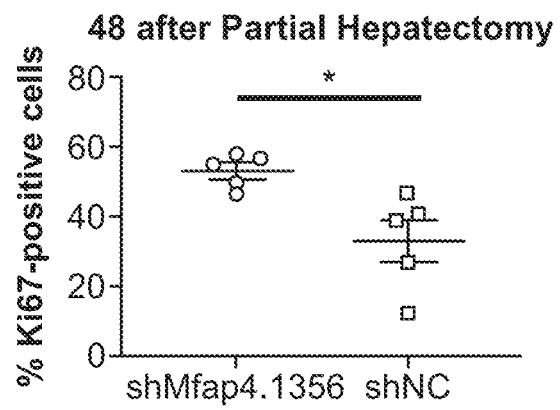
Figure 7D:
Figure 7E:
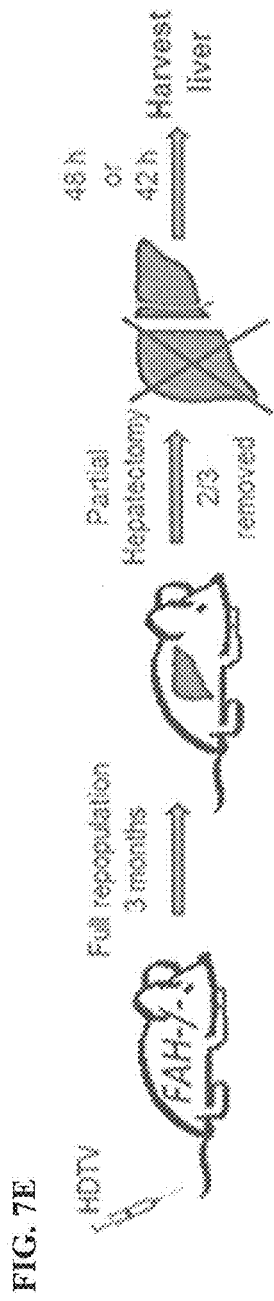
Figure 7F:
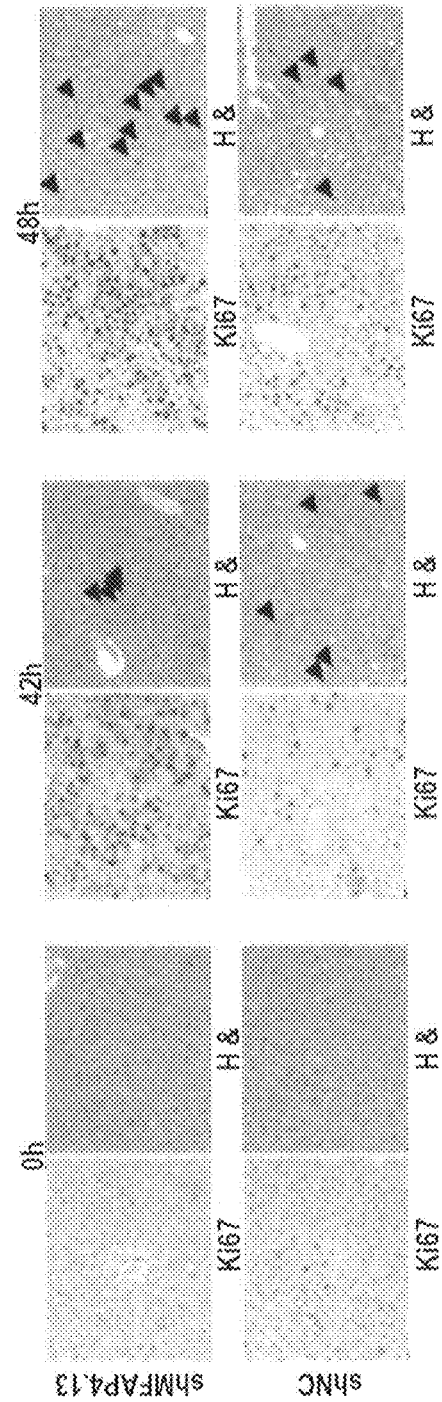
Figure 7G:
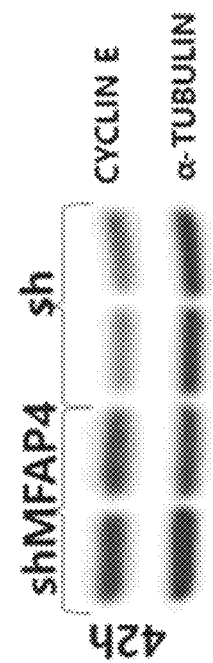
Figure 7H:
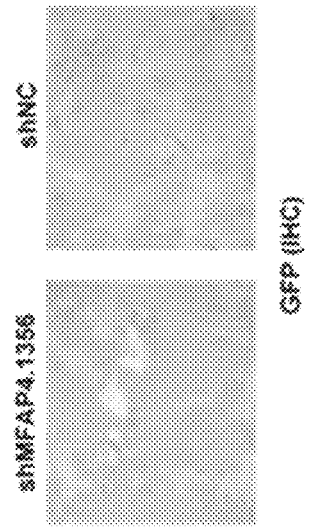
Figure 7I:
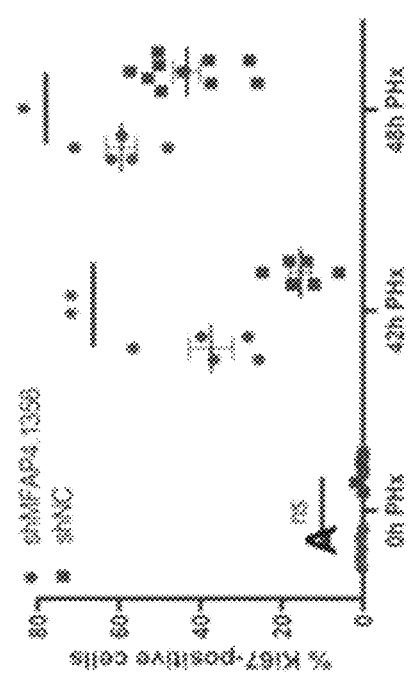
Figure 7J:
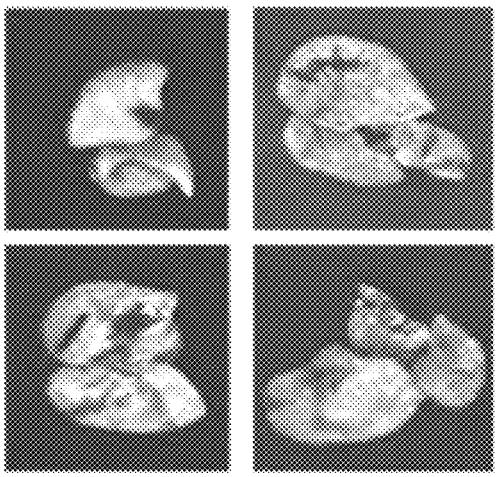

The "Western Diet" induces progressive NAFLD, leading to NASH and fibrosis (FIG. 4). The inventors repopulated FAH−/− mouse liver so that all hepatocytes express either a shRNA targeting Mfap4 or a non-targeting control shRNA. After full repopulation, the mice were exposed to the "Western Diet" (FIG. 5A). Knockdown of Mfap4 clearly attenuates disease progression, reflected in reduced fibrosis (FIG. 5B-5F). Chronic TAA exposure to shMfapp4 and shCTRL repopulated FAH mice (FIG. 6A) was also applied. Consistent with the screening results Mfap4 knockdown protects against TAA induced liver damage and fibrosis (FIG. 6B-6D). As an acute damage model, a ⅔ partial hepatectomy (PH) on repopulated mice (FIGS. 7A and 7E) was performed. Enhanced Ki67 staining (FIGS. 7B-7C and 7F-7G) as well as earlier activation of cyclin A (FIG. 7D) and cyclin E (FIG. 7H), respectively, after PH indicate faster regeneration. GFP-imaging (FIG. 7I) and DAB GFP staining (FIG. 7J) of FAH−/− livers after ⅔ surgical partial removal of livers indicated that mice were fully repopulated.

Figure 8E:
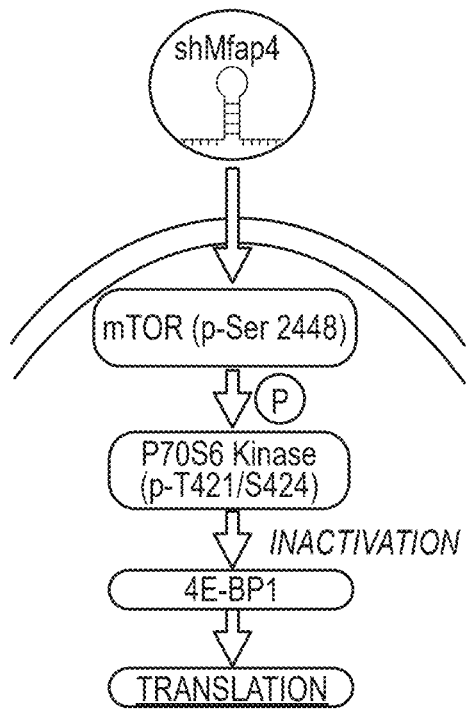
Figure 8F:
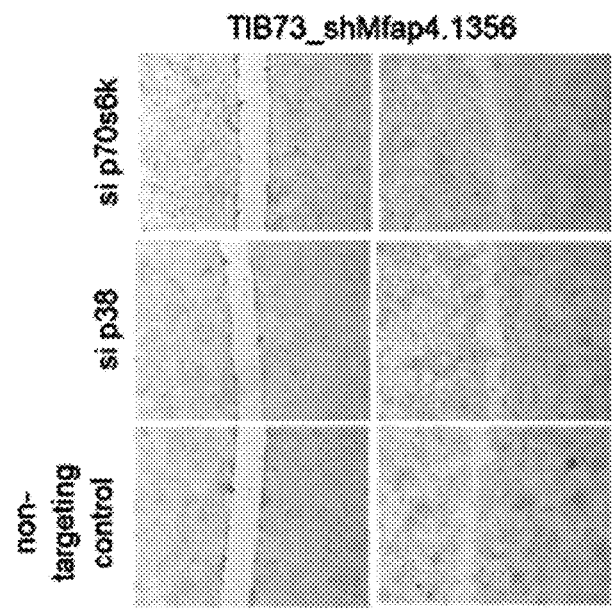
Figure 8G:
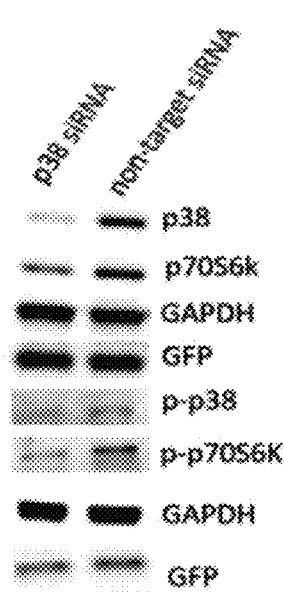
Figure 8H:
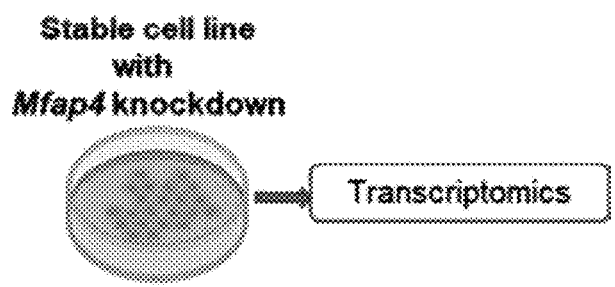
Figure 8I:
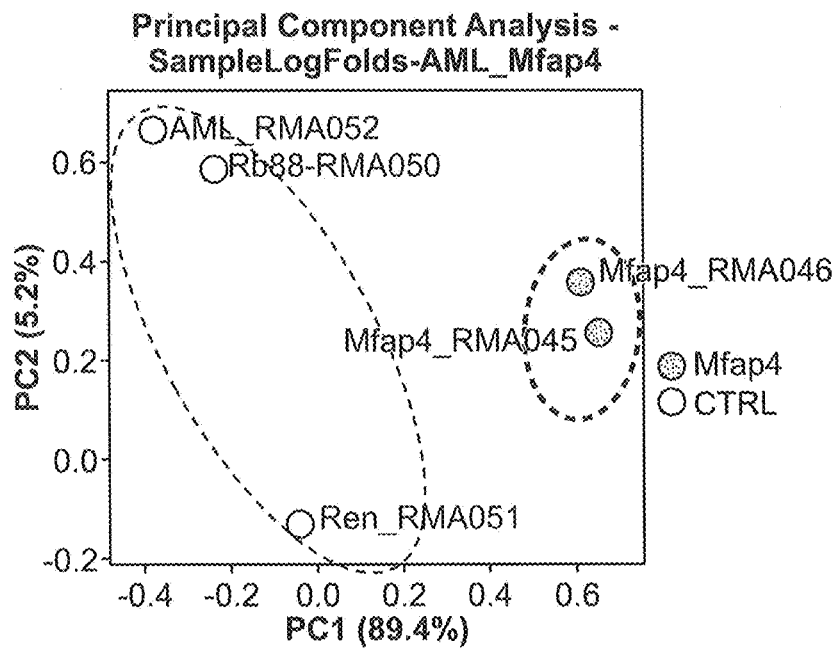
Figure 8J:
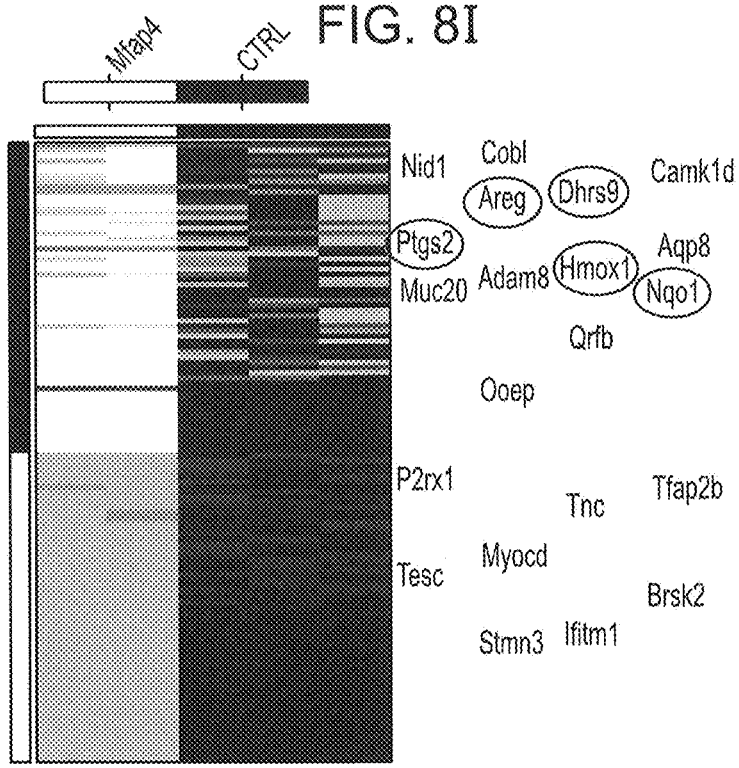
Figure 8K:
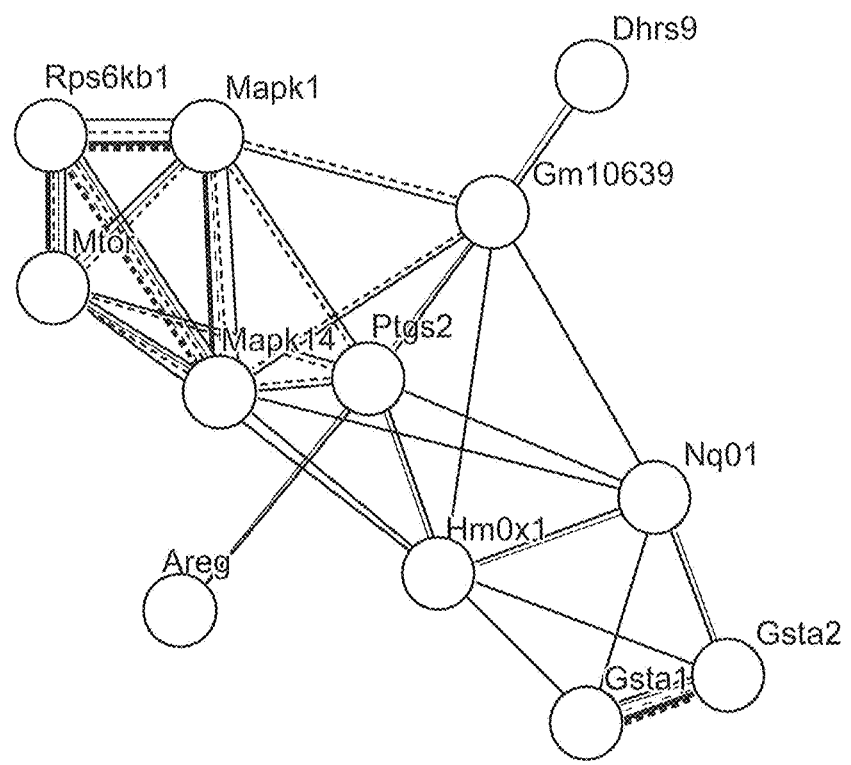

The inventors also checked for differences in pathway activation by protein arrays and Western blot after full repopulation with either shMfap4 or non-targeting control shRNA. Livers were collected and proteins for protein array and Western blot as well as RNA for transcriptomics were isolated (FIG. 8A-8H). Consistently with an enhanced regenerative capacity Mfap4 knockdown induces activation of mTOR, p70S6K, ERK and p38 (FIGS. 8B and 8D). The identified pathways are all linked (FIGS. 8C, 8E and 8K) based on STRING analysis (string-db.org) and impact cell growth and proliferation. P70S6K is a major substrate of mTOR (FIG. 8E) and contributes to liver regeneration. Furthermore, impairments in p70S6K and ERK signaling is linked to the age dependent decline of liver's regenerative capacity. Using the in vitro wound healing assay, double knockout experiments combining the stable shMfap4 or shCTRL expressing cell lines with siRNAs targeting either p70s6k or p38 (FIG. 8F-8G) were conducted. A slowdown in wound healing under such conditions was detected. This puts the knockdown of Mfap4 in line with enhancing regeneration and rejuvenating the liver. Principal component analysis for AML12-shMfap4.1356, AML12-shMfap4.760, and AML12-shNC shows cluster separation between experiment (shMfap4) and control (shNC). A heatmap comparison of Mfap4 and control indicates that genes known to be involved in liver regeneration according to the literature, such as Ptgs2, Areg, Dhrs9, Hmox1 and Nqo1, are upregulated after Mfap4 knockdown compared to control (FIG. 8H-8J). Furthermore, string analysis shows that the transcriptomic pathways coming from the cell line as well as the proteomic identified pathways from the repopulated liver are connected (FIG. 8K).

Figure 9A:
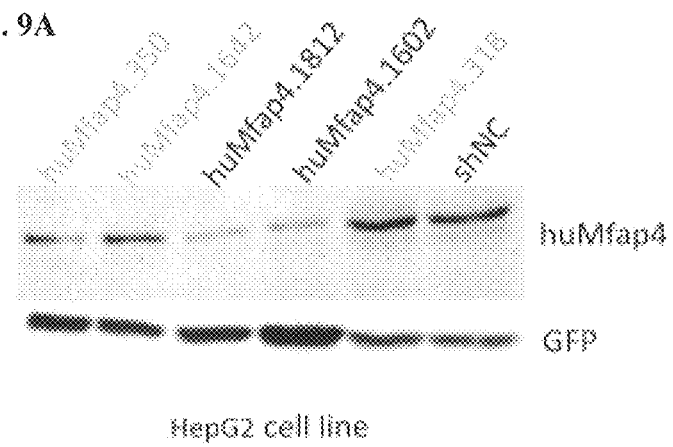
FIG. 9A, 9B, 9C, 9D, 9E, 9F, 9G, 9H, 9I, 9J, 9K, 9L, 9M, 9N, 9O: Mfap4 effect is conserved in human cells FIG. 9A) shRNAs were identified that efficiently targeting human Mfap4. Knockdown test by Western blot analysis using whole-cell lysates. HepG2 cells with stable expression of indicated shRNAs targeting human Mfap4 were generated by retroviral infection and selection. Tubulin serves as a loading control.
Figure 9B:
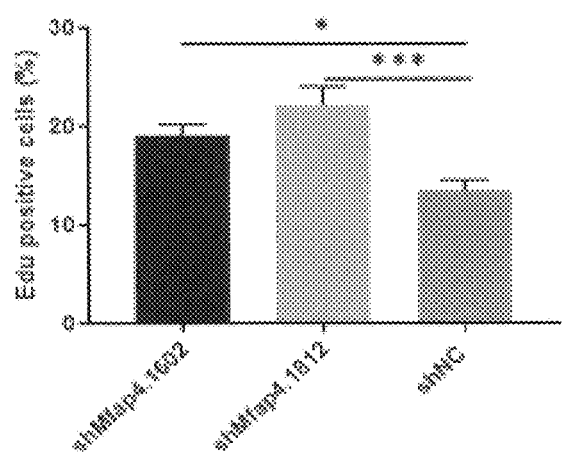
Figure 9C:
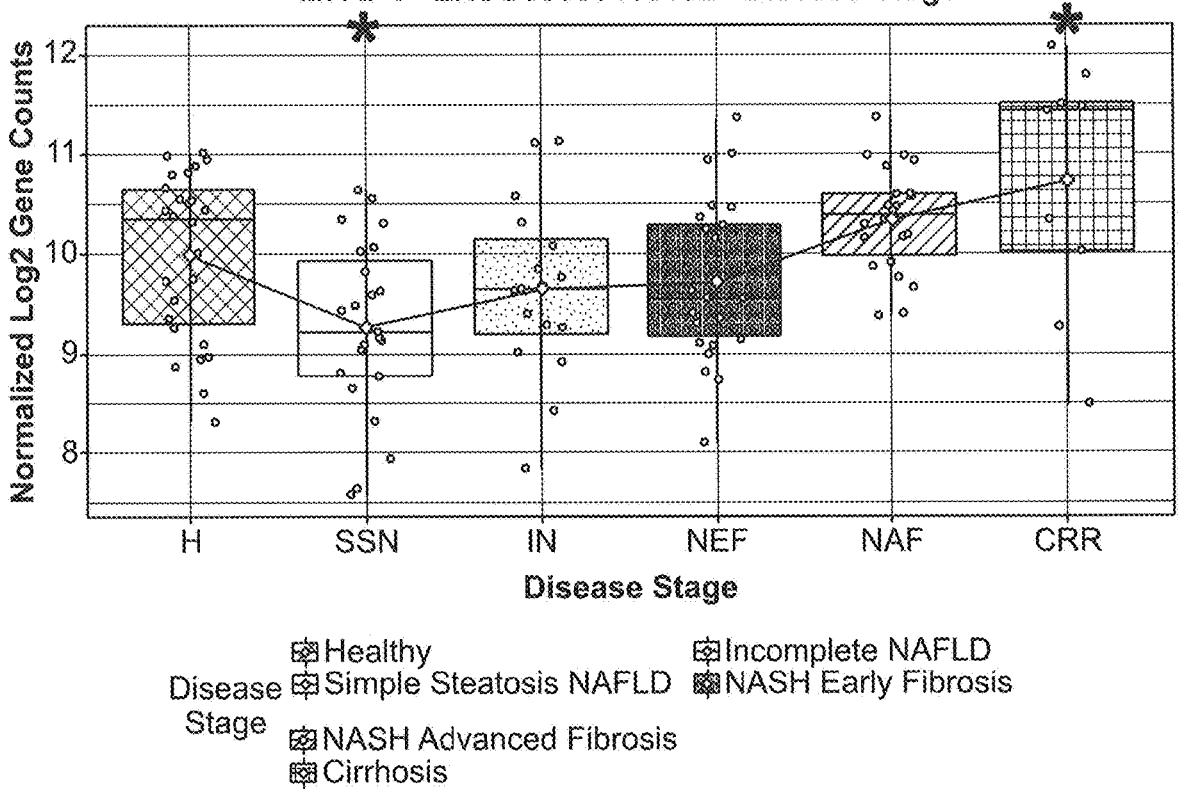
Figure 9D:
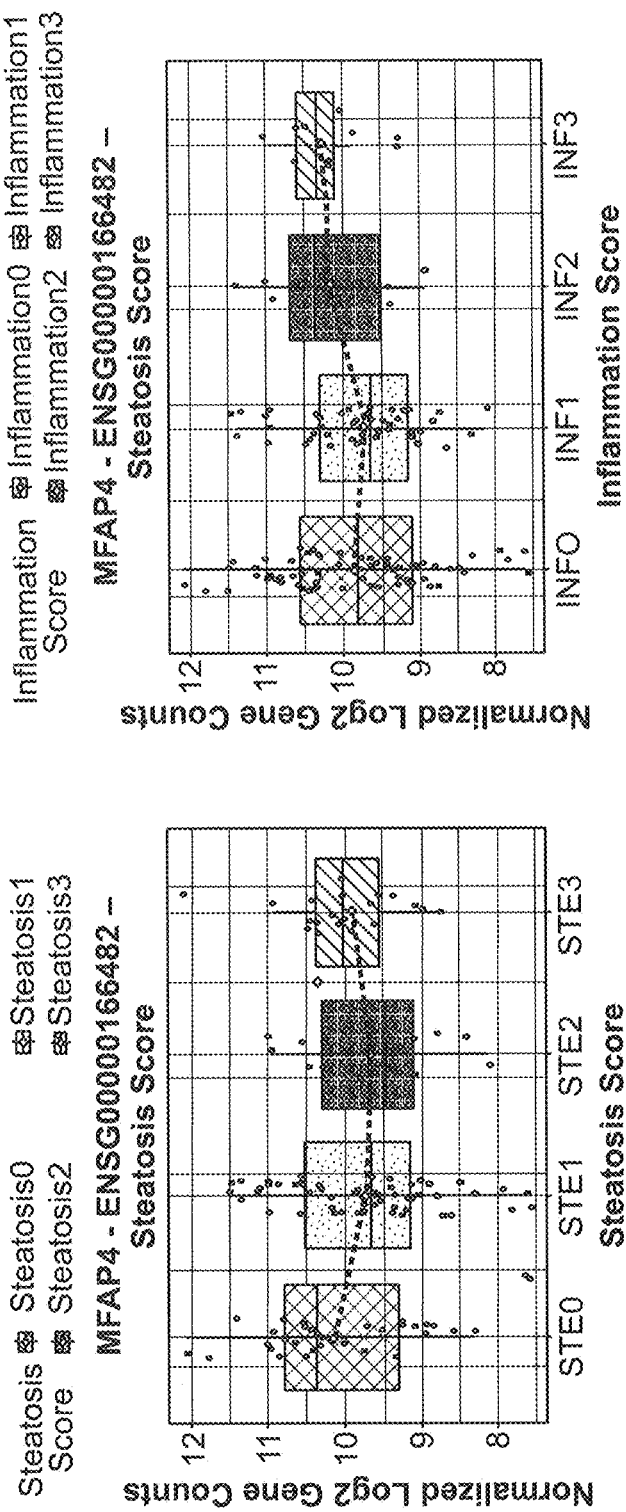
Figure 9E:
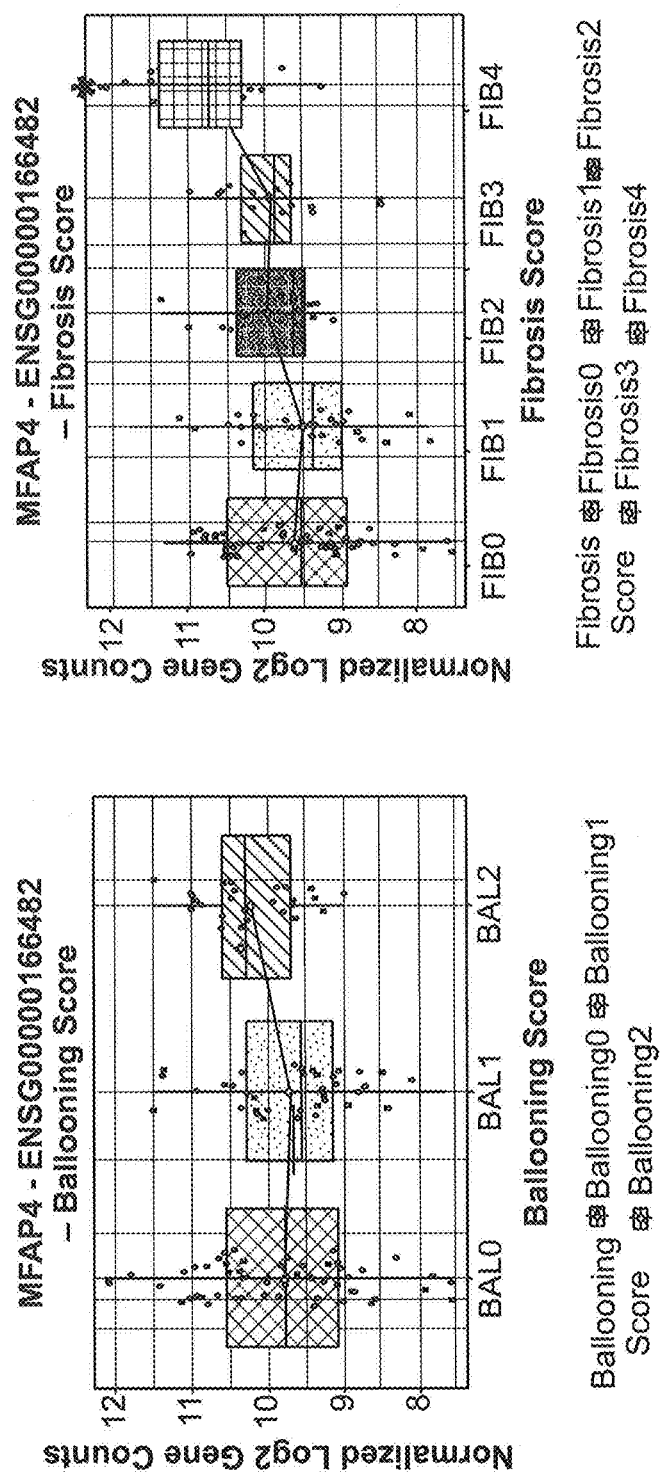
Figure 9F:
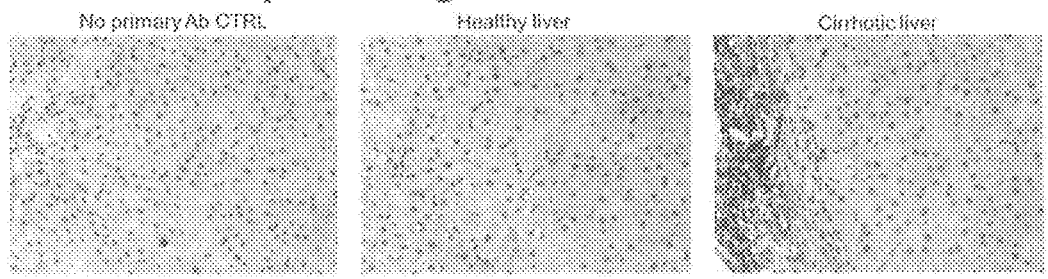
Figure 9G:
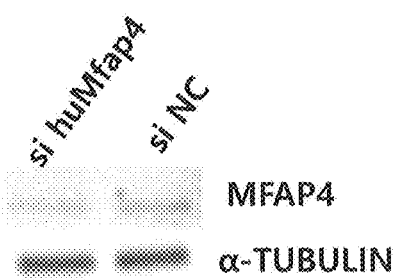
Figure 9H:
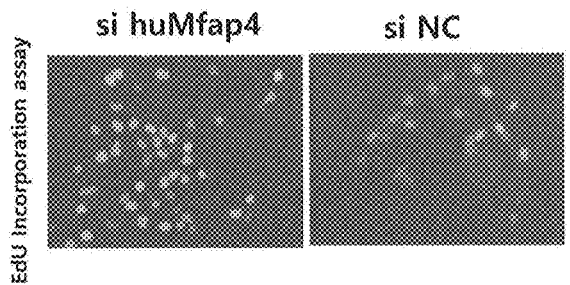
Figure 9I:
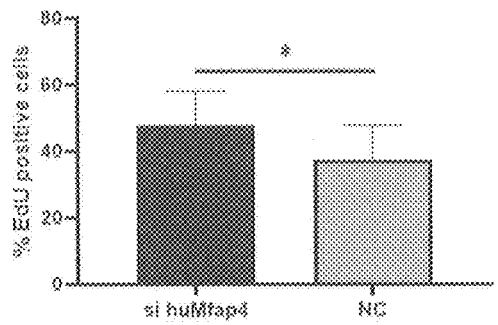
Figure 9J:
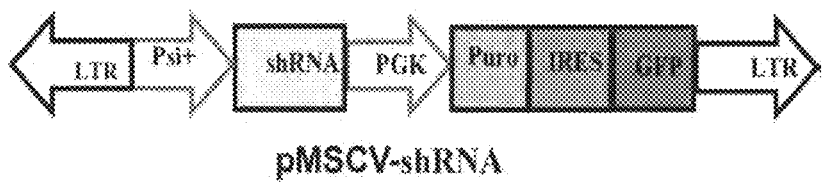
Figure 9K:
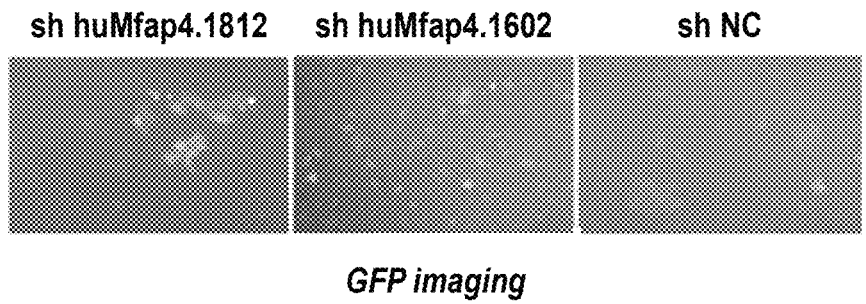
Figure 9L:
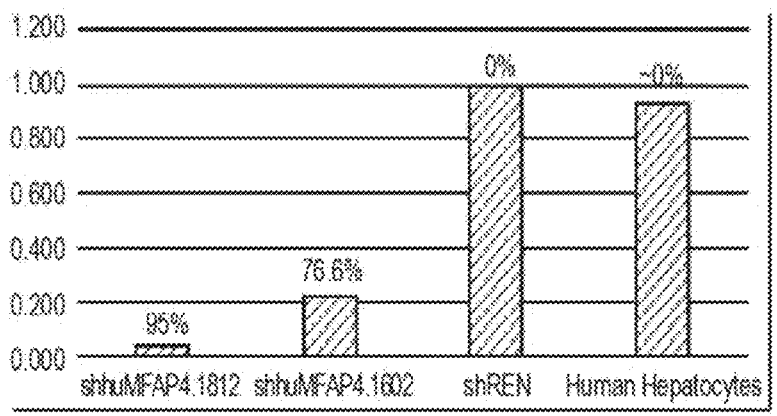
Figure 9M:
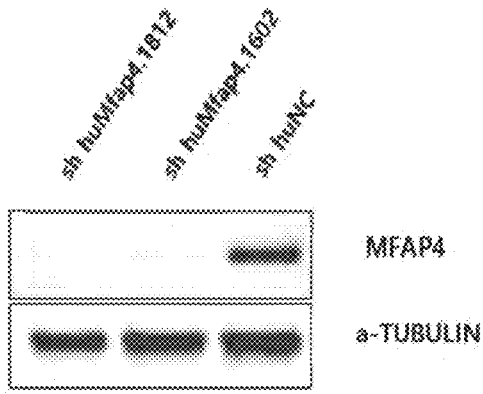
Figure 9N:
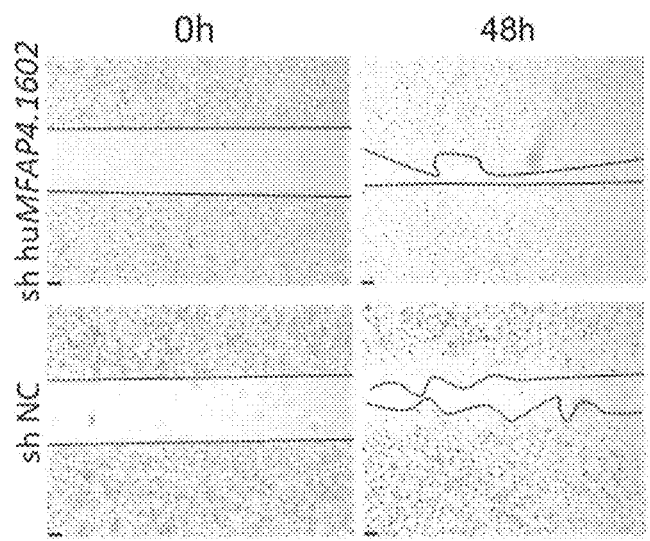
Figure 9O:
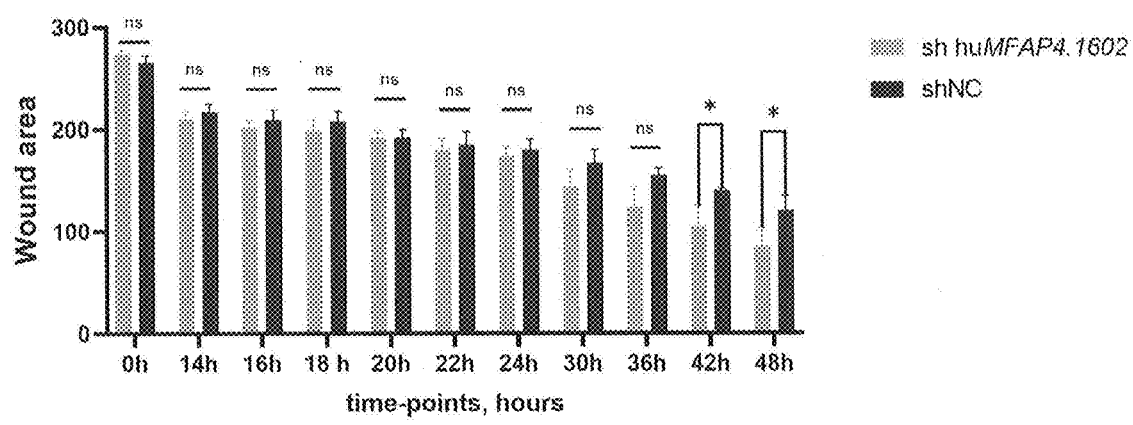

The inventors then identified 2 independent shRNAs targeting human Mfap4: huMfap4.1812 (SEQ ID NO: 7100) and huMfap4.1602 (SEQ ID NO: 7097). Efficient knockdown in the human liver cancer cell line HepG2 (FIG. 9A) was observed. Furthermore, both shRNAs show a strong on-target knockdown of huMfap4 compared to non-targeting control as determined by qPCR analysis (FIG. 9K) and Western blot (FIG. 9L) in immortalized human hepatocytes-SV40 (FIG. 9I-9J). Edu incorporation assay indicates a conserved mechanism between mouse and human, as higher EdU incorporation in human HepG2 cells with Mfap4 knockdown was seen (FIG. 9B), transient knockdown of Mfap4 by siRNA in immortalised human hepatocytes shows higher EdU incorporation (FIG. 9G-9H), and stable knockdown of Mfap4 in immortalised human hepatocytes enhances wound healing (FIG. 9M-9N).

Importantly expression of Mfap4 in the liver increases in NAFLD patients with cirrhosis (FIG. 9C-9D), based on a local patient cohort. This is consistent with previous studies indicating increased Mfap4 in liver and lung fibrosis. Interestingly, Mfap4 was suggested as potential biomarker for non-invasive assessment of hepatic fibrosis in hepatitis C patients. Staining for Mfap4 of human liver tissue from healthy and cirrhotic liver done by the inventors also showed increased detection in the diseased liver. Interestingly beside strong staining in fibrotic scar areas Mfap4 was also detected in the cytoplasm and nucleus of hepatocytes (FIG. 9E). Mfap4 is thought to be an extracellular matrix protein but not much is known about its role in hepatocytes. It represents therefore a new target for liver disease therapy, with new biology.

Figure 28A:
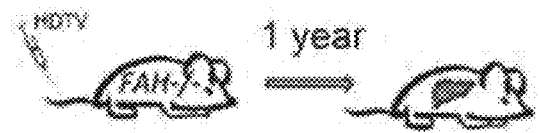
FIG. 28A, 28B, 28C, 28D, 28E: Mfap4 knockdown for 1 year does not lead to liver cancer FIG. 28A) Schematic representation of the experiment. FAH−/− mice were injected with p/T-FAHIG-shRNA & SB13 expressing constructs via HDTV; then, mice were kept for 1 year to observe any tumor formation or abnormal liver histology.
Figure 28B:
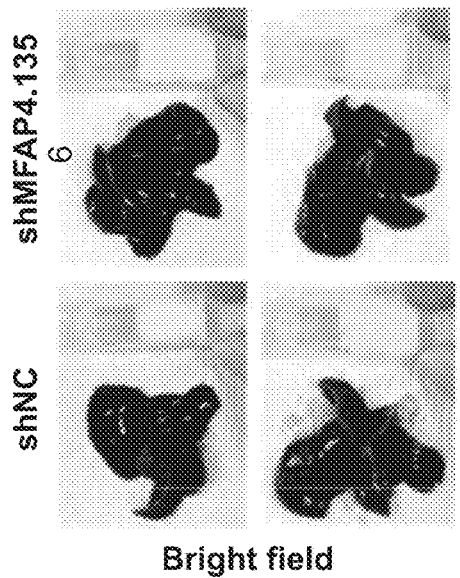
Figure 28C:
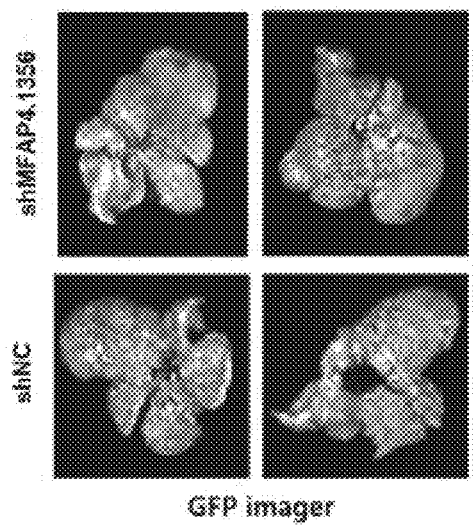
Figure 28D:
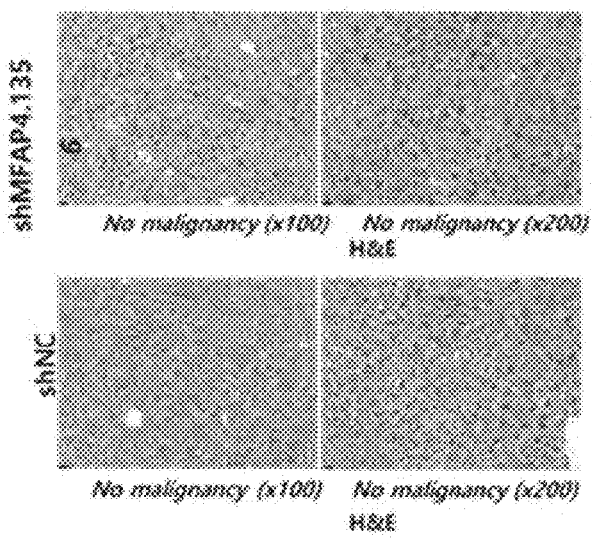
Figure 28E:
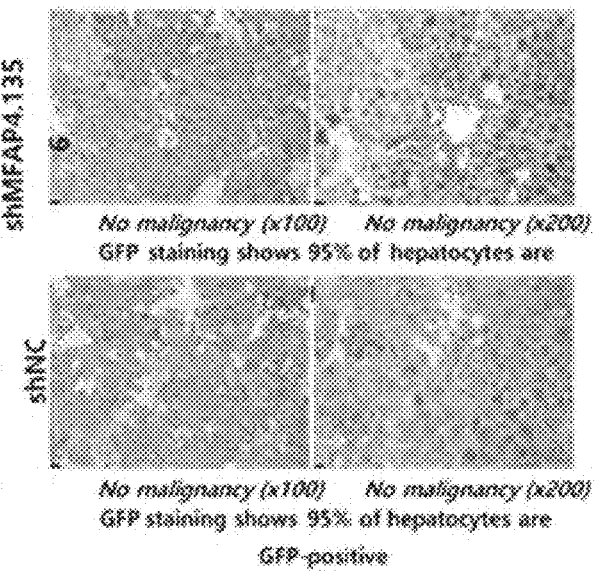

The inventors also investigated the development of liver cancer in Mfap4 treated mice. shMfap4 constructs were delivered by HDTV to FAH−/− mice. After keeping mice for 1 year, livers were harvested to determine any tumor formation in the liver (FIG. 28A). No GFP-positive tumor is observed and livers are fully repopulated as indicated by a strong GFP-positive signal (FIGS. 28B-28C and 28E). Around 95% of hepatocytes are GFP-positive. Also, Hematoxylin & Eosin staining did not reveal any malignant disease in both the shMfap4 and shNC treated group. Certified pathologists who conducted the evaluation did not find malignant lesions in the liver (FIG. 28D). The experiments show that Mfap4 knockdown for 1 year does not lead to liver cancer in mice.

Figure 29A:
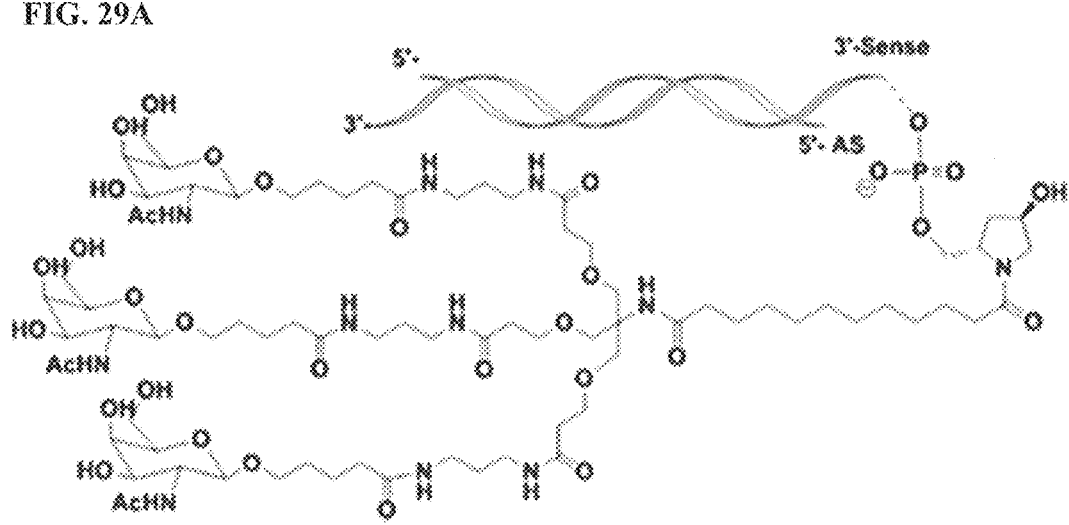
FIG. 29A, 29B, 29C: GalNAC conjugates with siRNA against Mfap4 (BNL CL.2 cell line; 72 h post-transfection) FIG. 29A) Structure of GalNAC-siRNA conjugate used in studies. Exact backbone modifications can be found in the sequence appendix (SEQ ID NOs: 7092 and 7093). The target sequence for the siRNA was based on the shRNA guide sequence.
Figure 29B:
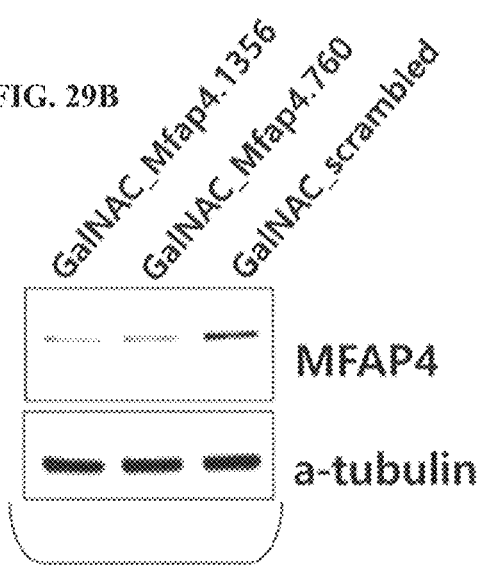
Figure 29C:
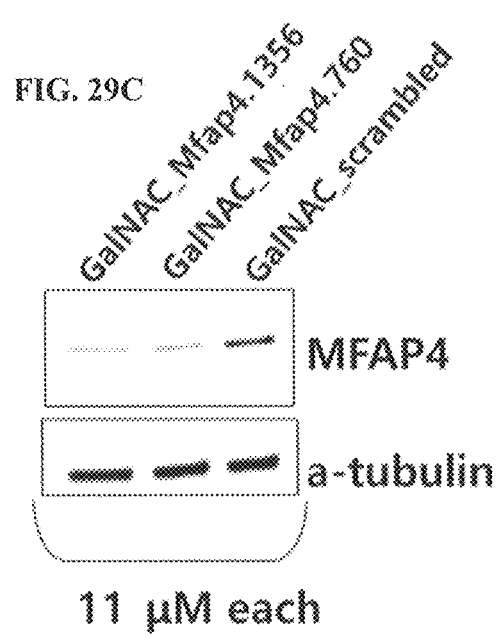

Modified siRNA-GalNAC conjugates targeting Mfap4 were generated (FIG. 29A; Table 11; SEQ ID NOs: 7092 and 7093). Human immortalised hepatocytes were treated for 72 h with siRNA and were then exposed for 4 h to EdU, then fixed and analysed. Western blot analysis with shows efficient knockdown of Mfap4 by two different conjugates GalNAC-si Mfap4.1356 and GalNAC-si Mfap4.760 compared to scrambled control.

Grhpr—Glyoxylate and Hydroxypyruvate Reductase

Figure 10A:
FIG. 10A, 10B, 10C, 10D: In vitro validation of targeting Grhpr for enhancing regeneration FIG. 10A) Outline of retroviral backbone for generating stable cell lines.
Figure 10B:
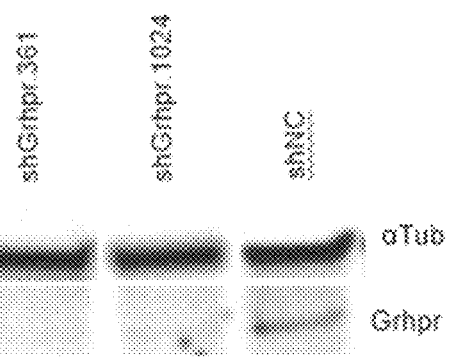
Figure 10C:
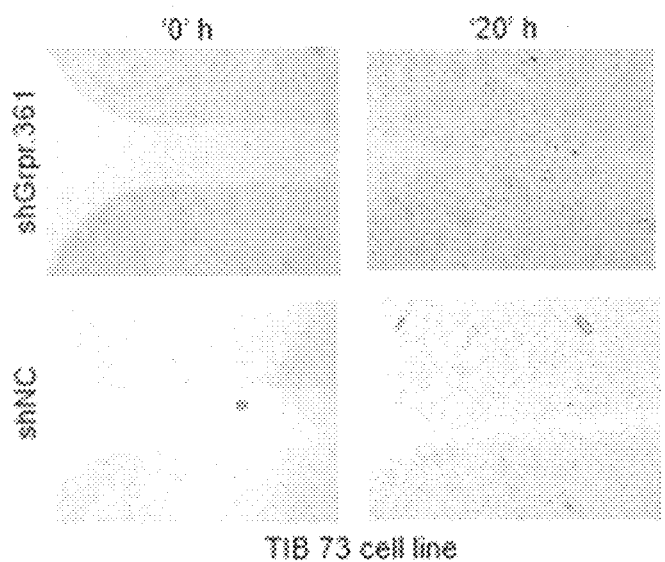
Figure 10D:
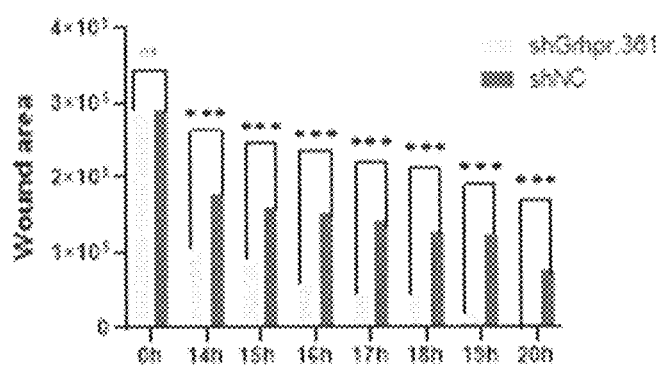
Figure 12A:
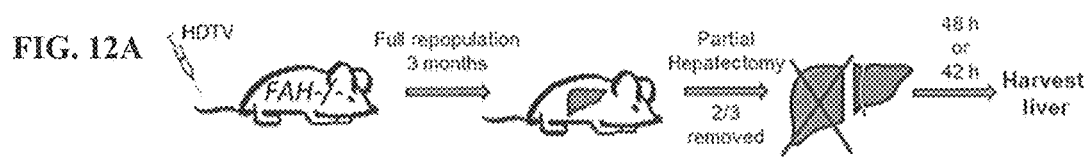
FIG. 12A, 12B, 12C, 12D: Grhpr knockdown accelerates liver regeneration after partial hepatectomy FIG. 12A) Experimental outline. FAH−/− mice were injected with our constructs, then, mice were kept for full repopulation for 3 months. After that ⅔ of the liver was surgically removed. The remaining regenerating liver was harvested at different time points after surgery.
Figure 12B:
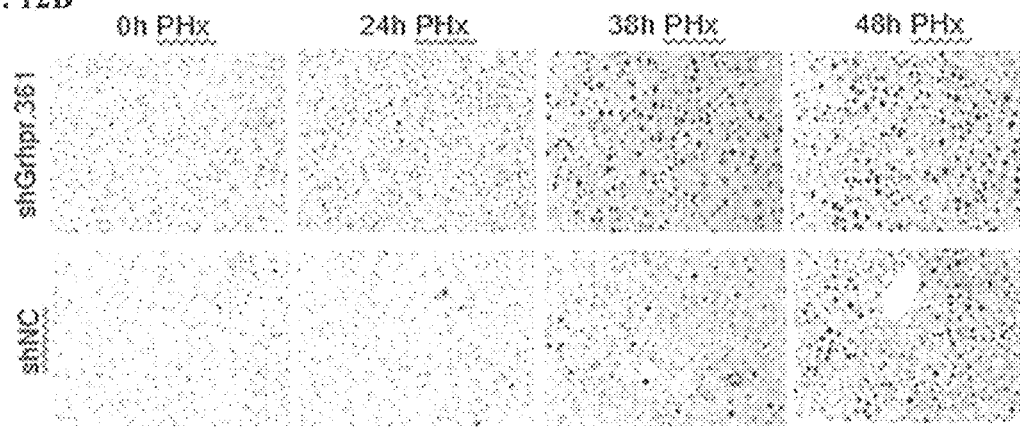
Figure 12C:
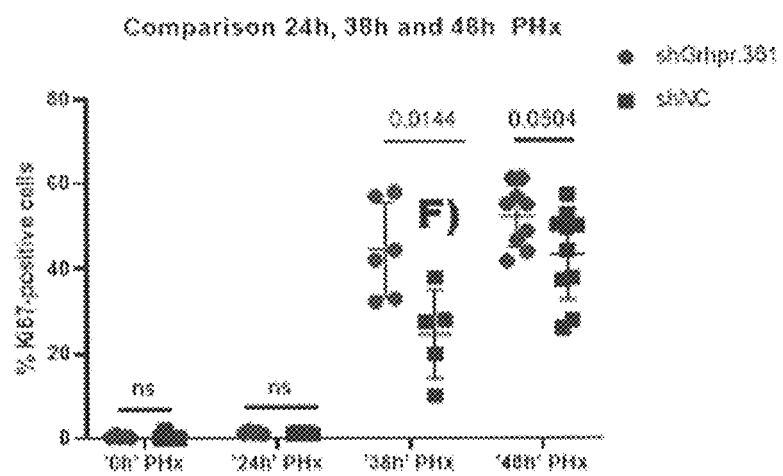
Figure 12D:
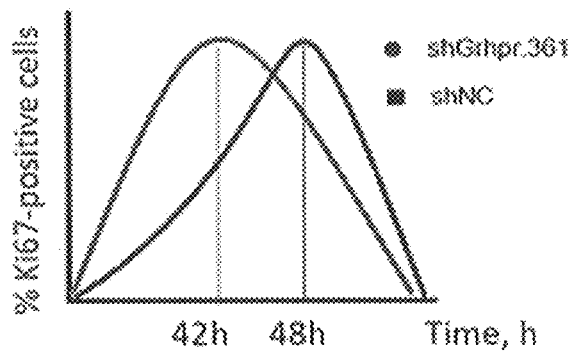
Figure 13A:
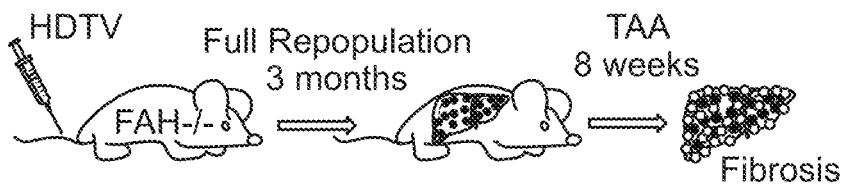
FIG. 13A, 13B, 13C, 13D: Grhpr knockdown attenuates chronic liver damage related liver fibrosis FIG. 13A) Experimental outline. FAH−/− mice were injected with our constructs, then, mice were kept for full repopulation for 3 months. After that chronic liver damage was induced by repetitive doses of thioacetamide administered intraperitoneal 3 times per week for 8 weeks. Livers were harvested, processed and analyzed.
Figure 13B:
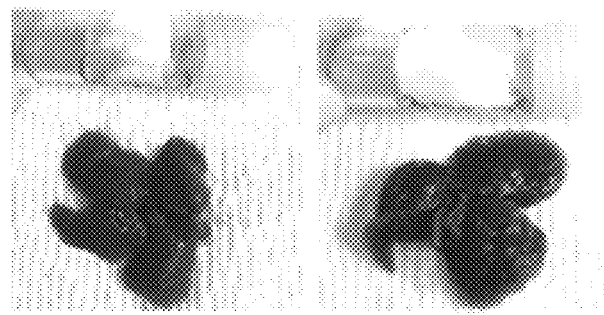
Figure 13C:
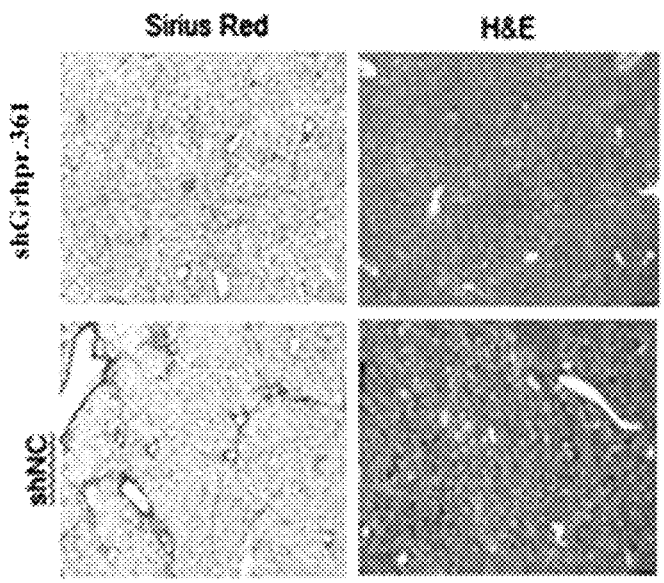
Figure 13D:
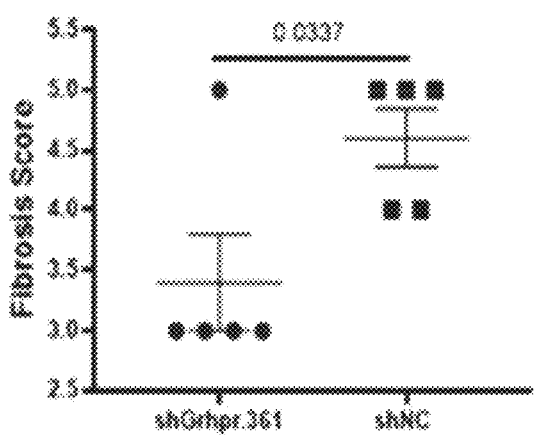
Figure 14A:
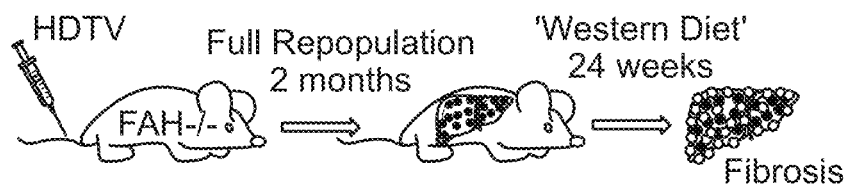
FIG. 14A, 14B, 14C, 14D: Grhpr knockdown does not protect against NASH related liver fibrosis FIG. 14A) Experimental outline. FAH−/− mice were injected with our constructs, then, mice were kept for full repopulation for 3 months. After full repopulation was reached mice were exposed to the "Western Diet" (high fat diet and 60% fructose) for 24 weeks. Livers were harvested, processed and analyzed.
Figure 14B:
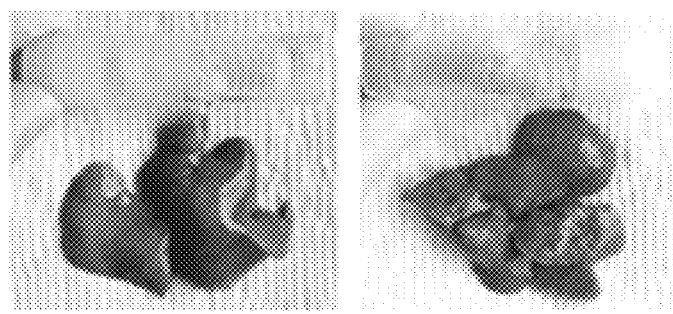
Figure 14C:
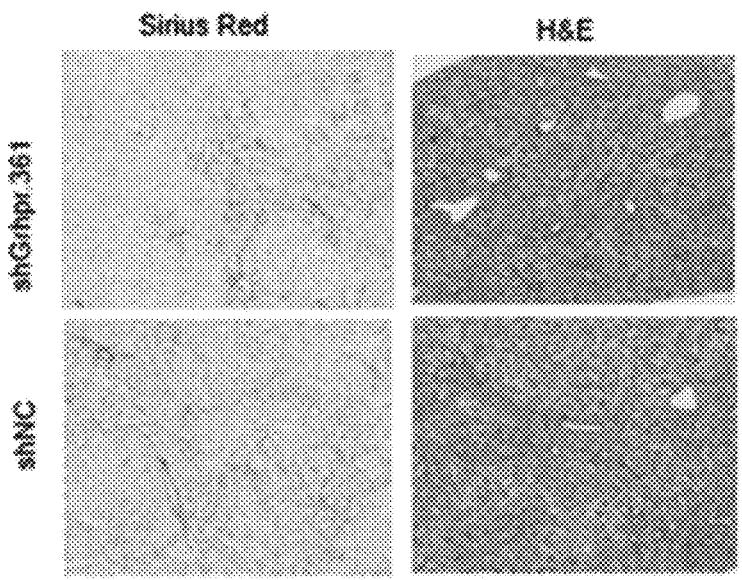
Figure 14D:
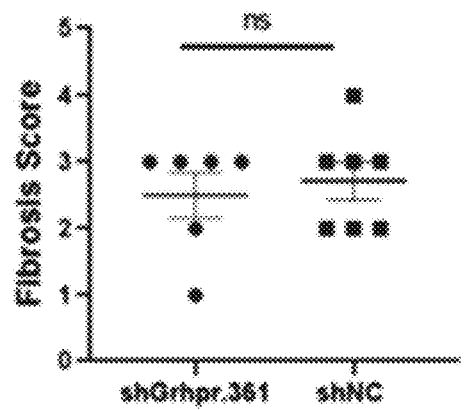

The second identified target is an enzyme with hydroxylpyruvate reductase, glyoxylate reductase and D-glycerate dehyrdrogenase enzymatic activities. Two shRNAs targeting Grhpr were strongly enriched in the screen (FIG. 1A-1D). Validation followed the same way as was described for Mfap4. First, stable cell lines were generated and the knockdown efficiency of the shRNAs was determined (FIG. 10A-10B). Both shRNAs show a strong on-target knockdown. The wound healing assay supported a faster healing and faster proliferation under Grhpr knockdown condition (FIG. 10C-10D). Again, taking advantage of the FAH−/− mice, repopulation between Grhpr targeting and control shRNA was compared. Grhpr knockdown accelerates liver repopulation under these conditions and all shGrhpr injected mice still survive at a 1:30 dilution whereas all control shNC injected mice die (FIG. 11A-11G). Next, the liver was completely repopulated so that every hepatocyte expresses shGrhpr or a non-targeting control shRNA (FIG. 12A). In the acute liver damaging model of ⅔ partial hepatectomy, Grhpr knockdown accelerates regeneration indicated by the earlier peak of Ki67 positive cells (FIG. 12B-12D). Furthermore, applying chronic TAA treatment to shGrhpr expressing repopulated FAH−/− mouse liver showed reduced liver injury and reduced fibrosis compared to control (FIG. 13A-13D). However, Grhpr knockdown does not seem to protect against NAFLD related disease progression and fibrosis development in the Western Diet mouse model (FIG. 14A-14D).

Figure 15A:
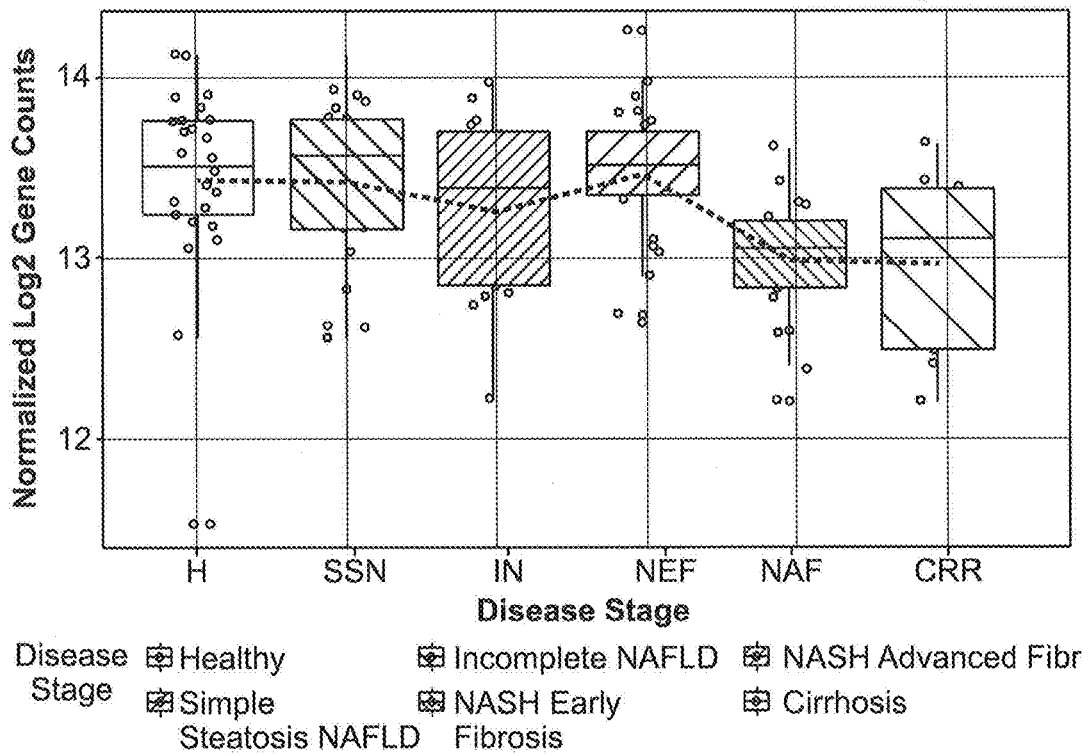
FIG. 15A, 15B, 15C: Grhpr expression changes in human NAFLD A) Transcriptomic analysis of liver samples from ~150 patients shows slight but significant decrease in Grhpr expression in NASH patients with advanced fibrosis and cirrhosis. Consistent with this we detected a significant reduction in patients with fibrosis 3 and 4 score (*$p<0.05$, $p<0.01$, *$p,0.005$).
Figure 15B:
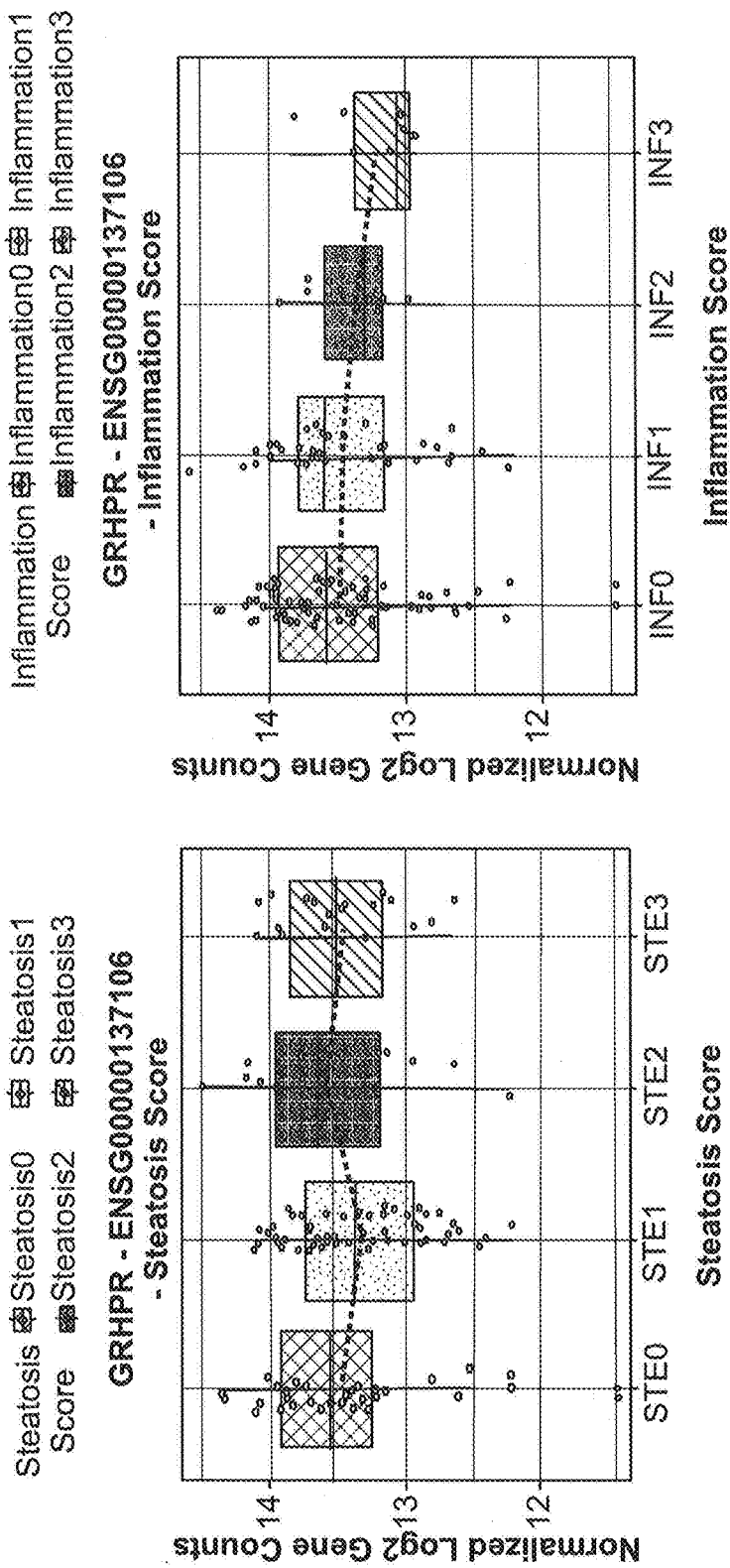
Figure 15C:
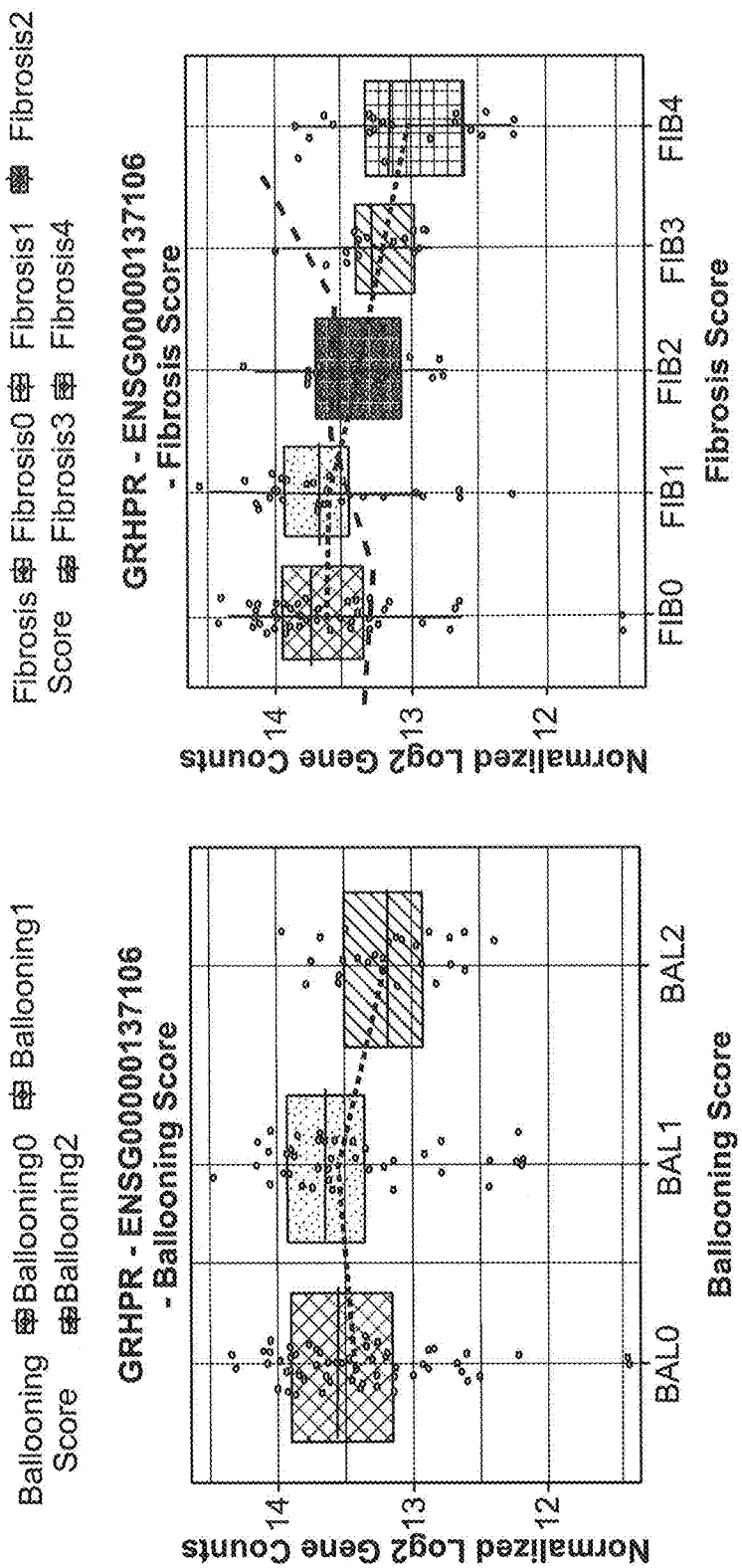

Interestingly, the NAFLD patient cohort showed a significant reduction in Grhpr expression in the liver at NASH advanced fibrosis and cirrhosis stages, but not very strongly (FIG. 15A-15C).

Figure 31A:
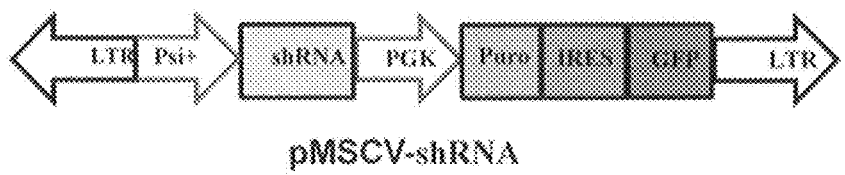
FIG. 31A, 31B, 31C: Grhpr expression in human hepatocytes (HpG2 cell line) FIG. 31A) Scheme of retroviral backbone for generating stable cell lines.
Figure 31B:
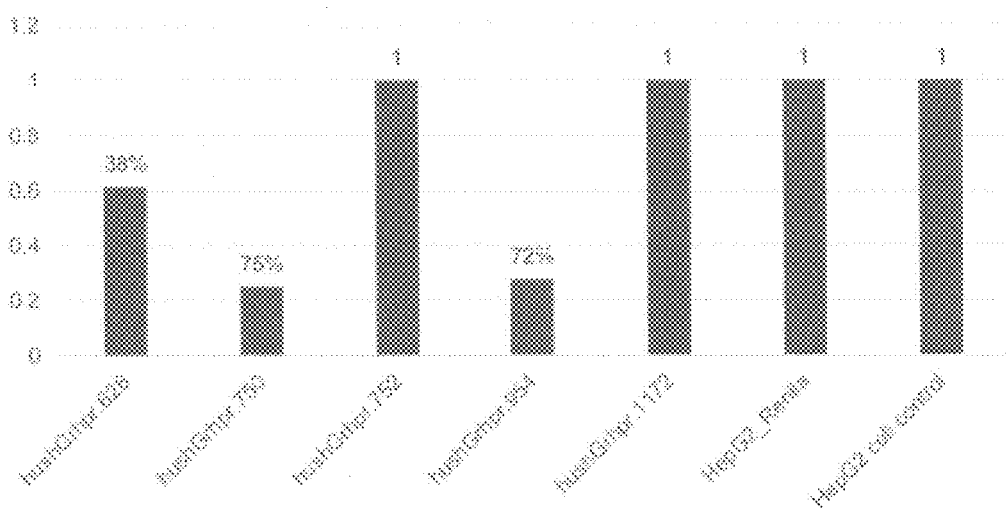
Figure 31C:
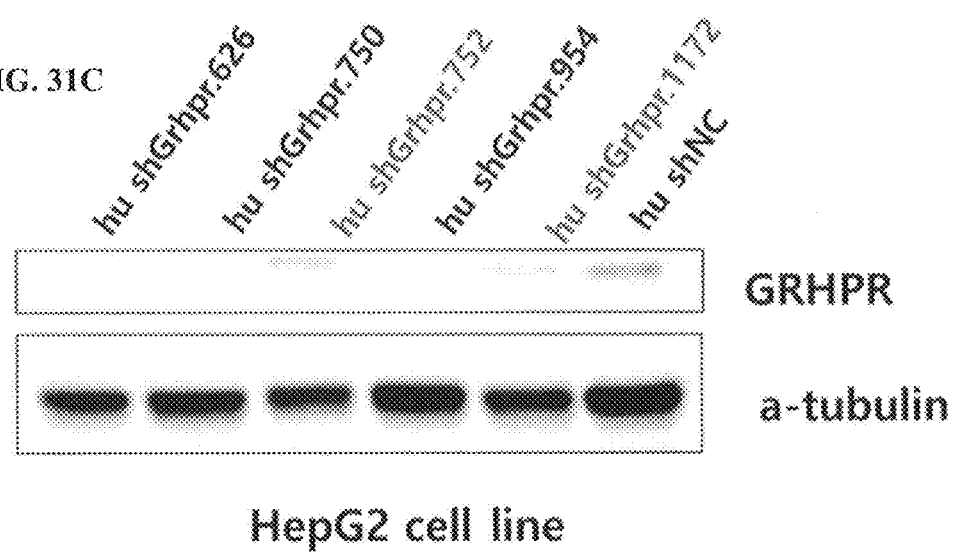

Similar to the experimental set up for targeting Mfap4, the development of liver cancer was investigated under Grhpr knockdown conditions (FIG. 30A). FAH−/− mice were injected with a combination of p?T-FAHIG-shGrhpr and SB13 plasmids for liver repopulation. Initially 5 to 10% of hepatocytes will have stable integration. After NTBC drug withdrawal after injection the liver will be repopulated, so that nearly every hepatocyte will express the shRNA targeting Grhpr. 1 year after injection livers were harvested and evaluated for liver tumor development. No GFP-positive tumor were observed in FAH−/− mice, and livers are fully repopulated (FIG. 30B-30C), indicating that long term Grhpr knockdown in the liver does not induce liver cancer and is safe Furthermore, HepG2 cells with stable expression of shRNAs were generated by retroviral transfection and selection (FIG. 31A). Grhpr knockdown was determined by qPCR and Western blot using RNA or whole-cell lysates (Tubulin was used as a loading control). Several independent shRNAs targeting human Grhpr were identified (FIG. 31B) that lead to efficient Grhpr knockdown in the human liver cancer cell line HepG2 (FIG. 31C).

Figure 32A:
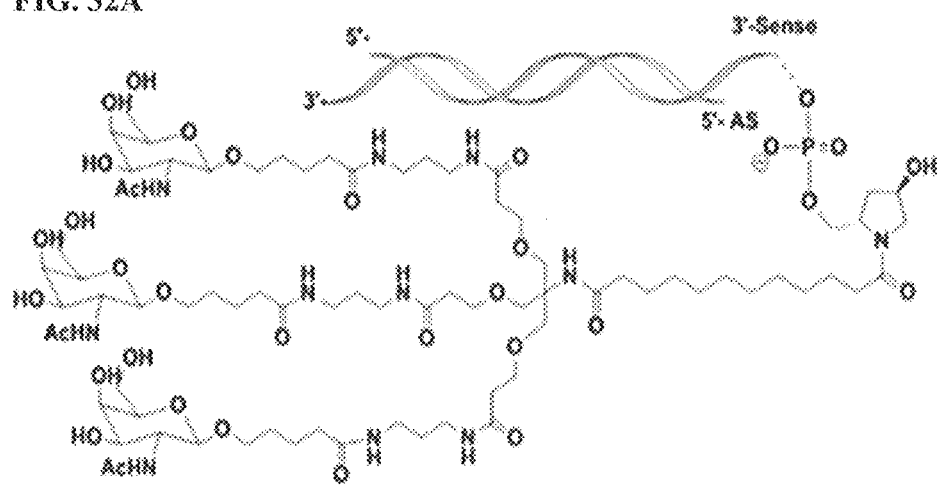
FIG. 32A, 32B: GalNAC conjugates with siRNA against Grhpr (BNL CL.2 cell line; 72 h post-transfection) FIG. 32A) Structure of GalNAC-siRNA conjugate used in studies. Exact backbone modifications can be found in the sequence appendix (SEQ ID NO: 7094). The target sequence for the siRNA was based on the shRNA guide sequence.
Figure 32B:
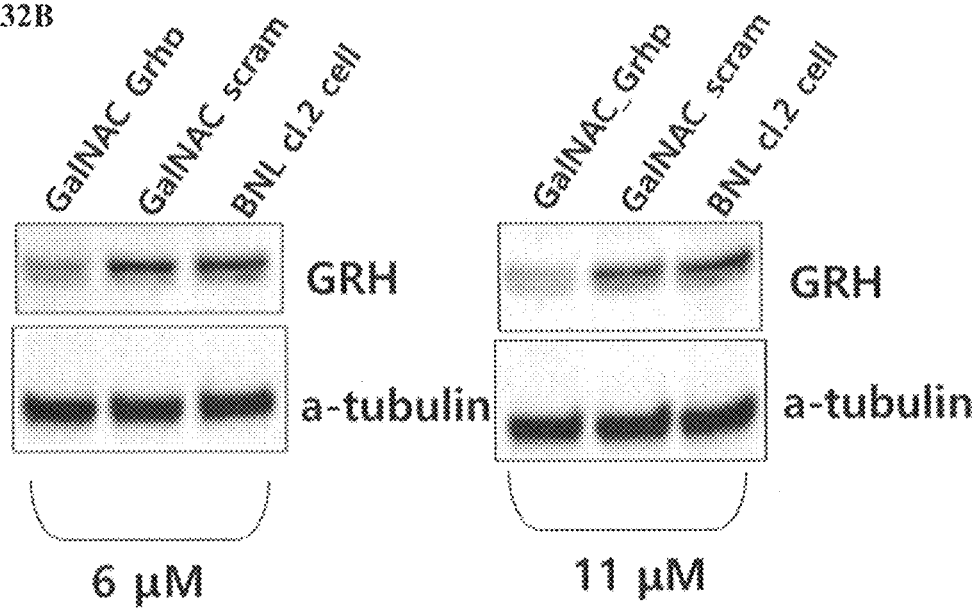

Modified siRNA-GalNAC conjugates targeting Grhpr were generated (FIG. 32A, Table 11; SEQ ID NO: 7094), following the same way as was described for Mfap4. BNL CL.2 cell line; 72 h post-transfection. Western blot analysis with 6 μM and 11 μM, respectively, shows efficient knockdown of Grhpr by conjugate GalNAC-si Grhpr.361 compared to scrambled control.

Itfg1—Integrin Alpha FG-GAP Repeat Containing 1

Figure 16D:
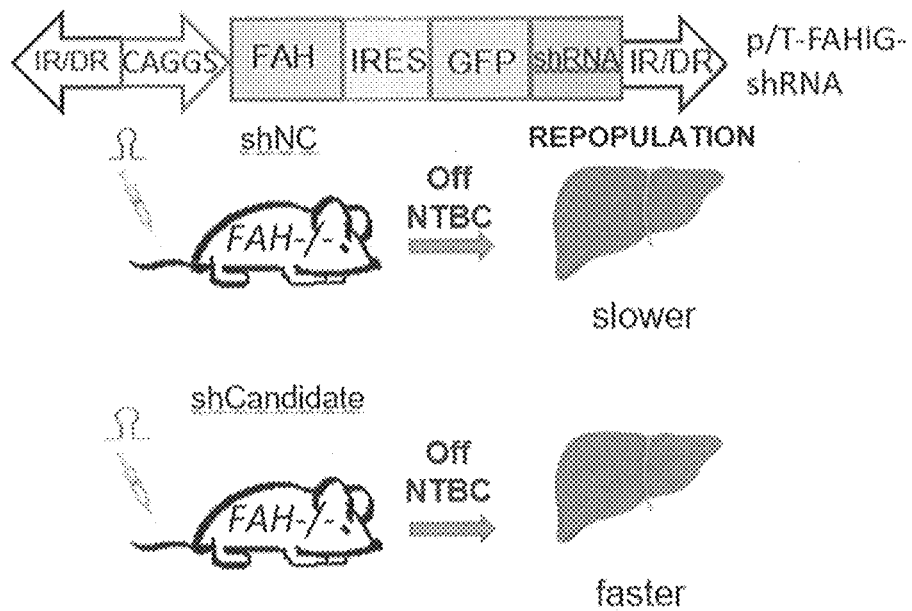
Figure 16E:
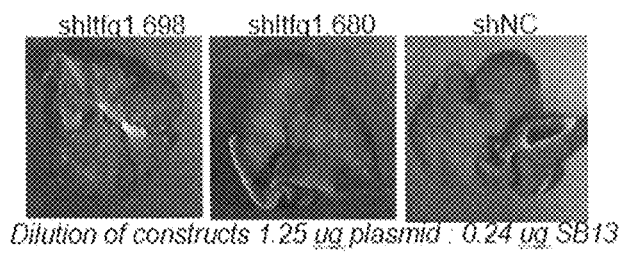
Figure 16F:
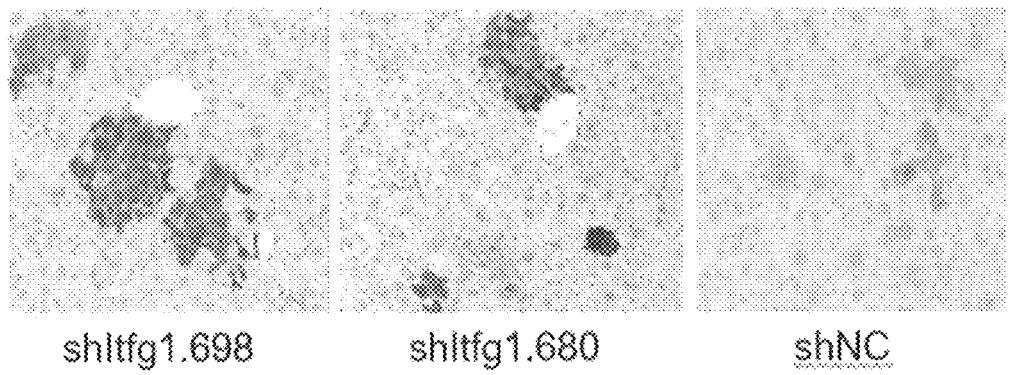
Figure 17A:
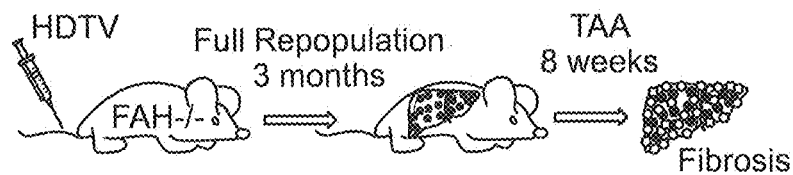
FIG. 17A, 17B, 17C, 17D, 17E: Itfg1 knockdown attenuates chronic liver damage related liver fibrosis FIG. 17A) Experimental outline. FAH−/− mice were injected with our constructs, then, mice were kept for full repopulation for 3 months. After that chronic liver damage was induced by repetitive doses of thioacetamide administered intraperitoneal 3 times per week for 8 weeks. Livers were harvested, processed and analyzed.
Figure 17B:
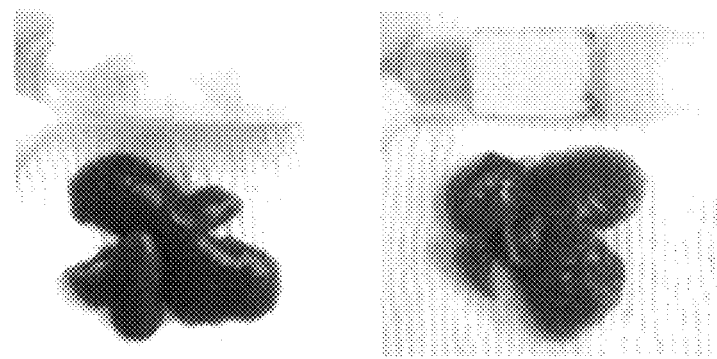
Figure 17C:
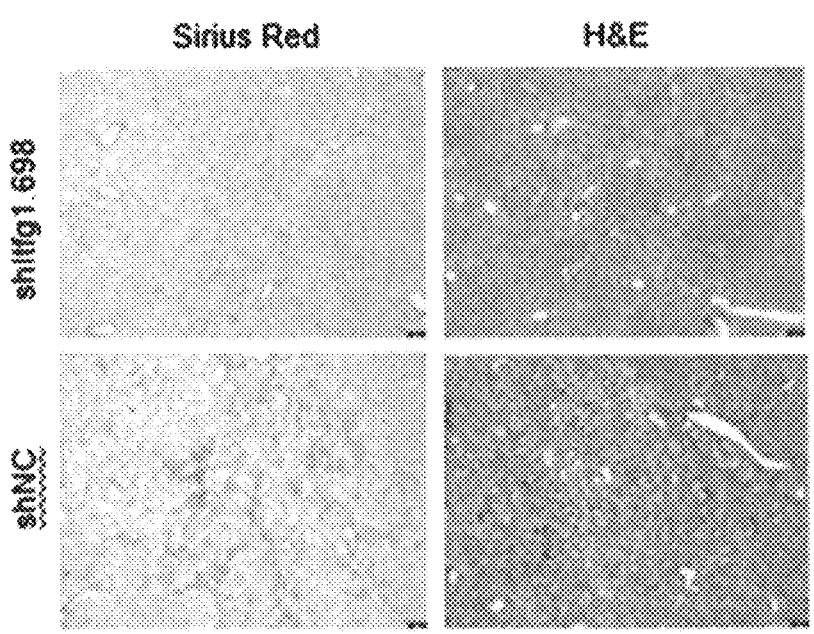
Figure 17D:
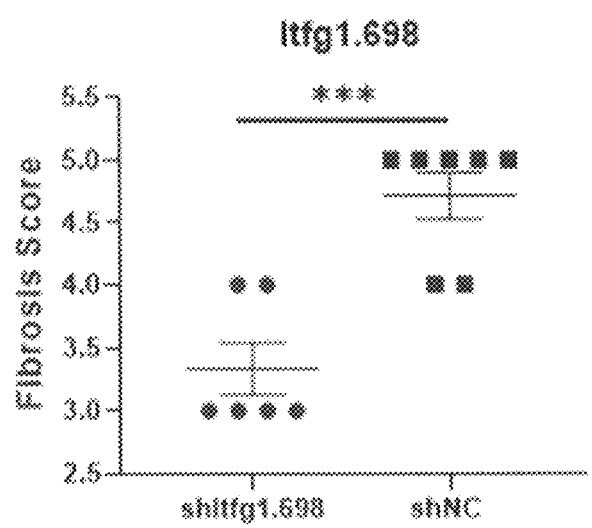
Figure 17E:
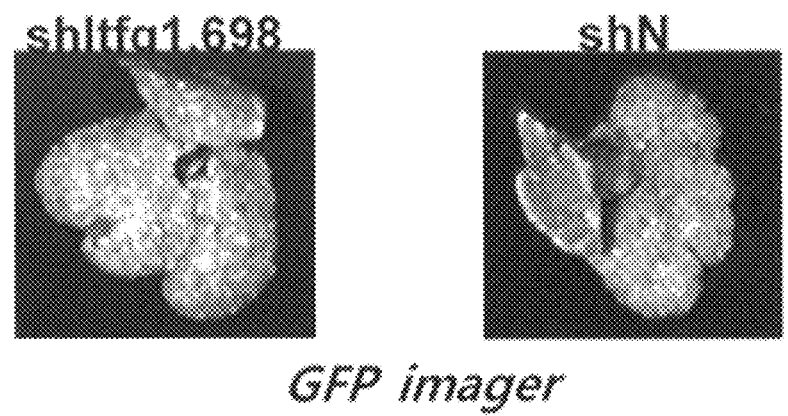

The on-target knockdown efficiency of the top enriched shRNA and an additional independent shRNA were first tested. Both shRNAs show a good on-target knockdown by qPCR and Western blot (FIG. 16A-16B). Itfg1 knockdown strongly accelerates wound healing in vitro, taking advantage of the stable cell lines (FIG. 16C). The inventors then took advantage of the FAH−/− mice and did a repopulation assay (FIG. 16D). Consistent with the screening results, both Itfg1 knockdowns accelerate repopulation (FIG. 16E-16G). Interestingly, if the plasmid input was further diluted, at some point, the amount of hepatocytes with stable integration should be not sufficient to compensate for hepatocyte loss after NTBC withdrawal (FIG. 16H right panel). At a 1:30 dilution still all shItfg1 injected mice survive whereas all shCTRL injected mice die (FIG. 16H left panel). This further supports the Itfg1 knockdown mediated acceleration, as only in case of shItfg1 the hepatocytes expand fast enough to compensate for hepatocyte loss. Consistent with this, after full liver repopulation, a protective effect of Itfg1 knockdown against chronic TAA induced liver damage and fibrosis (FIG. 17A-17E) was seen.

Figure 18A:
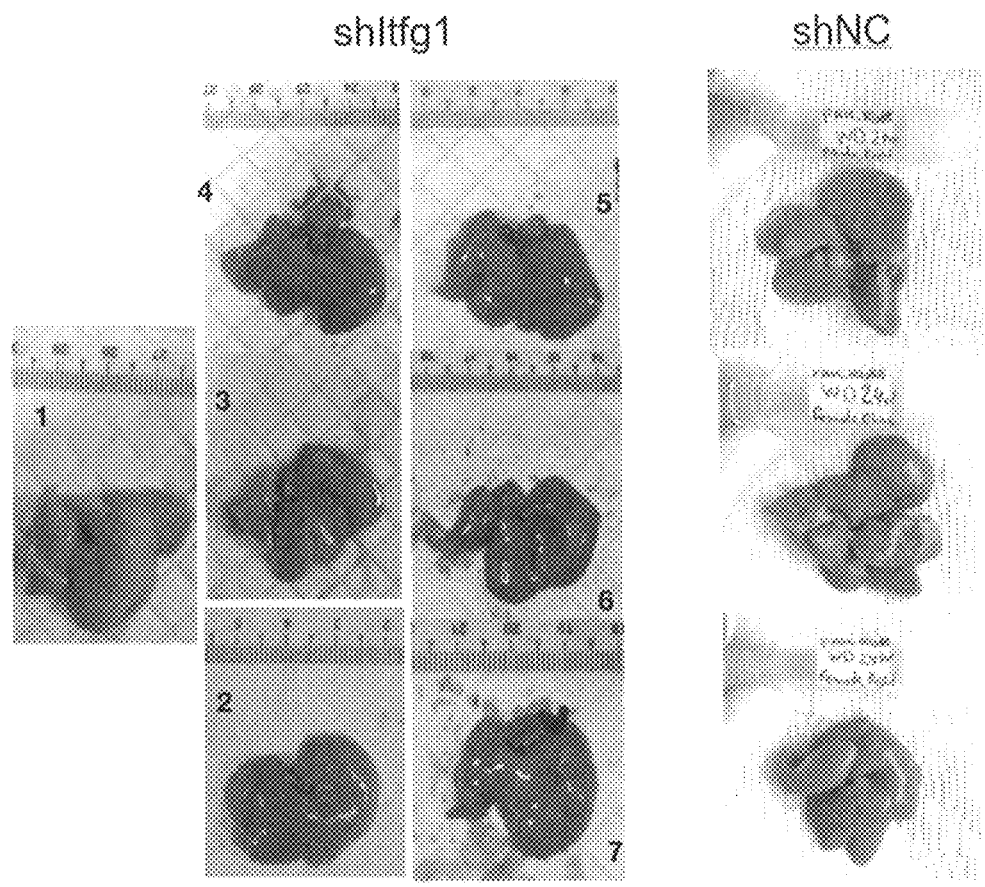
Figure 18C:
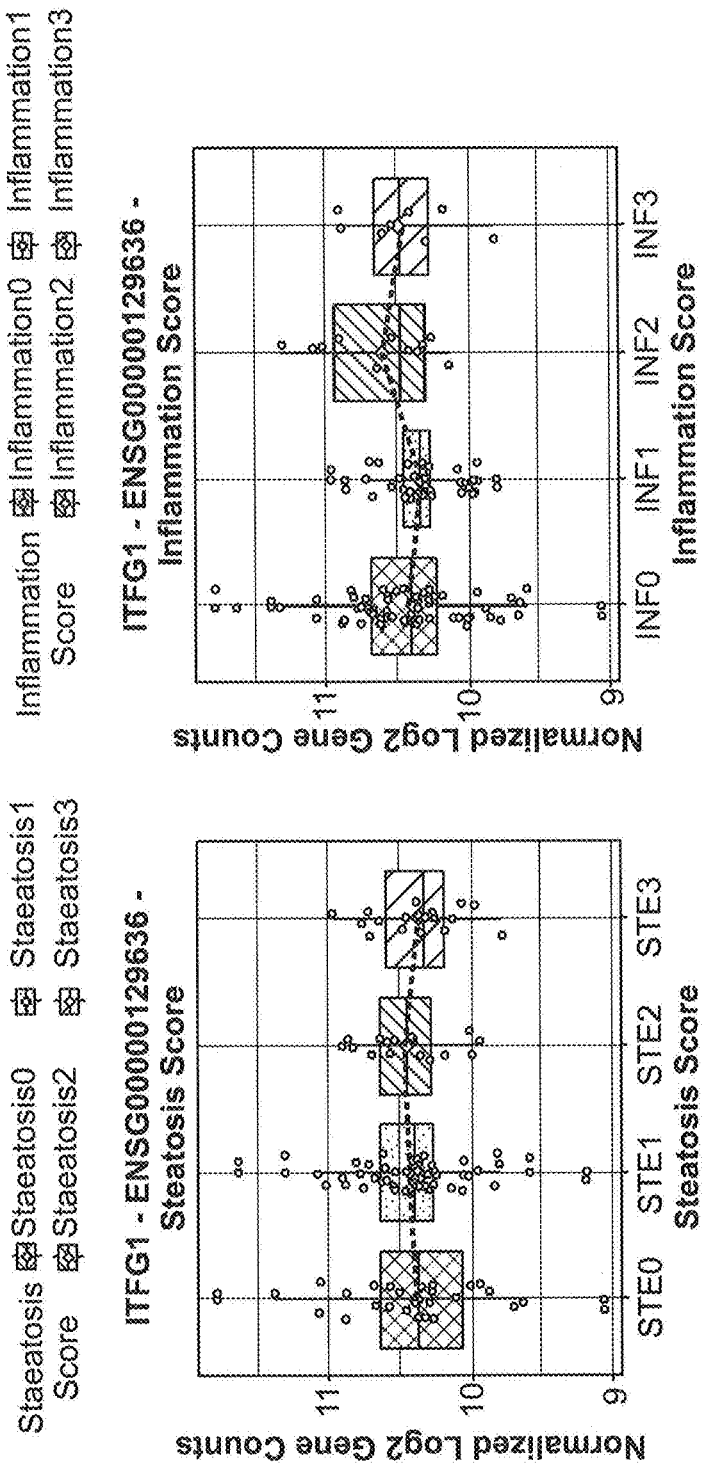
Figure 18D:
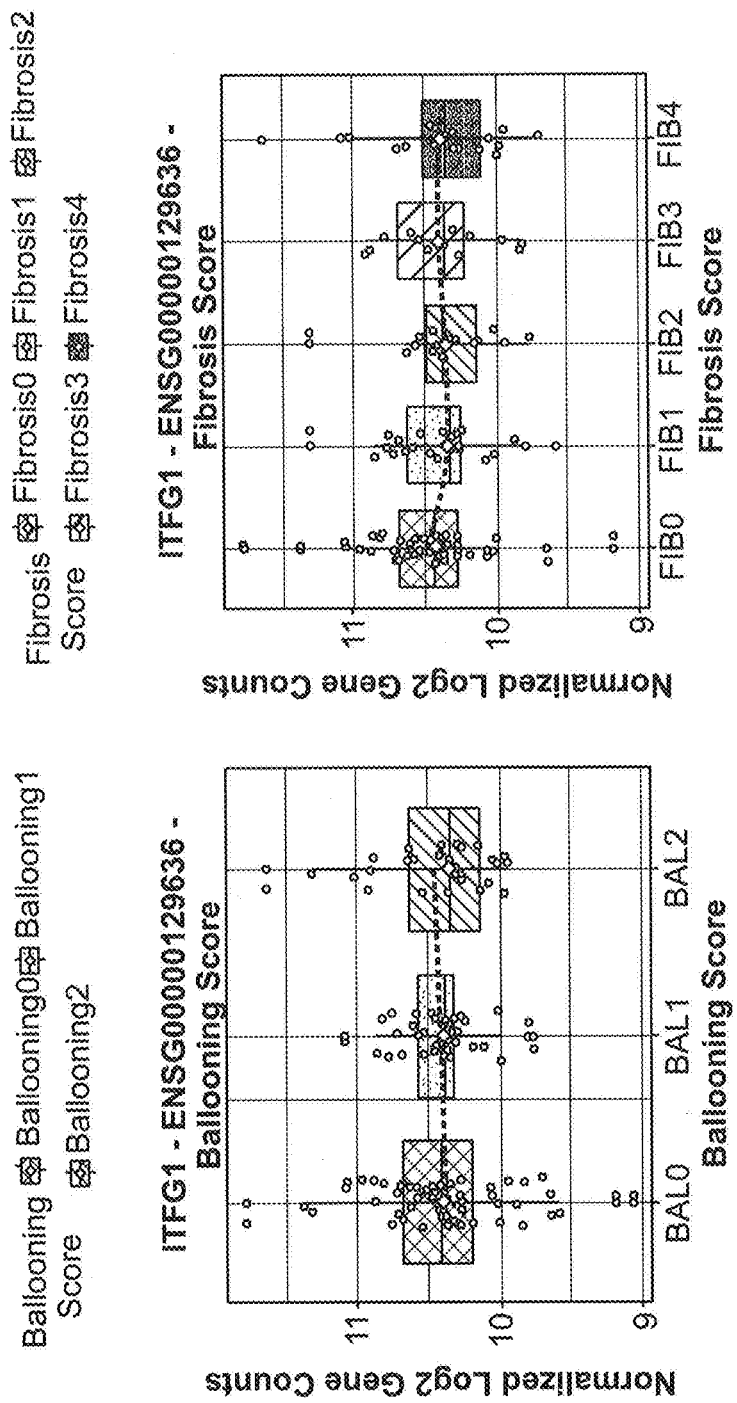
Figure 18E:
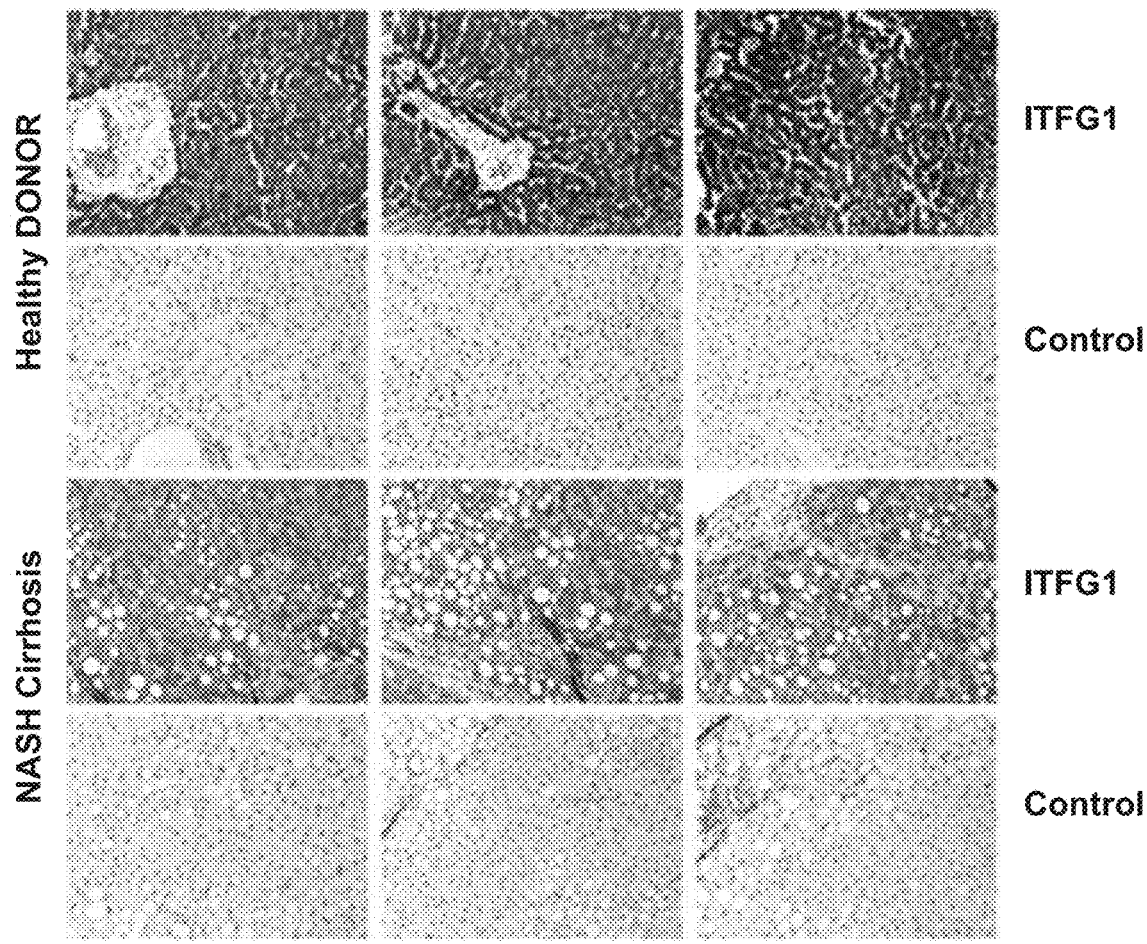
Figure 18F:
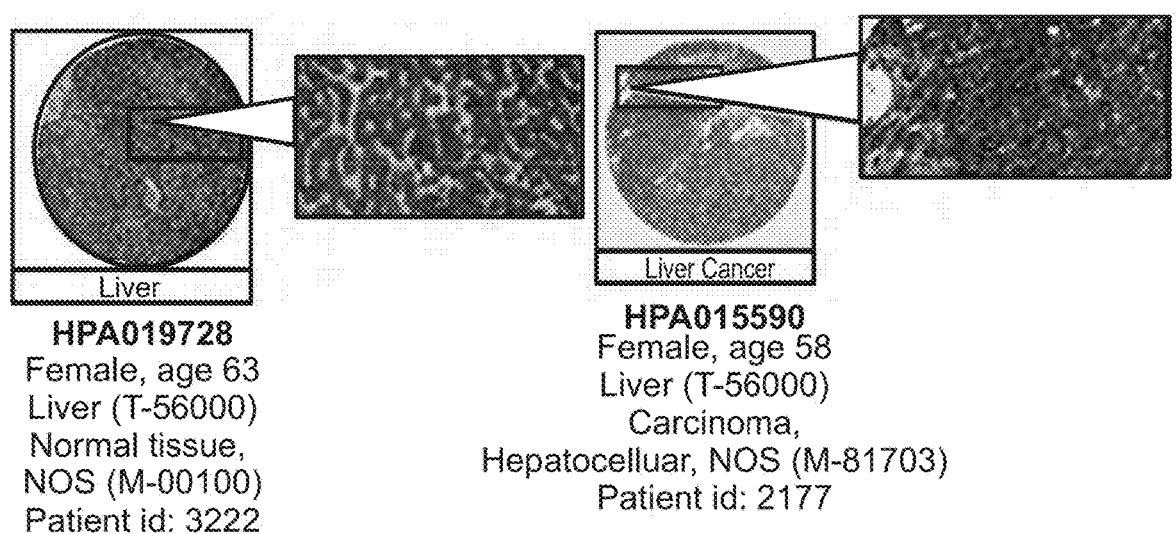
Figure 18G:
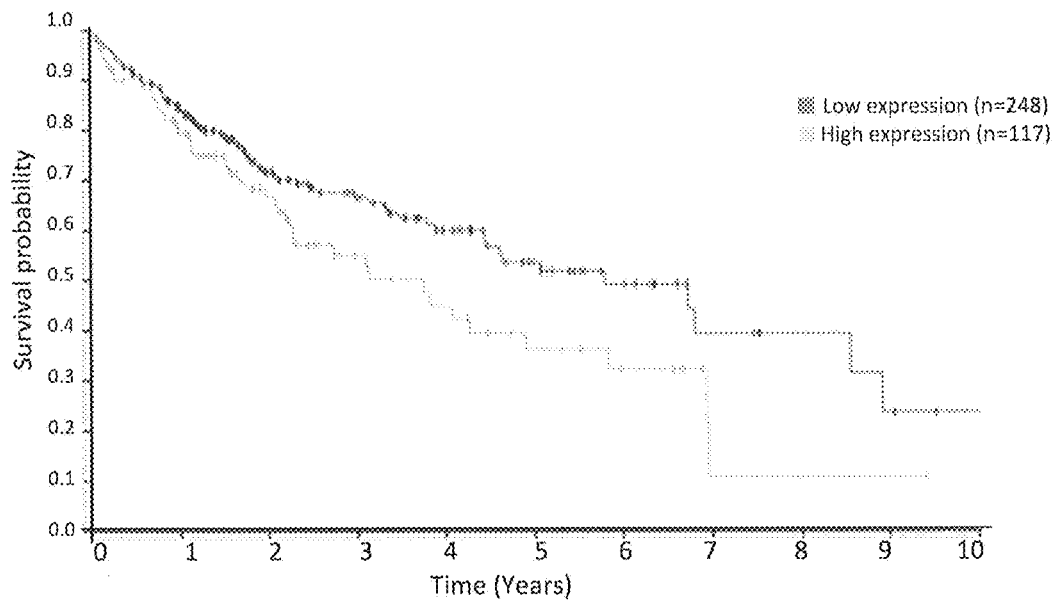
Figure 18H:
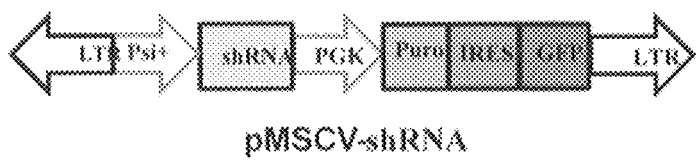
Figure 18I:
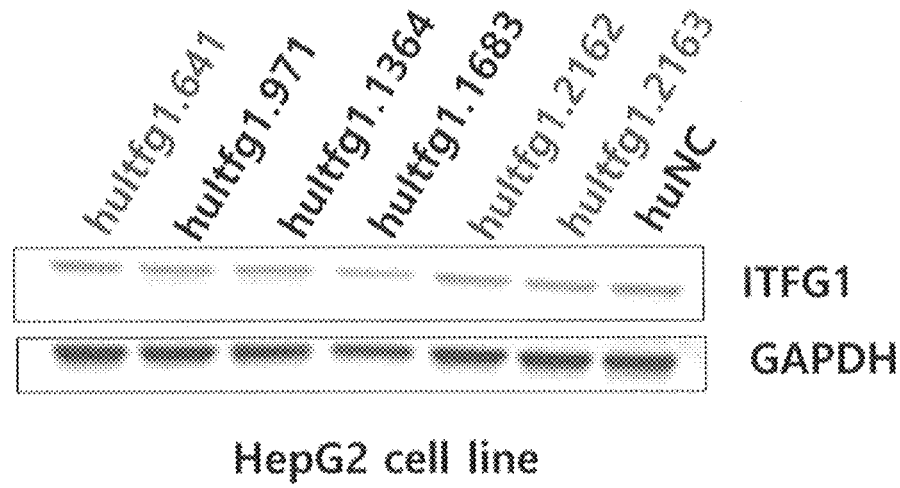
Figure 35A:
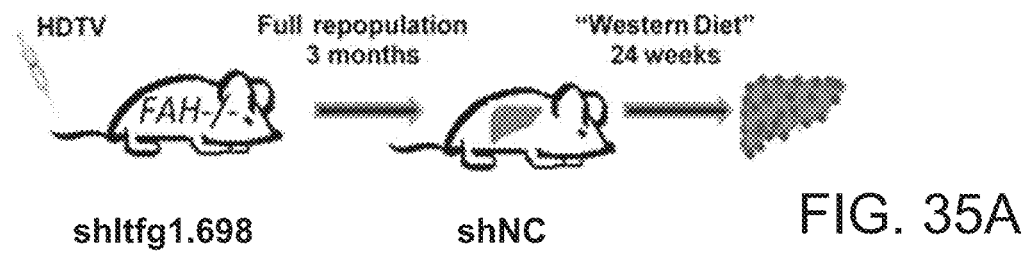
FIG. 35A, 35B, 35C, 35D, 35E, 35F: Itfg1 knockdown attenuates chronic liver damage related liver fibrosis in a NASH model FIG. 35A) Experimental outline. FAH−/− mice were injected with our constructs, then, mice were kept for full repopulation for 3 months. After full repopulation was reached mice were exposed to the "Western Diet" (high fat diet and 60% fructose) for 24 weeks. Livers were harvested, processed and analyzed.
Figure 35B:
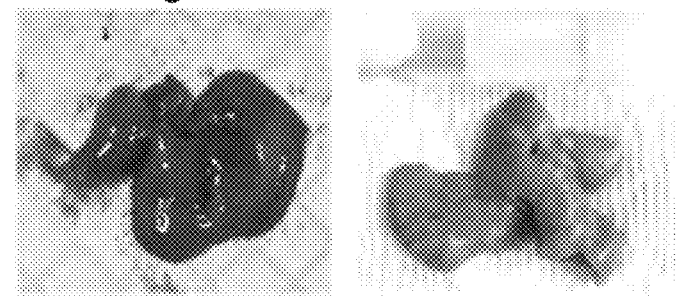
Figure 35C:
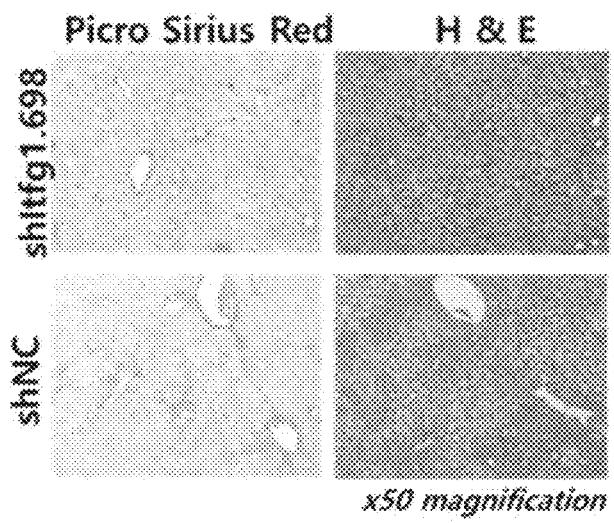
Figure 35E:
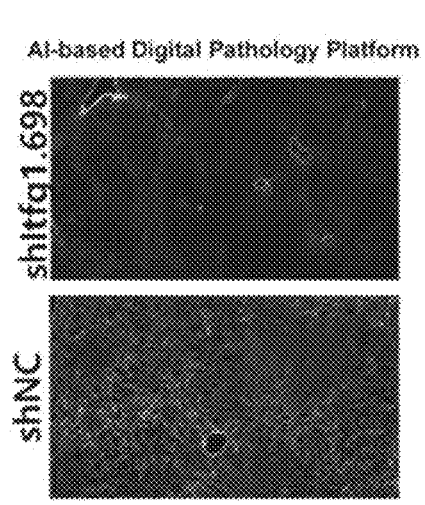
Figure 35D:
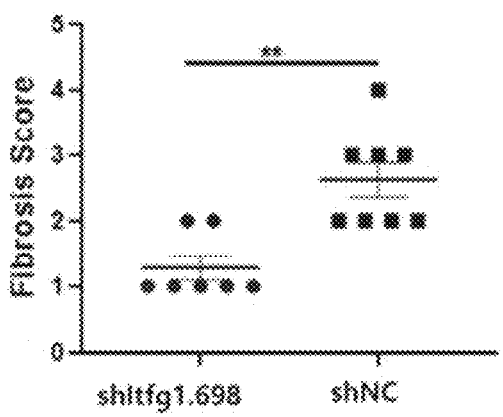
Figure 35F:
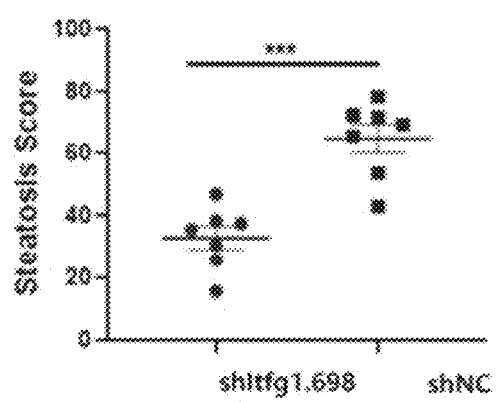

In the mouse Western Diet NAFLD model (FIG. 35A), knockdown of Itfg1 attenuates fibrosis development (FIG. 35B-35F), which could already be seen macroscopically (FIG. 18A). The rough surface on the liver of mice expressing a non-targeting control shRNA indicates advanced fibrosis. In contrast the surface of shItfg1 expressing livers indicates strong reduction in fibrosis. In addition objective analysis by HistoIndex with a proprietary AI pathology system, further showed significant reduction in steatosis by Itfg1 knockdown (FIG. 35E-35F). The expression data from our NAFLD patient cohort indicates no major expression changes in the liver during disease progression (FIG. 18B), suggesting a postranscriptional regulation. Itfg1 is expressed in healthy liver tissue and in NASH, Cirrhosis and hepatocellular carcinoma (FIG. 18C-18E). Data from The Human Protein Atlas show that low expression of Itfg1 is associated with increased survival in liver cancer patients (FIG. 18G). Interestingly, so far not much is known about Itfg1 and therefore it represents an interesting novel target for liver disease. Generating stable human HepG2 cell lines and determining the knockdown efficiency of different Itfg1 shRNAs showed a strong on-target knockdown (FIG. 18G-18H) for human Itfg1.

Figure 33A:
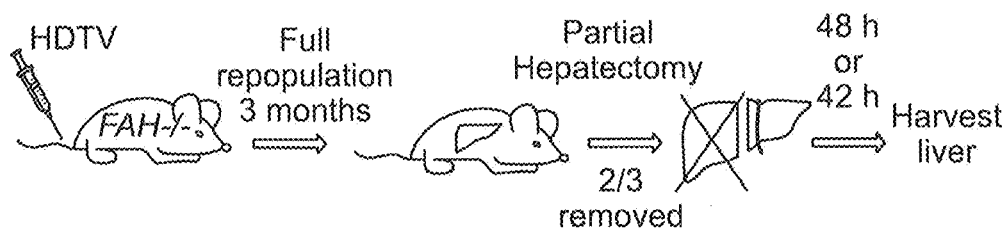
FIG. 33A, 33B, 33C: Itfg1 knockdown accelerates liver regeneration after partial hepatectomy (PH) FIG. 33A) Experimental outline. FAH−/− mice were injected with our constructs, then, mice were kept for full repopulation for 3 months. After that ⅔ of the liver was surgically removed. The remaining regenerating liver was harvested at 42 h and 48 h after surgery.
Figure 33B:
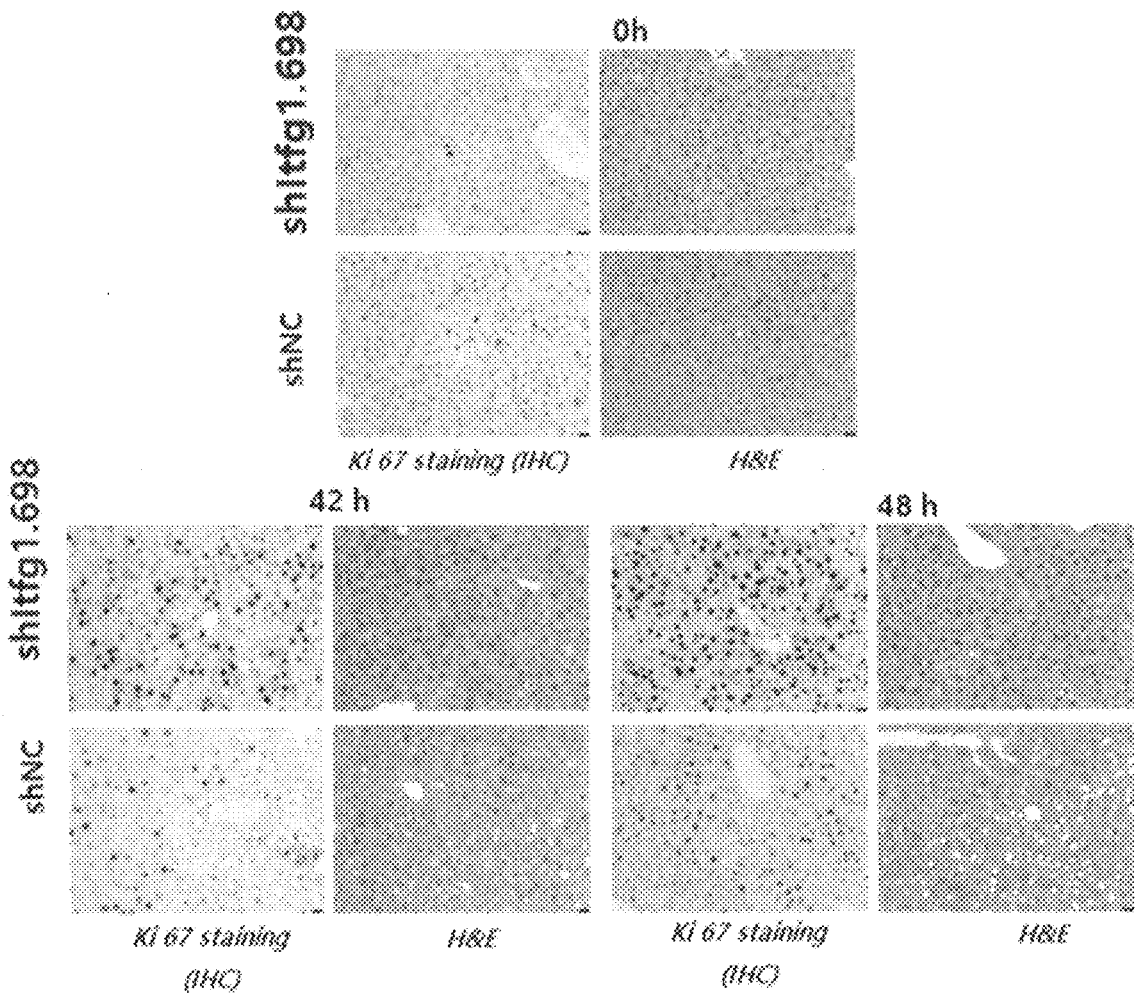
Figure 33C:
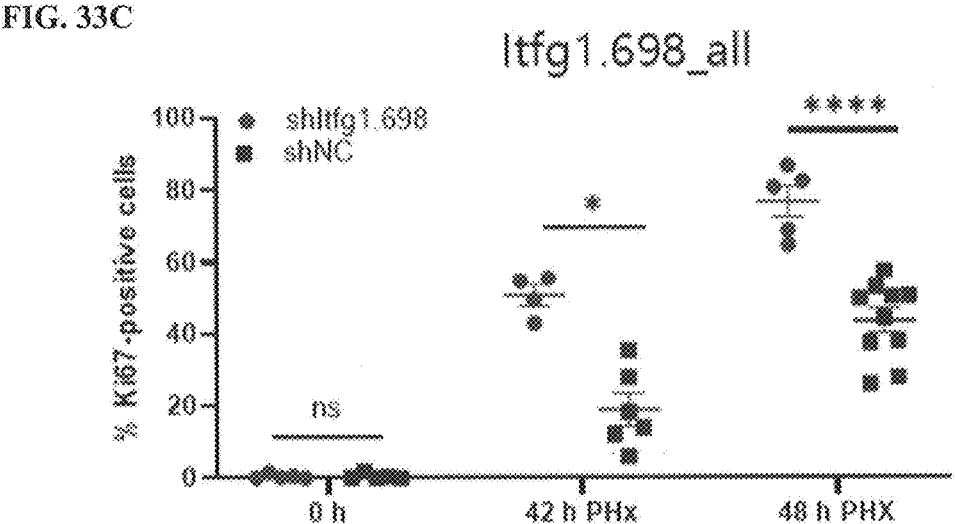
Figure 34D:
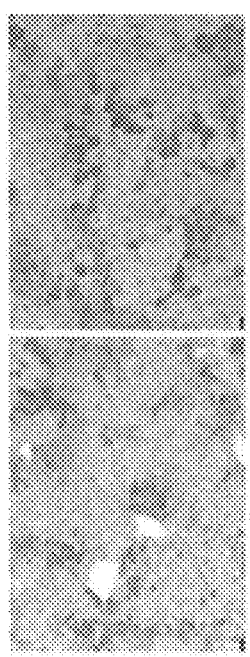
Figure 34E:
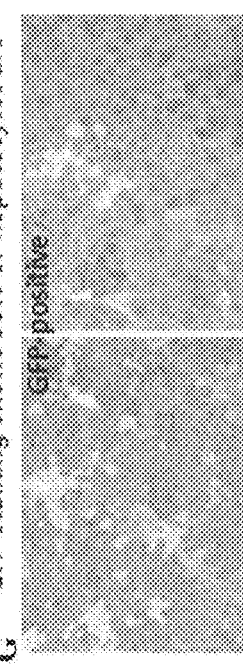
Figure 34F:
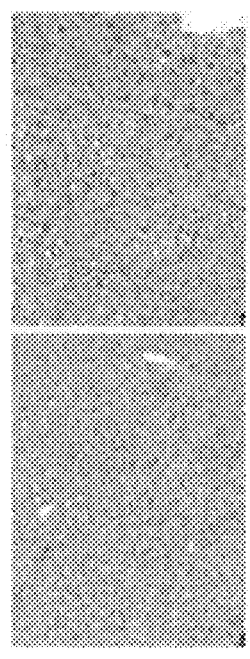
Figure 34G:
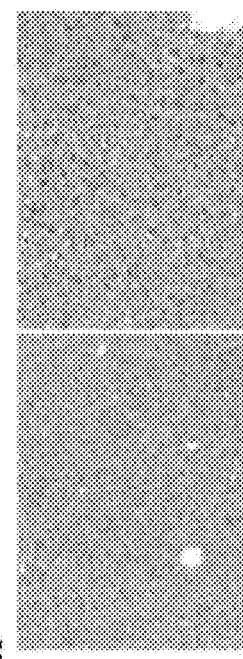

Again, taking advantage of the FAH−/− mice, the liver was completely repopulated for 3 months so that every hepatocyte expresses shItfg1 or a non-targeting control shRNA (shNC). Afterwards, ⅔ of the liver was removed and liver regeneration monitored (FIG. 33A). In the acute liver damaging model of ⅔ partial hepatectomy, Itfg1 knockdown accelerates regeneration after partial hepatectomy indicated by an earlier peak and higher amount of Ki67 positive cells (FIG. 33B-33C). No malignant disease and no GFP-positive tumor is observed 1 year after Itfg1 knockdown in mice (FIG. 34A-34E). Livers are fully repopulated in both the shItfg1 group and control group as indicated by around 95% GFP-positive hepatocytes.

Figure 36A:
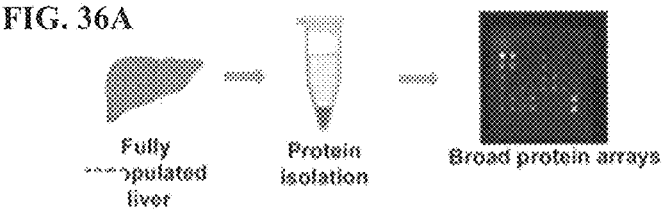
FIG. 36A, 36B, 36C: Knockdown of Itfg1 impacts MKK6, JNK, and RPS6 signaling FIG. 36A) Schematic outline of isolating proteins from full repopulated livers for further broad protein array analysis.
Figure 36B:
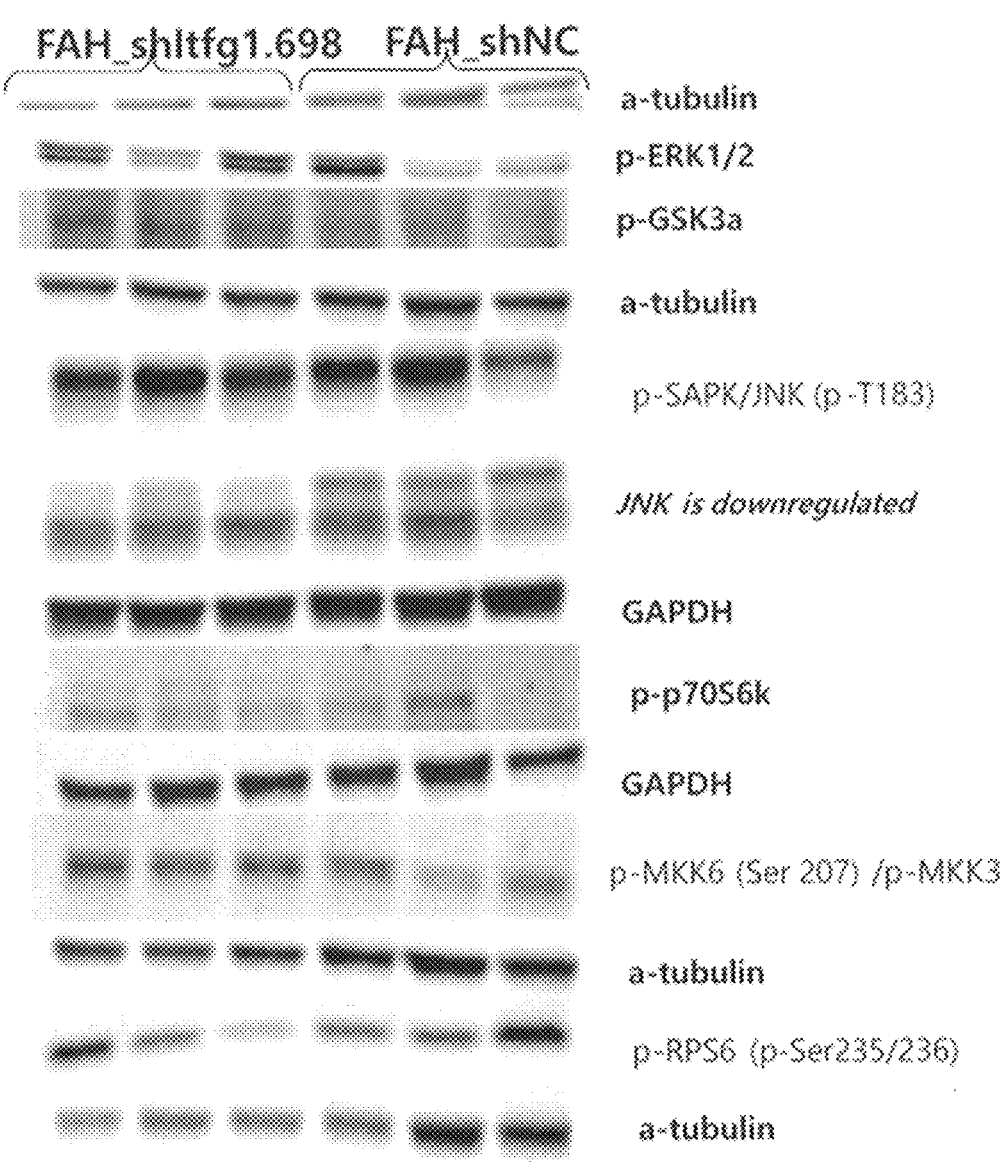
Figure 36C:
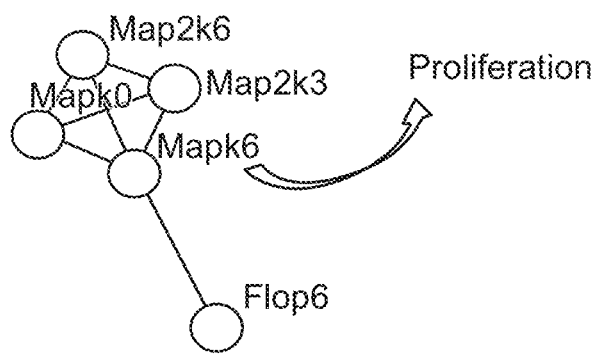

To investigate the differences in pathway activation after full repopulation with either shItfg1 or non-targeting control shRNA, proteins from full repopulated livers were isolated for further broad protein array analysis (FIG. 36A). After performing the broad protein array, focused Western blot experiments were carried out. It was observed that knockdown of ITFG1 impacts MKK6, JNK, and RPS6 signaling. In particular, P-MKK6/P-MKK3 are greater activated in case of Itfg1 knockdown compared to control (FIG. 36B). According to STRING database, all indicated proteins are interacting and are linked to cell growth and proliferation (FIG. 36C).

Figure 37A:
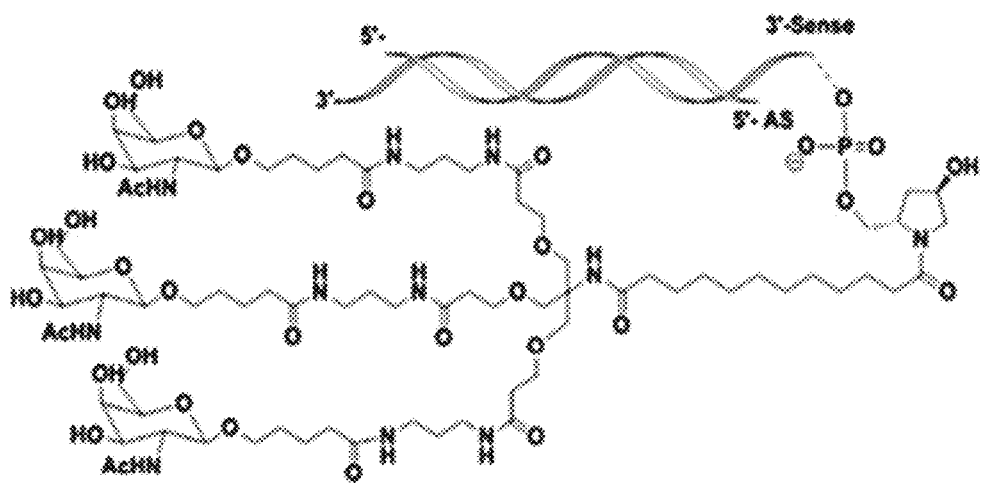
FIG. 37A, 37B: GalNAC conjugates with siRNA against Itfg1 (BNL CL.2 cell line; 72 h post-transfection) FIG. 37A) Structure of GalNAC-siRNA conjugate used in studies. Exact backbone modifications can be found in the sequence appendix (SEQ ID NOs: 7095 and 7096). The target sequence for the siRNA was based on the shRNA guide sequence.
Figure 37B:
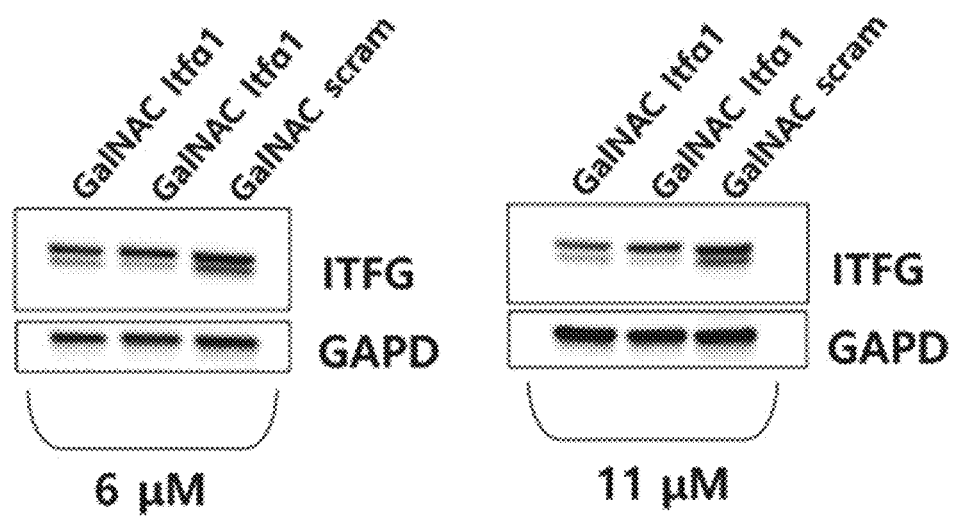

Modified siRNA-GalNAC conjugates were generated to target Itfg1 (FIG. 37A, Table 11; SEQ ID NOs: 7095 and 7096). Western blot analysis with 6 μM and 11 μM, respectively, shows efficient knockdown of Itfg1 by two different conjugates GalNAC-si Itfg1.698 and GalNAC-si Itfg1.680 compared to control (FIG. 37B).

Mfap4 or Itfg1 Knockdown in Mouse Lung Cell Line and Mouse Myoblast Cell Line

Figure 38A:
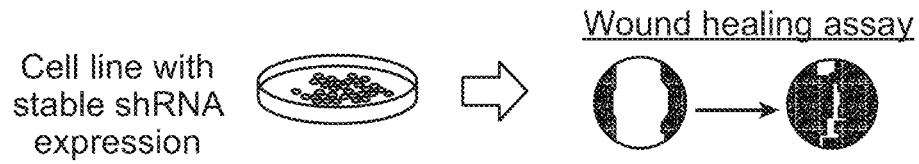
FIG. 38A, 38B, 38C: Mfap4 and Itfg1 knockdown enhances proliferation and regeneration beyond liver FIG. 38A) Outline of the wound healing assay. Stable cell lines were generated expressing the respective shRNAs.
Figure 38B:
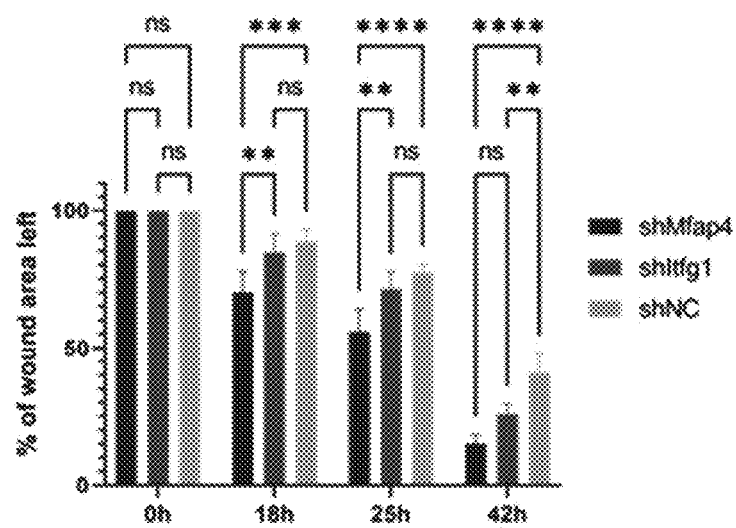
Figure 38C:
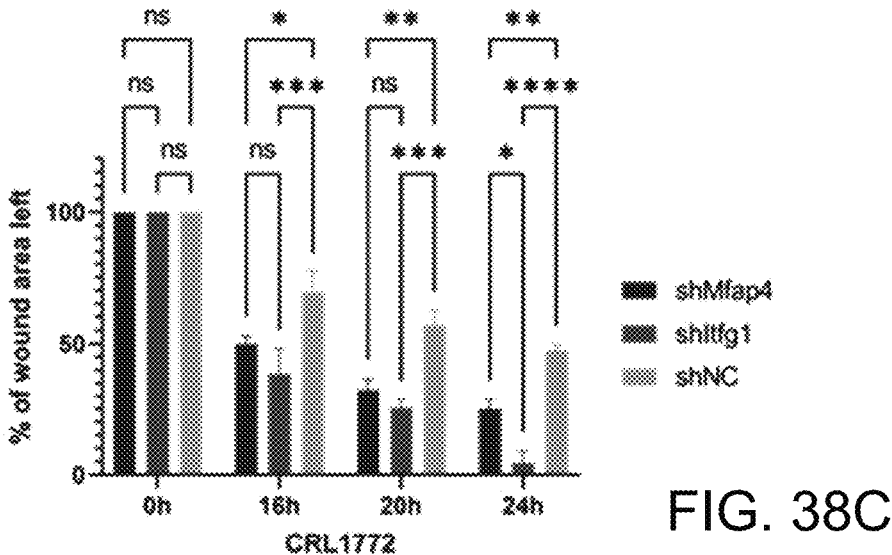

Stable cell lines using mouse lung cell line CCL206 and mouse myoblast cell line CRL1722 were generated expressing the respective shRNA—shMfap4, shItfg1 or control shNC (FIG. 38A). Knockdown of Mfap4 as well as the knockdown of Itfg1 accelerates wound healing of mouse lung cells as well as of mouse myoblast cells. These results suggest that Mfap4 and Itfg1 knockdown enhances proliferation and regeneration not only of liver but also of lung and myoblasts.

Example 3—EMULSION +500 Screen and Target Validation

Figure 19A:
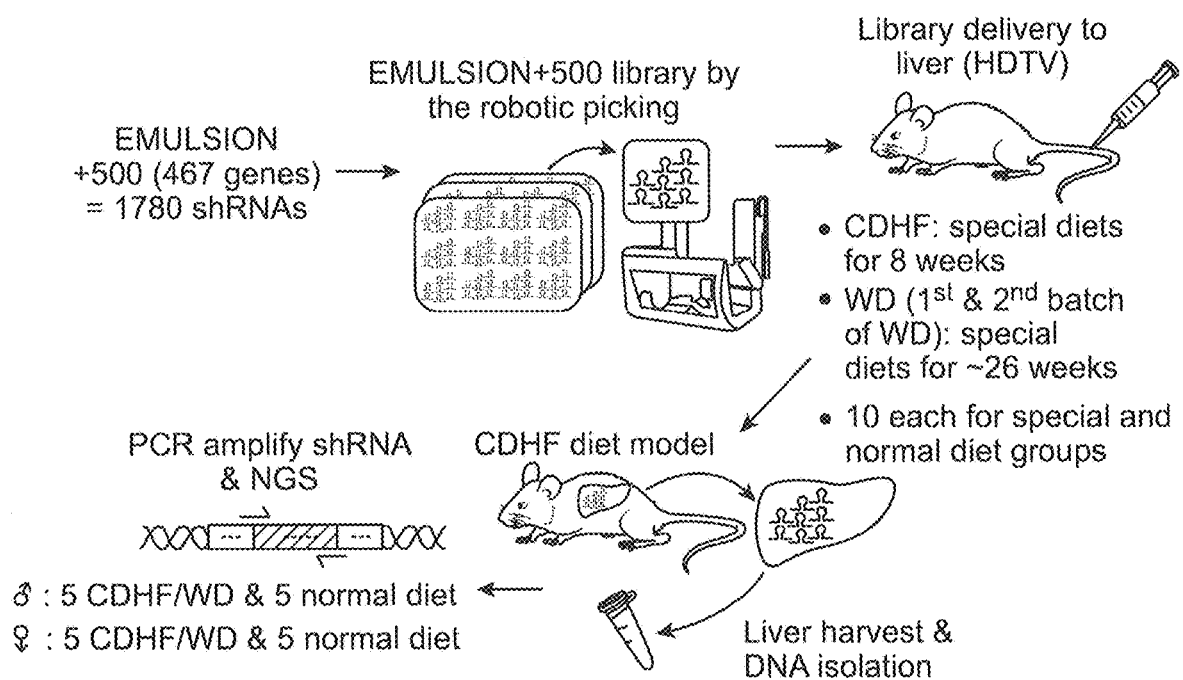
FIG. 19A, 19B, 19C, 19D: EMULSION +500 in vivo functional genetic screen FIG. 19A) Schematic outline of the screen. A pooled shRNA library screen targeting 467 genes, dysregulated in human NAFLD patients, is set up. The screen is conducted in mice of both gender using two diet based NAFLD models.

Independent of the TAA chronic damage-induced screen, a functional genetic screen using a focused shRNA library containing 1780 shRNAs targeting 467 genes was also conducted. These 467 genes are the mouse homologs corresponding to differentially up-regulated genes found in our NAFLD patient cohort (FIG. 19A). The screen was conducted in two diet-based mouse models of NAFLD, the "Western Diet" (WD) model (FIG. 4A-4H) and the Choline deficient L-amino acid defined high fat diet (CDHFD) model (FIGS. 20A and 20B). The CDHFD is a very aggressive and fast model leading to NASH with advanced fibrosis in 8 weeks. In contrast, the WD takes about half a year to reach this stage. Similar to the TAA screen, the shRNA library was delivered to the liver by hydro-dynamic tail vine injection (HDTV). The combination of transposon-based constructs with a sleeping beauty 13 transposase-expressing plasmid leads to the stable integration in about 5 to 10% of hepatocytes. After injection, the respective diet exposure was started until NASH with late fibrosis is reached. After harvesting the liver the genomic DNA is isolated, part of the shRNA expression cassette is amplified and the abundance sequenced by NGS. Enriched shRNAs are identified, which indicates an advantage by these shRNAs in the context of fatty liver disease.

Figure 19B:
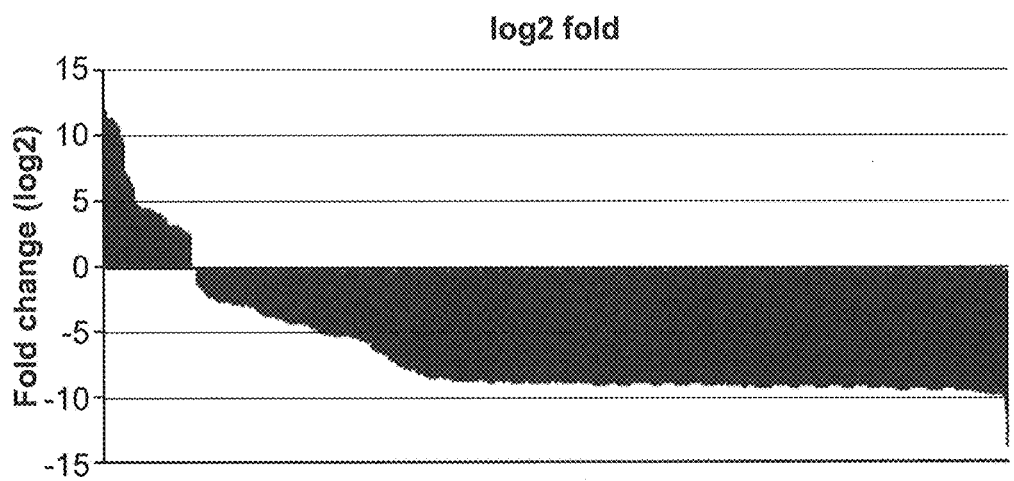
Figure 19C:
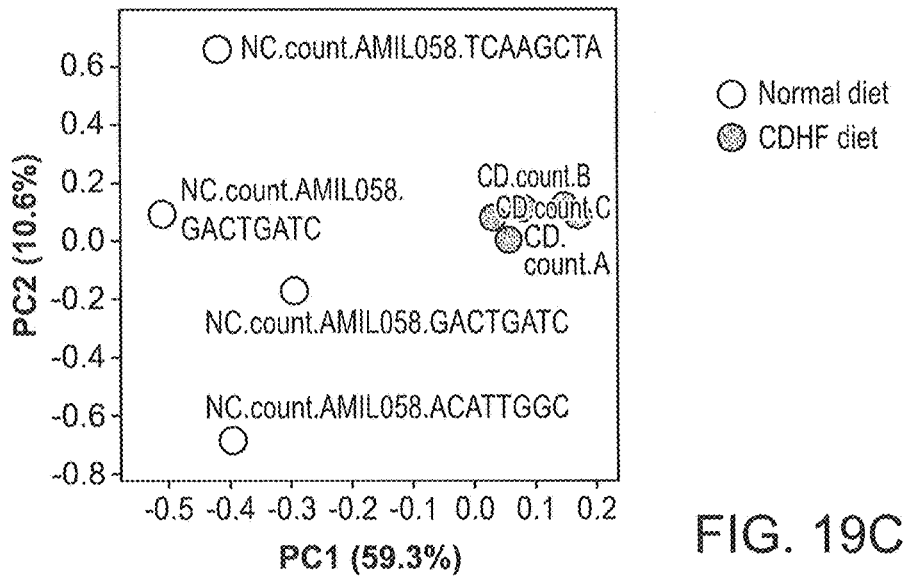
Figure 19D:
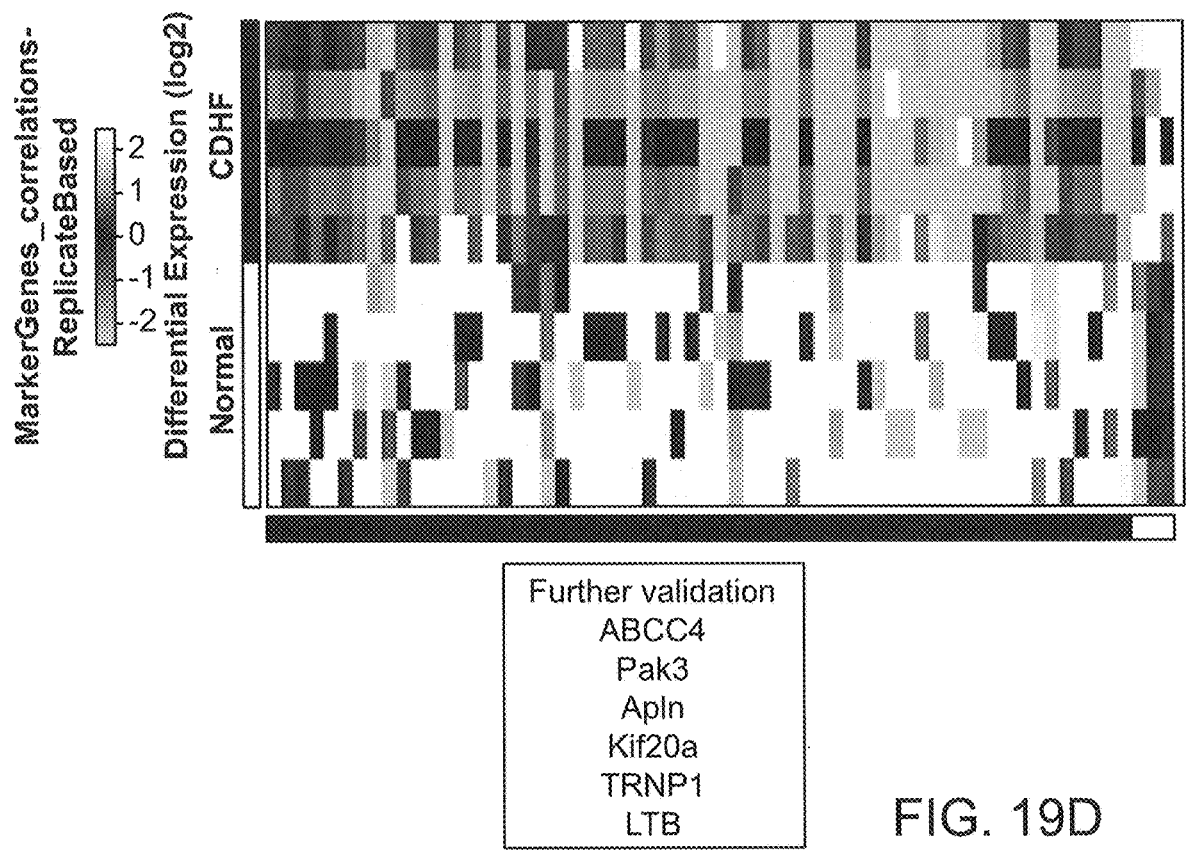

In the CDHFD model the majority of shRNAs were depleted (FIG. 19B). Interestingly, based on normalized shRNA abundance level in a principal component analysis, clear segregation between our CDHFD vs normal chow exposed mice (FIG. 19C) was seen. In-depth differential abundance shRNA analysis was then performed. Six shRNAs/targets for validation (FIG. 19D) were identified based on reliable enrichment in the majority of animals. Importantly, as the library was designed based on relevant human patient data and this is a functional genetic screen, scoring in the screen can already be seen as the first validation step.

ABCC4—ATP Binding Cassette Subfamily C Member 4 (MRP4)

Figures 21A, 21B:
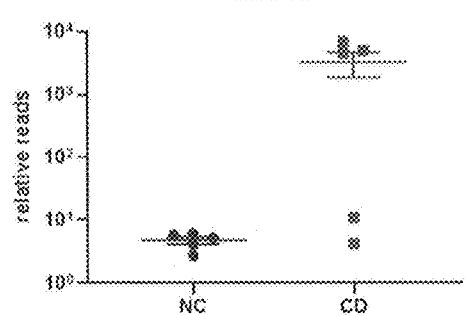
FIG. 21A, 21B, 21C, 21D, 21E: Abcc4 is a potential therapeutic target for NAFLD FIG. 21A) Shown is the relative read numbers for the shRNA expression cassette targeting Abcc4 for each animal (NC=normal chow, CD=CDHFD).
Figure 21C:
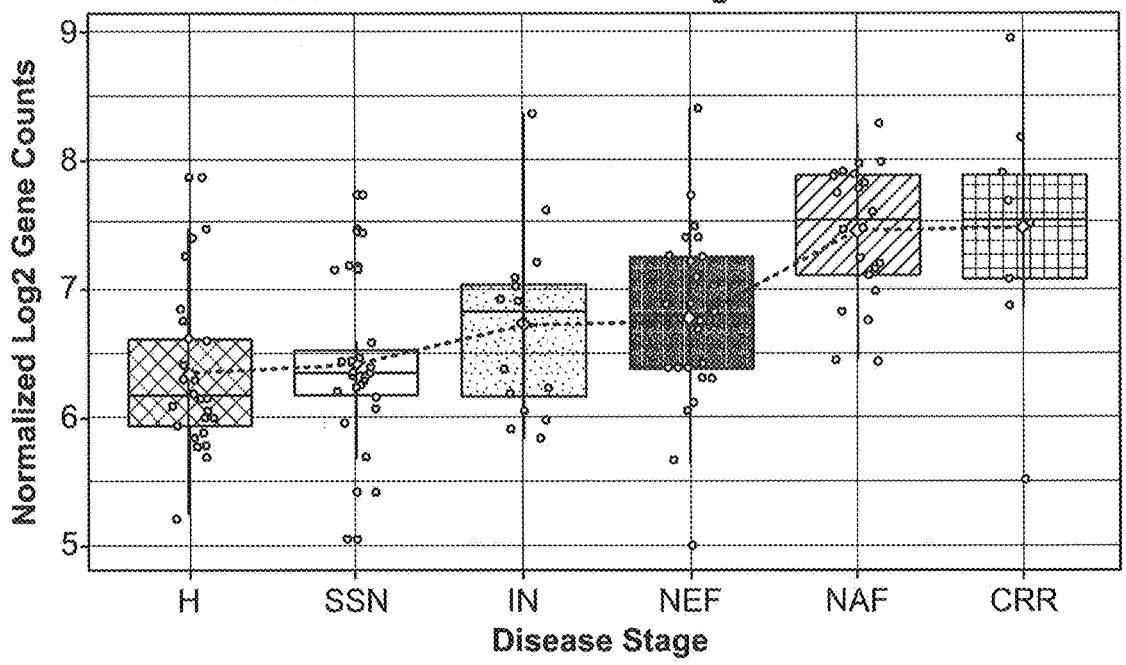
Figure 21D:
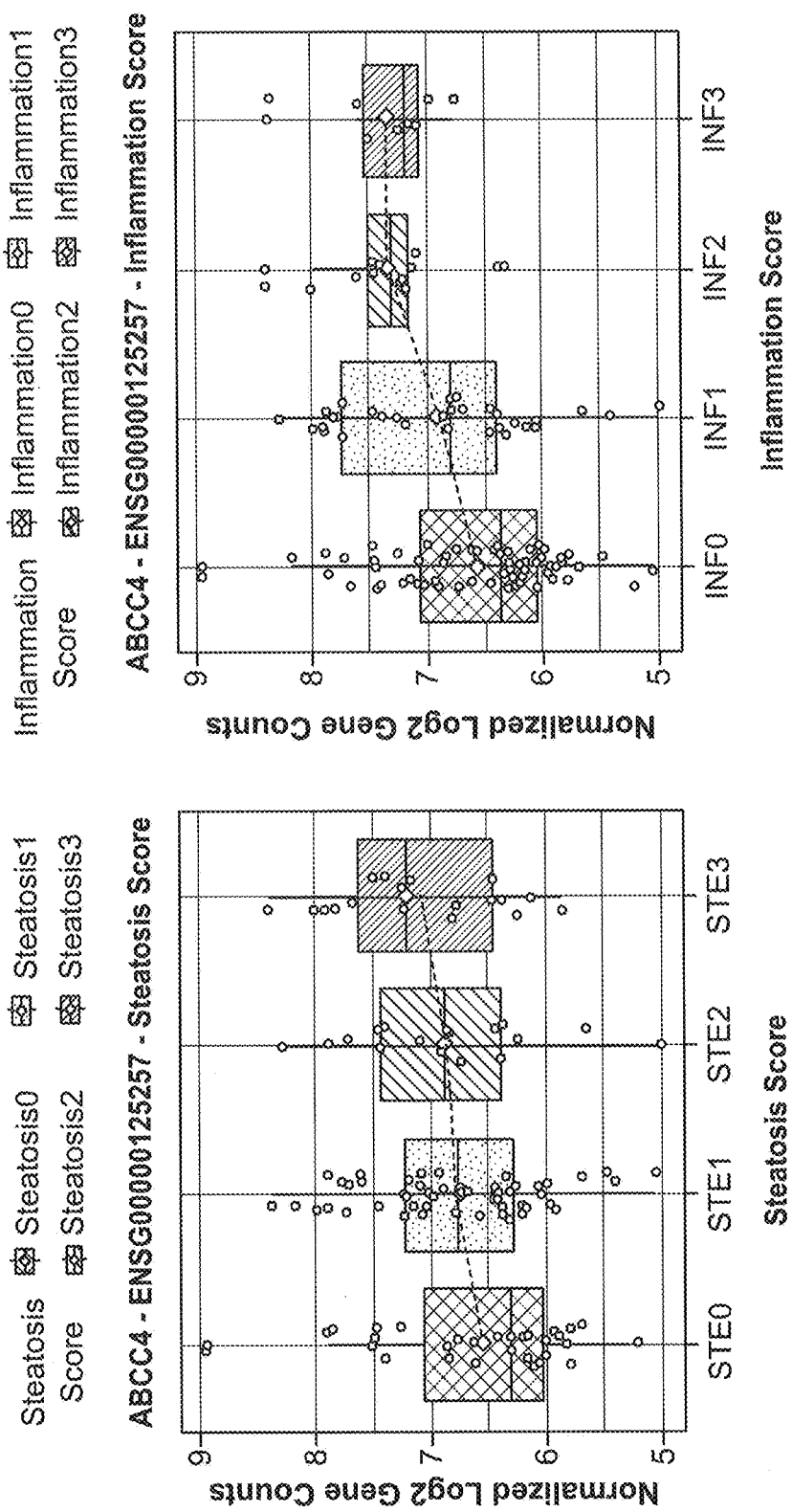
Figure 21E:
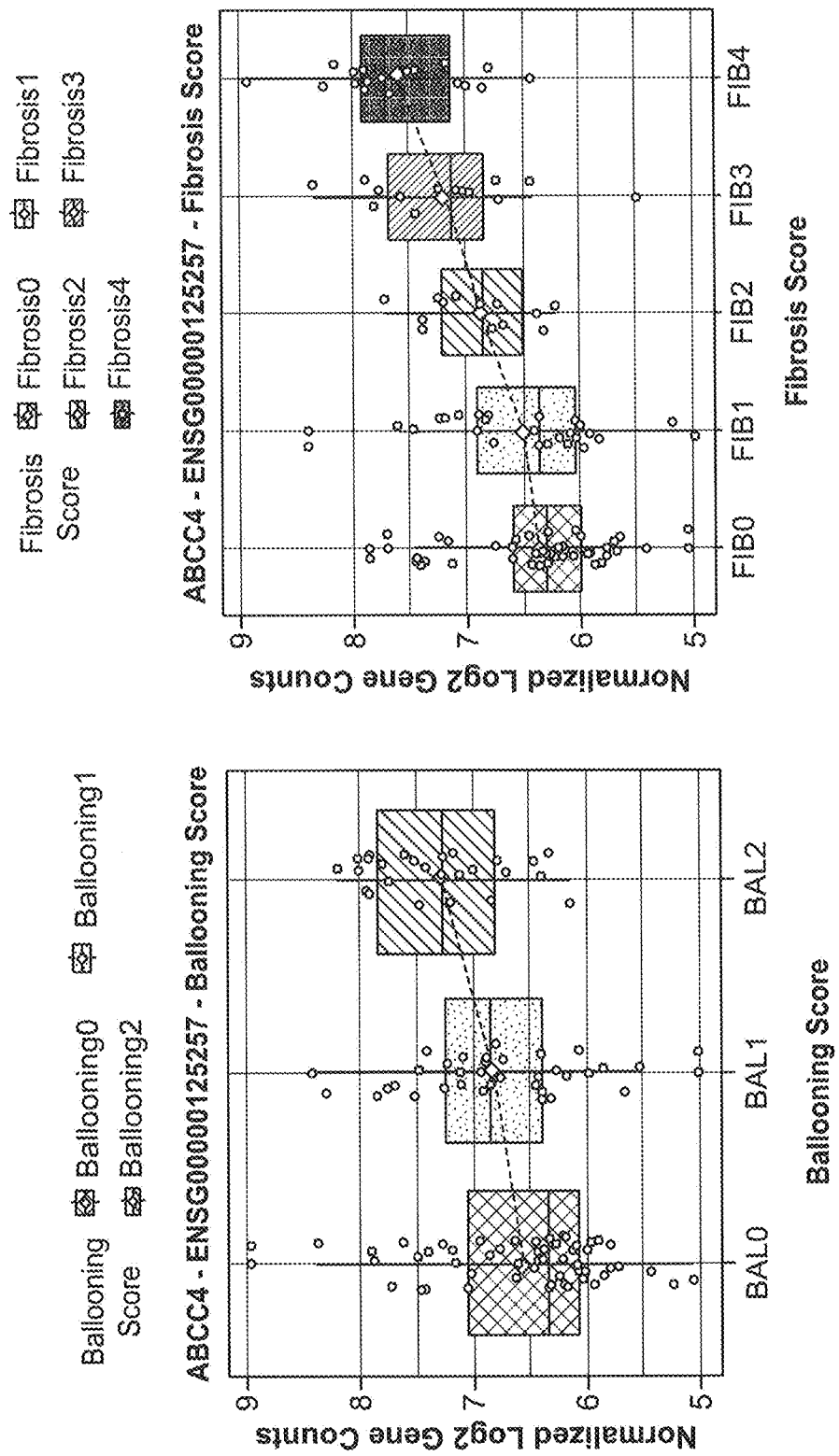

This target is a transporter that mediates the efflux of bile components into the blood. Interestingly in all control diet exposed mice, only a low number of relative reads was detected, whereas a strong enrichment in 3 out of 5 CDHFD mice was seen (FIG. 21A-21B). Furthermore, the expression of this gene increases during disease progression in the human patient cohort (FIG. 21C-21E). The expression also significantly increases in relation to the inflammation, fibrosis and ballooning score.

PAK3—P21 (RAC1) Activated Kinase 3

Figure 22A:
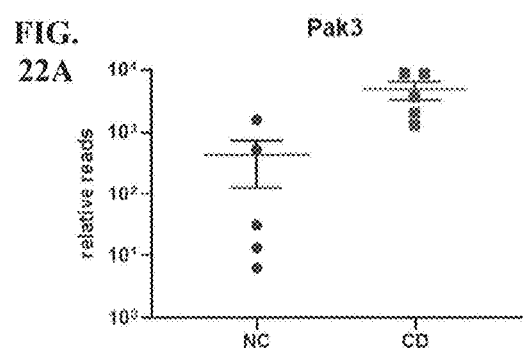
Figure 22B:
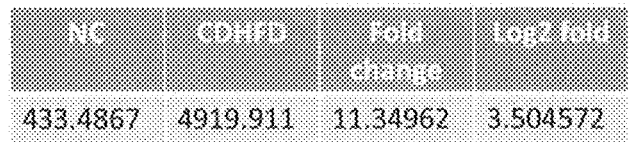
Figure 22D:
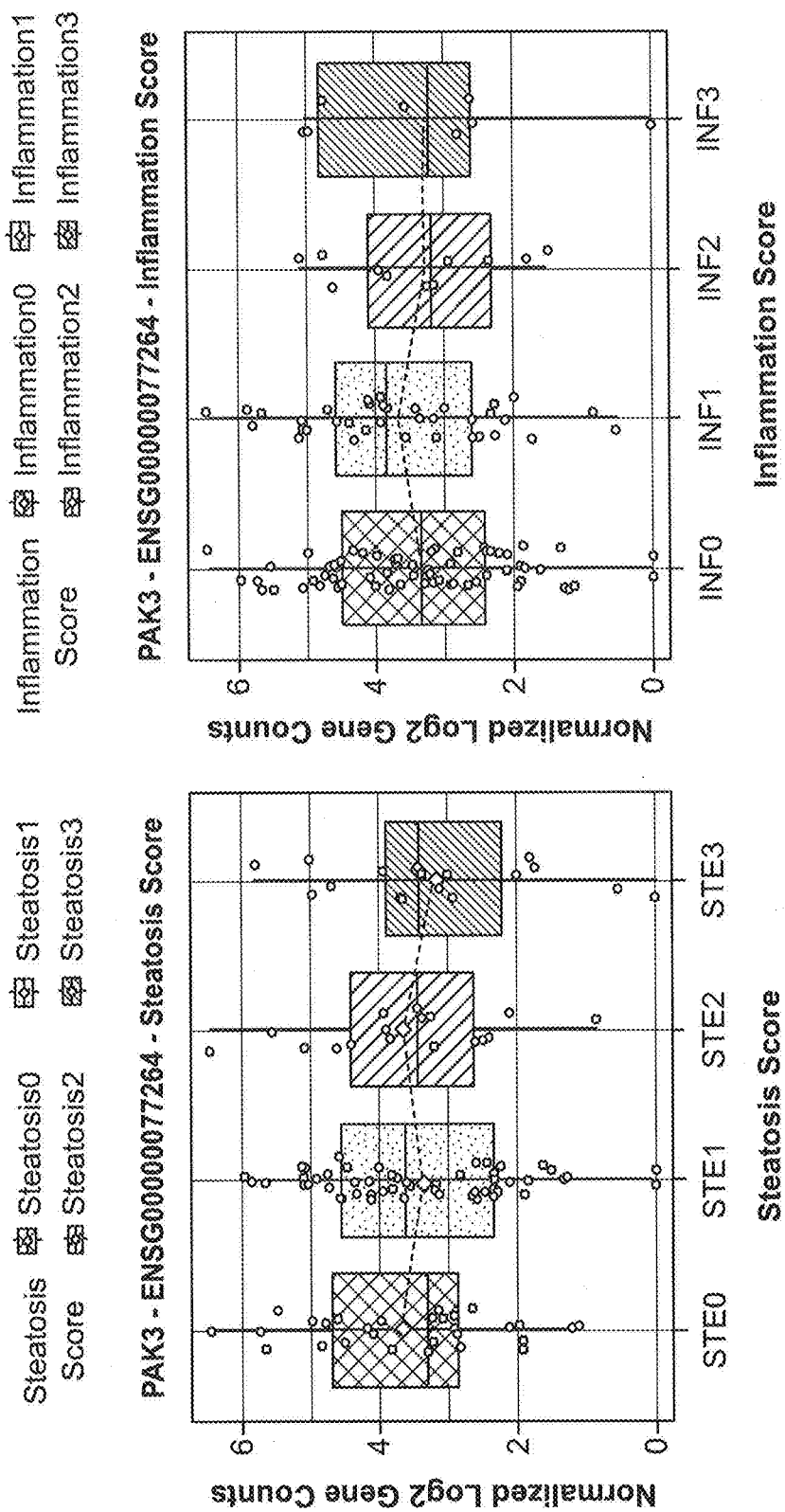
Figure 22E:
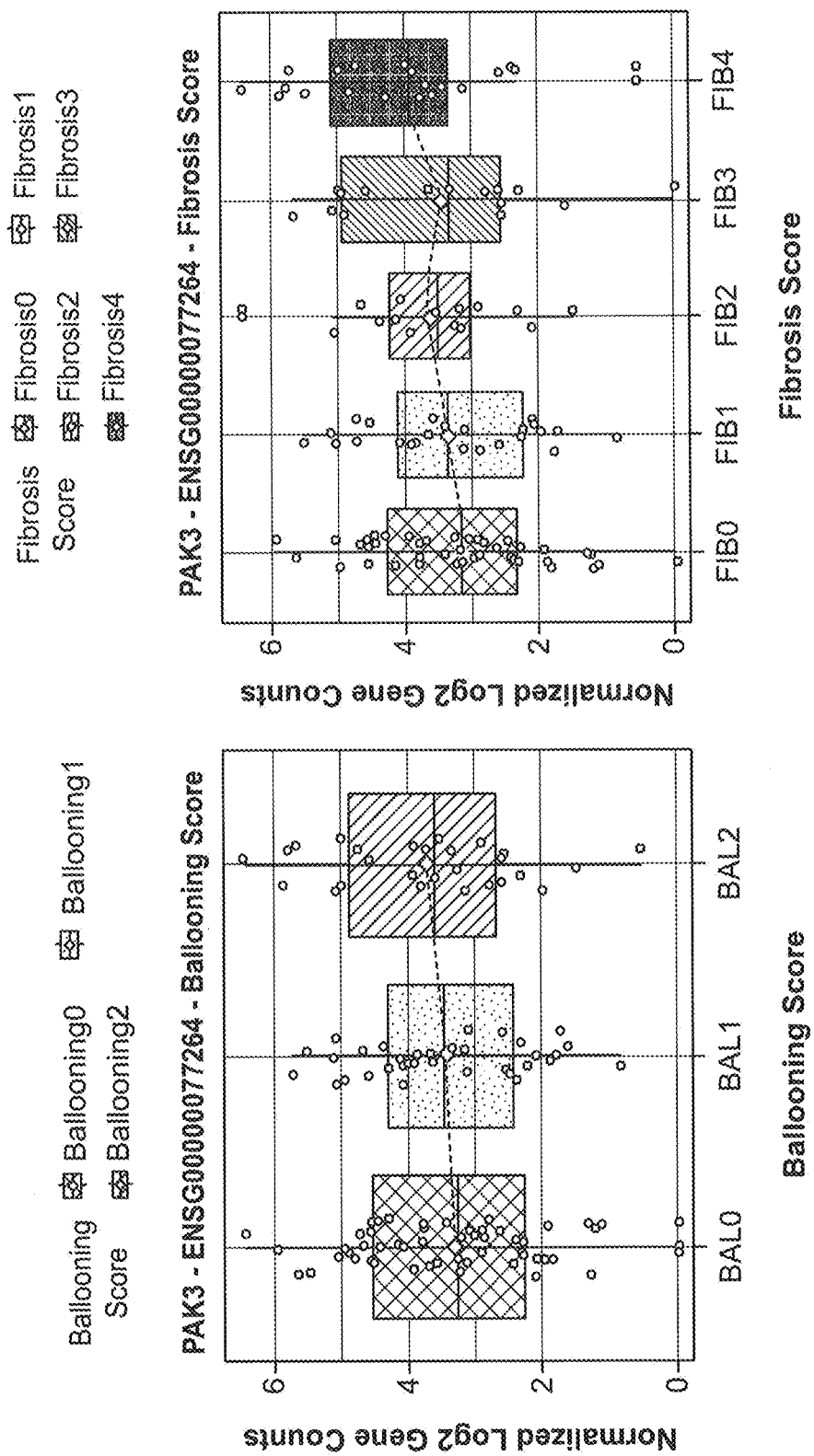
Figure 39:
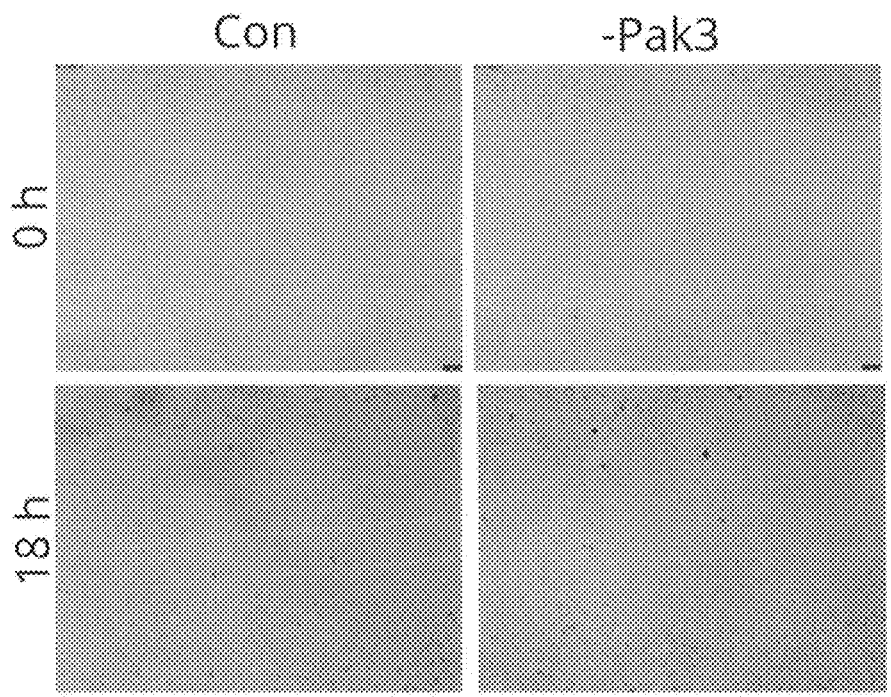
FIG. 39: Pak3 knockdown accelerates wound healing in vitro Stable knockdown of Pak3 in AML12 adult hepatocyte cell line accelerates wound healing (representative images are shown).

This target is a serine-threonine kinase. In 4 out of 5 mice enrichment for the shRNA targeting PAK3 (FIG. 22A-B; SEQ ID NO: 9) was seen. The expression of PAK3 is significantly upregulated in cirrhosis and fibrosis score 4 NAFLD patients (FIG. 22C-22E). As liver and pancreas both derive from the foregut endoderm during development, it is interesting that Pak 3 was described as a regulator of beta-cell differentiation. In that context, Pak3 promotes cell cycle exit and therefore would have an anti-proliferative function. Therefore, this is a highly interesting target for liver disease and regeneration, too, as confirmed by stable knockdown of Pak3 in the AML12 adult hepatocyte cell line, which accelerates wound healing (FIG. 39).

TRNP1—TMF1 Regulated Nuclear Protein 1

Figure 23A:
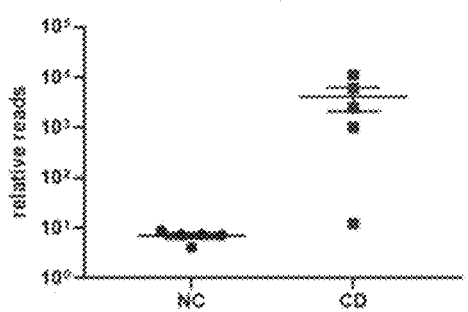
Figure 23B:
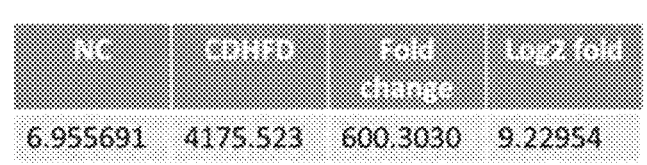
Figure 23D:
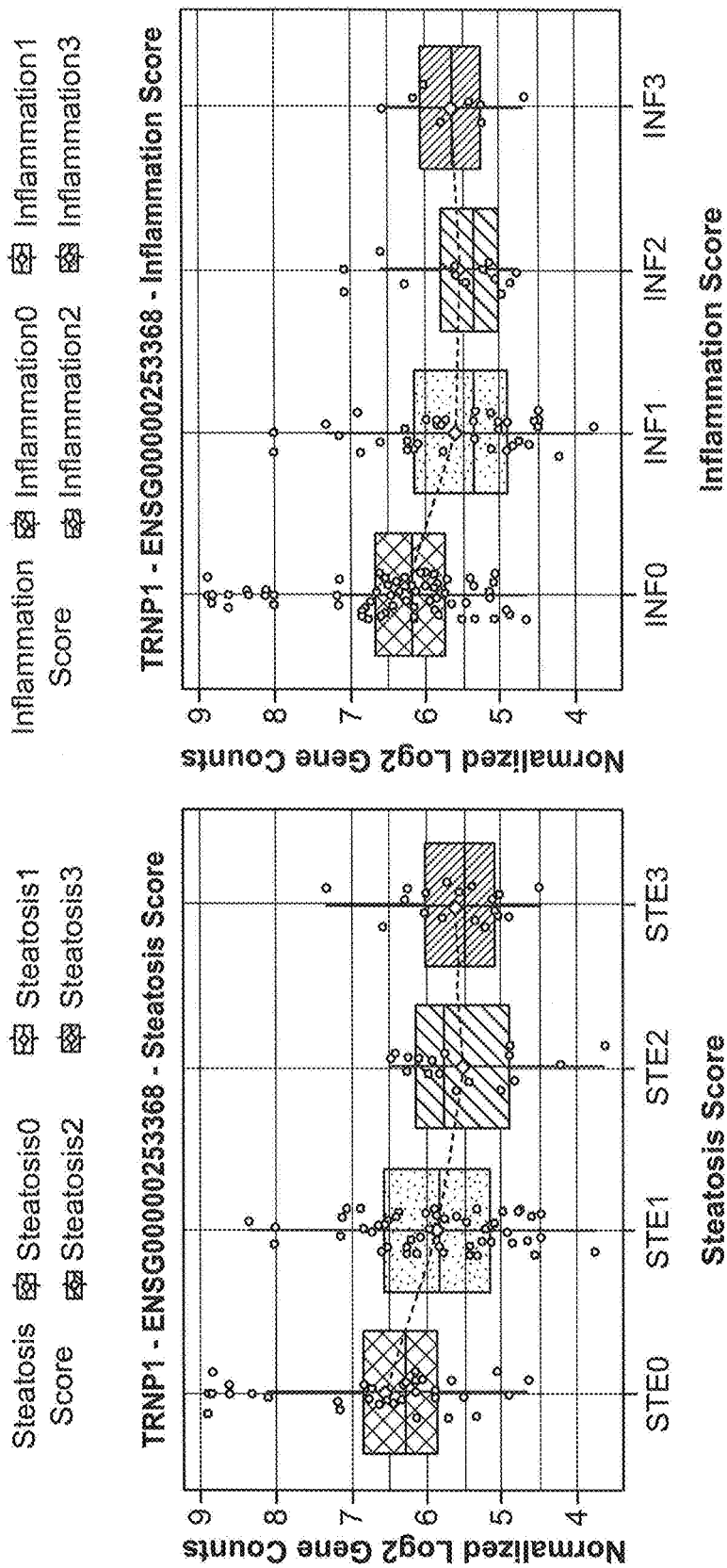
Figure 23E:
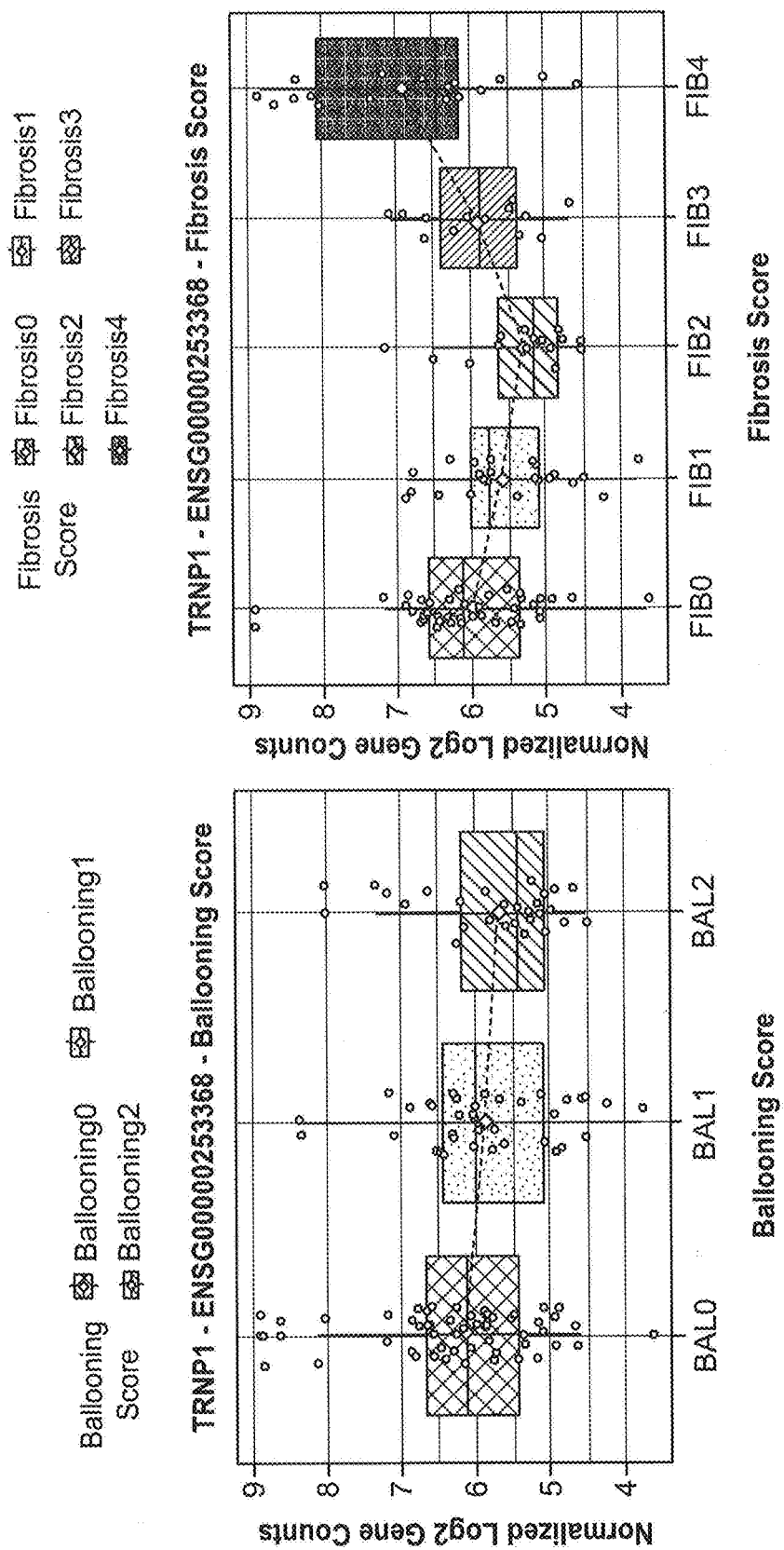

This target is a DNA-binding factor with a crucial role in brain development and accelerates cell-cycle progression. So far, no liver related function is described. In control fed mice, a consistent selection against shTrnp1 expressing cells (low relative reads) was detected. However, 4 out of 5 mice on CDHFD show enrichment for shTrnp1 (FIG. 23A-23B; SEQ ID NO: 13). Our human NAFLD patient cohort shows a complicated gene expression pattern of Trnp1 in the liver. In the earlier disease stages, we see a downregulation, but upregulation at the cirrhosis stage (FIG. 23C-23E). Consistent with this during steatosis we see a progressive downregulation.

APLN—Apelin

Figures 24A, 24B:
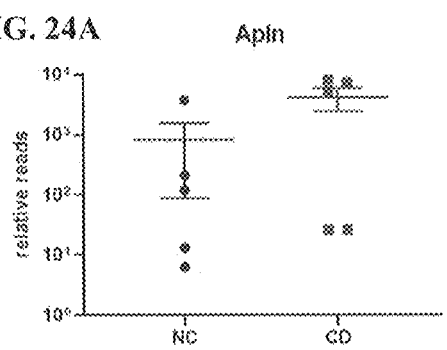
Figure 24D:
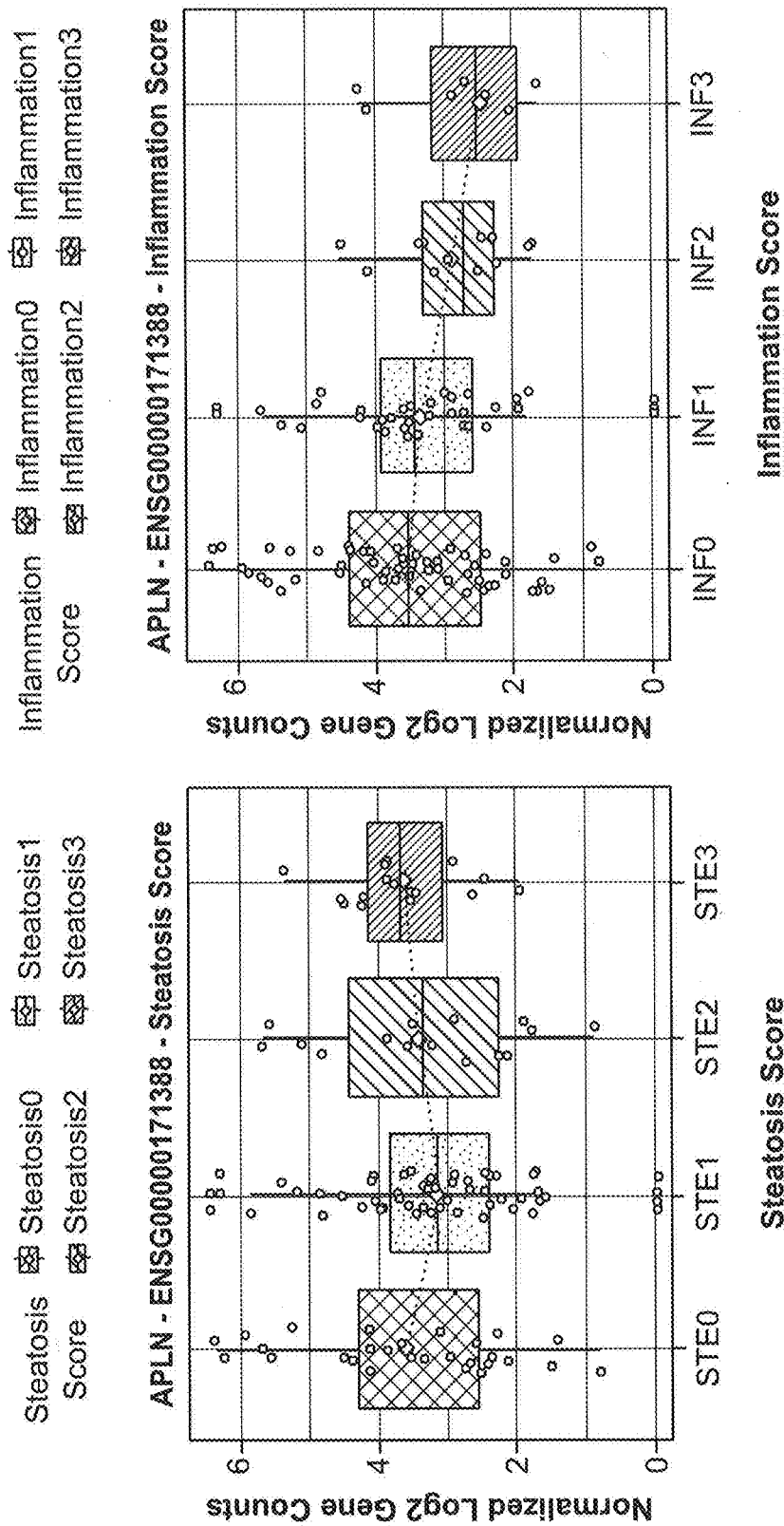
Figure 24E:
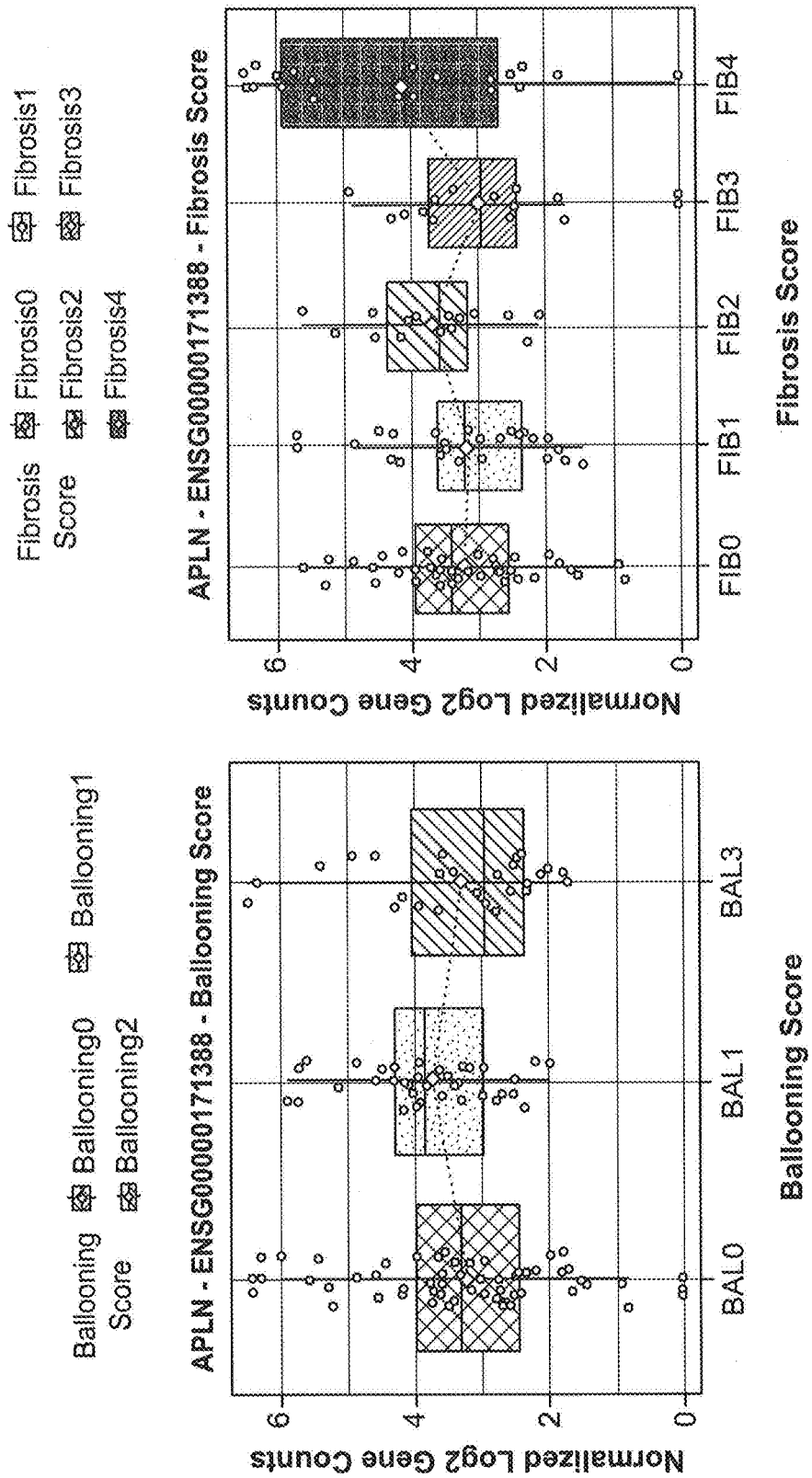

This target encodes a peptide that functions as an endogenous ligand for the G-protein coupled apelin receptor. In 3 out of 5 CDHFD mice, a strong enrichment for the shRNA targeting Apln compared to the control (FIG. 24A-24B; SEQ ID NO: 11) was seen. Based on the NAFLD patient cohort a significant upregulation at the cirrhosis stage is seen and consistent with this at a fibrotic score of 4 (FIG. 24C-24E). There is already a publication suggesting that Apln promotes hepatic fibrosis through ERK signaling. Also, Apln was described to be different in NAFLD patients and fatty liver rats and suggested as a diagnostic marker. Importantly, the encoded protein is processed into active peptide fragments, making it difficult to be targeted by classic drug approaches and ideal for RNAi based therapeutics.

KIF20A—Kinesin Family Member 20A

Figure 25A:
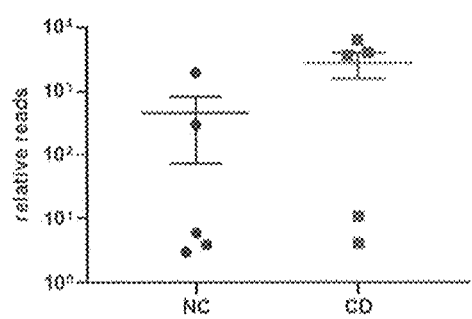
FIG. 25A, 25B, 25C, 25D, 25E: Kif20a is a potential therapeutic target for NAFLD FIG. 25A) Shown is the relative read numbers for the shRNA expression cassette targeting Kif20a for each animal (NC=normal chow, CD=CDHFD).
Figure 25B:
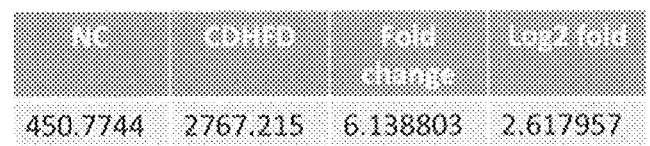
Figure 25C:
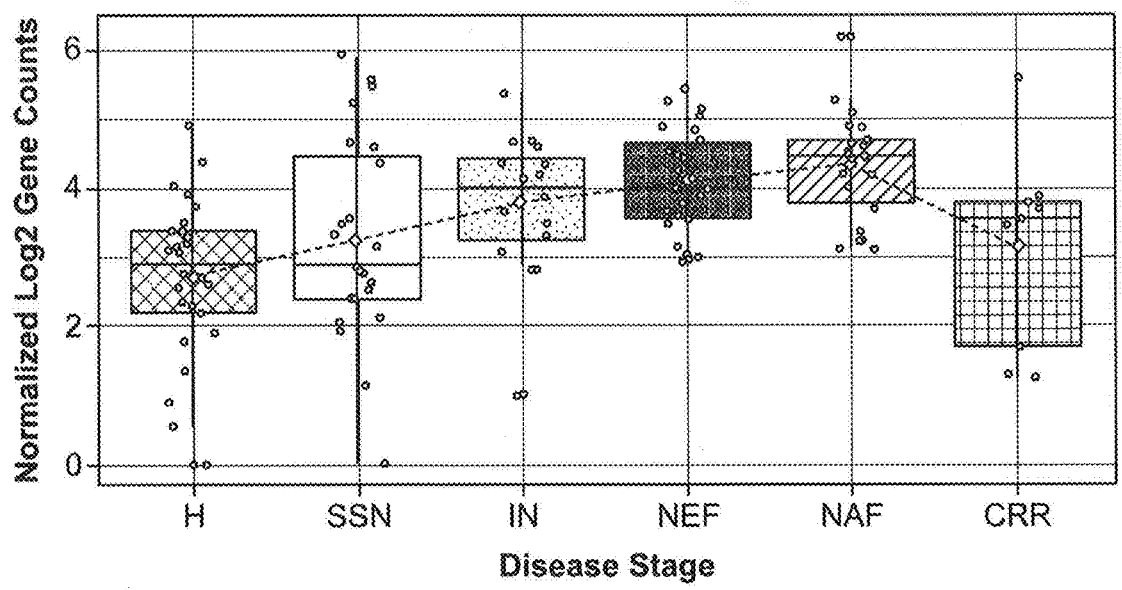
Figure 25D:
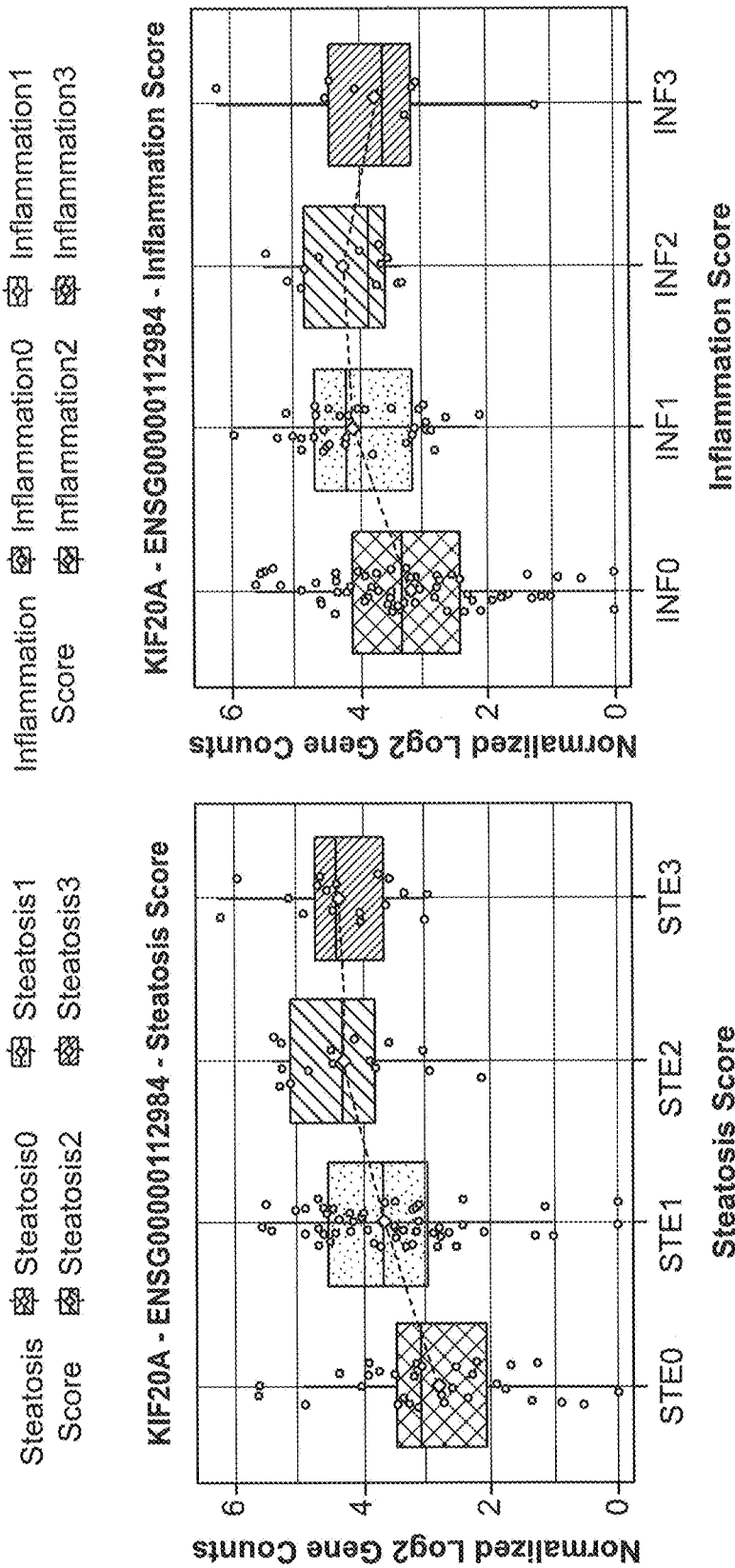
Figure 25E:
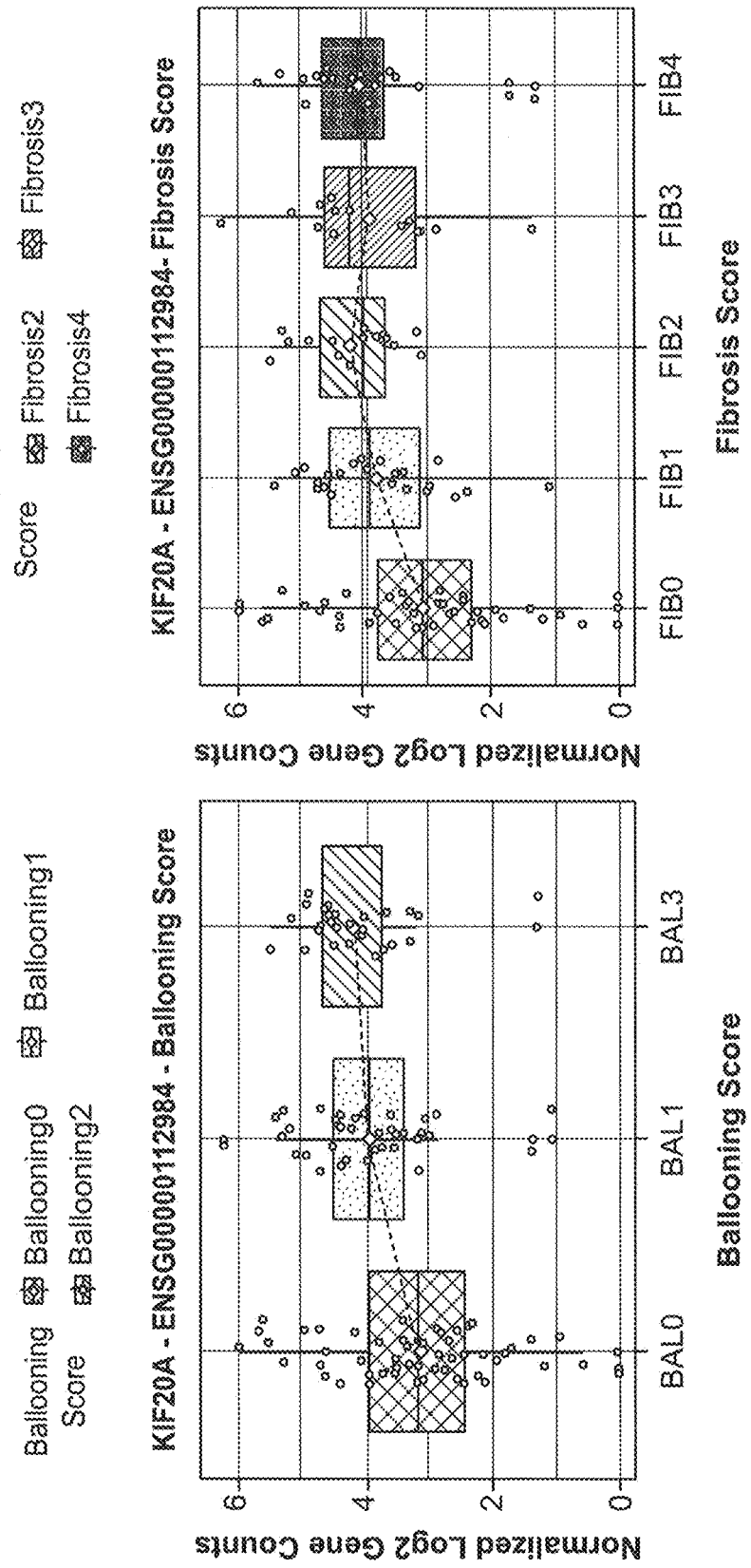

This target encodes a mitotic kinesin required for cytokinesis. In 3 out of 5 CDHFD mice, a strong enrichment for the shRNA targeting Kif20a compared to the control (FIG. 25A-25B; SEQ ID NO: 12) is seen. Based on the NAFLD patient cohort data, expression of Kif20a is increasing during disease progression (FIG. 25C-25E). Furthermore, high expression of Kif20a is associated with poor survival in case of HCC. Interestingly, Kif20a-knockdown affects cytokinesis leading to higher polyploidy. Higher polyploidy is also seen in many chronic liver diseases.

LTB—Lymphotoxin Beta

Figure 26A:
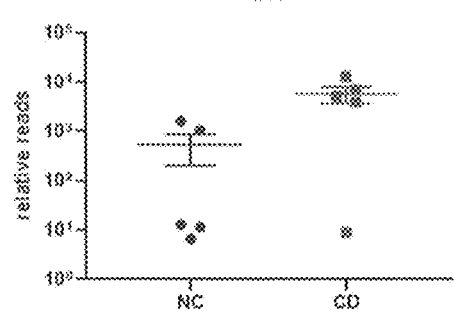
Figure 26B:
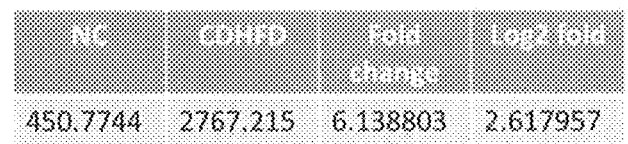
Figure 26D:
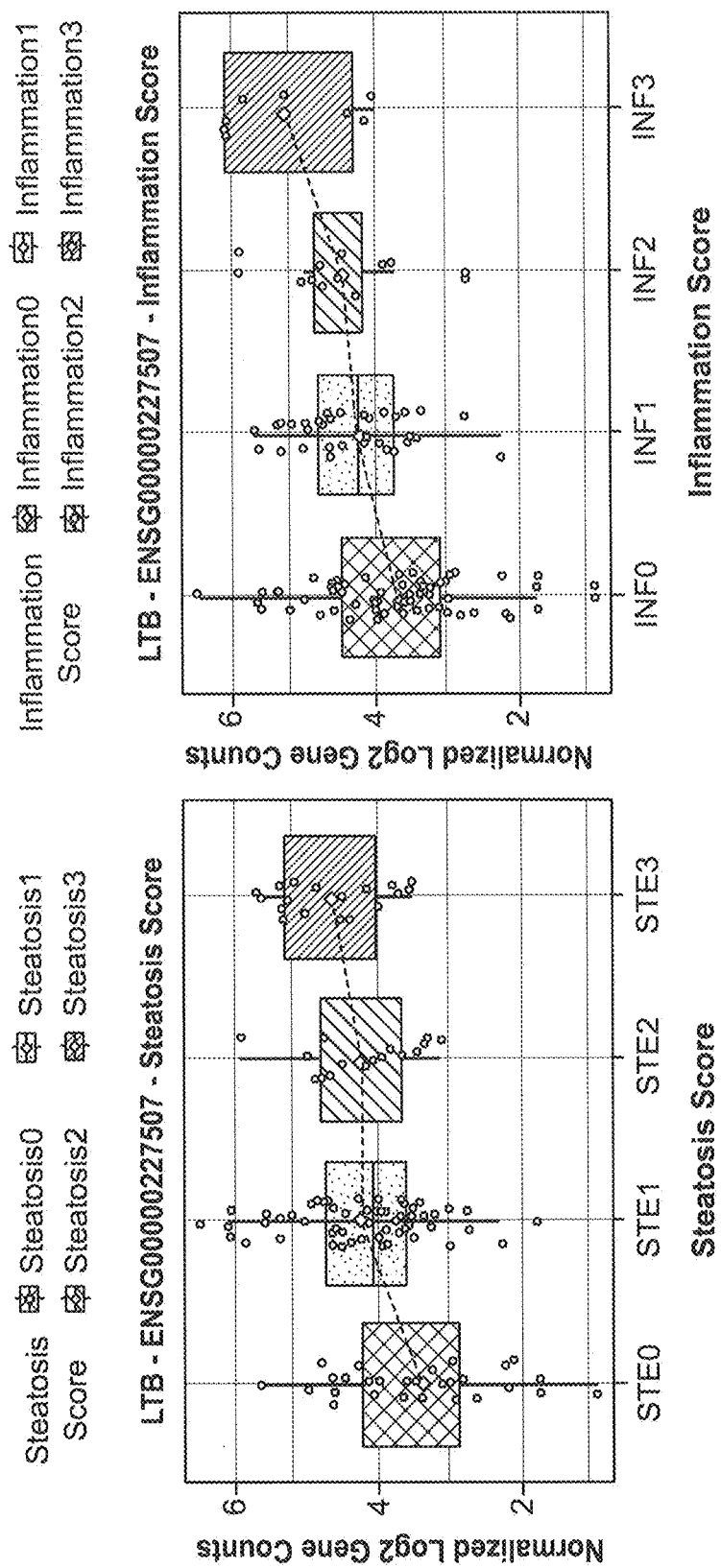
Figure 26E:
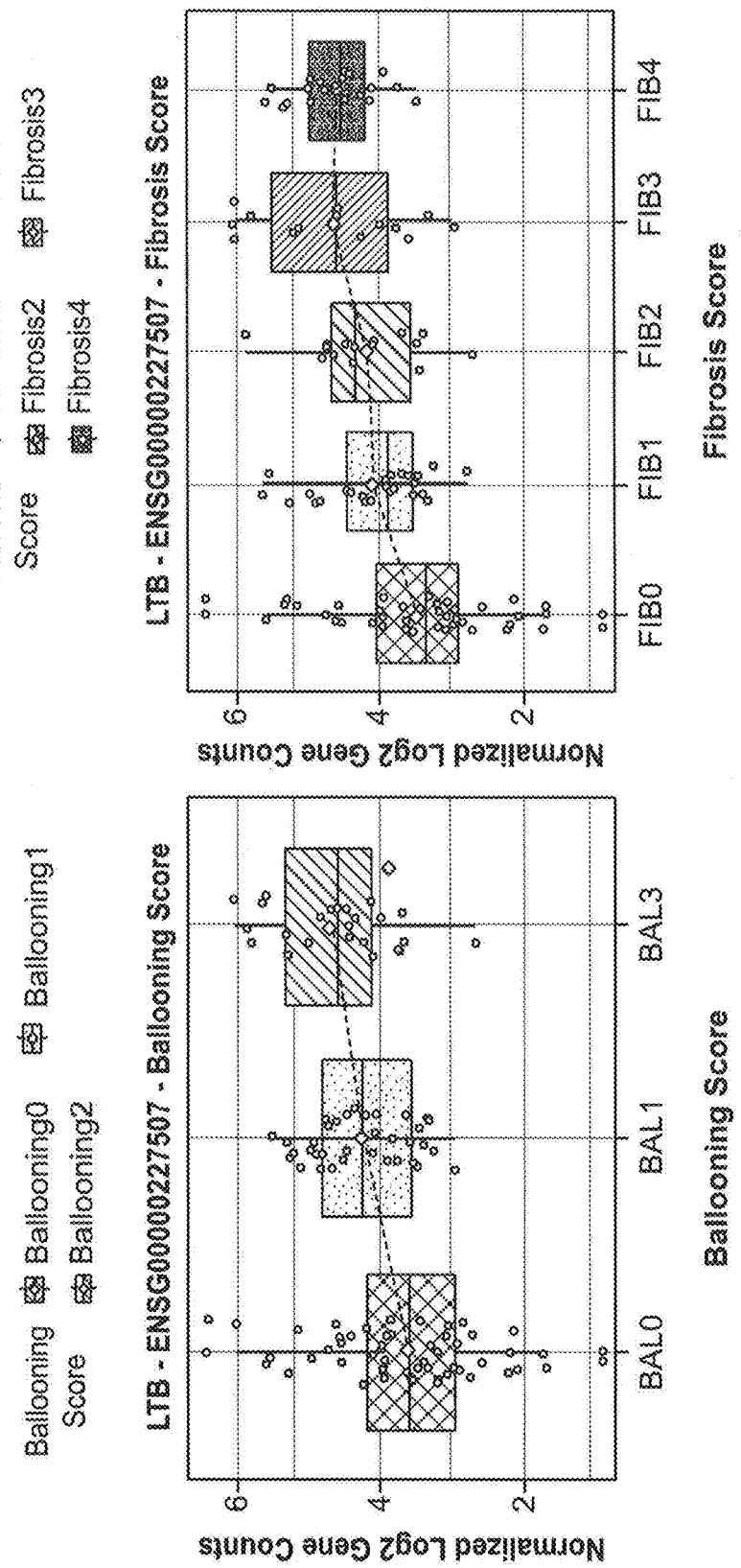

This target encodes a type II membrane protein of the TNF family. In 4 out of 5 CDHFD mice a strong enrichment for the shRNA targeting LTB compared to the control is seen (FIG. 26A-26B; SEQ ID NO: 10). Based on the NAFLD patient cohort data expression of LTB is consistently increasing during disease progression, except at the cirrhosis stage (FIG. 26C-26E). A significant expression increase based on steatosis, inflammation, ballooning and fibrosis score is also seen. Interestingly, LTB was found to regulate liver regeneration, is linked to obesity and animals lacking the lymphotoxin pathway were shown to resist diet-induced obesity.

Figure 27:
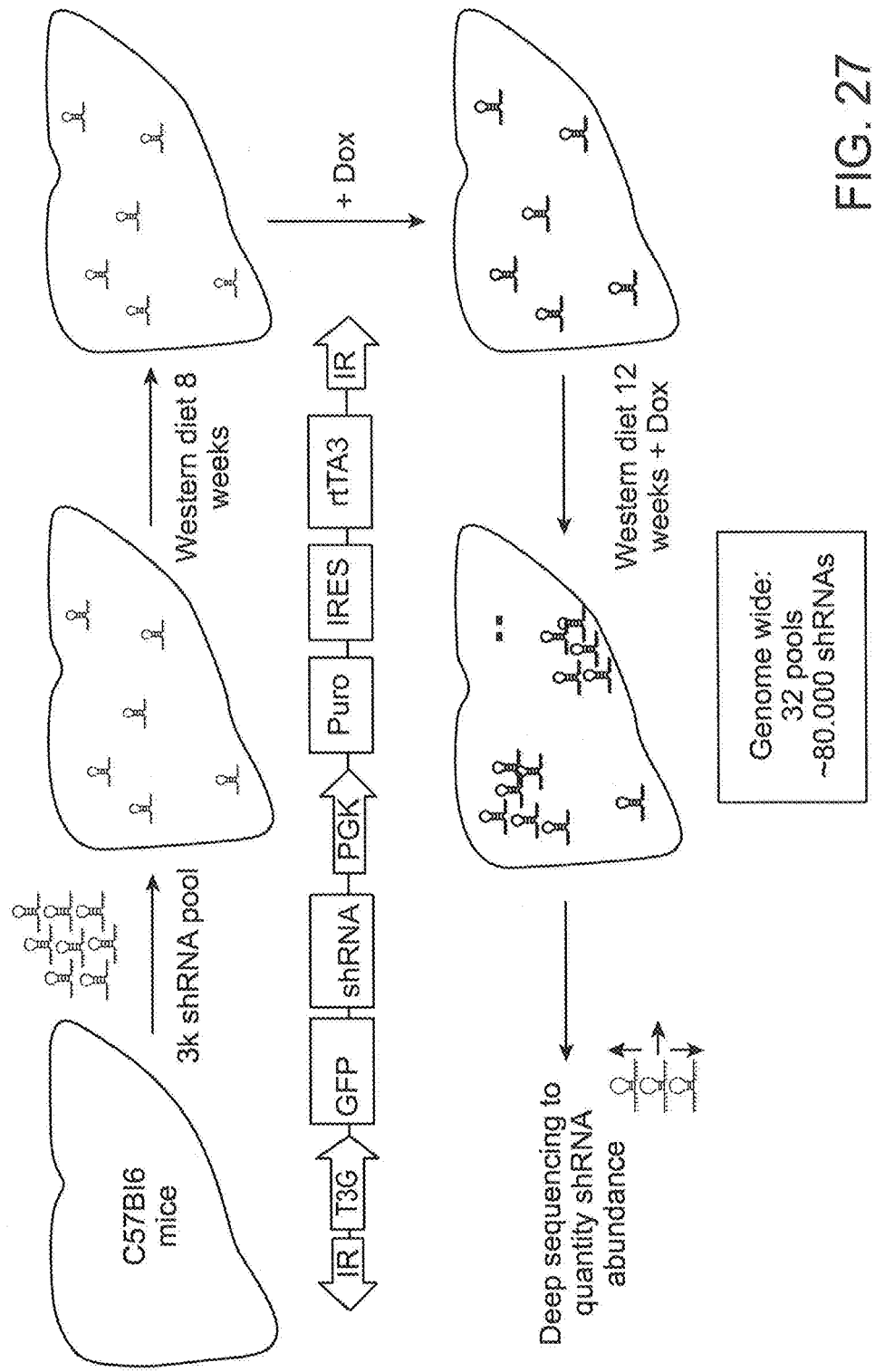
FIG. 27: Layout for NASH disease interception in vivo functional genetic screen FIG. 27) A genome wide in vivo functional genetic screen for disease interception. Nearly 80.000 shRNAs split into 32 sub-pools are screened. ShRNA expresses ion is inducible and only activated after liver shows steatosis but before NASH progression.

In addition, a functional genetic screen targeting the top down-regulated genes based on the NAFLD patient cohort is under the way. Also, a functional genomic screen is on the finishing line. In this set up, the inventors screen genome wide (32 shRNA pools of around 2500 to 3000 shRNAs in mice) specifically for modulators of NAFLD disease progression, by only inducing shRNA expression after steatosis is reached before progression to NASH (FIG. 27).

List of siRNA Guide Strands:

The siRNA guide strand is identical to the anti-sense strand of the sense-loop-anti-sense RNA structure. This sequence equals the reverse complement sequence of the targeting sequence in the mRNA. The list shows the 21 bp siRNA guide strand. SEQ ID NOs: 15 and 19 were used in the Examples. Light grey marked, bold and underlined are siRNA guide strands with top-DSIR prediction score and predicted by the genomewide sensor prediction algorithm (SEQ ID NOs: 349-351, 457, 465, 468, 470, 473, 1483, 1485, 1486, 1488-1490, 2209, 2225, 2234, 5061, 5062, 5390-5993, 5967, 5970, 5971, 6977, 6978 and 6993).

Sequence Identity

Pairwise and multiple sequence alignment for the purposes of determining percent identity between two or more amino acid or nucleic acid sequences can be achieved in various ways known to a person of skill in the art, for instance, using publicly available computer software such as ClustalOmega (Sdding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780) software. When using such software, the default parameters, e.g. for gap penalty and extension penalty, are preferably used.

Tables

TABLE 1

Mouse (mus musculus):

| SEQ ID NO | siRNA_id | siRNA guide strand/AS Sequence |
|---|---|---|
| 1 | Mfap4.1356 | UUCAGAGUUGAGCAGUAGCCG |
| 2 | Mfap4.760 | UUGAGGGAGUAAUAGAAGCCU |
| 3 | Grhpr.361 | UUCUGCAGUGGCAUCUGUCAG |
| 4 | Grhpr.1024 | UACAGCUUGAGUUCGCUGGGC |
| 5 | Grhpr.1025 | UUACAGCUUGAGUUCGCUGGG |
| 6 | Iftg1.698 | UUAGAGGCAGUCAAUGUCGUG |
| 7 | Itfg1.680 | UUGAAGUCCAUAAUCAGUGGU |
| 8 | Abcc4 | UCGAAUUUGUUCACGUCGUUG |
| 9 | Pak3 | UGUGUAAACAGUUCCUGAUGC |
| 10 | Ltb | UCUGGUGUAGAAUCCGCAGCU |
| 11 | Apln | UCAAGGAGAGCCAGAGCAGCA |
| 12 | Kif20a | UAAUUGACUUGUUUCAUCUAG |
| 13 | Trnp1 | UGACUUAGUGGGGUCGGAGU |

Human (Homo sapiens):

TABLE 2

Results for MFAP4. Score threshold: 70. Design: siRNA 21 nt.

| SEQ ID NO | siRNA_id | siRNA guide strand/AS Sequence |
|---|---|---|
| 14 | 1 | AUAGAUGUCGUCACAGUCCAG |
| 15 | 2 | UAUUAUGUUAUUAUUACACUG |
| 16 | 3 | UUGUAGUCAUUCCAGCCGCGG |
| 17 | 4 | UUAUUGAGACCUUCAGUCCCU |
| 18 | 5 | UAGAACCAUGUGCCUCUCGGA |
| 19 | 6 | UAUUGAGACCUUCAGUCCCUA |
| 20 | 7 | UCACACUGCACUGCUCAGCUU |
| 21 | 8 | UUCUGCACCUGACUCCAGGUG |
| 22 | 9 | UCGAAGGUAGAGAACUUCUGG |
| 23 | 10 | UCAGCUUAGCACACUAGGGUG |
| 24 | 11 | UAGGACACCAUCAGCAGGGGA |
| 25 | 12 | UUUAUUGAGACCUUCAGUCCC |
| 26 | 13 | UUGGAGGCAACUCAUUCUCAU |
| 27 | 14 | UAUGUUAUUAUUACACUGUCU |
| 28 | 15 | UCGCAGCUCAUACUUCUGCUU |
| 29 | 16 | UAGAUGUCGUCACAGUCCAGG |
| 30 | 17 | UUAUGUUAUUAUUACACUGUC |
| 31 | 18 | UUGGUGCUCGGGAAUCAGCAG |
| 32 | 19 | UAAACCUCUCAACACCCAGAG |
| 33 | 20 | UAGUAGAAGCCCUUCCACUGG |
| 34 | 21 | UGUAAGGAGUUGGUGCUCGGG |
| 35 | 22 | AUCAGCAGAAGCAUGCAUCAG |
| 36 | 23 | UGUUAUUAUUACACUGUCUUU |
| 37 | 24 | UUCAUUCAGGUUCUGAAGGUU |
| 38 | 25 | UUCUGCACAAAGAGGUCCUGG |
| 39 | 26 | UCUCCAGAGCAUCUCCUCGGA |
| 40 | 27 | UUUGAGAGCAGCCCAGAGGAG |
| 41 | 28 | UUGAGGGAGUAGUAGAAGCCC |
| 42 | 29 | UAUGAUAGUGAGGUGGGCUGG |
| 43 | 30 | UAGAAUACACCAUGGGCCCUG |
| 44 | 31 | UGUAACUUCAGGUGUAGGGGA |
| 45 | 32 | UUGUAAGGAGUUGGUGCUCGG |
| 46 | 33 | UUGUUCUCAAAGUCCUCCAAG |
| 47 | 34 | UGAGGGAGUAGUAGAAGCCCU |
| 48 | 35 | UUCUGCUUCAGUGUCAGGAGG |

TABLE 2-continued

Results for MFAP4. Score threshold: 70. Design: siRNA 21 nt.

| SEQ ID NO | siRNA_id | siRNA guide strand/AS Sequence |
|---|---|---|
| 49 | 36 | AUACUUCUGCUUCAGUGUCAG |
| 50 | 37 | UUAUUAUUACACUGUCUUUUU |
| 51 | 38 | AUGUCGUCACAGUCCAGGGGU |
| 52 | 39 | AUGUUAUUAUUACACUGUCUU |
| 53 | 40 | UCUGCGCUGACCGCGUUCGGG |
| 54 | 41 | UUCCACGGUACUCACCACAGG |
| 55 | 42 | AAGGUUUAUUGAGACCUUCAG |
| 56 | 43 | UAAGGAGUUGGUGCUCGGGAA |
| 57 | 44 | UGUCAGGAGGUGCAUGUUCUG |
| 58 | 45 | AUUAUGUUAUUAUUACACUGU |
| 59 | 46 | UCCUCCUCUGCGCUGACCGCG |
| 60 | 47 | UGAAGGUUUAUUGAGACCUUC |
| 61 | 48 | AAGAUGGACCACAAAGGCCUG |
| 62 | 49 | UUCAGUGUCAGGAGGUGCAUG |
| 63 | 50 | UAGAUGAGGUACACGCCGUCU |
| 64 | 51 | UCAUACUUCUGCUUCAGUGUC |
| 65 | 52 | UUAGGAAUGGAUGCCCUGGGU |
| 66 | 53 | AUGGAGACCAUGGGUGUCCAG |
| 67 | 54 | UACUUCUGCUUCAGUGUCAGG |
| 68 | 55 | UUCAUGCUGUCAGUUCUGCUC |
| 69 | 56 | AAGCAGGACAAGAUGGACCAC |
| 70 | 57 | AUUCUCAUGGAGCCCAGCCAG |
| 71 | 58 | UGCGGAACCAGAAGGCUCCUG |
| 72 | 59 | AGAGAUUGUCCUCUGCUCCCU |
| 73 | 60 | AAGUCCUCCAAGUCCACUCGC |
| 74 | 61 | UCCAAGUCCACUCGCAGCUCA |
| 75 | 62 | UUCAGUCCCUACCCACUCCCA |
| 76 | 63 | UGUUCACACUGCACUGCUCAG |
| 77 | 64 | UAGGAAUGGAUGCCCUGGGUG |
| 78 | 65 | AACCUCUCAACACCCAGAGGG |
| 79 | 66 | UGGGCAUAGAUGUCGUCACAG |
| 80 | 67 | UGGGACAUGGUUUGAGAGCAG |
| 81 | 68 | UCCACGGUACUCACCACAGGG |
| 82 | 69 | AAGACCUCAUAUGCAUGCCUA |
| 83 | 70 | AGCUUGUAGUCAUUCCAGCCG |
| 84 | 71 | UCAUGCUGUCAGUUCUGCUCA |
| 85 | 72 | UGUUGGGACAGGUUGGAGGCA |
| 86 | 73 | AAGCUGAGUAUGAUAGUGAGG |
| 87 | 74 | UGUUGUUCUCAAAGUCCUCCA |
| 88 | 75 | UCUGCUUCAGUGUCAGGAGGU |
| 89 | 76 | UGUUUCAGGGUGGUGUGCGGU |
| 90 | 77 | UGUGCCUCUCGGAAGAGGCCU |
| 91 | 78 | UGUAGUCAUUCCAGCCGCGGA |
| 92 | 79 | UAUUAUUAUUAUGUUAUUAUU |
| 93 | 80 | UAUUAUUAUGUUAUUAUUACA |
| 94 | 81 | UCAGUCCCUACCCACUCCCAG |
| 95 | 82 | UUAUUAUGUUAUUAUUACACU |
| 96 | 83 | UAGGACAGGGAGUCACCUGCC |
| 97 | 84 | UACUCUCCAUCAGCACGGCCG |
| 98 | 85 | UGAGUAUGAUAGUGAGGUGGG |
| 99 | 86 | AUGGAGAAGUCAGCGUACUUG |
| 100 | 87 | AUGAUAGUGAGGUGGGCUGGG |
| 101 | 88 | UGGUAGGACAGGGAGUCACCU |
| 102 | 89 | UGUCAGUUCUGCUCAGAGUGG |
| 103 | 90 | UCUCAAAGUCCUCCAAGUCCA |
| 104 | 91 | UCUGAAGGUUUAUUGAGACCU |
| 105 | 92 | AUUAUUAUUGUUAUUAUUA |
| 106 | 93 | UACACGCCGUCUGACUGGUAG |
| 107 | 94 | UUGUCCUCUGCUCCCUCAUGU |
| 108 | 95 | UGUGAAAUACAAGGUUCCCUU |
| 109 | 96 | UCCUGGUCCCGGUCGAAGGUA |
| 110 | 97 | AGCAGAAGCAUGCAUCAGGGG |
| 111 | 98 | GAUGUCGUCACAGUCCAGGGG |
| 112 | 99 | AUGAGGUACACGCCGUCUGAC |
| 113 | 100 | UUUCAGGGUGGUGUGCGGUAG |
| 114 | 101 | UCCACAGUGAGGAAGCAGGAC |
| 115 | 102 | UUUGAGGGAGUAGUAGAAGCC |
| 116 | 103 | UCGGAUCCCGGAGACCUGGGG |
| 117 | 104 | UUCCCUUCUGCACCUGACUCC |
| 118 | 105 | UGCAGAGAUUGUCCUCUGCUC |
| 119 | 106 | AUCUCAGUGCGUUUGAGGGAG |
| 120 | 107 | UCGGUGGUCAUGUCACAGAAG |
| 121 | 108 | CUGAGUAUGAUAGUGAGGUGG |

TABLE 2-continued

Results for MFAP4. Score threshold: 70. Design: siRNA 21 nt.

| SEQ ID NO | siRNA_id | siRNA guide strand/AS Sequence |
|---|---|---|
| 122 | 109 | UGAAAUACAAGGUUCCCUUCU |
| 123 | 110 | AGGUUCUGAAGGUUUAUUGAG |
| 124 | 111 | UGGUCAUGUCACAGAAGACGG |
| 125 | 112 | UUCCAGCCGCGGAAGAAACUU |
| 126 | 113 | UGAUAGUGAGGUGGGCUGGGG |
| 127 | 114 | CAUGCUGUCAGUUCUGCUCAG |
| 128 | 115 | UCAGCUGUUGGGACAGGUUGG |
| 129 | 116 | ACAUGGUUUGAGAGCAGCCCA |
| 130 | 117 | UAAGUUGGUGGGAGGGAUGCU |
| 131 | 118 | CAAGGUUCCCUUCUGCACCUG |
| 132 | 119 | CUCAGCUUAGCACACUAGGGU |
| 133 | 120 | AGAGCAUCUCCUCGGAUCCCG |
| 134 | 121 | UCCUCGGAUCCCGGAGACCUG |
| 135 | 122 | CAUAGAUGUCGUCACAGUCCA |
| 136 | 123 | AACCAGAAGGCUCCUGAGGAG |
| 137 | 124 | CUUGUAGUCAUUCCAGCCGCG |
| 138 | 125 | AGGCCUGUGAAAUACAAGGUU |
| 139 | 126 | UCCCUUCUGCACCUGACUCCA |
| 140 | 127 | UGUGGUAGGACAGGGAGUCAC |
| 141 | 128 | UGAGGAAGCAGGACAAGAUGG |
| 142 | 129 | AGCAUCUCCUCGGAUCCCGGA |
| 143 | 130 | AGAACCAUGUGCCUCUCGGAA |
| 144 | 131 | UGGUGCUCGGGAAUCAGCAGA |
| 145 | 132 | GUUCUGCACAAAGAGGUCCUG |
| 146 | 133 | GUCGAAGGUAGAGAACUUCUG |
| 147 | 134 | AGGUACACGCCGUCUGACUGG |
| 148 | 135 | AACUCAUUCUCAUGGAGCCCA |
| 149 | 136 | AUGCUGAAGAUGGGACAUGGU |
| 150 | 137 | UGCUGAAGAUGGGACAUGGUU |
| 151 | 138 | UGCGCAGUUCUGCACAAAGAG |
| 152 | 139 | UAGCCCUGGGCAUAGAUGUCG |
| 153 | 140 | AAGACGGGCACAGGCACACUG |
| 154 | 141 | AUGCUGUCAGUUCUGCUCAGA |
| 155 | 142 | AAAGUCCUCCAAGUCCACUCG |
| 156 | 143 | AGUAGAAGCCCUUCCACUGGG |
| 157 | 144 | UGUCCUCUGCUCCCUCAUGUG |
| 158 | 145 | UCCACUCGCAGCUCAUACUUC |
| 159 | 146 | UCGGGAAUCAGCAGAAGCAUG |
| 160 | 147 | AUCAGCACGGCCGAAGCCCAG |
| 161 | 148 | GUUAUUAUUACACUGUCUUUU |
| 162 | 149 | UGCGCUGACCGCGUUCGGGGA |
| 163 | 150 | ACAAAGAGGUCCUGGUCCCGG |
| 164 | 151 | AAGUUGGUGGGAGGGAUGCUG |
| 165 | 152 | UGCACCUGACUCCAGGUGUAA |
| 166 | 153 | UGCACUGCUCAGCUUAGCACA |
| 167 | 154 | AGUCCUCCAAGUCCACUCGCA |
| 168 | 155 | UUCACACUGCACUGCUCAGCU |
| 169 | 156 | UCAUAUGCAUGCCUACCUUGG |
| 170 | 157 | UGAGGAGAGCUGCGCAGUU |
| 171 | 158 | CAGCUCAUACUUCUGCUUCAG |
| 172 | 159 | UGUCACAGAAGACGGGCACAG |
| 173 | 160 | AAACCUCUCAACACCCAGAGG |
| 174 | 161 | UCUGCACCUGACUCCAGGUGU |
| 175 | 162 | ACAGUGAGGAAGCAGGACAAG |
| 176 | 163 | UGGUUUGAGAGCAGCCCAGAG |
| 177 | 164 | UCUGACUGGUAGCCCUGGGCA |
| 178 | 165 | UCAUCUCAGUGCGUUUGAGGG |
| 179 | 166 | UGAAGAUGGGACAUGGUUUGA |
| 180 | 167 | CAGCUUAGCACACUAGGGUGG |
| 181 | 168 | UCUGCACAAAGAGGUCCUGGU |
| 182 | 169 | UGCCUCUCGGAAGAGGCCUGG |
| 183 | 170 | UGCUCAGCUUAGCACACUAGG |
| 184 | 171 | ACUUCUGCUUCAGUGUCAGGA |
| 185 | 172 | AUUAUUAUGUUAUUAUUACAC |
| 186 | 173 | UCAUGUCACAGAAGACGGGCA |
| 187 | 174 | AGAUGAGGUACACGCCGUCUG |
| 188 | 175 | GUUGUUCUCAAAGUCCUCCAA |
| 189 | 176 | UCAACACCCAGAGGGUAUGGG |
| 190 | 177 | AUUCAGGUUCUGAAGGUUUAU |
| 191 | 178 | CUGAAGGUUUAUUGAGACCUU |
| 192 | 179 | UGGAGAGAAGCAGCAGCAGCG |
| 193 | 180 | UCAAAGUCCUCCAAGUCCACU |
| 194 | 181 | UUGAGAGCAGCCCAGAGGAGU |

TABLE 2-continued

Results for MFAP4. Score threshold: 70. Design: siRNA 21 nt.

| SEQ ID NO | siRNA_id | siRNA guide strand/AS Sequence |
|---|---|---|
| 195 | 182 | UUGGUGGGAGGGAUGCUGAAG |
| 196 | 183 | UAGUCAUUCCAGCCGCGGAAG |
| 197 | 184 | AUGGACCACAAAGGCCUGCAG |
| 198 | 185 | AAUACAAGGUUCCCUUCUGCA |
| 199 | 186 | CAUGGUUUGAGAGCAGCCCAG |
| 200 | 187 | UCAUUCAGGUUCUGAAGGUUU |
| 201 | 188 | UUAUUAUUAUGUUAUUAUUAC |
| 202 | 189 | AGGCAACUCAUUCUCAUGGAG |
| 203 | 190 | UGGAGAAGUCAGCGUACUUGG |
| 204 | 191 | AGUACUCCAUCAGCACGGC |
| 205 | 192 | AUACAAGGUUCCCUUCUGCAC |
| 206 | 193 | ACUGCUCAGCUUAGCACACUA |
| 207 | 194 | CUAGAAUACACCAUGGGCCCU |
| 208 | 195 | UCAGCAGAAGCAUGCAUCAGG |
| 209 | 196 | UCCUGAGGAGAGCUGCGCA |
| 210 | 197 | AUCCUCCUCUGCGCUGACCGC |
| 211 | 198 | CUCCAGAGCAUCUCCUCGGAU |
| 212 | 199 | AGUGCCUUCAUGCUGUCAGUU |
| 213 | 200 | CACACUGCACUGCUCAGCUUA |
| 214 | 201 | CUCUCCAGAGCAUCUCCUCGG |
| 215 | 202 | AAAUACAAGGUUCCCUUCUGC |
| 216 | 203 | UGGAGGCAACUCAUUCUCAUG |
| 217 | 204 | UUCAGGUUCUGAAGGUUUAUU |
| 218 | 205 | CUGCUCAGCUUAGCACACUAG |
| 219 | 206 | CACAAAGAGGUCCUGGUCCCG |
| 220 | 207 | UACACCAUGGGCCCUGUUCAC |
| 221 | 208 | UCAGGAGGUGCAUGUUCUGCA |
| 222 | 209 | UGUCAGCUGUUGGGACAGGUU |
| 223 | 210 | AGCAGGGGAGCACUCAUGGA |
| 224 | 211 | GAGACCUUCAGUCCCUACCCA |
| 225 | 212 | ACUCGCAGCUCAUACUUCUGC |
| 226 | 213 | ACUCAUUCUCAUGGAGCCCAG |
| 227 | 214 | UGGUCCCGGUCGAAGGUAGAG |
| 228 | 215 | CUGUGAAAUACAAGGUUCCCU |
| 229 | 216 | UACCCACUCCCAGCCCUGCAG |
| 230 | 217 | UUCUCAAAGUCCUCCAAGUCC |
| 231 | 218 | AGCCGCGGAAGAAACUUACUG |
| 232 | 219 | AGAUGUCGUCACAGUCCAGGG |
| 233 | 220 | AGCACUCAUGGAGACCAUGGG |
| 234 | 221 | ACUCUCCAUCAGCACGGCCGA |
| 235 | 222 | CUUCAGUGUCAGGAGGUGCAU |
| 236 | 223 | GAAGCUGAGUAUGAUAGUGAG |
| 237 | 224 | CAGGAGGUGCAUGUUCUGCAG |
| 238 | 225 | CAUCUCAGUGCGUUUGAGGGA |
| 239 | 226 | AGUGUAACUUCAGGUGUAGGG |
| 240 | 227 | ACAAGGUUCCCUUCUGCACCU |
| 241 | 228 | AGGUUUAUUGAGACCUUCAGU |
| 242 | 229 | CUCCUCUGCGCUGACCGCGUU |
| 243 | 230 | AUUGUCCUCUGCUCCCUCAUG |
| 244 | 231 | CACUCGCAGCUCAUACUUCUG |
| 245 | 232 | UCCACUUCCCGCCCUCGGUGG |
| 246 | 233 | CAGGCUAGAACCAUGUGCCUC |
| 247 | 234 | AAAGAGGUCCUGGUCCCGGUC |
| 248 | 235 | CUCGGGAAUCAGCAGAAGCAU |
| 249 | 236 | ACGGGCACAGGCACACUGGGG |
| 250 | 237 | CUCUCCAUCAGCACGGCCGAA |
| 251 | 238 | UCAGGUUCUGAAGGUUUAUUG |
| 252 | 239 | AGUUCUGCACAAAGAGGUCCU |
| 253 | 240 | UAGAAGCCCUUCCACUGGGCC |
| 254 | 241 | AGUAUGAUAGUGAGGUGGGCU |
| 255 | 242 | ACAGGUUGGAGGCAACUCAUU |
| 256 | 243 | ACCAUGUGCCUCUCGGAAGAG |
| 257 | 244 | AGCUGUUUGGGACAGGUUGGAG |
| 258 | 245 | ACCUCCAGAGCAUCUCCUC |
| 259 | 246 | UCCUCUGCGCUGACCGCGUUC |
| 260 | 247 | GGUCAUGUCACAGAAGACGGG |
| 261 | 248 | AUGGUUUGAGAGCAGCCCAGA |
| 262 | 249 | UCAGGGUGGUGUGCGGUAGCU |
| 263 | 250 | UACAAGGUUCCCUUCUGCACC |
| 264 | 251 | AAGAGGUCCUGGUCCCGGUCG |
| 265 | 252 | UCCAGCCGCGGAAGAAACUUA |
| 266 | 253 | CUCAUAUGCAUGCCUACCUUG |
| 267 | 254 | AAGGUUCCCUUCUGCACCUGA |

TABLE 2-continued

Results for MFAP4. Score threshold: 70. Design: siRNA 21 nt.

| SEQ ID NO | siRNA_id | siRNA guide strand/AS Sequence |
|---|---|---|
| 268 | 255 | UGCUGUCAGUUCUGCUCAGAG |
| 269 | 256 | AACACCCAGAGGGUAUGGGGA |
| 270 | 257 | GUAGAUGAGGUACACGCCGUC |
| 271 | 258 | UAGGCCGUGUUGUUCUCAAAG |
| 272 | 259 | AGAUGGGACAUGGUUUGAGAG |
| 273 | 260 | UUCCACUGGGCCCAGUUGAUG |
| 274 | 261 | CAGCUGUUGGGACAGGUUGGA |
| 275 | 262 | AGCCCUGCAGAGAUUGUCCUC |
| 276 | 263 | CAUACUUCUGCUUCAGUGUCA |
| 277 | 264 | UUCUGAAGGUUUAUUGAGACC |
| 278 | 265 | AGGACAGGGAGUCACCUGCCC |
| 279 | 266 | ACAAGAUGGACCACAAAGGCC |
| 280 | 267 | AGAGGUCCUGGUCCCGUCGA |
| 281 | 268 | AGCUGAGUAUGAUAGUGAGGU |
| 282 | 269 | UCCCUACCCACUCCCAGCCCU |
| 283 | 270 | AGGCUCCUGAGGAGAGAGCUG |
| 284 | 271 | AGACCAUGGGUGUCCAGGGA |
| 285 | 272 | GUCCACUCGCAGCUCAUACUU |
| 286 | 273 | AUUGAGACCUUCAGUCCCUAC |
| 287 | 274 | AUGAGGCCUGUGAAAUACAAG |
| 288 | 275 | UCACAGAAGACGGGCACAGGC |
| 289 | 276 | AGAUUGUCCUCUGCUCCCUCA |
| 290 | 277 | AGACCUUCAGUCCCUACCCAC |
| 291 | 278 | CUGUUCACACUGCACUGCUCA |
| 292 | 279 | GUAGGACACCAUCAGCAGGGG |
| 293 | 280 | GUGUAACUUCAGGUGUAGGGG |
| 294 | 281 | GAGACCAUGGGUGUCCAGGGG |
| 295 | 282 | CAACUCAUUCUCAUGGAGCCC |
| 296 | 283 | CUGACUGGUAGCCCUGGGCAU |
| 297 | 284 | GGAAGAAACUUACUGAGCCAU |
| 298 | 285 | CGGAAGAAACUUACUGAGCCA |
| 299 | 286 | CUGUCAGUUCUGCUCAGAGUG |
| 300 | 287 | CCCAGCUUGUAGUCAUUCCAG |
| 301 | 288 | AAGCCCUUCCACUGGGCCCAG |
| 302 | 289 | GUACACGCCGUCUGACUGGUA |
| 303 | 290 | GCUAAACCUCUCAACACCCAG |
| 304 | 291 | AGAAGCAGCAGCAGCGGCAGG |
| 305 | 292 | UCAGUGUCAGGAGGUGCAUGU |
| 306 | 293 | AGAGAAGCAGCAGCAGCGGCA |
| 307 | 294 | UGACUGGUAGCCCUGGGCAUA |
| 308 | 295 | CUGCUUCAGUGUCAGGAGGUG |
| 309 | 296 | CACGGUACUCACCACAGGGGA |
| 310 | 297 | CUCGGUGGUCAUGUCACAGAA |
| 311 | 298 | AAGGAGUUGGUGCUCGGGAAU |
| 312 | 299 | GAGUAUGAUAGUGAGGUGGGC |
| 313 | 300 | GGAAUCAGCAGAAGCAUGCAU |
| 314 | 301 | CUAGAACCAUGUGCCUCUCGG |
| 315 | 302 | CUCGCAGCUCAUACUUCUGCU |
| 316 | 303 | UGCUUCAGUGUCAGGAGGUGC |
| 317 | 304 | UCCUCCAAGUCCACUCGCAGC |
| 318 | 305 | AGGAGUGCCUUCAUGCUGUCA |
| 319 | 306 | GUCCUCCAAGUCCACUCGCAG |
| 320 | 307 | ACACUGCACUGCUCAGCUUAG |
| 321 | 308 | GAGUAGUAGAAGCCCUUCCAC |
| 322 | 309 | GUAGUCAUUCCAGCCGCGGAA |
| 323 | 310 | CUGCAGAGAUUGUCCUCUGCU |
| 324 | 311 | AUGGGCCCUGUUCACACUGCA |
| 325 | 312 | AUAGGCCGUGUUGUUCUCAAA |
| 326 | 313 | AUGGGACAUGGUUUGAGAGCA |
| 327 | 314 | GAGGGAGUAGUAGAAGCCCUU |
| 328 | 315 | GACAGGUUGGAGGCAACUCAU |
| 329 | 316 | CCUCAUAUGCAUGCCUACCUU |
| 330 | 317 | AAUCAGCAGAAGCAUGCAUCA |
| 331 | 318 | CCAGGCUAGAACCAUGUGCCU |
| 332 | 319 | UGCACAAAGAGGUCCUGGUCC |
| 333 | 320 | CGUGGAGAGAAGCAGCAGCAG |
| 334 | 321 | CUGCACCUGACUCCAGGUGUA |
| 335 | 322 | CUCCAAGUCCACUCGCAGCUC |
| 336 | 323 | AGUAGUAGAAGCCCUUCCACU |
| 337 | 324 | UCAGUGCGUUUGAGGGAGUAG |
| 338 | 325 | GGUAGGACAGGGAGUCACCUG |
| 339 | 326 | CAGGGUGGUGUGCGGUAGCUG |
| 340 | 327 | AGACGGGCACAGGCACACUGG |

TABLE 2-continued

Results for MFAP4. Score threshold: 70. Design: siRNA 21 nt.

| SEQ ID NO | siRNA_id | siRNA guide strand/AS Sequence |
|---|---|---|
| 341 | 328 | CACAGUGAGGAAGCAGGACAA |
| 342 | 329 | CUUCAUGCUGUCAGUUCUGCU |
| 343 | 330 | GGAGAGAAGCAGCAGCAGCGG |
| 344 | 331 | UGAGGUACACGCCGUCUGACU |
| 345 | 332 | CUCCUGAGGAGAGAGCUGCGC |
| 346 | 333 | AUCUCCUCGGAUCCCGGAGAC |
| 347 | 334 | UGAGACCUUCAGUCCCUACCC |

TABLE 3

Results for GRHPR. Score threshold: 70. Design: siRNA 21 nt.

| SEQ ID NO | siRNA_id | siRNA guide strand/AS Sequence |
|---|---|---|
| 348 | 1 | UUCUGGGCUCGUCACAUCCAG |
| 349 | 2 | UGAUGUUGAUGAACACAGCUG |
| 350 | 3 | AUGUUGAUGAACACAGCUGUU |
| 351 | 4 | UAGACACAAACUCUGCCUGGA |
| 352 | 5 | UUCUGGAAGAAGUCCUUGUUG |
| 353 | 6 | UUGUUGCAGAGUCCCUCGGUU |
| 354 | 7 | UCACAUCCAGUCCAGCAGCUG |
| 355 | 8 | AUCUUCUGGAAGAAGUCCUUG |
| 356 | 9 | UGGAAGAAGUCCUUGUUGCAG |
| 357 | 10 | UUUGUAGGCAGUGGUUCUGGG |
| 358 | 11 | UGUUGAUGAACACAGCUGUUU |
| 359 | 12 | AAUCUCUGGACACCGAAUGGU |
| 360 | 13 | UUCUGCUGCUUCCUCAGGCCU |
| 361 | 14 | UACAGAAAUCUCUGGACACCG |
| 362 | 15 | UCGUCACAUCCAGUCCAGCAG |
| 363 | 16 | UUGAUGAACACAGCUGUUUCC |
| 364 | 17 | UUGCAGAGUCCCUCGGUUGCA |
| 365 | 18 | UGAUGAACACAGCUGUUUCCU |
| 366 | 19 | UCAUCUUCUGGAAGAAGUCCU |
| 367 | 20 | UCUGCUGCUUCCUCAGGCCUG |
| 368 | 21 | UCGGUUGCAGGUGUUAAGGAG |
| 369 | 22 | UUGUAGGCAGUGGUUCUGGGC |
| 370 | 23 | UUCCUUCAUCUUCUGGAAGAA |
| 371 | 24 | UCUGCCUGGAAUUCUGCUGCU |
| 372 | 25 | UUCUUCAGGGUCAGGAGAGGG |
| 373 | 26 | UGGAAUUCUGCUGCUUCCUCA |
| 374 | 27 | AGCUGUUUCCUUCAUCUUCUG |
| 375 | 28 | UGUUUCCUUCAUCUUCUGGAA |
| 376 | 29 | UUCAUCUUCUGGAAGAAGUCC |
| 377 | 30 | AUGAACACAGCUGUUUCCUUC |
| 378 | 31 | ACAGAAAUCUCUGGACACCGA |
| 379 | 32 | UUGCAGGUGUUAAGGAGCAGG |
| 380 | 33 | UCUCUGGACACCGAAUGGUUU |
| 381 | 34 | UCUUCUGGAAGAAGUCCUUGU |
| 382 | 35 | UGGUACAGGUCGUCCUGGUUU |
| 383 | 36 | CUGAUGUUGAUGAACACAGCU |
| 384 | 37 | GUAGACACAAACUCUGCCUGG |
| 385 | 38 | AUGGUUUCAGAGCCGAGCAA |
| 386 | 39 | AACUCUGCCUGGAAUUCUGCU |
| 387 | 40 | AUCUCUGGACACCGAAUGGUU |
| 388 | 41 | UAGGCAGUGGUUCUGGGCUCG |
| 389 | 42 | UGUACAGAAAUCUCUGGACAC |
| 390 | 43 | UGUUGCAGAGUCCCUCGGUUG |
| 391 | 44 | UGCUGAUGUUGAUGAACACAG |
| 392 | 45 | UUCAGGGUCAGGAGAGGGUGG |
| 393 | 46 | CUUGUUGCAGAGUCCCUCGGU |
| 394 | 47 | ACUCUGCCUGGAAUUCUGCUG |
| 395 | 48 | CAGAAAUCUCUGGACACCGAA |
| 396 | 49 | UGAAAUCAGAUUGGGCAGCCA |
| 397 | 50 | CAUCUUCUGGAAGAAGUCCUU |
| 398 | 51 | UGCAGAGUCCCUCGGUUGCAG |
| 399 | 52 | AGUCCUUGUUGCAGAGUCCCU |
| 400 | 53 | AAGUCCUUGUUGCAGAGUCCC |
| 401 | 54 | UCCUGGUUUACGACGUCGCCC |
| 402 | 55 | GAUGUUGAUGAACACAGCUGU |
| 403 | 56 | AAAUCUCUGGACACCGAAUGG |
| 404 | 57 | UCAGGGUCAGGAGAGGGUGGU |
| 405 | 58 | UUUCCUUCAUCUUCUGGAAGA |
| 406 | 59 | AAGAAGUCCUUGUUGCAGAGU |
| 407 | 60 | CUGCCUGGAAUUCUGCUGCUU |

TABLE 3-continued

Results for GRHPR. Score threshold: 70. Design: siRNA 21 nt.

| SEQ ID NO | siRNA_id | siRNA guide strand/AS Sequence |
|---|---|---|
| 408 | 61 | UCGUCCUGGUUUACGACGUCG |
| 409 | 62 | UGAACACAGCUGUUUCCUUCA |
| 410 | 63 | GAACACAGCUGUUUCCUUCAU |
| 411 | 64 | CAGUCCAGCAGCUGCAAUCUU |
| 412 | 65 | ACAUCCAGUCCAGCAGCUGCA |
| 413 | 66 | UCCUUGUUGCAGAGUCCCUCG |
| 414 | 67 | AGACACAAACUCUGCCUGGAA |
| 415 | 68 | AGUCCAGCAGCUGCAAUCUUA |
| 416 | 69 | AAUUCUGCUGCUUCCUCAGGC |
| 417 | 70 | UGCUGCUUCCUCAGGCCUGGG |
| 418 | 71 | ACAGCUGUUUCCUUCAUCUUC |
| 419 | 72 | CUUCUGGAAGAAGUCCUUGUU |
| 420 | 73 | AAACUCUGCCUGGAAUUCUGC |
| 421 | 74 | CACAGCUGUUUCCUUCAUCUU |
| 422 | 75 | UCUGGGCUCGUCACAUCCAGU |
| 423 | 76 | AUCCAGUCCAGCAGCUGCAAU |
| 424 | 77 | AGCAGCUGCAAUCUUACCACU |
| 425 | 78 | UGCUUCCUCAGGCCUGGGCUG |
| 426 | 79 | UGUAGGCAGUGGUUCUGGGCU |
| 427 | 80 | UACAGGUCGUCCUGGUUUACG |
| 428 | 81 | CAUCCAGUCCAGCAGCUGCAA |
| 429 | 82 | AGAGUCCCUCGGUUGCAGGUG |
| 430 | 83 | UCUUCAGGGUCAGGAGAGGGU |
| 431 | 84 | UCCUUCAUCUUCUGGAAGAAG |
| 432 | 85 | CCUUGUUGCAGAGUCCCUCGG |
| 433 | 86 | AACACAGCUGUUUCCUUCAUC |
| 434 | 87 | AGUCCCUCGGUUGCAGGUGUU |
| 435 | 88 | GUUGCAGGUGUUAAGGAGCAG |
| 436 | 89 | UCUGGAAGAAGUCCUUGUUGC |
| 437 | 90 | GAUGAACACAGCUGUUUCCUU |
| 438 | 91 | CUGGUUUACGACGUCGCCCCU |
| 439 | 92 | CUGGUACAGGUCGUCCUGGUU |
| 440 | 93 | CUGUUUCCUUCAUCUUCUGGA |
| 441 | 94 | AGGCCUGGUACAGGUCGUCCU |
| 442 | 95 | ACGACGAUGAAAUCAGAUUGG |
| 443 | 96 | AUUCUGCUGCUUCCUCAGGCC |
| 444 | 97 | CAGCUGCAAUCUUACCACUGG |
| 445 | 98 | GCAGCUGCAAUCUUACCACUG |
| 446 | 99 | AGUUCUUCAGGGUCAGGAGAG |
| 447 | 100 | ACCGAAUGGUUUCAGACGCCG |
| 448 | 101 | ACAGUUCUUCAGGGUCAGGAG |
| 449 | 102 | GUCCUUGUUGCAGAGUCCCUC |
| 450 | 103 | GCUGUUUCCUUCAUCUUCUGG |
| 451 | 104 | AAUGGUUUCAGACGCCGAGCA |
| 452 | 105 | UCUGGACACCGAAUGGUUUCA |
| 453 | 106 | ACAAACUCUGCCUGGAAUUCU |
| 454 | 107 | UGGUUUGUAGGCAGUGGUUCU |
| 455 | 108 | CAAACUCUGCCUGGAAUUCUG |
| 456 | 109 | CUGCUGAUGUUGAUGAACACA |

TABLE 4

Results for ITFG1. Score threshold: 70. Design: siRNA 21 nt.

| SEQ ID NO | siRNA_id | siRNA guide strand/AS Sequence |
|---|---|---|
| 457 | 1 | UAUAAAUACACAAACACUGGA |
| 458 | 2 | UAGAUCACCAUUGAAAUCCAU |
| 459 | 3 | UAGAAUAAGAAGCAAGACCAA |
| 460 | 4 | UUGCAUUGAAGUCUGAAUGUA |
| 461 | 5 | UUGACCACUUACUCUGUGCUA |
| 462 | 6 | UUAAUGUUUACAGUAACUCAA |
| 463 | 7 | UAUACAUGAUAUAAGGUCCAG |
| 464 | 8 | UUAUCUUACGAGGACAGUCAU |
| 465 | 9 | UUAUAAAUACACAAACACUGG |
| 466 | 10 | UUUAGGUCUGUCAGCUCCCAG |
| 467 | 11 | UAUCAAUGCACUGUGAUUCUU |
| 468 | 12 | UAUUGCUGAAAUCUUGUAGGA |
| 469 | 13 | AUAUUGACCACUUACUCUGUG |
| 470 | 14 | UACUUGUAGUGGUCAAUGCUG |
| 471 | 15 | UUACUCUGUGCUAGGCACCAA |
| 472 | 16 | AUUUAUUUGAAUACUUUCCAA |
| 473 | 17 | UAUGGAAUGACAAUUAGCUGG |
| 474 | 18 | UAGGACUGGAACCCACUGCUU |
| 475 | 19 | UAAUAUGAGCAAGUAAAUCUU |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 476 | 20 | UAAGUCUAAUAAGAUCAUCUA |
| 477 | 21 | UUUACUUAGCACUACAAUGUC |
| 478 | 22 | UUAUAGACUUCUCCAAGUGUU |
| 479 | 23 | UGACCUGCUGUGAUGAAGCUG |
| 480 | 24 | AUACUUUCCAAUAAUUACCAU |
| 481 | 25 | UUGCGCUCCGACCUAAACCAA |
| 482 | 26 | UAGACUUUAAACAUUCGACGC |
| 483 | 27 | UUAUUAGCAUUGAUAAACUUU |
| 484 | 28 | UAGAACACAGACCACUAAGAA |
| 485 | 29 | UUCUUUAGUAUGACCAGAGCG |
| 486 | 30 | UAGCACUACAAUGUCCAAGAU |
| 487 | 31 | UGAGUAUGGUCAUAUUGUUA |
| 488 | 32 | UAUAGCAGUAAGCAGAACAAU |
| 489 | 33 | UGACUGUCCAACCACCAUCAU |
| 490 | 34 | AAUCUUUAUGUCAAUCACCAA |
| 491 | 35 | AUUAUUAGCAUUGAUAAACUU |
| 492 | 36 | UAUUGUAGUCUCCAAUAUGAA |
| 493 | 37 | UUAGUAUGACCAGAGCGUCUG |
| 494 | 38 | AUAAAUACACAAACACUGGAG |
| 495 | 39 | UUGAAUUAGGAGUUUAAGGCA |
| 496 | 40 | UUGUAGGACUGGAACCCACUG |
| 497 | 41 | UAGGAGUUUAAGGCAAGUCUG |
| 498 | 42 | UAUCAGGAAUUAGAUCACCAU |
| 499 | 43 | UCGUCAGGAAUAAAUCUGCUG |
| 500 | 44 | UUGAUUUAGGUCUGUCAGCUC |
| 501 | 45 | UAUUUAUUUGAAUACUUUCCA |
| 502 | 46 | UAUUUCUAUAAUUAGAUGUAU |
| 503 | 47 | UUGUAGUGGUCAAUGCUGGAU |
| 504 | 48 | UGGAAUGACAAUUAGCUGGGA |
| 505 | 49 | UUGUAUAUCCUUUACUUAGCA |
| 506 | 50 | AUUAUAAAUACACAAACACUG |
| 507 | 51 | UAUAGUACUGACAGAGAAGUU |
| 508 | 52 | UAAACAUUCGACGCGCCUCUU |
| 509 | 53 | AUUAAUAAUGACAACUACCAC |
| 510 | 54 | UUGUAUCAAUGCACGUGAU |
| 511 | 55 | UAUCAAGUCUAUGUAUUUCUA |
| 512 | 56 | UUGGAGAGCUAAAUGUGCGGA |
| 513 | 57 | UUUCCAAUAAUUACCAUGGGA |
| 514 | 58 | UAUUGUUAGGAUCUAAUGUUU |
| 515 | 59 | UAGUAUGACCAGAGCGUCUGG |
| 516 | 60 | UUAAUAAUGACAACUACCACA |
| 517 | 61 | UAAGGCAAGUCUGUCUUACUG |
| 518 | 62 | AAGUCUAAUAAGAUCAUCUAA |
| 519 | 63 | UAAGCAGAACAAUAUUACUUG |
| 520 | 64 | UUGAAAGAUACCUUUACUUUG |
| 521 | 65 | UACUGUGCUACCAAGUCAGAG |
| 522 | 66 | UAAGCACUUCACAUACAUCAU |
| 523 | 67 | UUUGGAAUGAUUGCAGUCCAC |
| 524 | 68 | UAUAAUUAGAUGUAUAAGUCU |
| 525 | 69 | UAAUUAGAUGUAUAAGUCUAA |
| 526 | 70 | UAAAUUAUAGACUUCUCCAAG |
| 527 | 71 | AUAUGUCAGAAGGACAUCCAU |
| 528 | 72 | UCUUUGUAUAUCCUUUACUUA |
| 529 | 73 | UUGGAGAGUACUAUAAUUUUU |
| 530 | 74 | UUAAUUCUUGGAGAGUACUAU |
| 531 | 75 | AUAAUUAGAUGUAUAAGUCUA |
| 532 | 76 | UAAGAAGCAAGACCAAGUCAA |
| 533 | 77 | UAGGGCACAUUAAUUCUUGGA |
| 534 | 78 | UCUGUCUUACUGUGCUACCAA |
| 535 | 79 | UUCUUUGUAUAUCCUUUACUU |
| 536 | 80 | UUAUAAAUAAUAUUUAAUCUC |
| 537 | 81 | UACAUCAUCCCAUUUAAUGUU |
| 538 | 82 | UUGCAUUAUUACAAGGGACGU |
| 539 | 83 | UAAUAAUGACAACUACCACAU |
| 540 | 84 | UUUGAUUUAGGUCUGUCAGCU |
| 541 | 85 | UUUCAGUUGGUUGCUGUUCAU |
| 542 | 86 | UGAUUCUUGAAAGAUACCUUU |
| 543 | 87 | UUGGUUGCUGUUCAUCCACAA |
| 544 | 88 | UUGCAUUCCCAGAUGCUGCCU |
| 545 | 89 | UAUAUCCUUUACUUAGCACUA |
| 546 | 90 | AAUGAUUGCAGUCCACUCUUG |
| 547 | 91 | UUGUAUACAUGAUAUAAGGUC |
| 548 | 92 | UUCAACUAAUCAAGUGAACAG |
| 549 | 93 | UUAAAGGCAAGUCACAUAGCA |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 550 | 94 | UUACAGUAACUCAAGUAUUAG |
| 551 | 95 | AAUAUGAGCAAGUAAAUCUUU |
| 552 | 96 | AAUAAUGACAACUACCACAUA |
| 553 | 97 | AUGUCGUCAGGAAUAAAUCUG |
| 554 | 98 | UAUCUUACGAGGACAGUCAUU |
| 555 | 99 | UUACUUAGCACUACAAUGUCC |
| 556 | 100 | AUUUAGGUCUGUCAGCUCCCA |
| 557 | 101 | UUUAUUUGAAUACUUUCCAAU |
| 558 | 102 | UCGAGGGACAUUGUGAGGGUA |
| 559 | 103 | UUCCAUCUUCGUAAAUGUCAA |
| 560 | 104 | AAGAAUAUUUCUUCAUGCCUG |
| 561 | 105 | AUCUUGUAGGACUGGAACCCA |
| 562 | 106 | UACUUAGCACUACAAUGUCCA |
| 563 | 107 | UAAUUGGAAUUGGUAUUUCAG |
| 564 | 108 | UUUAAUGUUUACAGUAACUCA |
| 565 | 109 | UUGCUGUUCAUCCACAAAUGG |
| 566 | 110 | UGAAUGCCUAAUGACUCCGUG |
| 567 | 111 | UCAAACUGGAAGGUACUAGUG |
| 568 | 112 | AACAGCUCCUAAUUCACUCUU |
| 569 | 113 | UCCAAUAUAGUACUGACAGAG |
| 570 | 114 | UUCAAGAAAUCAAAUGUUCUU |
| 571 | 115 | UUAAGAAGACAUGUUAACAUG |
| 572 | 116 | UAAAGGCAAGUCACAUAGCAU |
| 573 | 117 | UACACAAACACUGGAGUACAU |
| 574 | 118 | UGAAUUAGGAGUUUAAGGCAA |
| 575 | 119 | AAUUUGAUUUAGGUCUGUCAG |
| 576 | 120 | UUUACAGAGGUUAAACAAGAG |
| 577 | 121 | AAGAACAAUAACUUUAACAAA |
| 578 | 122 | UAAAUAAUAUUUAAUCUCCCC |
| 579 | 123 | AUAUUGUUAGGAUCUAAUGUU |
| 580 | 124 | UAUUUAUUAAGAAGACAUGUU |
| 581 | 125 | UAGAUGUAUAAGUCUAAUAAG |
| 582 | 126 | UAAGUAGAUGGUACUCUUUUG |
| 583 | 127 | AACUAAUCAAGUGAACAGCCA |
| 584 | 128 | UACAUGCAACACAUUCCACAA |
| 585 | 129 | UUUGCAUUGAAGUCUGAAUGU |
| 586 | 130 | UUUGAGAAUAGAAAUGUGAUU |
| 587 | 131 | UAAGUGGUUGAAUUAGGAGUU |
| 588 | 132 | UUUAUUAAGAAGACAUGUUAA |
| 589 | 133 | UUGGAAUUGGUAUUUCAGUUG |
| 590 | 134 | AUCAAGUCUAUGUAUUUCUAU |
| 591 | 135 | UUCAUUAUCACAUGAUAAGGA |
| 592 | 136 | AACAAUGACUUUGUAAGUGGU |
| 593 | 137 | AUUGAGUAUGGUCAUAUUGUU |
| 594 | 138 | UACAGUUGUAUACAUGAUAUA |
| 595 | 139 | UACCAAGUCAGAGUACCCGAU |
| 596 | 140 | UAUAAGUCUAAUAAGAUCAUC |
| 597 | 141 | UGGUAUUUCAGUUGGUUGCUG |
| 598 | 142 | AAGCAGAACAAUAUUACUUGG |
| 599 | 143 | AAAUACACAAACACUGGAGUA |
| 600 | 144 | UGCAUUAUUACAAGGGACGUU |
| 601 | 145 | UUGUAAGUGGUUGAAUUAGGA |
| 602 | 146 | UACUUGGUGUAAGAUACAGUU |
| 603 | 147 | UUAAUUUGAUUUAGGUCUGUC |
| 604 | 148 | AAUAAGAUUAUAAAUACACAA |
| 605 | 149 | UUGGAUUCAUUUGUGAUACCA |
| 606 | 150 | UAAGCAUCUGCUUCAAAGUUA |
| 607 | 151 | AGACUUUAAACAUUCGACGCG |
| 608 | 152 | ACAUAUUGACCACUUACUCUG |
| 609 | 153 | UGACAGAGAAGUUUCCAUCCA |
| 610 | 154 | UAGGUCUGUCAGCUCCCAGUA |
| 611 | 155 | AUCUACAGUUGUAUACAUGAU |
| 612 | 156 | UAUGUAUUUCUAUAAUUAGAU |
| 613 | 157 | ACCACUAAGAACAAUAACUUU |
| 614 | 158 | UGUGAUGAAGCUGAAUGCCUA |
| 615 | 159 | UCAGAUACCCAUUUGCAUCUA |
| 616 | 160 | AUUAGCAUUGAUAAACUUUUU |
| 617 | 161 | UAACAGCUCCUAAUUCACUCU |
| 618 | 162 | AUAAUGACAACUACCACAUAU |
| 619 | 163 | UAUUAAUGACAACUACCA |
| 620 | 164 | UAUUUGAAUACUUUCCAAUAA |
| 621 | 165 | UAAAUGCAUGAGAAUGUGGAA |
| 622 | 166 | UAAUGUUUACAGUAACUCAAG |
| 623 | 167 | UACAGCACUACAGAAUAGAGA |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 624 | 168 | UUGGUGUAAGAUACAGUUUGG |
| 625 | 169 | AAUGUGAUUGAAGAUUUGCAU |
| 626 | 170 | UGUAAGUGGUUGAAUUAGGAG |
| 627 | 171 | AUUACUGGUGUAAGAUACAG |
| 628 | 172 | UUUACAGUAACUCAAGUAUUA |
| 629 | 173 | UCGUAAAUGUCAAAGAAGGUG |
| 630 | 174 | UUGGUAUUUCAGUUGGUUGCU |
| 631 | 175 | ACACUUGUUAUCAAUGCACUG |
| 632 | 176 | UUCACAUACAUCAUCCCAUUU |
| 633 | 177 | AACUGGAAGGUACUAGUGGUG |
| 634 | 178 | UAGGAUCUAAUGUUUGAUUUU |
| 635 | 179 | UCUUUAGUAUGACCAGAGCGU |
| 636 | 180 | UUAUGUAAUAUUAAAGGCAAG |
| 637 | 181 | UACUGACAGAGAAGUUUCCAU |
| 638 | 182 | AUGACUUUGUAAGUGGUUGAA |
| 639 | 183 | AUUACAAGGGACGUUCUCCAG |
| 640 | 184 | UCUGUGCUAGGCACCAAGCUA |
| 641 | 185 | UACCCAUUUGCAUCUACAGUU |
| 642 | 186 | UGCAUCUACAGUUGUAUACAU |
| 643 | 187 | UCAUUCUUUGUAUAUCCUUUA |
| 644 | 188 | UUAGAUCACCAUUGAAAUCCA |
| 645 | 189 | UUGAGAAUAGAAAUGUGAUUG |
| 646 | 190 | UAUGUCAGAAGGACAUCCAUU |
| 647 | 191 | UAAGAACAAUAACUUUAACAA |
| 648 | 192 | UUGUGACAUAUUCAAACCAUA |
| 649 | 193 | UUUAGUAUGACCAGAGCGUCU |
| 650 | 194 | UUGUAUGGUAGUUUGGAGAGCU |
| 651 | 195 | UUGCAGUCCACUCUUGUUUUC |
| 652 | 196 | UAUUAGCAUUGAUAAACUUUU |
| 653 | 197 | UAGUCUCCAAUAUGAAGGGUA |
| 654 | 198 | UUUCAAACUGGAAGGUACUAG |
| 655 | 199 | AAUUAUAGACUUCUCCAAGUG |
| 656 | 200 | AUAAGCAUCUGCUUCAAAGUU |
| 657 | 201 | AAACUGGAAGGUACUAGUGGU |
| 658 | 202 | AUGACAACUACCACAUAUUGA |
| 659 | 203 | UGUAUUUCUAUAAUUAGAUGU |
| 660 | 204 | AAGUCUGCAAAUGCUGACUGU |
| 661 | 205 | UCUCUAUCAUCUGCUUUCUUU |
| 662 | 206 | ACAACUACCACAUAUUGACCA |
| 663 | 207 | UAUUCAAACCAUAUUUAUUUG |
| 664 | 208 | UUCGUAAAUGUCAAAGAAGGU |
| 665 | 209 | AUUGCUGAAAUCUUGUAGGAC |
| 666 | 210 | UUCGAGGGACAUUGUGAGGGU |
| 667 | 211 | AGUCAUUAGAACACAGACCAC |
| 668 | 212 | UAGACUUCUCCAAGUGUUUGA |
| 669 | 213 | UUAUUGCUGAAAUCUUGUAGG |
| 670 | 214 | ACUAAUCAAGUGAACAGCCAU |
| 671 | 215 | UUGAAGUCUGAAUGUAAAUUA |
| 672 | 216 | AUGAGAAUGUGGAAUUCGCAU |
| 673 | 217 | UGUAAAUUAUAGACUUCUCCA |
| 674 | 218 | UAUAGACUUCUCCAAGUGUUU |
| 675 | 219 | UUAGGAUCUAAUGUUUGAUUU |
| 676 | 220 | UCUUGUAGGACUGGAACCCAC |
| 677 | 221 | UGCUGACUGUCCAACCACCAU |
| 678 | 222 | UUAGAAUAAGAAGCAAGACCA |
| 679 | 223 | UGUUAGGAUCUAAUGUUUGAU |
| 680 | 224 | UGGUCAUAUUGUUAGGAUCUA |
| 681 | 225 | UUGAAUACUUUCCAAUAAUUA |
| 682 | 226 | UGAUUGCAGUCCACUCUUGUU |
| 683 | 227 | UUAAACAUUCGACGCGCCUCU |
| 684 | 228 | AUGUUUACAGUAACUCAAGUA |
| 685 | 229 | UUACUGUGCUACCAAGUCAGA |
| 686 | 230 | UUCUUCAUUAUCACAUGAUAA |
| 687 | 231 | UGAAUGUAAAUUAUAGACUUC |
| 688 | 232 | UAGCUGGGAAUUUGGAAUGAU |
| 689 | 233 | UAGGCAUCACAUGUCCAUUUG |
| 690 | 234 | UGAUAUAAGGUCCAGGUUGAU |
| 691 | 235 | UCUAUGUAUUUCUAUAAUUAG |
| 692 | 236 | UGCAACACAUUCCACAAAGGA |
| 693 | 237 | UUUAAACAUUCGACGCGCCUC |
| 694 | 238 | UUGAAGAUUUGCAUUCCCAGA |
| 695 | 239 | UGUGAUUCUUGAAAGAUACCU |
| 696 | 240 | GUAAAUUAUAGACUUCUCCAA |
| 697 | 241 | AAAUGCUGACUGUCCAACCAC |

TABLE 4-continued

Results for ITFG1.
Score threshold: 70. Design: siRNA 21 nt.

| SEQ ID NO | siRNA_id | siRNA guide strand/AS Sequence |
|---|---|---|
| 698 | 242 | UCUUGAAAGAUACCUUUACUU |
| 699 | 243 | UACUUUCCAAUAAUUACCAUG |
| 700 | 244 | AUUGAAGAUUUGCAUUCCCAG |
| 701 | 245 | UGCUGAAAUCUUGUAGGACUG |
| 702 | 246 | AUUCCCUCCUAAUAGUAUCUG |
| 703 | 247 | UGUAGUCUCCAAUAUGAAGGG |
| 704 | 248 | UGUUUCAACUAAUCAAGUGAA |
| 705 | 249 | UAUAAUUUGCAUCAUUAGAAU |
| 706 | 250 | AUUGUUAGGAUCUAAUGUUUG |
| 707 | 251 | AUAUCCUUUACUUAGCACUAC |
| 708 | 252 | UGUAUGGUAGUUGGAGAGCUA |
| 709 | 253 | AACAUGCUUAGAUACAAAGUA |
| 710 | 254 | AUGUUCUUCAUUAUCACAUGA |
| 711 | 255 | UACCCGAUCACUAUAUUGUAU |
| 712 | 256 | UGUUCUUCAUUAUCACAUGAU |
| 713 | 257 | UUAGCUGGGAAUUUGGAAUGA |
| 714 | 258 | UAAAUACACAAACACUGGAGU |
| 715 | 259 | AGGAAUUAGAUCACCAUUGAA |
| 716 | 260 | UUCCCUCCUAAUAGUAUCUGU |
| 717 | 261 | UUACUUGGUGUAAGAUACAGU |
| 718 | 262 | AAAGAUACCUUUACUUUGGGU |
| 719 | 263 | UUAGAUGUAUAAGUCUAAUAA |
| 720 | 264 | ACACAUUCCACAAAGGAACAA |
| 721 | 265 | UCUACAGUUGUAUACAUGAUA |
| 722 | 266 | UGUAUAUCCUUUACUUAGCAC |
| 723 | 267 | UUGUUAGGAUCUAAUGUUUGA |
| 724 | 268 | UCUGCAAAUGCUGACUGUCCA |
| 725 | 269 | UACCAACGUAGAGAUGGUCAA |
| 726 | 270 | UAAACCAAGCACGUUGUAUGG |
| 727 | 271 | AAGAAAUCAAAUGUUCUUCAU |
| 728 | 272 | UCACAUGAUAAGGAUAAGUUU |
| 729 | 273 | UGAAAUCUUGUAGGACUGGAA |
| 730 | 274 | UGUCAGAAGGACAUCCAUUUG |
| 731 | 275 | ACUUAGCACUACAAUGUCCAA |
| 732 | 276 | AACUUCGAGGGACAUUGUGAG |
| 733 | 277 | AUGGAAUGACAAUUAGCUGGG |
| 734 | 278 | AUAUUUAUUAAGAAGACAUGU |
| 735 | 279 | UACCAUGGGAUACAUCAUUUA |
| 736 | 280 | AUCUUCGUAAAUGUCAAAGAA |
| 737 | 281 | UCUUACUGUGCUACCAAGUCA |
| 738 | 282 | UCAUUAUCACAUGAUAAGGAU |
| 739 | 283 | UAAUUUGAUUUAGGUCUGUCA |
| 740 | 284 | AGUACAUGCAACACAUUCCAC |
| 741 | 285 | AUCAUUCUUUGUAUAUCCUUU |
| 742 | 286 | AAAUAUAUUUAAUCUCCCCU |
| 743 | 287 | CAAGUCUGUCUUACUGUGCUA |
| 744 | 288 | AAAGUCUGCAAAUGCUGACUG |
| 745 | 289 | AUGAUUGCAGUCCACUCUUGU |
| 746 | 290 | AAACCAAGCACGUUGUAUGGU |
| 747 | 291 | AUAAAUAAUAUUUAAUCUCCC |
| 748 | 292 | UUUGCAUCAUUAGAAUAAGAA |
| 749 | 293 | AACACAGACCACUAAGAACAA |
| 750 | 294 | ACAAUGACUUUGUAAGUGGUU |
| 751 | 295 | UUCUAUAAUUAGAUGUAUAAG |
| 752 | 296 | AUUUAUUAAGAAGACAUGUUA |
| 753 | 297 | AUUGAAAUCCAUAAUUAGUGG |
| 754 | 298 | AUUAUAGACUUCUCCAAGUGU |
| 755 | 299 | AAUGACAACUACCACAUAUUG |
| 756 | 300 | AAGUGGUUGAAUUAGGAGUUU |
| 757 | 301 | AUAGUACUGACAGAGAAGUUU |
| 758 | 302 | AAAGAAUAUUUCUUCAUGCCU |
| 759 | 303 | UCCAUCUCCAUCAAAGUCUGC |
| 760 | 304 | UGACAUAUUCAAACCAUAUUU |
| 761 | 305 | UAGCAGUAAGCAGAACAAUAU |
| 762 | 306 | UGACCACUUACUCUGUGCUAG |
| 763 | 307 | AUAAGGUCCAGGUUGAUUCAC |
| 764 | 308 | UAUAGGCAUCACAUGUCCAUU |
| 765 | 309 | UGUUUGAGAAUAGAAAUGUGA |
| 766 | 310 | AUAGACUUCUCCAAGUGUUUG |
| 767 | 311 | UGUCCAAGAUUCCAUCUUCGU |
| 768 | 312 | UUCUAUCAAGUCUAUGUAUUU |
| 769 | 313 | AGAAGACAUGUUAACAUGCUU |
| 770 | 314 | AUGUACAGCACUACAGAAUAG |
| 771 | 315 | UAGGCACCAAGCUAAGCACUU |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 772 | 316 | UCAUUAGAACACAGACCACUA |
| 773 | 317 | UCAUUUAUAAAUAAUAUUUAA |
| 774 | 318 | AGAAUCUCCAUCAUAAUCCCC |
| 775 | 319 | UAAUUCUUGGAGAGUACUAUA |
| 776 | 320 | AUCUCAGUGAACUAUAAAGAA |
| 777 | 321 | AUCCUUUACUUAGCACUACAA |
| 778 | 322 | AUGUCCAUUUGCAUACUAGAA |
| 779 | 323 | UAAAUCUUUAUGUCAAUCACC |
| 780 | 324 | UCCAUCUUCGUAAAUGUCAAA |
| 781 | 325 | UUUAAGGCAAGUCUGUCUUAC |
| 782 | 326 | ACUAAGUAGAUGGUACUCUUU |
| 783 | 327 | AUGCUGACUGUCCAACCACCA |
| 784 | 328 | UCAACUAAUCAAGUGAACAGC |
| 785 | 329 | UAUUACAAGGGACGUUCUCCA |
| 786 | 330 | UGAAGGGUAAUUGGAAUUGGU |
| 787 | 331 | UGAUUCACUCCAAAGGGUGUU |
| 788 | 332 | AUUAAUUCUUGGAGAGUACUA |
| 789 | 333 | AUUUGGAAUGAUUGCAGUCCA |
| 790 | 334 | UUAACAUGCUUAGAUACAAAG |
| 791 | 335 | AUAAGGAAUAUUUAUUAAGAA |
| 792 | 336 | UAAUUUGCAUCAUUAGAAUAA |
| 793 | 337 | AGCAGAACAAUAUUACUUGGU |
| 794 | 338 | CUUAAUUUGAUUUAGGUCUGU |
| 795 | 339 | AAUAGAAAUGUGAUUGAAGAU |
| 796 | 340 | UAUGAGCAAGUAAAUCUUUAU |
| 797 | 341 | UUUGAGAAUCUCCAUCAUAAU |
| 798 | 342 | AGUUCAAACAAUGACUUUGUA |
| 799 | 343 | UAGUUGGAGAGCUAAAUGUGC |
| 800 | 344 | AUAGGGUGCAUUCUGGUCUGC |
| 801 | 345 | UUGUAGUCUCCAAUAUGAAGG |
| 802 | 346 | AUAAGAGCAAGACCAAGUCA |
| 803 | 347 | AUUAUGUAAUAUUAAAGGCAA |
| 804 | 348 | UUCUUGGAGAGUACUAUAAUU |
| 805 | 349 | UACACUUGUUAUCAAUGCACU |
| 806 | 350 | AAGAAGACAUGUUAACAUGCU |
| 807 | 351 | UUACAAGGGACGUUCUCCAGU |
| 808 | 352 | CAUCAUUAGAAUAAGAAGCAA |
| 809 | 353 | UUCAAUAAGGAAUAUUUAUUA |
| 810 | 354 | UACAUGAUAUAAGGUCCAGGU |
| 811 | 355 | AUUAGAACACAGACCACUAAG |
| 812 | 356 | AUUAUUACAAGGGACGUUCUC |
| 813 | 357 | UAGUGGUCAAUGCUGGAUGCC |
| 814 | 358 | AUCCAUAUUGUAGUCUCCAAU |
| 815 | 359 | AUAUGAGCAAGUAAAUCUUUA |
| 816 | 360 | UUUGCAUCUACAGUUGUAUAC |
| 817 | 361 | AGUAUGACCAGAGCGUCUGGA |
| 818 | 362 | UACAAGGGACGUUCUCCAGUA |
| 819 | 363 | UUACGAGGACAGUCAUUAGAA |
| 820 | 364 | AUUAAGAAGACAUGUUAACAU |
| 821 | 365 | UGAAGUCUGAAUGUAAAUUAU |
| 822 | 366 | ACACAGACCACUAAGAACAAU |
| 823 | 367 | CACUACAGAAUAGAGAACCCA |
| 824 | 368 | UUCAAACCAUAUUUAUUUGAA |
| 825 | 369 | UCAAAUGUUCUUCAUUAUCAC |
| 826 | 370 | UCAGGAAUAAAUCUGCUGUAA |
| 827 | 371 | UAUAAGGUCCAGGUUGAUUCA |
| 828 | 372 | ACAAACACUGGAGUACAUGCA |
| 829 | 373 | UUUAUAAAUAAUAUUUAAUCU |
| 830 | 374 | ACAGAGGUUAAACAAGAGCCA |
| 831 | 375 | UGUAGGACUGGAACCCACUGC |
| 832 | 376 | UGUCCAACCACCAUCAUAUUU |
| 833 | 377 | CAGUAGACUUUAAACAUUCGA |
| 834 | 378 | ACAUGCAACACAUUCCACAAA |
| 835 | 379 | UCAGAAGGACAUCCAUUUGAG |
| 836 | 380 | UCUAUCAUCUGCUUUCUUUUC |
| 837 | 381 | AUCAAUGCACUGUGAUUCUUG |
| 838 | 382 | UUGCAUCAUUAGAAUAAGAAG |
| 839 | 383 | UCAAAGUCUGCAAAUGCUGAC |
| 840 | 384 | AGUCCAUUGAGUAUGGUCAU |
| 841 | 385 | UACCACAUAUUGACCACUUAC |
| 842 | 386 | AGUAACUCAAGUAUUAGCCCC |
| 843 | 387 | UAACAUGCUUAGAUACAAAGU |
| 844 | 388 | UCACAUACAUCAUCCCAUUUA |
| 845 | 389 | AUCAUUUAUAAAUAAUAUUUA |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 846 | 390 | CUUGUGACAUAUUCAAACCAU |
| 847 | 391 | UGAUUGAAGAUUUGCAUUCCC |
| 848 | 392 | ACUUGUUAUCAAUGCACUGUG |
| 849 | 393 | AGGCAAGUCACAUAGCAUCAA |
| 850 | 394 | UUGAUUCACUCCAAAGGGUGU |
| 851 | 395 | AAUGUGAAGUUCACAAUACAA |
| 852 | 396 | AGGACAGUCAUUAGAACACAG |
| 853 | 397 | UGUUCUUUAGUAUGACCAGAG |
| 854 | 398 | UAUUGAGUAUGGUCAUAUUGU |
| 855 | 399 | GUAGUCUCCAAUAUGAAGGGU |
| 856 | 400 | AUGUAUUUCUAUAAUUAGAUG |
| 857 | 401 | UACUCUGUGCUAGGCACCAAG |
| 858 | 402 | UGUUAACAUGCUUAGAUACAA |
| 859 | 403 | AUAAAUGCAUGAGAAUGUGGA |
| 860 | 404 | AUUUCAAACUGGAAGGUACUA |
| 861 | 405 | UCCAAGAUUCCAUCUUCGUAA |
| 862 | 406 | UCCUUUACUUAGCACUACAAU |
| 863 | 407 | AAUACCAACGUAGAGAUGGUC |
| 864 | 408 | ACAUGAUAUAAGGUCCAGGUU |
| 865 | 409 | AUCUUUAUGUCAAUCACCAAA |
| 866 | 410 | UGAAAGAUACCUUUACUUUGG |
| 867 | 411 | AAGGCAAGUCUGUCUUACUGU |
| 868 | 412 | UGGAAUUGGUAUUUCAGUUGG |
| 869 | 413 | UAUAAUAAUAUUUAAUCUCC |
| 870 | 414 | AUAAAUUCCUCCUAAUAGUA |
| 871 | 415 | AUAAUUUGCAUCAUUAGAAUA |
| 872 | 416 | ACUUGUAGUGGUCAAUGCUGG |
| 873 | 417 | AUCUGCUUCAAAGUUAUUUUU |
| 874 | 418 | UAAGAAGACAUGUUAACAUGC |
| 875 | 419 | AAGCACUUCACAUACAUCAUC |
| 876 | 420 | UACAUCAUUUAUAAAUAAUAU |
| 877 | 421 | AUUGACCACUUACUCUGUGCU |
| 878 | 422 | UUCAAUGUCGUCAGGAAUAAA |
| 879 | 423 | AUACAUGAUAUAAGGUCCAGG |
| 880 | 424 | AAAUGUUCUUCAUUAUCACAU |
| 881 | 425 | AUUCAAACCAUAUUUAUUUGA |
| 882 | 426 | CAUUAGAACACAGACCACUAA |
| 883 | 427 | UGCUGGUUGCUUCCAGAUGUG |
| 884 | 428 | AUUGGAAUUGGUAUUUCAGUU |
| 885 | 429 | UAAUAUUAAAGGCAAGUCACA |
| 886 | 430 | CACUUCACAUACAUCAUCCCA |
| 887 | 431 | UAUCCUUUACUUAGCACUACA |
| 888 | 432 | AAUACUUUCCAAUAAUUACCA |
| 889 | 433 | UCCCUCCUAAUAGUAUCUGUG |
| 890 | 434 | AUGUGAUUGAAGAUUUGCAUU |
| 891 | 435 | AGAACAAUAUUACUUGGUGUA |
| 892 | 436 | AAUAUUUAUUAAGAAGACAUG |
| 893 | 437 | UCUAUCAAGUCUAUGUAUUUC |
| 894 | 438 | AAUAUUAAAGGCAAGUCACAU |
| 895 | 439 | UAUUUCAGUUGGUUGCUGUUC |
| 896 | 440 | GUAUGGAAUGACAAUUAGCUG |
| 897 | 441 | UCACAGCUUGCAUUAUUACAA |
| 898 | 442 | AAGUCUGUCUUACUGUGCUAC |
| 899 | 443 | AGUAUGGUCAUAUUGUUAGGA |
| 900 | 444 | UCAAUAAGGAAUAUUUAUUAA |
| 901 | 445 | AAACAAUGACUUUGUAAGUGG |
| 902 | 446 | UGGAUUCAUUUGUGAUACCAA |
| 903 | 447 | UAUUAAAGGCAAGUCACAUAG |
| 904 | 448 | UGGGAAUUUGGAAUGAUUGCA |
| 905 | 449 | AAUCUUGUAGGACUGGAACCC |
| 906 | 450 | AUCUCCAUCAAAGUCUGCAAA |
| 907 | 451 | UUAGAACACAGACCACUAAGA |
| 908 | 452 | UCACUAAGUAGAUGGUACUCU |
| 909 | 453 | UUUCUAUAAUUAGAUGUAUAA |
| 910 | 454 | UGCAUUGAAGUCUGAAUGUAA |
| 911 | 455 | UUUGCGCUCCGACCUAAACCA |
| 912 | 456 | UGAUUUAGGUCUGUCAGCUCC |
| 913 | 457 | AACCGGUGGGCUUCUUGUCGU |
| 914 | 458 | UGAAGAUUUGCAUUCCCAGAU |
| 915 | 459 | UUAUUUGAAUACUUUCCAAUA |
| 916 | 460 | UCCCAGUAGACUUUAAACAUU |
| 917 | 461 | UCAGUCAGAUCAAUAAAUGCA |
| 918 | 462 | CAUCCAUUUGAGAAUCUCCAU |
| 919 | 463 | UAGAAAUGUGAUUGAAGAUUU |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 920 | 464 | ACAGCUCCUAAUUCACUCUUG |
| 921 | 465 | UUAGGUCUGUCAGCUCCCAGU |
| 922 | 466 | AAGACAUGUUAACAUGCUUAG |
| 923 | 467 | AUACCCAUUUGCAUCUACAGU |
| 924 | 468 | AAAUCUUUAUGUCAAUCACCA |
| 925 | 469 | CAGAGGUUAAACAAGAGCCAA |
| 926 | 470 | AUCAGGAAUUAGAUCACCAUU |
| 927 | 471 | UCCCAUUUAAUGUUUACAGUA |
| 928 | 472 | AGGCAAGUCUGUCUUACUGUG |
| 929 | 473 | UCUCAGUGAACUAUAAAGAAA |
| 930 | 474 | UAUUGACCACUUACUCUGUGC |
| 931 | 475 | AUGUAAAUUAUAGACUUCUCC |
| 932 | 476 | UCAGAUCAAUAAAUGCAUGAG |
| 933 | 477 | UGAGAAUGUGGAAUUCGCAUU |
| 934 | 478 | UUGCAUCUACAGUUGUAUACA |
| 935 | 479 | CUUAUUGCUGAAAUCUUGUAG |
| 936 | 480 | ACUUGGUGUAAGAUACAGUUU |
| 937 | 481 | AUAUUGUAGUCUCCAAUAUGA |
| 938 | 482 | ACAUCCAUUUGAGAAUCUCCA |
| 939 | 483 | UUAUCAAUGCACUGUGAUUCU |
| 940 | 484 | AUUACCAUGGGAUACAUCAUU |
| 941 | 485 | ACUUCACAUACAUCAUCCCAU |
| 942 | 486 | AUCAAAGUCUGCAAAUGCUGA |
| 943 | 487 | AUCCUUAAUUUGAUUUAGGUC |
| 944 | 488 | UGAAGCUGAAUGCCUAAUGAC |
| 945 | 489 | AGCAAGACCAAGUCAAGUGGA |
| 946 | 490 | AUUGCAGUCCACUCUUGUUUU |
| 947 | 491 | CAAACAAUGACUUUGUAAGUG |
| 948 | 492 | UCUAAUAAGAUCAUCUAAAAU |
| 949 | 493 | AUAACAGCUCCUAAUUCACUC |
| 950 | 494 | UAGGAAUAUUUAUUAAGAAG |
| 951 | 495 | AAGGGUGUUAUCUUACGAGGA |
| 952 | 496 | UAAUGACAACUACCACAUAUU |
| 953 | 497 | UAUUACUUGGUGUAAGAUACA |
| 954 | 498 | AUCAUUAGAAUAAGAAGCAAG |
| 955 | 499 | CAAUAUAGUACUGACAGAGAA |
| 956 | 500 | AUUGUAGUCUCCAAUAUGAAG |
| 957 | 501 | UGACAACUACCACAUAUUGAC |
| 958 | 502 | ACUACAAUGUCCAAGAUUCCA |
| 959 | 503 | UCAGGAAUUAGAUCACCAUUG |
| 960 | 504 | ACCGGUGGGCUUCUUGUCGUU |
| 961 | 505 | AUGUCCAAGAUUCCAUCUUCG |
| 962 | 506 | AAUAAAUGCAUGAGAAUGUGG |
| 963 | 507 | AAGCAAGACCAAGUCAAGUGG |
| 964 | 508 | UCUUCGUAAAUGUCAAAGAAG |
| 965 | 509 | UUACCAUGGGAUACAUCAUUU |
| 966 | 510 | UUACAGAGGUUAAACAAGAGC |
| 967 | 511 | UUGCUGAAAUCUUGUAGGACU |
| 968 | 512 | UUGGAAUGAUUGCAGUCCACU |
| 969 | 513 | UAUGAAGGGUAAUUGGAAUUG |
| 970 | 514 | AUGAGCAAGUAAAUCUUUAUG |
| 971 | 515 | UUUGUAAGUGGUUGAAUUAGG |
| 972 | 516 | AACUACCACAUAUUGACCACU |
| 973 | 517 | UCAAACAAUGACUUUGUAAGU |
| 974 | 518 | AAUUCUUGGAGAGUACUAUAA |
| 975 | 519 | CUUACUGUGCUACCAAGUCAG |
| 976 | 520 | ACAAUUAGCUGGGAAUUUGGA |
| 977 | 521 | UGGAGUACAUGCAACACAUUC |
| 978 | 522 | AGAAAUGUGAUUGAAGAUUUG |
| 979 | 523 | UGCAUUCCCAGAUGCUGCCUA |
| 980 | 524 | UAAAUUCCUCCUAAUAGUAU |
| 981 | 525 | AUUCUUUGUAUAUCCUUUACU |
| 982 | 526 | UUCCAUAAUUACCAUGGGAU |
| 983 | 527 | UUCUUGAAAGAUACCUUUACU |
| 984 | 528 | UGAGCAAGUAAAUCUUUAUGU |
| 985 | 529 | CUGAAUGUAAAUUAUAGACUU |
| 986 | 530 | UGUGAGGGUAUGGAAUGACAA |
| 987 | 531 | AAUGUUCUUCAUUAUCACAUG |
| 988 | 532 | ACAGACACCGAUGAGAGCUAU |
| 989 | 533 | CCAACUUCGAGGGACAUUGUG |
| 990 | 534 | UAGUACUGACAGAGAAGUUUC |
| 991 | 535 | UUCACAGCUUGCAUUAUUACA |
| 992 | 536 | CAUAUUGACCACUUACUCUGU |
| 993 | 537 | AGGGACUACACUUGUUAUCAA |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 994 | 538 | UUAUCACAUGAUAAGGAUAAG |
| 995 | 539 | AAUUACCAUGGGAUACAUCAU |
| 996 | 540 | ACUACACUUGUUAUCAAUGCA |
| 997 | 541 | UACAAUGUCCAAGAUUCCAUC |
| 998 | 542 | AUUUGCAUUGAAGUCUGAAUG |
| 999 | 543 | AUGAAGGGUAAUUGGAAUUGG |
| 1000 | 544 | ACUACAGAAUAGAGAACCCAA |
| 1001 | 545 | GAGAGCUAUAGCAGUAAGCAG |
| 1002 | 546 | AGAAUGUGGAAUUCGCAUUUU |
| 1003 | 547 | UCCAGGUUGAUUCACUCCAAA |
| 1004 | 548 | UUUCAAGAAAUCAAAUGUUCU |
| 1005 | 549 | ACCUAAACCAAGCACGUUGUA |
| 1006 | 550 | AAUAUAGUACUGACAGAGAAG |
| 1007 | 551 | GAUCUCACUAAGUAGAUGGUA |
| 1008 | 552 | UGUACAGCACUACAGAAUAGA |
| 1009 | 553 | UGUAAUAUUAAAGGCAAGUCA |
| 1010 | 554 | UUCCUUUCAAGAAAUCAAAUG |
| 1011 | 555 | AUCCAUUUGAGAAUCUCCAUC |
| 1012 | 556 | UAUCACAUGAUAAGGAUAAGU |
| 1013 | 557 | CAAUGCACUGUGAUUCUUGAA |
| 1014 | 558 | UGGAGAGCUAAAUGUGCGGAU |
| 1015 | 559 | UAAGAUUAUAAAUACACAAAC |
| 1016 | 560 | AUAAGAUUAUAAAUACACAAA |
| 1017 | 561 | UCUUGGAGAGUACUAUAAUUU |
| 1018 | 562 | AACAAUAUUACUUGGUGUAAG |
| 1019 | 563 | UCAAGAAAUCAAAUGUUCUUC |
| 1020 | 564 | UGUCGUCAGGAAUAAAUCUGC |
| 1021 | 565 | GAGUACAUGCAACACAUUCCA |
| 1022 | 566 | UAUGACCAGAGCGUCUGGAUA |
| 1023 | 567 | UCCAACCACCAUCAUAUUUUG |
| 1024 | 568 | CUGCAAAUGCUGACUGUCCAA |
| 1025 | 569 | UCCGACCUAAACCAAGCACGU |
| 1026 | 570 | UGUCAGCUCCCAGUAGACUUU |
| 1027 | 571 | AUUCUAUCAAGUCUAUGUAUU |
| 1028 | 572 | CUUAGCACUACAAUGUCCAAG |
| 1029 | 573 | UGAGAAUAGAAAUGUGAUUGA |
| 1030 | 574 | AAGCACGUUGUAUGGUAGUUG |
| 1031 | 575 | UAGGGUGCAUUCUGGUCUGCC |
| 1032 | 576 | UCAAUGCACUGUGAUUCUUGA |
| 1033 | 577 | UCCAAGUGUUUGAGAAUAGAA |
| 1034 | 578 | UCCAAUAUGAAGGGUAAUUGG |
| 1035 | 579 | CUUUCCAAUAAUUACCAUGGG |
| 1036 | 580 | UUAAUAUGAGCAAGUAAAUCU |
| 1037 | 581 | UUUCCUUUCAAGAAAUCAAAU |
| 1038 | 582 | UGACUUUGUAAGUGGUUGAAU |
| 1039 | 583 | GUAAGCAGAACAAUAUUACUU |
| 1040 | 584 | AUUCCAUCUUCGUAAAUGUCA |
| 1041 | 585 | UCUUACGAGGACAGUCAUUAG |
| 1042 | 586 | AAAUGUGAUUGAAGAUUUGCA |
| 1043 | 587 | ACAUAUUCAAACCAUAUUUAU |
| 1044 | 588 | UGUGACAUAUUCAAACCAUAU |
| 1045 | 589 | UUUGAAUACUUUCCAAUAAUU |
| 1046 | 590 | AAUGCCUAAUGACUCCGUGAU |
| 1047 | 591 | AUUUGAUUUAGGUCUGUCAGC |
| 1048 | 592 | AUAGGCAUCACAUGUCCAUUU |
| 1049 | 593 | UCAUGAUGCAAAUAAGAUUAU |
| 1050 | 594 | AGUUGGUUGCUGUUCAUCCAC |
| 1051 | 595 | AAGUCUAUGUAUUUCUAUAAU |
| 1052 | 596 | UGCACUGUGAUUCUUGAAAGA |
| 1053 | 597 | UGACAAUUAGCUGGGAAUUUG |
| 1054 | 598 | UGUCCAUUUGCAUACUAGAAA |
| 1055 | 599 | AUAGAAAUGUGAUUGAAGAUU |
| 1056 | 600 | UCCAACUUCGAGGGACAUUGU |
| 1057 | 601 | UUGAGAAUCUCCAUCAUAAUC |
| 1058 | 602 | GAUCACUAUAUUGUAUGCCAU |
| 1059 | 603 | UUCAUCCCAGAUCUCACUAAG |
| 1060 | 604 | UGAGUAUGGUCAUAUUGUUAG |
| 1061 | 605 | UGUGCUACCAAGUCAGAGUAC |
| 1062 | 606 | CAAACUGGAAGGUACUAGUGG |
| 1063 | 607 | ACACAAACACUGGAGUACAUG |
| 1064 | 608 | AUAUCAGGAAUUAGAUCACCA |
| 1065 | 609 | AAUGUUUACAGUAACUCAAGU |
| 1066 | 610 | UGUUUACAGUAACUCAAGUAU |
| 1067 | 611 | ACAUGCUUAGAUACAAAGUAA |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 1068 | 612 | AUCACCAUUGAAAUCCAUAAU |
| 1069 | 613 | UAUUUCUUCAUGCCUGAAAAU |
| 1070 | 614 | UCAAGUCUAUGUAUUUCUAUA |
| 1071 | 615 | CAGAACAAUAUUACUUGGUGU |
| 1072 | 616 | UAGUUAAUAUGAGCAAGUAAA |
| 1073 | 617 | CUGAAAUCUUGUAGGACUGGA |
| 1074 | 618 | AAACAUUCGACGCGCCUCUUC |
| 1075 | 619 | UUCCUGCUCAUUUAAUUAUUU |
| 1076 | 620 | UGGGAAGAUAUGUCAGAAGGA |
| 1077 | 621 | UUUCAAUAAGGAAUAUUUAUU |
| 1078 | 622 | AUGACUCCGUGAUAUAUUCAC |
| 1079 | 623 | CAAACACUGGAGUACAUGCAA |
| 1080 | 624 | AAUGACUUUGUAAGUGGUUGA |
| 1081 | 625 | AAUGUCGUCAGGAAUAAAUCU |
| 1082 | 626 | UUCCAUUAUGUAAUAUUAAAG |
| 1083 | 627 | UUUGCAUUCCCAGAUGCUGCC |
| 1084 | 628 | UCAUAUUGUUAGGAUCUAAUG |
| 1085 | 629 | AAGUGUUUGAGAAUAGAAAUG |
| 1086 | 630 | AAGAUAACAGCUCCUAAUUCA |
| 1087 | 631 | AUUCUUGAAAGAUACCUUUAC |
| 1088 | 632 | AGUUUAAGGCAAGUCUGUCUU |
| 1089 | 633 | ACUACCACAUAUUGACCACUU |
| 1090 | 634 | AGGAGUUUAAGGCAAGUCUGU |
| 1091 | 635 | UUCAGUUGGUUGCUGUUCAUC |
| 1092 | 636 | AUUUAAUGUUUACAGUAACUC |
| 1093 | 637 | UCACAUGUCCAUUUGCAUACU |
| 1094 | 638 | UGCCCUUAUUGCUGAAAUCUU |
| 1095 | 639 | UGUAUAAGUCUAAUAAGAUCA |
| 1096 | 640 | UACAGAGGUUUAAACAAGAGCC |
| 1097 | 641 | AAUUAGAUGUAUAAGUCUAAU |
| 1098 | 642 | GAGAAUAGAAAUGUGAUUGAA |
| 1099 | 643 | UGUCCAUCUCCAUCAAAGUCU |
| 1100 | 644 | UUCAAACAAUGACUUUGUAAG |
| 1101 | 645 | AAUGUAAAUUAUAGACUUCUC |
| 1102 | 646 | GUAUACAUGAUAUAAGGUCCA |
| 1103 | 647 | AGACUUCUCCAAGUGUUUGAG |
| 1104 | 648 | UACAGAAUAGAGAACCCAAAU |
| 1105 | 649 | CUUGUAGUGGUCAAUGCUGGA |
| 1106 | 650 | UUUGUAUAUCCUUUACUUAGC |
| 1107 | 651 | UUCUCCAAGUGUUUGAGAAUA |
| 1108 | 652 | UCAAACCAUAUUUAUUUGAAU |
| 1109 | 653 | AAUGACUCCGUGAUAUAUUCA |
| 1110 | 654 | AUUCUUGGAGAGUACUAUAAU |
| 1111 | 655 | CAUCAAAGUCUGCAAAUGCUG |
| 1112 | 656 | AGACAUGUUAACAUGCUUAGA |
| 1113 | 657 | UGUGAUUGAAGAUUUGCAUUC |
| 1114 | 658 | AAGAUACCUUUACUUUGGGUU |
| 1115 | 659 | AGAAUAUUUCUUCAUGCCUGA |
| 1116 | 660 | AUUUGCAUCUACAGUUGUAUA |
| 1117 | 661 | UCCAUUUGAGAAUCUCCAUCA |
| 1118 | 662 | UCCAAAGAAUAUUUCUUCAUG |
| 1119 | 663 | AAUAAUUACCAUGGGAUACAU |
| 1120 | 664 | UGGAAAUGUGAAGUUCACAAU |
| 1121 | 665 | ACACCGAUGAGAGCUAUAGCA |
| 1122 | 666 | ACUGGAGUACAUGCAACACAU |
| 1123 | 667 | AGGUCUGUCAGCUCCCAGUAG |
| 1124 | 668 | UUAGGAGUUUAAGGCAAGUCU |
| 1125 | 669 | AUAUAGUACUGACAGAGAAGU |
| 1126 | 670 | CCAUUUGAGAAUCUCCAUCAU |
| 1127 | 671 | UGUCUUACUGUGCUACCAAGU |
| 1128 | 672 | ACAGCUUGCAUUAUUACAAGG |
| 1129 | 673 | AGUAGACUUUAAACAUUCGAC |
| 1130 | 674 | UACAGUAACUCAAGUAUUAGC |
| 1131 | 675 | UGAGAGCUAUAGCAGUAAGCA |
| 1132 | 676 | ACCAUUGAAAUCCAUAAUUAG |
| 1133 | 677 | AGCUUGCAUUAUUACAAGGGA |
| 1134 | 678 | CAUAUUUCAAACUGGAAGGUA |
| 1135 | 679 | AACCAAGCACGUUGUAUGGUA |
| 1136 | 680 | UCUGAAUGUAAAUUAUAGACU |
| 1137 | 681 | ACCAUAUUUAUUUGAAUACUU |
| 1138 | 682 | CUUGUUAUCAAUGCACUGUGA |
| 1139 | 683 | AAAUCAAAUGUUCUUCAUUAU |
| 1140 | 684 | UAUGGUCAUAUUGUUAGGAUC |
| 1141 | 685 | AUCUUCAGUCAGAUCAAUAAA |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 1142 | 686 | UAUGGUAGUUGGAGAGCUAAA |
| 1143 | 687 | UCCUUAAUUUGAUUUAGGUCU |
| 1144 | 688 | AUCCCAGAUCUCACUAAGUAG |
| 1145 | 689 | AAUAAGAAGCAAGACCAAGUC |
| 1146 | 690 | AAACCGGUGGGCUUCUUGUCG |
| 1147 | 691 | AGAUCUCACUAAGUAGAUGGU |
| 1148 | 692 | AUUUCUAUAAUUAGAUGUAUA |
| 1149 | 693 | UGGAAUGAUUGCAGUCCACUC |
| 1150 | 694 | UUCAGUCAGAUCAAUAAAUGC |
| 1151 | 695 | CACAUGUCCAUUUGCAUACUA |
| 1152 | 696 | GUCAGGAAUAAAUCUGCUGUA |
| 1153 | 697 | ACCCAUUUGCAUCUACAGUUG |
| 1154 | 698 | AGGAUCUAAUGUUUGAUUUUG |
| 1155 | 699 | AUAUUCAAACCAUAUUUAUUU |
| 1156 | 700 | AGGUUGAUUCACUCCAAAGGG |
| 1157 | 701 | GAAUGAUUGCAGUCCACUCUU |
| 1158 | 702 | UCGACGCGCCUCUUCACAGCU |
| 1159 | 703 | AUGACAAUUAGCUGGGAAUUU |
| 1160 | 704 | AGAAUAAGAAGCAAGACCAAG |
| 1161 | 705 | AGCUAAGCACUUCACAUACAU |
| 1162 | 706 | UCCAUUUGCAUACUAGAAAAU |
| 1163 | 707 | CACAUAUUGACCACUUACUCU |
| 1164 | 708 | AUAUUUAUUUGAAUACUUUCC |
| 1165 | 709 | AAUUGGUAUUUCAGUUGGUUG |
| 1166 | 710 | AGCACUACAAUGUCCAAGAUU |
| 1167 | 711 | AUGCCUAAUGACUCCGUGAUA |
| 1168 | 712 | UCAUCAUGAUGCAAAUAAGAU |
| 1169 | 713 | ACCUGCUGUGAUGAAGCUGAA |
| 1170 | 714 | AAACACUGGAGUACAUGCAAC |
| 1171 | 715 | UGCAUGAGAAUGUGGAAUUCG |
| 1172 | 716 | GUCCAAGAUUCCAUCUUCGUA |
| 1173 | 717 | CUACCACAUAUUGACCACUUA |
| 1174 | 718 | UCCAUCAUGAUGCAAAUA |
| 1175 | 719 | CAAUGUCCAAGAUUCCAUCUU |
| 1176 | 720 | UUAUAAGAAGACAUGUUAAC |
| 1177 | 721 | AGAAGGACAUCCAUUUGAGAA |
| 1178 | 722 | UCAGAGUACCCGAUCACUAUA |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 1179 | 723 | AAUACACAAACACUGGAGUAC |
| 1180 | 724 | CUGAAUGCCUAAUGACUCCGU |
| 1181 | 725 | AUGUGAAGUUCACAAUACAAA |
| 1182 | 726 | AGCAAGUAAAUCUUUAUGUCA |
| 1183 | 727 | AAUUGGAAUUGGUAUUUCAGU |
| 1184 | 728 | AAUAUUACUUGGUGUAAGAUA |
| 1185 | 729 | CUUGGUGUAAGAUACAGUUUG |
| 1186 | 730 | GUGAUUCUUGAAAGAUACCUU |
| 1187 | 731 | UCACCAUUGAAAUCCAUAAUU |
| 1188 | 732 | UGUAGUGGUCAAUGCUGGAUG |
| 1189 | 733 | UCUUCAUUAUCACAUGAUAAG |
| 1190 | 734 | AAGUUCAAACAAUGACUUUGU |
| 1191 | 735 | UAUUUCAAACUGGAAGGUACU |
| 1192 | 736 | AAGUCUGAAUGUAAAUUAUAG |
| 1193 | 737 | AAUGUCCAAGAUUCCAUCUUC |
| 1194 | 738 | UGUUAUCUUACGAGGACAGUC |
| 1195 | 739 | GUGUUUGAGAAUAGAAAUGUG |
| 1196 | 740 | AGACCUUGUGACAUAUUCAAA |
| 1197 | 741 | AGAGCUAUAGCAGUAAGCAGA |
| 1198 | 742 | AAGGGUAAUUGGAAUUGGUAU |
| 1199 | 743 | UCCUGCUCAUUUAAUUAUUUU |
| 1200 | 744 | CUGGAGUACAUGCAACACAUU |
| 1201 | 745 | ACACAGACACCGAUGAGAGCU |
| 1202 | 746 | AUCAUGAUGCAAAUAAGAUUA |
| 1203 | 747 | AUUUGAAUACUUUCCAAUAAU |
| 1204 | 748 | AGAUUAUAAAUACACAAACAC |
| 1205 | 749 | GUAGUUGGAGAGCUAAAUGUG |
| 1206 | 750 | AGUCAGAUCAAUAAAUGCAUG |
| 1207 | 751 | UUUCAACUAAUCAAGUGAACA |
| 1208 | 752 | ACUUCGAGGGACAUUGUGAGG |
| 1209 | 753 | UUAUUACAAGGACGUUCUCC |
| 1210 | 754 | UGGUUGCUGUUCAUCCACAAA |
| 1211 | 755 | ACAUGUCCAUUUGCAUACUAG |
| 1212 | 756 | ACAGUUGUAUACAUGAUAUAA |
| 1213 | 757 | UGCUGCCUACAGCAGUUUCCU |
| 1214 | 758 | AUUAGAUGUAUAAGUCUAAUA |
| 1215 | 759 | UUCGACGCGCCUCUUCACAGC |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 1216 | 760 | AAAUGCAUGAGAAUGUGGAAU |
| 1217 | 761 | UCUAUAAUUAGAUGUAUAAGU |
| 1218 | 762 | GACAGAGAAGUUUCCAUCCAA |
| 1219 | 763 | UACAGCAGUUUCCUUUCAAGA |
| 1220 | 764 | CUAUUGAGUAUGGUCAUAUUG |
| 1221 | 765 | GUAUAAGUCUAAUAAGAUCAU |
| 1222 | 766 | CAGUCAUUAGAACACAGACCA |
| 1223 | 767 | AUUCAAUGUCGUCAGGAAUAA |
| 1224 | 768 | AUGAUAUAAGGUCCAGGUUGA |
| 1225 | 769 | AUUAUCACAUGAUAAGGAUAA |
| 1226 | 770 | GUGUUCUUUAGUAUGACCAGA |
| 1227 | 771 | CAGAGUGUGCCCUUAUUGCUG |
| 1228 | 772 | AAGCUAAGCACUUCACAUACA |
| 1229 | 773 | CUUUAGUAUGACCAGAGCGUC |
| 1230 | 774 | UACGAGGACAGUCAUUAGAAC |
| 1231 | 775 | AUGUAUAAGUCUAAUAAGAUC |
| 1232 | 776 | CAUAUUGUUAGGAUCUAAUGU |
| 1233 | 777 | AUGUCAGAAGGACAUCCAUUU |
| 1234 | 778 | UGUGCUAGGCACCAAGCUAAG |
| 1235 | 779 | AUUUGCAUCAUUAGAAUAAGA |
| 1236 | 780 | CAAAGGGUGUUAUCUUACGAG |
| 1237 | 781 | AGCAGUAAGCAGAACAAUAUU |
| 1238 | 782 | AGAACAAUAACUUUAACAAAA |
| 1239 | 783 | CAUUUGAGAAUCUCCAUCAUA |
| 1240 | 784 | AUGCACUGUGAUUCUUGAAAG |
| 1241 | 785 | ACACUGGAGUACAUGCAACAC |
| 1242 | 786 | CCUUAUUGCUGAAAUCUUGUA |
| 1243 | 787 | AUGACCAGAGCGUCUGGAUAG |
| 1244 | 788 | AGGCCUGCUGGUUGCUUCCAG |
| 1245 | 789 | AGGUUUACAGAGGUUAAACAA |
| 1246 | 790 | AAAUUAUAGACUUCUCCAAGU |
| 1247 | 791 | AGAUGCUGCCUACAGCAGUUU |
| 1248 | 792 | UGGUUGGAUUCAUUUGUGAUA |
| 1249 | 793 | CAUGAGAAUGUGGAAUUCGCA |
| 1250 | 794 | GUACUGACAGAGAAGUUUCCA |
| 1251 | 795 | GUCCAGGUUGAUUCACUCCAA |
| 1252 | 796 | CCGACCUAAACCAAGCACGUU |
| 1253 | 797 | AGUUGGAGAGCUAAAUGUGCG |
| 1254 | 798 | CAUAUUGUAGUCUCCAAUAUG |
| 1255 | 799 | CAUUAUGUAAUAUUAAAGGCA |
| 1256 | 800 | CUACACUUGUUAUCAAUGCAC |
| 1257 | 801 | AACCAUAUUUAUUUGAAUACU |
| 1258 | 802 | AUAUUAAAGGCAAGUCACAUA |
| 1259 | 803 | ACCAAGCUAAGCACUUCACAU |
| 1260 | 804 | GAAAGAUACCUUUACUUUGGG |
| 1261 | 805 | UUAAGGCAAGUCUGUCUUACU |
| 1262 | 806 | AAUUGCAUCAUUAGAAUAAG |
| 1263 | 807 | CAUGAUAUAAGGUCCAGGUUG |
| 1264 | 808 | AUAGCAGUAAGCAGAACAAUA |
| 1265 | 809 | CAAUAAAUGCAUGAGAAUGUG |
| 1266 | 810 | AGAAGUUUCCAUCCAAAUUUU |
| 1267 | 811 | AAGCAUCUGCUUCAAAGUUAU |
| 1268 | 812 | CACUUGUUAUCAAUGCACUGU |
| 1269 | 813 | AUUCGACGCGCCUCUUCACAG |
| 1270 | 814 | AAGCUGAAUGCCUAAUGACUC |
| 1271 | 815 | UCCAUAUUGUAGUCUCCAAUA |
| 1272 | 816 | AUAUUAAUAAUGACAACUACC |
| 1273 | 817 | CUUUAAACAUUCGACGCGCCU |
| 1274 | 818 | CUUCGAGGGACAUUGUGAGGG |
| 1275 | 819 | AUGAAGCUGAAUGCCUAAUGA |
| 1276 | 820 | GAACCCACUGCUUCAUCCCAG |
| 1277 | 821 | AAAUGUGAAGUUCACAAUACA |
| 1278 | 822 | ACCGAUGAGAGCUAUAGCAGU |
| 1279 | 823 | CUUUGUAUAUCCUUUACUUAG |
| 1280 | 824 | GUCGUCAGGAAUAAAUCUGCU |
| 1281 | 825 | AGUCUGCAAAUGCUGACUGUC |
| 1282 | 826 | UGUUAUCAAUGCACUGUGAUU |
| 1283 | 827 | AUACACAAACACUGGAGUACA |
| 1284 | 828 | GUUGGAGAGCUAAAUGUGCGG |
| 1285 | 829 | AUUGAAGUCUGAAUGUAAAUU |
| 1286 | 830 | CCUUGUGACAUAUUCAAACCA |
| 1287 | 831 | UCAGCUCCCAGUAGACUUUAA |
| 1288 | 832 | ACAGCACUACAGAAAUAGAGAA |
| 1289 | 833 | CUACAAUGUCCAAGAUUCCAU |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 1290 | 834 | ACUGCUUCAUCCCAGAUCUCA |
| 1291 | 835 | ACCACUUACUCUGUGCUAGGC |
| 1292 | 836 | AGAAUAGAGAACCCAAAUUUU |
| 1293 | 837 | ACUAAGAACAAUAACUUUAAC |
| 1294 | 838 | AUUGUGAGGGUAUGGAAUGAC |
| 1295 | 839 | ACAUCAUUUAUAAAUAAUAUU |
| 1296 | 840 | UUCAAACUGGAAGGUACUAGU |
| 1297 | 841 | ACUCCAAAGGGUGUUAUCUUA |
| 1298 | 842 | UGAGGGUAUGGAAUGACAAUU |
| 1299 | 843 | ACAAUGUCCAAGAUUCCAUCU |
| 1300 | 844 | CUAAGUAGAUGGUACUCUUUU |
| 1301 | 845 | CCAUUUGCAUCUACAGUUGUA |
| 1302 | 846 | AAGAAGCAAGACCAAGUCAAG |
| 1303 | 847 | AGUGGUUGAAUUAGGAGUUUA |
| 1304 | 848 | UAUGUAAUAUUAAAGGCAAGU |
| 1305 | 849 | AAGAUUAUAAAUACACAAACA |
| 1306 | 850 | AAUCUCAGUGAACUAUAAAGA |
| 1307 | 851 | CAACUACCACAUAUUGACCAC |
| 1308 | 852 | ACAAGGGACGUUCUCCAGUAA |
| 1309 | 853 | UGACUCCGUGAUAUAUUCACA |
| 1310 | 854 | CUACCAAGUCAGAGUACCCGA |
| 1311 | 855 | AUGAAACCGGUGGGCUUCUUG |
| 1312 | 856 | UGUGAAGUUCACAAUACAAAA |
| 1313 | 857 | ACUGGAAGGUACUAGUGGUGG |
| 1314 | 858 | UAUUAAGAAGCAUGUUAACA |
| 1315 | 859 | UCUUCACAGCUUGCAUUAUUA |
| 1316 | 860 | ACAUGUUAACAUGCUUAGAUA |
| 1317 | 861 | AAGAUAUGUCAGAAGGACAUC |
| 1318 | 862 | GUUUAAGGCAAGUCUGUCUUA |
| 1319 | 863 | AUUCCUGCUCAUUUAAUUAUU |
| 1320 | 864 | GAAGACAUGUUAACAUGCUUA |
| 1321 | 865 | AAUAUGAAGGGUAAUUGGAAU |
| 1322 | 866 | CAAAUGCUGACUGUCCAACCA |
| 1323 | 867 | UAUAUACAAAGUGCUUUAAAA |
| 1324 | 868 | UAAUGACUCCGUGAUAUAUUC |
| 1325 | 869 | GUCAUUAGAACACAGACCACU |
| 1326 | 870 | AUCCCAUUUAAUGUUUACAGU |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 1327 | 871 | ACAUCAUCCCAUUUAAUGUUU |
| 1328 | 872 | AUACCUUUACUUUGGGUUUAA |
| 1329 | 873 | GAAUAUUCUUCAUGCCUGAA |
| 1330 | 874 | GUCUGUCUUACUGUGCUACCA |
| 1331 | 875 | AGUGUUUGAGAAUAGAAAUGU |
| 1332 | 876 | AUCAUCAUGAUGCAAAUAAGA |
| 1333 | 877 | GUAACUCAAGUAUUAGCCCCA |
| 1334 | 878 | GUUGUAUACAUGAUAUAAGGU |
| 1335 | 879 | UCUCACUAAGUAGAUGGUACU |
| 1336 | 880 | UGAUGAAGCUGAAUGCCUAAU |
| 1337 | 881 | UGCGCUCCGACCUAAACCAAG |
| 1338 | 882 | CAGCUUGCAUUAUUACAAGGG |
| 1339 | 883 | UGGAACCCACUGCUUCAUCCC |
| 1340 | 884 | AUAAGUCUAAUAAGAUCAUCU |
| 1341 | 885 | AAAGGGUGUUAUCUUACGAGG |
| 1342 | 886 | AACGUAGAGAUGGUCAAGAAA |
| 1343 | 887 | AGGGUAUGGAAUGACAAUUAG |
| 1344 | 888 | AUUAGCUGGGAAUUUGGAAUG |
| 1345 | 889 | ACUUCUCCAAGUGUUUGAGAA |
| 1346 | 890 | UCAGUGAACUAUAAAGAAAAA |
| 1347 | 891 | UCUUCAGUCAGAUCAAUAAAU |
| 1348 | 892 | UGGUUGAAUUAGGAGUUUAAG |
| 1349 | 893 | AUGGGAUACAUCAUUUAUAAA |
| 1350 | 894 | CCUUAAUUUGAUUUAGGUCUG |
| 1351 | 895 | AUCAAUAAAUGCAUGAGAAUG |
| 1352 | 896 | AUUUGAGAAUCUCCAUCAUAA |
| 1353 | 897 | UUAGCACUACAAUGUCCAAGA |
| 1354 | 898 | AGAGUGUGCCCUUAUUGCUGA |
| 1355 | 899 | UCCCAUAUUUCAAACUGGAAG |
| 1356 | 900 | GACUUUAAACAUUCGACGCGC |
| 1357 | 901 | GAUUGCAGUCCACUCUUGUUU |
| 1358 | 902 | GUCCAUCUCCAUCAAAGUCUG |
| 1359 | 903 | ACUUUAAACAUUCGACGCGCC |
| 1360 | 904 | CUGUGCUACCAAGUCAGAGUA |
| 1361 | 905 | UCCUAUUGAGUAUGGUCAUAU |
| 1362 | 906 | AGUAUAAUUUGCAUCAUUAGA |
| 1363 | 907 | ACCAACGUAGAGAUGGUCAAG |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 1364 | 908 | ACAUUCGACGCGCCUCUUCAC |
| 1365 | 909 | CAGUUGGUUGCUGUUCAUCCA |
| 1366 | 910 | CUGUCUUACUGUGCUACCAAG |
| 1367 | 911 | AUGCAACACAUUCCACAAAGG |
| 1368 | 912 | AGGACUGGAACCCACUGCUUC |
| 1369 | 913 | UCUCCAAGUGUUUGAGAAUAG |
| 1370 | 914 | UGCUUCAUCCCAGAUCUCACU |
| 1371 | 915 | AAUAUUCUUCAUGCCUGAAA |
| 1372 | 916 | AGAAAUCAAAUGUUCUUCAUU |
| 1373 | 917 | UCUCCAUCAAAGUCUGCAAAU |
| 1374 | 918 | UCAAUAAAUGCAUGAGAAUGU |
| 1375 | 919 | AUCACAUGAUAAGGAUAAGUU |
| 1376 | 920 | ACAGUCAUUAGAACACAGACC |
| 1377 | 921 | UCUGUCAGCUCCCAGUAGACU |
| 1378 | 922 | CAUUGAAAUCCAUAAUUAGUG |
| 1379 | 923 | CUUUGUAAGUGGUUGAAUUAG |
| 1380 | 924 | AAGGCAAGUCACAUAGCAUCA |
| 1381 | 925 | ACUUUGUAAGUGGUUGAAUUA |
| 1382 | 926 | AAAUAAGAUUAUAAAUACACA |
| 1383 | 927 | AUACAUCAUCCCAUUUAAUGU |
| 1384 | 928 | UAAGGUCCAGGUUGAUUCACU |
| 1385 | 929 | GACCACUAAGAACAAUAACUU |
| 1386 | 930 | CUGUGAUGAAGCUGAAUGCCU |
| 1387 | 931 | UGCUAGGCACCAAGCUAAGCA |
| 1388 | 932 | GUACCCGAUCACUAUAUUGUA |
| 1389 | 933 | CACCGAUGAGAGCUAUAGCAG |
| 1390 | 934 | UCCCAGAUGCUGCCUACAGCA |
| 1391 | 935 | CAGUCAGAUCAAUAAAUGCAU |
| 1392 | 936 | AUGCAUGAGAAUGUGGAAUUC |
| 1393 | 937 | UGUAUACAUGAUAUAAGGUCC |
| 1394 | 938 | UCCAAUAAUUACCAUGGGAUA |
| 1395 | 939 | CAAUAUUACUUGGUGUAAGAU |
| 1396 | 940 | AAAGGCAAGUCACAUAGCAUC |
| 1397 | 941 | AUGGUAUUUCAGUUGGUUGC |
| 1398 | 942 | UCCUUUCAAGAAAUCAAAUGU |
| 1399 | 943 | GUAUUUCUAUAAUUAGAUGUA |
| 1400 | 944 | UCCAUUAUGUAAUAUUAAAGG |
| 1401 | 945 | AACACUGGAGUACAUGCAACA |
| 1402 | 946 | AAGAUUUGCAUUCCCAGAUGC |
| 1403 | 947 | GUAGACUUUAAACAUUCGACG |
| 1404 | 948 | CCACUAAGAACAAUAACUUUA |
| 1405 | 949 | GAUUCUUGAAAGAUACCUUUA |
| 1406 | 950 | CAAUUAGCUGGGAAUUUGGAA |
| 1407 | 951 | AGUCUAUGUAUUUCUAUAAUU |
| 1408 | 952 | CACGUUGUAUGGUAGUUGGAG |
| 1409 | 953 | UGCCUAAUGACUCCGUGAUAU |
| 1410 | 954 | UGAAACCGGUGGGCUUCUUGU |
| 1411 | 955 | GUUGAUUCACUCCAAAGGGUG |
| 1412 | 956 | AAUUAGAUCACCAUUGAAAUC |
| 1413 | 957 | UGAUAAAUUCCCUCCUAAUAG |
| 1414 | 958 | AUUCACUCCAAAGGGUGUUAU |
| 1415 | 959 | UGAAUACUUUCCAAUAAUUAC |
| 1416 | 960 | AAUGCUGACUGUCCAACCACC |
| 1417 | 961 | AAUGCACGUGAUUCUUGAAA |
| 1418 | 962 | GAAUUGGUAUUUCAGUUGGUU |
| 1419 | 963 | AUAAUUACCAUGGGAUACAUC |
| 1420 | 964 | AGAUCAAUAAAUGCAUGAGAA |
| 1421 | 965 | GCUGAAAUCUUGUAGGACUGG |
| 1422 | 966 | AUUCAUUUGUGAUACCAAAAA |
| 1423 | 967 | GUUCAAACAAUGACUUUGUAA |
| 1424 | 968 | AUUCCAUUAUGUAAUAUUAAA |
| 1425 | 969 | GUACAUGCAACACAUUCCACA |
| 1426 | 970 | AUUCCCAGAUGCUGCCUACAG |
| 1427 | 971 | AGUCUGAAUGUAAAUUAUAGA |
| 1428 | 972 | CACAGCUUGCAUUAUUACAAG |
| 1429 | 973 | CAAUAUGAAGGGUAAUUGGAA |
| 1430 | 974 | CAUCUCCAUCAAAGUCUGCAA |
| 1431 | 975 | AGUCUAAUAAGAUCAUCUAAA |
| 1432 | 976 | UGCUGUGAUGAAGCUGAAUGC |
| 1433 | 977 | CUUUACUUAGCACUACAAUGU |
| 1434 | 978 | AUGUUAACAUGCUUAGAUACA |
| 1435 | 979 | UGCUUAGAUACAAAGUAAAAA |
| 1436 | 980 | AUGGUCAUAUUGUUAGGAUCU |
| 1437 | 981 | AACAUUCGACGCGCCUCUUCA |

TABLE 4-continued

Results for ITFG1.
Score threshold: 70. Design: siRNA 21 nt.

| SEQ ID NO | siRNA_id | siRNA guide strand/ AS Sequence |
|---|---|---|
| 1438 | 982 | UACCUUUACUUUGGGUUUAAA |
| 1439 | 983 | GUGAUGAAGCUGAAUGCCUAA |
| 1440 | 984 | AGGGCACAUUAAUUCUUGGAG |
| 1441 | 985 | ACAGCAGUUUCCUUUCAAGAA |
| 1442 | 986 | AUGCUUAGAUACAAAGUAAAA |
| 1443 | 987 | ACUCCGUGAUAUAUUCACAAA |
| 1444 | 988 | UCUUUAUGUCAAUCACCAAAA |
| 1445 | 989 | GAUUGAAGAUUUGCAUUCCCA |
| 1446 | 990 | AUUAGGAGUUUAAGGCAAGUC |
| 1447 | 991 | AAUUUGGAAUGAUUGCAGUCC |
| 1448 | 992 | UCCCAGAUCUCACUAAGUAGA |
| 1449 | 993 | CACUAAGUAGAUGGUACUCUU |
| 1450 | 994 | UGCAUCAUUAGAAUAAGAAGC |
| 1451 | 995 | AGAUGUAUAAGUCUAAUAAGA |
| 1452 | 996 | UUGUGAGGGUAUGGAAUGACA |
| 1453 | 997 | AGUCAGAGUACCCGAUCACUA |
| 1454 | 998 | CUGUGCUAGGCACCAAGCUAA |
| 1455 | 999 | GUAUAAUUUGCAUCAUUAGAA |
| 1456 | 1000 | UAAUUACCAUGGGAUACAUCA |
| 1457 | 1001 | CACAUUAAUUCUUGGAGAGUA |
| 1458 | 1002 | CUUGAAAGAUACCUUUACUUU |
| 1459 | 1003 | CUGCCUACAGCAGUUUCCUUU |
| 1460 | 1004 | AAGACCAAGUCAAGUGGACAC |
| 1461 | 1005 | GGAAUUGGUAUUUCAGUUGGU |
| 1462 | 1006 | CCAUAUUUCAAACUGGAAGGU |
| 1463 | 1007 | GAACAAUAUUACUUGGUGUAA |
| 1464 | 1008 | CAAGUCUAUGUAUUUCUAUAA |
| 1465 | 1009 | AAGAUUCCAUCUUCGUAAAUG |
| 1466 | 1010 | ACAUGAUAAGGAUAAGUUUUU |
| 1467 | 1011 | ACAUACAUCAUCCCAUUUAAU |
| 1468 | 1012 | GACAUGUUAACAUGCUUAGAU |
| 1469 | 1013 | UGGUAGUUGGAGAGCUAAAUG |
| 1470 | 1014 | CUAUAGCAGUAAGCAGAACAA |
| 1471 | 1015 | CUUCAUCCCAGAUCUCACUAA |
| 1472 | 1016 | CUCUGUGCUAGGCACCAAGCU |
| 1473 | 1017 | AAGGUCCAGGUUGAUUCACUC |
| 1474 | 1018 | GACUGGAACCCACUGCUUCAU |
| 1475 | 1019 | AUCACAUGUCCAUUUGCAUAC |
| 1476 | 1020 | CUACAGAAUAGAGAACCCAAA |
| 1477 | 1021 | AAUGACAAUUAGCUGGGAAUU |
| 1478 | 1022 | GUAAAUCUUUAUGUCAAUCAC |
| 1479 | 1023 | GUAUGGUAGUUGGAGAGCUAA |
| 1480 | 1024 | CAUCCUUAAUUUGAUUUAGGU |
| 1481 | 1025 | AUCUUACGAGGACAGUCAUUA |
| 1482 | 1026 | CACAUGAUAAGGAUAAGUUUU |

TABLE 5

Results for ABCC4.
Score threshold: 70. Design: siRNA 21 nt.

| SEQ ID NO | siRNA_id | siRNA guide strand/ AS Sequence |
|---|---|---|
| 1483 | 1 | UUAACAGUGAUGACUUCCCUG |
| 1484 | 2 | UUGACAAAUACACAGUUCGAA |
| 1485 | 3 | UUAAGAUCUAGCUUCUCGGUU |
| 1486 | 4 | UAACACUUUAUGAUUGCUCUU |
| 1487 | 5 | UUCACUUUCCUCAUUAUCCUU |
| 1488 | 6 | UUCAAUAUCAGAAUCUGACUU |
| 1489 | 7 | UUAAACCUGAAUAAAUUCCUA |
| 1490 | 8 | UAGAAUACCAAUAGAGAUCUU |
| 1491 | 9 | UGCACUGAGAGGAUCGUCCAG |
| 1492 | 10 | UCAUCUUCCUCUAAUCUCCGU |
| 1493 | 11 | UAUAACUUCAUUCAUGGUCCU |
| 1494 | 12 | UUUGACAAAUACACAGUUCGA |
| 1495 | 13 | AUAACUUCAUUCAUGGUCCUG |
| 1496 | 14 | UUAAAGAAGGCUUCUGUGCGU |
| 1497 | 15 | UGUAAGAACACUGUCACCUGA |
| 1498 | 16 | UAAGAUUUCCAGUAACACUUU |
| 1499 | 17 | UCAUUCAUGGUCCUGAUCCUG |
| 1500 | 18 | UCAGAAUCUGACUUGCAGCUU |
| 1501 | 19 | UACACGGGCAGCAUCUUGCCG |
| 1502 | 20 | AUACAUAUCAUCUUCCUCUAA |
| 1503 | 21 | UGAAGAGUUAACAAGGACGUA |
| 1504 | 22 | UUUGUGAAGAGUUAACAAGGA |
| 1505 | 23 | UCUAUCAAAGAAUAAUACCGG |

TABLE 5-continued

Results for ABCC4.
Score threshold: 70. Design: siRNA 21 nt.

| SEQ ID NO | siRNA_id | siRNA guide strand/ AS Sequence |
|---|---|---|
| 1506 | 24 | UGAUAUCUCAUCAAGUAGCAA |
| 1507 | 25 | UGACAUUUAGCAUACUUUGUU |
| 1508 | 26 | AAACUUGUUCACAUCAUUGGA |
| 1509 | 27 | UUUACAGUGACAUUUAGCAUA |
| 1510 | 28 | AUUUACAGUGACAUUUAGCAU |
| 1511 | 29 | AAGCACAUAGGCAACAUCUUG |
| 1512 | 30 | UUCUCGGUUACAUUUCCUCCU |
| 1513 | 31 | UAAACCUGAAUAAAUUCCUAA |
| 1514 | 32 | AAUCUUGGAAAUCUCCUUCUU |
| 1515 | 33 | UAUUACUCCUCAGAGUUCCCG |
| 1516 | 34 | UUCCUAUUGGAUUUCUAUCAA |
| 1517 | 35 | AUACCAAUAGAGAUCUUGCUA |
| 1518 | 36 | UUUCCAGUAACACUUUAUGAU |
| 1519 | 37 | UUGCUCUUGUUAAAGAAGGCU |
| 1520 | 38 | UAUCAAAGAAUAAUACCGGAG |
| 1521 | 39 | UGAGGUACUGCAACUGAUGAG |
| 1522 | 40 | UUCCGCAUCUACUGCACUGAG |
| 1523 | 41 | UGAAUACAUAUCAUCUUCCUC |
| 1524 | 42 | AUCACCAUCCUCCAACAGCUG |
| 1525 | 43 | UUGCAACUCCUCUCCAAGGUG |
| 1526 | 44 | UUGUUAAAGAAGGCUUCUGUG |
| 1527 | 45 | UCUUGAUACACUGCUCUUGCA |
| 1528 | 46 | UUUCAGAAUUGACUCAAACAU |
| 1529 | 47 | AGUGAUGAGAACAACUUCCCA |
| 1530 | 48 | UCAAUAUCAGAAUCUGACUUG |
| 1531 | 49 | AAUCUUGAAGCACAUAGGCAA |
| 1532 | 50 | UCUUCCAUGCACGCUGACCAG |
| 1533 | 51 | AAGAUUCCAGUAACACUUUA |
| 1534 | 52 | UACUGCACUGAGAGGAUCGUC |
| 1535 | 53 | UAAGAUCUAGCUUCUCGGUUA |
| 1536 | 54 | UUAGUGUGGGAGUUCCUGGAA |
| 1537 | 55 | AACACUUUAUGAUUGCUCUUG |
| 1538 | 56 | UACACUGCUCUUGCAAGGUUU |
| 1539 | 57 | AUAUCAGAAUCUGACUUGCAG |
| 1540 | 58 | AUAGAGAUCUUGCUAUGCCAA |
| 1541 | 59 | AAUACAUAUCAUCUUCCUCUA |
| 1542 | 60 | UACACAGUUCGAACAAGUGUC |
| 1543 | 61 | UAUUGGAUUUCUAUCAAAGAA |
| 1544 | 62 | AUCAUCUUCCUCUAAUCUCCG |
| 1545 | 63 | UAGAAGAUUGUUGAGACCAAA |
| 1546 | 64 | UACCAAUAGAGAUCUUGCUAU |
| 1547 | 65 | UUGUGAAGAGUUAACAAGGAC |
| 1548 | 66 | UGCUCUUGCAAGGUUUACCCG |
| 1549 | 67 | AUACUUUGUUUGUUUGCCCAG |
| 1550 | 68 | UUUAUACCAGUUAUAACUUCAU |
| 1551 | 69 | UAAAUUCCUAAGUACCAGUUA |
| 1552 | 70 | UUGCCUCUGACACCCUCUCAA |
| 1553 | 71 | UAACUUCCGCAUCUACUGCAC |
| 1554 | 72 | UAUUCCUAUCUCCAUCCAGAG |
| 1555 | 73 | AUACACAGUUCGAACAAGUGU |
| 1556 | 74 | UUACUCCUCAGAGUUCCCGAG |
| 1557 | 75 | AACAAGGACGUAGAAUACCAA |
| 1558 | 76 | UUUAGCAUACUUUGUUUGUUU |
| 1559 | 77 | UCAGCAUCUUGAUACACUGCU |
| 1560 | 78 | UGCAGCUUUGAGGUACUGCAA |
| 1561 | 79 | AGAUUGUUGAGACCAAACCGA |
| 1562 | 80 | UUGAGGUACUGCAACUGAUGA |
| 1563 | 81 | UAUACCAGUUAUAACUUCAUU |
| 1564 | 82 | UUAGCAUACUUUGUUUGUUUG |
| 1565 | 83 | UUCUUUAUCCCAGAACCCUUG |
| 1566 | 84 | AAUACCAAUAGAGAUCUUGCU |
| 1567 | 85 | UUCAGAAUUGACUCAAACAUU |
| 1568 | 86 | UCUGAGGCAGGAACUUCUCAG |
| 1569 | 87 | UGUCACCUGAUCAAACUUGUU |
| 1570 | 88 | UCUUUCAAUAUCAGAAUCUGA |
| 1571 | 89 | UUGGAAAUCUCCUUCUUUCUC |
| 1572 | 90 | UUACAUUUCCUCCUCCAUUUA |
| 1573 | 91 | AUCUUGGAAAUCUCCUUCUUU |
| 1574 | 92 | UUCUAUCAAGAAUAAUACCG |
| 1575 | 93 | UGCGCUGUGAUAUCUCAUCAA |
| 1576 | 94 | AAGAUUGUUGAGACCAAACCG |
| 1577 | 95 | UUGCAAGGUUUACCCGUGCUU |
| 1578 | 96 | UCCAUUUCAGUGACAUUUAG |
| 1579 | 97 | UGAGACACAUAGGCAAUUCUU |

TABLE 5-continued

Results for ABCC4.
Score threshold: 70. Design: siRNA 21 nt.

| SEQ ID NO | siRNA_id | siRNA guide strand/ AS Sequence |
|---|---|---|
| 1580 | 98 | UAAGUACCAGUUAAGAUCUAG |
| 1581 | 99 | AUUUAGCAUACUUUGUUUGUU |
| 1582 | 100 | UCUUGUUAAAGAAGGCUUCUG |
| 1583 | 101 | AAUAGAGAUCUUGCUAUGCCA |
| 1584 | 102 | UGUCAGCAUCUUGAUACACUG |
| 1585 | 103 | UACAGUGACAUUUAGCAUACU |
| 1586 | 104 | UGAGCAGAGGUUCGCGUCCUG |
| 1587 | 105 | UGACAGUAAAGGAAAGGCCUU |
| 1588 | 106 | ACAAGUGUCUGCUAACUUCCG |
| 1589 | 107 | AUACACUGCUCUUGCAAGGUU |
| 1590 | 108 | UCACAGUCAGAUCACCAUCCU |
| 1591 | 109 | UUUGAGGUACUGCAACUGAUG |
| 1592 | 110 | ACACAUAGGCAAUUCUUCCAU |
| 1593 | 111 | AUAGAUGUCAGCAUCUUGAUA |
| 1594 | 112 | UUUACCCGUGCUUUCUGCCCU |
| 1595 | 113 | UUCCUGGAACUGGAGGUUGUU |
| 1596 | 114 | AGUCAGAUCACCAUCCUCCAA |
| 1597 | 115 | UUUAUCCCAGAACCCUUGCAA |
| 1598 | 116 | UUCCUAUCUCCAUCCAGAUA |
| 1599 | 117 | UUCCUCAUUAUCCUUCUUUAA |
| 1600 | 118 | AAUCUGACUUGCAGCUUUGAG |
| 1601 | 119 | CACAGUUCGAACAAGUGUCUG |
| 1602 | 120 | UACCAGUUAAGAUCUAGCUUC |
| 1603 | 121 | AGUUCGAACAAGUGUCUGCUA |
| 1604 | 122 | AAGUGUCUGCUAACUUCCGCA |
| 1605 | 123 | UCUGACUUGCAGCUUUGAGGU |
| 1606 | 124 | UCUCGGUUACAUUUCCUCCUC |
| 1607 | 125 | UUCAUUCAUGGUCCUGAUCCU |
| 1608 | 126 | UACGAUUCCUUAGUGUGGGAG |
| 1609 | 127 | UCCAACAGCUGUAAAUCCUUU |
| 1610 | 128 | UUGUGCAAAGUUUGUGAAGAG |
| 1611 | 129 | AAUAUCAGAAUCUGACUUGCA |
| 1612 | 130 | UCUUCCUCUAAUCUCCGUUUA |
| 1613 | 131 | AUAAGAUUUCCAGUAACACUU |
| 1614 | 132 | AUCCUGCACAUGCACCAUCUU |
| 1615 | 133 | AUCUUUCAUAUCAGAAUCUG |
| 1616 | 134 | UCCUGCACAUGCACCAUCUUU |
| 1617 | 135 | AACCCUUGCAACUCCUCUCCA |
| 1618 | 136 | UCCUUCUUUCUCAAAUUGGUA |
| 1619 | 137 | UACUAAGACGAAGUGCCUCAA |
| 1620 | 138 | UCACCAUCCUCCAACAGCUGU |
| 1621 | 139 | UGUCUUUGGAGAAACGAUUUA |
| 1622 | 140 | UGUGAUCACACUGCCGAGGAG |
| 1623 | 141 | ACCACAGCUAACAUUCGCCA |
| 1624 | 142 | UUCACAUCAUUGGACAGCAGA |
| 1625 | 143 | UUCUGCCCUCCACUCAGCGUG |
| 1626 | 144 | UUUAUGAUUGCUCUUGUUAAA |
| 1627 | 145 | ACCAGUUAUAACUUCAUUCAU |
| 1628 | 146 | UCUCCAUCCAGAGUAGGGCAG |
| 1629 | 147 | CAUCUUGAUACACUGCUCUUG |
| 1630 | 148 | UUCAAGGAGGGUCUAGAAGAU |
| 1631 | 149 | UAAAGAAGGCUUCUGUGCGUC |
| 1632 | 150 | UUGAUACACUGCUCUUGCAAG |
| 1633 | 151 | UUUCCUCCUCCAUUUACAGUG |
| 1634 | 152 | AAGUGUCCAAUGUCUUUGGAG |
| 1635 | 153 | UCUGAGAAGGUACGAUUCCUU |
| 1636 | 154 | ACAAAUACACAGUUCGAACAA |
| 1637 | 155 | UCAGAAUCUUGGAAAUCUCCU |
| 1638 | 156 | UUUCUGCCCUCCACUCAGCGU |
| 1639 | 157 | AGUGUCUGCUAACUUCCGCAU |
| 1640 | 158 | UAAAGGAAAGGCCUUGUAGAG |
| 1641 | 159 | UUCUGUGCGUCAUUCUCAGCU |
| 1642 | 160 | UCCUUAGUGGGAGUUCCUG |
| 1643 | 161 | CUGACUUGCAGCUUUGAGGUA |
| 1644 | 162 | AACAGUGAUGACUUCCCUGCU |
| 1645 | 163 | UCUAGCUUCUCGGUUACAUUU |
| 1646 | 164 | UCUAGAAGAUUGUUGAGACCA |
| 1647 | 165 | UAACCGUCAGCCGCACAGCCC |
| 1648 | 166 | UUGGACAGCAGAUUGACUAUC |
| 1649 | 167 | UAGGAACUCAGUGUAAGUCCC |
| 1650 | 168 | AUGCACGCUGACCAGCCCGUG |
| 1651 | 169 | AUAUCAUCUUCCUCUAAUCUC |
| 1652 | 170 | UUCCAGUAACACUUUAUGAUU |
| 1653 | 171 | ACUGAGAGGAUCGUCCAGGAG |

TABLE 5-continued

Results for ABCC4.
Score threshold: 70. Design: siRNA 21 nt.

| SEQ ID NO | siRNA_id | siRNA guide strand/ AS Sequence |
|---|---|---|
| 1654 | 172 | UUACCCGUGCUUUCUGCCCUC |
| 1655 | 173 | UAUCAUCUUCCUCUAAUCUCC |
| 1656 | 174 | CUUAACAGUGAUGACUUCCCU |
| 1657 | 175 | AAAUUCAUCCCUCUGAGGCAG |
| 1658 | 176 | UCCAAGUGUCCAAUGUCUUUG |
| 1659 | 177 | AUGAUUGCUCUUGUUAAAGAA |
| 1660 | 178 | UGUGCGUCAUUCUCAGCUCUU |
| 1661 | 179 | UGAGGCAGGAACUUCUCAGAA |
| 1662 | 180 | UUCACCUCCUGGUACACGGGC |
| 1663 | 181 | UCCAGUAACACUUUAUGAUUG |
| 1664 | 182 | UCAAACUUGUUCACAUCAUUG |
| 1665 | 183 | UAACAGUGAUGACUUCCCUGC |
| 1666 | 184 | UAUCACAGUCGAUCACCAUC |
| 1667 | 185 | UAGCAUACUUUGUUUGUUUGC |
| 1668 | 186 | AAGACUCUGAGAAGGUACGAU |
| 1669 | 187 | AACUUGUUCACAUCAUUGGAC |
| 1670 | 188 | AGCAUCUUGAUACACUGCUCU |
| 1671 | 189 | UUGCGCUGUGAUAUCUCAUCA |
| 1672 | 190 | UGGAGGUUGUUCACUUUCCUC |
| 1673 | 191 | UAUCUCAUCAAGUAGCAAAAA |
| 1674 | 192 | UGGUGAAGGUCACAAACACGA |
| 1675 | 193 | AAGAGGGUAACCGUCAGCCGC |
| 1676 | 194 | UAUCAGAAUCGACUUGCAGC |
| 1677 | 195 | ACAUUUAGCAUACUUUGUUUG |
| 1678 | 196 | UAACAAGGACGUAGAAUACCA |
| 1679 | 197 | UUGCAGCUUUGAGGUACUGCA |
| 1680 | 198 | GUUAAGAUCUAGCUUCUCGGU |
| 1681 | 199 | AGGGUCUAGAAGAUUGUUGAG |
| 1682 | 200 | UAACUUCAUUCAUGGUCCUGA |
| 1683 | 201 | AUAAAUUCCUAAGUACCAGUU |
| 1684 | 202 | UUCCUUAGUGUGGGAGUUCCU |
| 1685 | 203 | AGAAUGACUCAAACAUUUUG |
| 1686 | 204 | UGUUACUAAGACGAAGUGCCU |
| 1687 | 205 | AGUCACUGCAAUCGCCUGCAG |
| 1688 | 206 | AGGAAGUGUAAGAACACUGUC |
| 1689 | 207 | CUUGAUACACUGCUCUUGCAA |
| 1690 | 208 | UCGGUUACAUUUCCUCCUCCA |

TABLE 5-continued

Results for ABCC4.
Score threshold: 70. Design: siRNA 21 nt.

| SEQ ID NO | siRNA_id | siRNA guide strand/ AS Sequence |
|---|---|---|
| 1691 | 209 | UAGGGCAGUCACUGCAAUCGC |
| 1692 | 210 | UCAAAGAAUAAUACCGGAGCU |
| 1693 | 211 | UUCUUCCUAUUGGAUUUCUAU |
| 1694 | 212 | UCAGAAUUGACUCAAACAUUU |
| 1695 | 213 | UUGUUCACAUCAUUGGACAGC |
| 1696 | 214 | UAUUAUCCUUAUACCAGUUAU |
| 1697 | 215 | UUGAAGCACAUAGGCAACAUC |
| 1698 | 216 | UGCUAACUUCCGCAUCUACUG |
| 1699 | 217 | GUGAUGAGAACAACUUCCCAA |
| 1700 | 218 | UCUCCAAGGUGCUGUGAGCGG |
| 1701 | 219 | UAUCUCCAUCCAGAGUAGGGC |
| 1702 | 220 | UACCAUCUUUCAAUAUCAGAA |
| 1703 | 221 | UCGUCCAGGAGAUAGAUGUCA |
| 1704 | 222 | AUCCAAGUGUCCAAUGUCUUU |
| 1705 | 223 | AGCUUUGAGGUACUGCAACUG |
| 1706 | 224 | AUUGCCUCUGACACCCUCUCA |
| 1707 | 225 | CAGAAUCUUGGAAAUCUCCUU |
| 1708 | 226 | UCUCCUUCUUUCUCAAAUUGG |
| 1709 | 227 | ACUUCUUUAUCCCAGAACCCU |
| 1710 | 228 | ACUUCCUCAUUAUCCUUCUU |
| 1711 | 229 | UACAUAUCAUCUUCCUCUAAU |
| 1712 | 230 | CUAACUUCCGCAUCUACUGCA |
| 1713 | 231 | UCGGAUGCUGACGAUUGCCUC |
| 1714 | 232 | AAUACACAGUUCGAACAAGUG |
| 1715 | 233 | AAGUUUGUGAAGAGUUAACAA |
| 1716 | 234 | UCAAAUGGUAAUAAGAUUUG |
| 1717 | 235 | ACUUGCAGCUUUGAGGUACUG |
| 1718 | 236 | UUGCAAGGGCAGGAGAAUGAU |
| 1719 | 237 | GAUAUUCCUAUCUCCAUCCAG |
| 1720 | 238 | UCCUAUUGGAUUUCUAUCAAA |
| 1721 | 239 | UGGUACACGGGCAGCAUCUUG |
| 1722 | 240 | ACUGUCACCUGAUCAAACUUG |
| 1723 | 241 | UGGAAAUCUCCUUCUUUCUCA |
| 1724 | 242 | AGUUAAGAUCUAGCUUCUCGG |
| 1725 | 243 | AUUUCCAGUAACACUUUAUGA |
| 1726 | 244 | AUCAGAAUCUGACUUGCAGCU |
| 1727 | 245 | AAGAAGGCUUCUGUGCGUCAU |

TABLE 5-continued

Results for ABCC4.
Score threshold: 70. Design: siRNA 21 nt.

| SEQ ID NO | siRNA_id | siRNA guide strand/ AS Sequence |
|---|---|---|
| 1728 | 246 | ACCCUUGCAACUCCUCUCCAA |
| 1729 | 247 | UGACCAGCCCGUGACUUGGGG |
| 1730 | 248 | CUAAGUACCAGUUAAGAUCUA |
| 1731 | 249 | UUCCCGAGAACACCCAGGGCU |
| 1732 | 250 | UACUUUGUUUGUUUGCCCAGU |
| 1733 | 251 | AAUUCUUCCAUGCACGCUGAC |
| 1734 | 252 | UCAGUGAUGAGAACAACUUCC |
| 1735 | 253 | AUGACUUCCCUGCUCCCACGG |
| 1736 | 254 | AUUCUUCCUAUUGGAUUUCUA |
| 1737 | 255 | UUUCCUCAUUAUCCUUCUUUA |
| 1738 | 256 | UACCGGAGCUUUCAGAAUUGA |
| 1739 | 257 | AUAGGCAAUUCUUCCAUGCAC |
| 1740 | 258 | UUUCAAUAUCAGAAUCUGACU |
| 1741 | 259 | AGUUAUAACUUCAUUCAUGGU |
| 1742 | 260 | UUCGGAUGCUGACGAUUGCCU |
| 1743 | 261 | CAAGUGUCUGCUAACUUCCGC |
| 1744 | 262 | UCUGCUAACUUCCGCAUCUAC |
| 1745 | 263 | UGGGAGUUCCUGGAACUGGAG |
| 1746 | 264 | CUAUCAAAGAAUAAUACCGGA |
| 1747 | 265 | ACUUCCGCAUCUACUGCACUG |
| 1748 | 266 | UUCUCAAAUUGGUAAUAAGAU |
| 1749 | 267 | AUUGUUGAGACCAAACCGAAG |
| 1750 | 268 | CAAUCUUGAAGCACAUAGGCA |
| 1751 | 269 | UGUCCGCUCGGCUGGAGCCUG |
| 1752 | 270 | AGGAGGGUCUAGAAGAUUGUU |
| 1753 | 271 | UGCUCUUGUUAAAGAAGGCUU |
| 1754 | 272 | UUUGUUUGUUUGCCCAGUAUG |
| 1755 | 273 | UUCCUAAGUACCAGUUAAGAU |
| 1756 | 274 | UCUCCUAUCACAGUCAGAUCA |
| 1757 | 275 | UCACAUCAUUGGACAGCAGAU |
| 1758 | 276 | UACCAGUUAUAACUUCAUUCA |
| 1759 | 277 | UUACAGUGACAUUUAGCAUAC |
| 1760 | 278 | UGACUUCCCUGCUCCCACGGG |
| 1761 | 279 | UAGCUUCUCGGUUACAUUUCC |
| 1762 | 280 | AAAUUGGUAAUAAGAUUUGAA |
| 1763 | 281 | ACAGUGACAUUUAGCAUACUU |
| 1764 | 282 | CAAGUGUCCAAUGUCUUUGGA |
| 1765 | 283 | AGAGUUAACAAGGACGUAGAA |
| 1766 | 284 | GUACCAGUUAAGAUCUAGCUU |
| 1767 | 285 | AUUGGACAGCAGAUUGACUAU |
| 1768 | 286 | AGAAUCUGACUUGCAGCUUUG |
| 1769 | 287 | UGGAUUUCUAUCAAAGAAUAA |
| 1770 | 288 | AGAAUACCAAUAGAGAUCUUG |
| 1771 | 289 | UGAAUAAAUUCCUAAGUACCA |
| 1772 | 290 | AUCAAACUUGUUCACAUCAUU |
| 1773 | 291 | AUCAUUGGACAGCAGAUUGAC |
| 1774 | 292 | UCAGCGGCAGCAAAUCAUCCA |
| 1775 | 293 | AGUGACAUUUAGCAUACUUUG |
| 1776 | 294 | CACUUUAUGAUUGCUCUUGUU |
| 1777 | 295 | UAGAUGUCAGCAUCUUGAUAC |
| 1778 | 296 | CAUCUUCCUCUAAUCUCCGUU |
| 1779 | 297 | CUGAAUACAUAUCAUCUUCCU |
| 1780 | 298 | ACAGUGAUGACUUCCCUGCUC |
| 1781 | 299 | UUAUCCUUAUACCAGUUAUAA |
| 1782 | 300 | UCCUUAUACCAGUUAUAACUU |
| 1783 | 301 | UGUUGUGCAAAGUUUGUGAAG |
| 1784 | 302 | UGACUUGCAGCUUUGAGGUAC |
| 1785 | 303 | ACUGCAACUGAUGAGUCACUA |
| 1786 | 304 | ACACGGGCAGCAUCUUGCCGG |
| 1787 | 305 | UGUUUGUUUGCCCAGUAUGAA |
| 1788 | 306 | AUUUGACAAAUACACAGUUCG |
| 1789 | 307 | UUCGCGUCCUGCAGCGGGUUG |
| 1790 | 308 | UUAUGAUUGCUCUUGUUAAAG |
| 1791 | 309 | UCUGUGCGUCAUUCUCAGCUC |
| 1792 | 310 | AAGGUCACAAACACGAUGAUU |
| 1793 | 311 | UUCCUCCUCCAUUUACAGUGA |
| 1794 | 312 | UCUCAGAAUCUUGGAAAUCUC |
| 1795 | 313 | UGAUACACUGCUCUUGCAAGG |
| 1796 | 314 | UUGUUGAGACCAAACCGAAGA |
| 1797 | 315 | AUUGUGAUCUUCUCAUGCAAA |
| 1798 | 316 | AGAGUUCCCGAGAACACCCAG |
| 1799 | 317 | ACAGGAAGUGUAAGAACACUG |
| 1800 | 318 | AAGAACACUGUCACCUGAUCA |
| 1801 | 319 | UUACUAAGACGAAGUGCCUCA |

TABLE 5-continued

Results for ABCC4.
Score threshold: 70. Design: siRNA 21 nt.

| SEQ ID NO | siRNA_id | siRNA guide strand/ AS Sequence |
|---|---|---|
| 1802 | 320 | AUCUCCUUCUUUCUCAAAUUG |
| 1803 | 321 | ACACAGUUCGAACAAGUGUCU |
| 1804 | 322 | AUCUUCCUCUAAUCUCCGUUU |
| 1805 | 323 | UCACCUGAUCAAACUUGUUCA |
| 1806 | 324 | UACUGCAACUGAUGAGUCACU |
| 1807 | 325 | UCAAGGAGGGUCUAGAAGAUU |
| 1808 | 326 | UGAGAGGAUCGUCCAGGAGAU |
| 1809 | 327 | AGUGUAAGAACACUGUCACCU |
| 1810 | 328 | UCCUCCUCCAUUUACAGUGAC |
| 1811 | 329 | UAGCUACAGUUAAACCUGAAU |
| 1812 | 330 | UGAGAAGGUACGAUUCCUUAG |
| 1813 | 331 | UUCUUUCUCAAAUUGGUAAUA |
| 1814 | 332 | UCCAGAGUAGGGCAGUCACUG |
| 1815 | 333 | AAAGGCCUUGUAGAGUUGGGG |
| 1816 | 334 | UUAACAAGGACGUAGAAUACC |
| 1817 | 335 | UUGGAUUUCUAUCAAAGAAUA |
| 1818 | 336 | UGCUUUCUGCCCUCCACUCAG |
| 1819 | 337 | UUGUUUGUUUGCCCAGUAUGA |
| 1820 | 338 | UUCAUCCCUCUGAGGCAGGAA |
| 1821 | 339 | AGAAUCUUGGAAAUCUCCUUC |
| 1822 | 340 | UACCAUCUGACGGCAGCUGAC |
| 1823 | 341 | AUUACUCCUCAGAGUUCCCGA |
| 1824 | 342 | GAGAAUGAUUAGAACUGCCAU |
| 1825 | 343 | ACGUAGAAUACCAAUAGAGAU |
| 1826 | 344 | UUGUGAUCUUCUCAUGCAAAA |
| 1827 | 345 | UACAUUCCUCCUCCAUUUAC |
| 1828 | 346 | UGAUCAAACUUGUUCACAUCA |
| 1829 | 347 | GAACUUCUCAGAAUCUUGGAA |
| 1830 | 348 | UUCCUCUAAUCUCCGUUUAUG |
| 1831 | 349 | UAGGCAAUUCUUCCAUGCACG |
| 1832 | 350 | UGUGGGAGUUCCUGGAACUGG |
| 1833 | 351 | AUCUCCAUCCAGAGUAGGGCA |
| 1834 | 352 | AUUCCUAUCUCCAUCCAGAGU |
| 1835 | 353 | UGAAGGUCACAAACACGAUGA |
| 1836 | 354 | UCACUUUCCUCAUUAUCCUUC |
| 1837 | 355 | AAGUGUAAGAACACUGUCACC |
| 1838 | 356 | AGAACACUGUCACCUGAUCAA |
| 1839 | 357 | AACUUCAUUCAUGGUCCUGAU |
| 1840 | 358 | AAGGUUUACCCGUGCUUUCUG |
| 1841 | 359 | UCACUGCAAUCGCCUGCAGUG |
| 1842 | 360 | UCGCCUGCAGUGGUCCUGCCC |
| 1843 | 361 | UCCGCAUCUACUGCACUGAGA |
| 1844 | 362 | UGAGACCAAACCGAAGACUCU |
| 1845 | 363 | UCUUUCAAGGAGGGUCUAGAA |
| 1846 | 364 | AGCUUCUCGGUUACAUUUCCU |
| 1847 | 365 | AACAAGUGUCUGCUAACUUCC |
| 1848 | 366 | GUGUAAGAACACUGUCACCUG |
| 1849 | 367 | CUUUGAGGUACUGCAACUGAU |
| 1850 | 368 | UGAAGCACAUAGGCAACAUCU |
| 1851 | 369 | UUCUUCCAUGCACGCUGACCA |
| 1852 | 370 | AAUAAUACCGGAGCUUUCAGA |
| 1853 | 371 | CAGAUCACCAUCCUCCAACAG |
| 1854 | 372 | UUGAGACCAAACCGAAGACUC |
| 1855 | 373 | AAGAUCUAGCUUCUCGGUUAC |
| 1856 | 374 | AGGAACUUCUCAGAAUCUUGG |
| 1857 | 375 | UCAUCCAAGUGUCCAAUGUCU |
| 1858 | 376 | AUGUCUUUGGAGAAACGAUUU |
| 1859 | 377 | AGGAACUCAGUGUAAGUCCCC |
| 1860 | 378 | CAAAGAAUAAUACCGGAGCUU |
| 1861 | 379 | UGGAACUGGAGGUUGUUCACU |
| 1862 | 380 | AGCACAUAGGCAACAUCUUGG |
| 1863 | 381 | ACGAUUGCCUCUGACACCCUC |
| 1864 | 382 | UGAUGAGAACAACUUCCCAAA |
| 1865 | 383 | UUGGUAAUAAGAUUUGAAAAU |
| 1866 | 384 | UAAUACCGGAGCUUUCAGAAU |
| 1867 | 385 | CAAUCGCCUGCAGUGGUCCUG |
| 1868 | 386 | UGCAAAGUUUGUGAAGAGUUA |
| 1869 | 387 | AAGAACACGCGUGAGCAGAGG |
| 1870 | 388 | UCCUAUCUCCAUCCAGAGUAG |
| 1871 | 389 | AACUUCCGCAUCUACUGCACU |
| 1872 | 390 | AGAAGGUACGAUUCCUUAGUG |
| 1873 | 391 | UGCAACUGAUGAGUCACUAAA |
| 1874 | 392 | UGUCUGCUAACUUCCGCAUCU |
| 1875 | 393 | UCACACUGCCGAGGAGCACGU |

TABLE 5-continued

Results for ABCC4.
Score threshold: 70. Design: siRNA 21 nt.

| SEQ ID NO | siRNA_id | siRNA guide strand/ AS Sequence |
|---|---|---|
| 1876 | 394 | AUGCUGACGAUUGCCUCUGAC |
| 1877 | 395 | GUCUGCUAACUUCCGCAUCUA |
| 1878 | 396 | CAUACUUUGUUUGUUUGCCCA |
| 1879 | 397 | AGUAACACUUUAUGAUUGCUC |
| 1880 | 398 | GAAUAAAUUCCUAAGUACCAG |
| 1881 | 399 | UCUGGAUUCUUCGGAUGCUGA |
| 1882 | 400 | GACAGCAGAUUGACUAUCUGG |
| 1883 | 401 | CUCCAGAGCACCAUCUUUCAA |
| 1884 | 402 | CAGAAGAACACGCGUGAGCAG |
| 1885 | 403 | GUUCACAUCAUUGGACAGCAG |
| 1886 | 404 | UCUCAAAUUGGUAAUAAGAUU |
| 1887 | 405 | UCUGACGGCAGCUGACGGUUG |
| 1888 | 406 | UUGUUCACUUUCCUCAUUAUC |
| 1889 | 407 | AGCACGGCACUUAACAGUGAU |
| 1890 | 408 | GUAGCUACAGUUAAACCUGAA |
| 1891 | 409 | UUUGCCCAGUAUGAAAGCCAC |
| 1892 | 410 | UGGUCCUGCCCACAGGAAGUG |
| 1893 | 411 | AGUUUGUGAAGAGUUAACAAG |
| 1894 | 412 | GAUUGUUGAGACCAAACCGAA |
| 1895 | 413 | CCACAGCUAACAAUUCGCCAG |
| 1896 | 414 | AUCCCUCUGAGGCAGGAACUU |
| 1897 | 415 | CACAGUCAGAUCACCAUCCUC |
| 1898 | 416 | AACUCCUCUCCAAGGUGCUGU |
| 1899 | 417 | UCGAACAAGUGUCUGCUAACU |
| 1900 | 418 | UCUGACAGUAAAGGAAAGGCC |
| 1901 | 419 | UUGGGCUUCACCUCCUGGUAC |
| 1902 | 420 | AUUCUUCGGAUGCUGACGAUU |
| 1903 | 421 | GCACUGAAUACAUAUCAUCUU |
| 1904 | 422 | UAAGACGAAGUGCCUCAAUUA |
| 1905 | 423 | AAUGUCUUUGGAGAAACGAUU |
| 1906 | 424 | CUUGUUCACAUCAUUGGACAG |
| 1907 | 425 | AUCAUCCAAGUGUCCAAUGUC |
| 1908 | 426 | UAAGAACACUGUCACCUGAUC |
| 1909 | 427 | AUCUGACGGCAGCUGACGGUU |
| 1910 | 428 | AGGAUCGUCCAGGAGAUAGAU |
| 1911 | 429 | CAGAAUCUGACUUGCAGCUUU |
| 1912 | 430 | AGCACAAGCCUUUAUGACUUU |
| 1913 | 431 | GAGCUUUCAGAAUUGACUCAA |
| 1914 | 432 | AUCCGUGAAAGUUGCAGUUUU |
| 1915 | 433 | UCCAGGAGAUAGAUGUCAGCA |
| 1916 | 434 | ACACUUUAUGAUUGCUCUUGU |
| 1917 | 435 | UGCAAGGUUUACCCGUGCUUU |
| 1918 | 436 | UGGACCUCAAGCAGGGAUGCU |
| 1919 | 437 | AAAUUCCUAAGUACCAGUUAA |
| 1920 | 438 | GAGACCAAACCGAAGACUCUG |
| 1921 | 439 | ACUUUAUGAUUGCUCUUGUUA |
| 1922 | 440 | UCCUCUCCAAGGUGCUGUGAG |
| 1923 | 441 | AGGUUCGCGUCCUGCAGCGGG |
| 1924 | 442 | UACAGUUAAACCUGAAUAAAU |
| 1925 | 443 | CAGAGCACCAUCUUUCAAGGA |
| 1926 | 444 | ACGGUAGCUACAGUUAAACCU |
| 1927 | 445 | AAGGUACGAUUCCUUAGUGUG |
| 1928 | 446 | AACUUCUCAGAAUCUUGGAAA |
| 1929 | 447 | CUCAGUGAUGAGAACAACUUC |
| 1930 | 448 | CACACUGCCGAGGAGCACGUA |
| 1931 | 449 | AUCUGACUUGCAGCUUUGAGG |
| 1932 | 450 | GAUUCUUCGGAUGCUGACGAU |
| 1933 | 451 | ACUGCAAUCGCCUGCAGUGGU |
| 1934 | 452 | UCCUCCAUUUACAGUGACAUU |
| 1935 | 453 | CAACUCCUCUCCAAGGUGCUG |
| 1936 | 454 | UUCUUCGGAUGCUGACGAUUG |
| 1937 | 455 | AAACCGAAGACUCUGAGAAGG |
| 1938 | 456 | CAGCAUCUUGAUACACUGCUC |
| 1939 | 457 | UCUCCAGAGCACCAUCUUUCA |
| 1940 | 458 | CAAACUUGUUCACAUCAUUGG |
| 1941 | 459 | AGAGUAGGGCAGUCACUGCAA |
| 1942 | 460 | UCUGGAAAUCUCCUUCUUUC |
| 1943 | 461 | UUUCUAUCAAAGAAUAAUACC |
| 1944 | 462 | UCACCUCCUGGUACACGGGCA |
| 1945 | 463 | AUCUACUGCACUGAGAGGAUC |
| 1946 | 464 | UCCGCUCGGCUGGAGCCUGUG |
| 1947 | 465 | AUCUUGAUACACUGCUCUUGC |
| 1948 | 466 | GUUCGAACAAGUGUCUGCUAA |
| 1949 | 467 | AUUCCUCCUCCAUUUACAGU |

TABLE 5-continued

Results for ABCC4.
Score threshold: 70. Design: siRNA 21 nt.

| SEQ ID NO | siRNA_id | siRNA guide strand/ AS Sequence |
|---|---|---|
| 1950 | 468 | UCUUGAAGCACAUAGGCAACA |
| 1951 | 469 | UCCGUGAAAGUUGCAGUUUUA |
| 1952 | 470 | UGACGGCAGCUGACGGUUGCG |
| 1953 | 471 | UCCUGGACCUCAAGCAGGGAU |
| 1954 | 472 | CAUCUGACGGCAGCUGACGGU |
| 1955 | 473 | AAGGAGGGUCUAGAAGAUUGU |
| 1956 | 474 | CUUCUUUAUCCCAGAACCCUU |
| 1957 | 475 | UCCAGAGCACCAUCUUUCAAG |
| 1958 | 476 | ACCGAAGACUCUGAGAAGGUA |
| 1959 | 477 | AAUCAUCCAAGUGUCCAAUGU |
| 1960 | 478 | AAUAAGAUUUCCAGUAACACU |
| 1961 | 479 | CUAGAAGAUUGUUGAGACCAA |
| 1962 | 480 | AAGGACGUAGAAUACCAAUAG |
| 1963 | 481 | UCUUUCUCAAAUUGGUAAUAA |
| 1964 | 482 | UCUCUGAUGCCUUAUCCCAAA |
| 1965 | 483 | UCCAUGCACGCUGACCAGCCC |
| 1966 | 484 | AUUGCUCUUGUUAAAGAAGGC |
| 1967 | 485 | GGAACUUCUCAGAAUCUUGGA |
| 1968 | 486 | UGCGUCAUUCUCAGCUCUUAA |
| 1969 | 487 | UUUCUCAAAUUGGUAAUAAGA |
| 1970 | 488 | AUCGUCCAGGAGAUAGAUGUC |
| 1971 | 489 | UGCAGUGGUCCUGCCCACAGG |
| 1972 | 490 | GUCUGGAUUCUUCGGAUGCUG |
| 1973 | 491 | UGACGAUUGCCUCUGACACCC |
| 1974 | 492 | AAUAAAUUCCUAAGUACCAGU |
| 1975 | 493 | AGCACCAUCUUUCAAGGAGGG |
| 1976 | 494 | GUAAGAACACUGUCACCUGAU |
| 1977 | 495 | UCUUGCAAGGUUUACCCGUGC |
| 1978 | 496 | AGGUUGUUCACUUUCCUCAUU |
| 1979 | 497 | GCAUCUUGAUACACUGCUCUU |
| 1980 | 498 | ACAGUUCGAACAAGUGUCUGC |
| 1981 | 499 | AGCAAAUCAUCCAAGUGUCCA |
| 1982 | 500 | UAGGUGGUGAAGGUCACAAAC |
| 1983 | 501 | CAGAGUUCCCGAGAACACCCA |
| 1984 | 502 | UGUUGAGACCAAACCGAAGAC |
| 1985 | 503 | ACCAAUAGAGAUCUUGCUAUG |
| 1986 | 504 | CAGUUCGAACAAGUGUCUGCU |
| 1987 | 505 | AAAGAAUAAUACCGGAGCUUU |
| 1988 | 506 | UGGAUUCUUCGGAUGCUGACG |
| 1989 | 507 | AUCUAGCUUCUCGGUUACAUU |
| 1990 | 508 | AUAAUACCGGAGCUUUCAGAA |
| 1991 | 509 | GUGACAUUUAGCAUACUUUGU |
| 1992 | 510 | UCAUUGGACAGCAGAUUGACU |
| 1993 | 511 | CUGCACUGAGAGGAUCGUCCA |
| 1994 | 512 | UAUGAUUGCUCUUGUUAAAGA |
| 1995 | 513 | AUCUUGAAGCACAUAGGCAAC |
| 1996 | 514 | UCUACUGCACUGAGAGGAUCG |
| 1997 | 515 | UGUCCAAUGUCUUUGGAGAAA |
| 1998 | 516 | AGUACCAGUUAAGAUCUAGCU |
| 1999 | 517 | CUUAGUGUGGGAGUUCCUGGA |
| 2000 | 518 | UGAUUGCUCUUGUUAAAGAAG |
| 2001 | 519 | CAAAUUGGUAAUAAGAUUUGA |
| 2002 | 520 | GAUAGAUGUCAGCAUCUUGAU |
| 2003 | 521 | UACUCCUCAGAGUUCCCGAGA |
| 2004 | 522 | UCUUCGGAUGCUGACGAUUGC |
| 2005 | 523 | GAAGCACAUAGGCAACAUCUU |
| 2006 | 524 | GAAGACUCUGAGAAGGUACGA |
| 2007 | 525 | CUGUGCGUCAUUCUCAGCUCU |
| 2008 | 526 | AGAGCACCAUCUUUCAAGGAG |
| 2009 | 527 | GACAUUUAGCAUACUUUGUUU |
| 2010 | 528 | CUGCCGAGGAGCACGUAGGUG |
| 2011 | 529 | CUCCAACAGCUGUAAAUCCUU |
| 2012 | 530 | AUUGGUAAUAAGAUUUGAAAA |
| 2013 | 531 | CAGAAUUGACUCAAACAUUUU |
| 2014 | 532 | CUAUCACGUCAGAUCACCAU |
| 2015 | 533 | CUGUGAUAUCUCAUCAAGUAG |
| 2016 | 534 | AGAUAGAUGUCAGCAUCUUGA |
| 2017 | 535 | AUUAUCCUUAUACCAGUUAUA |
| 2018 | 536 | AGAACCCUGCAACUCCCUCUC |
| 2019 | 537 | AUACCGGAGCUUUCAGAAUUG |
| 2020 | 538 | ACGCGUGAGCAGAGGUUCGCG |
| 2021 | 539 | ACAAGGACGUAGAAUACCAAU |
| 2022 | 540 | GUGAAGGUCACAAACACGAUG |
| 2023 | 541 | AAGGCCUUGUAGAGUUGGGGU |

TABLE 5-continued

Results for ABCC4.
Score threshold: 70. Design: siRNA 21 nt.

| SEQ ID NO | siRNA_id | siRNA guide strand/ AS Sequence |
|---|---|---|
| 2024 | 542 | AACCGUCAGCCGCACAGCCCC |
| 2025 | 543 | GAGAUAGAUGUCAGCAUCUUG |
| 2026 | 544 | AAACCUGAAUAAAUUCCUAAG |
| 2027 | 545 | ACGAAGUGCCUCAAUUAACGU |
| 2028 | 546 | UCGUAUUUCUUCCCAAAUAAA |
| 2029 | 547 | UCGCGCUGAUCAGGCGGCGGU |
| 2030 | 548 | UGCUGAGACACAUAGGCAAUU |
| 2031 | 549 | AGAGGGUAACCGUCAGCCGCA |
| 2032 | 550 | GAUCAAACUUGUUCACAUCAU |
| 2033 | 551 | UGUGCAAAGUUUGUGAAGAGU |
| 2034 | 552 | CAGCAAGGCACGAUAUUCCUA |
| 2035 | 553 | UUAUAACUUCAUUCAUGGUCC |
| 2036 | 554 | UUCGAACAAGUGUCUGCUAAC |
| 2037 | 555 | UUUCAAGGAGGGUCUAGAAGA |
| 2038 | 556 | ACAGCUUUGCAAGGGCAGGAG |
| 2039 | 557 | GUGAUGACUUCCCUGCUCCCA |
| 2040 | 558 | UAGUGUGGGAGUUCCUGGAAC |
| 2041 | 559 | UGUGAAGAGUUAACAAGGACG |
| 2042 | 560 | CAAAUACACAGUUCGAACAAG |
| 2043 | 561 | AUACCAGUUAUAACUUCAUUC |
| 2044 | 562 | AUAUUCCUAUCUCCAUCCAGA |
| 2045 | 563 | AAGAAGAGGGUAACCGUCAGC |
| 2046 | 564 | UGCAACUCCUCUCCAAGGUGC |
| 2047 | 565 | GUUACUAAGACGAAGUGCCUC |
| 2048 | 566 | ACGCCUGUCCGCUCGGCUGGA |
| 2049 | 567 | CAUCCAAGUGUCCAAUGUCUU |
| 2050 | 568 | ACCGUCAGCCGCACAGCCCCA |
| 2051 | 569 | CAUUGGACAGCAGAUUGACUA |
| 2052 | 570 | UGUUCACAUCAUUGGACAGCA |
| 2053 | 571 | ACCUGAAUAAAUUCCUAAGUA |
| 2054 | 572 | AUUGGAUUUCUAUCAAAGAAU |
| 2055 | 573 | UUUGUUUGCCCAGUAUGAAAG |
| 2056 | 574 | CAAGGUGCUGUGAGCGGUCUU |
| 2057 | 575 | AACUGGAGGUUGUUCACUUUC |
| 2058 | 576 | GUGCUGUGAGCGGUCUUCUGG |
| 2059 | 577 | CUACUGCACUGAGAGGAUCGU |
| 2060 | 578 | UCCCGAGAACACCCAGGGCUG |
| 2061 | 579 | AACCGAAGACUCUGAGAAGGU |
| 2062 | 580 | AAAUACACAGUUCGAACAAGU |
| 2063 | 581 | UUCUCAGAAUCUUGGAAAUCU |
| 2064 | 582 | AUUCAUCCCUCUGAGGCAGGA |
| 2065 | 583 | ACCUCAAGCAGGGAUGCUGGG |
| 2066 | 584 | GACACAUAGGCAAUUCUUCCA |
| 2067 | 585 | UCAGAGCACAAGCCUUUAUGA |
| 2068 | 586 | ACUAAAUAAGAUUUCCAGUAA |
| 2069 | 587 | AGUUCCUGGAACUGGAGGUUG |
| 2070 | 588 | CAGAGUAGGGCAGUCACUGCA |
| 2071 | 589 | GUCUCUGAUGCCUUAUCCCAA |
| 2072 | 590 | CAUCUUUCAAGGAGGGUCUAG |
| 2073 | 591 | CCAUCUUUCAAGGAGGGUCUA |
| 2074 | 592 | UACUCCUCAGUGAUGAGAACA |
| 2075 | 593 | AACCUGAAUAAAUUCCUAAGU |
| 2076 | 594 | AUUUCUAUCAAAGAAUAUAC |
| 2077 | 595 | CGGUAGCUACAGUUAAACCUG |
| 2078 | 596 | GAAGAAGAGGGUAACCGUCAG |
| 2079 | 597 | UCCAAGGUGCUGUGAGCGGUC |
| 2080 | 598 | UGUUAAAGAAGGCUUCUGUGC |
| 2081 | 599 | ACGCUGACCAGCCCGUGACUU |
| 2082 | 600 | AAGACGAAGUGCCUCAAUUAA |
| 2083 | 601 | AGGACGUAGAAUACCAAUAGA |
| 2084 | 602 | UAUCCUUAUACCAGUUAUAAC |
| 2085 | 603 | GCUGCUGAGACACAUAGGCAA |
| 2086 | 604 | CACCUGAUCAAACUUGUUCAC |
| 2087 | 605 | GAGGUUCGCGUCCUGCAGCGG |
| 2088 | 606 | UGUGAUAUCUCAUCAAGUAGC |
| 2089 | 607 | CACUGUCACCUGAUCAAACUU |
| 2090 | 608 | CUUUCCUCAUUAUCCUUCUUU |
| 2091 | 609 | UCCACUCAGCGUGGUUCCCCG |
| 2092 | 610 | AGAGGUUCGCGUCCUGCAGCG |
| 2093 | 611 | CUUCCGCAUCUACUGCACUGA |
| 2094 | 612 | GUCACAAACACGAUGAUUUUG |
| 2095 | 613 | CCAAUCUUGAAGCACAUAGGC |
| 2096 | 614 | CACUGAAUACAUCAUCUUCUU |
| 2097 | 615 | ACCAGUUAAGAUCUAGCUUCU |

TABLE 5-continued

Results for ABCC4.
Score threshold: 70. Design: siRNA 21 nt.

| SEQ ID NO | siRNA_id | siRNA guide strand/ AS Sequence |
|---|---|---|
| 2098 | 616 | AGGGCAGUCACUGCAAUCGCC |
| 2099 | 617 | AAAUAAGAUUUCCAGUAACAC |
| 2100 | 618 | AGCACGUAGGUGGUGAAGGUC |
| 2101 | 619 | GAAUCUGACUUGCAGCUUUGA |
| 2102 | 620 | GUCAGCAUCUUGAUACACUGC |
| 2103 | 621 | AAGAAUAAUACCGGAGCUUUC |
| 2104 | 622 | AGAUUUCCAGUAACACUUUAU |
| 2105 | 623 | ACAUCAUUGGACAGCAGAUUG |
| 2106 | 624 | UCCUCUAAUCUCCGUUUAUGG |
| 2107 | 625 | AGACCAAACCGAAGACUCUGA |
| 2108 | 626 | CUUCACCUCCUGGUACACGGG |
| 2109 | 627 | UUUGGAGAAACGAUUUAAAAU |
| 2110 | 628 | UCGCGUCCUGCAGCGGGUUGG |
| 2111 | 629 | ACUGCCGAGGAGCACGUAGGU |
| 2112 | 630 | AGGUACGAUUCCUUAGUGUGG |
| 2113 | 631 | CUUGCAACUCCUCUCCAAGGU |
| 2114 | 632 | UCUUUAUCCCAGAACCCUUGC |
| 2115 | 633 | GAAGUGUAAGAACACUGUCAC |
| 2116 | 634 | CUGGAGGUUGUUCACUUUCCU |
| 2117 | 635 | UAUCCCAGAACCCUUGCAACU |
| 2118 | 636 | GGUAGCUACAGUUAAACCUGA |
| 2119 | 637 | AUGUCAGCAUCUUGAUACACU |
| 2120 | 638 | CCAGUUAAGAUCUAGCUUCUC |
| 2121 | 639 | CUCCAAGGUGCUGUGAGCGGU |
| 2122 | 640 | CAGUAACACUUUAUGAUUGCU |
| 2123 | 641 | AUCCAGAGUAGGGCAGUCACU |
| 2124 | 642 | GUGAAGAGUUAACAAGGACGU |
| 2125 | 643 | GGACAGCAGAUUGACUAUCUG |
| 2126 | 644 | GUGAGCAGAGGUUCGCGUCCU |
| 2127 | 645 | CUCUGAGGCAGGAACUUCUCA |
| 2128 | 646 | CAAUUCUUCCAUGCACGCUGA |
| 2129 | 647 | GAAGGUCACAAACACGAUGAU |
| 2130 | 648 | AGGAGAAUGAUUAGAACUGCC |
| 2131 | 649 | CAGGAAGUGUAAGAACACUGU |
| 2132 | 650 | AGAAGAACACGCGUGAGCAGA |
| 2133 | 651 | GAACUGGAGGUUGUUCACUUU |
| 2134 | 652 | CGAAGUGCCUCAAUUAACGUA |
| 2135 | 653 | ACCAUCCUCCAACAGCUGUAA |
| 2136 | 654 | CAUCCGUGAAAGUUGCAGUUU |
| 2137 | 655 | AUCGCCUGCAGUGGUCCUGCC |
| 2138 | 656 | CCGAGGAGCACGUAGGUGGUG |
| 2139 | 657 | CUGCACAUGCACCAUCUUUUU |
| 2140 | 658 | ACUUUGUUUGUUUGCCCAGUA |
| 2141 | 659 | GAUGUCAGCAUCUUGAUACAC |
| 2142 | 660 | GAGGUUGUUCACUUUCCUCAU |
| 2143 | 661 | UUAUCCCAGAACCCUUGCAAC |
| 2144 | 662 | AAUUGGUAAUAAGAUUUGAAA |
| 2145 | 663 | UCCUAUCAGUCAGAUCACC |
| 2146 | 664 | CUGACAGUAAAGGAAAGGCCU |
| 2147 | 665 | CAUCAUUGGACAGCAGAUUGA |
| 2148 | 666 | ACCAAUCUUGAAGCACAUAGG |
| 2149 | 667 | AGAUCUAGCUUCUCGGUUACA |
| 2150 | 668 | UACCCGUGCUUUCUGCCCUCC |
| 2151 | 669 | CUGUCCGCUCGGCUGGAGCCU |
| 2152 | 670 | AAGGUGCUGUGAGCGGUCUUC |
| 2153 | 671 | AAUUCCUAAGUACCAGUUAAG |
| 2154 | 672 | ACUGAAUACAUAUCAUCUUCC |
| 2155 | 673 | GCUCUUGCAAGGUUUACCCGU |
| 2156 | 674 | GAAUACAUAUCAUCUUCCUCU |
| 2157 | 675 | UCUGCCCUCCACUCAGCUGGG |
| 2158 | 676 | UCUUCCUAUUGGAUUUCUAUC |
| 2159 | 677 | UGGACAGCAGAUUGACUAUCU |
| 2160 | 678 | CAAUGUCUUUGGAGAAACGAU |
| 2161 | 679 | UUCCAUGCACGCUGACCAGCC |
| 2162 | 680 | AGAACACCCAGGGCUGCUGAG |
| 2163 | 681 | UGUGAUCUUCUCAUGCAAAAU |
| 2164 | 682 | ACGGGCAGCAUCUUGCCGGGC |
| 2165 | 683 | GAACAAGUGUCUGCUAACUUC |
| 2166 | 684 | UGCCUCUGACACCCUCUCAAU |
| 2167 | 685 | CCAUGCACGCUGACCAGCCCG |
| 2168 | 686 | AAGGAAAGGCCUUGUAGAGUU |
| 2169 | 687 | CACCAUCCUCCAACAGCUGUA |
| 2170 | 688 | CGAACAAGUGUCUGCUAACUU |
| 2171 | 689 | GAAGAGGGUAACCGUCAGCCG |

TABLE 5-continued

Results for ABCC4.
Score threshold: 70. Design: siRNA 21 nt.

| SEQ ID NO | siRNA_id | siRNA guide strand/ AS Sequence |
|---|---|---|
| 2172 | 690 | ACUCCUCUCCAAGGUGCUGUG |
| 2173 | 691 | GAAUCUUGGAAAUCUCCUUCU |
| 2174 | 692 | CAGCGGCAGCAAAUCAUCCAA |
| 2175 | 693 | AAGGGCAGGAGAAUGAUUAGA |
| 2176 | 694 | AUAUCUCAUCAAGUAGCAAAA |
| 2177 | 695 | UUUGCAAGGGCAGGAGAAUGA |
| 2178 | 696 | AAAUCAUCCAAGUGUCCAAUG |
| 2179 | 697 | CGAUAUUCCUAUCUCCAUCCA |
| 2180 | 698 | UAAAUAAGAUUCCAGUAACA |
| 2181 | 699 | CUUGAAGCACAUAGGCAACAU |
| 2182 | 700 | AGGAAAGGCCUUGUAGAGUUG |
| 2183 | 701 | UGCACGCUGACCAGCCCGUGA |
| 2184 | 702 | UCCCUCUGAGGCAGGAACUUC |
| 2185 | 703 | ACACUGCUCUUGCAAGGUUUA |
| 2186 | 704 | CAGGAGAAUGAUUAGAACUGC |
| 2187 | 705 | CACAUAGGCAAUUCUUCCAUG |
| 2188 | 706 | GCAUCUACUGCACUGAGAGGA |
| 2189 | 707 | CACUGCAAUCGCCUGCAGUGG |
| 2190 | 708 | GAACACUGUCACCUGAUCAAA |
| 2191 | 709 | AAGGCUUCUGUGCGUCAUUCU |
| 2192 | 710 | GUGUCCAAUGUCUUUGGAGAA |
| 2193 | 711 | AUCCCAGAACCCUUGCAACUC |
| 2194 | 712 | UCAGAGUUCCCGAGAACACCC |
| 2195 | 713 | CCAAUGUCUUUGGAGAAACGA |
| 2196 | 714 | ACGUCAGCGGCAGCAAAUCAU |
| 2197 | 715 | AGAACGGUAGCUACAGUUAAA |
| 2198 | 716 | GACCAAACCGAAGACUCUGAG |
| 2199 | 717 | GAACACGCGUGAGCAGAGGUU |
| 2200 | 718 | CUCUUGCAAGGUUUACCCGUG |
| 2201 | 719 | CAGUGAUGAACAACUUCCC |
| 2202 | 720 | AACACGCGUGAGCAGAGGUUC |
| 2203 | 721 | GUGAUAUCUCAUCAAGUAGCA |
| 2204 | 722 | GCAGGAACUUCUCAGAAUCUU |
| 2205 | 723 | CUUUAUCCCAGAACCCUUGCA |
| 2206 | 724 | ACCAUCUUUCAAUAUCAGAAU |
| 2207 | 725 | ACCUGAUCAAACUUGUUCACA |
| 2208 | 726 | AAUACCGGAGCUUUCAGAAUU |

TABLE 6

Results for PAK3.
Score threshold: 70. Design: siRNA 21 nt.

| SEQ ID NO | siRNA_id | siRNA guide strand/ AS Sequence |
|---|---|---|
| 2209 | 1 | UAUAUCUCUAUGGAUCACCUG |
| 2210 | 2 | UUAUCUUGCAAGUUCAACCCA |
| 2211 | 3 | UUAGGUAUCAUUAUCUUUGUU |
| 2212 | 4 | UAAUGUAUCUAUUCCUCCUG |
| 2213 | 5 | UAAUUUGUCAACAUUUCUCAA |
| 2214 | 6 | UUUACAAUGACACACACACGA |
| 2215 | 7 | UUCUGUAUUGAGAAUGACCAA |
| 2216 | 8 | AUUAAGGAGAUUAACAACCUG |
| 2217 | 9 | UCUAAUAGUGACAUCUCCCUA |
| 2218 | 10 | UUAAUAUUAAACACAUUCCCA |
| 2219 | 11 | UUACAAUGACACACACACGAG |
| 2220 | 12 | UAAAUAAUCUCUACUGUGCUU |
| 2221 | 13 | UUAACUGAAUAUUAACUGCAA |
| 2222 | 14 | UUCAUUAAUAAUUAAUUCCUU |
| 2223 | 15 | UUCUCUACUAUCGCUGUUGAU |
| 2224 | 16 | ACAACUACUGCAAACAACCUA |
| 2225 | 17 | UUGAGUGCUGAAGAAUCCCGG |
| 2226 | 18 | UAAUAUUAAACACAUUCCCAA |
| 2227 | 19 | AUGAUAUACAGUAAUAUCCUG |
| 2228 | 20 | UAUCUUGCAAGUUCAACCCAA |
| 2229 | 21 | UCAUUCUCUACUAUCGCUGUU |
| 2230 | 22 | UUCAGAACCUGAACUCACCUA |
| 2231 | 23 | UUCCUGAACACACAUAUUCCU |
| 2232 | 24 | UAUACAGACAACAGGAAGCAA |
| 2233 | 25 | UUAUGGGAUAGCAUUUGCCUG |
| 2234 | 26 | UUGCUGUUGAAGGUUCAUCUG |
| 2235 | 27 | UUUACAGAUAACACAUUCUGA |
| 2236 | 28 | UAUAGAAUCUCUCAGAACUGG |
| 2237 | 29 | UUAGAGAAACAACUUUCUGUA |
| 2238 | 30 | UAAGUGUUUAGGUUCACUCUU |
| 2239 | 31 | UGAUAUUAUAGAAUCUCUCAG |
| 2240 | 32 | UUAAUAAUUAAUUCCUUCUUG |
| 2241 | 33 | UAUUAUUAUCAAAUCUUGGUA |
| 2242 | 34 | UACUAUAUCACCUUUCUCUAG |
| 2243 | 35 | UUGAGUUAAAUCUUCUUACAU |
| 2244 | 36 | UAGAAUACUCGUACACACAGG |
| 2245 | 37 | UUUACAUACAGACUGUAUGGA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2246 | 38 | UAUUAUGAACUUCAUUUGCUU |
| 2247 | 39 | UUUGGUUAGAUGGUCUCCCUU |
| 2248 | 40 | UUUGCAAUACUUUAGGUCCAA |
| 2249 | 41 | UUCUAAUAGUGACAUCUCCCU |
| 2250 | 42 | UUAUAGAAUCUCUCAGAACUG |
| 2251 | 43 | UUUCUUACAGAGUUGAAUGUU |
| 2252 | 44 | UAAGGCUUGCAGUCUUAGCGG |
| 2253 | 45 | UAUAGUUUGCUGAAACUCUAA |
| 2254 | 46 | UUGCCUAGCGUCACAUAGCAA |
| 2255 | 47 | UAACUUAUAGAUAAUAGUCUC |
| 2256 | 48 | UUAUAGAUAAUAGUCUCCUAA |
| 2257 | 49 | AUUAACAGAACUAUAACUGAA |
| 2258 | 50 | UAAAUAAAUAAUCUCUACUGU |
| 2259 | 51 | UAAAUUACAUAAUCUGAGGGA |
| 2260 | 52 | AAGUUGUAUAGAAUACUCGUA |
| 2261 | 53 | UUUAAUAUUAAACACAUUCCC |
| 2262 | 54 | UAGAGAAACAACUUUCUGUAA |
| 2263 | 55 | UAUAAUUAUUUACACGAUCUU |
| 2264 | 56 | UGUAACUAGCAAAUAUCUCUG |
| 2265 | 57 | UAGACAAAUAUCUCAAACUAU |
| 2266 | 58 | AUUUACACGAUCUUUGAGCUG |
| 2267 | 59 | AUAAUUAACAAUAUUAGGGUU |
| 2268 | 60 | UUGUUGACUGUUUCUUUGGAA |
| 2269 | 61 | UUGGGUACUAAAUCUGUUGAA |
| 2270 | 62 | UUAAUUUGUCAACAUUUCUCA |
| 2271 | 63 | UCUACUGUGCUUCUCACCCUU |
| 2272 | 64 | UAUAUUAUUAUCAAAUCUUGG |
| 2273 | 65 | UAAUUUAGGUAUCAUUAUCUU |
| 2274 | 66 | UUACUAUUCAUCCUCAGUGGA |
| 2275 | 67 | UUAAGGAGAUUAACAACCUGG |
| 2276 | 68 | UUUGAGAACAUCUAGAACAGC |
| 2277 | 69 | UACAGAUGAGGAAACAGCCAU |
| 2278 | 70 | UUAAUGUAUCUAUUUCCUCCU |
| 2279 | 71 | UGGAAUAAUUGUAACUAGCAA |
| 2280 | 72 | UUCUAUAACACAAAUUGUUAG |
| 2281 | 73 | UAACUGAAUAUUAACUGCAAG |
| 2282 | 74 | AAGACCAAGAGAUUCAACCGG |
| 2283 | 75 | UUAACAACCUGGUUUACUCAA |
| 2284 | 76 | UUCUCUAUGUUGGUCAGGCUG |
| 2285 | 77 | UAUUUCUGGUUGUUGACUGUU |
| 2286 | 78 | AAUAUUAACUGCAAGUAGCUU |
| 2287 | 79 | UAUUGCUUCAACCACAAUUUA |
| 2288 | 80 | UUUAUUUAGAUAUACAGUUUU |
| 2289 | 81 | UUAACUGCAAGUAGCUUAGAU |
| 2290 | 82 | AUAGAAUUUGAGAACAUCUAG |
| 2291 | 83 | UUUCAUAGGAGAAAUAUUCCA |
| 2292 | 84 | UUGUUUAAUAUUAAACACAUU |
| 2293 | 85 | UUAACUUAUAGAUAAUAGUCU |
| 2294 | 86 | UAUCGCUGUUGAUUUCCUCUU |
| 2295 | 87 | UUACUAUAUCACCUUUCUCUA |
| 2296 | 88 | UAGUGCUUCGUUUACUUUGCU |
| 2297 | 89 | UAUAGCAGGCUGAAUUUGCAA |
| 2298 | 90 | UUUGGAAUCAUAGAAUUUGAG |
| 2299 | 91 | UACUUGAGUUAAAUCUUCUUA |
| 2300 | 92 | UACAUAGUUGUAAUCCCUGUU |
| 2301 | 93 | UACACUAUAUAGUUUGCUGAA |
| 2302 | 94 | AAUCUGUUGAACAUGUUGCCA |
| 2303 | 95 | UUGUCCUGUUGCAAUGUCUAG |
| 2304 | 96 | UAUCUCAGGGCACACUAGCAA |
| 2305 | 97 | UCUAGCAAGUGUGACAGUGUG |
| 2306 | 98 | UAAAGCUCAUAUUAGACUCCG |
| 2307 | 99 | UUAUAUUCUAGCAAGUGUGAC |
| 2308 | 100 | UUACCCAACAUGGUGACUGAU |
| 2309 | 101 | UAUUUCAGUCUUACUCAUGAG |
| 2310 | 102 | UCUCCUGAACAUAAACACGUA |
| 2311 | 103 | UUAGAUGGAUGGAUGUACCUU |
| 2312 | 104 | UUCCUUUGCAGCGAUAAUCAG |
| 2313 | 105 | UAUGACAACGCACUGGAUCCU |
| 2314 | 106 | UUACUUAAUGUCCAACAAGGA |
| 2315 | 107 | UCUCUCUGCAACUUGUAAGUG |
| 2316 | 108 | UAUGCUCUGGUCUUGGUGCGA |
| 2317 | 109 | UUGUAUAGAAUACUCGUACAC |
| 2318 | 110 | UUGCUCUGGAAUUCCAGUGAA |
| 2319 | 111 | UAGAAUUUGAGAACAUCUAGA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2320 | 112 | UUAUUUGGUACUGCUGGUGAA |
| 2321 | 113 | AUUAUUUACACGAUCUUUGAG |
| 2322 | 114 | UAAUUGCUUCCUUUGCAGCGA |
| 2323 | 115 | AUAAAUUACAUAAUCUGAGGG |
| 2324 | 116 | UUAAACACAUUCCCAAUGCAU |
| 2325 | 117 | UUUCUUAUUCUUCUCUUCAGG |
| 2326 | 118 | AUUUCCUAGGUUCAGAACCUG |
| 2327 | 119 | AUGAGAAACAGCUUCUUUCUA |
| 2328 | 120 | UUCUCCUAUGAGGAUUCCUA |
| 2329 | 121 | UUCUCCUUCUUCUUAUUGGUU |
| 2330 | 122 | UAUCCCACUACAUCUGACUCA |
| 2331 | 123 | UUAGCUUCUCUAAGAUCUCCU |
| 2332 | 124 | UGGAAGUUUGGAGUAAUCGUG |
| 2333 | 125 | UAUAGUUCCCUUUCUGCUGUU |
| 2334 | 126 | UUACAGAUAACACAUUCUGAC |
| 2335 | 127 | UUACUCAUGAGGGAGAUGGUG |
| 2336 | 128 | UCAUCUAGUCCAAUACACUUA |
| 2337 | 129 | UUGUCACUCUUUAUAUCUCUA |
| 2338 | 130 | UUCAGUCUUACUCAUGAGGGA |
| 2339 | 131 | UAUCUGAGGUGACUACCUCAU |
| 2340 | 132 | UAGAACAGCUUGUGGGUUCUU |
| 2341 | 133 | UAUUUAUCCCACUACAUCUGA |
| 2342 | 134 | UAAGAUCUCCUCAUCUGUCAU |
| 2343 | 135 | UAGUCCAAUACACUUAUUUUA |
| 2344 | 136 | UUACAUACAGACUGUAUGGAA |
| 2345 | 137 | UGAGAACAUCUAGAACAGCUU |
| 2346 | 138 | AUAAGUUCUGUUUAGAUUCUU |
| 2347 | 139 | UACUCGAUUGUACCAAAUGUG |
| 2348 | 140 | UAACAUAAAGAAUAAAUACUU |
| 2349 | 141 | UUGUACCAAAUGUGAAUCCUU |
| 2350 | 142 | UCUUAUUCUUCUCUUCAGGGG |
| 2351 | 143 | UUCUCUGCCUACAGUGAUCUG |
| 2352 | 144 | UAUAACACAAAUUGUUAGUUU |
| 2353 | 145 | UUAAGUGACUUGCCUAGCGUC |
| 2354 | 146 | UUUAGGUUCACUCUUAGCAGU |
| 2355 | 147 | UAUUAUUGAACUUCAUUUG |
| 2356 | 148 | AUAGGUACACAAACCAAGCCA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2357 | 149 | AAGAAUUUCACUACACAUGGU |
| 2358 | 150 | UACAAUGACACACACACGAGA |
| 2359 | 151 | AAGUAUUCCAUGACUACCCAU |
| 2360 | 152 | UAUCUCUAUGGAUCACCUGGU |
| 2361 | 153 | UAAGGAAUUCUGUCGGACUGA |
| 2362 | 154 | AUAUAGUUUGCUGAAACUCUA |
| 2363 | 155 | AUCUAGAACAGCUUGUGGGUU |
| 2364 | 156 | UACUUAAUGUCCAACAAGGAU |
| 2365 | 157 | UUCCUCUUCAUCUUCUUCUUC |
| 2366 | 158 | AACAUCUAGAACAGCUUGUGG |
| 2367 | 159 | UCAUAUAAGGAAUUCUGUCGG |
| 2368 | 160 | UUAGGUCCAAGUUUCAAACUG |
| 2369 | 161 | UUUCUCCUUCUUCUUAUUGGU |
| 2370 | 162 | UUCCUGUACAAAGUACUGGAA |
| 2371 | 163 | AUUAGUAGCUACAGGAUUCUG |
| 2372 | 164 | UAAUGAAUAUGGUAUUUGCGG |
| 2373 | 165 | UUGAGAACAUCUAGAACAGCU |
| 2374 | 166 | AUCUUCUUCUUCUUCUUCCUC |
| 2375 | 167 | UAUUCUACAUUUAUCUGGUUU |
| 2376 | 168 | UGAAACUAAGCAGCAUAUCUG |
| 2377 | 169 | UUCAUAGGAGAAAUAUUCCAU |
| 2378 | 170 | AAGACAUUUAUGAAUAUGCUU |
| 2379 | 171 | UCUAGUGCUGUAUAAACAGUA |
| 2380 | 172 | UAGCCUUCACUGACCUCCCAU |
| 2381 | 173 | UAUUUAACUGCAACAUAAGAG |
| 2382 | 174 | UUUCUAUUCAUUUGAAAGGUA |
| 2383 | 175 | UAGCUUCUCUAAGAUCUCCUC |
| 2384 | 176 | UUAUUAUGAACUUCAUUUGCU |
| 2385 | 177 | UUUACAAAGCUGAAUUUCAG |
| 2386 | 178 | UUAUAAGAAGUUUCUAUUCAU |
| 2387 | 179 | UCAGUAUUCUACAUUUAUCUG |
| 2388 | 180 | UUUAUGGUCACUUCAACAUUG |
| 2389 | 181 | AUUGUUAAUAUGCUGAACUGA |
| 2390 | 182 | UUGCAGUCUUAGCGGCUGCUG |
| 2391 | 183 | AUACAGCUGACAGUCUCUCAG |
| 2392 | 184 | UAAAUACUUGAGUUAAAUCUU |
| 2393 | 185 | UAGUAGCUACAGGAUUCUGUG |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2394 | 186 | CUUGCUAACAACAUUAACGUU |
| 2395 | 187 | AUGGUCACUUCAACAUUGCUG |
| 2396 | 188 | UUCGUUUACUUUGCUCAGGAG |
| 2397 | 189 | UCACAUAAUUCCACCACCCUA |
| 2398 | 190 | AUAUACAGUAAUAUCCUGUUG |
| 2399 | 191 | UAUCACCUUUCUCUAGAUCUU |
| 2400 | 192 | UAUGAACUUCAUUUGCUUGAG |
| 2401 | 193 | UUAGAAAUAUACAUAACUCUC |
| 2402 | 194 | UAUUAUAACAAUAUCAAAUAA |
| 2403 | 195 | UAACUUCUAUUGAAAUUAGUG |
| 2404 | 196 | UUCUUCUUCCUCUUCAUCUUC |
| 2405 | 197 | UUGUCAACAUUUCUCAAUGCU |
| 2406 | 198 | UUCUGCUGUUUAUUUAUUGUA |
| 2407 | 199 | UAGAUGGUCUCCCUUGCUCUU |
| 2408 | 200 | AUACUCUACACACAGGUGUG |
| 2409 | 201 | UUCUUCUUCUUCUUCCUCUUC |
| 2410 | 202 | AUACUUGAGUUAAAUCUUCUU |
| 2411 | 203 | UUGUAACUAGCAAAUAUCUCU |
| 2412 | 204 | UUCACAUAAUUCCACCACCCU |
| 2413 | 205 | UAAAGCUCAUGUAUUUCUGGU |
| 2414 | 206 | UAACUAGCAAAUAUCUCUGCC |
| 2415 | 207 | UAUUGAUUGGGAUGUAGCCUU |
| 2416 | 208 | AUAAUCUCUACUGUGCUUCUC |
| 2417 | 209 | UAAUCGUGCCCAUUGCUCUGG |
| 2418 | 210 | UUAGUAGCUACAGGAUUCUGU |
| 2419 | 211 | AAGGAGAUUAACAACCUGGUU |
| 2420 | 212 | UAAAGAAUAAAUACUUGAGUU |
| 2421 | 213 | UUUAACUGCAACAUAAGAGAC |
| 2422 | 214 | UCUAGGUAUAGGGUCUGCUUU |
| 2423 | 215 | AUGAACACACCAUAUUCCGAA |
| 2424 | 216 | UUGGAGUUCUAAUAGUGACAU |
| 2425 | 217 | AUAGUGACAUCUCCCUAGCUU |
| 2426 | 218 | UCACACAGUACUUGCUCUGGU |
| 2427 | 219 | UUUAGGUACAUUAUCUUUGU |
| 2428 | 220 | UAUUUCUGUAUUGAGAAUGAC |
| 2429 | 221 | UCUAUGACAAUGCAAGUGAA |
| 2430 | 222 | UUCACACAGUACUUGCUCUGG |
| 2431 | 223 | UUCUUCUUCAGACACAGGAGG |
| 2432 | 224 | UCUGUCGGACUGACAUUUCUU |
| 2433 | 225 | UUCUUAUUCUUCUCUUCAGGG |
| 2434 | 226 | AAGGCUUAGAGAAACAACUUU |
| 2435 | 227 | UAAUAUGCUGAACUGAAAGCA |
| 2436 | 228 | UUAAUUGCUUCCUUUGCAGCG |
| 2437 | 229 | UUGUUCAGAGCUCAGAGACUG |
| 2438 | 230 | ACAUCUAGAACAGCUUGUGGG |
| 2439 | 231 | AUCUGUUGAACAUGUUGCCAG |
| 2440 | 232 | AAAUAAAUAAUCUCUACUGUG |
| 2441 | 233 | UUACAACUAAUUUCACAGCUC |
| 2442 | 234 | AUAGAAUACUCGUACACACAG |
| 2443 | 235 | UUACACGAUCUUUGAGCUGAG |
| 2444 | 236 | UAUGGUCACUUCAACAUUGCU |
| 2445 | 237 | UAUUCUAGCAAGUGUGACAGU |
| 2446 | 238 | UAAUAGUCUCCUAAGAAAGCG |
| 2447 | 239 | AACUAAGCAUGAACACACCAU |
| 2448 | 240 | UUUCAUAAGCACAAGAGAGGA |
| 2449 | 241 | UACUUUAGGUCCAAGUUUCAA |
| 2450 | 242 | UAUUAUCAAAUCUUGGUACAA |
| 2451 | 243 | UUUCGCUUCACGGUGGAAGUG |
| 2452 | 244 | UUAUACAGACAACAGGAAGCA |
| 2453 | 245 | UCGGACUGACAUUUCUUGGGA |
| 2454 | 246 | UCUUCUUCUUCAGACACAGGA |
| 2455 | 247 | UAUAUGGUGAAAUAGUAGUCA |
| 2456 | 248 | UUUCUCAAUGCUAAUAGCAUG |
| 2457 | 249 | UUUGUCCAUAUGCAUUUCUUU |
| 2458 | 250 | UUGCUAACAACAUUAACGUUC |
| 2459 | 251 | UCUAUAGUUCCCUUUCUGCUG |
| 2460 | 252 | UAGGUUCAGAACCUGAACUCA |
| 2461 | 253 | UCAUCUUACAUAGUUCUUUUA |
| 2462 | 254 | UUUAUAGACAAAUAUCUCAAA |
| 2463 | 255 | AAACUAAGCAGCAUAUCUGAG |
| 2464 | 256 | ACUCUUAGCAGUCUCAGCCAU |
| 2465 | 257 | AAAGCUUGCAGGCACUCUCUG |
| 2466 | 258 | UUAUGUUGGAAGUUUGGAGUA |
| 2467 | 259 | AUACUUAUUAGAAAUAUACAU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2468 | 260 | UCUUUGGUGAGUUAGAAGGAA |
| 2469 | 261 | UAGAUAAUAGUCUCCUAAGAA |
| 2470 | 262 | AUCACCUUUCUCUAGAUCUUU |
| 2471 | 263 | UGAAGGAAGAGAGAUCUCUGG |
| 2472 | 264 | UCAUCCAUACAGGUCUCUGUG |
| 2473 | 265 | UACCAAAUGUGAAUCCUUCAG |
| 2474 | 266 | AUUCUGUGAAGAUCUUAUCAU |
| 2475 | 267 | UUCUUAAUUGCUUCCUUUGCA |
| 2476 | 268 | UAAGGAGAUUAACAACCUGGU |
| 2477 | 269 | UGAAUGUACAUAAGUUCUGUU |
| 2478 | 270 | UUUACUAUAUCACCUUUCUCU |
| 2479 | 271 | AUAAUUAUUUACACGAUCUUU |
| 2480 | 272 | UCAUCUGUCAUCUUGGAUUUU |
| 2481 | 273 | AUCAUCUAGUCCAAUACACUU |
| 2482 | 274 | AUAGUCUCCUAAGAAAGCGUG |
| 2483 | 275 | AUCUCCUGAACAUAAACACGU |
| 2484 | 276 | UAAGGGAUGCUAACUAAUGAA |
| 2485 | 277 | ACAACAGGAAGCAAUUUCGUG |
| 2486 | 278 | UGAAAUAGUAGUCAAAUUUUG |
| 2487 | 279 | UAUGUAACUGAUCUCUUUCCC |
| 2488 | 280 | AUUAACAAUAUUAGGGUUCUU |
| 2489 | 281 | UUUACUUUGCUCAGGAGUGAU |
| 2490 | 282 | UUGGUCACUUAAAGGAGUGUG |
| 2491 | 283 | UAUACAGUAAUAUCCUGUUGG |
| 2492 | 284 | UACAGUAAUAUCCUGUUGGAC |
| 2493 | 285 | AAGCACACCACACACAAGCAC |
| 2494 | 286 | AUUAUGAACUUCAUUUGCUUG |
| 2495 | 287 | UAAUUAAUUCCUUCUUGGGUU |
| 2496 | 288 | UAAAUAAUUAACAAUAUUAGG |
| 2497 | 289 | UUCUACAUUUAUCUGGUUUUG |
| 2498 | 290 | UUGCAAUGUCUAGUGCUGUAU |
| 2499 | 291 | UGUGCAUCUUUGAGAAACCUU |
| 2500 | 292 | UACAGCUGACAGUCUCUCAGG |
| 2501 | 293 | UGUAACUGAUCUCUUUCCCU |
| 2502 | 294 | UCAAGUACAGUUAUAUUCUAG |
| 2503 | 295 | UGGACAUCUAAUGACAAUGCA |
| 2504 | 296 | ACUCAUUCUCUACUAUCGCUG |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2505 | 297 | UUGAGAAUUAAACUCUAGAAA |
| 2506 | 298 | UGAAUAGGGCUUCCUAACCAG |
| 2507 | 299 | AUUCUAGCAAGUGUGACAGUG |
| 2508 | 300 | UAAUGAUUUCAAAGUCAGCUU |
| 2509 | 301 | UAGCAAUUUAGUAAUAAAGCU |
| 2510 | 302 | UGACAGUCUCUCAGGAUUCUG |
| 2511 | 303 | AUCGCUGUUGAUUCCUCUUG |
| 2512 | 304 | UGUUCCUGUACAAAGUACUGG |
| 2513 | 305 | UACAAUUCUGAUAAACAAUGA |
| 2514 | 306 | AUAAUUAAUUCCUUCUUGGGU |
| 2515 | 307 | AUUAAUAAUUAAUUCCUUCUU |
| 2516 | 308 | UUCUUCUUCUGUUCCAAUUUU |
| 2517 | 309 | AAGCAGAGGGCAGACAACCUG |
| 2518 | 310 | UUCUCUUCAUUAUCCAGACCG |
| 2519 | 311 | UUCUUUGGUGAGUUAGAAGGA |
| 2520 | 312 | UACAUCUGACUCAUUCUCUAC |
| 2521 | 313 | AAACACAACACUAUGAAGAGG |
| 2522 | 314 | UCUUAAUUGCUUCCUUUGCAG |
| 2523 | 315 | AUUUGAGAACAUCUAGAACAG |
| 2524 | 316 | UCGAACUCCUGACCUCAGGUG |
| 2525 | 317 | UAUGCUCAAAGUCUGAAGGAA |
| 2526 | 318 | UAGUUCAUCACCCACCAAGUA |
| 2527 | 319 | AUUUAUAGACAAAUAUCUCAA |
| 2528 | 320 | UAGAAAUAUACAUAACUCUCC |
| 2529 | 321 | UAGAUGUAAGGAUCAGGUGGU |
| 2530 | 322 | AAUUUAGGUAUCAUUAUCUUU |
| 2531 | 323 | AUAUAUUAUUAUCAAAUCUUG |
| 2532 | 324 | UCUGCAGACAGCUGCUAUCUG |
| 2533 | 325 | UAUCUUUGUUUACUUAAUGUC |
| 2534 | 326 | UAUUCCGAAACAGAAAUAGGU |
| 2535 | 327 | UAUCAUUAUCUUUGUUUACUU |
| 2536 | 328 | UGAACAUAAACACGUACACUA |
| 2537 | 329 | UUGAUUUCCUCUUGGGUACUA |
| 2538 | 330 | UAAACAGUACCUGAUGCCCCU |
| 2539 | 331 | UAGAAGGAAGUUAUCCUUUGG |
| 2540 | 332 | AAUAAUUAACAAUAUUAGGGU |
| 2541 | 333 | UCUUUGUUUACUUAAUGUCCA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2542 | 334 | UGAACUGAAAGCAUAAGAGAG |
| 2543 | 335 | UAGAUAUAUGGUGAAAUAGUA |
| 2544 | 336 | UAGACAUCACUACCCUGUGAU |
| 2545 | 337 | AUAAAUAAUCUCUACUGUGCU |
| 2546 | 338 | UGCUAUCUGUCCUUCAUCCAU |
| 2547 | 339 | UUAGACAUUGUUUAAUAUUAA |
| 2548 | 340 | UUAUGAACUUCAUUUGCUUGA |
| 2549 | 341 | UUUCAUUAAUAAUUAAUUCCU |
| 2550 | 342 | UAACACAACUGAUUUCAAUUA |
| 2551 | 343 | AUUAGAAAUAUACAUAACUCU |
| 2552 | 344 | UUCAUCUUCUUCUUCAGACAC |
| 2553 | 345 | UUAAUGUCCAACAAGGAUUUC |
| 2554 | 346 | UCUUGGUACAAAGUGGUAGUA |
| 2555 | 347 | UACAGUGAUCUGAAGGGUCAC |
| 2556 | 348 | AUGCAACGCACUGGAUCCUU |
| 2557 | 349 | UUUAACUUAUAGAUAAUAGUC |
| 2558 | 350 | UUGGUACUGCUGGUGAAGCAA |
| 2559 | 351 | UGUUUAUUUAUUGUAAAGCAA |
| 2560 | 352 | UUGCAAGUCAUAACUUCUAUU |
| 2561 | 353 | AACACGUACACUAUAUAGUUU |
| 2562 | 354 | UUCAUAAGCACAAGAGAGGAU |
| 2563 | 355 | AACAACUGUAAAUGAAUUGGA |
| 2564 | 356 | UUCCCAUUUAUUUCCUUCCCA |
| 2565 | 357 | UUGGUGAGUUAGAAGGAAGUU |
| 2566 | 358 | UUUAUUGUAAAGCAAUAUUAU |
| 2567 | 359 | UAAGUAUUUCUGUAUUGAGAA |
| 2568 | 360 | UCUGGUUGUUGACUGUUUCUU |
| 2569 | 361 | AAUUGCAAGUCAUAACUUCUA |
| 2570 | 362 | AGACUUUACAUACAGACUGUA |
| 2571 | 363 | UAACACAAAUUGUUAGUUUUU |
| 2572 | 364 | UGGUUAAACUCAAACAUUGGG |
| 2573 | 365 | UUUCUCUCUGCAACUUGUAAG |
| 2574 | 366 | UAAUAAUUAAUUCCUUCUUGG |
| 2575 | 367 | UACUCGUACACACAGGUGUGC |
| 2576 | 368 | UGAUAUACAGUAAUAUCCUGU |
| 2577 | 369 | UCCUCGCCUAUCCACAUCCAU |
| 2578 | 370 | AUUUGCAAUACUUUAGGUCCA |
| 2579 | 371 | AUAAUCAGAGGAGUCAGGCUG |
| 2580 | 372 | UGUAUCUAUUCCUCCUGGUA |
| 2581 | 373 | UAUAUGGAUGGUUAGAUGGAU |
| 2582 | 374 | UACUAUUCAUCCUCAGUGGAG |
| 2583 | 375 | AUAAGGAAUUCUGUCGGACUG |
| 2584 | 376 | AGAACUAUAACUGAAUGCCAA |
| 2585 | 377 | ACAAGCACACAUUGAACUU |
| 2586 | 378 | UCACCUAGCAGGAUGUCACAG |
| 2587 | 379 | UUUGCAGCGAUAAUCAGAGGA |
| 2588 | 380 | UAACAGAACUAUAACUGAAUG |
| 2589 | 381 | UUGCUCAGGAGUGAUCUGGGC |
| 2590 | 382 | UUGGGAUGUAGCCUUCACUGA |
| 2591 | 383 | AUAUUGAUUGGGAUGUAGCCU |
| 2592 | 384 | UUAUUUAGAUAUACAGUUUUU |
| 2593 | 385 | UGUUGCAAUGCUAGUGCUGU |
| 2594 | 386 | AACAGCUUCUUUCUAAUACUU |
| 2595 | 387 | UAGGUAUCAUUAUCUUUGUUU |
| 2596 | 388 | AUUGUAACUAGCAAAUAUCUC |
| 2597 | 389 | UUAGAAGGAAGUUAUCCUUUG |
| 2598 | 390 | AUUUCUUGGGAUAUGAUUGUA |
| 2599 | 391 | UUGAAGGUUCAUCUGCUUUAU |
| 2600 | 392 | UUAUCCUUUGGUUAGAUGGUC |
| 2601 | 393 | UCUUUAUUUGGUACUGCUGGU |
| 2602 | 394 | UCAUCAAUAAUGAAUAUGGUA |
| 2603 | 395 | UUUCAGUCUUACUCAUGAGGG |
| 2604 | 396 | UUAGAAGCUGUUCUCAUUUGA |
| 2605 | 397 | UCUUCUUCUUCUUCUUCCUCU |
| 2606 | 398 | UUAACAGAACUAUAACUGAAU |
| 2607 | 399 | UAAUAGCAUGUAAUUACUUUU |
| 2608 | 400 | AUAGACAAAUAUCUCAAACUA |
| 2609 | 401 | ACUCUCUGCAGACAGCUGCUA |
| 2610 | 402 | UUAUAUUCAUUUGGUCACUUA |
| 2611 | 403 | UCAGUCAAUUUAACAGAGCCA |
| 2612 | 404 | UUACAUAAUCUGAGGGAGUAG |
| 2613 | 405 | UUUAGAAGCUGUUCUCAUUUG |
| 2614 | 406 | ACUUCUAUUGAAAUUAGUGGG |
| 2615 | 407 | UUAACUGCAACAUAAGAGACU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2616 | 408 | UUUGUAUCAUAAGUAAAUGAU |
| 2617 | 409 | UCUUCUUCAGACACAGGAGGG |
| 2618 | 410 | UUCACUGACCUCCCAUUUCUU |
| 2619 | 411 | UCCUCUUGGGUACUAAAUCUG |
| 2620 | 412 | AUCCCUCAUCUGUCAUCUUG |
| 2621 | 413 | AAUAAUUAAUUCCUUCUUGGG |
| 2622 | 414 | AUUGUCACUCUUUAUAUCUCU |
| 2623 | 415 | UGUCGGACUGACAUUUCUUGG |
| 2624 | 416 | UGAAUUUGCAAGGCAACCUAU |
| 2625 | 417 | UUUACAUGAAUACAAAUUUAU |
| 2626 | 418 | UAUUAGGGCAUGGACUUCCAC |
| 2627 | 419 | UUUCCCGGCACUAUGAGUGAA |
| 2628 | 420 | UACAUAACUCUCCAAUACAGG |
| 2629 | 421 | ACAAAUAUCUCAAACUAUCAA |
| 2630 | 422 | UAGGUACACAAACCAAGCCAC |
| 2631 | 423 | UUCUGUCGGACUGACAUUUCU |
| 2632 | 424 | UUCAACAUUGCUGCCCUGUUU |
| 2633 | 425 | UGAAGAGGGAGUGUGCAUCUU |
| 2634 | 426 | UGAAACUCUAAAGAAAGUGCU |
| 2635 | 427 | UGUCACUCUUUAUAUCUCUAU |
| 2636 | 428 | UUCAUUUGGUCACUUAAAGGA |
| 2637 | 429 | AAGCUCAUAUUAGACUCCGGG |
| 2638 | 430 | AUACAUAACUCUCCAAUACAG |
| 2639 | 431 | UGUCUAGUGCUGUAUAAACAG |
| 2640 | 432 | UAGUGACAUCUCCCUAGCUUU |
| 2641 | 433 | UUCUAUUGAAAUUAGUGGGAC |
| 2642 | 434 | UUAUUUAUUGUAAAGCAAUAU |
| 2643 | 435 | AUAUGGUGAAAUAGUAGUCAA |
| 2644 | 436 | UGAAGCAAUGGAUUCAACCAC |
| 2645 | 437 | UUGUCCAUAUGCAUUUCUUUU |
| 2646 | 438 | UUCCGAAACAGAAAUAGGUGA |
| 2647 | 439 | AUUAGAAAUAAACCCAUUGAG |
| 2648 | 440 | UAAUUCCUUCUUGGGUUGCUG |
| 2649 | 441 | UGGGAUUAUGACAACGCACUG |
| 2650 | 442 | UUCAUUAUCCAGACCGUCAGA |
| 2651 | 443 | UCUCUUCAUUAUCCAGACCGU |
| 2652 | 444 | UUCUUUGGAAUCAUAGAAUUU |
| 2653 | 445 | AUAUUCUAGCAAGUGUGACAG |
| 2654 | 446 | UACUGCAAAUUAAGAAGCCUU |
| 2655 | 447 | AAAUAAAUUACAUAAUCUGAG |
| 2656 | 448 | AAAGUAUAACAUAGUAUGCUU |
| 2657 | 449 | UGACUCAUUCUCUACUAUCGC |
| 2658 | 450 | AGUACAGUUAUAUUCUAGCAA |
| 2659 | 451 | AACAUUAACGUUCUUUCCUUU |
| 2660 | 452 | UUAUCAUCAAUAAUGAAUAUG |
| 2661 | 453 | UUUAUUUCCUUCCCAGUCCAC |
| 2662 | 454 | UAGCGUCACAUAGCAAUUUAG |
| 2663 | 455 | UACAGGUCUCUGUGACCACAU |
| 2664 | 456 | UUUCCCACUGCCCUAUUCCUA |
| 2665 | 457 | UAUGUAUCCAUGUGCACUUUU |
| 2666 | 458 | UCAGUCUUACUCAUGAGGGAG |
| 2667 | 459 | AUAGGAAAUACACCAGUGGGG |
| 2668 | 460 | AAACAACCUAUAAAUAGGCAG |
| 2669 | 461 | AUCAUUAUCUUUGUUUACUUA |
| 2670 | 462 | UAUAGAAUACUCGUACACACA |
| 2671 | 463 | AAUAGUGACAUCUCCCUAGCU |
| 2672 | 464 | AUCUCUAUGGAUCACCUGGUU |
| 2673 | 465 | UUAACAAUAUUAGGGUUCUUA |
| 2674 | 466 | UCUCUAAGAUCUCCUCAUCUG |
| 2675 | 467 | UCCUCAUCUGUCAUCUUGGAU |
| 2676 | 468 | UUCAUCCAUACAGGUCUCUGU |
| 2677 | 469 | UGAAUGUUUACUAUAUCACCU |
| 2678 | 470 | ACAGAUAACACAUUCUGACAA |
| 2679 | 471 | UUUACACGAUCUUUGAGCUGA |
| 2680 | 472 | AAUACUCGUACACACAGGUGU |
| 2681 | 473 | AAAUCUUGGUACAAAGUGGUA |
| 2682 | 474 | AUAUCUGAGGUGACUACCUCA |
| 2683 | 475 | UCUCUCAUUAGAGCAGUGUGG |
| 2684 | 476 | UUGGAAGUUUGGAGUAAUCGU |
| 2685 | 477 | UUGGUUAGAUGGUCUCCCUUG |
| 2686 | 478 | UUUGAGCUGAGAAAUAUCAUU |
| 2687 | 479 | UUGAUUGGGAUGUAGCCUUCA |
| 2688 | 480 | UGACCUCAGGUGAUCCGCCUG |
| 2689 | 481 | AAUAUUUACAAUGACACACAC |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2690 | 482 | UGGAUUCAACCACAGAACGAG |
| 2691 | 483 | UUUCUGUAUUGAGAAUGACCA |
| 2692 | 484 | UUGUUAAUAUGCUGAACUGAA |
| 2693 | 485 | ACAACUGAUUUCAAUUAUCUG |
| 2694 | 486 | UGCUUAACUGAAUAUUAACUG |
| 2695 | 487 | AUUGCAAGUCAUAACUUCUAU |
| 2696 | 488 | AAUGUUUACUAUAUCACCUUU |
| 2697 | 489 | UGCUUCGUUUACUUUGCUCAG |
| 2698 | 490 | AAAGCUCAUAUUAGACUCCGG |
| 2699 | 491 | UGUCAGUUUACAAAUGCUGAA |
| 2700 | 492 | UGAACUUCAUUUGCUUGAGUU |
| 2701 | 493 | UCCACCACCCUAACACAACUG |
| 2702 | 494 | UAUGGUGAAAUAGUAGUCAAA |
| 2703 | 495 | AAUGAUUUCAAAGUCAGCUUU |
| 2704 | 496 | UCACUCUUGUUGCCGAGGCUG |
| 2705 | 497 | AAGAACGAAGUCAUUACCCAA |
| 2706 | 498 | UUUAAAUGUGGUUUCUCCUAU |
| 2707 | 499 | AACAUAAAGAAUAAAUACUUG |
| 2708 | 500 | AUGCAUUAGUAGCUACAGGAU |
| 2709 | 501 | UCGCCUAUCCACAUCCAUCUC |
| 2710 | 502 | AAUGUAUCUAUUUCCUCCUGG |
| 2711 | 503 | UAUUGUCACUCUUUAUAUCUC |
| 2712 | 504 | UAUUCAUCCUCAGUGGAGGAG |
| 2713 | 505 | UGAGUGCUGAAGAAUCCCGGU |
| 2714 | 506 | UGACUUCUCUAGGUAUAGGGU |
| 2715 | 507 | UCAUUGGUCACUUAAAGGAG |
| 2716 | 508 | UUAUCUUUGUUUACUUAAUGU |
| 2717 | 509 | AUAUUAUUAUCAAAUCUUGGU |
| 2718 | 510 | UAAGCAUGAACACACCAUAUU |
| 2719 | 511 | AUGAAUAUGGUAUUUGCGGGU |
| 2720 | 512 | UUAUUGUAAAGCAAUAUUAUA |
| 2721 | 513 | UGUUUCUUUGGAAUCUAGAA |
| 2722 | 514 | UACUCUCAGAAGAUUCAGGAA |
| 2723 | 515 | UCCUGAACACACAUAUUCCUC |
| 2724 | 516 | AUGGAUUCAACCACAGAACGA |
| 2725 | 517 | UGCAAGAGGGACUACUCUCUA |
| 2726 | 518 | UUCCUAACUCAGGACAUUUUG |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2727 | 519 | UAUAACAUAGUAUGCUUCAAA |
| 2728 | 520 | AAUUUCAGUCCUCUUGUUCAG |
| 2729 | 521 | UUAGUAAUAAAGCUCAUAUUA |
| 2730 | 522 | UCACUCUUUAUAUCUCUAUGG |
| 2731 | 523 | UUUCUCUAUGUUGGUCAGGCU |
| 2732 | 524 | UAUUAAGGAGAUUAACAACCU |
| 2733 | 525 | UCGCUGUUGAUUUCCUCUUGG |
| 2734 | 526 | UAUGUUGGAAGUUUGGAGUAA |
| 2735 | 527 | UACCUGAAUGAUAUACAGUAA |
| 2736 | 528 | UACACUCAAGACACAGUCAUG |
| 2737 | 529 | UCUCUGCCUACAGUGAUCUGA |
| 2738 | 530 | UUGGGUUAUAUUCAUUUGGUC |
| 2739 | 531 | UAGGUAUAGGGUCUGCUUUUA |
| 2740 | 532 | UUCAAAUUAAUAUUACCGUUU |
| 2741 | 533 | UAUAUAGUUUGCUGAAACUCU |
| 2742 | 534 | UAGUCUCCUAAGAAAGCGUGU |
| 2743 | 535 | AAUCGUAUGCUCAAAGUCUGA |
| 2744 | 536 | AUCAGAAAUGCUAUCUUUGGU |
| 2745 | 537 | UAGAAGCUGUUCUCAUUUGAA |
| 2746 | 538 | UUUAGUAAUAAAGCUCAUAUU |
| 2747 | 539 | AAACACGUACACUAUAUAGUU |
| 2748 | 540 | AAUGCUUCUUAGCUUCUCUAA |
| 2749 | 541 | UAUUGAAAUUAGUGGGACUUG |
| 2750 | 542 | AUUGGAUAGACUCACCUGUG |
| 2751 | 543 | UAUCUAAAUAAUUAACAAUAU |
| 2752 | 544 | UUUCCUAGGUUCAGAACCUGA |
| 2753 | 545 | AUAAUGAAUAUGGUAUUUGCG |
| 2754 | 546 | UAAGAAGUUUCUAUUCAUUUG |
| 2755 | 547 | UAAAGCAAUAUUAUAACAAUA |
| 2756 | 548 | AACAGGAAGCAAUUUCGUGUU |
| 2757 | 549 | UUCACUCUUGUUGCCGAGGCU |
| 2758 | 550 | UUAAUGAUUUCAAAGUCAGCU |
| 2759 | 551 | UAAGCAGCAUAUCUGAGGUGA |
| 2760 | 552 | UAUGGGAUAGCAUUUGCCUGA |
| 2761 | 553 | UCUCAGAGAAAGUCCCAUCUU |
| 2762 | 554 | UUGCAGAUUCAGUUAGACAUU |
| 2763 | 555 | UAGCAAUGGAAUGUGCUUCAC |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2764 | 556 | UCCAUUAUUUCCAAGUUCCCA |
| 2765 | 557 | UUCACAGGAAAGGAGAAGCUC |
| 2766 | 558 | UGACUGUUUCUUUGGAAUCAU |
| 2767 | 559 | UAUGUUUCAUAAGCACAAGAG |
| 2768 | 560 | AGUAGCUUAGAUAAAGACCAA |
| 2769 | 561 | UGUGCUUCUCACCCUUCCCUG |
| 2770 | 562 | UUUAUCUUGCAAGUUCAACCC |
| 2771 | 563 | AAAUAAUUAACAAUAUUAGGG |
| 2772 | 564 | UCCACAUCCAUCUCAAGACAG |
| 2773 | 565 | ACACAGUCAUGCACAAUCCAU |
| 2774 | 566 | AUUAAUUUGUCAACAUUUCUC |
| 2775 | 567 | UCUGAAGGGUCACUGCUCCAA |
| 2776 | 568 | AACAGCUUGUGGGUUCUUCUU |
| 2777 | 569 | UAGGAAAUACACCAGUGGGGU |
| 2778 | 570 | AUAUUAUAGAAUCUCUCAGAA |
| 2779 | 571 | UGAGAAACAGCUUCUUUCUAA |
| 2780 | 572 | UGGGAUUACAGGUAUGAGCCA |
| 2781 | 573 | UUAGGUUCACUCUUAGCAGUC |
| 2782 | 574 | UGCUGUAUAAACAGUACCUGA |
| 2783 | 575 | UAGAUGGAUGGAUGUACCUUG |
| 2784 | 576 | UCUUCUUCUGUAUUCCAAUUUUG |
| 2785 | 577 | UGGUCUCGAACUCCUGACCUC |
| 2786 | 578 | UAAUCCAAAGUUACAGAAGAA |
| 2787 | 579 | AUAUUAACUGCAAGUAGCUUA |
| 2788 | 580 | AAGGAUUUCAGUAUUCUACAU |
| 2789 | 581 | UUGAGCUGAGAAAUAUCAUUU |
| 2790 | 582 | UGGAGCUGUGGUUGAGUGCUG |
| 2791 | 583 | UUCCUAACCAGGUAUUGGGCU |
| 2792 | 584 | AUCAUCAAUAAUGAAUAUGGU |
| 2793 | 585 | AGAACAUCUAGAACAGCUUGU |
| 2794 | 586 | UACCUCAUUAUUAAAGUUCUC |
| 2795 | 587 | UCAUUUAUAGACAAAUAUCUC |
| 2796 | 588 | AAUAAACUGUUAACAAUCUGG |
| 2797 | 589 | UACUGCUGGUGAAGCAAUGGA |
| 2798 | 590 | UCUCCUAUGAGGAUUUCCUAG |
| 2799 | 591 | UAACUCUCCAAUACAGGGAAG |
| 2800 | 592 | ACAAUUCUGAUAAACAAUGAA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2801 | 593 | UAUUAGAAAUAUACAUAACUC |
| 2802 | 594 | AUAGAUGUAAGGAUCAGGUGG |
| 2803 | 595 | UGUAUUUCUGGUUGUUGACUG |
| 2804 | 596 | AUGGUGACUGAUUUGAGGGGA |
| 2805 | 597 | AAUGAAUAUGGUAUUUGCGGG |
| 2806 | 598 | ACUCUUUAUAUCUCUAUGGAU |
| 2807 | 599 | UUCCAGCAGUGUACUCAUCAU |
| 2808 | 600 | UUGUAUCAUAAGUAAAUGAUG |
| 2809 | 601 | UAAUCUCUACUGUGCUUCUCA |
| 2810 | 602 | AUGUUCACACAGUACUUGCUC |
| 2811 | 603 | UUUGAGUGCAGGAAAUCCAAA |
| 2812 | 604 | AAUGGAAUGUGCUUCACCGGG |
| 2813 | 605 | UCUCUCAGGAUUCUGGAGCUC |
| 2814 | 606 | AAACUCUAAAGAAAGUGCUUU |
| 2815 | 607 | UCUUGGGUACUAAAUCUGUUG |
| 2816 | 608 | AAUUAAACUCUAGAAAGCCCA |
| 2817 | 609 | AUAUUUACAAUGACACACACA |
| 2818 | 610 | UUCUUCCUCUUCAUCUUCUUC |
| 2819 | 611 | UAUCUCCGAUGUAAAGCUCA |
| 2820 | 612 | UUUGCUGAAACUCUAAAGAAA |
| 2821 | 613 | UUGGUGCGAUAACUGGUGGUG |
| 2822 | 614 | UAAUUAUUUACACGAUCUUUG |
| 2823 | 615 | UAUUUCCUCCUGGUAUGCCUA |
| 2824 | 616 | ACAAAUAAAUUACAUAAUCUG |
| 2825 | 617 | AUUUACAUGAAUACAAAUUUA |
| 2826 | 618 | UACACAGACACUCCGCAGAUA |
| 2827 | 619 | UGGGUUCUUCUUCUGUUCCAA |
| 2828 | 620 | UGGAUCCUUGCUAACAACAUU |
| 2829 | 621 | UCUCUGCAACUUGUAAGUGUU |
| 2830 | 622 | UACAUGAAUACAAAUUUAUAA |
| 2831 | 623 | UCAAGUUACUCGAUUGUACCA |
| 2832 | 624 | UCUGUGACCACAUCAGUCAGA |
| 2833 | 625 | AUAACUCUCCAAUACAGGGAA |
| 2834 | 626 | UUCACUACACAUGGUUUACAG |
| 2835 | 627 | UAACUGCAACAUAAGAGACUC |
| 2836 | 628 | AACUGAUUUCAAUUAUCUGUG |
| 2837 | 629 | UGCUGUUCUUAAUUGCUUCCU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2838 | 630 | UCUCAAUGCUAAUAGCAUGUA |
| 2839 | 631 | AUUUACAAUGACACACACACG |
| 2840 | 632 | AUACAGUAAUAUCCUGUUGGA |
| 2841 | 633 | AUGAGGAUUUCCUAGGUUCAG |
| 2842 | 634 | AACUUCUAUUGAAAUUAGUGG |
| 2843 | 635 | UGCAUCUUUGAGAAACCUUUU |
| 2844 | 636 | UCAGAAAUGCUAUCUUUGGUU |
| 2845 | 637 | AUCUGCAACAGAUGUUAUCAA |
| 2846 | 638 | AUUGCAACUCUAUUAGGGCAU |
| 2847 | 639 | UGUAAAGCUCAUGUAUUUCUG |
| 2848 | 640 | AGAUUUGGAUAGACUCACCUG |
| 2849 | 641 | UUCCACCAUUUCAAUUGCCAU |
| 2850 | 642 | UUACUCGAUUGUACCAAAUGU |
| 2851 | 643 | UUUGCUCAGGAGUGAUCUGGG |
| 2852 | 644 | UAACAUAGUAUGCUUCAAAUU |
| 2853 | 645 | UCAAAUCUUGGUACAAAGUGG |
| 2854 | 646 | AAUCUUGGUACAAAGUGGUAG |
| 2855 | 647 | UUCCUUCUUGGGUUGCUGUUG |
| 2856 | 648 | GAGAACAUCUAGAACAGCUUG |
| 2857 | 649 | AUUAUUAAAGUUCUCACCUAA |
| 2858 | 650 | AAGGCUUGCAGUCUUAGCGGC |
| 2859 | 651 | UGCAUUAGUAGCUACAGGAUU |
| 2860 | 652 | AGAAUUUCACUACACAUGGUU |
| 2861 | 653 | UUGUAAUCCCUGUUUAUGUUA |
| 2862 | 654 | UGGUUGUUGACUGUUUCUUUG |
| 2863 | 655 | UUAGAUGGUCUCCCUUGCUCU |
| 2864 | 656 | UCUGGAGCUCUGGAGUUCCAU |
| 2865 | 657 | ACUCACAAUGCUUCUUAGCUU |
| 2866 | 658 | AUAACUUCUAUUGAAAUUAGU |
| 2867 | 659 | UCAACAUUGAAAGAUGUGCCC |
| 2868 | 660 | UCAUCACCCACCAAGUAGCUA |
| 2869 | 661 | AAGUCAGUCAAUUUAACAGAG |
| 2870 | 662 | UAGGGCAUGGACUUCCACAUG |
| 2871 | 663 | AUCUCAGCUCACCACAACCUC |
| 2872 | 664 | AUGUUAUGAGUAUAAUCCCAG |
| 2873 | 665 | UUUCAUUGAAUUUCCCGGCAC |
| 2874 | 666 | UAUUCCAUUAUUUCCAAGUUC |
| 2875 | 667 | AAGAAUAUUGUCACUCUUUAU |
| 2876 | 668 | AGAAAUAUACAUAACUCUCCA |
| 2877 | 669 | UUACAGAAGAAUUUCACUACA |
| 2878 | 670 | UAUAAUCCCAGUAGACAUCAC |
| 2879 | 671 | UUUGUCAACAUUUCUCAAUGC |
| 2880 | 672 | UGGUCUUGGUGCGAUAACUGG |
| 2881 | 673 | AAGUAAAUGAUGAUUAAUGUA |
| 2882 | 674 | UACUUAUUAGAAAUAUACAUA |
| 2883 | 675 | AUAUCUCUAUGGAUCACCUGG |
| 2884 | 676 | UUGACUGUUUCUUUGGAAUCA |
| 2885 | 677 | UCUGUAUUGAGAAUGACCAAU |
| 2886 | 678 | UUCAACCUGAGAGUCUGUUAA |
| 2887 | 679 | UUGUUUAAUGAUUUCAAAGUC |
| 2888 | 680 | AUUCCGAAACAGAAAUAGGUG |
| 2889 | 681 | ACUAAAUCUGUUGAACAUGUU |
| 2890 | 682 | UAAUCAGAGGAGUCAGGCUGG |
| 2891 | 683 | AAGUAUAACAUAGUAUGCUUC |
| 2892 | 684 | UACACGAUCUUUGAGCUGAGA |
| 2893 | 685 | AAAUGCUGAAUUUCAGUCCUC |
| 2894 | 686 | CUAAGCAGCAUAUCUGAGGUG |
| 2895 | 687 | UUCUAUUCAUUUGAAAGGUAA |
| 2896 | 688 | UUUGCAGAUUCAGUUAGACAU |
| 2897 | 689 | UAGCUUUAACUUUAUAGAUAAU |
| 2898 | 690 | UAAUCCCAGUAGACAUCACUA |
| 2899 | 691 | UAUAUUCAUUUGGUCACUUAA |
| 2900 | 692 | UAGUAAUAAAGCUCAUAUUAG |
| 2901 | 693 | UUCUCUAGGUAUAGGGUCUGC |
| 2902 | 694 | UCAAUGCAUUAGUAGCUACAG |
| 2903 | 695 | GUGCUGUAUAAACAGUACCUG |
| 2904 | 696 | AAUAUGCUGAACUGAAAGCAU |
| 2905 | 697 | UAAUAAAUAGAUAUAUGGUGA |
| 2906 | 698 | AUUAAACUCUAGAAAGCCCAG |
| 2907 | 699 | AUCUGACUCAUUCUCUACUAU |
| 2908 | 700 | AGACAGCUGCUAUCUGUCCUU |
| 2909 | 701 | AAUUCUGUCGGACUGACAUUU |
| 2910 | 702 | UAUUUGUUUAAUGAUUUCAAA |
| 2911 | 703 | UGUCAACAUUUCUCAAUGCUA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2912 | 704 | UAGUUUGCUGAAACUCUAAAG |
| 2913 | 705 | UGUUUCAUAAGCACAAGAGAG |
| 2914 | 706 | AUGUGACAGGAUUUCACCGUU |
| 2915 | 707 | AUACUGCAAAUUAAGAAGCCU |
| 2916 | 708 | UAAUUGCAAGUCAUAACUUCU |
| 2917 | 709 | UUAUCCAGACCGUCAGACAUU |
| 2918 | 710 | UUUAUUGGUACUGCUGGUGA |
| 2919 | 711 | AAUUGCUUCCUUUGCAGCGAU |
| 2920 | 712 | UAAGUGACUUGCCUAGCGUCA |
| 2921 | 713 | AUCAAAUCUUGGUACAAAGUG |
| 2922 | 714 | UCAUGGGAUUAUGACAACGCA |
| 2923 | 715 | UACAGUUAUAUUCUAGCAAGU |
| 2924 | 716 | ACAAGUUGUAUAGAAUACUCG |
| 2925 | 717 | AGAAUUUGAGAACAUCUAGAA |
| 2926 | 718 | UUCAGUUAGACAUUGUUUAAU |
| 2927 | 719 | UAAAUGAUGAUUAAUGUAUCU |
| 2928 | 720 | AAUGAUAUACAGUAAUAUCCU |
| 2929 | 721 | AAGUCAUUACCCAACAUGGUG |
| 2930 | 722 | UCUUCUUCUUCUUCCUCUUCA |
| 2931 | 723 | UAUUAACUGCAAGUAGCUUAG |
| 2932 | 724 | UGGUAGUAAAGAAGUACCUGG |
| 2933 | 725 | UAAGUUCUGUUUAGAUUCUUU |
| 2934 | 726 | UAUAAGAAGUUUCUAUUCAUU |
| 2935 | 727 | ACAACAUUAACGUUCUUUCCU |
| 2936 | 728 | UUCAAGACAUUUAUGAAUAUG |
| 2937 | 729 | ACAACUGUAAAUGAAUUGGAA |
| 2938 | 730 | AUUGUUUAAUAUUAAACACAU |
| 2939 | 731 | UAAAUCUGUUGAACAUGUUGC |
| 2940 | 732 | AACAUUGCUGCCCUGUUUGGG |
| 2941 | 733 | UUUCUUUGGAAUCAUAGAAUU |
| 2942 | 734 | UGAGUUCACUUCAAAUCCCAG |
| 2943 | 735 | UAAACGUUAUAAAUUGUCAAA |
| 2944 | 736 | UAGGGCUUCCUAACCAGGUAU |
| 2945 | 737 | UGUAAAGCAAUAUUAUAACAA |
| 2946 | 738 | UUAAAUGUGGUUUCUCCUAUG |
| 2947 | 739 | UCUUGGUGCGAUAACUGGUGG |
| 2948 | 740 | UCAGAACCUGAACUCACCUAG |
| 2949 | 741 | UUUCUUGGGAUAUGAUUGUAA |
| 2950 | 742 | UUAAUAUUACCGUUUCAUUUU |
| 2951 | 743 | UGAGCUGAGAAAUAUCAUUUA |
| 2952 | 744 | UUGUGGGUUCUUCUUCUGUUC |
| 2953 | 745 | UUGAGCUUUAUUUAGAUAUAC |
| 2954 | 746 | AGACCAGAUAUCAACUUUCGG |
| 2955 | 747 | GAAAUAUACAUAACUCUCCAA |
| 2956 | 748 | AAGAUUUGGAUAGACUCACCU |
| 2957 | 749 | UCUACUAUCGCUGUUGAUUUC |
| 2958 | 750 | AUGGUUUACAGAUAACACAUU |
| 2959 | 751 | UAUCAUAAGUAAAUGAUGAUU |
| 2960 | 752 | AUAAAGCACACCACACACAAG |
| 2961 | 753 | UCAGCUCACCACAACCUCCGC |
| 2962 | 754 | AAUAGUCUCCUAAGAAAGCGU |
| 2963 | 755 | UACAGAGUUGAAUGUUUACUA |
| 2964 | 756 | UUCCUAGGUUCAGAACCUGAA |
| 2965 | 757 | UUUGGUCACUUAAAGGAGUGU |
| 2966 | 758 | AAAGGCUUAGAGAAACAACUU |
| 2967 | 759 | AAAUUAGGGGACUUGCCCUA |
| 2968 | 760 | AAAUUACAUAAUCUGAGGGAG |
| 2969 | 761 | AUUGCUUCAACCACAAUUUAA |
| 2970 | 762 | UACAAGUUGUAUAGAAUACUC |
| 2971 | 763 | UAAUUAACAAUAUUAGGGUUC |
| 2972 | 764 | AACAUAAACACGUACACUAUA |
| 2973 | 765 | AACUUUCGGACCAUAAGCUUU |
| 2974 | 766 | UUAUGAGUAUAAUCCCAGUAG |
| 2975 | 767 | UCUCAGAAGAUUCAGGAAGUG |
| 2976 | 768 | UGAUUAAUGUAUCUAUUUCCU |
| 2977 | 769 | AAUCAUAGAAUUUGAGAACAU |
| 2978 | 770 | ACAGCUGACAGUCUCUCAGGA |
| 2979 | 771 | UCAUCCUCAGUGGAGGAGCCG |
| 2980 | 772 | ACUAGCAACAUCAAAGAUUUG |
| 2981 | 773 | UAGCAACAUCAAAGAUUUGGA |
| 2982 | 774 | CAGUAUUCUACAUUUAUCUGG |
| 2983 | 775 | AACACACAUAUUCCUCUCCAC |
| 2984 | 776 | UUAAACUCUAGAAAGCCCAGC |
| 2985 | 777 | AACACAACUGAUUUCAAUUAU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 2986 | 778 | UAGAAAUAAACCCAUUGAGCA |
| 2987 | 779 | UACAGAUAACACAUUCUGACA |
| 2988 | 780 | UUGGAGCUGUGGUUGAGUGCU |
| 2989 | 781 | AACGAGUAUAGAUUGAUUUUG |
| 2990 | 782 | UGAUCUGGGCACAGAACCCAA |
| 2991 | 783 | AUGGAGACCAUCCCAAGCCAA |
| 2992 | 784 | AGUUAGAAGGAAGUUAUCCUU |
| 2993 | 785 | CUUAUAGAUAAUAGUCUCCUA |
| 2994 | 786 | UACCUUUGCUUAACUGAAUAU |
| 2995 | 787 | UUCUCUAAGAUCUCCUCAUCU |
| 2996 | 788 | UCAAGCACAGUCAUGCACAA |
| 2997 | 789 | AUGACACACACGAGAUCAG |
| 2998 | 790 | UGGAAUUCCAGUGAAUUCCCC |
| 2999 | 791 | UCUCUCUCUCAUUAGAGCAGU |
| 3000 | 792 | UGAAUCCUUCAGCAUCACUGU |
| 3001 | 793 | AUUAACUGCAAGUAGCUUAGA |
| 3002 | 794 | UUCCAAGAGACCAGAUAUCAA |
| 3003 | 795 | AUAAUUGUAACUAGCAAAUAU |
| 3004 | 796 | UUCAGAGCUCAGAGACUGGGA |
| 3005 | 797 | UUAUCCCACUACAUCUGACUC |
| 3006 | 798 | AAUAAAUAGAUAUAUGGUGAA |
| 3007 | 799 | UCUCAGUUCCCGCAUUUGCAG |
| 3008 | 800 | UUACAAAUGCUGAAUUUCAGU |
| 3009 | 801 | UGUAAAUGAAUUGGAAGGCUG |
| 3010 | 802 | UAGGUUCACUCUUAGCAGUCU |
| 3011 | 803 | UUACCCUCUUUCCAGCAGUGU |
| 3012 | 804 | UGUUGAAGGUUCAUCUGCUUU |
| 3013 | 805 | UUUCAGUCCUCUUGUUCAGAG |
| 3014 | 806 | UCUUUGGAAUCAUAGAAUUUG |
| 3015 | 807 | UAACUCCCAGUUUACCCUCUU |
| 3016 | 808 | UCUCCUUCUUCUUAUUGGUUU |
| 3017 | 809 | UAGGCUAGUAUUUAUCCCACU |
| 3018 | 810 | UUAUCUCAGGGCACACUAGCA |
| 3019 | 811 | AAAUACUUGAGUUAAAUCUUC |
| 3020 | 812 | AGUUAUAUUCUAGCAAGUGUG |
| 3021 | 813 | UAAACCCAUUGAGCAAAGGAA |
| 3022 | 814 | UACUAUCGCUGUUGAUUUCCU |
| 3023 | 815 | AAUACAGCUGACAGUCUCUCA |
| 3024 | 816 | UCUUUCUCCUUCUUCUUAUUG |
| 3025 | 817 | UCAACUUUCGGACCAUAAGCU |
| 3026 | 818 | UUGAGCAAAGGAAUAUAAUUA |
| 3027 | 819 | UUGAAAGAUGUGCCCUCGUUA |
| 3028 | 820 | AUUUCUCUCUGCAACUUGUAA |
| 3029 | 821 | UGAAAGAAAUCUGAAUAACAU |
| 3030 | 822 | UCUUUCUAAUACUUAUUAGAA |
| 3031 | 823 | AACUGCAACAUAAGAGACUCA |
| 3032 | 824 | UUAAUUUAGGUAUCAUUAUCU |
| 3033 | 825 | AGAAAUAUCAUUUAUAGACAA |
| 3034 | 826 | CAUAUAAGGAAUUCUGUCGGA |
| 3035 | 827 | AAGUGUUUAGGUUCACUCUUA |
| 3036 | 828 | UGAUCUGAAGGGUCACUGCUC |
| 3037 | 829 | UGACCUCUUUAUUGGUACUG |
| 3038 | 830 | UACUCGAAGGAUGGGCUGCUA |
| 3039 | 831 | AUUAACAACCUGGUUUACUCA |
| 3040 | 832 | UGAGUUAAAUCUUCUUACAUG |
| 3041 | 833 | AUUCCUUCUUGGGUUGCUGUU |
| 3042 | 834 | AAUGCAUUAGUAGCUACAGGA |
| 3043 | 835 | ACUAGCAAAUAUCUCUGCCCU |
| 3044 | 836 | UGUGACAGGAUUUCACCGUUU |
| 3045 | 837 | AACACAUUCCCAAUGCAUGUU |
| 3046 | 838 | AAUAAUUUGUAUCAUAAGUAA |
| 3047 | 839 | AUUAUUAUGAACUUCAUUUGC |
| 3048 | 840 | UAUGCUGAACUGAAAGCAUAA |
| 3049 | 841 | AUAAACACGUACACUAUAUAG |
| 3050 | 842 | UUACUGCUGGUAUUAUGGGAU |
| 3051 | 843 | AUCUAGUCCAAUACACUUAUU |
| 3052 | 844 | UCUUAGCUUCUCUAAGAUCUC |
| 3053 | 845 | UGCUGAAUUUCAGUCCUCUUG |
| 3054 | 846 | ACUAUCGCUGUUGAUUUCCUC |
| 3055 | 847 | ACACAUAUUCCUCUCCACUUU |
| 3056 | 848 | UUCUUUCUAAUACUUAUUAGA |
| 3057 | 849 | UGGAAUGUGCUUCACCGGGGA |
| 3058 | 850 | UCAUUGAUGUUUGUCAUUUUU |
| 3059 | 851 | AAAUGAUGAUUAAUGUAUCUA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3060 | 852 | AAUUUGUCAACAUUUCUCAAU |
| 3061 | 853 | UUCAGUAUUCUACAUUUAUCU |
| 3062 | 854 | UCUAGUCCAAUACACUUAUUU |
| 3063 | 855 | ACAACUUUCUGUAAUUUACAA |
| 3064 | 856 | UUCUGGUUGUUGACUGUUUCU |
| 3065 | 857 | UUCUGUGAAGAUCUUAUCAUC |
| 3066 | 858 | UUAAUUCCUUCUUGGGUUGCU |
| 3067 | 859 | AUCUCUGCCCUGCAUGCUCUG |
| 3068 | 860 | UGUGGUUUCUCCUAUGAGGAU |
| 3069 | 861 | AUGUAACUGAUCUCUUUCCCC |
| 3070 | 862 | UACAGAAGAAUUUCACUACAC |
| 3071 | 863 | UUAAGAAGCCUUCUAUAACAC |
| 3072 | 864 | AAAUGCUAUCUUUGGUUCCCA |
| 3073 | 865 | UAAGAAGCCUUCUAUAACACA |
| 3074 | 866 | UUUGGAGUAAUCGUGCCCAUU |
| 3075 | 867 | AUUAAGGCCUCUCUCUCUCAU |
| 3076 | 868 | AUUUGAAAGGUAAAGAACCCC |
| 3077 | 869 | UUUGUUUAAAUGUGGUUUCUC |
| 3078 | 870 | UAUCAGAUACAAUGCCCUGAG |
| 3079 | 871 | UUUGGUACUGCUGGUGAAGCA |
| 3080 | 872 | AACACAACACUAUGAAGAGGG |
| 3081 | 873 | UUUCAAGACAUUUAUGAAUAU |
| 3082 | 874 | UGGAUCCUUCUCAACUUGUUU |
| 3083 | 875 | UAUAACAGUACCUGAUGCCC |
| 3084 | 876 | UAGCAGGAUGUCACAGUUUCA |
| 3085 | 877 | AAAUCUGUUGAACAUGUUGCC |
| 3086 | 878 | UUCAACCACAGAACGAGUAUA |
| 3087 | 879 | AUGUACAUAAGUUCUGUUUAG |
| 3088 | 880 | UCUGAAGGAAGAGAGAUCUCU |
| 3089 | 881 | UGUCAUCAGAAAUGCUAUCUU |
| 3090 | 882 | AUCGUAUGCUCAAAGUCUGAA |
| 3091 | 883 | UUCUUCUUCUUCCUCUUCAUC |
| 3092 | 884 | UCUCUCUCAUUAGAGCAGUGU |
| 3093 | 885 | CACACAAGCACACACAUUGAA |
| 3094 | 886 | AUGGGAAGUGGUUUGGAGCUG |
| 3095 | 887 | UAUAGAUAAUAGUCUCCUAAG |
| 3096 | 888 | GAAUAAACUGUUAACAAUCUG |
| 3097 | 889 | UGCAUGUUGGGUUAUAUUCAU |
| 3098 | 890 | UCUAAGAUCUCCUCAUCUGUC |
| 3099 | 891 | UGGAAGUGACCACUUUAUGGU |
| 3100 | 892 | UCUCUAGGUAUAGGGUCUGCU |
| 3101 | 893 | UCUGCAACUUGUAAGUGUUUA |
| 3102 | 894 | UAUUGUAAAGCAAUAUUAUAA |
| 3103 | 895 | AUAUGCUGAACUGAAAGCAUA |
| 3104 | 896 | AAAUCUGAAUAACAUAAAGAA |
| 3105 | 897 | UUCAUCACCCACCAAGUAGCU |
| 3106 | 898 | AGUAGCUACAGGAUUCUGUGA |
| 3107 | 899 | ACAGUUAUACAGACAACAGGA |
| 3108 | 900 | AGAGGUUAAGUGACUUGCCUA |
| 3109 | 901 | UAGACAUUGUUUAAUAUUAAA |
| 3110 | 902 | UGAACACACAUAUUCCUCUCC |
| 3111 | 903 | UUCACUUCAAAUCCCAGGCCC |
| 3112 | 904 | UAUUCCAUGACUACCCAUAGU |
| 3113 | 905 | UGGGAGAUACUUGCACUACUG |
| 3114 | 906 | AACAAGGAUUUCAGUAUUCUA |
| 3115 | 907 | ACAGGUGUGCACAUGGAGGUG |
| 3116 | 908 | UCCAAUCUAAAGCAACCACAA |
| 3117 | 909 | AAUUCCACCACCCUAACACAA |
| 3118 | 910 | UCUUGGGUUGCUGUUGAAGGU |
| 3119 | 911 | AAAGUCUGAAGGAAGAGAGAU |
| 3120 | 912 | UAUUUACAAUGACACACACAC |
| 3121 | 913 | GUAUUCUACAUUUAUCUGGUU |
| 3122 | 914 | UGUUACUAUUCAUCCUCAGUG |
| 3123 | 915 | AAUACCUUUAAUCCAAAGUUA |
| 3124 | 916 | UAAAGAAAGUGCUUUCAUUUU |
| 3125 | 917 | AGAUAUCAACUUUCGGACCAU |
| 3126 | 918 | AACAAAUUAAUUUGUCAACAU |
| 3127 | 919 | UGGUUUGGAGCUGUGGUUGAG |
| 3128 | 920 | ACACAUUGAACUUGAAUUUUG |
| 3129 | 921 | UCAAAGAUUUGGAUAGACUCA |
| 3130 | 922 | UGGAAUCUAGAAUUUGAGAA |
| 3131 | 923 | AGCACACAUUGAACUUGAA |
| 3132 | 924 | UUGCAGCGAUAAUCAGAGGAG |
| 3133 | 925 | AUAAUUUGUAUCAUAAGUAAA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3134 | 926 | AGAGGGACUACUCUCUAACUU |
| 3135 | 927 | CUAGCAAAUAUCUCUGCCCUG |
| 3136 | 928 | AAUUUCACUACACAUGGUUUA |
| 3137 | 929 | UUCUAGCAAGUGUGACAGUGU |
| 3138 | 930 | UUUACUUAAUGUCCAACAAGG |
| 3139 | 931 | AAUCAGAGGAGUCAGGCUGGA |
| 3140 | 932 | AAGCACACACAUUGAACUUGA |
| 3141 | 933 | UUGGGAUAUGAUUGUAAGUUA |
| 3142 | 934 | UCACUUCAACAUUGCUGCCCU |
| 3143 | 935 | GAACAUCUAGAACAGCUUGUG |
| 3144 | 936 | UAGUGAAACUAAGCAGCAUAU |
| 3145 | 937 | AAGUACAGUUAUAUUCUAGCA |
| 3146 | 938 | UGAAUUUCCCGGCACUAUGAG |
| 3147 | 939 | AAGUUUGGAGUAAUCGUGCCC |
| 3148 | 940 | UAUGAGUAUAAUCCCAGUAGA |
| 3149 | 941 | AACAUGGACACACAAAUAUUU |
| 3150 | 942 | UUCUUCCUAGGCUAGUAUUUA |
| 3151 | 943 | AAGCCCUUCCUGAACACACAU |
| 3152 | 944 | ACAUUUAUGAAUAUGCUUUUG |
| 3153 | 945 | ACUGUCAGUUUACAAAUGCUG |
| 3154 | 946 | UAUUAUGGGAUAGCAUUUGCC |
| 3155 | 947 | AUUUAUUUCCUUCCCAGUCCA |
| 3156 | 948 | ACACACACACGAGAUCAGCAA |
| 3157 | 949 | UGUCCAACAAGGAUUUCAGUA |
| 3158 | 950 | UGUAUUGAGAAUGACCAAUAA |
| 3159 | 951 | UUUCUGGUUGUUGACUGUUUC |
| 3160 | 952 | ACACAGUCACUAAUGUACUGA |
| 3161 | 953 | UUCCCGCAUUUGCAGAUUCAG |
| 3162 | 954 | UUCUUACAGAGUUGAAUGUUU |
| 3163 | 955 | AAUGCUACAAGUUGUAUAGAA |
| 3164 | 956 | AAUCCUUCAGCAUCACUGUGG |
| 3165 | 957 | AGUUUCACUCUUGUUGCCGAG |
| 3166 | 958 | UCAUCUUCUUCUUCAGACACA |
| 3167 | 959 | UUGCAAUACUUUAGGUCCAAG |
| 3168 | 960 | UAUGUUGGUCAGGCUGGUCUC |
| 3169 | 961 | UUUACCCUCUUUCCAGCAGUG |
| 3170 | 962 | UCUACACAGACACUCCGCAGA |
| 3171 | 963 | ACAGCUUCUUUCUAAUACUUA |
| 3172 | 964 | CAACUUUCGGACCAUAAGCUU |
| 3173 | 965 | AAAGCCUAUGGAAUAAUUGUA |
| 3174 | 966 | AUGAUUUCAAAGUCAGCUUUU |
| 3175 | 967 | UUCCUUCCCAGUCCACAUGCA |
| 3176 | 968 | AUGUUGGUCAGGCUGGUCUCG |
| 3177 | 969 | UAUCUGUCCUUCAUCCAUACA |
| 3178 | 970 | UUGCAACUCUAUUAGGGCAUG |
| 3179 | 971 | AUGCUAACUAAUGAAUAGGGC |
| 3180 | 972 | UGUUCUUAAUUGCUUCCUUUG |
| 3181 | 973 | AUCUGAAGGGUCACUGCUCCA |
| 3182 | 974 | UACUAAAUCUGUUGAACAUGU |
| 3183 | 975 | ACUUAUAGAUAAUAGUCUCCU |
| 3184 | 976 | AUCUUCUUCUUCAGACACAGG |
| 3185 | 977 | AACUACUGCAAACAACCUAUA |
| 3186 | 978 | UCUCUAUGGAUCACCUGGUUU |
| 3187 | 979 | AUUGUACCAAAUGUGAAUCCU |
| 3188 | 980 | UUCUCAAUGCUAAUAGCAUGU |
| 3189 | 981 | AUUUCUUACAGAGUUGAAUGU |
| 3190 | 982 | UAUAUCACCUUUCUCUAGAUC |
| 3191 | 983 | AAUUAAUUUGUCAACAUUUCU |
| 3192 | 984 | UGUUUACUUAAUGUCCAACAA |
| 3193 | 985 | UCAGUUACAACUAAUUUCACA |
| 3194 | 986 | UCUAAUACUUAUUAGAAAUAU |
| 3195 | 987 | ACGUACACUAUAUAGUUUGCU |
| 3196 | 988 | UGCAACAGAUGUUAUCAAGGG |
| 3197 | 989 | UUCUGGAGCUCUGGAGUUCCA |
| 3198 | 990 | UUACAUGAAUACAAAUUUAUA |
| 3199 | 991 | UUAUGGUCACUUCAACAUUGC |
| 3200 | 992 | AAGUCAUAUAAGGAAUUCUGU |
| 3201 | 993 | UAACUGCAAGUAGCUUAGAUA |
| 3202 | 994 | ACAGUUAUAUUCUAGCAAGUG |
| 3203 | 995 | AAGUGGUUUGGAGCUGUGGUU |
| 3204 | 996 | UCUGAGGUGACUACCUCAUUA |
| 3205 | 997 | AACACUCACAAUGCUUCUUAG |
| 3206 | 998 | UAUAACAAUAUCAAUAAAAU |
| 3207 | 999 | ACACACAUUGAACUUGAAUUU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3208 | 1000 | AAUAGCAUGUAAUUACUUUUU |
| 3209 | 1001 | UUAUUAUCAAAUCUUGGUACA |
| 3210 | 1002 | AAAGAAUAAAUACUUGAGUUA |
| 3211 | 1003 | CUGAAUUUCAGUCCUCUUGUU |
| 3212 | 1004 | AUGAACUUCAUUUGCUUGAGU |
| 3213 | 1005 | ACAUCCAUCUCAAGACAGCGA |
| 3214 | 1006 | UAUUUGGUACUGCUGGUGAAG |
| 3215 | 1007 | AGGAUUUCAUUGAAUUUCCCG |
| 3216 | 1008 | UUAGAUAAAGACCAAGAGAUU |
| 3217 | 1009 | AAGAGACCAGAUAUCAACUUU |
| 3218 | 1010 | AUCAUCUUACAUAGUUCUUUU |
| 3219 | 1011 | AUAACACAAAUUGUUAGUUUU |
| 3220 | 1012 | CACUUCAACAUUGCUGCCCUG |
| 3221 | 1013 | AGACAGUCCUACAUAUUUGUU |
| 3222 | 1014 | UAGUGCUGUAUAAACAGUACC |
| 3223 | 1015 | UAUACUGCAAAUUAAGAAGCC |
| 3224 | 1016 | AUUUAGGUAUCAUUAUCUUUG |
| 3225 | 1017 | AAACAGAAAUAGGUGAUACAU |
| 3226 | 1018 | UCUUCUUCCUCUUCAUCUUCU |
| 3227 | 1019 | UCAUUUCUCUCUGCAACUUGU |
| 3228 | 1020 | AAUAAUUGUAACUAGCAAAUA |
| 3229 | 1021 | AACUUCAUUUGCUUGAGUUUU |
| 3230 | 1022 | UGUUCACACAGUACUUGCUCU |
| 3231 | 1023 | UAUCCAGACCGUCAGACAUUU |
| 3232 | 1024 | AAAGCUCAUGUAUUUCUGGUU |
| 3233 | 1025 | UCACGGAAUACAGCUGACAGU |
| 3234 | 1026 | UGGAACCAUACCAUCAGCAGG |
| 3235 | 1027 | UUGGAAUCAUAGAAUUGAGA |
| 3236 | 1028 | UAAACACGUACACUAUAUAGU |
| 3237 | 1029 | CACAACACUAUGAAGAGGGAG |
| 3238 | 1030 | CACACUAGCAACAUCAAAGAU |
| 3239 | 1031 | UCCAUCUUUCCUGCAGCAGAG |
| 3240 | 1032 | AUAUAAGGAAUUCUGUCGGAC |
| 3241 | 1033 | CAACAUUAACGUUCUUUCCUU |
| 3242 | 1034 | UGGUGUGACCUCUUUAUUUGG |
| 3243 | 1035 | AUAAAGAAUAAAUACUUGAGU |
| 3244 | 1036 | UAUACAUAACUCUCCAAUACA |
| 3245 | 1037 | UGUUGGGUUAUAUUCAUUUGG |
| 3246 | 1038 | UCCUAUGAGGAUUUCCUAGGU |
| 3247 | 1039 | UUCUAAAGGAGACUCCGAUGG |
| 3248 | 1040 | UCCUGAUGUAAAGCUCAUGUA |
| 3249 | 1041 | AUUUCAUUGAAUUUCCCGGCA |
| 3250 | 1042 | AAUCUCUACUGUGCUUCUCAC |
| 3251 | 1043 | AUCUGUCCUUCAUCCAUACAG |
| 3252 | 1044 | AUCUCCUGAUGUAAAGCUCAU |
| 3253 | 1045 | UCCAGCAGUGUACUCAUCAUA |
| 3254 | 1046 | UGCAUGGGCUCUGCUAUCUUG |
| 3255 | 1047 | AAUGCUAUCUUUGGUUCCCAA |
| 3256 | 1048 | AUGCUGAAUUUCAGUCCUCUU |
| 3257 | 1049 | UCUCCUGAUGUAAAGCUCAUG |
| 3258 | 1050 | UACCCAUAGUUCAUCACCCAC |
| 3259 | 1051 | UACAUAUUUGUUUAAUGAUUU |
| 3260 | 1052 | AUGGAAUGUGCUUCACCGGGG |
| 3261 | 1053 | UCUGCCUACAGUGAUCUGAAG |
| 3262 | 1054 | CAAGUCAUAACUUCUAUUGAA |
| 3263 | 1055 | CUUUCUUAUUCUUCUCUUCAG |
| 3264 | 1056 | ACACACAAGCACACACAUUGA |
| 3265 | 1057 | UGCAAAUUAAGAAGCCUUCUA |
| 3266 | 1058 | UCAUUAUCUUUGUUUACUUAA |
| 3267 | 1059 | AAUCUGAAUAACAUAAAGAAU |
| 3268 | 1060 | UAAAUGUGGUUUCUCCUAUGA |
| 3269 | 1061 | UCCUCUUUCAGGUAUUAAGGA |
| 3270 | 1062 | AACACUAUGAAGAGGGAGUGU |
| 3271 | 1063 | UAAUAUUACCGUUUCAUUUUC |
| 3272 | 1064 | UCAUCAGAAAUGCUAUCUUUG |
| 3273 | 1065 | UUAUUCCAAGUUCCCAUUUA |
| 3274 | 1066 | UAUCCUUCUAGUCCUCCAAAA |
| 3275 | 1067 | UUCCCAACAAAUUAAUUUGUC |
| 3276 | 1068 | AUCCUCGCCUAUCCACAUCCA |
| 3277 | 1069 | UUAUAUCUCUAUGGAUCACCU |
| 3278 | 1070 | CUUUGUUUACUUAAUGUCCAA |
| 3279 | 1071 | AUUGAAAGAUGUGCCCUCGUU |
| 3280 | 1072 | UAUUCCUAACUCAGGACAUUU |
| 3281 | 1073 | CUUCUCUAGGUAUAGGGUCUG |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3282 | 1074 | UCACCUUUCUCUAGAUCUUUA |
| 3283 | 1075 | AACUUAUAGAUAAUAGUCUCC |
| 3284 | 1076 | UGGACACACAAAUAUUUACAA |
| 3285 | 1077 | UUCUUCAGACACAGGAGGGGC |
| 3286 | 1078 | UCUCGAACUCCUGACCUCAGG |
| 3287 | 1079 | UUGCAAGUUCAACCCAAUUAA |
| 3288 | 1080 | UGUGAAGAUCUUAUCAUCAAU |
| 3289 | 1081 | UCAUUAUUAAAGUUCUCACCU |
| 3290 | 1082 | AUUAUGGGAUAGCAUUUGCCU |
| 3291 | 1083 | AAAUACACGUUCAGAAUUGUG |
| 3292 | 1084 | AGCUUGUGGGUUCUUCUUCUG |
| 3293 | 1085 | UAUUUACACGAUCUUUGAGCU |
| 3294 | 1086 | UGAAUUUCAGUCCUCUUGUUC |
| 3295 | 1087 | UCUCUGUGACCACAUCAGUCA |
| 3296 | 1088 | UAAAUGAAUUGGAAGGCUGCC |
| 3297 | 1089 | UCAGAUACAAUGCCCUGAGUG |
| 3298 | 1090 | CAAGCACACACAUUGAACUUG |
| 3299 | 1091 | UGCUGUUGAAGGUUCAUCUGC |
| 3300 | 1092 | UUCCCACCAUAGUGCUUCGUU |
| 3301 | 1093 | UGUUAUGUUGGAAGUUUGGAG |
| 3302 | 1094 | AUUAUCCAGACCGUCAGACAU |
| 3303 | 1095 | UUGAAUGUUUACUAUAUCACC |
| 3304 | 1096 | AUGAAUAGGGCUUCCUAACCA |
| 3305 | 1097 | AGCAACAUCAAAGAUUUGGAU |
| 3306 | 1098 | UGAAAUUAGUGGGACUUGCCC |
| 3307 | 1099 | UAACCAGGUAUGGGCUCUCU |
| 3308 | 1100 | UCAAUAAUGAAUAUGGUAUUU |
| 3309 | 1101 | AAGAAGUUUCUAUUCAUUUGA |
| 3310 | 1102 | UGGAGACGAAGUUUCACUCUU |
| 3311 | 1103 | CAACAUAAGAGACUCAGGCUU |
| 3312 | 1104 | UAAAUAAUUUGUAUCAUAAGU |
| 3313 | 1105 | UAAUAUCCUGUUGGACAAGAA |
| 3314 | 1106 | GAAUCCUUCAGCAUCACUGUG |
| 3315 | 1107 | UGCAGAUUCAGUUAGACAUUG |
| 3316 | 1108 | UAUUAUAGAAUCUCUCAGAAC |
| 3317 | 1109 | AUUGGGACCAUCCACUAACUC |
| 3318 | 1110 | AAAUAUUCCAUUAUUUCCAAG |
| 3319 | 1111 | AGAAAUAGGUGAUACAUAGGA |
| 3320 | 1112 | UCUAUUGCUUCAACCACAAUU |
| 3321 | 1113 | UUUAUUUAUUGUAAAGCAAUA |
| 3322 | 1114 | UUUAAUCCAAAGUUACAGAAG |
| 3323 | 1115 | CAAGUUACUCGAUUGUACCAA |
| 3324 | 1116 | AUAAGCACAAGAGAGGAUUAA |
| 3325 | 1117 | UCAGCCUCCCAAGUAGCUGGG |
| 3326 | 1118 | AUUUCUCAAUGCUAAUAGCAU |
| 3327 | 1119 | AAGACCCUAAGGAUCAUCUAG |
| 3328 | 1120 | GAGAAGAAUAUUGUCACUCUU |
| 3329 | 1121 | UCUAUAACACAAAUUGUUAGU |
| 3330 | 1122 | UCACUGCUCCAAGGUCUCCAA |
| 3331 | 1123 | AUUUGGUCACUUAAAGGAGUG |
| 3332 | 1124 | UCCUUCAUCCAUACAGGUCUC |
| 3333 | 1125 | CUACAUCGACUCAUUCUCUA |
| 3334 | 1126 | UCUUCCAUCUUUCCUGCAGCA |
| 3335 | 1127 | ACUGCAACAUAAGAGACUCAG |
| 3336 | 1128 | AAGCAAUGGAUUCAACCACAG |
| 3337 | 1129 | CUCUGUGACCACAUCAGUCAG |
| 3338 | 1130 | AUCCCGGUUGUUACUAUUCAU |
| 3339 | 1131 | AGAAGAUUCAGGAAGUGCCAA |
| 3340 | 1132 | AAGCCCAGCACUACUUCACAG |
| 3341 | 1133 | AAAUGUGGUUUCUCCUAUGAG |
| 3342 | 1134 | AUCUAAAUAAUUAACAAUAUU |
| 3343 | 1135 | UAUCUCUGCCCUGCAUGCUCU |
| 3344 | 1136 | AUUAAACACAUUCCCAAUGCA |
| 3345 | 1137 | UAGUAUGCUUCAAAUUAAUAU |
| 3346 | 1138 | UCCUAGAAAGCGUGUGCCAU |
| 3347 | 1139 | AGAAGGAUGGAACCAUACCAU |
| 3348 | 1140 | UUAGGGCAUGGACUUCCACAU |
| 3349 | 1141 | AAACUCUAGAAAGCCCAGCAC |
| 3350 | 1142 | AACAUGGUGACUGAUUUGAGG |
| 3351 | 1143 | AAAUAAUUUGUAUCAUAAGUA |
| 3352 | 1144 | CUUAACUGAAUAUUAACUGCA |
| 3353 | 1145 | AGAAAUAAACCCAUUGAGCAA |
| 3354 | 1146 | UAGAAAGCCCAGCACUACUUC |
| 3355 | 1147 | UCCUGUUGCAAUGUCUAGUGC |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3356 | 1148 | AAGAAGCCUUCUAUAACACAA |
| 3357 | 1149 | CACAUGUUCACACAGUACUUG |
| 3358 | 1150 | CAUUAUUAAAGUUCUCACCUA |
| 3359 | 1151 | UUGUUACUAUUCAUCCUCAGU |
| 3360 | 1152 | UGGGAAGAUAGAGCGAAGCCU |
| 3361 | 1153 | AGAAUACUCGUACACACAGGU |
| 3362 | 1154 | UCUUCCUCUUCAUCUUCUUCU |
| 3363 | 1155 | UCAUGCACAAUCCAUAUUUCA |
| 3364 | 1156 | AACUAGCAAAUAUCUCUGCCC |
| 3365 | 1157 | UUUCUCUUCAUUAUCCAGACC |
| 3366 | 1158 | AAUGCUAAUAGCAUGUAAUUA |
| 3367 | 1159 | UCAGAGCUCAGAGACUGGGAG |
| 3368 | 1160 | UUUGGAGUUCUAAUAGUGACA |
| 3369 | 1161 | UCACUGACCUCCCAUUUCUUA |
| 3370 | 1162 | UAAUGUCCAACAAGGAUUUCA |
| 3371 | 1163 | UCCUUCUUCUUUAUUGGUUUUA |
| 3372 | 1164 | UGCAAGUCAUAACUUCUAUUG |
| 3373 | 1165 | UAAGAUGUGGAUAUAUGGAUG |
| 3374 | 1166 | ACGUGGAUCCUUCUCAACUUG |
| 3375 | 1167 | AAUACUUGAGUUAAAUCUUCU |
| 3376 | 1168 | AGUGUACUCAUCAUACAACUG |
| 3377 | 1169 | UCUCAGGAUUCUGGAGCUCUG |
| 3378 | 1170 | UCCUACCUGAAUGAUAUACAG |
| 3379 | 1171 | AUAGGGCUUCCUAACCAGGUA |
| 3380 | 1172 | AUAUAUGGUGAAAUAGUAGUC |
| 3381 | 1173 | AGUGAUAUUAUAGAAUCUCUC |
| 3382 | 1174 | AUGUAUCUAUUCCUCCUGGU |
| 3383 | 1175 | AAAGUCAGUCAAUUUAACAGA |
| 3384 | 1176 | UUUGGGCUGCGAUUCAGGCUU |
| 3385 | 1177 | UCUUUGUCCAUAUGCAUUUCU |
| 3386 | 1178 | UUUGAAUGCAAGAGGGACUAC |
| 3387 | 1179 | AUUUAUUGUAAAGCAAUAUUA |
| 3388 | 1180 | UUUCUGCUGUUUAUUUAUUGU |
| 3389 | 1181 | AAUAUCUCUGCCCUGCAUGCU |
| 3390 | 1182 | UUUGUUUACUUAAUGUCCAAC |
| 3391 | 1183 | AUAUGGUAUUUGCGGGUCCAU |
| 3392 | 1184 | AUUAUUAUCAAAUCUUGGUAC |
| 3393 | 1185 | UAAAUGCUACAAGUUGUAUAG |
| 3394 | 1186 | AUAGUUUGCUGAAACUCUAAA |
| 3395 | 1187 | UGCUAACUAAUGAAUAGGGCU |
| 3396 | 1188 | UUCCAGAAAGGCAAUAUCUGC |
| 3397 | 1189 | AGAACCUGAACUCACCUAGCA |
| 3398 | 1190 | UGAUGAUUAAUGUAUCUAUUU |
| 3399 | 1191 | UCCGAAACAGAAAUAGGUGAU |
| 3400 | 1192 | UUGUCAUCAGAAAUGCUAUCU |
| 3401 | 1193 | UUUGAAAGGUAAAGAACCCCC |
| 3402 | 1194 | CUUAGAGAAACAACUUUCUGU |
| 3403 | 1195 | AUAUCAUUUAUAGACAAAUAU |
| 3404 | 1196 | AGGAUUUCACCGUUUGAGCUU |
| 3405 | 1197 | UAGUGGGACUUGCCCUAUUGG |
| 3406 | 1198 | AUAUUUGUUUAAUGAUUUCAA |
| 3407 | 1199 | UCACAUAGCAAUUUAGUAAUA |
| 3408 | 1200 | GAAUACUCGUACACACAGGUG |
| 3409 | 1201 | UUCCACAUGUUCACACAGUAC |
| 3410 | 1202 | AACCUGAACUCACCUAGCAGG |
| 3411 | 1203 | UCUUACAGAGUUGAAUGUUUA |
| 3412 | 1204 | UACUUCACAGGAAAGGAGAAG |
| 3413 | 1205 | CAACUUGUAAGUGUUUAGGUU |
| 3414 | 1206 | GCUAACAACAUUAACGUUCUU |
| 3415 | 1207 | AUUCAGUUAGACAUUGUUUAA |
| 3416 | 1208 | UACAAAGUGGUAGUAAAGAAG |
| 3417 | 1209 | UACAUAAGUUCUGUUUAGAUU |
| 3418 | 1210 | AAAUAUACAUAACUCUCCAAU |
| 3419 | 1211 | UGUCCUUCAUCCAUACAGGUC |
| 3420 | 1212 | AUGCUCUGGUCUUGGUGCGAU |
| 3421 | 1213 | AGUAUUCUACAUUUAUCUGGU |
| 3422 | 1214 | AUAAACAGUACCUGAUGCCCC |
| 3423 | 1215 | UCAUCUCCUGAACAUAAACAC |
| 3424 | 1216 | UAGUAUUUAUCCCACUACAUC |
| 3425 | 1217 | AUCCCACUACAUCUGACUCAU |
| 3426 | 1218 | CAUAGAAUUUGAGAACAUCUA |
| 3427 | 1219 | UACACACAGGUGUGCACAUGG |
| 3428 | 1220 | AACGAAGUCAUUACCCAACAU |
| 3429 | 1221 | UUGAGUGCAGGAAAUCCAAAG |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3430 | 1222 | UAGGCAGGGCAUUGGGACCAU |
| 3431 | 1223 | AUGUGAAUCCUUCAGCAUCAC |
| 3432 | 1224 | ACACACAGGUGUGCACAUGGA |
| 3433 | 1225 | UCAUAGGAGAAAUAUUCCAUU |
| 3434 | 1226 | UCUGCUGUUUAUUUAUUGUAA |
| 3435 | 1227 | CUUCAAAUUAAUAUUACCGUU |
| 3436 | 1228 | UCUCGGGCGCUCUUUCUCCU |
| 3437 | 1229 | UCCUAGGCUAGUAUUUAUCCC |
| 3438 | 1230 | UUUCUCUGCCUACAGUGAUCU |
| 3439 | 1231 | CAACAUUGAAAGAUGUGCCCU |
| 3440 | 1232 | UUCUUAGCUUCUCUAAGAUCU |
| 3441 | 1233 | ACAGUCUCUCAGGAUUCUGGA |
| 3442 | 1234 | UGGUUUACUCAAUUAUCUUUU |
| 3443 | 1235 | AGUUCUAAUAGUGACAUCUCC |
| 3444 | 1236 | ACCACACACAAGCACACACAU |
| 3445 | 1237 | UCUCUAUGUUGGUCAGGCUGG |
| 3446 | 1238 | UCAAGUCUGAAGGAAGAGAG |
| 3447 | 1239 | AGACCAAGAGAUUCAACCGGG |
| 3448 | 1240 | UUCACCUUCCACCAUUUCAAU |
| 3449 | 1241 | CAAAGUAUAACAUAGUAUGCU |
| 3450 | 1242 | UAGCUACAGGAUUCUGUGAAG |
| 3451 | 1243 | AAUAUCUGCAACAGAUGUUAU |
| 3452 | 1244 | ACAAUGACACACACGAGAU |
| 3453 | 1245 | AAGUUCACUCUUGUUGCCGA |
| 3454 | 1246 | AACAUUGAAAGAUGUGCCCUC |
| 3455 | 1247 | UCUGCAACAGAUGUUAUCAAG |
| 3456 | 1248 | GUGGUAGUAAAGAAGUACCUG |
| 3457 | 1249 | AUGCUUCUUAGCUUCUCUAAG |
| 3458 | 1250 | UGCUGAAGAAUCCCGGUUGUU |
| 3459 | 1251 | ACUACAUCUGACUCAUUCUCU |
| 3460 | 1252 | UUCGCUUCACGGUGGAAGUGA |
| 3461 | 1253 | AAGCUCAUGUAUUUCUGGUUG |
| 3462 | 1254 | UCUCCUCAUCUGUCAUCUUGG |
| 3463 | 1255 | AUUACAUAAUCUGAGGGAGUA |
| 3464 | 1256 | AUUCUCUACUAUCGCUGUUGA |
| 3465 | 1257 | AUCACAUUGGGUAAGGAGUUU |
| 3466 | 1258 | UUUCUUUGGUGAGUUAGAAGG |
| 3467 | 1259 | CAAUUUAGUAAUAAAGCUCAU |
| 3468 | 1260 | AUUGCUGCCCUGUUUGGGCUG |
| 3469 | 1261 | AUCUUUGUUUAAAUGUGGUUU |
| 3470 | 1262 | ACAGGAAGCAAUUUCGUGUUU |
| 3471 | 1263 | UUCAAGCGAUUCUCCCACCUC |
| 3472 | 1264 | AUACAGGUCUCUGUGACCACA |
| 3473 | 1265 | AAACAACUGUAAAUGAAUUGG |
| 3474 | 1266 | UAACAACCUGGUUUACUCAAU |
| 3475 | 1267 | AUAGUUGUAAUCCCUGUUUAU |
| 3476 | 1268 | GAACCUGAACUCACCUAGCAG |
| 3477 | 1269 | AUGAUGAUUAAUGUAUCUAUU |
| 3478 | 1270 | AAGAGAGGAUUAAUUUAGGUA |
| 3479 | 1271 | GUUUACAGAUAACACAUUCUG |
| 3480 | 1272 | UAUCUAUUCCUCCUGGUAUG |
| 3481 | 1273 | AUAGAUAAUAGUCUCCUAAGA |
| 3482 | 1274 | UAUCCCACUGUGGACAUUUUC |
| 3483 | 1275 | UUGAAUUUCCCGGCACUAUGA |
| 3484 | 1276 | AAUUUAGUAAUAAAGCUCAUA |
| 3485 | 1277 | UUGCAUCCCAGGAUUUCAUUG |
| 3486 | 1278 | UCUUUCCAGCAGUGUACUCAU |
| 3487 | 1279 | UACCAUCAGCAGGUCUACAAA |
| 3488 | 1280 | UCAUCUUCUUCUUCUUCUUCC |
| 3489 | 1281 | AUCCAUACAGGUCUCUGUGAC |
| 3490 | 1282 | UAGCAAAUAUCUCUGCCCUGC |
| 3491 | 1283 | UCAGGUGAUCCGCCUGCCUUG |
| 3492 | 1284 | AGAGACUCAGGCUUAAACGUG |
| 3493 | 1285 | UCUGUGAAGAUCUUAUCAUCA |
| 3494 | 1286 | UUAUUAGAAAUAUACAUAACU |
| 3495 | 1287 | AGCUUCUCUAAGAUCUCCUCA |
| 3496 | 1288 | AACCACAGAACGAGUAUAGAU |
| 3497 | 1289 | UCAGGAUUCUGGAGCUCUGGA |
| 3498 | 1290 | UACAAAUAAUUCAUAAUCU |
| 3499 | 1291 | UCAUUAAUAAUUAAUUCCUUC |
| 3500 | 1292 | UAAUUGUAACUAGCAAAUAUC |
| 3501 | 1293 | UUAAGGCCUCUCUCUCUCAUU |
| 3502 | 1294 | CAUUUCUCUCUGCAACUUGUA |
| 3503 | 1295 | UCUAAAUAAUUAACAAUAUUA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3504 | 1296 | ACAACCUAUAAAUAGGCAGAA |
| 3505 | 1297 | UUGGGCUGCGAUUCAGGCUUA |
| 3506 | 1298 | AAGAGAAUAAACUGUUAACAA |
| 3507 | 1299 | AUUUGUAUCAUAAGUAAAUGA |
| 3508 | 1300 | UGCAACAUAAGAGACUCAGGC |
| 3509 | 1301 | UUAGUGGGACUUGCCCUAUUG |
| 3510 | 1302 | AUGGAACCAUACCAUCAGCAG |
| 3511 | 1303 | CCAGUAGACAUCACUACCCUG |
| 3512 | 1304 | UCCCAUUUAUUCCUUCCCAG |
| 3513 | 1305 | GAACUAAGCAUGAACACACCA |
| 3514 | 1306 | CUUUAUUGGUACUGCUGGUG |
| 3515 | 1307 | AAUAAAUUACAUAAUCUGAGG |
| 3516 | 1308 | UUCCAUUAUUUCCAAGUUCCC |
| 3517 | 1309 | AUCAGCAAGAACGAAGUCAUU |
| 3518 | 1310 | CUAACAACAUUAACGUUCUUU |
| 3519 | 1311 | AACAGAACUAUAACUGAAUGC |
| 3520 | 1312 | ACAAUUAAUUUGUCAACAUU |
| 3521 | 1313 | UCGUACACACAGGUGUGCACA |
| 3522 | 1314 | GUUCACACAGUACUUGCUCUG |
| 3523 | 1315 | ACACGUACACUAUAUAGUUUG |
| 3524 | 1316 | AAAGACCCUAAGGAUCAUCUA |
| 3525 | 1317 | UUACAGGCCCAGAUUCGUUUU |
| 3526 | 1318 | CUCAAGUACAGUUAUAUUCUA |
| 3527 | 1319 | UGGAAAGACCCUAAGGAUCAU |
| 3528 | 1320 | AAAGGCAAUAUCUGCAACAGA |
| 3529 | 1321 | CAUGAACACACCAUAUUCCGA |
| 3530 | 1322 | ACUUAAGGAGUGUGGAUCAG |
| 3531 | 1323 | UUGCAGGCACUCUCUGCAGAC |
| 3532 | 1324 | UGUUUGGAGUUCUAAUAGUGA |
| 3533 | 1325 | UGACAUUUCUUGGGAUAUGAU |
| 3534 | 1326 | UUCACUCUUAGCAGUCUCAGC |
| 3535 | 1327 | UACAAAUGCUGAAUUUCAGUC |
| 3536 | 1328 | AAAUAAUCUCUACUGUGCUUC |
| 3537 | 1329 | AAGAAUAAAUACUUGAGUUAA |
| 3538 | 1330 | UCACAGUUUCAGUUUCAGUGU |
| 3539 | 1331 | ACUACUGCAAACAACCUAUAA |
| 3540 | 1332 | AUUGGGAUGUAGCCUUCACUG |
| 3541 | 1333 | AAGUAGCUUAGAUAAAGACCA |
| 3542 | 1334 | AAUGAUGAUUAAUGUAUCUAU |
| 3543 | 1335 | ACAGGAUUCUGUGAAGAUCUU |
| 3544 | 1336 | UAGGUCCAAGUUUCAAACUGC |
| 3545 | 1337 | AGCUUCUAAAGGAGACUCCGA |
| 3546 | 1338 | AAUCACUGUGGGAGUUGUCAU |
| 3547 | 1339 | UAAACUCUAGAAAGCCCAGCA |
| 3548 | 1340 | UCAGGCUGGUCUCGAACUCCU |
| 3549 | 1341 | AUGUCCAACAAGGAUUUCAGU |
| 3550 | 1342 | UUUGGAGCUGUGGUUGAGUGC |
| 3551 | 1343 | CAGGCUGGUCUCGAACUCCUG |
| 3552 | 1344 | UGAAUCGUAUGCUCAAAGUCU |
| 3553 | 1345 | UCACCGUUUGAGCUUUAUUUA |
| 3554 | 1346 | AAUCGUGCCCAUUGCUCUGGA |
| 3555 | 1347 | GAAUGUUUACUAUAUCACCUU |
| 3556 | 1348 | UGUAUCAUAAGUAAAUGAUGA |
| 3557 | 1349 | UAACAAUAUUAGGGUUCUUAU |
| 3558 | 1350 | CUGAAUUUGCAAGGCAACCUA |
| 3559 | 1351 | UUGUAAAGCAAUAUUAUAACA |
| 3560 | 1352 | UACCCUCUUUCCAGCAGUGUA |
| 3561 | 1353 | AACAAUAUUAGGGUUCUUAUU |
| 3562 | 1354 | AAUUAAUUCCUUCUUGGGUUG |
| 3563 | 1355 | UCAGAGACUGGGAGAUACUUG |
| 3564 | 1356 | CAAGUUGUAUAGAAUACUCGU |
| 3565 | 1357 | UUCUCUCUGCAACUUGUAAGU |
| 3566 | 1358 | UCACAAUGCUUCUUAGCUUCU |
| 3567 | 1359 | UGUCCAUAUGCAUUUCUUUUU |
| 3568 | 1360 | AACAUAAGAGACUCAGGCUUA |
| 3569 | 1361 | UUGAAAUUAGUGGGACUUGCC |
| 3570 | 1362 | UCCUUCCCAGUCCACAUGCAA |
| 3571 | 1363 | AAUAUUAAACACAUUCCCAAU |
| 3572 | 1364 | UGUAUAGAAUACUCGUACACA |
| 3573 | 1365 | CUGUUGAAGGUUCAUCUGCUU |
| 3574 | 1366 | UAGGAGAAAUAUUCCAUUAUU |
| 3575 | 1367 | CACACAUUGAACUUGAAUUUU |
| 3576 | 1368 | GUUGUUACUAUUCAUCCUCAG |
| 3577 | 1369 | ACAGAGUUGAAUGUUUACUAU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3578 | 1370 | UUCACCGUUUGAGCUUUAUUU |
| 3579 | 1371 | CAAUGGAAUGUGCUUCACCGG |
| 3580 | 1372 | UGUUGGUCAGGCUGGUCUCGA |
| 3581 | 1373 | UGUCCUGUUGCAAUGUCUAGU |
| 3582 | 1374 | CUUCUAUUGAAAUUAGUGGGA |
| 3583 | 1375 | UAUAUUCUAGCAAGUGUGACA |
| 3584 | 1376 | UAAAGGAGUGUGGAUCAGAAA |
| 3585 | 1377 | UUGCUGAAACUCUAAAGAAAG |
| 3586 | 1378 | UUUCUAAUACUUAUUAGAAAU |
| 3587 | 1379 | UUUGCUUAACUGAAUAUUAAC |
| 3588 | 1380 | UUCACGGUGGAAGUGACCACU |
| 3589 | 1381 | AGGUCUCUGUGACCACAUCAG |
| 3590 | 1382 | UGACAACGCACUGGAUCCUUG |
| 3591 | 1383 | UCCUCUUCAUCUUCUUCUUCA |
| 3592 | 1384 | AUACAGACAACAGGAAGCAAU |
| 3593 | 1385 | GAUGUUAUGAGUAUAAUCCCA |
| 3594 | 1386 | AUUUAUCCCACUACAUCUGAC |
| 3595 | 1387 | AUAUAUGGAUGGUUAGAUGGA |
| 3596 | 1388 | UAAGUAAAUGAUGAUUAAUGU |
| 3597 | 1389 | AUUAUCUUUGUUUACUUAAUG |
| 3598 | 1390 | CAGAACUAUAACUGAAUGCCA |
| 3599 | 1391 | AAAGCAUAAGAGAGAAGCCAU |
| 3600 | 1392 | AGAAGUUUCUAUUCAUUUGAA |
| 3601 | 1393 | AAUUAUUUACACGAUCUUUGA |
| 3602 | 1394 | UGCUGAGGUCAGAAGGAUGGA |
| 3603 | 1395 | AAAUUAAUAUUACCGUUUCAU |
| 3604 | 1396 | UCAUUGAAUUUCCCGGCACUA |
| 3605 | 1397 | UUAUUUACACGAUCUUUGAGC |
| 3606 | 1398 | UUGGAUGCUGAGGUCAGAAGG |
| 3607 | 1399 | UUUAUGAUUUCAAAGUCAGC |
| 3608 | 1400 | AAGUUCAACCCAAUUAAGUGG |
| 3609 | 1401 | AAAUGAGAUACAAUUCUGAUA |
| 3610 | 1402 | GUAGCCUUCACUGACCUCCCA |
| 3611 | 1403 | AGGAUGGAACCAUACCAUCAG |
| 3612 | 1404 | AUCCUUGCUAACAACAUUAAC |
| 3613 | 1405 | UUCAGGCUUACAAAUAAAUUA |
| 3614 | 1406 | UCUUGUCCUGUUGCAAUGUCU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3615 | 1407 | ACAGACAACAGGAAGCAAUUU |
| 3616 | 1408 | UUACAGAGUUGAAUGUUUACU |
| 3617 | 1409 | AACAACAUUAACGUUCUUUCC |
| 3618 | 1410 | AUCUGAGGUGACUACCUCAUU |
| 3619 | 1411 | AAUCCCAGUAGACAUCACUAC |
| 3620 | 1412 | AAGUAUUUCUGUAUUGAGAAU |
| 3621 | 1413 | AUUAAUAUUACCGUUUCAUUU |
| 3622 | 1414 | UAUCCUUUGGUUAGAUGGUCU |
| 3623 | 1415 | AGAAGAAUAUUGUCACUCUUU |
| 3624 | 1416 | CUUCUUCUUCUUCUUCCUCUU |
| 3625 | 1417 | UCAUUAGAAAUAAACCCAUUG |
| 3626 | 1418 | UUAUAGACAAAUAUCUCAAAC |
| 3627 | 1419 | AACUGAAAGCAUAAGAGAGAA |
| 3628 | 1420 | AUUUCAGUAUUCUACAUUUAU |
| 3629 | 1421 | AUCAUUUAUAGACAAAUAUCU |
| 3630 | 1422 | UCAUAACUUCUAUUGAAAUUA |
| 3631 | 1423 | CAUAACUCUCCAAUACAGGGA |
| 3632 | 1424 | AAAUAGGUGAUACAUAGGAAA |
| 3633 | 1425 | AUCACAACUACUGCAAACAAC |
| 3634 | 1426 | AUGAAUCGUAUGCUCAAAGUC |
| 3635 | 1427 | UGGAGUUCUAAUAGUGACAUC |
| 3636 | 1428 | UAUUUAUUGUAAAGCAAUAUU |
| 3637 | 1429 | CAAAUGUGAAUCCUUCAGCAU |
| 3638 | 1430 | AUUGCUCUGGAAUUCCAGUGA |
| 3639 | 1431 | AUUUCUGGUUGUUGACUGUUU |
| 3640 | 1432 | GUAUUUAUCCCACUACAUCUG |
| 3641 | 1433 | UUCCCAGUCUUUGUCCAUAUG |
| 3642 | 1434 | CUAAUAGUGACAUCUCCCUAG |
| 3643 | 1435 | UGUUUAAAUGUGGUUUCUCCU |
| 3644 | 1436 | UUCCUCUUGGGUACUAAAUCU |
| 3645 | 1437 | AGCAGUGUACUCAUCAUACAA |
| 3646 | 1438 | UCGUUAUCUCAGGGCACACUA |
| 3647 | 1439 | CUCUACUGUGCUUCUCACCCU |
| 3648 | 1440 | GUAACUAGCAAAUAUCUCUGC |
| 3649 | 1441 | UGGUGAGUUAGAAGGAAGUUA |
| 3650 | 1442 | CAAUGCUUCUUAGCUUCUCUA |
| 3651 | 1443 | AUAAAUAAUUUGUAUCAUAAG |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3652 | 1444 | AAGUUCUGUUUAGAUUCUUUU |
| 3653 | 1445 | CAACGCACUGGAUCCUUGCUA |
| 3654 | 1446 | UGAUUUCAAAGUCAGCUUUUA |
| 3655 | 1447 | UAAAGCACACCACACAAGC |
| 3656 | 1448 | UUGCGGGUCCAUAAAGCACAC |
| 3657 | 1449 | UUUGAGCUUUAUUUAGAUAUA |
| 3658 | 1450 | AUGGAAUAAUUGUAACUAGCA |
| 3659 | 1451 | UUGCUUAACUGAAUAUUAACU |
| 3660 | 1452 | CACAGUUUCAGUUUCAGUGUG |
| 3661 | 1453 | AUCGUGCCCAUUGCUCUGGAA |
| 3662 | 1454 | UCACGGUGGAAGUGACCACUU |
| 3663 | 1455 | CUAAAUCUGUUGAACAUGUUG |
| 3664 | 1456 | AGCAAUUUAGUAAUAAAGCUC |
| 3665 | 1457 | UGGGAUAUGAUUGUAAGUUAA |
| 3666 | 1458 | UAGCAGGCUGAAUUUGCAAGG |
| 3667 | 1459 | UACAGUGCAUAUGUUUCAUAA |
| 3668 | 1460 | UUCAAAUCCCAGGCCCAUCAA |
| 3669 | 1461 | UUCUCCCACCUCAGCCUCCCA |
| 3670 | 1462 | UUAAAGGAGUGUGGAUCAGAA |
| 3671 | 1463 | UAGAUAAAGACCAAGAGAUUC |
| 3672 | 1464 | UCAACAUUGCUGCCCUGUUUG |
| 3673 | 1465 | UCCAUAAAGCACACCACACAC |
| 3674 | 1466 | UGCAACUCUAUUAGGGCAUGG |
| 3675 | 1467 | AUGUUUACUAUAUCACCUUUC |
| 3676 | 1468 | UGAAGGUUCAUCUGCUUUAUG |
| 3677 | 1469 | UAGUUGUAAUCCCUGUUUAUG |
| 3678 | 1470 | GAUCUUAUCAUCAAUAAUGAA |
| 3679 | 1471 | AUGGAGAGGUUAAGUGACUUG |
| 3680 | 1472 | UAUGGAAUAAUUGUAACUAGC |
| 3681 | 1473 | AUGCAUGGGCUCUGCUAUCUU |
| 3682 | 1474 | UCGAUUGUACCAAAUGUGAAU |
| 3683 | 1475 | CAUAUCUGAGGUGACUACCUC |
| 3684 | 1476 | AAGAACUAAGCAUGAACACAC |
| 3685 | 1477 | UUUAUCCCACUACAUCUGACU |
| 3686 | 1478 | AUUCCAUGACUACCCAUAGUU |
| 3687 | 1479 | UAAACACAUUCCCAAUGCAUG |
| 3688 | 1480 | AUUCAUUUGAAAGGUAAAGAA |
| 3689 | 1481 | AUAGGAGAAAUAUUCCAUUAU |
| 3690 | 1482 | UCUUAGCGGCUGCUGUUCUUA |
| 3691 | 1483 | UAUGCUUCAAAUUAAUAUUAC |
| 3692 | 1484 | UGGAUGGUUAGAUGGAUGGAU |
| 3693 | 1485 | AAAGAACUAAGCAUGAACACA |
| 3694 | 1486 | AAGGAGGUUUGAAUGCAAGAG |
| 3695 | 1487 | UCUAUGGAUCACCUGGUUUGA |
| 3696 | 1488 | AUGGAUGGUUAGAUGGAUGGA |
| 3697 | 1489 | ACACACCAUAUUCCGAAACAG |
| 3698 | 1490 | AUGGUUAGAUGGAUGGAUGUA |
| 3699 | 1491 | AGAUACAAUUCUGAUAAACAA |
| 3700 | 1492 | AGUAGCUAUCUAAAUAAUUAA |
| 3701 | 1493 | UCCACAUGCAAAUACACGUUC |
| 3702 | 1494 | AGUUACAGAAGAAUUUCACUA |
| 3703 | 1495 | UUGAAUGCAAGAGGGACUACU |
| 3704 | 1496 | CAGGAUUCUGUGAAGAUCUUA |
| 3705 | 1497 | CUGAACACACAUAUUCCCUCUC |
| 3706 | 1498 | ACUCAAGACACAGUCAUGCAC |
| 3707 | 1499 | AUUAUAACAAUAUCAAAUAAA |
| 3708 | 1500 | UCUUUCAGGUAUUAAGGAGAU |
| 3709 | 1501 | UCCCAUCUUUGUUUAAAUGUG |
| 3710 | 1502 | AAUUGUAACUAGCAAAUAUCU |
| 3711 | 1503 | AACUAGCAGCAUAUCUGAGG |
| 3712 | 1504 | AGAUGUAAGGAUCAGGUGGUU |
| 3713 | 1505 | AAUUAGUGGGACUUGCCCUAU |
| 3714 | 1506 | AGUUUGGAGUAAUCGUGCCCA |
| 3715 | 1507 | CAAAUCUUGGUACAAAGUGGU |
| 3716 | 1508 | ACUUUGCUCAGGAGUGAUCUG |
| 3717 | 1509 | UCUUCAAAGUGAAUGCACAAA |
| 3718 | 1510 | AUUAUUUCCAAGUUCCCAUUU |
| 3719 | 1511 | UCAACAUUUCUCAAUGCUAAU |
| 3720 | 1512 | AGGAGGUCAAGCCUCUCCCAA |
| 3721 | 1513 | AGUAGACAUCACUACCCUGUG |
| 3722 | 1514 | UGACAGGAUUUCACCGUUUGA |
| 3723 | 1515 | UCUUCCUAGGCUAGUAUUUAU |
| 3724 | 1516 | UCAACAUGUAAGGGAUGCUAA |
| 3725 | 1517 | CAUCUUCUUCUUCUUCUUCCU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3726 | 1518 | UAAUAGUGACAUCUCCCUAGC |
| 3727 | 1519 | GCUUAGAGAAACAACUUUCUG |
| 3728 | 1520 | CAUCUAGAACAGCUUGUGGGU |
| 3729 | 1521 | UCUUCAUCUUCUUCUUCAGAC |
| 3730 | 1522 | AAAUGCUACAAGUUGUAUAGA |
| 3731 | 1523 | UUUGGUUCCCAACAAAUUAAU |
| 3732 | 1524 | UAUCAACUUUCGGACCAUAAG |
| 3733 | 1525 | AAGCUUGCAGGCACUCUCUGC |
| 3734 | 1526 | CUAUGUAUCCAUGUGCACUUU |
| 3735 | 1527 | AUGGGAUAGCAUUUGCCUGAU |
| 3736 | 1528 | UAAAGCCUAUGGAAUAAUUGU |
| 3737 | 1529 | UAGCUGGGAUUACAGGCGCCC |
| 3738 | 1530 | UCAGGAGUGAUCUGGGCACAG |
| 3739 | 1531 | AGUGCUUCGUUUACUUUGCUC |
| 3740 | 1532 | UCGUUUACUUUGCUCAGGAGU |
| 3741 | 1533 | UCACUCUUAGCAGUCUCAGCC |
| 3742 | 1534 | UAUGAGGAUUUCCUAGGUUCA |
| 3743 | 1535 | UAAUUUGUAUCAUAAGUAAAU |
| 3744 | 1536 | AUUAAUGUAUCUAUUUCCUCC |
| 3745 | 1537 | ACACAACACUAUGAAGAGGGA |
| 3746 | 1538 | AAAUGAAUUGGAAGGCUGCCA |
| 3747 | 1539 | AAGUAGCUGGGAUUACAGGCG |
| 3748 | 1540 | CAUCUAUGACAAUGCAAGUG |
| 3749 | 1541 | UCUAUGUUGGUCAGGCUGGUC |
| 3750 | 1542 | CUGAGUUCACUUCAAAUCCCA |
| 3751 | 1543 | UCAGAGAAAGUCCCAUCUUUG |
| 3752 | 1544 | AUCCUCAGUGGAGGAGCCGGG |
| 3753 | 1545 | AAGCAAUUUCGUGUUUCUUUU |
| 3754 | 1546 | AUGAGAUACAAUUCUGAUAAA |
| 3755 | 1547 | UACAUAAUCUGAGGGAGUAGG |
| 3756 | 1548 | UCUUUGGUUCCCAACAAAUUA |
| 3757 | 1549 | UGAAGAUCUUAUCAUCAAUAA |
| 3758 | 1550 | AUAUUGUCACUCUUUAUAUCU |
| 3759 | 1551 | UGGUUUACAGAUAACACAUUC |
| 3760 | 1552 | UCUUCUUCUUCCUCUUCAUCU |
| 3761 | 1553 | CUGUCGGACUGACAUUUCUUG |
| 3762 | 1554 | CUCCUCAUUGUUAAUAUGCUG |
| 3763 | 1555 | AAAGAAAUCUGAAUAACAUAA |
| 3764 | 1556 | GACACAGUCACUAAUGUACUG |
| 3765 | 1557 | UGGGUUCAAGCGAUUCUCCCA |
| 3766 | 1558 | AACCAUACCAUCAGCAGGUCU |
| 3767 | 1559 | GUAUAACAUAGUAUGCUUCAA |
| 3768 | 1560 | AUACUUUAGGUCCAAGUUUCA |
| 3769 | 1561 | ACAUGGUGACUGAUUUGAGGG |
| 3770 | 1562 | UGUUUAGGUUCACUCUUAGCA |
| 3771 | 1563 | AGAAGGAAGUUAUCCUUUGGU |
| 3772 | 1564 | ACUAAUGAAUAGGGCUUCCUA |
| 3773 | 1565 | UCCAUGACUACCCAUAGUUCA |
| 3774 | 1566 | AAGGAAGAGAGAUCUCUGGGC |
| 3775 | 1567 | UCUAAAGAAAGUGCUUUCAUU |
| 3776 | 1568 | CUGAAUGUACAUAAGUUCUGU |
| 3777 | 1569 | UGUACAAAGUACUGGAAUUGG |
| 3778 | 1570 | GUGUACUCAUCAUACAACUGG |
| 3779 | 1571 | UCCAGAAAGGCAAUAUCUGCA |
| 3780 | 1572 | AAUAUGGUAUUUGCGGGUCCA |
| 3781 | 1573 | AAUAGAUAUAUGGUGAAAUAG |
| 3782 | 1574 | AUUUCCUUCCCAGUCCACAUG |
| 3783 | 1575 | CAGACUUUACAUACAGACUGU |
| 3784 | 1576 | CUUACUGCUGGUAUUAUGGGA |
| 3785 | 1577 | UCAUAAGUAAAUGAUGAUUAA |
| 3786 | 1578 | UCUGUCCUUCAUCCAUACAGG |
| 3787 | 1579 | UGACUUGCCUAGCGUCACAUA |
| 3788 | 1580 | CAUCUGACUCAUUCUCUACUA |
| 3789 | 1581 | AUGAGGGAGAUGGUGAGGUGU |
| 3790 | 1582 | GUACACUAUAUAGUUUGCUGA |
| 3791 | 1583 | UUUCACUCUUGUUGCCGAGGC |
| 3792 | 1584 | UACUGCAAACAACCUAUAAAU |
| 3793 | 1585 | CAACUGAUUUCAAUUAUCUGU |
| 3794 | 1586 | ACAUUGUUUAAUAUUAAACAC |
| 3795 | 1587 | CAGUUAUACAGACAACAGGAA |
| 3796 | 1588 | UUUGCAUCCCAGGAUUUCAUU |
| 3797 | 1589 | UAUCAUUUAUAGACAAAUAUC |
| 3798 | 1590 | UCCCACUACAUCUGACUCAUU |
| 3799 | 1591 | UACAGGCCCAGAUUCGUUUUU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3800 | 1592 | UCUACUCUCAGAAGAUUCAGG |
| 3801 | 1593 | AUUUCAGUCUUACUCAUGAGG |
| 3802 | 1594 | GAAACUAAGCAGCAUAUCUGA |
| 3803 | 1595 | AAGGAAGUUAUCCUUUGGUUA |
| 3804 | 1596 | CUUCUUCAGACACAGGAGGGG |
| 3805 | 1597 | UUAGCGGCUGCUGUUCUUAAU |
| 3806 | 1598 | UUUCACUACACAUGGUUUACA |
| 3807 | 1599 | UGGAACAUGGACACACAAAUA |
| 3808 | 1600 | AUGUCACAGUUUCAGUUUCAG |
| 3809 | 1601 | UUAAUCCAAAGUUACAGAAGA |
| 3810 | 1602 | UCUCCCACCUCAGCCUCCCAA |
| 3811 | 1603 | AAUAGGGCUUCCUAACCAGGU |
| 3812 | 1604 | AGCACAUGGAGACCAUCCCAA |
| 3813 | 1605 | UGCAACUUGUAAGUGUUUAGG |
| 3814 | 1606 | AAGAGACUCAGGCUUAAACGU |
| 3815 | 1607 | AAUAAAGCUCAUAUUAGACUC |
| 3816 | 1608 | UAGCUAUCUAAAUAAUUAACA |
| 3817 | 1609 | AUGCUGAACUGAAAGCAUAAG |
| 3818 | 1610 | AUGAGUAUAAUCCCAGUAGAC |
| 3819 | 1611 | ACUAAGCAUGAACACACCAUA |
| 3820 | 1612 | AGUGCAGGAAAUCCAAAGCUU |
| 3821 | 1613 | UGAUAUCUCAGUUCCCGCAUU |
| 3822 | 1614 | AAUAUUAUAACAAUAUCAAAU |
| 3823 | 1615 | AGUAAUAUCCUGUUGGACAAG |
| 3824 | 1616 | AAUGCUGAAUUUCAGUCCUCU |
| 3825 | 1617 | UCCUCAUUGUUAAUAUGCUGA |
| 3826 | 1618 | UGCAAAGUAUAACAUAGUAUG |
| 3827 | 1619 | CAGACAGCUGCUAUCUGUCCU |
| 3828 | 1620 | AUAGUUCCCUUUCUGCUGUUU |
| 3829 | 1621 | CAGGACACAGUCACUAAUGUA |
| 3830 | 1622 | ACAUAACUCUCCAAUACAGGG |
| 3831 | 1623 | UAUUCAUUUGGUCACUUAAAG |
| 3832 | 1624 | UAUCUGCAACAGAUGUUAUCA |
| 3833 | 1625 | AGAAAUAUUCCAUUAUUUCCA |
| 3834 | 1626 | UGAGGUGUAAGGCUUGCAGUC |
| 3835 | 1627 | UGCCCUAUUCCUAACUCAGGA |
| 3836 | 1628 | UUUCCAGCAGUGUACUCAUCA |
| 3837 | 1629 | AAAGAAAGUGCUUUCAUUUUA |
| 3838 | 1630 | AUCUAAUGACAAUGCAAGUGA |
| 3839 | 1631 | AACUAAUGAAUAGGGCUUCCU |
| 3840 | 1632 | CCUUCUAUAACACAAAUUGUU |
| 3841 | 1633 | UCCAUCUCAAGACAGCGAUUU |
| 3842 | 1634 | AUAUUCCAUUAUUUCCAAGUU |
| 3843 | 1635 | UCACAUUGGGUAAGGAGUUUU |
| 3844 | 1636 | ACCAUAAAUACCUUUAAUCCA |
| 3845 | 1637 | GUGAUCUGGGCACAGAACCCA |
| 3846 | 1638 | AAAGUGCUGGGAUUACAGGUA |
| 3847 | 1639 | AAGAAAUCUGAAUAACAUAAA |
| 3848 | 1640 | AUUGAUUGGGAUGUAGCCUUC |
| 3849 | 1641 | ACUCGUACACACAGGUGUGCA |
| 3850 | 1642 | AUGUGGUUUCUCCUAUGAGGA |
| 3851 | 1643 | UACAUACAGACUGUAUGGAAA |
| 3852 | 1644 | UAUUUCCUUCCCAGUCCACAU |
| 3853 | 1645 | AACUGUCAGUUUACAAAUGCU |
| 3854 | 1646 | AGGUGUAAGGCUUGCAGUCUU |
| 3855 | 1647 | GACACAGUCAUGCACAAUCCA |
| 3856 | 1648 | AGGAGAUUAACAACCUGGUUU |
| 3857 | 1649 | AGAAACAACUUUCUGUAAUUU |
| 3858 | 1650 | UGCUGUAGGCAGGGCAUUGGG |
| 3859 | 1651 | UGUGCCCUCGUUAUCUCAGGG |
| 3860 | 1652 | ACAUAGUUGUAAUCCCUGUUU |
| 3861 | 1653 | UCAGCAAGAACGAAGUCAUUA |
| 3862 | 1654 | AGACAUUUAUGAAUAUGCUUU |
| 3863 | 1655 | UCCAACAAGGAUUUCAGUAUU |
| 3864 | 1656 | AGCAAUUCGUGUUUCUUUUU |
| 3865 | 1657 | UUCCAUCUUUCCUGCAGCAGA |
| 3866 | 1658 | AAUUUCAAGACAUUUAUGAAU |
| 3867 | 1659 | UUCUAAUACUUAUUAGAAAUA |
| 3868 | 1660 | CUUCUUCCUCUUCAUCUUCUU |
| 3869 | 1661 | UCACUACACAUGGUUUACAGA |
| 3870 | 1662 | UCAACCUGAGAGCUGUUAAA |
| 3871 | 1663 | UUCCAUGACUACCCAUAGUUC |
| 3872 | 1664 | UGGAUGCUGAGGUCAGAAGGA |
| 3873 | 1665 | ACACAGUACUUGCUCUGGUAU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3874 | 1666 | UUAUCAAAUCUUGGUACAAAG |
| 3875 | 1667 | AUAAAUAGAUAUAUGGUGAAA |
| 3876 | 1668 | CUUCUUCUUCCUCUUCAUCUU |
| 3877 | 1669 | UGCUUCAAAUUAAUAUUACCG |
| 3878 | 1670 | AUAUACAUAACUCUCCAAUAC |
| 3879 | 1671 | UAAUUCCACCACCCUAACACA |
| 3880 | 1672 | AAGGCAAUAUCUGCAACAGAU |
| 3881 | 1673 | UGUUUAAUGAUUUCAAAGUCA |
| 3882 | 1674 | UGAUGUAAAGCUCAUGUAUUU |
| 3883 | 1675 | AUACCAUCAGCAGGUCUACAA |
| 3884 | 1676 | UGACACACACGAGAUCAGC |
| 3885 | 1677 | CUUCUUUCUAAUACUUAUUAG |
| 3886 | 1678 | AAUUUGAGAACAUCUAGAACA |
| 3887 | 1679 | AGCAGGAUGUCACAGUUUCAG |
| 3888 | 1680 | CACGAGAUCAGCAAGAACAA |
| 3889 | 1681 | UCUUGUUCAGAGCUCAGAGAC |
| 3890 | 1682 | UUCUCACCCUUCCCUGACUUU |
| 3891 | 1683 | CUGAAUAUUAACUGCAAGUAG |
| 3892 | 1684 | AAUGUACAUAAGUUCUGUUUA |
| 3893 | 1685 | UACUUUGCUCAGGAGUGAUCU |
| 3894 | 1686 | UGGGCGCUCUUUCUCCUUCUU |
| 3895 | 1687 | UCCCAGUUUACCCUCUUUCCA |
| 3896 | 1688 | CACAACUACUGCAAACAACCU |
| 3897 | 1689 | UGCAGUCUUAGCGGCUGCUGU |
| 3898 | 1690 | ACUGAAUAUUAACUGCAAGUA |
| 3899 | 1691 | UCACUUCAAAUCCCAGGCCCA |
| 3900 | 1692 | AGGGAUAGAUGUAAGGAUCAG |
| 3901 | 1693 | UUGGAGUAAUCGUGCCCAUUG |
| 3902 | 1694 | UCUGAAUAACAUAAAGAAUAA |
| 3903 | 1695 | UGAGCAAAGGAAUAUAAUUAU |
| 3904 | 1696 | UGAGGUGACUACCUCAUUAUU |
| 3905 | 1697 | AGAGACAGUCCUACAUAUUUG |
| 3906 | 1698 | UUUCUCCUAUGAGGAUUUCCU |
| 3907 | 1699 | UGUUCAGAGCUCAGAGACUGG |
| 3908 | 1700 | UGUAUAAACAGUACCUGAUGC |
| 3909 | 1701 | UGUUAUGAGUAUAAUCCCAGU |
| 3910 | 1702 | UGACUACCCAUAGUUCAUCAC |
| 3911 | 1703 | UCUCAGCUCACCACAACCUCC |
| 3912 | 1704 | UUUAGGUCCAAGUUUCAAACU |
| 3913 | 1705 | AGAGAAAGUCCCAUCUUUGUU |
| 3914 | 1706 | AAAGUUACAGAAGAAUUUCAC |
| 3915 | 1707 | UCCUCAGUGGAGGAGCCGGGG |
| 3916 | 1708 | AUAAAGCUCAUAUUAGACUCC |
| 3917 | 1709 | UAUCAAAUCUUGGUACAAAGU |
| 3918 | 1710 | UUAUUAAAGUUCUCACCUAAA |
| 3919 | 1711 | UCAGUCCUCUUGUUCAGAGCU |
| 3920 | 1712 | UCACCUGGUUUGAGUGCAGGA |
| 3921 | 1713 | CAUCUUCUUCUUCAGACACAG |
| 3922 | 1714 | UUCCCUGACUUUCCCACUGCC |
| 3923 | 1715 | GAAUCGUAUGCUCAAAGUCUG |
| 3924 | 1716 | UCAAGCGAUUCUCCCACCUCA |
| 3925 | 1717 | ACAGUCACUAAUGUACUGAUU |
| 3926 | 1718 | UAACCAACAGAAAGAUUAUAU |
| 3927 | 1719 | GUUCACUCUUAGCAGUCUCAG |
| 3928 | 1720 | AACAUAGUAUGCUUCAAAUUA |
| 3929 | 1721 | AAGCCUUCUAUAACACAAAUU |
| 3930 | 1722 | AUGUUGGGUUAUAUUCAUUUG |
| 3931 | 1723 | AAAGGAGAAGCUCAAGUACAG |
| 3932 | 1724 | CUUCUUCUUCAGACACAGGAG |
| 3933 | 1725 | CUUCCUCUUCAUCUUCUUCUU |
| 3934 | 1726 | AACAGAAAUAGGUGAUACAUA |
| 3935 | 1727 | UCACAGGAAAGGAGAAGCUCA |
| 3936 | 1728 | UAACUAAUGAAUAGGGCUUCC |
| 3937 | 1729 | AUCCUUUGGUUAGAUGGUCUC |
| 3938 | 1730 | UCCCAUUUCUUACAGAGUUGA |
| 3939 | 1731 | AGUGGUAGUAAAGAAGUACCU |
| 3940 | 1732 | AUUUCAGUCCUCUUGUUCAGA |
| 3941 | 1733 | UGGGAUGUAGCCUUCACUGAC |
| 3942 | 1734 | AUACCUUUGCUUAACUGAAUA |
| 3943 | 1735 | CACUCUUAGCAGUCUCAGCCA |
| 3944 | 1736 | CUUCAUUAUCCAGACCGUCAG |
| 3945 | 1737 | AUAUUAAACACAUUCCCAAUG |
| 3946 | 1738 | ACUCUUGUUGCCGAGGCUGGA |
| 3947 | 1739 | GACUCAUUCUCUACUAUCGCU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 3948 | 1740 | CUAUGGAAUAAUUGUAACUAG |
| 3949 | 1741 | UCGUAUGCUCAAAGUCUGAAG |
| 3950 | 1742 | AUCUUUCCUGCAGCAGAGUUU |
| 3951 | 1743 | AUGCAAGAGGGACUACUCUCU |
| 3952 | 1744 | CUUCUUCUUCUUCCUCUUCAU |
| 3953 | 1745 | UAAUAAAGCUCAUAUUAGACU |
| 3954 | 1746 | UGAGAAUUAAACUCUAGAAAG |
| 3955 | 1747 | AAGAGGGAGUGUGCAUCUUUG |
| 3956 | 1748 | AUGAUUAAUGUAUCUAUUUCC |
| 3957 | 1749 | UAUUUGCGGGUCCAUAAAGCA |
| 3958 | 1750 | AACUUGUAAGUGUUUAGGUUC |
| 3959 | 1751 | UUGUAAGUGUUUAGGUUCACU |
| 3960 | 1752 | CUCUUGGGUACUAAAUCUGUU |
| 3961 | 1753 | GUUAAGUGACUUGCCUAGCGU |
| 3962 | 1754 | AAGGAGAAGCUCAAGUACAGU |
| 3963 | 1755 | AUACAAUUCUGAUAAACAAUG |
| 3964 | 1756 | AAAGCACACCACACACAAGCA |
| 3965 | 1757 | ACCACUUUAUGGUCACUUCAA |
| 3966 | 1758 | AGUCUCCUAAGAAAGCGUGUG |
| 3967 | 1759 | AAGUGCUGGGAUUACAGGUAU |
| 3968 | 1760 | CAGUCAUUUAACAGAGCCAU |
| 3969 | 1761 | UAUCCACAUCCAUCUCAAGAC |
| 3970 | 1762 | AGUCAUAUAAGGAAUUCUGUC |
| 3971 | 1763 | ACAAGCCUGAAAGAAAUCUGA |
| 3972 | 1764 | ACAUAUUCCUCUCCACUUUUG |
| 3973 | 1765 | ACUGCUGGUGAAGCAAUGGAU |
| 3974 | 1766 | GUGUCUAUAGUUCCCUUUCUG |
| 3975 | 1767 | UUCUUGGGAUAUGAUUGUAAG |
| 3976 | 1768 | ACUAAGCAGCAUAUCUGAGGU |
| 3977 | 1769 | AAUGCAAGAGGGACUACUCUC |
| 3978 | 1770 | UUCUUUCAUAGGAGAAAUAUU |
| 3979 | 1771 | GACAACAGGAAGCAAUUUCGU |
| 3980 | 1772 | UUUCAGUAUUCUACAUUUAUC |
| 3981 | 1773 | UUUGCAAGGCAACCUAUAAUG |
| 3982 | 1774 | UCAGGCUUAAACGUGAUAUUU |
| 3983 | 1775 | GUAAUCGUGCCCAUUGCUCUG |
| 3984 | 1776 | AGUUAUACAGACAACAGGAAG |
| 3985 | 1777 | ACAGAACCCAAAGUCAGUCAA |
| 3986 | 1778 | GAAACUCUAAAGAAAGUGCUU |
| 3987 | 1779 | UCCUGUACAAAGUACUGGAAU |
| 3988 | 1780 | UCAUAGAAUUUGAGAACAUCU |
| 3989 | 1781 | AUUAUCAAAUCUUGGUACAAA |
| 3990 | 1782 | UUACAAAUAAAUUACAUAAUC |
| 3991 | 1783 | UGAAUAUGGUAUUUGCGGGUC |
| 3992 | 1784 | ACUUAUUAGAAAUAUACAUAA |
| 3993 | 1785 | CAUUUAUGACAAAUAUCUCA |
| 3994 | 1786 | AAUAUUGUCACUCUUUAUAUC |
| 3995 | 1787 | UGGACUUCCACAUGUUCACAC |
| 3996 | 1788 | ACAUAAAGAAUAAAUACUUGA |
| 3997 | 1789 | AGCUAUCUAAAUAAUUAACAA |
| 3998 | 1790 | ACAAAUAUUUACAAUGACACA |
| 3999 | 1791 | GUUGUUGACUGUUUCUUUGGA |
| 4000 | 1792 | AGGCUGGUCUCGAACUCCUGA |
| 4001 | 1793 | CUGUUGCAAUGUCUAGUGCUG |
| 4002 | 1794 | UUGCUUCAACCACAAUUUAAA |
| 4003 | 1795 | AUUCACAUAAUUCCACCACCC |
| 4004 | 1796 | UUGGGACCAUCCACUAACUCC |
| 4005 | 1797 | UCCUCUUGUUCAGAGCUCAGA |
| 4006 | 1798 | AGACGAAGUUUCACUCUUGUU |
| 4007 | 1799 | CAAUACUUUAGGUCCAAGUUU |
| 4008 | 1800 | UGCUCAGGAGUGAUCUGGGCA |
| 4009 | 1801 | CAAGAGACCAGAUAUCAACUU |
| 4010 | 1802 | CUGUCCUUCAUCCAUACAGGU |
| 4011 | 1803 | UAAUACUUAUUAGAAAUAUAC |
| 4012 | 1804 | UAAUUCCAAGAGACCAGAUAU |
| 4013 | 1805 | UUUCCUUCCCAGUCCACAUGC |
| 4014 | 1806 | UAAUCUGAGGGAGUAGGAAAA |
| 4015 | 1807 | UUGGGUUGCUGUUGAAGGUUC |
| 4016 | 1808 | AGAUAUGGUGAAAUAGUAG |
| 4017 | 1809 | AGGAUUUCAGUAUUCUACAUU |
| 4018 | 1810 | CAAUAUUAUAACAAUAUCAAA |
| 4019 | 1811 | GUUUAGGUUCACUCUUAGCAG |
| 4020 | 1812 | UCUAGAACAGCUUGUGGGUUC |
| 4021 | 1813 | UAUAAGGAAUUCUGUCGGACU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4022 | 1814 | AUGGAGGUGAUAUCUCAGUUC |
| 4023 | 1815 | ACUAUGAAGAGGGAGUGUGCA |
| 4024 | 1816 | UGUGGUUGAGUGCUGAAGAAU |
| 4025 | 1817 | AAACACAUUCCCAAUGCAUGU |
| 4026 | 1818 | UAUCUUUGGUUCCCAACAAAU |
| 4027 | 1819 | AAGCCUAUGGAAUAAUUGUAA |
| 4028 | 1820 | AAUGACACACACACGAGAUCA |
| 4029 | 1821 | CUUCCAUCUUUCCUGCAGCAG |
| 4030 | 1822 | AUAAAUACUUGAGUUAAAUCU |
| 4031 | 1823 | UCCUUCUUCCUAGGCUAGUAU |
| 4032 | 1824 | UCAUUACCAGACCGUCAGAC |
| 4033 | 1825 | UGGGAUAGCAUUUGCCUGAUG |
| 4034 | 1826 | UCCUUUGCAGCGAUAAUCAGA |
| 4035 | 1827 | UUUAUAUCUCUAUGGAUCACC |
| 4036 | 1828 | GAAGUUUCACUCUUGUUGCCG |
| 4037 | 1829 | CAUCUUUGUUUAAAUGUGGUU |
| 4038 | 1830 | ACACUAUGAAGAGGGAGUGUG |
| 4039 | 1831 | AUGCACAAUCCAUAUUUCAAU |
| 4040 | 1832 | CUGUUCUUAAUUGCUUCCUUU |
| 4041 | 1833 | CUUUGCUCAGGAGUGAUCUGG |
| 4042 | 1834 | UACAGGAUUCUGUGAAGAUCU |
| 4043 | 1835 | AAAUACCUUUAAUCCAAAGUU |
| 4044 | 1836 | AGCUCUAUUAGACUCCGGGG |
| 4045 | 1837 | AACUGCAAGUAGCUUAGAUAA |
| 4046 | 1838 | AACAACUUUCUGUAAUUUACA |
| 4047 | 1839 | UAACAACAUUAACGUUCUUUC |
| 4048 | 1840 | CAUGGUGACUGAUUUGAGGGG |
| 4049 | 1841 | UUUGCGGGUCCAUAAAGCACA |
| 4050 | 1842 | AGUGCUGUAUAAACAGUACCU |
| 4051 | 1843 | UGAAGGAGGUUUGAAUGCAAG |
| 4052 | 1844 | UUGCUUCCUUUGCAGCGAUAA |
| 4053 | 1845 | UCUCUACAUCGCUGUUGAUU |
| 4054 | 1846 | AUAGGUGAUACAUAGGAAAAA |
| 4055 | 1847 | AUUCAACCUGAGAGUCUGUUA |
| 4056 | 1848 | AUUCUGUCGGACUGACAUUUC |
| 4057 | 1849 | GUAGACAUCACUACCCUGUGA |
| 4058 | 1850 | AGAUGGUCUCCCUUGCUCUUU |
| 4059 | 1851 | UCCCACCAUAGUGCUUCGUUU |
| 4060 | 1852 | UGUACCAAAUGUGAAUCCUUC |
| 4061 | 1853 | UGGUAUUAUGGGAUAGCAUUU |
| 4062 | 1854 | AAUAUUAGGGUUCUUAUUUUC |
| 4063 | 1855 | UCAGGCUGGAGAGAGGCUUGG |
| 4064 | 1856 | GUAGCUACAGGAUUCUGUGAA |
| 4065 | 1857 | UCUCCUAAGAAAGCGUGUGCC |
| 4066 | 1858 | CACUCUUUAUAUCUCUAUGGA |
| 4067 | 1859 | ACAACCUCCGCCUCCUGGGUU |
| 4068 | 1860 | UGACCUCCCAUUUCUUACAGA |
| 4069 | 1861 | ACAACGCACUGGAUCCUUGCU |
| 4070 | 1862 | UAUGGUAUUUGCGGGUCCAUA |
| 4071 | 1863 | CUUGGUGCGAUAACUGGUGGU |
| 4072 | 1864 | CUCUUCAUUAUCCAGACCGUC |
| 4073 | 1865 | CUCCUCAUCUGUCAUCUUGGA |
| 4074 | 1866 | UCUUUCCUGCAGCAGAGUUUU |
| 4075 | 1867 | UAUCAUCAAUAAUGAAUAUGG |
| 4076 | 1868 | ACACUAGCAACAUCAAAGAUU |
| 4077 | 1869 | CACACAGUACUUGCUCUGGUA |
| 4078 | 1870 | AUUCCUAACUCAGGACAUUUU |
| 4079 | 1871 | UCCUGACCUCAGGUGAUCCGC |
| 4080 | 1872 | UCAACCACAGAACGAGUAUAG |
| 4081 | 1873 | ACAAACACAACACUAUGAAGA |
| 4082 | 1874 | AGAUUCAGUUAGACAUUGUUU |
| 4083 | 1875 | UCCACUGGAGAGAAUUUCAAG |
| 4084 | 1876 | ACUAACUCCCAGUUUACCCUC |
| 4085 | 1877 | CACACAGGUGUGCACAUGGAG |
| 4086 | 1878 | CCAGACUUUACAUACAGACUG |
| 4087 | 1879 | AUCACCUGGUUUGAGUGCAGG |
| 4088 | 1880 | AAAGACCAAGAGAUUCAACCG |
| 4089 | 1881 | CUGCAGACAGCUGCUAUCUGU |
| 4090 | 1882 | AUUUCCUCCUGGUAUGCCUAU |
| 4091 | 1883 | AUGUUUCAUAAGCACAAGAGA |
| 4092 | 1884 | UUCCCAAUGCAUGUUGGGUUA |
| 4093 | 1885 | ACAUGGACACACAAAUAUUUA |
| 4094 | 1886 | GAACACACAUAUUCCUCUCCA |
| 4095 | 1887 | UCUUUGAGCUGAGAAAUAUCA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4096 | 1888 | AGAAGAAUUUCACUACACAUG |
| 4097 | 1889 | UAUCCUGUUGGACAAGAAAAU |
| 4098 | 1890 | AGGAAGAGAGAUCUCUGGGCG |
| 4099 | 1891 | CAGCUGACAGUCUCUCAGGAU |
| 4100 | 1892 | CCUAAGGAUCAUCUAGUCCAA |
| 4101 | 1893 | UGUUAAUAUGCUGAACUGAAA |
| 4102 | 1894 | UCACCCACCAAGUAGCUAUCU |
| 4103 | 1895 | UCCCAGUAGACAUCACUACCC |
| 4104 | 1896 | AUAAGAAGUUUCUAUUCAUUU |
| 4105 | 1897 | ACAGAACGAGUAUAGAUUGAU |
| 4106 | 1898 | AUGGGCUCUGCUAUCUUGUGC |
| 4107 | 1899 | CUAAGGAUCAUCUAGUCCAAU |
| 4108 | 1900 | UAUUUCCAAGUUCCCAUUUAU |
| 4109 | 1901 | AUCCAGACCGUCAGACAUUUU |
| 4110 | 1902 | CAUCCAUCUCAAGACAGCGAU |
| 4111 | 1903 | AUUUGCAUCCCAGGAUUUCAU |
| 4112 | 1904 | AUCAAUAAUGAAUAUGGUAUU |
| 4113 | 1905 | UUCAUUUGAAAGGUAAAGAAC |
| 4114 | 1906 | AUCAGAGGAGUCAGGCUGGAG |
| 4115 | 1907 | AUGGUCUCCCUUGCUCUUUAA |
| 4116 | 1908 | UGGUGCGAUAACUGGUGGUGG |
| 4117 | 1909 | ACAAUGCUUCUUAGCUUCUCU |
| 4118 | 1910 | AAGCAUGAACACACCAUAUUC |
| 4119 | 1911 | UAAGGCCUCUCUCUCUCAUUA |
| 4120 | 1912 | UGCAAGGCAACCUAUAAUGCC |
| 4121 | 1913 | UUCAUUGAAUUUCCCGGCACU |
| 4122 | 1914 | AGGCUUGCAGUCUUAGCGGCU |
| 4123 | 1915 | AGGAAUAUAAUUAUUUACACG |
| 4124 | 1916 | AUUCAACCACAGAACGAGUAU |
| 4125 | 1917 | ACAGCUUGUGGGUUCUUCUUC |
| 4126 | 1918 | CUGCUAUCUGUCCUUCAUCCA |
| 4127 | 1919 | CUGAACAUAAACACGUACACU |
| 4128 | 1920 | AAUUCCUUCUUGGGUUGCUGU |
| 4129 | 1921 | UGAACACACCAUAUUCCGAAA |
| 4130 | 1922 | AAGUCAUAACUUCUAUUGAAA |
| 4131 | 1923 | AUCAACAUUGAAAGAUGUGCC |
| 4132 | 1924 | AUCAUAGAAUUUGAGAACAUC |
| 4133 | 1925 | GAACAUAAACACGUACACUAU |
| 4134 | 1926 | UACUGCUGGUAUUAUGGGAUA |
| 4135 | 1927 | UGGUGAGGUGUAAGGCUUGCA |
| 4136 | 1928 | GAAUAUAAUUAUUUACACGAU |
| 4137 | 1929 | AUAGCAGGCUGAAUUUGCAAG |
| 4138 | 1930 | GUCGGACUGACAUUUCUUGGG |
| 4139 | 1931 | CUUGAGAAUUAAACUCUAGAA |
| 4140 | 1932 | AGAUGGUGAGGUGUAAGGCUU |
| 4141 | 1933 | AUAACAUAAAGAAUAAAUACU |
| 4142 | 1934 | CACAUGGAGGUGAUAUCUCAG |
| 4143 | 1935 | CCAUAGUUCAUCACCCACCAA |
| 4144 | 1936 | AAGAUGUGGAUAUAUGGAUGG |
| 4145 | 1937 | UUAGAAAUAAACCCAUUGAGC |
| 4146 | 1938 | CAGUCUCUCAGGAUUCUGGAG |
| 4147 | 1939 | CAUAGUGCUUCGUUUACUUUG |
| 4148 | 1940 | ACACUAUAUAGUUUGCUGAAA |
| 4149 | 1941 | UUUCAGGUAUUAAGGAGAUUA |
| 4150 | 1942 | AAUGAGAUACAAUUCUGAUAA |
| 4151 | 1943 | GUGACUUCUCUAGGUAUAGGG |
| 4152 | 1944 | CUGGUCUCGAACUCCUGACCU |
| 4153 | 1945 | AGUUCUGUUUAGAUUCUUUUA |
| 4154 | 1946 | UGCACAUGGAGGUGAUAUCUC |
| 4155 | 1947 | UGCUUCUUAGCUUCUCUAAGA |
| 4156 | 1948 | UUCAGGUAUUAAGGAGAUUAA |
| 4157 | 1949 | UCUCCCUAGCUUUAACUUAUA |
| 4158 | 1950 | AUUCUACAUUUAUCUGGUUUU |
| 4159 | 1951 | GUCCACAUGCAAAUACACGUU |
| 4160 | 1952 | AACAUUCUCAAUGCUAAUAG |
| 4161 | 1953 | AUCCACAUCCAUCUCAAGACA |
| 4162 | 1954 | UGAUUCCUCUUGGGUACUAA |
| 4163 | 1955 | AUAAUCCCAGUAGACAUCACU |
| 4164 | 1956 | AUAUGUUUCAUAAGCACAAGA |
| 4165 | 1957 | AGUGUUUAGGUUCACUCUUAG |
| 4166 | 1958 | UAUUAAACACAUUCCCAAUGC |
| 4167 | 1959 | GAUUAUGACAACGCACUGGAU |
| 4168 | 1960 | UCUGGACAUCUAAUGACAAUG |
| 4169 | 1961 | CUAUAACACAAAUUGUUAGUU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4170 | 1962 | UGGAGCUCUGGAGUUCCAUUA |
| 4171 | 1963 | UGAACUCACCUAGCAGGAUGU |
| 4172 | 1964 | AUGGACUUCCACAUGUUCACA |
| 4173 | 1965 | UGCCUACAGUGAUCUGAAGGG |
| 4174 | 1966 | UGUACAUAAGUUCUGUUUAGA |
| 4175 | 1967 | AAAUAUUUACAAUGACACACA |
| 4176 | 1968 | AGCAAUAUUAUAACAAUAUCA |
| 4177 | 1969 | CACUACAUCUGACUCAUUCUC |
| 4178 | 1970 | UUCAAAGUGAAUGCACAAAAU |
| 4179 | 1971 | UCUAUUGAAAUUAGUGGGACU |
| 4180 | 1972 | ACAUCUCCCUAGCUUUAACUU |
| 4181 | 1973 | AUUAAUUUAGGUAUCAUUAUC |
| 4182 | 1974 | CUCUCUCUCUCAUUAGAGCAG |
| 4183 | 1975 | UCAGUUCCCGCAUUUGCAGAU |
| 4184 | 1976 | UGCAAUGUCUAGUGCUGUAUA |
| 4185 | 1977 | CUUUGAGCUGAGAAAUAUCAU |
| 4186 | 1978 | AAUAAAUAAUCUCUACUGUGC |
| 4187 | 1979 | AGUAGCUGGGAUUACAGGCGC |
| 4188 | 1980 | AAUGUCCAACAAGGAUUUCAG |
| 4189 | 1981 | AUUUCUUUGGUGAGUUAGAAG |
| 4190 | 1982 | UCUUUAUAUCUCUAUGGAUCA |
| 4191 | 1983 | UAUUUGCAAUACUUUAGGUCC |
| 4192 | 1984 | AGAUACAAUGCCCUGAGUGGA |
| 4193 | 1985 | AUUUGCGGUCCAUAAAGCAC |
| 4194 | 1986 | CAAAUAAAUUACAUAAUCUGA |
| 4195 | 1987 | UUGCAAGGCAACCUAUAAUGC |
| 4196 | 1988 | CUGUGAAGAUCUUAUCAUCAA |
| 4197 | 1989 | UCCCUUUCUGCUGUUUAUUUA |
| 4198 | 1990 | AGAGACUGGGAGAUACUUGCA |
| 4199 | 1991 | UGGGCUGCUAUGUAUCCAUGU |
| 4200 | 1992 | UCAUGUAUUUCUGGUUGUUGA |
| 4201 | 1993 | AAGUGACUUGCCUAGCGUCAC |
| 4202 | 1994 | GAAAGCAUAAGAGAGAAGCCA |
| 4203 | 1995 | GAAAUUAGUGGGACUUGCCCU |
| 4204 | 1996 | GAGAGGUUAAGUGACUUGCCU |
| 4205 | 1997 | CUAAUAGCAUGUAAUUACUUU |
| 4206 | 1998 | UCUUGGGAUAUGAUUGUAAGU |
| 4207 | 1999 | UGUCUAUAGUUCCCUUUCUGC |
| 4208 | 2000 | UCAAACUGUCAGUUUACAAAU |
| 4209 | 2001 | AUAAUUCCAAGAGACCAGAUA |
| 4210 | 2002 | AGGUUCACUCUUAGCAGUCUC |
| 4211 | 2003 | CUACCCAUAGUUCAUCACCCA |
| 4212 | 2004 | CUUGGGUUGCUGUUGAAGGUU |
| 4213 | 2005 | GACCAGAUAUCAACUUUCGGA |
| 4214 | 2006 | AAUAAUCUCUACUGUGCUUCU |
| 4215 | 2007 | GUUACAACUAAUUUCACAGCU |
| 4216 | 2008 | GUCACUUCAACAUUGCUGCCC |
| 4217 | 2009 | CUCAUUCUCUACUAUCGCUGU |
| 4218 | 2010 | AGUGACAUCUCCCUAGCUUUA |
| 4219 | 2011 | UUUGGUGAGUUAGAAGGAAGU |
| 4220 | 2012 | CUUUAUUUAGAUAUACAGUUU |
| 4221 | 2013 | UACUGUGCUUCUCACCCUUCC |
| 4222 | 2014 | UAAGGAUCAUCUAGUCCAAUA |
| 4223 | 2015 | CAUUCUCUACUAUCGCUGUUG |
| 4224 | 2016 | UGCAGACAGCUGCUAUCUGUC |
| 4225 | 2017 | CAUCACUACCCUGUGAUCUGG |
| 4226 | 2018 | CUCUUUAUUUGGUACUGCUGG |
| 4227 | 2019 | ACAUUCCCAAUGCAUGUUGGG |
| 4228 | 2020 | UGCUGGGAUUACAGGUAUGAG |
| 4229 | 2021 | ACAUGGUUUACAGAUAACACA |
| 4230 | 2022 | UUAAUAUGCUGAACUGAAAGC |
| 4231 | 2023 | GUACUAAAUCUGUUGAACAUG |
| 4232 | 2024 | AAGGAAUUCUGUCGGACUGAC |
| 4233 | 2025 | ACAGCUGCUAUCUGUCCUUCA |
| 4234 | 2026 | GUCAUCAGAAAUGCUAUCUUU |
| 4235 | 2027 | CUGGUUUACUCAAUUAUCUUU |
| 4236 | 2028 | AAAUUAAUUUGUCAACAUUUC |
| 4237 | 2029 | ACAUAGUAUGCUUCAAAUUAA |
| 4238 | 2030 | CAUUGUUAAUAUGCUGAACUG |
| 4239 | 2031 | AUGGAGGCUCAGAUGCUGUUU |
| 4240 | 2032 | CAAAGUGGUAGUAAAGAAGUA |
| 4241 | 2033 | UUUCCUCCUGGUAUGCCUAUU |
| 4242 | 2034 | AACUCUAGAAAGCCCAGCACU |
| 4243 | 2035 | UCACCACAACCUCCGCCUCCU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4244 | 2036 | AUUUAACUGCAACAUAAGAGA |
| 4245 | 2037 | UUAUUUCCUUCCCAGUCCACA |
| 4246 | 2038 | GUGAUCUGAAGGGUCACUGCU |
| 4247 | 2039 | UCACUAUAGCAGGCUGAAUUU |
| 4248 | 2040 | AUGUAUUUCUGGUUGUUGACU |
| 4249 | 2041 | AAUACUUUAGGUCCAAGUUUC |
| 4250 | 2042 | CUAAGCAUGAACACACCAUAU |
| 4251 | 2043 | AUGGAUCACCUGGUUUGAGUG |
| 4252 | 2044 | UUUGUUUAAUGAUUUCAAAGU |
| 4253 | 2045 | AUCUCUACUGUGCUUCUCACC |
| 4254 | 2046 | AAGAUCUCCUCAUCUGUCAUC |
| 4255 | 2047 | CAAACAACCUAUAAAUAGGCA |
| 4256 | 2048 | AUUAUGACAACGCACUGGAUC |
| 4257 | 2049 | ACAUGUAAGGGAUGCUAACUA |
| 4258 | 2050 | GAAAUAUUCCAUUAUUUCCAA |
| 4259 | 2051 | AUUCUUUCAUAGGAGAAAUAU |
| 4260 | 2052 | CCAGUCUUUGUCCAUAUGCAU |
| 4261 | 2053 | UCUGACUCAUUCUCUACUAUC |
| 4262 | 2054 | AACAUCAAAGAUUUGGAUAGA |
| 4263 | 2055 | CACAAUGCUUCUUAGCUUCUC |
| 4264 | 2056 | CAGAUAUCAACUUUCGGACCA |
| 4265 | 2057 | AUAUCUGCAACAGAUGUUAUC |
| 4266 | 2058 | AGGCCUAUGUAACUGAUCUCU |
| 4267 | 2059 | UCCUUUGGUUAGAUGGUCUCC |
| 4268 | 2060 | AAUCCCAGGCCCAUCAAACUG |
| 4269 | 2061 | UCCAAAGUUACAGAAGAAUUU |
| 4270 | 2062 | AGAGAAUAAACUGUUAACAAU |
| 4271 | 2063 | UAGUUCCCUUUCUGCUGUUUA |
| 4272 | 2064 | AUGAUCUCAGCUCACCACAAC |
| 4273 | 2065 | UGAGAAAUAUCAUUUAUAGAC |
| 4274 | 2066 | ACUUUAUGGUCACUUCAACAU |
| 4275 | 2067 | AUGUAUCCAUGUGCACUUUUA |
| 4276 | 2068 | AUUGCUUCCUUUGCAGCGAUA |
| 4277 | 2069 | AGUAUUUCUGUAUUGAAAUG |
| 4278 | 2070 | CAUAAAGCACACCACACACAA |
| 4279 | 2071 | UGGUCACUUCAACAUUGCUGC |
| 4280 | 2072 | CUUGUGGGUUCUUCUUCUGUU |
| 4281 | 2073 | AUCUCCCUAGCUUUAACUUAU |
| 4282 | 2074 | UUGCCGAGGCUGGAGUGCAAU |
| 4283 | 2075 | AGUAUAACAUAGUAUGCUUCA |
| 4284 | 2076 | AGGGACUACUCUCUAACUUAA |
| 4285 | 2077 | AGAACGAGUAUAGAUUGAUUU |
| 4286 | 2078 | AAUAUAAUUAUUUACACGAUC |
| 4287 | 2079 | UUGGUUCCCAACAAAUUAAUU |
| 4288 | 2080 | AAGGCCUCUCUCUCUCAUUAG |
| 4289 | 2081 | GAUAGAUGUAAGGAUCAGGUG |
| 4290 | 2082 | AUCCAUCUCAAGACAGCGAUU |
| 4291 | 2083 | AUCUGAAUAACAUAAAGAAUA |
| 4292 | 2084 | UGUUUAAUAUUAAACACAUUC |
| 4293 | 2085 | CUUCUAUAACACAAAUUGUUA |
| 4294 | 2086 | AAUAACAUAAAGAAUAAAUAC |
| 4295 | 2087 | CAAUGCAUUAGUAGCUACAGG |
| 4296 | 2088 | AAGCCUGAAAGAAAUCUGAAU |
| 4297 | 2089 | UGAAGGGUCACUGCUCCAAGG |
| 4298 | 2090 | UAUAGACAAAUAUCUCAAACU |
| 4299 | 2091 | GUUGAGUGCUGAAGAAUCCCG |
| 4300 | 2092 | ACCAAGAGAUUCAACCGGGGA |
| 4301 | 2093 | CUUUAUAUCUCUAUGGAUCAC |
| 4302 | 2094 | AUAAAUACCUUUAAUCCAAAG |
| 4303 | 2095 | AAAGUGGUAGUAAAGAAGUAC |
| 4304 | 2096 | AAGGAAUAUAAUUAUUUACAC |
| 4305 | 2097 | AGGCUUACAAAUAAAUUACAU |
| 4306 | 2098 | UCUCAACAUGUAAGGGAUGCU |
| 4307 | 2099 | GAUUAAUGUAUCUAUUUCCUC |
| 4308 | 2100 | ACCUGAACUCACCUAGCAGGA |
| 4309 | 2101 | AGUAAAUGCUACAAGUUGUAU |
| 4310 | 2102 | AGUUGUAUAGAAUACUCGUAC |
| 4311 | 2103 | UCAUAAGCACAAGAGAGGAUU |
| 4312 | 2104 | UGCUAUGUAUCCAUGUGCACU |
| 4313 | 2105 | CAGAAGAAUUUCACUACACAU |
| 4314 | 2106 | AUAUCUCUGCCCUGCAUGCUC |
| 4315 | 2107 | ACCUUUAAUCCAAAGUUACAG |
| 4316 | 2108 | AUCCUCAUGGGAUUAUGACAA |
| 4317 | 2109 | AAUUUGUAUCAUAAGUAAAUG |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4318 | 2110 | AGUCACUAAUGUACUGAUUUU |
| 4319 | 2111 | UCAAAUUAAUAUUACCGUUUC |
| 4320 | 2112 | GAUUUGGAUAGACUCACCUGU |
| 4321 | 2113 | UUGUUGCCGAGGCUGGAGUGC |
| 4322 | 2114 | CUACACAGACACUCCGCAGAU |
| 4323 | 2115 | AAAUCCAAAGCUUGCAGGCAC |
| 4324 | 2116 | AUAUCUCAGUUCCCGCAUUUG |
| 4325 | 2117 | AGUCUUUGUCCAUAUGCAUUU |
| 4326 | 2118 | AUUAAUUCCUUCUUGGGUUGC |
| 4327 | 2119 | UGUGGAUAUAUGGAUGGUUAG |
| 4328 | 2120 | UUGUUUAAAUGUGGUUUCUCC |
| 4329 | 2121 | AGACACUCCGCAGAUAUUUUU |
| 4330 | 2122 | UGUGAAUCCUUCAGCAUCACU |
| 4331 | 2123 | CAUCUAGUCCAAUACACUUAU |
| 4332 | 2124 | CUCGAUUGUACCAAAUGUGAA |
| 4333 | 2125 | AUCUUUGUUUACUUAAUGUCC |
| 4334 | 2126 | UAACCCUGUUUAUGUUAUUU |
| 4335 | 2127 | AUUACCCAACAUGGUGACUGA |
| 4336 | 2128 | CAUAAUCUGAGGGAGUAGGAA |
| 4337 | 2129 | AUAAACCCAUUGAGCAAAGGA |
| 4338 | 2130 | AGAUGUGGAUAUAUGGAUGGU |
| 4339 | 2131 | AGCUUAGAUAAAGACCAAGAG |
| 4340 | 2132 | UGGAGAGAAUUUCAAGACAUU |
| 4341 | 2133 | ACACAUUCCCAAUGCAUGUUG |
| 4342 | 2134 | CAAGUUCCCAUUUAUUUCCUU |
| 4343 | 2135 | CAACACUCACAAUGCUUCUUA |
| 4344 | 2136 | AUGAAUACAAAUUUAUAAAAG |
| 4345 | 2137 | UGAAUAUUAACUGCAAGUAGC |
| 4346 | 2138 | AGAGGGUGGUGUGACCUCUUU |
| 4347 | 2139 | UGCAGCGAUAAUCAGAGGAGU |
| 4348 | 2140 | AUAUUCAUUUGGUCACUUAAA |
| 4349 | 2141 | UGCAAGUUCAACCCAAUUAAG |
| 4350 | 2142 | GAAUCAACAUUGAAAGAUGUG |
| 4351 | 2143 | UAAAUAGAUAUAUGGUGAAAU |
| 4352 | 2144 | AGAUGUUAUGAGUAUAAUCCC |
| 4353 | 2145 | GUAGCUUAGAUAAAGACCAAG |
| 4354 | 2146 | AGUCAGGCUGGAGAGAGGCUU |
| 4355 | 2147 | AUCUUAUCAUCAAUAAUGAAU |
| 4356 | 2148 | CAACAUGGUGACUGAUUUGAG |
| 4357 | 2149 | UGGGAAGUGGUUUGGAGCUGU |
| 4358 | 2150 | AAGAUCUUAUCAUCAAUAAUG |
| 4359 | 2151 | CAUUGCUCUGGAAUUCCAGUG |
| 4360 | 2152 | AGAAAUCUGAAUAACAUAAAG |
| 4361 | 2153 | ACAUUAACGUUCUUUCCUUUU |
| 4362 | 2154 | AGGGAAAGAGAAUAAACUGUU |
| 4363 | 2155 | CAGGAUUCUGGAGCUCUGGAG |
| 4364 | 2156 | CAAAUGCUGAAUUUCAGUCCU |
| 4365 | 2157 | CAACACUAUGAAGAGGGAGUG |
| 4366 | 2158 | AGGGCACACUAGCAACAUCAA |
| 4367 | 2159 | GAAGUCAUUACCCAACAUGGU |
| 4368 | 2160 | CAACUUUCUGUAAUUUACAAA |
| 4369 | 2161 | CAUCUCCCUAGCUUUAACUUA |
| 4370 | 2162 | GAAAUAGGUGAUACAUAGGAA |
| 4371 | 2163 | AACAACCAUAAAAUAGGCAGA |
| 4372 | 2164 | UGUGACCACAUCAGUCAGAGA |
| 4373 | 2165 | UACAAUGCCCUGAGUGGAUUU |
| 4374 | 2166 | AGUCCACAUGCAAAUACACGU |
| 4375 | 2167 | AGUCUUACUCAUGAGGGAGAU |
| 4376 | 2168 | UAGCUUAGAUAAAGACCAAGA |
| 4377 | 2169 | AUUUGCAAGGCAACCUAUAAU |
| 4378 | 2170 | AUUUGUCAACAUUCUCAAUG |
| 4379 | 2171 | GUAUGCUCUGGUCUUGGUGCG |
| 4380 | 2172 | CACUAUAGCAGGCUGAAUUUG |
| 4381 | 2173 | CAGAUUCAGUUAGACAUUGUU |
| 4382 | 2174 | UAUGGAUGGUUAGAUGGAUGG |
| 4383 | 2175 | CUUAGCUUCUCUAAGAUCUCC |
| 4384 | 2176 | UCCUCCUGGGAAGAUAGAGCG |
| 4385 | 2177 | AGGUCAGAAGGAUGGAACCAU |
| 4386 | 2178 | CAACAGAUGUUAUCAAGGGGG |
| 4387 | 2179 | CAACUACUGCAAACAACCUAU |
| 4388 | 2180 | UCACCUUCCACCAUUUCAAUU |
| 4389 | 2181 | AAUGGAGGCUCAGAUGCUGUU |
| 4390 | 2182 | CUAGUAUUAUCCCACUACAUU |
| 4391 | 2183 | CAUGUUCACACAGUACUUGCU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4392 | 2184 | GUACACACAGGUGUGCACAUG |
| 4393 | 2185 | ACACGAGAUCAGCAAGAACGA |
| 4394 | 2186 | ACUUCAACAUUGCUGCCCUGU |
| 4395 | 2187 | GUUCCCACCAUAGUGCUUCGU |
| 4396 | 2188 | AAUUCUGAUAAACAAUGAAAA |
| 4397 | 2189 | AACAGGCAGAGACAGUCCUAC |
| 4398 | 2190 | CUGUGCUUCUCACCCUUCCCU |
| 4399 | 2191 | AAUUACAUAAUCUGAGGGAGU |
| 4400 | 2192 | AGCGAUAAUCAGAGGGAGUCAG |
| 4401 | 2193 | UGAUUGGGAUGUAGCCUUCAC |
| 4402 | 2194 | UGGGACUUGCCCUAUUGGUUA |
| 4403 | 2195 | UGGAUCACCUGGUUUGAGUGC |
| 4404 | 2196 | UUGGUCAGGCUGGUCUCGAAC |
| 4405 | 2197 | UCCUACAUAUUUGUUUAAUGA |
| 4406 | 2198 | ACCACAUCAGUCAGAGAGCCA |
| 4407 | 2199 | AGAGAAACAACUUUCUGUAAU |
| 4408 | 2200 | UCCUUCUUGGGUUGCUGUUGA |
| 4409 | 2201 | UACAGACAACAGGAAGCAAUU |
| 4410 | 2202 | UGGAAUCAACAUUGAAAGAUG |
| 4411 | 2203 | AUAAUCUGAGGGAGUAGGAAA |
| 4412 | 2204 | AGUGGUUUGGAGCUGUGGGUUG |
| 4413 | 2205 | UGCCUAGCGUCACAUAGCAAU |
| 4414 | 2206 | AUCCCGAGAAGAAUAUUGUCA |
| 4415 | 2207 | UAUUAAAGUUCUCACCUAAAA |
| 4416 | 2208 | AAAGCAAUAUUAUAACAAUAU |
| 4417 | 2209 | AUCCCAAUGCAUGUUGGGUU |
| 4418 | 2210 | CUAGCUUUAACUUAUAGAUAA |
| 4419 | 2211 | CAUCCAUACAGGUCUCUGUGA |
| 4420 | 2212 | UGUACUCGAAGGAUGGGCUGC |
| 4421 | 2213 | UCCAAAGCUUGCAGGCACUCU |
| 4422 | 2214 | AGGUGGUUAAACUCAAACAUU |
| 4423 | 2215 | AUUUGUUUAAUGAUUUCAAAG |
| 4424 | 2216 | UUGGUACAAAGUGGUAGUAAA |
| 4425 | 2217 | UAUGAAGAGGGAGUGUGCAUC |
| 4426 | 2218 | CAAAUAUUUACAAUGACACAC |
| 4427 | 2219 | CUGAAGGAAGAGAGAUCUCUG |
| 4428 | 2220 | UGCUCUGGAAUUCCAGUGAAU |
| 4429 | 2221 | AGAGAGGCCUAUGUAACUGAU |
| 4430 | 2222 | GAAUACAGCUGACAGUCUCUC |
| 4431 | 2223 | AAGUUUCAAACUGCAAUAUUU |
| 4432 | 2224 | CUGACCUCAGGUGAUCCGCCU |
| 4433 | 2225 | ACUGGGAACAGUCAACAGAAA |
| 4434 | 2226 | GUUAUGAGUAUAAUCCCAGUA |
| 4435 | 2227 | UUGUUUACUUAAUGUCCAACA |
| 4436 | 2228 | CUAUAUAGUUUGCUGAAACUC |
| 4437 | 2229 | AUUCAUUUGGUCACUUAAAGG |
| 4438 | 2230 | CUUAAACGUGAUAUUUGCCAU |
| 4439 | 2231 | CACCACAACCUCCGCCUCCUG |
| 4440 | 2232 | AAUGUGGUUUCUCCUAUGAGG |
| 4441 | 2233 | UGAGGGAGAUGGUGAGGUGUA |
| 4442 | 2234 | UGGGUUAUAUUCAUUUGGUCA |
| 4443 | 2235 | AACGCACUGGAUCCUUGCUAA |
| 4444 | 2236 | UUACUUUGCUCAGGAGUGAUC |
| 4445 | 2237 | CUCUGCAACUUGUAAGUGUUU |
| 4446 | 2238 | CUCUAAGAUCUCCUCAUCUGU |
| 4447 | 2239 | AGGAUGUCACAGUUUCAGUUU |
| 4448 | 2240 | UCUCUACUGUGCUUCUCACCC |
| 4449 | 2241 | AGAAUUUCAAGACAUUUAUGA |
| 4450 | 2242 | UCACUGUGGGAGUUGUCAUCA |
| 4451 | 2243 | AAUACUUAUUAGAAAUAUACA |
| 4452 | 2244 | AGUCCUCUUGUUCAGAGCUCA |
| 4453 | 2245 | CAAACACAACACUAUGAAGAG |
| 4454 | 2246 | CAGCUUCUAAAGGAGACUCCG |
| 4455 | 2247 | UGGGACCAUCCACUAACUCCC |
| 4456 | 2248 | AUCAAAGAUUUGGAUAGACUC |
| 4457 | 2249 | UGGGAUUACAGGCGCCCGCCA |
| 4458 | 2250 | CUAACCAACAGAAAGAUUAUA |
| 4459 | 2251 | AAGUAGCUAUCUAAAUAAUUA |
| 4460 | 2252 | CUUUAUGGUCACUUCAACAUU |
| 4461 | 2253 | AGGUAUUAAGGAGAUUAACAA |
| 4462 | 2254 | AAAUUAAGAAGCCUUCUAUAA |
| 4463 | 2255 | ACAGUCAUGCACAAUCCAUAU |
| 4464 | 2256 | UCAGGGCACACUAGCAACAUC |
| 4465 | 2257 | AGACUCAGGCUUAAACGUGAU |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4466 | 2258 | GGACCAUCCACUAACUCCCAG |
| 4467 | 2259 | CUGAAUAACAUAAAGAAUAAA |
| 4468 | 2260 | UGGGUUGCUGUUGAAGGUUCA |
| 4469 | 2261 | UGCUACAAGUUGUAUAGAAUA |
| 4470 | 2262 | CUAUAGUUCCCUUUCUGCUGU |
| 4471 | 2263 | GUGUGCAUCUUUGAGAAACCU |
| 4472 | 2264 | CUAGGUAUAGGGUCUGCUUUU |
| 4473 | 2265 | UCUAUUUCCUCCUGGUAUGCC |
| 4474 | 2266 | AAUAUACAUAACUCUCCAAUA |
| 4475 | 2267 | GUAAAGCUCAUGUAUUUCUGG |
| 4476 | 2268 | UUCCCUUUCUGCUGUUUAUUU |
| 4477 | 2269 | CACAUGCAAAUACACGUUCAG |
| 4478 | 2270 | UCGAGUCACCACCUCAGGUGC |
| 4479 | 2271 | GAGGUGAUAUCUCAGUUCCCG |
| 4480 | 2272 | GUCUUGGUGCGAUAACUGGUG |
| 4481 | 2273 | GUUUACUAUAUCACCUUUCUC |
| 4482 | 2274 | CUCUCUGCAACUUGUAAGUGU |
| 4483 | 2275 | ACUUUCGGACCAUAAGCUUUU |
| 4484 | 2276 | AAUAUUGAUUGGGAUGUAGCC |
| 4485 | 2277 | GUUUGAGUGCAGGAAAUCCAA |
| 4486 | 2278 | CAGAAUUUCAUUAUAAUUAA |
| 4487 | 2279 | AGUACUUGCUCUGGUAUUUUU |
| 4488 | 2280 | UUUCCAAGUUCCCAUUUAUUU |
| 4489 | 2281 | AAACAGCUUCUUUCUAAUACU |
| 4490 | 2282 | UGCUAACAACAUUAACGUUCU |
| 4491 | 2283 | AGGUCCAAGUUUCAAACUGCA |
| 4492 | 2284 | UUCAGUCCUCUUGUUCAGAGC |
| 4493 | 2285 | UUCUCAACAUGUAAGGGAUGC |
| 4494 | 2286 | GAAGGAAGAGAGAUCUCUGGG |
| 4495 | 2287 | UGUAGAUGUUAUGAGUAUAAU |
| 4496 | 2288 | AGGCACUCUCUGCAGACAGCU |
| 4497 | 2289 | ACAUCUGACUCAUUCUCUACU |
| 4498 | 2290 | CCUCUUUAUUUGGUACUGCUG |
| 4499 | 2291 | UCAAGCCUCUCCCAACUUUUA |
| 4500 | 2292 | UCAUGAGGGAGAUGGUGAGGU |
| 4501 | 2293 | ACAUUGAAAGAUGUGCCCUCG |
| 4502 | 2294 | UCUGCCCUGCAUGCUCUGCGC |
| 4503 | 2295 | CUCUGGGCGCUCUUUCUCCUU |
| 4504 | 2296 | CACCACCCUAACACAACUGAU |
| 4505 | 2297 | ACAUAAUCUGAGGGAGUAGGA |
| 4506 | 2298 | CAAUAUCUGCAACAGAUGUUA |
| 4507 | 2299 | UCAAUGCUAAUAGCAUGUAAU |
| 4508 | 2300 | CAUGGUUUACAGAUAACACAU |
| 4509 | 2301 | UGUAAGUGUUUAGGUUCACUC |
| 4510 | 2302 | AUAUUAUAACAAUAUCAAAUA |
| 4511 | 2303 | UCUAUUCAUUUGAAAGGUAAA |
| 4512 | 2304 | AUGGGCUGCUAUGUAUCCAUG |
| 4513 | 2305 | GAUAUAUUAUUAUCAAAUCUU |
| 4514 | 2306 | CUCAGGAUUCUGGAGCUCUGG |
| 4515 | 2307 | AUGUAAGGGAUGCUAACUAAU |
| 4516 | 2308 | AAACUGUCAGUUUACAAAUGC |
| 4517 | 2309 | GAAUUCUGUCGGACUGACAUU |
| 4518 | 2310 | AUAGUGCUUCGUUUACUUUGC |
| 4519 | 2311 | AUCUCAGUUCCCGCAUUUGCA |
| 4520 | 2312 | UAUUGAGAAUGACCAAUAAAA |
| 4521 | 2313 | UGGUCACUAAAGGAGUGUGG |
| 4522 | 2314 | GAGUGCUGAAGAAUCCCGGUU |
| 4523 | 2315 | UACCUUUAAUCCAAAGUUACA |
| 4524 | 2316 | ACAUCUAAUGACAAUGCAAGU |
| 4525 | 2317 | CCACACACAAGCACACACAUU |
| 4526 | 2318 | CAGGUGGUUAAACUCAAACAU |
| 4527 | 2319 | UCCACAUGUUCACACAGUACU |
| 4528 | 2320 | UUAUAACAAUAUCAAAUAAAA |
| 4529 | 2321 | UCUUGCAAGUUCAACCCAAUU |
| 4530 | 2322 | CAGUAAAUGCUACAAGUUGUA |
| 4531 | 2323 | UGCAUAUGUUUCAUAAGCACA |
| 4532 | 2324 | CAGCUCACCACAACCUCCGCC |
| 4533 | 2325 | ACUUCCACAUGUUCACACAGU |
| 4534 | 2326 | GUUUACUUAAUGUCCAACAAG |
| 4535 | 2327 | UAAAUACCUUUAAUCCAAAGU |
| 4536 | 2328 | CUAGCAACAUCAAAGAUUUGG |
| 4537 | 2329 | ACUCUAGAAAGCCCAGCACUA |
| 4538 | 2330 | AUACCUUUAAUCCAAAGUUAC |
| 4539 | 2331 | AGAAAGUCCCAUCUUUGUUUA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4540 | 2332 | CAAGGCAACCUAUAAUGCCAU |
| 4541 | 2333 | CCUCAUUAGAAAUAAACCCAU |
| 4542 | 2334 | AGGAAAUCCAAAGCUUGCAGG |
| 4543 | 2335 | UCUUCAUUAUCCAGACCGUCA |
| 4544 | 2336 | ACAUAAACACGUACACUAUAU |
| 4545 | 2337 | GUGUUUGGAGUUCUAAUAGUG |
| 4546 | 2338 | ACAGACACUCCGCAGAUAUUU |
| 4547 | 2339 | CUAAAUAAUUAACAAUAUUAG |
| 4548 | 2340 | CUGUUGAUUCCUCUUGGGUA |
| 4549 | 2341 | AGCUCUGGAGUUCCAUUAGUG |
| 4550 | 2342 | GUGAUAUUAUAGAAUCUCUCA |
| 4551 | 2343 | ACCUAGCAGGAUGUCACAGUU |
| 4552 | 2344 | UUUCACCGUUUGAGCUUUAUU |
| 4553 | 2345 | UGUCACAGUUUCAGUUUCAGU |
| 4554 | 2346 | CCUUGCUAACAACAUUAACGU |
| 4555 | 2347 | AGCUUUAUUUAGAUAUACAGU |
| 4556 | 2348 | UAUUUGCAUCCCAGGAUUUCA |
| 4557 | 2349 | AUUGAAAUUAGUGGGACUUGC |
| 4558 | 2350 | UGUAUGCUCUGGUCUUGGUGC |
| 4559 | 2351 | UCACCCUUCCCUGACUUUCCC |
| 4560 | 2352 | GUGAUAUCUCAGUUCCCGCAU |
| 4561 | 2353 | CAACAGGAAGCAAUUUCGUGU |
| 4562 | 2354 | CUACCGAAUGAUAUACAGUA |
| 4563 | 2355 | CUCUUCAUCUUCUUCUUCAGA |
| 4564 | 2356 | CACUGUGGGAGUUGUCAUCAG |
| 4565 | 2357 | AAGGAUGGAACCAUACCAUCA |
| 4566 | 2358 | UGUUCCAGUCUUUGUCCAUA |
| 4567 | 2359 | AUUACAGGCCCAGAUUCGUUU |
| 4568 | 2360 | GUUUGGAGUAAUCGUGCCCAU |
| 4569 | 2361 | UGAAAGAUGUGCCCUCGUUAU |
| 4570 | 2362 | AAUGUGAAUCCUUCAGCAUCA |
| 4571 | 2363 | CUCUAGGUAUAGGGUCUGCUU |
| 4572 | 2364 | GUUUCUAUUCAUUUGAAAGGU |
| 4573 | 2365 | ACUCAUGAGGGAGAUGGUGAG |
| 4574 | 2366 | CUCAGCUCACCACAACCUCCG |
| 4575 | 2367 | ACACCAUAUUCCGAAACAGAA |
| 4576 | 2368 | AAUUUCAUUAAUAAUUAAUUC |
| 4577 | 2369 | ACACCACACACAAGCACACAC |
| 4578 | 2370 | AGAGGGAGUGUGCAUCUUUGA |
| 4579 | 2371 | AAACGUUAUAAAUUGUCAAAA |
| 4580 | 2372 | AGUCAUGCACAAUCCAUAUUU |
| 4581 | 2373 | GUAUUUCUGGUUGUUGACUGU |
| 4582 | 2374 | UAUCUCAGUUCCCGCAUUUGC |
| 4583 | 2375 | AGUGCUGAAGAAUCCCGGUUG |
| 4584 | 2376 | GAGUUGUCAUCAGAAAUGCUA |
| 4585 | 2377 | CACUACUUCACAGGAAAGGAG |
| 4586 | 2378 | CUCUAUGUUGGUCAGGCUGGU |
| 4587 | 2379 | UCGAAGGAUGGGCUGCUAUGU |
| 4588 | 2380 | AGAAUUAAACUCUAGAAAGCC |
| 4589 | 2381 | AUCACUGUGGGAGUUGUCAUC |
| 4590 | 2382 | CUAUAUCACCUUUCUCUAGAU |
| 4591 | 2383 | AAAUGUGAAUCCUUCAGCAUC |
| 4592 | 2384 | ACACACAAAUAUUUACAAUGA |
| 4593 | 2385 | ACUCGAUUGUACCAAAUGUGA |
| 4594 | 2386 | AAGAAUCCUACCUGAAUGAUA |
| 4595 | 2387 | CAUAAAGAAUAAAUACUUGAG |
| 4596 | 2388 | AUCAGAUACAAUGCCCUGAGU |
| 4597 | 2389 | ACAUCACUACCCGUGAUCUG |
| 4598 | 2390 | UGCAAACAACCUAUAAAUAGG |
| 4599 | 2391 | CAUAGUUGUAAUCCCUGUUUA |
| 4600 | 2392 | ACAGUCCUACAUAUUUGUUUA |
| 4601 | 2393 | GGGAUUAUGACAACGCACUGG |
| 4602 | 2394 | UCCUUGCUAACAACAUUAACG |
| 4603 | 2395 | ACGAAGUCAUUACCCAACAUG |
| 4604 | 2396 | UACUCAUGAGGGAGAUGGUGA |
| 4605 | 2397 | AGAACUAAGCAUGAACACACC |
| 4606 | 2398 | AAUCAACAUUGAAAGAUGUGC |
| 4607 | 2399 | UCUUUGUUUAAAUGUGGUUUC |
| 4608 | 2400 | CUUUGGUUAGAUGGUCUCCCU |
| 4609 | 2401 | AGAUCAGCAAGAACGAAGUCA |
| 4610 | 2402 | GUUUGCUGAAACUCUAAAGAA |
| 4611 | 2403 | AGAAGCCUUCUAUAACACAAA |
| 4612 | 2404 | CUUUGCUUAACUGAAUAUUAA |
| 4613 | 2405 | AUAUCAACUUUCGGACCAUAA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4614 | 2406 | ACACACAUAUUCCUCUCCACU |
| 4615 | 2407 | AUAACAUAGUAUGCUUCAAAU |
| 4616 | 2408 | CAAGACACAGUCAUGCACAAU |
| 4617 | 2409 | CAGAUAACACAUUCUGACAAA |
| 4618 | 2410 | GUUUAAAUGUGGUUUCUCCUA |
| 4619 | 2411 | AAGCAGCAUAUCUGAGGUGAC |
| 4620 | 2412 | UGGAGUAAUCGUGCCCAUUGC |
| 4621 | 2413 | ACGGUGGAAGUGACCACUUUA |
| 4622 | 2414 | ACCACAACCUCCGCCUCCUGG |
| 4623 | 2415 | AGCAAUGGAUUCAACCACAGA |
| 4624 | 2416 | AUUAGUGGGACUUGCCCUAUU |
| 4625 | 2417 | AGUUUACCCUCUUUCCAGCAG |
| 4626 | 2418 | CCUCUUCAUCUUCUUCUUCAG |
| 4627 | 2419 | AGUGGGACUUGCCCUAUUGGU |
| 4628 | 2420 | GUGUUCCCAGUCUUUGUCCAU |
| 4629 | 2421 | AGGUUCAGAACCUGAACUCAC |
| 4630 | 2422 | GAGGAGGUCAAGCCUCUCCCA |
| 4631 | 2423 | CUGGUUGUUGACUGUUUCUUU |
| 4632 | 2424 | CCUAUGAGGAUUUCCUAGGUU |
| 4633 | 2425 | AAGGGUCACUGCUCCAAGGUC |
| 4634 | 2426 | CUAUUGAAAUUAGUGGGACUU |
| 4635 | 2427 | AAGAGAGAUCUCUGGGCGCUC |
| 4636 | 2428 | AACCCAAAGUCAGUCAAUUUA |
| 4637 | 2429 | CUAAUGAAUAGGGCUUCCUAA |
| 4638 | 2430 | UGGAUAUAUGGAUGGUUAGAU |
| 4639 | 2431 | UCCUAACCAGGUAUUGGGCUC |
| 4640 | 2432 | UCAUGACCAGAAUUUCAUUAA |
| 4641 | 2433 | AUAAGCCUAUGGAAUAAUUG |
| 4642 | 2434 | CAUCUCCUGAACAUAAACACG |
| 4643 | 2435 | UGAGAUACAAUUCUGAUAAAC |
| 4644 | 2436 | GAUCUCCUCAUCUGUCAUCUU |
| 4645 | 2437 | GUGACUUGCCUAGCGUCACAU |
| 4646 | 2438 | UAGAUGUUAUGAGUAUAAUCC |
| 4647 | 2439 | GUCACUAAUGUACUGAUUUUU |
| 4648 | 2440 | UCCAAGUUUCAAACUGCAAUA |
| 4649 | 2441 | AGCUUCUUUCUAAUACUUAUU |
| 4650 | 2442 | UCCUGGGUUCAAGCGAUUCUC |
| 4651 | 2443 | CGGACUGACAUUUCUUGGGAU |
| 4652 | 2444 | GGAAGAGGUACUUAGAGCCAA |
| 4653 | 2445 | CUUAUCAUCAAUAAUGAAUAU |
| 4654 | 2446 | GACUUCUCUAGGUAUAGGGUC |
| 4655 | 2447 | AGGCUAGUAUUUAUCCCACUA |
| 4656 | 2448 | AGAUGUGCCCUCGUUAUCUCA |
| 4657 | 2449 | UGUAGCCUUCACUGACCUCCC |
| 4658 | 2450 | UAUUCAUUUGAAAGGUAAAGA |
| 4659 | 2451 | AAUGAAUUGGAAGGCUGCCAC |
| 4660 | 2452 | CAAGCCUGAAAGAAAUCUGAA |
| 4661 | 2453 | CUGUGGUUGAGUGCUGAAGAA |
| 4662 | 2454 | AACUGAAUAUUAACUGCAAGU |
| 4663 | 2455 | GUAUGCUCAAAGUCUGAAGGA |
| 4664 | 2456 | AAAUAUCUCAAACUAUCAAAA |
| 4665 | 2457 | CUUGUCCUGUUGCAAUGUCUA |
| 4666 | 2458 | UGAAAGCCCUUCCUGAACACA |
| 4667 | 2459 | AAUAUCCUGUUGGACAAGAAA |
| 4668 | 2460 | UGAGGAUUUCCUAGGUUCAGA |
| 4669 | 2461 | ACAGAAAUAGGUGAUACAUAG |
| 4670 | 2462 | AGAAGCUCAAGUACAGUUAUA |
| 4671 | 2463 | UCUGCUGUAGGCAGGGCAUUG |
| 4672 | 2464 | CUAACUAUGAAUAGGGCUUC |
| 4673 | 2465 | UACCCAACAUGGUGACUGAUU |
| 4674 | 2466 | AGUCAUUACCCAACAUGGUGA |
| 4675 | 2467 | GAUUUCAGUAUUCUACAUUUA |
| 4676 | 2468 | CUCAACAUGUAAGGGAUGCUA |
| 4677 | 2469 | GGACAUCUAAUGACAAUGCAA |
| 4678 | 2470 | UCUUUCAUAGGAGAAAUAUUC |
| 4679 | 2471 | AUGUAGCCUUCACUGACCUCC |
| 4680 | 2472 | CUUCAUCCAUACAGGUCUCUG |
| 4681 | 2473 | AGGCUUAUAAGAAGUUUCUAU |
| 4682 | 2474 | GCAACAGAUGUUAUCAAGGGG |
| 4683 | 2475 | CAGUAGACAUCACUACCCUGU |
| 4684 | 2476 | CUGCUAUGUAUCCAUGUGCAC |
| 4685 | 2477 | CAAGAGAGGAUUAAUUUAGGU |
| 4686 | 2478 | UGUUUACUAUAUCACCUUUCU |
| 4687 | 2479 | AUCCAAAGCUUGCAGGCACUC |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4688 | 2480 | AUGCAUGUUGGGUUAUAUUCA |
| 4689 | 2481 | AUGGACACACAAAUAUUUACA |
| 4690 | 2482 | AUUUCAUUAAUAAUUAAUUCC |
| 4691 | 2483 | CAGUCCUACAUAUUUGUUUAA |
| 4692 | 2484 | UGGUACUGCUGGUGAAGCAAU |
| 4693 | 2485 | ACCAGAUAUCAACUUUCGGAC |
| 4694 | 2486 | AGAAACAGCUUCUUUCUAAUA |
| 4695 | 2487 | GAGGUUUGAAUGCAAGAGGGA |
| 4696 | 2488 | ACCAUAGUGCUUCGUUUACUU |
| 4697 | 2489 | AACUCCCAGUUUACCCUCUUU |
| 4698 | 2490 | AAGAAUCCCGGUUGUUACUAU |
| 4699 | 2491 | CACACAAAUAUUUACAAUGAC |
| 4700 | 2492 | CUGUAUAAACAGUACCUGAUG |
| 4701 | 2493 | UUCCCAGUCCACAUGCAAAUA |
| 4702 | 2494 | GCAAUAUCUGCAACAGAUGUU |
| 4703 | 2495 | CAAAGAACUAAGCAUGAACAC |
| 4704 | 2496 | ACACGAUCUUUGAGCUGAGAA |
| 4705 | 2497 | UCCCAACAAAUUAAUUUGUCA |
| 4706 | 2498 | UGCCCUGCAUGCUCUGCGCUC |
| 4707 | 2499 | UUCUUGGGUUGCUGUUGAAGG |
| 4708 | 2500 | AGGCUUAGAGAAACAACUUUC |
| 4709 | 2501 | CUCAAUGCUAAUAGCAUGUAA |
| 4710 | 2502 | ACAUGGAGGUGAUAUCUCAGU |
| 4711 | 2503 | CAAGUCAUAUAAGGAAUUCUG |
| 4712 | 2504 | ACAUAAGAGACUCAGGCUUAA |
| 4713 | 2505 | AAGUGACCACUUUAUGGUCAC |
| 4714 | 2506 | AGAAGGAGAGAGGCCUAUGUA |
| 4715 | 2507 | UCCUGAACAUAAACACGUACA |
| 4716 | 2508 | GCUGAAUGUACAUAAGUUCUG |
| 4717 | 2509 | ACUGUGGAGUUGUCAUCAGA |
| 4718 | 2510 | CAUGGGAUUAUGACAACGCAC |
| 4719 | 2511 | CAGCUGCUAUCUGUCCUUCAU |
| 4720 | 2512 | AGAGAAUUUCAAGACAUUUAU |
| 4721 | 2513 | CUGACCUCCCAUUUCUUACAG |
| 4722 | 2514 | UCAGUUUACAAAUGCUGAAUU |
| 4723 | 2515 | AGAUCUUAUCAUCAAUAAUGA |
| 4724 | 2516 | ACUAUAUCACCUUUCUCUAGA |
| 4725 | 2517 | CAUAACUUCUAUUGAAAUUAG |
| 4726 | 2518 | GACUUCCACAUGUUCACACAG |
| 4727 | 2519 | AGCAGAGGGCAGACAACCUGU |
| 4728 | 2520 | ACUCAAUGCAUUAGUAGCUAC |
| 4729 | 2521 | CAUACAGGUCUCUGUGACCAC |
| 4730 | 2522 | CCCAGUAGACAUCACUACCCU |
| 4731 | 2523 | UGUGGGAGUUGUCAUCAGAAA |
| 4732 | 2524 | AUCAAACUGUCAGUUUACAAA |
| 4733 | 2525 | CUAUCAGAUACAAUGCCCUGA |
| 4734 | 2526 | CUUUACAUACAGACUGUAUGG |
| 4735 | 2527 | AGGCCCAUCAAACUGUCAGUU |
| 4736 | 2528 | AGAAUAUUGUCACUCUUUAUA |
| 4737 | 2529 | GAUCCUUCUCAACUUGUUUUG |
| 4738 | 2530 | CAGGAAAUCCAAAGCUUGCAG |
| 4739 | 2531 | CUUUAAUCCAAAGUUACAGAA |
| 4740 | 2532 | ACUCUAUUAGGGCAUGGACUU |
| 4741 | 2533 | UCUCUGCCCUGCAUGCUCUGC |
| 4742 | 2534 | CUAUCUUUGGUUCCCAACAAA |
| 4743 | 2535 | GUUACUAUUCAUCCUCAGUGG |
| 4744 | 2536 | UUCAAGUUACUCGAUUGUACC |
| 4745 | 2537 | UCAUUACCCAACAUGGUGACU |
| 4746 | 2538 | ACAAUAUUAGGGUUCUUAUUU |
| 4747 | 2539 | CAAAUUAAUUUGUCAACAUUU |
| 4748 | 2540 | UUCCACCACCCUAACACAACU |
| 4749 | 2541 | GUUCAGAGCUCAGAGACUGGG |
| 4750 | 2542 | ACUUCUCUAGGUAUAGGGUCU |
| 4751 | 2543 | CAUAUGUUUCAUAAGCACAAG |
| 4752 | 2544 | AACUGUAAAUGAAUUGGAAGG |
| 4753 | 2545 | CAAAGUGCUGGGAUUACAGGU |
| 4754 | 2546 | ACCAAGUAGCUAUCUAAAUAA |
| 4755 | 2547 | GUUAGAAGGAAGUUAUCCUUU |
| 4756 | 2548 | CAGAAGAUUCAGGAAGUGCCA |
| 4757 | 2549 | CACACAUAUUCCUCUCCACUU |
| 4758 | 2550 | GAAACAACUGUAAAUGAAUUG |
| 4759 | 2551 | GAUAUUAUAGAAUCUCUCAGA |
| 4760 | 2552 | GUCUAGUGCUGUAUAAACAGU |
| 4761 | 2553 | AUGCUGAGGUCAGAAGGAUGG |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4762 | 2554 | ACCUUUGCUUAACUGAAUAUU |
| 4763 | 2555 | AAGCAAUAUUAUAACAAUAUC |
| 4764 | 2556 | AGGAUCAGGUGGUUAAACUCA |
| 4765 | 2557 | CUAUGGAUCACCUGGUUUGAG |
| 4766 | 2558 | UUCCCACUGCCCUAUUCCUAA |
| 4767 | 2559 | UACACAUGGUUUACAGAUAAC |
| 4768 | 2560 | ACUGCCCUAUUCCUAACUCAG |
| 4769 | 2561 | UGCACAAUCCAUAUUUCAAUU |
| 4770 | 2562 | CAGGAUGUCACAGUUUCAGUU |
| 4771 | 2563 | AACUCACCUAGCAGGAUGUCA |
| 4772 | 2564 | GAUCCUUGCUAACAACAUUAA |
| 4773 | 2565 | CACACCACACACAAGCACACA |
| 4774 | 2566 | AGGAGAAGCUCAAGUACAGUU |
| 4775 | 2567 | CCUGUUGCAAUGUCUAGUGCU |
| 4776 | 2568 | GUUGCAAUGUCUAGUGCUGUA |
| 4777 | 2569 | ACUUGAGUUAAAUCUUCUUAC |
| 4778 | 2570 | GCUAAUAGCAUGUAAUUACUU |
| 4779 | 2571 | UCCUCCUGGUAUGCCUAUUUU |
| 4780 | 2572 | CUGGAUCCUUGCUAACAACAU |
| 4781 | 2573 | UCCCUGACUUUCCCACUGCCC |
| 4782 | 2574 | CAAAUAUCUCAAACUAUCAAA |
| 4783 | 2575 | GUGACCACAUCAGUCAGAGAG |
| 4784 | 2576 | AAUAGGUGAUACAUAGGAAAA |
| 4785 | 2577 | UGCAAAUACACGUUCAGAAUU |
| 4786 | 2578 | GUAUUGGGCUCUCUCCACUGG |
| 4787 | 2579 | AUGUCUAGUGCUGUAUAAACA |
| 4788 | 2580 | GUCUCGAACUCCUGACCUCAG |
| 4789 | 2581 | AAACAACUUUCUGUAAUUUAC |
| 4790 | 2582 | UGGUGAAAUAGUAGUCAAAUU |
| 4791 | 2583 | ACUUACAUACAGACUGUAUG |
| 4792 | 2584 | UCCCGAGAAGAAUAUUGUCAC |
| 4793 | 2585 | ACAACCUGGUUUACUCAAUUA |
| 4794 | 2586 | UGUUGAUUCCUCUUGGGUAC |
| 4795 | 2587 | AUAAUUCCACCACCCUAACAC |
| 4796 | 2588 | CCACAUGUUCACACAGUACUU |
| 4797 | 2589 | UGGAGAGGUUAAGUGACUUGC |
| 4798 | 2590 | GAAAGAAAUCUGAAUAACAUA |
| 4799 | 2591 | AUCAUAAGUAAAUGAUGAUUA |
| 4800 | 2592 | GAGCUUUAUUUAGAUAUACAG |
| 4801 | 2593 | AGUUGUCAUCAGAAAUGCUAU |
| 4802 | 2594 | CCGGUUGUUACUAUUCAUCCU |
| 4803 | 2595 | GACAGUCCUACAUAUUUGUUU |
| 4804 | 2596 | CUCCUGGGAAGAUAGAGCGAA |
| 4805 | 2597 | AUGUGCCCUCGUUAUCUCAGG |
| 4806 | 2598 | AGUGACUUCUCUAGGUAUAGG |
| 4807 | 2599 | UGCUGUUUAUUUAAUUGUAAAG |
| 4808 | 2600 | GUGGGUUCUUCUUCUGUUCCA |
| 4809 | 2601 | CUUGCCUAGCGUCACAUAGCA |
| 4810 | 2602 | ACCCAGGCAAGCAUAAAGCCU |
| 4811 | 2603 | ACAUAUUUGUUUAAUGAUUUC |
| 4812 | 2604 | GUUAAACUCAAACAUUGGGGU |
| 4813 | 2605 | GCAUCUUUGAGAAACCUUUUU |
| 4814 | 2606 | UGUAAGGGAUGCUAACUAAUG |
| 4815 | 2607 | UUCCAAGUUCCAUUUUAUUUC |
| 4816 | 2608 | GUGCAUCUUUGAGAAACCUUU |
| 4817 | 2609 | CAAGAACGAAGUCAUUACCCA |
| 4818 | 2610 | AGGUCAAGCCUCUCCCAACUU |
| 4819 | 2611 | GUUCAGAACCUGAACUCACCU |
| 4820 | 2612 | CACGGUGGAAGUGACCACUUU |
| 4821 | 2613 | AUCUUGCAAGUUCAACCCAAU |
| 4822 | 2614 | UGGGCUCUGCUAUCUUGUGCC |
| 4823 | 2615 | CUAGGUUCAGAACCUGAACUC |
| 4824 | 2616 | CUAGCGUCACAUAGCAAUUUA |
| 4825 | 2617 | CACAUAUUCCUCUCCACUUUU |
| 4826 | 2618 | CUGAAUGAUAUACAGUAAUAU |
| 4827 | 2619 | AUGACCAGAAUUUCAUUAAUA |
| 4828 | 2620 | CACAGAACGAGUAUAGAUUGA |
| 4829 | 2621 | AAACCCAUUGAGCAAAGGAAU |
| 4830 | 2622 | UGGUACAAAGUGGUAGUAAAG |
| 4831 | 2623 | AACUCUAAAGAAAGUGCUUUC |
| 4832 | 2624 | AACAGAAAGAUUAUAUCAAAA |
| 4833 | 2625 | CUGAACUGAAAGCAUAAGAGA |
| 4834 | 2626 | AAGAUGUGCCCUCGUUAUCUC |
| 4835 | 2627 | UCCCUAGCUUUAACUUAUAGA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4836 | 2628 | CAUUUCUCAAUGCUAAUAGCA |
| 4837 | 2629 | CAAAUUAAUAUUACCGUUUCA |
| 4838 | 2630 | AGCCCUUCCUGAACACACAUA |
| 4839 | 2631 | UAUGGAUCACCUGGUUUGAGU |
| 4840 | 2632 | UGUGGGUUCUUCUUCUGUUCC |
| 4841 | 2633 | AGCUUGCAGGCACUCUCUGCA |
| 4842 | 2634 | AAUAUCAUUUAUAGACAAAUA |
| 4843 | 2635 | CUCCUGAACAUAAACACGUAC |
| 4844 | 2636 | AAUGGAUUCAACCACAGAACG |
| 4845 | 2637 | AAUUUCCCGGCACUAUGAGUG |
| 4846 | 2638 | AGUAUUUAUCCCACUACAUCU |
| 4847 | 2639 | AUUUCACCGUUUGAGCUUUAU |
| 4848 | 2640 | AUUUAGUAAUAAAGCUCAUAU |
| 4849 | 2641 | ACUUGUAAGUGUUUAGGUUCA |
| 4850 | 2642 | CUCUCCAAUACAGGGAAGGGG |
| 4851 | 2643 | CUUUCUAAUACUUAUUAGAAA |
| 4852 | 2644 | UGCCCUCGUUAUCUCAGGGCA |
| 4853 | 2645 | ACUCUAAAGAAAGUGCUUUCA |
| 4854 | 2646 | AUAUUCCGAAACAGAAAUAGG |
| 4855 | 2647 | UCACAAGCCUGAAAGAAAUCU |
| 4856 | 2648 | AGGAUCAUCUAGUCCAAUACA |
| 4857 | 2649 | ACCUCUUUAUUUGGUACUGCU |
| 4858 | 2650 | AUCCCUGUUUAUGUUAUUUAA |
| 4859 | 2651 | AGUUUCAAACUGCAAUAUUUU |
| 4860 | 2652 | AGAUUGGAUGCUGAGGUCAGA |
| 4861 | 2653 | ACACUCAAGACACAGUCAUGC |
| 4862 | 2654 | GUGGAUCCUUCUCAACUUGUU |
| 4863 | 2655 | AUGACUACCCAUAGUUCAUCA |
| 4864 | 2656 | AUAUCACCUUUCUCUAGAUCU |
| 4865 | 2657 | GUUAUAUUCUAGCAAGUGUGA |
| 4866 | 2658 | AAAGCAGAGGGCAGACAACCU |
| 4867 | 2659 | ACAAGGAUUUCAGUAUUCUAC |
| 4868 | 2660 | GAAUGUACAUAAGUUCUGUUU |
| 4869 | 2661 | ACAGAACUAUAACUGAAUGCC |
| 4870 | 2662 | AAUCCUACCUGAAUGAUAUAC |
| 4871 | 2663 | UGAGUUAGAAGGAAGUUAUCC |
| 4872 | 2664 | ACUUAAUGUCCAACAAGGAUU |
| 4873 | 2665 | AAUUUGCAAGGCAACCUAUAA |
| 4874 | 2666 | UCUCUGCAGACAGCUGCUAUC |
| 4875 | 2667 | ACUUGAGAAUUAAACUCUAGA |
| 4876 | 2668 | ACUGCAAGUAGCUUAGAUAAA |
| 4877 | 2669 | CUCUCUCUCAUUAGAGCAGUG |
| 4878 | 2670 | CACAUGAAUCGUAUGCUCAAA |
| 4879 | 2671 | AUCUUGGUACAAAGUGGUAGU |
| 4880 | 2672 | GAGACUGGGAGAUACUUGCAC |
| 4881 | 2673 | UGUAAGGAUCAGGUGGUUAAA |
| 4882 | 2674 | CUUAUUCUUCUCUUCAGGGGC |
| 4883 | 2675 | UCUUACUCAUGAGGGAGAUGG |
| 4884 | 2676 | AAGUUACUCGAUUGUACCAAA |
| 4885 | 2677 | CGGAAUACAGCUGACAGUCUC |
| 4886 | 2678 | UGUGACCUCUUUAUUUGGUAC |
| 4887 | 2679 | GUAUAGAAUACUCUGUACACAC |
| 4888 | 2680 | CAUUGUUUAAUAUUAAACACA |
| 4889 | 2681 | UAAGCACAAGAGAGGAUUAAU |
| 4890 | 2682 | CACAUCCAUCUCAAGACAGCG |
| 4891 | 2683 | GAUGUAGCCUUCACUGACCUC |
| 4892 | 2684 | CUUUGUCCAUAUGCAUUUCUU |
| 4893 | 2685 | CAGGGAAAGAGAAUAAACUGU |
| 4894 | 2686 | UAAUGACAAUGCAAGUGAAAA |
| 4895 | 2687 | ACUUCAUUUGCUUGAGUUUUU |
| 4896 | 2688 | CUCAGAGAAAGUCCCAUCUUU |
| 4897 | 2689 | AUCUAUUUCCUCCUGGUAUGC |
| 4898 | 2690 | AGGUAUCAUUAUCUUUGUUUA |
| 4899 | 2691 | CAAAGAUUUGGAUAGACUCAC |
| 4900 | 2692 | UGCUUCUCACCCUUCCCUGAC |
| 4901 | 2693 | UCUGGAAUUCCAGUGAAUUCC |
| 4902 | 2694 | UGCUGAACUGAAAGCAUAAGA |
| 4903 | 2695 | GUAUCAUAAGUAAAUGAUGAU |
| 4904 | 2696 | GUUAUAUUCAUUUGGUCACUU |
| 4905 | 2697 | CAAAGUCAGUCAAUUUAACAG |
| 4906 | 2698 | CACCUUUCUCUAGAUCUUUAA |
| 4907 | 2699 | GUGCAGGAAAUCCAAAGCUUG |
| 4908 | 2700 | GUCAACAUUUCUCAAUGCUAA |
| 4909 | 2701 | CACACACAAGCACACACAUUG |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4910 | 2702 | GCUAUCAGAUACAAUGCCCUG |
| 4911 | 2703 | UGUAAUCCCUGUUUAUGUUAU |
| 4912 | 2704 | CUAAGUAUUCUGUAUUGAGA |
| 4913 | 2705 | ACAGUACUUGCUCUGGUAUUU |
| 4914 | 2706 | ACCAUCCACUAACUCCCAGUU |
| 4915 | 2707 | CAGAAGGAUGGAACCAUACCA |
| 4916 | 2708 | UGGUAUUUGCGGGUCCAUAAA |
| 4917 | 2709 | UGAAUGAUAUACAGUAAUAUC |
| 4918 | 2710 | UGCUUCAACCACAAUUUAAAA |
| 4919 | 2711 | CAUGAUCUCAGCUCACCACAA |
| 4920 | 2712 | CAGUCCUCUUGUUCAGAGCUC |
| 4921 | 2713 | AAUCCCGGUUGUUACUAUUCA |
| 4922 | 2714 | AUAUAAUUAUUUACACGAUCU |
| 4923 | 2715 | GCUGUUCUUAAUUGCUUCCUU |
| 4924 | 2716 | UUGCUGCCCUGUUUGGGCUGC |
| 4925 | 2717 | UCAGGUAUUAAGGAGAUUAAC |
| 4926 | 2718 | UCUCAGGGCACACUAGCAACA |
| 4927 | 2719 | ACUGUUUCUUUGGAAUCAUAG |
| 4928 | 2720 | CUCAGGGCACACUAGCAACAU |
| 4929 | 2721 | CUGUAAAUGAAUUGGAAGGCU |
| 4930 | 2722 | AAGUUACAGAAGAAUUUCACU |
| 4931 | 2723 | AGAGAGGAUUAAUUUAGGUAU |
| 4932 | 2724 | UCUAUUAGGGCAUGGACUUCC |
| 4933 | 2725 | UGGUUCCCAACAAAUUAAUUU |
| 4934 | 2726 | GACAUUUAUGAAUAUGCUUUU |
| 4935 | 2727 | ACCAACAGAAAGAUUAUAUCA |
| 4936 | 2728 | GUUCCUGUACAAAGUACUGGA |
| 4937 | 2729 | ACAUGUUCACACAGUACUUGC |
| 4938 | 2730 | UGCUAAUAGCAUGUAAUUACU |
| 4939 | 2731 | AUAGAUAUAUGGUGAAAUAGU |
| 4940 | 2732 | GUACAGUUAUAUUCUAGCAAG |
| 4941 | 2733 | UAGCGGCUGCUGUUCUUAAUU |
| 4942 | 2734 | CACCGUUUGAGCUUUAUUUAG |
| 4943 | 2735 | ACCAUACCAUCAGCAGGUCUA |
| 4944 | 2736 | CAAGACAUUUAUGAAUAUGCU |
| 4945 | 2737 | GACUGGGAGAUACUUGCACUA |
| 4946 | 2738 | CUUGUAAGUGUUUAGGUUCAC |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4947 | 2739 | AGUAAUCGUGCCCAUUGCUCU |
| 4948 | 2740 | UAAGAGACUCAGGCUUAAACG |
| 4949 | 2741 | ACAUGCAAAUACACGUUCAGA |
| 4950 | 2742 | AAUCCAAAGUUACAGAAGAAU |
| 4951 | 2743 | UCUUUCGCUUCACGGUGGAAG |
| 4952 | 2744 | AUGCUCAAAGUCUGAAGGAAG |
| 4953 | 2745 | AUGGAACAUGGACACACAAAU |
| 4954 | 2746 | AUCAACUUUCGGACCAUAAGC |
| 4955 | 2747 | AGUUACAACUAAUUUCACAGC |
| 4956 | 2748 | AGAUAACACAUUCUGACAAAA |
| 4957 | 2749 | UCCAAUACAAAUGCAGAAAAA |
| 4958 | 2750 | AGCUCAUGUAUUUCUGGUUGU |
| 4959 | 2751 | UCCCAGGAUUUCAUUGAAUUU |
| 4960 | 2752 | CGCUCUUUCUCCUUCUUCUUA |
| 4961 | 2753 | ACAGGAAAGGAGAAGCUCAAG |
| 4962 | 2754 | AGAAUAAACUGUUAACAAUCU |
| 4963 | 2755 | CACAGGAAAGGAGAAGCUCAA |
| 4964 | 2756 | UUCCUCCUGGUAUGCCUAUUU |
| 4965 | 2757 | CAUCUUUCCUGCAGCAGAGUU |
| 4966 | 2758 | CUAGGCUAGUAUUUAUCCCAC |
| 4967 | 2759 | AGAAGAAUCCUACCUGAAUGA |
| 4968 | 2760 | ACCCUAACACAACUGAUUUCA |
| 4969 | 2761 | ACUCUCAGAAGAUUCAGGAAG |
| 4970 | 2762 | AGAGAUCUCUGGGCGCUCUUU |
| 4971 | 2763 | AAAUAUCAUUUAUAGACAAAU |
| 4972 | 2764 | UCCCAAUGCAUGUUGGGUUAU |
| 4973 | 2765 | GUUCUAAUAGUGACAUCUCCC |
| 4974 | 2766 | AUAUCCUGUUGGACAAGAAAA |
| 4975 | 2767 | AUUAUAGAAUCUCUCAGAACU |
| 4976 | 2768 | UCAGGCUUACAAAUAAAUUAC |
| 4977 | 2769 | AUCUCUGGGCGCUCUUUCUCC |
| 4978 | 2770 | CUCUCUCAUUAGAGCAGUGUG |
| 4979 | 2771 | CUCAGGUGAUCCGCCUGCCUU |
| 4980 | 2772 | AGGAGUGAUCUGGGCACAGAA |
| 4981 | 2773 | AUUUCCCGGCACUAUGAGUGA |
| 4982 | 2774 | CCAAUCUAAAGCAACCACAAA |
| 4983 | 2775 | CUAAGAUCUCCUCAUCUGUCA |

TABLE 6-continued

Results for PAK3.
Score threshold: 70. Design: siRNA 21 nt.

| SEQ ID NO | siRNA_id | siRNA guide strand/ AS Sequence |
|---|---|---|
| 4984 | 2776 | UGGAGGUGAUAUCUCAGUUCC |
| 4985 | 2777 | CUUCCACAUGUUCACACAGUA |
| 4986 | 2778 | AGAUGGAUGGAUGUACCUUGG |
| 4987 | 2779 | ACUGCUGGUAUUAUGGGAUAG |
| 4988 | 2780 | UGCUCGGUCUUGGUGCGAUA |
| 4989 | 2781 | AAUAUCUCAAACUAUCAAAAC |
| 4990 | 2782 | AACUCUAUUAGGGCAUGGACU |
| 4991 | 2783 | GAAUAUUAACUGCAAGUAGCU |
| 4992 | 2784 | CCAUAAAUACCUUUAAUCCAA |
| 4993 | 2785 | AAGGAUCAGGUGGUUAAACUC |
| 4994 | 2786 | CUCUCUGCAGACAGCUGCUAU |
| 4995 | 2787 | GAGGGAGUGUGCAUCUUUGAG |
| 4996 | 2788 | UCUUAUCAUCAAUAAUGAAUA |
| 4997 | 2789 | UAAUGAAUAGGGCUUCCUAAC |
| 4998 | 2790 | CCUAGGCUAGUAUUUAUCCCA |
| 4999 | 2791 | AACUUUCUGUAAUUUACAAAA |
| 5000 | 2792 | AUUGAGCAAAGGAAUAUAAUU |
| 5001 | 2793 | AUUCUGAUAAACAAUGAAAAC |
| 5002 | 2794 | AGGCAGAGACAGUCCUACAUA |
| 5003 | 2795 | ACACAGGUGUGCACAUGGAGG |
| 5004 | 2796 | AUUAGGGCAUGGACUUCCACA |
| 5005 | 2797 | GACCAAGAGAUUCAACCGGGG |
| 5006 | 2798 | AGAAAUGCUAUCUUUGGUUCC |
| 5007 | 2799 | GUAAGUGUUUAGGUUCACUCU |
| 5008 | 2800 | AGCAUGAACACACCAUAUUCC |
| 5009 | 2801 | CCAACAGAAAGAUUAUAUCAA |
| 5010 | 2802 | ACCUGAAUGAUAUACAGUAAU |
| 5011 | 2803 | AAGGGAUGCUAACUAAUGAAU |
| 5012 | 2804 | CACAGGUGUGCACAUGGAGGU |
| 5013 | 2805 | CUUCUCAACAUGUAAGGGAUG |
| 5014 | 2806 | UGCUGGUAUUAUGGGAUAGCA |
| 5015 | 2807 | CUGGAGAGAAUUUCAAGACAU |
| 5016 | 2808 | GAAGAAUCCUACCUGAAUGAU |
| 5017 | 2809 | AUGUAAAGCUCAUGUAUUUCU |
| 5018 | 2810 | AUAGUAUGCUUCAAAUUAAUA |
| 5019 | 2811 | AUGGUGAAAUAGUAGUCAAAU |
| 5020 | 2812 | GUCUCUGUGACCACAUCAGUC |
| 5021 | 2813 | GCAUGAACACACCAUAUUCCG |
| 5022 | 2814 | CUUGGUACAAAGUGGUAGUAA |
| 5023 | 2815 | CAUGGGCUCUGCUAUCUUGUG |
| 5024 | 2816 | GCCUAUGUAACUGAUCUCUUU |
| 5025 | 2817 | AAAGAGAAUAAACUGUUAACA |
| 5026 | 2818 | AGUUAGACAUUGUUUAAUAUU |
| 5027 | 2819 | ACCCACCAAGUAGCUAUCUAA |
| 5028 | 2820 | GAUGCUAACUAAUGAAUAGGG |
| 5029 | 2821 | CUAUUCCUAACUCAGGACAUU |
| 5030 | 2822 | AGGAAGUUAUCCUUUGGUUAG |
| 5031 | 2823 | AUGGUGAGGUGUAAGGCUUGC |
| 5032 | 2824 | UCUGGGCGCUCUUUCUCCUUC |
| 5033 | 2825 | AGCUCACCACAACCUCCGCCU |
| 5034 | 2826 | UCAGUUAGACAUUGUUUAAUA |
| 5035 | 2827 | CAGUCUUUGUCCAUAUGCAUU |
| 5036 | 2828 | UUCAUCCUCAGUGGAGGAGCC |
| 5037 | 2829 | ACUGUAAAUGAAUUGGAAGGC |
| 5038 | 2830 | AGUAAAUGAUGAUUAAUGUAU |
| 5039 | 2831 | AGUAAUAAAGCUCAUAUUAGA |
| 5040 | 2832 | UCCUAGGUUCAGAACCUGAAC |
| 5041 | 2833 | AUGCUACAAGUUGUAUAGAAU |
| 5042 | 2834 | GAUACAAUUCUGAUAAACAAU |
| 5043 | 2835 | CAGAGGGCAGACAACCUGUUU |
| 5044 | 2836 | GCUUGCAGGCACUCUCUGCAG |
| 5045 | 2837 | AGUCACCACCUCAGGUGCCAU |
| 5046 | 2838 | CUGCCCUGCAUGCUCUGCGCU |
| 5047 | 2839 | GGGACCAUCCACUAACUCCCA |
| 5048 | 2840 | CAUUAGUAGCUACAGGAUUCU |
| 5049 | 2841 | AGGCAAUAUCUGCAACAGAUG |
| 5050 | 2842 | AGGAUUAAUUUAGGUAUCAUU |
| 5051 | 2843 | GAUUCAACCACAGAACGAGUA |
| 5052 | 2844 | CAUCACAUUGGGUAAGGAGUU |
| 5053 | 2845 | UGUUGACUGUUUCUUUGGAAU |
| 5054 | 2846 | ACAAAUGCUGAAUUUCAGUCC |
| 5055 | 2847 | UGAGUAUAAUCCCAGUAGACA |
| 5056 | 2848 | UGUGCUGAGUUCACUUCAAAU |
| 5057 | 2849 | ACCACCCUAACACAACUGAUU |

TABLE 6-continued

Results for PAK3.
Score threshold: 70. Design: siRNA 21 nt.

| SEQ ID NO | siRNA_id | siRNA guide strand/AS Sequence |
|---|---|---|
| 5058 | 2850 | CUACUCUCAGAAGAUUCAGGA |
| 5059 | 2851 | CAAAGCUUGCAGGCACUCUCU |
| 5060 | 2852 | GAAACAACUUUCUGUAAUUUA |

TABLE 7

Results for TRNP1. Score threshold: 70.
Design: siRNA 21 nt.

| SEQ ID NO | siRNA_id | siRNA guide strand/AS Sequence |
|---|---|---|
| 5061 | 1 | UUUAAUGAGGAAGACUUCCUG |
| 5062 | 2 | UCAAUUCUCAACGUCUUCCUG |
| 5063 | 3 | UUGUUUAAGAAUGAUGACGAU |
| 5064 | 4 | UAAUCUGAUUGCAUCUCAGGG |
| 5065 | 5 | UUAGACUUGAAGCAAUGACAU |
| 5066 | 6 | UUAAUGAGGAAGACUUCCUGA |
| 5067 | 7 | UAAUUCAAUAUACAUUCACUA |
| 5068 | 8 | UAUGGAAAUUUAUUCCUCCUG |
| 5069 | 9 | AACGAAACUAAAUACAAGCUG |
| 5070 | 10 | UAGAGUGGAGGUUCUGAGGAG |
| 5071 | 11 | AUGCUUGCUACGCUUAAUCUG |
| 5072 | 12 | UGUAGCAACAUCUCCAAUUGU |
| 5073 | 13 | UAGGAGUCAAGGUCGGAGUUG |
| 5074 | 14 | UUAAUCUGAUUGCAUCUCAGG |
| 5075 | 15 | UAAUGAGGAAGACUUCCUGAG |
| 5076 | 16 | UAAGGCAGGAGACUAAUUCAA |
| 5077 | 17 | AUCCGUAGUCCUUCCAGCCGG |
| 5078 | 18 | UAGACUUGAAGCAAUGACAUC |
| 5079 | 19 | UGUAAGGUCAAUUCUCAACGU |
| 5080 | 20 | AACAUCUCCAAUUGUACAGUG |
| 5081 | 21 | UAUAUGAAGAAAUUCAGAGCA |
| 5082 | 22 | AAUCUGAUUGCAUCUCAGGGA |
| 5083 | 23 | UCAAUAUACAUUCACUAUGCA |
| 5084 | 24 | ACUAAAUACAAGCUGCUCCAG |
| 5085 | 25 | AAUUCUACAAGUUCUGGGCUA |
| 5086 | 26 | UUGGUCUGCAAAUCAAAGUCA |
| 5087 | 27 | UGCAGAAUUCUACAAGUUCUG |
| 5088 | 28 | UGAAGCAAUGACAUCUAUUAA |
| 5089 | 29 | UGGUCUGCAAAUCAAAGUCAA |

TABLE 7-continued

Results for TRNP1. Score threshold: 70.
Design: siRNA 21 nt.

| SEQ ID NO | siRNA_id | siRNA guide strand/AS Sequence |
|---|---|---|
| 5090 | 30 | UUAUGGAAAUUUAUUCCUCCU |
| 5091 | 31 | UAUACAUUCACUAUGCAGAAU |
| 5092 | 32 | UCACUAUGCAGAAUUCUACAA |
| 5093 | 33 | UUGCAUCUCAGGGACCUGUAG |
| 5094 | 34 | AGGAUGACCACAGCACACCCG |
| 5095 | 35 | UAAAGUGAAAGGCUCCUGUGA |
| 5096 | 36 | AAGAAUGAUGACGAUAUCUUG |
| 5097 | 37 | AUAGACACAGAGGAAAGGCAG |
| 5098 | 38 | UGAAGAAAUUCAGAGCAUCAG |
| 5099 | 39 | UGAUUGCAUCUCAGGGACCUG |
| 5100 | 40 | UUAUCAGGAUGUUUAAAUGUG |
| 5101 | 41 | ACUUGAAGCAAUGACAUCUAU |
| 5102 | 42 | AUAUGAAGAAAUUCAGAGCAU |
| 5103 | 43 | UCGGUCGGUCGGCACCUCGGC |
| 5104 | 44 | AUCCAUAGAGUGGAGGUUCUG |
| 5105 | 45 | AAUCCAGAGGUCCAGAUCCAU |
| 5106 | 46 | UGCAAAUCAAAGUCAACAGGG |
| 5107 | 47 | UCUUCCUGAAGGCAGUGCCCA |
| 5108 | 48 | UACAAGCUGCUCCAGGAACCG |
| 5109 | 49 | UUGAAGCAAUGACAUCUAUUA |
| 5110 | 50 | AAGGUCAAUUCUCAACGUCUU |
| 5111 | 51 | AUAUACAUUCACUAUGCAGAA |
| 5112 | 52 | UCAACGUCUUCCUGAAGGCAG |
| 5113 | 53 | AAGCCGAAUCCAGAGGUCCAG |
| 5114 | 54 | AUGAGGAAGACUUCCUGAGGA |
| 5115 | 55 | AUCACAUCCUUUAAUGAGGAA |
| 5116 | 56 | UCCUGCGGAUCCGUAGUCCUU |
| 5117 | 57 | UUGGAAGGAGCUCAGCCUCCU |
| 5118 | 58 | AUAGAGUGGAGGUUCUGAGGA |
| 5119 | 59 | AAUCAAAGUCAACAGGGCCAG |
| 5120 | 60 | AAAUACAAGCUGCUCCAGGAA |
| 5121 | 61 | UCAGUCGGUCGGUCGGCACCU |
| 5122 | 62 | ACAAGCUGCUCCAGGAACCGU |
| 5123 | 63 | UGAGGAAGACUUCCUGAGGAG |
| 5124 | 64 | AAAGUGAACCUCAGAACCCCA |
| 5125 | 65 | CAAUUGUACAGUGUAAGCCAA |
| 5126 | 66 | ACCUCGGCGAAGCUUGUCGGG |

TABLE 7-continued

Results for TRNP1. Score threshold: 70.
Design: siRNA 21 nt.

| SEQ ID NO | siRNA_id | siRNA guide strand/AS Sequence |
|---|---|---|
| 5127 | 67 | UGGAAAUUUAUUCCUCCUGAA |
| 5128 | 68 | UAAGAAUGAUGACGAUAUCUU |
| 5129 | 69 | UUAAGAAUGAUGACGAUAUCU |
| 5130 | 70 | UAAAUACAAGCUGCUCCAGGA |
| 5131 | 71 | AAUUUAUUCCUCCUGAAUGUA |
| 5132 | 72 | ACUAAUUCAAUAUACAUUCAC |
| 5133 | 73 | AACGUCUUCCUGAAGGCAGUG |
| 5134 | 74 | AACUAAAUACAAGCUGCUCCA |
| 5135 | 75 | UCCUCCUGAAUGUAUAAGGCA |
| 5136 | 76 | AUUCAAUAUACAUUCACUAUG |
| 5137 | 77 | AAUUCAAUAUACAUUCACUAU |
| 5138 | 78 | UAAUAGACACAGAGGAAAGGC |
| 5139 | 79 | UAUGCAGAAUUCUACAAGUUC |
| 5140 | 80 | AUCUCCAAUUGUACAGUGUAA |
| 5141 | 81 | CAAUAUACAUUCACUAUGCAG |
| 5142 | 82 | UUGCUACGCUUAAUCUGAUUG |
| 5143 | 83 | CUUAAUCGAUUGCAUCUCAG |
| 5144 | 84 | UUCACUAUGCAGAAUUCUACA |
| 5145 | 85 | ACCGUCAACUUAAAGAGCCAU |
| 5146 | 86 | UUCCUGCGGAUCCGUAGUCCU |
| 5147 | 87 | AUUCUCAACGUCUUCCUGAAG |
| 5148 | 88 | UCAAGGGAGAAUUGGUCUGCA |
| 5149 | 89 | UGCGGAUCCGUAGUCCUUCCA |
| 5150 | 90 | UCUGCAAAUCAAAGUCAACAG |
| 5151 | 91 | UUGCCUUACAUUAUGGAAAUU |
| 5152 | 92 | AGCUGCUCCAGGAACCGUCAA |
| 5153 | 93 | AACCGUCAACUUAAAGAGCCA |
| 5154 | 94 | UGCUCCAGGAACCGUCAACUU |
| 5155 | 95 | UGCCUCUUCCUGCGGAUCCGU |
| 5156 | 96 | ACCGUAGCAACAUCUCCAAU |
| 5157 | 97 | UCCAGCUCCGACACCAGGCGC |
| 5158 | 98 | UCUGCGGCUGUAGGUGCGCAG |
| 5159 | 99 | AAUUCUCAACGUCUUCCUGAA |
| 5160 | 100 | AGAAAUUCAGAGCAUCAGCCA |
| 5161 | 101 | UAUUCCUCCUGAAUGUAUAAG |
| 5162 | 102 | UGGAGAACAAGGGCAGUGGAU |
| 5163 | 103 | UUAAGAAUGUUGUUUAAGAAU |
| 5164 | 104 | UAAGGUCAAUUCUCAACGUCU |
| 5165 | 105 | GACCUGUAGCAACAUCUCCAA |
| 5166 | 106 | UGCAGCUGCAGCACGCGGCUC |
| 5167 | 107 | CAGAAUUCUACAAGUUCUGGG |
| 5168 | 108 | AUGUUGUUUAAGAAUGAUGAC |
| 5169 | 109 | UGCUUGCUACGCUUAAUCUGA |
| 5170 | 110 | UUCAAUAUACAUUCACUAUGC |
| 5171 | 111 | UAGCAACAUCUCCAAUUGUAC |
| 5172 | 112 | UCCAAUUGUACAGUGUAAGCC |
| 5173 | 113 | UUAUUCCUCCUGAAUGUAUAA |
| 5174 | 114 | UUCUUGAGGCGCGACCCGUGA |
| 5175 | 115 | UGUUGUUUAAGAAUGAUGACG |
| 5176 | 116 | AAAGUGAAAGGCUCCUGUGAG |
| 5177 | 117 | AAAUCAAAGUCAACAGGGCCA |
| 5178 | 118 | AGAAUGUUGUUUAAGAAUGAU |
| 5179 | 119 | UGGAGGUUCUGAGGAGUUGGA |
| 5180 | 120 | ACAUUAUGGAAAUUUAUUCCU |
| 5181 | 121 | AUCUGAUUGCAUCUCAGGGAC |
| 5182 | 122 | UAUGAAGAAAUUCAGAGCAUC |
| 5183 | 123 | UUACAUUAUGGAAAUUUAUUC |
| 5184 | 124 | AAUGAUGACGAUAUCUUGAAA |
| 5185 | 125 | ACAUCUCCAAUUGUACAGUGU |
| 5186 | 126 | UGGAGGUCAGCGCUGCGGGA |
| 5187 | 127 | GAAAUUCAGAGCAUCAGCCAG |
| 5188 | 128 | UCCACCUCCAGCAGCCGCCGC |
| 5189 | 129 | UCUUGAGGCGCGACCCGUGAG |
| 5190 | 130 | UGCAUUUGCCUUACAUUAUGG |
| 5191 | 131 | AUGCAUUUGCCUUACAUUAUG |
| 5192 | 132 | UACAUUAUGGAAAUUUAUUCC |
| 5193 | 133 | UGUAAGUGAAAGGCUCCUGU |
| 5194 | 134 | UCCGUAGUCCUUCCAGCCGGC |
| 5195 | 135 | AAACGAAACUAAAUACAAGCU |
| 5196 | 136 | UCUCCAAUUGUACAGUGUAAG |
| 5197 | 137 | UCCGCGAUCAGUCGGUCGGUC |
| 5198 | 138 | UGGAAGGAGCUCAGCCUCCUC |
| 5199 | 139 | AUAAUAGACACAGAGGAAAGG |
| 5200 | 140 | AUGGAAAUUUAUUCCUCCUGA |

TABLE 7-continued

Results for TRNP1. Score threshold: 70.
Design: siRNA 21 nt.

| SEQ ID NO | siRNA_id | siRNA guide strand/AS Sequence |
|---|---|---|
| 5201 | 141 | UCUUCCUGCGGAUCCGUAGUC |
| 5202 | 142 | AUUGCAUCUCAGGGACCUGUA |
| 5203 | 143 | UCCUGAAUGUAUAAGGCAGGA |
| 5204 | 144 | UUCUCAACGUCUUCCUGAAGG |
| 5205 | 145 | AGAAUGAUGACGAUAUCUUGA |
| 5206 | 146 | AUUAUCAGGAUGUUUAAAUGU |
| 5207 | 147 | UCCGUCAUCACAUCCUUUAAU |
| 5208 | 148 | CACCCGAACAGCUAGACACGG |
| 5209 | 149 | AAUAGACACAGAGGAAAGGCA |
| 5210 | 150 | UCCUUUAAUGAGGAAGACUUC |
| 5211 | 151 | GUAAGGUCAAUUCUCAACGUC |
| 5212 | 152 | UUCUACAAGUUCUGGGCUAUG |
| 5213 | 153 | AUGCAGAAUUCUACAAGUUCU |
| 5214 | 154 | UCCCUCAAACAGGCCUCCCGG |
| 5215 | 155 | UUCCUGAAGGCAGUGCCCAGG |
| 5216 | 156 | GUAGCAACAUCUCCAAUUGUA |
| 5217 | 157 | UUUAUUCCUCCUGAAUGUAUA |
| 5218 | 158 | AUUCACUAUGCAGAAUUCUAC |
| 5219 | 159 | ACAUUCACUAUGCAGAAUUCU |
| 5220 | 160 | UACGCUUAAUCUGAUUGCAUC |
| 5221 | 161 | CAAUUCUCAACGUCUUCCUGA |
| 5222 | 162 | UCCGACACCAGGCGCCGGCGG |
| 5223 | 163 | CACAGCACACCCGAACAGCUA |
| 5224 | 164 | UCCCACGUGGAGAACAAGGGC |
| 5225 | 165 | AAUGAGGAAGACUUCCUGAGG |
| 5226 | 166 | ACAAGCACACUCCCACGUGGA |
| 5227 | 167 | UCCAGAUCCAUAGAGUGGAGG |
| 5228 | 168 | AAGAAUGUUGUUUAAGAAUGA |
| 5229 | 169 | CUAUGCAGAAUUCUACAAGUU |
| 5230 | 170 | UUCCUCCUGAAUGUAUAAGGC |
| 5231 | 171 | UGAGGAGUUGGAAGGAGCUCA |
| 5232 | 172 | UCCAUAGAGUGGAGGUUCUGA |
| 5233 | 173 | UGUUUAAGAAUGAUGACGAUA |
| 5234 | 174 | UUUAAGAAUGAUGACGAUAUC |
| 5235 | 175 | AUGUAUAAGGCAGGAGACUAA |
| 5236 | 176 | CUACGCUUAAUCUGAUUGCAU |
| 5237 | 177 | UCCUGGUCCUCGGCCGCGCCU |
| 5238 | 178 | ACUUGCAAAGUGAACCUCAGA |
| 5239 | 179 | AUUGGUCUGCAAAUCAAAGUC |
| 5240 | 180 | CAUCUCAGGGACCUGUAGCAA |
| 5241 | 181 | UGAGGCGCGACCCGUGAGCCG |
| 5242 | 182 | UAGGUGCGCAGGGAGGAUGAC |
| 5243 | 183 | AGUCGGUCGGUCGGCACCUCG |
| 5244 | 184 | AAACUAAAUACAAGCUGCUCC |
| 5245 | 185 | CAGAGGUCCAGAUCCAUAGAG |
| 5246 | 186 | UCCAUUAUCAGGAUGUUUAAA |
| 5247 | 187 | ACAGCACACCCGAACAGCUAG |
| 5248 | 188 | UAAGAAUGUUGUUUAAGAAUG |
| 5249 | 189 | AGUUGGAAGGAGCUCAGCCUC |
| 5250 | 190 | UCAGGUCAAGGGAGAAUUGGU |
| 5251 | 191 | UGCGGCUGUAGGUGCGCAGGG |
| 5252 | 192 | UCCUGUGAGGAGGCGCUGGG |
| 5253 | 193 | UCACAUCCUUUAAUGAGGAAG |
| 5254 | 194 | AUUCUACAAGUUCUGGGCUAU |
| 5255 | 195 | AUUUAUUCCUCCUGAAUGUAU |
| 5256 | 196 | UCGGUCGGCACCUCGGCGAAG |
| 5257 | 197 | GAAACUAAAUACAAGCUGCUC |
| 5258 | 198 | GUCCGCGAUCAGUCGGUCGGU |
| 5259 | 199 | UCUGAGGAGUUGGAAGGAGCU |
| 5260 | 200 | UGAAUGUAUAAGGCAGGAGAC |
| 5261 | 201 | UCCAGGAACCGUCAACUUAAA |
| 5262 | 202 | UAGACACAGAGGAAAGGCAGC |
| 5263 | 203 | AGCUCCGACACCAGGCGCCGG |
| 5264 | 204 | AAAUUUAUUCCUCCUGAAUGU |
| 5265 | 205 | ACCUCUGCUCUGCCGUCCCCU |
| 5266 | 206 | UUGCAAAGUGAACCUCAGAAC |
| 5267 | 207 | UGCAGCUCCUGGUCCUCGGCC |
| 5268 | 208 | CUGUAAAGUGAAAGGCUCCUG |
| 5269 | 209 | UGAAAGGCUCCUGUGAGGAGG |
| 5270 | 210 | AUGAUGACGAUAUCUUGAAAA |
| 5271 | 211 | AUCCUUUAAUGAGGAAGACUU |
| 5272 | 212 | AUUAUGGAAAUUUAUUCCUCC |
| 5273 | 213 | AAUGUAUAAGGCAGGAGACUA |
| 5274 | 214 | AGACUUGAAGCAAUGACAUCU |

TABLE 7-continued

Results for TRNP1. Score threshold: 70.
Design: siRNA 21 nt.

| SEQ ID NO | siRNA_id | siRNA guide strand/AS Sequence |
|---|---|---|
| 5275 | 215 | UAUAAGGCAGGAGACUAAUUC |
| 5276 | 216 | AGGUCAAUUCUCAACGUCUUC |
| 5277 | 217 | GAAUUCUACAAGUUCUGGGCU |
| 5278 | 218 | AGAAUUGGUCUGCAAAUCAAA |
| 5279 | 219 | CAAAGUGAACCUCAGAACCCC |
| 5280 | 220 | GAGAAUUGGUCUGCAAAUCAA |
| 5281 | 221 | AGGAACCGUCAACUUAAAGAG |
| 5282 | 222 | ACAGAGGAAAGGCAGCAAGGG |
| 5283 | 223 | CUGCAAAUCAAAGUCAACAGG |
| 5284 | 224 | UCAGGGACCUGUAGCAACAUC |
| 5285 | 225 | UCAUCACAUCCUUUAAUGAGG |
| 5286 | 226 | CAGACUAUCUUUCUGAGGGGC |
| 5287 | 227 | UUUGCCUUACAUUAUGGAAAU |
| 5288 | 228 | AGAAUUCUACAAGUUCUGGGC |
| 5289 | 229 | GAUCCUAGUCCUUCCAGCCG |
| 5290 | 230 | UACAUUCACUAUGCAGAAUUC |
| 5291 | 231 | AGCAGACUAUCUUUCUGAGGG |
| 5292 | 232 | CUGUGAGUCAGGUCAAGGGAG |
| 5293 | 233 | ACUGUAAAGUGAAAGGCUCCU |
| 5294 | 234 | GACUUGAAGCAAUGACAUCUA |
| 5295 | 235 | CACUUGCAAAGUGAACCUCAG |
| 5296 | 236 | CAGAUCCAUAGAGUGGAGGUU |
| 5297 | 237 | CUCAACGUCUUCCUGAAGGCA |
| 5298 | 238 | AGGUCCAGAUCCAUAGAGUGG |
| 5299 | 239 | GUCAUCACAUCCUUUAAUGAG |
| 5300 | 240 | AGCUCAGCCUCCUCUACUGGG |
| 5301 | 241 | AGAACAAGGGCAGUGGAUGAA |
| 5302 | 242 | GCAGACUAUCUUUCUGAGGGG |
| 5303 | 243 | UCAGCCUCCUCUACUGGGCCC |
| 5304 | 244 | CAUCUCCAAUUGUACAGUGUA |
| 5305 | 245 | CAGUCGGUCGGUCGGCACCUC |
| 5306 | 246 | GUAGGAGUCAAGGUCGGAGUU |
| 5307 | 247 | AAGGCAGCAAGGGCACUUGCA |
| 5308 | 248 | AAUAUACAUUCACUAUGCAGA |
| 5309 | 249 | UAGUCCUUCCAGCCGGCGUCC |
| 5310 | 250 | AGCAAGGGCACUUGCAAAGUG |
| 5311 | 251 | AAAGGCUCCUGUGAGGAGGGC |
| 5312 | 252 | UCUCCAGCUCCGACACCAGGC |
| 5313 | 253 | UCCUCGGCCGCGCCUGCUGAA |
| 5314 | 254 | GUAAAGUGAAAGGCUCCUGUG |
| 5315 | 255 | UGGUCCUCGGCCGCGCCUGCU |
| 5316 | 256 | UCUCAACGUCUUCCUGAAGGC |
| 5317 | 257 | UCCCUCCAUUAUCAGGAUGUU |
| 5318 | 258 | CAUUAUGGAAAUUUAUUCCUC |
| 5319 | 259 | AUAAGGCAGGAGACUAAUUCA |
| 5320 | 260 | UGCUACGCUUAAUCUGAUUGC |
| 5321 | 261 | ACAUCCUUUAAUGAGGAAGAC |
| 5322 | 262 | AAUUGGUCUGCAAAUCAAAGU |
| 5323 | 263 | GAUGACCACAGCACACCCGAA |
| 5324 | 264 | ACCUCCAGCAGCCGCCGCCGU |
| 5325 | 265 | CAAGGGAGAAUUGGUCUGCAA |
| 5326 | 266 | UGCGGCGGAAGGGCGAGUCGG |
| 5327 | 267 | AGUUCUCCAGAACCAGCCCCU |
| 5328 | 268 | UCAGGCUCUCCGCGCGGUGCG |
| 5329 | 269 | UGUAUAAGGCAGGAGACUAAU |
| 5330 | 270 | UGUGAGUCAGGUCAAGGGAGA |
| 5331 | 271 | CAACAUCUCCAAUUGUACAGU |
| 5332 | 272 | UCCUUCCAGCCGGCGUCCGCG |
| 5333 | 273 | AAGAAAUUCAGAGCAUCAGCC |
| 5334 | 274 | GACCACAGCACACCCGAACAG |
| 5335 | 275 | AAAGCCGAAUCCAGAGGUCCA |
| 5336 | 276 | UCUGAUUGCAUCUCAGGGACC |
| 5337 | 277 | GCAACAUCUCCAAUUGUACAG |
| 5338 | 278 | GUCAAUUCUCAACGUCUUCCU |
| 5339 | 279 | AGCUCCUGGUCCUCGGCCGCG |
| 5340 | 280 | ACAAGGGCAGUGGAUGAAGGG |
| 5341 | 281 | AAUGUUGUUUAAGAAUGAUGA |
| 5342 | 282 | AGGGACCUGUAGCAACAUCUC |
| 5343 | 283 | UGUAGGUGCGCAGGGAGGAUG |
| 5344 | 284 | GUUCUGAGGAGUUGGAAGGAG |
| 5345 | 285 | AUACAUUCACUAUGCAGAAUU |
| 5346 | 286 | ACACCCGAACAGCUAGACACG |
| 5347 | 287 | CUGAGGAGUUGGAAGGAGCUC |
| 5348 | 288 | AGACACAGAGGAAAGGCAGCA |

TABLE 7-continued

Results for TRNP1. Score threshold: 70.
Design: siRNA 21 nt.

| SEQ ID NO | siRNA_id | siRNA guide strand/AS Sequence |
|---|---|---|
| 5349 | 289 | AGUCAAGGUCGGAGUUGGGGG |
| 5350 | 290 | CUAAAUACAAGCUGCUCCAGG |
| 5351 | 291 | AGCGCUGCAGCUCCUGGUCCU |
| 5352 | 292 | UCCAGAGGUCCAGAUCCAUAG |
| 5353 | 293 | ACGUGGAGAACAAGGGCAGUG |
| 5354 | 294 | CAUCACAUCCUUUAAUGAGGA |
| 5355 | 295 | CGAAACUAAAUACAAGCUGCU |
| 5356 | 296 | AGUCCUUCCAGCCGGCGUCCG |
| 5357 | 297 | AAGUGAAAGGCUCCUGUGAGG |
| 5358 | 298 | AAGGAGCUCAGCCUCCUCUAC |
| 5359 | 299 | AGUGGAGGUUCUGAGGAGUUG |
| 5360 | 300 | GGACCUGUAGCAACAUCUCCA |
| 5361 | 301 | ACGCUUAAUCUGAUUGCAUCU |
| 5362 | 302 | CUCAGGGACCUGUAGCAACAU |
| 5363 | 303 | GGCACUUGCAAAGUGAACCUC |
| 5364 | 304 | CACCUCGGCGAAGCUUGUCGG |
| 5365 | 305 | AAGGCUCCUGUGAGGAGGGCG |
| 5366 | 306 | UCUACAAGUUCUGGGCUAUGU |
| 5367 | 307 | AGCUGCGUCCGGCAGCGGCGG |
| 5368 | 308 | AAGCUGCUCCAGGAACCGUCA |
| 5369 | 309 | AAUGCUUGCUACGCUUAAUCU |
| 5370 | 310 | CUUGCUACGCUUAAUCUGAUU |
| 5371 | 311 | AGGAAGACUUCCUGAGGAGGG |
| 5372 | 312 | CCAAUUGUACAGUGUAAGCCA |
| 5373 | 313 | CACUAUGCAGAAUUCUACAAG |
| 5374 | 314 | CUUGAAGCAAUGACAUCUAUU |
| 5375 | 315 | GUGGAGGUCAGCGCUGCGGGG |
| 5376 | 316 | AGCAACAUCUCCAAUUGUACA |
| 5377 | 317 | ACGAAACUAAAUACAAGCUGC |
| 5378 | 318 | AAGGGCGAGUCGGGCUCGGGG |
| 5379 | 319 | UAAGAGCAGGCGGCUGUGAGU |
| 5380 | 320 | UCCAGCAGCCGCCGCCGUGCU |
| 5381 | 321 | AAGGGCAGUGGAUGAAGGGAA |
| 5382 | 322 | AGUGGAUGAAGGGAACGGGGA |
| 5383 | 323 | CUGAUUGCAUCUCAGGGACCU |
| 5384 | 324 | AUUUGCCUUACAUUAUGGAAA |
| 5385 | 325 | AAACAGGCCUCCCGGCGCCGU |
| 5386 | 326 | UCAAACAGGCCUCCCGGCGCC |
| 5387 | 327 | AAGCACACUCCCACGUGGAGA |
| 5388 | 328 | AAGGGAGAAUUGGUCUGCAAA |
| 5389 | 329 | GAAUGAUGACGAUAUCUUGAA |

TABLE 8

Results for APLN. Score threshold: 70.
Design: siRNA 21 nt.

| SEQ ID NO | siRNA_id | siRNA guide strand/AS Sequence |
|---|---|---|
| 5390 | 1 | UUACAAACAUUGAACACAGGG |
| 5391 | 2 | UUUACAAACAUUGAACACAGG |
| 5392 | 3 | UUUCUUAAUGAACAGGGCCUU |
| 5393 | 4 | AUAUUUACACAGAACAAUCUU |
| 5394 | 5 | UAUUUACACAGAACAAUCUUU |
| 5395 | 6 | UAGUAUAAGAAUCAUAAACAA |
| 5396 | 7 | UAUAAAGACAUAUUUACACAG |
| 5397 | 8 | UACAAACAUUGAACACAGGGG |
| 5398 | 9 | UUCAUCAAGCAACUCUACUUU |
| 5399 | 10 | UAGGUCUCCAAAGUCAGUCCA |
| 5400 | 11 | UAUCUUUGUAUAAAUUAGUAU |
| 5401 | 12 | UUAUAUUGAACUCUUUGCAUU |
| 5402 | 13 | UUGACCUAGAACCGAUUUGGG |
| 5403 | 14 | AUAAGAAUCAUAAACAACCAC |
| 5404 | 15 | UCUUGUCUUCUCUUUCUCCCU |
| 5405 | 16 | UAACUAGAGUCUCUCCUUGCU |
| 5406 | 17 | UAUUAGAGUACCCUGGGUCUG |
| 5407 | 18 | UAUCAAAUGUAUUUAUUGCUG |
| 5408 | 19 | UCUUAACUAGAGUCUCUCCUU |
| 5409 | 20 | ACAAUCUUUACAAACAUUGAA |
| 5410 | 21 | UUCUUCAAAUGACACUGCCAA |
| 5411 | 22 | UAUAAGAAUCAUAAACAACCA |
| 5412 | 23 | AACUAGAGUCUCUCCUUGCUU |
| 5413 | 24 | AUGUUCUUAAAUAAACUGCUU |
| 5414 | 25 | UUUAAGCAGCAGCAGCAGCAG |
| 5415 | 26 | AACAGGACAGUUCACAGCCAG |
| 5416 | 27 | UUAUGGAACCUUCCAGCCCAG |

TABLE 8-continued

Results for APLN. Score threshold: 70.
Design: siRNA 21 nt.

| SEQ ID NO | siRNA_id | siRNA guide strand/AS Sequence |
|---|---|---|
| 5417 | 28 | UGGAGGAGACAUAACCGCCGG |
| 5418 | 29 | AAUCAUCCAAACUACAGCCAG |
| 5419 | 30 | UUUAUUAUAAAGCAUAUUUA |
| 5420 | 31 | AUAAAUUAGUAUAAGAAUCAU |
| 5421 | 32 | UAUAUUGAACUCUUUGCAUUU |
| 5422 | 33 | UUCUGUUCCUUUGCUUUCUUU |
| 5423 | 34 | UUAACUGAGCAAACGCUGAUG |
| 5424 | 35 | UACACAGAACAAUCUUUACAA |
| 5425 | 36 | UAAAGACAUAUUUACACAGAA |
| 5426 | 37 | ACAAACAUUGAACACAGGGGA |
| 5427 | 38 | UCUAACAUUCUGUGAUUCUUG |
| 5428 | 39 | UGAGCCUUUAAGCAGCAGCAG |
| 5429 | 40 | UUAUCAAAUGUAUUUAUUGCU |
| 5430 | 41 | UAUGUUCUUAAAUAAACUGCU |
| 5431 | 42 | UACAAACAAAGUCAUUAUCAA |
| 5432 | 43 | UAAAUUAGUAUAAGAAUCAUA |
| 5433 | 44 | UCAUCAAGCAACUCUACUUUG |
| 5434 | 45 | UGUUCUUAAAUAAACUGCUUU |
| 5435 | 46 | UUGAGCGGUAGUCUCAGUGCC |
| 5436 | 47 | UAAGUGACCUUCAAGGGUCCU |
| 5437 | 48 | UCUUCUGUUCCCUAUCUCCCA |
| 5438 | 49 | UUACACAGAACAAUCUUUACA |
| 5439 | 50 | UUAACUAGAGUCUCUCCUUGC |
| 5440 | 51 | UUCUCUUUCUCCCUCCUGGGA |
| 5441 | 52 | AACAAUUUCUUAAUGAACAGG |
| 5442 | 53 | UAUUGAACUCUUUGCAUUUUA |
| 5443 | 54 | UCAGCUCUAACAUUCUGUGAU |
| 5444 | 55 | AGAAUCAUAAACAACCACUUU |
| 5445 | 56 | UGACCUAGAACCGAUUUGGGA |
| 5446 | 57 | UUGUGAGAACGGGAAUCAU |
| 5447 | 58 | UUCCCUUCCUUCUUCUCCCCU |
| 5448 | 59 | UCAAGCAACUCUACUUUGUGA |
| 5449 | 60 | UUCCUGCUGCACUUCCUCCCA |
| 5450 | 61 | AUCUUUACAAACAUUGAACAC |
| 5451 | 62 | UUGGGAGGCACACUAAGGCAA |
| 5452 | 63 | UUGUAUAAAUUAGUAUAAGAA |
| 5453 | 64 | UUCCAGCCCAUUCCCAUCGGG |
| 5454 | 65 | UCUUUCUUUCCUUCCUUCUGU |
| 5455 | 66 | AUAGCAGAAGACACCCACCAA |
| 5456 | 67 | UCAGGCUCUUGUCUUCUCUUU |
| 5457 | 68 | UAAACAACCACUUUAAAUAAG |
| 5458 | 69 | UGUCAGCUCUAACAUUCUGUG |
| 5459 | 70 | UUCUUAAAUAAACUGCUUUAA |
| 5460 | 71 | UAAUAUCUUUGUAUAAAUUAG |
| 5461 | 72 | AUGGAGGAGACAUAACCGCCG |
| 5462 | 73 | UUAAGCAUAGGGAUUCAUUUU |
| 5463 | 74 | UUAAUAUCUUUGUAUAAAUUA |
| 5464 | 75 | AUAUUGAACUCUUUGCAUUUU |
| 5465 | 76 | UCUACCUCUCCCUUAACUGAG |
| 5466 | 77 | AUAUCUUUGUAUAAAUUAGUA |
| 5467 | 78 | AUCAAGCAACUCUACUUUGUG |
| 5468 | 79 | UCAAAUGUAUUUAUUGCUGAA |
| 5469 | 80 | UAGCAGAAGACACCCACCAAG |
| 5470 | 81 | UCCUGCUGCACUUCCUCCCAU |
| 5471 | 82 | UCUCCCAGCUUUCUUAGCCAU |
| 5472 | 83 | AAGAAUCAUAAACAACCACUU |
| 5473 | 84 | AUCUUUCUUUCCUUCCUUCUG |
| 5474 | 85 | AUUCUUGUGAGAACGGGAA |
| 5475 | 86 | AUUUACACAGAACAAUCUUUA |
| 5476 | 87 | AUUCUUCAAAUGACACUGCCA |
| 5477 | 88 | UUGUCUUCUCUUUCUCCCUCC |
| 5478 | 89 | UCAGGCUAUCUCAUUCAUCAA |
| 5479 | 90 | UUCUUAAUGAACAGGGCUUA |
| 5480 | 91 | UUAGAGUACCCUGGGUCUGGG |
| 5481 | 92 | UGGAGCUUGGGCUAGCUGGGG |
| 5482 | 93 | UAGAGUACCCUGGGUCUGGGA |
| 5483 | 94 | UGGACUGGACGGAUUCUUGUG |
| 5484 | 95 | UUGAAGGCUACCUCGGACUCC |
| 5485 | 96 | UCUGCAAUGACUCUGAGCAGG |
| 5486 | 97 | UCAAGGGUCCUGUCAGCUCUA |
| 5487 | 98 | UAAGCAUAGGGAUUCAUUUUG |
| 5488 | 99 | UUGCCUAAGAAGGCUAAGUGA |
| 5489 | 100 | UUUCCUUCCUUCUGUUCCUUU |
| 5490 | 101 | UGAGCGGUAGUCUCAGUGCCU |

TABLE 8-continued

Results for APLN. Score threshold: 70.
Design: siRNA 21 nt.

| SEQ ID NO | siRNA_id | siRNA guide strand/AS Sequence |
|---|---|---|
| 5491 | 102 | CUUAACUAGAGUCUCUCCUUG |
| 5492 | 103 | UUUACACAGAACAAUCUUUAC |
| 5493 | 104 | UAGUCUCAGUGCCUGAGCCGC |
| 5494 | 105 | UCUAUGGAGGAGACAUAACCG |
| 5495 | 106 | UUCAAGGGUCCUGUCAGCUCU |
| 5496 | 107 | UAUGGAGGAGACAUAACCGCC |
| 5497 | 108 | UGUGACCUGGUCAUUAAGCAU |
| 5498 | 109 | UUCUGCAGCCUCCUCUCCCGC |
| 5499 | 110 | UUUCUUUCCUUCCUUCUGUUC |
| 5500 | 111 | UAAGGGCGAACUGUCAGCUUU |
| 5501 | 112 | UGAGAGAACGGGAAUCAUCCA |
| 5502 | 113 | AUGCAGGCACUUACCUCCCUG |
| 5503 | 114 | UGACCCUCUGGGCUGCACCAG |
| 5504 | 115 | UCAUUCAUCAAGCAACUCUAC |
| 5505 | 116 | UAACUGUUUAUUAUAAAGACA |
| 5506 | 117 | AUUCAUCAAGCAACUCUACUU |
| 5507 | 118 | UUCCUUCUGUUCCUUUGCUUU |
| 5508 | 119 | AUCAAAUGUAUUUAUUGCUGA |
| 5509 | 120 | UAGAACCGAUUUGGGAUGCAG |
| 5510 | 121 | AAGUAGGAGAUGGGAGACCUG |
| 5511 | 122 | UAAGAAUCAUAAACAACCACU |
| 5512 | 123 | UAGCCCACCCACUACCCUCUU |
| 5513 | 124 | AUCAGGCUCUUGUCUUCUCUU |
| 5514 | 125 | UUUCCUCCGACCUCCCUGCCA |
| 5515 | 126 | UUGGGCAUCAGGCUCUUGUCU |
| 5516 | 127 | AACAAUCUUUACAAACAUUGA |
| 5517 | 128 | UCUUUACAAACAUUGAACACA |
| 5518 | 129 | UGUCUUCUCUUUCUCCCUCCU |
| 5519 | 130 | UCAUUAAGCAUAGGGAUUCAU |
| 5520 | 131 | UUAAUCAGUAUGUUCUUAAAU |
| 5521 | 132 | UACCUCUCCCUUAACUGAGCA |
| 5522 | 133 | AUUUCUUAAUGAACAGGGCCU |
| 5523 | 134 | UCCCUUAACUGAGCAAACGCU |
| 5524 | 135 | UUAAGCAGCAGCAGCAGCAGC |
| 5525 | 136 | UUAUAAAGACAUAUUUACACA |
| 5526 | 137 | UCUUUGUAUAAAUUAGUAUAA |
| 5527 | 138 | UGGGAUGCAGGCACUUACCU |
| 5528 | 139 | UGAGCAAACGCUGAUGCUCCA |
| 5529 | 140 | UAGAGUCUCUCCUUGCUUUUC |
| 5530 | 141 | AAGCAGCAGCAGCAGCAGCAG |
| 5531 | 142 | AGUGACAAAGGACUUCACGGG |
| 5532 | 143 | AAGAGAAGUGACAAAGGACUU |
| 5533 | 144 | UUCAUGCUGCUCCUUGGGCCG |
| 5534 | 145 | UGCUGCACUUCCUCCCAUCUU |
| 5535 | 146 | UCUCAUUCAUCAAGCAACUCU |
| 5536 | 147 | AUCUCAUUCAUCAAGCAACUC |
| 5537 | 148 | AAUUUCUUAAUGAACAGGGCC |
| 5538 | 149 | AGUAUGUUCUUAAAUAAACUG |
| 5539 | 150 | UAAGCAGCAGCAGCAGCAGCA |
| 5540 | 151 | AGACAUAUUACACAGAACAA |
| 5541 | 152 | UUAGAUGAGACAGGCAGGGAC |
| 5542 | 153 | UGAACAGGGCCUUAAUAUCUU |
| 5543 | 154 | AUAAAGACAUAUUUACACAGA |
| 5544 | 155 | ACACAGAACAAUCUUUACAAA |
| 5545 | 156 | UAGGACACCCAAACAGAUGCC |
| 5546 | 157 | UCCUCCCAUCUUUCUUUCCUU |
| 5547 | 158 | UAGGAGAUGGGAGACCUGGUC |
| 5548 | 159 | UGAACAUGACCUCCAAGAGUA |
| 5549 | 160 | UGCAAUGACUCUGAGCAGGUC |
| 5550 | 161 | UCUCCAAAGUCAGUCCAGGGA |
| 5551 | 162 | AGCAGCAGCAGCAGCAGCGUU |
| 5552 | 163 | UUCAGAAAGGCAUGGGUCCCU |
| 5553 | 164 | UCUUUCCUUCCUUCUGUUCCU |
| 5554 | 165 | AGUGAUUGAAGGCUACCUCGG |
| 5555 | 166 | AUUCCUUGACCCUCUGGGCUG |
| 5556 | 167 | UAAGGCAAGAGAAGUGACAAA |
| 5557 | 168 | UUCCUCCUUCCUUCUGCCCU |
| 5558 | 169 | UGGAACCUUCCAGCCCAGCUG |
| 5559 | 170 | AGAACAAUCUUUACAAACAUU |
| 5560 | 171 | UCUUCUCUUUCUCCCUCCUGG |
| 5561 | 172 | UUCCUUCCUUCUGUUCCUUUG |
| 5562 | 173 | UUUAUUAAAGACAUAUUUAC |
| 5563 | 174 | UCUACUUUGUGAAACAUAAAA |
| 5564 | 175 | UGCACGUGCAAUAUGUGGGCA |

TABLE 8-continued

Results for APLN. Score threshold: 70.
Design: siRNA 21 nt.

| SEQ ID NO | siRNA_id | siRNA guide strand/AS Sequence |
|---|---|---|
| 5565 | 176 | UUCCUCCCAUCUUUCUUUCCU |
| 5566 | 177 | AACUCUACUUUGUGAAACAUA |
| 5567 | 178 | UUCUUGUGAGAGAACGGGAAU |
| 5568 | 179 | UCUCUGCAUUCUUCCCUGGAG |
| 5569 | 180 | ACAAUUUCUUAAUGAACAGGG |
| 5570 | 181 | AUAAACAACCACUUUAAAUAA |
| 5571 | 182 | AGGUCUCCAAAGUCAGUCCAG |
| 5572 | 183 | AGAAGCAGACCAAUCUAUGGA |
| 5573 | 184 | AACAAAGUCAUUAUCAAAUGU |
| 5574 | 185 | AUGCUCCACCCACUUCACCAG |
| 5575 | 186 | AAUCAUAAACAACCACUUUAA |
| 5576 | 187 | UGAUUGAAGGCUACCUCGGAC |
| 5577 | 188 | UAAGAAGGCUAAGUGACCUUC |
| 5578 | 189 | CAGAACAAUCUUUACAAACAU |
| 5579 | 190 | AACUGAGCAAACGCUGAUGCU |
| 5580 | 191 | CUCUUAACUAGAGUCUCUCCU |
| 5581 | 192 | ACAACCACUUUAAAUAAGGCA |
| 5582 | 193 | UAUAAAUUAGUAUAAGAAUCA |
| 5583 | 194 | UUUCUCCCUCCUGGGAACCCU |
| 5584 | 195 | UCUCUUUCUCCCUCCUGGGAA |
| 5585 | 196 | UUUGCCUAAGAAGGCUAAGUG |
| 5586 | 197 | UAUUCCUGCUGCACUUCCUCC |
| 5587 | 198 | ACUAGAGUCUCUCCUUGCUUU |
| 5588 | 199 | AAGAAGGGAGGCUUUCUGGGG |
| 5589 | 200 | AUUGGGAGGCACACUAAGGCA |
| 5590 | 201 | UUCUCCCUCCUGGGAACCCUG |
| 5591 | 202 | UGGGUCUGGGAAUGCUGCCAG |
| 5592 | 203 | UCAGGGACCUCCACACACCG |
| 5593 | 204 | UGAGUGUGCGCGCUGAGCCCC |
| 5594 | 205 | AAGUGACAAAGGACUUCACGG |
| 5595 | 206 | AAUAUCUUUGUAUAAAUUAGU |
| 5596 | 207 | CUCUGCAAUGACUCUGAGCAG |
| 5597 | 208 | CUUUCCUUCCUUCUGUUCCUU |
| 5598 | 209 | AGAUUCAUGCUGCUCCUUGGG |
| 5599 | 210 | CAACAGGACAGUUCACAGCCA |
| 5600 | 211 | UUAGCAGCAGCAUAGGUAAAG |
| 5601 | 212 | AACUGUUUAUUAUAAAGACAU |
| 5602 | 213 | AAGUGACCUUCAAGGGUCCUG |
| 5603 | 214 | UUCCUCCGACCUCCCUGCCAG |
| 5604 | 215 | GUCUUCUCUUUCUCCCUCCUG |
| 5605 | 216 | CUUAACGAGCAAACGCUGAU |
| 5606 | 217 | UAUUAUAAAGACAUAUUUACA |
| 5607 | 218 | AUUCCCAUCGGGAAGCGGCAU |
| 5608 | 219 | AUCAUAAACAACCACUUUAAA |
| 5609 | 220 | UAUGGGAGGCACACUAAGGC |
| 5610 | 221 | AAGGCUACCUCGGACUCCUGA |
| 5611 | 222 | GUGAUUGAAGGCUACCUCGGA |
| 5612 | 223 | UCCCAUCUUUCUUUCCUUCCU |
| 5613 | 224 | UCAUAAAGUAGGAGAUGGGAG |
| 5614 | 225 | ACAAAGUCAUUAUCAAAUGUA |
| 5615 | 226 | UGACCUUCAAGGGUCCUGUCA |
| 5616 | 227 | AAAGUUGGGCAUCAGGCUCUU |
| 5617 | 228 | ACUCUGAGCAGGUCACUCCCC |
| 5618 | 229 | AUCUUUGUAUAAAUUAGUAUA |
| 5619 | 230 | UGAUACAAACAAAGUCAUUAU |
| 5620 | 231 | CUUCCUUCUGUUCCUUUGCUU |
| 5621 | 232 | UCCUGGGAGGGUAUAUAGCCA |
| 5622 | 233 | CAACUCUACUUUGUGAAACAU |
| 5623 | 234 | UUUGUAUAAAUUAGUAUAAGA |
| 5624 | 235 | CUUGUCUUCUCUUUCUCCCUC |
| 5625 | 236 | UGGGAUGCAGGCACUUACCUC |
| 5626 | 237 | UCUUCUGCAGCCUCCUCUCCC |
| 5627 | 238 | AUGACCUCCAAGAGUAAGGGC |
| 5628 | 239 | AAUUAGUAUAAGAAUCAUAAA |
| 5629 | 240 | UGGGCAUCAGGCUCUUGUCUU |
| 5630 | 241 | UCUCUACCUCUCCCUUAACUG |
| 5631 | 242 | AUUAUAAAGACAUAUUUACAC |
| 5632 | 243 | UAACUGAGCAAACGCUGAUGC |
| 5633 | 244 | UCAUCAAGAGGGAAGAGGGCG |
| 5634 | 245 | UCUGUUCCUUUGCUUUCUUUU |
| 5635 | 246 | AUCUCCCAGCUUUCUUAGCCA |
| 5636 | 247 | UGCUGGAGCCCACAGAAGGGA |
| 5637 | 248 | UUCUGGGCACCGACCAGUCCC |
| 5638 | 249 | UGGAUAGGCAAACAUUGGGGC |

TABLE 8-continued

Results for APLN. Score threshold: 70.
Design: siRNA 21 nt.

| SEQ ID NO | siRNA_id | siRNA guide strand/AS Sequence |
|---|---|---|
| 5639 | 250 | UCCGCUCUUCUGCAGCCUCCU |
| 5640 | 251 | UGACCUCCAAGAGUAAGGGCG |
| 5641 | 252 | UAGGUCAGGGAGGUGGGAGCA |
| 5642 | 253 | AAGUUGGGCAUCAGGCUCUUG |
| 5643 | 254 | AUUAGGACACCCAAACAGAUG |
| 5644 | 255 | UUUAAUCAGUAUGUUCUUAAA |
| 5645 | 256 | UUAAUGAACAGGGCCUUAAUA |
| 5646 | 257 | GUCAGCUCUAACAUUCUGUGA |
| 5647 | 258 | CCUGUCAGCUCUAACAUUCUG |
| 5648 | 259 | ACCUCUUAACUAGAGUCUCUC |
| 5649 | 260 | UCAACACGAAGGGAAGGCCAU |
| 5650 | 261 | CUAUGGAGGAGACAUAACCGC |
| 5651 | 262 | UCCAAGAGUAAGGGCGAACUG |
| 5652 | 263 | CUUCUGUUCCCUAUCUCCCAG |
| 5653 | 264 | AAUGACUCUGAGCAGGUCACU |
| 5654 | 265 | ACAAACAAAGUCAUUAUCAAA |
| 5655 | 266 | AUUCCUGCUGCACUUCCUCCC |
| 5656 | 267 | ACCGCGGUCAAGGAGAGCCAG |
| 5657 | 268 | GAAUCAUCCAAACUACAGCCA |
| 5658 | 269 | UACAGCAGGUGCGAGGUGAGA |
| 5659 | 270 | AGGAAGGUCCGGUCAACACGA |
| 5660 | 271 | AUGAUACAAACAAAGUCAUUA |
| 5661 | 272 | CUUUACAAACAUUGAACACAG |
| 5662 | 273 | UCAUGCUGCUCCUUGGGCCGC |
| 5663 | 274 | AGCCCUGGAAGGAAGGUCCGG |
| 5664 | 275 | UGAGAGCUGAAUGGACGUGAG |
| 5665 | 276 | UUAAAUAAACUGCUUUAAAAA |
| 5666 | 277 | ACAUUGCCGUCUUCCAGCCCA |
| 5667 | 278 | AAUCUUUACAAACAUUGAACA |
| 5668 | 279 | AUGACUCUGAGCAGGUCACUC |
| 5669 | 280 | AUUAGAGUACCCUGGGUCUGG |
| 5670 | 281 | AAACGCUGAUGCUCCACCCAC |
| 5671 | 282 | AAGCAGACCAAUCUAUGGAGG |
| 5672 | 283 | UCCUUCCUUCUGCCCUUCCCU |
| 5673 | 284 | CUUUCUUCCUUCCUUCUGUU |
| 5674 | 285 | UUGACCCUCUGGGCUGCACCA |
| 5675 | 286 | UUCCUUGACCCUCUGGGCUGC |

TABLE 8-continued

Results for APLN. Score threshold: 70.
Design: siRNA 21 nt.

| SEQ ID NO | siRNA_id | siRNA guide strand/AS Sequence |
|---|---|---|
| 5676 | 287 | AACAGGGCCUUAAUAUCUUUG |
| 5677 | 288 | UUCCCUAUCUCCCAGCUUUCU |
| 5678 | 289 | AUCAUCAAGAGGGAAGAGGGC |
| 5679 | 290 | AUCGGGAAGCGGCAUCAGGGA |
| 5680 | 291 | UGAAUGGACGUGAGGCCUCCA |
| 5681 | 292 | CAUUUAAUCAGUAUGUUCUUA |
| 5682 | 293 | AAGAGACUUUCUGGGCACCGA |
| 5683 | 294 | UGAGACAGGCAGGGACUAGGG |
| 5684 | 295 | AUGGACUGGACGGAUUCUUGU |
| 5685 | 296 | AGAAGGCUAAGUGACCUUCAA |
| 5686 | 297 | AAAGUCAUUAUCAAAUGUAUU |
| 5687 | 298 | UGACCUGGUCAUUAAGCAUAG |
| 5688 | 299 | AGCGUUAGCAGCAGCAUAGGU |
| 5689 | 300 | UAGUAGCGAUCCUGCAUUUAA |
| 5690 | 301 | GAACAAUUUCUUAAUGAACAG |
| 5691 | 302 | AACAUGACCUCCAAGAGUAAG |
| 5692 | 303 | UGAAGGCUACCUCGGACUCCU |
| 5693 | 304 | CUGUCAGCUCUAACAUUCUGU |
| 5694 | 305 | UGUAUAAAUUAGUAUAAGAAU |
| 5695 | 306 | ACACACAAAGUUGGGCAUCAG |
| 5696 | 307 | GAGAGAACGGGAAUCAUCCAA |
| 5697 | 308 | UCCAGUGAUUGAAGGCUACCU |
| 5698 | 309 | UAUCUCAUUCAUCAAGCAACU |
| 5699 | 310 | AGAGUAAGGGCGAACUGUCAG |
| 5700 | 311 | UCCCUCCUUCCUUCUGCCCUU |
| 5701 | 312 | UCCUGCUUCAGAAAGGCAUGG |
| 5702 | 313 | UUUCGGGCACCGACCAGUCC |
| 5703 | 314 | AGGCACUUCAUUUGCUUUGAA |
| 5704 | 315 | UCUGCCCUUCCCUUCCUUCUU |
| 5705 | 316 | CUAACAUUCUGUGAUUCUUGG |
| 5706 | 317 | UAUCUCCCAGCUUUCUUAGCC |
| 5707 | 318 | CAAGCAACUCUACUUUGUGAA |
| 5708 | 319 | AACCGAUUUGGGAUGCAGGCA |
| 5709 | 320 | AUACAAACAAAGUCAUUAUCA |
| 5710 | 321 | UCCUUCUGCCCUUCCCUUCCU |
| 5711 | 322 | ACAUGAGGAAGGAAGGCCCAA |
| 5712 | 323 | GAAGGGAGCACUUCCACCCCG |

TABLE 8-continued

Results for APLN. Score threshold: 70.
Design: siRNA 21 nt.

| SEQ ID NO | siRNA_id | siRNA guide strand/AS Sequence |
|---|---|---|
| 5713 | 324 | GUAGUCUCAGUGCCUGAGCCG |
| 5714 | 325 | UCCUGUCAGCUCUAACAUUCU |
| 5715 | 326 | UCCCUAUCUCCCAGCUUUCUU |
| 5716 | 327 | CUAAGAAGGCUAAGUGACCUU |
| 5717 | 328 | AGGACACCCAAACAGAUGCCA |
| 5718 | 329 | AAUCAGUAUGUUCUUAAAUAA |
| 5719 | 330 | AGUUGACCUAGAACCGAUUUG |
| 5720 | 331 | CAAACGCUGAUGCUCCACCCA |
| 5721 | 332 | AGCAGCAGCAUAGGUAAAGGG |
| 5722 | 333 | AACCUUCCAGCCCAGCUGGGG |
| 5723 | 334 | CUGGUCAUUAAGCAUAGGGAU |
| 5724 | 335 | UCAUAAACAACCACUUUAAAU |
| 5725 | 336 | AGAGAAGUGACAAAGGACUUC |
| 5726 | 337 | CAGAGCCGCAGAUUCAUGCUG |
| 5727 | 338 | AAGGGAACAAUUUCUUAAUGA |
| 5728 | 339 | CUAGAGUCUCUCCUUGCUUUU |
| 5729 | 340 | UCAGAAAGGCAUGGGUCCCUU |
| 5730 | 341 | UAGCGAUCCUGCAUUUAAUCA |
| 5731 | 342 | UUCUGUUCCCUAUCUCCCAGC |
| 5732 | 343 | UGGAGUCCAGUGAUUGAAGGC |
| 5733 | 344 | AGUCAUUAUCAAAUGUAUUUA |
| 5734 | 345 | GAAUCAUAAACAACCACUUUA |
| 5735 | 346 | AGGUCCGGUCAACACGAAGGG |
| 5736 | 347 | AGUUAUGGAACCUUCCAGCCC |
| 5737 | 348 | GAGAGGGUGCUAUUCCUGCUG |
| 5738 | 349 | AGGAAGAAGGGAGUAUUGGGA |
| 5739 | 350 | CUCUAACAUUCUGUGAUUCUU |
| 5740 | 351 | AGAAGUGACAAAGGACUUCAC |
| 5741 | 352 | UCAGGGAGGUGGGAGCAGCUC |
| 5742 | 353 | AGGAGACACAGAAAGGAAGGG |
| 5743 | 354 | UGCACUUCCUCCCAUCUUUCU |
| 5744 | 355 | AUUGAAGGCUACCUCGGACUC |
| 5745 | 356 | AGAAGGGAGCACUUCCACCCC |
| 5746 | 357 | UCCCUUAUGGGAGAGGCGGGG |
| 5747 | 358 | UGACAAAGGACUUCACGGGCC |
| 5748 | 359 | UGCAAUAUGUGGGCAUGGGGA |
| 5749 | 360 | ACAGGCAGGGACUAGGGCGGA |
| 5750 | 361 | ACUGAGCAAACGCUGAUGCUC |
| 5751 | 362 | UGCGAGGUGAGAGCUGAAUGG |
| 5752 | 363 | ACCUCUCCCUUAACUGAGCAA |
| 5753 | 364 | UGCUCCACCCACUUCACCAGA |
| 5754 | 365 | CUUCUGUUCCUUUGCUUUCUU |
| 5755 | 366 | UCAUUAUCAAAUGUAUUUAUU |
| 5756 | 367 | UGACUCUGAGCAGGUCACUCC |
| 5757 | 368 | AAGGAAGGUCCGGUCAACACG |
| 5758 | 369 | AGUAGGAGAUGGGAGACCUGG |
| 5759 | 370 | UGGUCAUUAAGCAUAGGGAUU |
| 5760 | 371 | GAGCGGUAGUCUCAGUGCCUG |
| 5761 | 372 | UAAUGAACAGGGCCUUAAUAU |
| 5762 | 373 | UCCCUGCACGUGCAAUAUGUG |
| 5763 | 374 | AGCACCUCUUAACUAGAGUCU |
| 5764 | 375 | ACAAAGUGGGCAUCAGGCUC |
| 5765 | 376 | CAGAGAAGCAGACCAAUCUAU |
| 5766 | 377 | AUGGACGUGAGGCCUCCAGAG |
| 5767 | 378 | AUCAGUAUGUUCUUAAAUAAA |
| 5768 | 379 | AGCGAUCCUGCAUUUAAUCAG |
| 5769 | 380 | UGAGGCAGGAGACACAGAAAG |
| 5770 | 381 | AAGAGUAAGGGCGAACUGUCA |
| 5771 | 382 | UUGCCUCUCCCUUCCCUUCCC |
| 5772 | 383 | CUUCUCUUUCUCCCUCCUGGG |
| 5773 | 384 | CUCAUUCAUCAAGCAACUCUA |
| 5774 | 385 | AGGCAGGAGACACAGAAGGA |
| 5775 | 386 | UUAGUAUAAGAAUCAUAAACA |
| 5776 | 387 | UUACCUCCCUGCACGUGCAAU |
| 5777 | 388 | AAGCAACUCUACUUUGUGAAA |
| 5778 | 389 | ACCUCCAAGAGUAAGGGCGAA |
| 5779 | 390 | UAAUCAGUAUGUUCUUAAAUA |
| 5780 | 391 | AGUCCUGCUUCAGAAAGGCAU |
| 5781 | 392 | AGGCAGGUGAGAGAGCUGGG |
| 5782 | 393 | GUGGAUAGGCAAACAUUGGGG |
| 5783 | 394 | GGAUUCUUGUGAGAGAACGGG |
| 5784 | 395 | UCUCAGUGCCUGAGCCGCCCC |
| 5785 | 396 | ACUGUUUAUUAUAAAGACAUA |
| 5786 | 397 | UCCUGCAUUUAAUCAGUAUGU |

TABLE 8-continued

Results for APLN. Score threshold: 70.
Design: siRNA 21 nt.

| SEQ ID NO | siRNA_id | siRNA guide strand/AS Sequence |
|---|---|---|
| 5787 | 398 | UUCAGUCCUGCUUCAGAAAGG |
| 5788 | 399 | AUUUAAUCAGUAUGUUCUUAA |
| 5789 | 400 | AUUAGUAUAAGAAUCAUAAAC |
| 5790 | 401 | AUAAAGUAGGAGAUGGGAGAC |
| 5791 | 402 | CAAGCAUGAGCCUUUAAGCAG |
| 5792 | 403 | GACAUAUUUACACAGAACAAU |
| 5793 | 404 | UAGAUGAGACAGGCAGGGACU |
| 5794 | 405 | UGUUCCCUAUCUCCCAGCUUU |
| 5795 | 406 | AGCAGGAGCGCCUGCACGCAG |
| 5796 | 407 | UUAGGACACCCAAACAGAUGC |
| 5797 | 408 | UCUUAAAUAAACUGCUUUAAA |
| 5798 | 409 | UCCUUCUGUUCCUUUGCUUUC |
| 5799 | 410 | CCCAUCUUUCUUUCCUUCCUU |
| 5800 | 411 | AAGUCAUUAUCAAAUGUAUUU |
| 5801 | 412 | UUCUUUCCUUCCUUCUGUUCC |
| 5802 | 413 | AUGGAGUCCAGUGAUUGAAGG |
| 5803 | 414 | ACGGAAGCUAGGGCCUCCCGG |
| 5804 | 415 | UACCCUGGGUCUGGGAAUGCU |
| 5805 | 416 | ACAAGGGAUCUGCUGGAGCCC |
| 5806 | 417 | AGAUGGACUGGACGGAUUCUU |
| 5807 | 418 | AUCAAGAGGGAAGAGGGCGUC |
| 5808 | 419 | ACCUGGAGCUUGGGCUAGCUG |
| 5809 | 420 | UCUUAUGAACAGGGCCUUAA |
| 5810 | 421 | GAUUCUUGUGAGAGAACGGGA |
| 5811 | 422 | AUUGCCGUCUUCCAGCCCAUU |
| 5812 | 423 | AUUAUCAAAUGUAUUUAUUGC |
| 5813 | 424 | AGACAGGCAGGGACUAGGGCG |
| 5814 | 425 | UGCAUUUAAUCAGUAUGUUCU |
| 5815 | 426 | CGCAGAUUCAUGCUGCUCCUU |
| 5816 | 427 | AUUAAGCAUAGGGAUUCAUUU |
| 5817 | 428 | AUUCAUGCUGCUCCUUGGGCC |
| 5818 | 429 | CACCUCUUAACUAGAGUCUCU |
| 5819 | 430 | AACAACCACUUUAAAUAAGGC |
| 5820 | 431 | UCCAAAGUCAGUCCAGGGAGG |
| 5821 | 432 | AGAUGAGACAGGCAGGGACUA |
| 5822 | 433 | GCUAUCUCAUUCAUCAAGCAA |
| 5823 | 434 | AACGGGAAUCAUCCAAACUAC |
| 5824 | 435 | ACUACCCUCUUCUGUUCCCUA |
| 5825 | 436 | AAGAAGGCUAAGUGACCUUCA |
| 5826 | 437 | UCUGUUCCCUAUCUCCCAGCU |
| 5827 | 438 | AGGUGAGAGCUGAAUGGACGU |
| 5828 | 439 | AGGGACCCUCCACACACCGCG |
| 5829 | 440 | CUGAACAUGACCUCCAAGAGU |
| 5830 | 441 | AGUAUUGGGAGGCACACUAAG |
| 5831 | 442 | AGGCUCUUGUCUUCUCUUUCU |
| 5832 | 443 | UGCAUUCUUCCCUGGAGGCCA |
| 5833 | 444 | CACUUCACCAGAGCUCCUGAA |
| 5834 | 445 | CAUCAGGCUCUUGUCUUCUCU |
| 5835 | 446 | GUUAUGGAACCUUCCAGCCCA |
| 5836 | 447 | CAGCAGCAGCAGCAGCAGCAG |
| 5837 | 448 | CUUACCUCCCUGCACGUGCAA |
| 5838 | 449 | GGAGGAGACAUAACCGCCGGG |
| 5839 | 450 | GUAAGGGCGAACUGUCAGCUU |
| 5840 | 451 | CUGACCUGGAGCUUGGGCUAG |
| 5841 | 452 | AGGUGGAUAGGCAAACAUUGG |
| 5842 | 453 | CUCUUGUCUUCUCUUUCUCCC |
| 5843 | 454 | CAUAUUUACACAGAACAAUCU |
| 5844 | 455 | AAGGGCGAACUGUCAGCUUUU |
| 5845 | 456 | AGACUUUCUGGGCACCGACCA |
| 5846 | 457 | AAACAAAGUCAUUAUCAAAUG |
| 5847 | 458 | ACACUAAGGCAAGAGAAGUGA |
| 5848 | 459 | UCCUUGACCCUCUGGGCUGCA |
| 5849 | 460 | CAAUUUCUUAUGAACAGGGC |
| 5850 | 461 | CAUCAAGCAACUCUACUUUGU |
| 5851 | 462 | AGAAGAAGGGAGGCUUUCUGG |
| 5852 | 463 | CAGCAGCAGCAGCAGCAGCGU |
| 5853 | 464 | GAACAAUCUUUACAAACAUUG |
| 5854 | 465 | AGGCUAAGUGACCUUCAAGGG |
| 5855 | 466 | UCGGGAAGCGGCAUCAGGGAC |
| 5856 | 467 | UAGCAGCAGCAUAGGUAAAGG |
| 5857 | 468 | AAGGCAUGGGUCCCUUAUGGG |
| 5858 | 469 | UCUGCAGCCUCCUCUCCCGCC |
| 5859 | 470 | GAAGCAGACCAAUCUAUGGAG |
| 5860 | 471 | AUGAGCCUUUAAGCAGCAGCA |

TABLE 8-continued

Results for APLN. Score threshold: 70.
Design: siRNA 21 nt.

| SEQ ID NO | siRNA_id | siRNA guide strand/AS Sequence |
|---|---|---|
| 5861 | 472 | AGCUGAAUGGACGUGAGGCCU |
| 5862 | 473 | GAAGGCUACCUCGGACUCCUG |
| 5863 | 474 | CUGUUCCCUAUCUCCCAGCUU |
| 5864 | 475 | AGCUCUAACAUUCUGUGAUUC |
| 5865 | 476 | AGCAGCGUUAGCAGCAGCAUA |
| 5866 | 477 | UCUGGGCACCGACCAGUCCCC |
| 5867 | 478 | AGGAAGAUGGACUGGACGGAU |
| 5868 | 479 | ACCUGGUCAUUAAGCAUAGGG |
| 5869 | 480 | GAUGCAGGCACUUACCUCCCU |
| 5870 | 481 | AUCUGCUGGAGCCCACAGAAG |
| 5871 | 482 | CUAUUCCUGCUGCACUUCCUC |
| 5872 | 483 | AUCCUGCAUUUAAUCAGUAUG |
| 5873 | 484 | CAGAAGACACCCACCAAGGAU |
| 5874 | 485 | ACAACAGGACAGUUCACAGCC |
| 5875 | 486 | UGCAGCCUCCUCUCCCGCCGC |
| 5876 | 487 | UCAGUCCUGCUUCAGAAAGGC |
| 5877 | 488 | ACGCUGAUGCUCCACCCACUU |
| 5878 | 489 | CAGCAGCAGCGUUAGCAGCAG |
| 5879 | 490 | GAACCUUCCAGCCCAGCUGGG |
| 5880 | 491 | UAUGGAACCUUCCAGCCCAGC |
| 5881 | 492 | AAAUUAGUAUAAGAAUCAUAA |
| 5882 | 493 | CUCCUGAACAUGACCUCCAAG |
| 5883 | 494 | UCCUGACCUGGAGCUUGGGCU |
| 5884 | 495 | CUGUUUAUUAUAAAGACAUAU |
| 5885 | 496 | GCGGACAUUGCCGUCUUCCAG |
| 5886 | 497 | CUCUGAGCAGGUCACUCCCCU |
| 5887 | 498 | CACACACACAAAGUUGGGCAU |
| 5888 | 499 | CCAGAGAAGCAGACCAAUCUA |
| 5889 | 500 | AUGUGACCUGGUCAUUAAGCA |
| 5890 | 501 | AGGAAGGCCCAAAUGAAGGUU |
| 5891 | 502 | UCUCCCUUAACUGAGCAAACG |
| 5892 | 503 | AGCGGUAGUCUCAGUGCCUGA |
| 5893 | 504 | UCUGCAUUCUUCCCUGGAGGC |
| 5894 | 505 | UCCACCCACUUCACCAGAGCU |
| 5895 | 506 | UACUCCUGGGAGGGUAUAUAG |
| 5896 | 507 | CAGUGAUUGAAGGCUACCUCG |
| 5897 | 508 | GACUUUCUGGGCACCGACCAG |
| 5898 | 509 | CUUUGUAUAAAUUAGUAUAAG |
| 5899 | 510 | AUGAACAGGGCCUUAAUAUCU |
| 5900 | 511 | ACCCACUUCACCAGAGCUCCU |
| 5901 | 512 | CUUCUGCAGCCUCCUCUCCCG |
| 5902 | 513 | AAGAUGGACUGGACGGAUUCU |
| 5903 | 514 | UGUGCCCUGUCUGGAUCCCCG |
| 5904 | 515 | AGGCACACUAAGGCAAGAGAA |
| 5905 | 516 | AGUAUAAGAAUCAUAAACAAC |
| 5906 | 517 | UGCGGGCGCAGAGCUCGGGAG |
| 5907 | 518 | AUGUGCCCUGUCUGGAUCCCC |
| 5908 | 519 | AAGAGCUGGGCCCACUGGUGG |
| 5909 | 520 | AGCGCCUGCACGCAGAGCCGC |
| 5910 | 521 | UAAAGUAGGAGAUGGGAGACC |
| 5911 | 522 | AUUUCCUCCGACCUCCCUGCC |
| 5912 | 523 | GACAUUGCCGUCUUCCAGCCC |
| 5913 | 524 | AAAGAAGGCCCAAUCCCUGAU |
| 5914 | 525 | AUGCUGCUCCUUGGGCCGCCG |
| 5915 | 526 | AGGAGACAUAACCGCCGGGGG |
| 5916 | 527 | AAGACAUAUUUACACAGAACA |
| 5917 | 528 | UCCGGGAGCGGCAGCGGCGAG |
| 5918 | 529 | AGAUGGGAGACCUGGUCCCCA |
| 5919 | 530 | UGCCUCUCCCUUCCCUUCCCC |
| 5920 | 531 | AAGAAGGGAGUAUUGGGAGGC |
| 5921 | 532 | CUGGAAGGAAGGUCCGGUCAA |
| 5922 | 533 | GAACAGGGCCUUAAUAUCUUU |
| 5923 | 534 | CCCACUUCACCAGAGCUCCUG |
| 5924 | 535 | AAAGACAUAUUUACACAGAAC |
| 5925 | 536 | GAAUUCCUCCGACCUCCCUG |
| 5926 | 537 | UGGACGGAUUCUUGUGAGAGA |
| 5927 | 538 | AGGGCAGACAUGAGGAAGGAA |
| 5928 | 539 | GAGGAGACAUAACCGCCGGGG |
| 5929 | 540 | UGCUUCAGAAAGGCAUGGGUC |
| 5930 | 541 | CAAGGGUCCUGUCAGCUCUAA |
| 5931 | 542 | UCUUGUGAGAACGGGAAUC |
| 5932 | 543 | AGCAGACCAAUCUAUGGAGGA |
| 5933 | 544 | GAGUCCAGUGAUUGAAGGCUA |
| 5934 | 545 | AGGUGAGAAGAGCUGGGCCCA |

TABLE 8-continued

Results for APLN. Score threshold: 70. Design: siRNA 21 nt.

| SEQ ID NO | siRNA_id | siRNA guide strand/AS Sequence |
|---|---|---|
| 5935 | 546 | UCCAGCCCAUUCCCAUCGGGA |
| 5936 | 547 | AGGCGUUUGCCUAAGAAGGCU |
| 5937 | 548 | CCCUUAACUGAGCAAACGCUG |
| 5938 | 549 | CGGCUCUGCAAUGACUCUGAG |
| 5939 | 550 | AGGGAACAAUUUCUUAAUGAA |
| 5940 | 551 | UCCCGGCUCUGCAAUGACUCU |
| 5941 | 552 | CUGGGAACCCUGCUCAAGCAA |
| 5942 | 553 | AGGGCCUUAAUAUCUUUGUAU |
| 5943 | 554 | AGCAUGAGCCUUUAAGCAGCA |
| 5944 | 555 | UGAGAAGAGCUGGGCCCACUG |
| 5945 | 556 | AGUAAGGGCGAACUGUCAGCU |
| 5946 | 557 | AACCACUUUAAAUAAGGCAGC |
| 5947 | 558 | AGGUCAGGGAGGUGGGAGCAG |
| 5948 | 559 | UGCCUAAGAAGGCUAAGUGAC |
| 5949 | 560 | CCACACACCGCGGUCAAGGAG |
| 5950 | 561 | CAGCUCUAACAUUCUGUGAUU |
| 5951 | 562 | UGGGAGGCACACUAAGGCAAG |
| 5952 | 563 | GGUGAGAGCUGAAUGGACGUG |
| 5953 | 564 | GAGGGCGUCAUAAAGUAGGAG |
| 5954 | 565 | AGCUUGCCUCUCCCUUCCCUU |
| 5955 | 566 | UCUUCCCUCCUUCCUUCUGCC |
| 5956 | 567 | AGAAGAGCUGGGCCCACUGGU |
| 5957 | 568 | GGAAGGUCCGGUCAACACGAA |
| 5958 | 569 | CAUUCCUUGACCCUCUGGGCU |
| 5959 | 570 | AUGAGGCAGGAGACACAGAAA |
| 5960 | 571 | GCAUUUAAUCAGUAUGUUCUU |
| 5961 | 572 | CUUCCCUUCCUUCUUCUCCCC |
| 5962 | 573 | CACUACCCUCUUCUGUUCCCU |
| 5963 | 574 | GACAUGAGGAAGGAAGGCCCA |
| 5964 | 575 | UGAUGCUCCACCCACUUCACC |
| 5965 | 576 | AAAGUAGGAGAUGGGAGACCU |
| 5966 | 577 | CACAGAAGGGAGCACUUCCAC |

TABLE 9

Results for KIF20A. Score threshold: 70. Design: siRNA 21 nt.

| SEQ ID NO | siRNA_id | AS Sequence |
|---|---|---|
| 5967 | 1 | UAAUUUAGCUUUAACCUCCUG |
| 5968 | 2 | UUCACAUUGACAAUCAUGCAG |
| 5969 | 3 | UUUGAGUACAUCCUUUACCAU |
| 5970 | 4 | UUCUUGUCCACAUCAAUGGUG |
| 5971 | 5 | UUGACAAUCAUGCAGGAACGG |
| 5972 | 6 | UAGCUCUGCUUUGCACUGCUG |
| 5973 | 7 | UAGGUCAUAAAGCAGUUCGUU |
| 5974 | 8 | AACUACGACAUCGUCAUCGGA |
| 5975 | 9 | UACCUGAAGACUAUGUUCCUU |
| 5976 | 10 | UUGAUGGUACCUUGAAUCGUG |
| 5977 | 11 | UUUCCUGCUUCCUUCAACCGU |
| 5978 | 12 | UAAGAUGUCAUCACAAGUGGU |
| 5979 | 13 | UUACUCACACCUAGUCGCCGA |
| 5980 | 14 | UUGCACAUGAAUCCAGUUGAG |
| 5981 | 15 | UUCGAUGUAGACACUCCUCUU |
| 5982 | 16 | UCUGAUAGCAGGUUCUUGCGU |
| 5983 | 17 | UUCACCACUCUUCUGAUCUUU |
| 5984 | 18 | UCGAUGACUUGUUUCAUCCAG |
| 5985 | 19 | UUUAACCUCCUGAAGCUGCUG |
| 5986 | 20 | UUGUAGAUCUCAAAGAAUGAG |
| 5987 | 21 | UUGAGAUCUUUCACAUAGGGA |
| 5988 | 22 | AAUAUCUUUAAUAUAACUGUU |
| 5989 | 23 | UACGACAUCGUCAUCGGACAG |
| 5990 | 24 | UUCUAAUAGGUCAUAAAGCAG |
| 5991 | 25 | UUUCAACACAGUAUGAUACUG |
| 5992 | 26 | AUGACUUGUUUCAUCCAGCUG |
| 5993 | 27 | UGGAACACUCGAGUCAACUUG |
| 5994 | 28 | UACAUCCUUUACCAUCUCCUU |
| 5995 | 29 | AUCUGCUUGCUGUCUAGCCAG |
| 5996 | 30 | AACACUCGAGUCAACUUGCUG |
| 5997 | 31 | UUCACUGCACCACUGUUCCCG |
| 5998 | 32 | UUAUGCAACUCUUCAGUGGUA |
| 5999 | 33 | UUGGAGGCUAUUGAAGAUCAG |
| 6000 | 34 | UUCAGGAGAGUAGCUGACCCA |
| 6001 | 35 | UAUAAUUCCUGAUAUAUGGUA |
| 6002 | 36 | UUGAUUAAGAUGUCAUCACAA |
| 6003 | 37 | UCACAGAGUGACAGCUCGCUG |

TABLE 9-continued

Results for KIF20A.
Score threshold: 70. Design: siRNA 21 nt.

| SEQ ID NO | siRNA_id | AS Sequence |
|---|---|---|
| 6004 | 38 | UUCCACAACUUGUAGGAGCUC |
| 6005 | 39 | UUGUAGAACAAGGGUCUCCAC |
| 6006 | 40 | UUUCACUAGCACCAUGUUGUU |
| 6007 | 41 | UUUACCAUCUCCUUCACAGUU |
| 6008 | 42 | UGUUCUACCAUCUCAUUGCAA |
| 6009 | 43 | UAAUCUUUAAUAUAACUGU |
| 6010 | 44 | UUGUCCUCUAGGGAGGUAGAG |
| 6011 | 45 | UUUCUGAAGCUCUGUCCGCAA |
| 6012 | 46 | UUCUUCAUUUCCUCCUGUCGG |
| 6013 | 47 | AUCUCGGAGAUGCAUCUCCAG |
| 6014 | 48 | UACUUAUGCAACUCUUCAGUG |
| 6015 | 49 | UAGCACCAUGUUGUUCUGCAG |
| 6016 | 50 | AUACAUGCUGCCUUCUUCCGA |
| 6017 | 51 | UUAGGUUGAAGAAGGAUGCCU |
| 6018 | 52 | UCUGAUACUUAUGCAACUCUU |
| 6019 | 53 | UUAAGAUGUCAUCACAAGUGG |
| 6020 | 54 | UGCACUGCUGUAAUUUAGCUU |
| 6021 | 55 | UAUACUUUCACCUUCUCCAUA |
| 6022 | 56 | UUUCGAUGUAGACACUCCUCU |
| 6023 | 57 | UUUAGCUCUGCUUUGCACUGC |
| 6024 | 58 | UCGGAGAUGCAUCUCCAGCUG |
| 6025 | 59 | UACUGCUGGUACACUGACUGA |
| 6026 | 60 | UUCGUUGUAGAUCUCAAAGAA |
| 6027 | 61 | UAGAACAAGGGUCUCCACAUU |
| 6028 | 62 | UUCAUCUCGGAGAUGCAUCUC |
| 6029 | 63 | UAACUUCUUGUCCACAUCAAU |
| 6030 | 64 | UUCAGUGGUAGAGUUUAGCUC |
| 6031 | 65 | UCUCAAUACGGACACAACCCU |
| 6032 | 66 | UAGCAGGGACAGCUUCUUCAU |
| 6033 | 67 | UGUCUGAGUAUUGCAUCCUGG |
| 6034 | 68 | AUUUCUUCAGGAGAGUAGCUG |
| 6035 | 69 | AUCCUGAUUGAGAAGAUGCUG |
| 6036 | 70 | UUCUGGUUGAGGUGGGUGCUG |
| 6037 | 71 | UUGUCAGUGACUCCUUGAGGA |
| 6038 | 72 | UUCCUGUCGUUCCAACUCUGA |
| 6039 | 73 | UGACAGCUCGCUGAUCUUGGG |
| 6040 | 74 | UCUGAAGGUAACAAGGGCCUA |
| 6041 | 75 | UAUCUUUAAUAUAACUGUUUU |
| 6042 | 76 | UUAACCUCCUGAAGCUGCUGG |
| 6043 | 77 | UGUCGUUCCAACUCUGAAGGU |
| 6044 | 78 | UAGACACUCCUCUUCAAGGAA |
| 6045 | 79 | UUCCUUGAUGAACGAGUGCAG |
| 6046 | 80 | AUAUCUUUAAUAUAACUGUUU |
| 6047 | 81 | AUCUCAAAGAAUGAGAUCCAG |
| 6048 | 82 | UUUAGCUUUAACCUCCUGAAG |
| 6049 | 83 | UAACCUCCUGAAGCUGCUGGG |
| 6050 | 84 | UACUCACACCUAGUCGCCGAA |
| 6051 | 85 | UUGCAUCUGUUCUACCAUCUC |
| 6052 | 86 | UUCCUGCUUCCUUCAACCGUU |
| 6053 | 87 | UGACUGAUAGAAGAGAGCCCA |
| 6054 | 88 | UCUUCAUUUCCUCCUGUCGGA |
| 6055 | 89 | UAGUCGCCGAAGCUGGACUUU |
| 6056 | 90 | UUGAUGAACGAGUGCAGGGAU |
| 6057 | 91 | UUUCAUCUAGGUAGAUGCAC |
| 6058 | 92 | UAGGUUGAAGAAGGAUGCCUG |
| 6059 | 93 | UGACUUGUUUCAUCCAGCUGG |
| 6060 | 94 | UUCACUAGCACCAUGUUGUUC |
| 6061 | 95 | UCUUCUGAUCUUUGCAGCGCU |
| 6062 | 96 | UGGUAGAGUUUAGCUCUGCUU |
| 6063 | 97 | UCUGAGUAUUGCAUCCUGGAU |
| 6064 | 98 | AUAAUAUCUUUAAUAUAACUG |
| 6065 | 99 | UAGCAGGUUCUUGCGUACCAC |
| 6066 | 100 | UUCCUCCUGUCGGAUCUGCUU |
| 6067 | 101 | UUAGCUCUGCUUUGCACUGCU |
| 6068 | 102 | AACCCGAUCUUCCUGUCGUU |
| 6069 | 103 | UAGGCGGUUCUAAUAGGUCAU |
| 6070 | 104 | UCAUCGGACAGCAAGCCCGCU |
| 6071 | 105 | AUUCACAUUGACAAUCAUGCA |
| 6072 | 106 | UAAAUUUCGAAGGAAUGGUUU |
| 6073 | 107 | UCUUGCACAUGAAUCCAGUUG |
| 6074 | 108 | UUGGAGGCCUCCAUUUAGCAG |
| 6075 | 109 | UCCUGUCGGAUCUGCUUGCUG |
| 6076 | 110 | UUGGAGAGACUCACCAAGUUU |

TABLE 9-continued

Results for KIF20A.
Score threshold: 70. Design: siRNA 21 nt.

| SEQ ID NO | siRNA_id | AS Sequence |
|---|---|---|
| 6077 | 111 | UCGAUGUAGACACUCCUCUUC |
| 6078 | 112 | UUGCACUGCUGUAAUUUAGCU |
| 6079 | 113 | AAGCUCUCUCUGCUGAUUGGA |
| 6080 | 114 | UACAUGCUGCCUUCUUCCGAA |
| 6081 | 115 | UACUGCUCAGCAAUACAUGCU |
| 6082 | 116 | AUUGAGAAGAUGCUGUGACUG |
| 6083 | 117 | AACUUGUAGGAGCUCCUCUUU |
| 6084 | 118 | UAGAGACGACAGAGCAGUCUG |
| 6085 | 119 | UAAUAGGUCAUAAAGCAGUUC |
| 6086 | 120 | UUGGAGUUUCAACACAGUAUG |
| 6087 | 121 | UUACCAUCUCCUUCACAGUUA |
| 6088 | 122 | UCCAUAUGUAUAGAUGAGCCA |
| 6089 | 123 | UGCAUCUGUUCUACCAUCUCA |
| 6090 | 124 | AUCACAGAGUGACAGCUCGCU |
| 6091 | 125 | UGCUUGUAGAACAAGGGUCUC |
| 6092 | 126 | UUCUUGCGUACCACAGACCCC |
| 6093 | 127 | UAGCCGCAAAGUCUGCCUCUU |
| 6094 | 128 | UUUGUGACCGCCGUAGGGCCA |
| 6095 | 129 | AUGCAUCUCCAGCUGUAGCUU |
| 6096 | 130 | AGCUCUGUCCGCAACAGCCUU |
| 6097 | 131 | UUUGCCGGGACAGGUAGUGGG |
| 6098 | 132 | UACGGACACAACCCUGAUCUU |
| 6099 | 133 | UCUUCCUGUCGUUCCAACUCU |
| 6100 | 134 | UGUUGUUCUGCAGUUCAGCCA |
| 6101 | 135 | UACACUGACUGAUAGAAGAGA |
| 6102 | 136 | AAGAAUGAGAUCCAGAUGGAG |
| 6103 | 137 | AACAGCCUUAUAUUCUUCGG |
| 6104 | 138 | UCAUAGGUAGAUGCACAGGGA |
| 6105 | 139 | UCUUGCGUACCACAGACCCCA |
| 6106 | 140 | AUCUUUAAUAUAACUGUUUUU |
| 6107 | 141 | UUCUGAUCUUUGCAGCGCUCU |
| 6108 | 142 | AGAAACCUUGGAACACUCGAG |
| 6109 | 143 | UUGGAACACUCGAGUCAACUU |
| 6110 | 144 | AUUGCAAAUUUCAUCUCGGAG |
| 6111 | 145 | UGUAGGAGCUCCUCUUUGCCA |
| 6112 | 146 | UGCAUCUCCAGCUGUAGCUUU |
| 6113 | 147 | UUCUUCAGGAGAGUAGCUGAC |
| 6114 | 148 | UCACCUUCUCCAUACUGUCCU |
| 6115 | 149 | UUAGUGACUCCAUAUGUAUAG |
| 6116 | 150 | UGAAGAAGGAUGCCUGUCCCA |
| 6117 | 151 | AAUUUCAUCUCGGAGAUGCAU |
| 6118 | 152 | AAGCUCUGUCCGCAACAGCCU |
| 6119 | 153 | UCUCAUUGCAAAUUUCAUCUC |
| 6120 | 154 | UCAUUGCAAAUUUCAUCUCGG |
| 6121 | 155 | UUGCCGGGACAGGUAGUGGGG |
| 6122 | 156 | UCGGAUCUGCUUGCUGUCUAG |
| 6123 | 157 | ACAUUGACAAUCAUGCAGGAA |
| 6124 | 158 | UAUGCAACUCUUCAGUGGUAG |
| 6125 | 159 | UACCUCAUUGGAGAGCAAGGG |
| 6126 | 160 | AAGUUUCUGAAGCUCUGUCCG |
| 6127 | 161 | AAGAAACCUUGGAACACUCGA |
| 6128 | 162 | UAUUUCUUCAGGAGAGUAGCU |
| 6129 | 163 | AUGUGAACAAUAAUAUCUUUA |
| 6130 | 164 | UGAUAGAAGAGAGCCCAGCAA |
| 6131 | 165 | UCUAACUUCUUGUCCACAUCA |
| 6132 | 166 | AAUAUCAUCAUCAAGGCCUGU |
| 6133 | 167 | UCUGAUCUUUGCAGCGCUCUG |
| 6134 | 168 | UCUUCUAACUUCUUGUCCACA |
| 6135 | 169 | UGGUACCUUGAAUCGUGUGGG |
| 6136 | 170 | UUUCUUCAGGAGAGUAGCUGA |
| 6137 | 171 | ACACAGUAUGAUACUGCUCAG |
| 6138 | 172 | UUUAGCAGGGACAGCUUCUUC |
| 6139 | 173 | UAGCUUUAACCUCCUGAAGCU |
| 6140 | 174 | AUCUGUUCUACCAUCUCAUUG |
| 6141 | 175 | AUCGAUGACUUGUUUCAUCCA |
| 6142 | 176 | UGAUCUUUGCAGCGCUCUGAG |
| 6143 | 177 | UCCUCCUGUCGGAUCUGCUUG |
| 6144 | 178 | UUUGAUUAAGAUGUCAUCACA |
| 6145 | 179 | AUGAAUCCAGUUGAGAUCUUU |
| 6146 | 180 | AGCUUCUAGCUCUUCAAUCUU |
| 6147 | 181 | UUGUAGGAGCUCCUCUUUGCC |
| 6148 | 182 | AUCUCCUUCACAGUUAGGUUG |
| 6149 | 183 | UGUCAGUGACUCCUUGAGGAU |

TABLE 9-continued

Results for KIF20A.
Score threshold: 70. Design: siRNA 21 nt.

| SEQ ID NO | siRNA_id | AS Sequence |
|---|---|---|
| 6150 | 184 | UUCUCCAUACUGUCCUCAGAU |
| 6151 | 185 | AUCUUGCACAUGAAUCCAGUU |
| 6152 | 186 | AGCAUCUUGCACAUGAAUCCA |
| 6153 | 187 | UUCACAGUUAGGUUGAAGAAG |
| 6154 | 188 | AGUGACAGCUCGCUGAUCUUG |
| 6155 | 189 | UAACAAGGGCCUAACCCUCAA |
| 6156 | 190 | UAGAGUUUAGCUCUGCUUUGC |
| 6157 | 191 | AUGAGAGUUUCAUCAUAGGU |
| 6158 | 192 | ACUGCUGGUACACUGACUGAU |
| 6159 | 193 | UGCUGCUUGUCCUCUAGGGAG |
| 6160 | 194 | UCAUCAUAGGUAGAUGCACAG |
| 6161 | 195 | UUGAGUACAUCCUUUACCAUC |
| 6162 | 196 | UGGACUUUCGCAGCCGCAGAG |
| 6163 | 197 | AACUCUGAAGGUAACAAGGGC |
| 6164 | 198 | UGAGAAGAUGCUGUGACUGCG |
| 6165 | 199 | UGCAACUCUUCAGUGGUAGAG |
| 6166 | 200 | UUGUCCACAUCAAUGGUGAAG |
| 6167 | 201 | ACCAGGUUCUGCUUUGACCGG |
| 6168 | 202 | AUAGGUCAUAAAGCAGUUCGU |
| 6169 | 203 | UUAGCAGGGACAGCUUCUUCA |
| 6170 | 204 | UUCAACACAGUAUGAUACUGC |
| 6171 | 205 | AAGUGGUCAAGGCUUGACGAA |
| 6172 | 206 | CUAACUUCUUGUCCACAUCAA |
| 6173 | 207 | AGCUUUAACCUCCUGAAGCUG |
| 6174 | 208 | UAGAUGCACAGGGAUUCACAU |
| 6175 | 209 | AUUAAGAUGUCAUCACAAGUG |
| 6176 | 210 | UGGUUGUGGUUUGGUUGCUG |
| 6177 | 211 | UAAGGGCUGCAGUCUGUUGAG |
| 6178 | 212 | AUACCUGAAGACUAUGUUCCU |
| 6179 | 213 | UGAAGAGUUUCAUCAUAGGUA |
| 6180 | 214 | AAGACUAUGUUCCUUGAUGAA |
| 6181 | 215 | UGCUUUGACCGGUUCUGCUGG |
| 6182 | 216 | UGGAGUUUCAACACAGUAUGA |
| 6183 | 217 | UCAUAAAGCAGUUCGUUGUAG |
| 6184 | 218 | ACUUUCGAUGUAGACACUCCU |
| 6185 | 219 | AUCAUAGGUAGAUGCACAGGG |
| 6186 | 220 | UCCAGUUUCACUAGCACCAUG |
| 6187 | 221 | AAACAUGGGAGAAACUACGAC |
| 6188 | 222 | AACCUUGGAACACUCGAGUCA |
| 6189 | 223 | AACAACAUGAGAUUACAUAGG |
| 6190 | 224 | UGCCUUCUUCCGAAGGUCCAG |
| 6191 | 225 | UUUCGCAGCCGCAGAGCACAA |
| 6192 | 226 | AUACUUAUGCAACUCUUCAGU |
| 6193 | 227 | UCCUGAUAUAUGGUAAAGCAU |
| 6194 | 228 | AAUGUUUCCUGCUUCCUUCAA |
| 6195 | 229 | UGGAACCUGCUGCUUGUCCUC |
| 6196 | 230 | AAACCUUGGAACACUCGAGUC |
| 6197 | 231 | AACAUGAGAUUACAUAGGUGG |
| 6198 | 232 | AUGACUGCUCUUCUCUUUCCC |
| 6199 | 233 | AGGUGUAGGAUCCUGAUUGAG |
| 6200 | 234 | UCAAGGAAGUGGACAGCUCCU |
| 6201 | 235 | UUAAUGUUUCCUGCUUCCUUC |
| 6202 | 236 | CAACAUGAGAUUACAUAGGUG |
| 6203 | 237 | AAGCAGUUCGUUGUAGAUCUC |
| 6204 | 238 | UGAGAUCUUUCACAUAGGGAU |
| 6205 | 239 | UGAAGGUGUAGGAUCCUGAUU |
| 6206 | 240 | AACAAUAAUAUCUUUAAUAUA |
| 6207 | 241 | AUUUAGCAGGGACAGCUUCUU |
| 6208 | 242 | UUGAAGAAGGAUGCCUGUCCC |
| 6209 | 243 | UACAUGGAGAUGUCAGCUUCA |
| 6210 | 244 | AUAUAAUUCCUGAUAUAUGGU |
| 6211 | 245 | UGCAAGAGAGCUUCUAGCUCU |
| 6212 | 246 | UAACCCUCAAGUAUACUUUCA |
| 6213 | 247 | CUGAUCUUCCUGUCGUUCCAA |
| 6214 | 248 | UGCAGCUGUGGACUCAAACAU |
| 6215 | 249 | UAGGGAGGUAGAGACGACAGA |
| 6216 | 250 | AAAUGUUCACUGCACCACUGU |
| 6217 | 251 | UUGUGACCGCCGUAGGGCCAA |
| 6218 | 252 | UCCAUUUAGCAGGGACAGCUU |
| 6219 | 253 | UCCAGUUGAGAUCUUUCACAU |
| 6220 | 254 | UGAUGGUACCUUGAAUCGUGU |
| 6221 | 255 | UUGACCGGUUCUGCUGGUUUU |
| 6222 | 256 | ACAACAUGAGAUUACAUAGGU |

TABLE 9-continued

Results for KIF20A.
Score threshold: 70. Design: siRNA 21 nt.

| SEQ ID NO | siRNA_id | AS Sequence |
|---|---|---|
| 6223 | 257 | UGGACAGCUCCUCCUCUUGGA |
| 6224 | 258 | AGUGUCUGAGUAUUGCAUCCU |
| 6225 | 259 | UCCUGUCGUUCCAACUCUGAA |
| 6226 | 260 | UGUCGGAUCUGCUUGCUGUCU |
| 6227 | 261 | UACCAUCUCCUUCACAGUUAG |
| 6228 | 262 | UGCCCUUUGAGUACAUCCUUU |
| 6229 | 263 | AAUACAUGCUGCCUUCUUCCG |
| 6230 | 264 | UCUUUGCAGCGCUCUGAGCCA |
| 6231 | 265 | UCACAUUGACAAUCAUGCAGG |
| 6232 | 266 | UCAACACAGUAUGAUACUGCU |
| 6233 | 267 | AAGUGGACAGCUCCUCCUCUU |
| 6234 | 268 | UUUCACCUUCUCCAUACUGUC |
| 6235 | 269 | UGCUGGUACCUAUCCGACUUU |
| 6236 | 270 | UCGGCCUGUGAAGAAACCUUG |
| 6237 | 271 | UAAUGUUCCUGCUUCCUUCA |
| 6238 | 272 | AACAGGGUCUCCACAUUCUC |
| 6239 | 273 | AUCCUGGAUAUAAUUCCUGAU |
| 6240 | 274 | AAUCCCUCCAUCCUUGAUGGU |
| 6241 | 275 | CUUGAUGGUACCUUGAAUCGU |
| 6242 | 276 | AAAGUCUGCCUCUUGCGCUGU |
| 6243 | 277 | UCAGAUGGAACCUGCUGCUUG |
| 6244 | 278 | AACCGUUCACCACUCUUCUGA |
| 6245 | 279 | UUUCCUCCAAUAGUUCCUUUU |
| 6246 | 280 | UGCACCACUGUUCCCGCUGUU |
| 6247 | 281 | AAUGUUCACUGCACCACUGUU |
| 6248 | 282 | UGCAGGAACGGCCUCGGCCUG |
| 6249 | 283 | AAUUUAGCUUUAACCUCCUGA |
| 6250 | 284 | CUUACUCACACCUAGUCGCCG |
| 6251 | 285 | CUAUGUUCCUUGAUGAACGAG |
| 6252 | 286 | UUGUUGGUUUGGUUGCUGAUU |
| 6253 | 287 | AGUUUACUAGCACCAUGUUG |
| 6254 | 288 | UCGUCAUCGGACAGCAAGCCC |
| 6255 | 289 | UUCUAACUUCUUGUCCACAUC |
| 6256 | 290 | UCUGCUUUGACCGGUUCUGCU |
| 6257 | 291 | UGAUGGAGAGACUCACCAAG |
| 6258 | 292 | UCAGUGGUAGAGUUUAGCUCU |
| 6259 | 293 | UCAAUAUCAUCAUCAAGGCCU |
| 6260 | 294 | CUCAAUACGGACACAACCCUG |
| 6261 | 295 | UGAGUUAGUGACUCCAUAUGU |
| 6262 | 296 | UGGAGUUCUGGUUGAGGUGGG |
| 6263 | 297 | ACAACUUGUAGGAGCUCCUCU |
| 6264 | 298 | UACUGUCCUCAGAUGGAACCU |
| 6265 | 299 | AAAUCUGCAGCUGUGGACUCA |
| 6266 | 300 | CUUCUUGUCCACAUCAAUGGU |
| 6267 | 301 | UGCUUGUCCUCUAGGGAGGUA |
| 6268 | 302 | UCUAAUAGGUCAUAAAGCAGU |
| 6269 | 303 | UGCAUAGAAAUCAUAUAAGUA |
| 6270 | 304 | AGUUUCUGAAGCUCUGUCCGC |
| 6271 | 305 | ACAGAGUGACAGCUCGCUGAU |
| 6272 | 306 | UGAUACUGCUCAGCAAUACAU |
| 6273 | 307 | ACACUCGAGUCAACUUGCUGU |
| 6274 | 308 | UGAUACUUAUGCAACUCUUCA |
| 6275 | 309 | CAACCGUUCACCACUCUUCUG |
| 6276 | 310 | UCCUUGAGGAUAUUUAGUUUU |
| 6277 | 311 | UUCUAGCUCUUCAAUCUUUUC |
| 6278 | 312 | GUGUCUGAGUAUUGCAUCCUG |
| 6279 | 313 | ACUUAUGCAACUCUUCAGUGG |
| 6280 | 314 | CUUCCUGUCGUUCCAACUCUG |
| 6281 | 315 | ACUUGUAGGAGCUCCUCUUUG |
| 6282 | 316 | UAUCCGACUUUCGAUGUAGAC |
| 6283 | 317 | AAACUACGACAUCGUCAUCGG |
| 6284 | 318 | ACUGCUCAGCAAUACAUGCUG |
| 6285 | 319 | AUUCAGACCCUGAUUGCUGAU |
| 6286 | 320 | UGUAAUUUAGCUUUAACCUCC |
| 6287 | 321 | UCCUGUUUGAUUAAGAUGUCA |
| 6288 | 322 | UCGCAUAGCCGCAAAGUCUGC |
| 6289 | 323 | UGGGUGCUUGUAGAACAAGGG |
| 6290 | 324 | AACUCUUCAGUGGUAGAGUUU |
| 6291 | 325 | AUUGGAGAGACUCACCAAGUU |
| 6292 | 326 | AUUUCCUCCAAUAGUUCCUUU |
| 6293 | 327 | UUCUGCUUUGACCGGUUCUGC |
| 6294 | 328 | UCCAACUCUGAAGGUAACAAG |
| 6295 | 329 | UGACUGCUCUUCUCUUUCCCC |

TABLE 9-continued

Results for KIF20A.
Score threshold: 70. Design: siRNA 21 nt.

| SEQ ID NO | siRNA_id | AS Sequence |
|---|---|---|
| 6296 | 330 | UUUCCUCCUGUCGGAUCUGCU |
| 6297 | 331 | GACACAACCCUGAUCUUCCUG |
| 6298 | 332 | UUGCAAAUUUCAUCUCGGAGA |
| 6299 | 333 | AUGUAGACACUCCUCUUCAAG |
| 6300 | 334 | AAGGGAACCAGGUUCUGCUUU |
| 6301 | 335 | UUCAUUGCUCUUCAGGGCAAA |
| 6302 | 336 | AAGUCUGCCUCUUGCGCUGUU |
| 6303 | 337 | AAUCCCAGUUGCAUAGGUGGG |
| 6304 | 338 | ACUAUGUUCCUUGAUGAACGA |
| 6305 | 339 | ACAGUUAGGUUGAAGAAGGAU |
| 6306 | 340 | UUCCUGCAAGAGAGCUUCUAG |
| 6307 | 341 | UGUAGGAUCCUGAUUGAGAAG |
| 6308 | 342 | UUCCAACUCUGAAGGUAACAA |
| 6309 | 343 | UAGGAUCCUGAUUGAGAAGAU |
| 6310 | 344 | AUCAGGUGUUGGAUGAAGUUG |
| 6311 | 345 | AACACAGUAUGAUACUGCUCA |
| 6312 | 346 | UCCUUGAUGAACGAGUGCAGG |
| 6313 | 347 | UAGAUCUCAAAGAAUGAGAUC |
| 6314 | 348 | ACUGUCCUCAGAUGGAACCUG |
| 6315 | 349 | ACCUUGGAACACUCGAGUCAA |
| 6316 | 350 | AACCUCCUGAAGCUGCUGGGU |
| 6317 | 351 | UCUGGUUCUUACGACCCACUU |
| 6318 | 352 | UCAAUACGGACACAACCCUGA |
| 6319 | 353 | UACCUUGAAUCGUGUGGGUUU |
| 6320 | 354 | GAUACUUAUGCAACUCUUCAG |
| 6321 | 355 | UAGUGUCUGAGUAUUGCAUCC |
| 6322 | 356 | UCGUUGUAGAUCUCAAAGAAU |
| 6323 | 357 | AACCUGCUGCUUGUCCUCUAG |
| 6324 | 358 | AUCCCAGUUGCAUAGGUGGGG |
| 6325 | 359 | AGAGCAGUCUGAUAGCAGGUU |
| 6326 | 360 | UGUAGAGAGGUGUUAAUGUUU |
| 6327 | 361 | UCUCCACAUUCUCAAUACGGA |
| 6328 | 362 | UCCCUGAGUUAGUGACUCCAU |
| 6329 | 363 | AUCAAGUGGUCAAGGCUUG |
| 6330 | 364 | ACUUUCACCUUCUCCAUACUG |
| 6331 | 365 | CUUUGCAGCGCUCUGAGCCAG |
| 6332 | 366 | AAGAUGCUGUGACUGCGGCUG |
| 6333 | 367 | AUGGUACCUUGAAUCGUGUGG |
| 6334 | 368 | CAACACAGUAUGAUACUGCUC |
| 6335 | 369 | AUCCUUUACCAUCUCCUUCAC |
| 6336 | 370 | UCUUCAUACAUUUCCUCCAAU |
| 6337 | 371 | UUCAAGGAAGUGGACAGCUCC |
| 6338 | 372 | UACCUAUCCGACUUUCGAUGU |
| 6339 | 373 | CUGCCCUUUGAGUACAUCCUU |
| 6340 | 374 | UUGAGAAGAUGCUGUGACUGC |
| 6341 | 375 | UCAAAGAAUGAGAUCCAGAUG |
| 6342 | 376 | UUGGUUUGGUUGCUGAUUUUC |
| 6343 | 377 | AUAGCCGCAAAGUCUGCCUCU |
| 6344 | 378 | UGCAAAUUUCAUCUCGGAGAU |
| 6345 | 379 | UCAGGAGAGUAGCUGACCCAC |
| 6346 | 380 | UGUAGAACAAGGGUCUCCACA |
| 6347 | 381 | CUGAUUGGAGAGACUCACCAA |
| 6348 | 382 | UCUUUCACAUAGGGAUUGCCA |
| 6349 | 383 | UCAAGUAUACUUUCACCUUCU |
| 6350 | 384 | AUUUAGCUUUAACCUCCUGAA |
| 6351 | 385 | AUCCCUUGCGACAUGACGGCA |
| 6352 | 386 | UGCUGGUACACUGACUGAUAG |
| 6353 | 387 | AAUCCAGUUGAGAUCUUUCAC |
| 6354 | 388 | CUGAAGACUAUGUUCCUUGAU |
| 6355 | 389 | AGCAGUUCGUUGUAGAUCUCA |
| 6356 | 390 | UUGGGUGCUUGUAGAACAAGG |
| 6357 | 391 | UACAUUUGGAAUUCAAUAAAA |
| 6358 | 392 | UCCUGAUCUCUUCUUGGUAA |
| 6359 | 393 | UGAACGAGUGCAGGGAUGGGA |
| 6360 | 394 | UGCAUCCUGGAUAUAAUUCCU |
| 6361 | 395 | AUUUCGAAGGAAUGGUUUCUU |
| 6362 | 396 | UGUUAAUGUUCCUGCUUCCU |
| 6363 | 397 | ACUCUUCUGAUCUUUGCAGCG |
| 6364 | 398 | UGUUCCUUGAUGAACGAGUGC |
| 6365 | 399 | CUGUAAUUUAGCUUUAACCUC |
| 6366 | 400 | GAACACUCGAGUCAACUUGCU |
| 6367 | 401 | UGGUACCUAUCCGACUUUCGA |
| 6368 | 402 | UCAACCGUUCACCACUCUUCU |

TABLE 9-continued

Results for KIF20A.
Score threshold: 70. Design: siRNA 21 nt.

| SEQ ID NO | siRNA_id | AS Sequence |
|---|---|---|
| 6369 | 403 | UCCACAUCAAUGGUGAAGGGC |
| 6370 | 404 | UCGAGUCAACUUGCUGUCACG |
| 6371 | 405 | UUCUCAAUACGGACACAACCC |
| 6372 | 406 | ACAGCUUCUUCAUUUCCUCCU |
| 6373 | 407 | CAACUUGUAGGAGCUCCUCUU |
| 6374 | 408 | UGAAGCUGCGGGUGGAGGCA |
| 6375 | 409 | UGGGAGAAACUACGACAUCGU |
| 6376 | 410 | UAGGUGGUUAUAAUACAAAAG |
| 6377 | 411 | GACAGCUCGCUGAUCUUGGGG |
| 6378 | 412 | ACCAAGUUUCUGAAGCUCUGU |
| 6379 | 413 | UAAAGCAGUUCGUUGUAGAUC |
| 6380 | 414 | ACUUGUCAGUGACUCCUUGAG |
| 6381 | 415 | UUCACCUUCUCCAUACUGUCC |
| 6382 | 416 | GUAUACUUUCACCUUCUCCAU |
| 6383 | 417 | CAGUGGUAGAGUUUAGCUCUG |
| 6384 | 418 | UCCAAAUGUUCACUGCACCAC |
| 6385 | 419 | AUGGUUUCUUCCCUGGUGGUU |
| 6386 | 420 | AGAGACGACAGAGCAGUCUGA |
| 6387 | 421 | UGUGAAGAAACCUUGGAACAC |
| 6388 | 422 | UUCAACCGUUCACCACUCUUC |
| 6389 | 423 | UGCACAGGGAUUCACAUUGAC |
| 6390 | 424 | UGACAAUCAUGCAGGAACGGC |
| 6391 | 425 | AUACAUGGAGAUGUCAGCUUC |
| 6392 | 426 | AUAAAGCAGUUCGUUGUAGAU |
| 6393 | 427 | CAUGAGAUUACAUAGGUGGUU |
| 6394 | 428 | CUCUUCUAACUUCUUGUCCAC |
| 6395 | 429 | CACACCUAGUCGCCGAAGCUG |
| 6396 | 430 | GACAUCGUCAUCGGACAGCAA |
| 6397 | 431 | ACUAGCACCAUGUUGUUCUGC |
| 6398 | 432 | UAGCUGACCCACCUCAGGGCC |
| 6399 | 433 | ACUCGAGUCAACUUGCUGUCA |
| 6400 | 434 | AAGGGCUUCAGAUCAGGUGUU |
| 6401 | 435 | AACCAGGUUCUGCUUUGACCG |
| 6402 | 436 | UGAACAAUAAUAUCUUUAAUA |
| 6403 | 437 | UUCAUCAUAGGUAGAUGCACA |
| 6404 | 438 | UGAGGGUGGUGGUUCUAACAU |
| 6405 | 439 | UCAGAUCAGGUGUUGGAUGAA |
| 6406 | 440 | UUCCUCCAAUAGUUCCUUUUG |
| 6407 | 441 | AGCUUCUUCAUUUCCUCCUGU |
| 6408 | 442 | ACAUCGUCAUCGGACAGCAAG |
| 6409 | 443 | AGAGAGCUUCUAGCUCUUCAA |
| 6410 | 444 | CAUUGCAAAUUUCAUCUCGGA |
| 6411 | 445 | AAGAGUUUCAUCAUAGGUAGA |
| 6412 | 446 | AAGCUGGACUUUCGCAGCCGC |
| 6413 | 447 | AUCGUCAUCGGACAGCAAGCC |
| 6414 | 448 | UUUCGAAGGAAUGGUUUCUUC |
| 6415 | 449 | UCCUUUACCAUCUCCUUCACA |
| 6416 | 450 | CAGCUUCUUCAUUUCCUCCUG |
| 6417 | 451 | CAACUCUGAAGGUAACAAGGG |
| 6418 | 452 | UGGGUGUCCAAAUGUUCACUG |
| 6419 | 453 | UAGGAUCCGGGCAUAAGGGCU |
| 6420 | 454 | ACAUGAGAUUACAUAGGUGGU |
| 6421 | 455 | ACCACUCUUCUGAUCUUUGCA |
| 6422 | 456 | UACCAUCUCAUUGCAAAUUUC |
| 6423 | 457 | ACAUCCUUUACCAUCUCCUUC |
| 6424 | 458 | UGAAGAAACCUUGGAACACUC |
| 6425 | 459 | UCUUGUCCACAUCAAUGGUGA |
| 6426 | 460 | UAGUGACUCCAUAUGUAUAGA |
| 6427 | 461 | UCAUCACAAGUGGUCAAGGCU |
| 6428 | 462 | CACAACUUGUAGGAGCUCCUC |
| 6429 | 463 | AAGAUGUCAUCACAAGUGGUC |
| 6430 | 464 | AAUCUGCAGCUGUGGACUCAA |
| 6431 | 465 | UCCAUCCUUGAUGGUACCUUG |
| 6432 | 466 | UGGAGAAGCGAAUGUUUGCCG |
| 6433 | 467 | UACAUUUCCUCCAAUAGUUCC |
| 6434 | 468 | UCGAAGCUGGUGCUGGUACCU |
| 6435 | 469 | AUGAACGAGUGCAGGGAUGGG |
| 6436 | 470 | AGCUGUGGACUCAAACAUGGG |
| 6437 | 471 | UCUGCUGAUUGGAGAGACUCA |
| 6438 | 472 | ACCUUUGUGACCGCCGUAGGG |
| 6439 | 473 | CACAUUGACAAUCAUGCAGGA |
| 6440 | 474 | CAGUAUGAUACUGCUCAGCAA |
| 6441 | 475 | UGACCGGUUCUGCUGGUUUUG |

TABLE 9-continued

Results for KIF20A.
Score threshold: 70. Design: siRNA 21 nt.

| SEQ ID NO | siRNA_id | AS Sequence |
|---|---|---|
| 6442 | 476 | UGAGAUUACAUAGGUGGUUAU |
| 6443 | 477 | AAAGAAUGAGAUCCAGAUGGA |
| 6444 | 478 | AUGUUCCUUGAUGAACGAGUG |
| 6445 | 479 | UCUCCUUCACAGUUAGGUUGA |
| 6446 | 480 | UCUCUCUGCUGAUUGGAGAGA |
| 6447 | 481 | UCACAAGUGGUCAAGGCUUGA |
| 6448 | 482 | CUGUUGCAUCUGUUCUACCAU |
| 6449 | 483 | UUUCAUCUCGGAGAUGCAUCU |
| 6450 | 484 | UAUUGCAUCCUGGAUAUAAUU |
| 6451 | 485 | CUGCUUUGACCGUUCUGCUG |
| 6452 | 486 | AGCUCUGGUUCUUACGACCCA |
| 6453 | 487 | AAGUAUACUUUCACCUUCUCC |
| 6454 | 488 | ACACUGACUGAUAGAAGAGAG |
| 6455 | 489 | ACAUAGGUGGUUAUAAUACAA |
| 6456 | 490 | GCAUCUUGCACAUGAAUCCAG |
| 6457 | 491 | UCUGCCCUUUGAGUACAUCCU |
| 6458 | 492 | UUGGAGAGCAAGGGCUUCAGA |
| 6459 | 493 | AGGUGUUAAUGUUUCCUGCUU |
| 6460 | 494 | CUCCUGAAUCUCUUCUUGGUA |
| 6461 | 495 | UGAAGCUCUGUCCGCAACAGC |
| 6462 | 496 | UCCUGAUUGAGAAGAUGCUGU |
| 6463 | 497 | UUCUGAAGCUCUGUCCGCAAC |
| 6464 | 498 | AUGGAACCUGCUGCUUGUCCU |
| 6465 | 499 | AGGAAGUGGACAGCUCCUCCU |
| 6466 | 500 | CUGAUCUUUGCAGCGCUCUGA |
| 6467 | 501 | UAUGAUACUGCUCAGCAAUAC |
| 6468 | 502 | CAUAGGUAGAUGCACAGGGAU |
| 6469 | 503 | ACCUAUCCGACUUUCGAUGUA |
| 6470 | 504 | AAGGUGUAGGAUCCUGAUUGA |
| 6471 | 505 | UGUCCUCAGAUGGAACCUGCU |
| 6472 | 506 | AUAUCAUCAAGGCCUGUG |
| 6473 | 507 | UCUUCAAGGAAGUGGACAGCU |
| 6474 | 508 | UGUUUGAUUAAGAUGUCAUCA |
| 6475 | 509 | UGAUUAAGAUGCAUCACAAG |
| 6476 | 510 | UCUGGUUGAGGUGGGUGCUGG |
| 6477 | 511 | UUUGACCGGUUCUGCUGGUUU |
| 6478 | 512 | UAAUUCCUGAUAUAUGGUAAA |
| 6479 | 513 | UGACUCCUUGAGGAUAUUUAG |
| 6480 | 514 | AGCUAGUGUCUGAGUAUUGCA |
| 6481 | 515 | UCGCCGAAGCUGGACUUUCGC |
| 6482 | 516 | UCACACCUAGUCGCCGAAGCU |
| 6483 | 517 | CUUUCGAUGUAGACACUCCUC |
| 6484 | 518 | UGUUGCAUCUGUUCUACCAUC |
| 6485 | 519 | UCCCUUGCGACAUGACGGCAG |
| 6486 | 520 | UGUCACGGAAGGGAACCAGGU |
| 6487 | 521 | ACAUGGAGAUGUCAGCUUCAU |
| 6488 | 522 | ACUGCUGUAAUUUAGCUUUAA |
| 6489 | 523 | AAUGGUUUCUUCCCUGGUGGU |
| 6490 | 524 | ACAACAACAUGAGAUUACAUA |
| 6491 | 525 | UCAUGCAGGAACGGCCUCGGC |
| 6492 | 526 | UUGCUCCUCCUGGGAUACUGG |
| 6493 | 527 | UGGGUGCUGGUACCUAUCCGAC |
| 6494 | 528 | UGUGAACAAUAAUAUCUUUAA |
| 6495 | 529 | ACCUUCUCCAUACUGUCCUCA |
| 6496 | 530 | ACUUCUUGUCCACAUCAAUGG |
| 6497 | 531 | UGCACAUGAAUCCAGUUGAGA |
| 6498 | 532 | UAGGAGCUUCCAGGCCUCCUC |
| 6499 | 533 | CUUCCUGCAAGAGAGCUUCUA |
| 6500 | 534 | UCUUCCCUGGUGGUUGUUGGU |
| 6501 | 535 | AUAAUUCCUGAUAUAUGGUAA |
| 6502 | 536 | GUACCUUGAAUCGUGUGGGUU |
| 6503 | 537 | AUGUCAUCACAAGUGGUCAAG |
| 6504 | 538 | ACAGCUCGCUGAUCUUGGGA |
| 6505 | 539 | UACAUAGGUGGUUAUAAUACA |
| 6506 | 540 | UGAUAUAUGGUAAAGCAUAAA |
| 6507 | 541 | AGAGUAGCUGACCCACCUCAG |
| 6508 | 542 | UCAUUGGAGAGCAAGGGCUUC |
| 6509 | 543 | UGGAGAUGUCAGCUUCAUUUU |
| 6510 | 544 | UGACUCCAUAUGUAUAGAUGA |
| 6511 | 545 | CUGAUAGCAGGUUCUUGCGUA |
| 6512 | 546 | AUAAGGGCUGCAGUCUGUUGA |
| 6513 | 547 | AGAUCUUUCACAUAGGGAUUG |
| 6514 | 548 | UGAUUGAGAAGAUGCUGUGAC |

TABLE 9-continued

Results for KIF20A.
Score threshold: 70. Design: siRNA 21 nt.

| SEQ ID NO | siRNA_id | AS Sequence |
|---|---|---|
| 6515 | 549 | UGUUUGCCGGGACAGGUAGUG |
| 6516 | 550 | UCAACUUGCUGUCACGGAAGG |
| 6517 | 551 | AGCUCUGCUUUGCACUGCUGU |
| 6518 | 552 | UAGAAAUCAUAUAAGUAAAUA |
| 6519 | 553 | ACAUUCUCAAUACGGACACAA |
| 6520 | 554 | AUGCACAGGGAUUCACAUUGA |
| 6521 | 555 | GUCCAGUUUCACUAGCACCAU |
| 6522 | 556 | CUCAUUGCAAAUUUCAUCUCG |
| 6523 | 557 | GUUGAGAUCUUUCACAUAGGG |
| 6524 | 558 | CAGUCUGAUAGCAGGUUCUUG |
| 6525 | 559 | AGUCAACUUGCUGUCACGGAA |
| 6526 | 560 | UUUCUUCCCUGGUGGUUGUUG |
| 6527 | 561 | ACACCUAGUCGCCGAAGCUGG |
| 6528 | 562 | AUACAUUCCUCCAAUAGUUC |
| 6529 | 563 | AUCCAGUUGAGAUCUUUCACA |
| 6530 | 564 | GAUGGUACCUUGAAUCGUGUG |
| 6531 | 565 | AACAAGCUCUCUCUGCUGAUU |
| 6532 | 566 | UUAGCUUUAACCUCCUGAAGC |
| 6533 | 567 | ACAAUCAUGCAGGAACGGCCU |
| 6534 | 568 | CAAAUGUUCACUGCACCACUG |
| 6535 | 569 | ACAAGGGUCUCCACAUUCUCA |
| 6536 | 570 | AUCUUCCUGUCGUUCCAACUC |
| 6537 | 571 | AACUUCUUGUCCACAUCAAUG |
| 6538 | 572 | AUGAGAUUACAUAGGUGGUUA |
| 6539 | 573 | AAUCAUGCAGGAACGGCCUCG |
| 6540 | 574 | UUCAGAUCAGGUGUUGGAUGA |
| 6541 | 575 | CUGAUUGAGAAGAUGCUGUGA |
| 6542 | 576 | CAACUUGCUGUCACGGAAGGG |
| 6543 | 577 | AUUACCCAUUGGAGAGCAAG |
| 6544 | 578 | GUAAUUUAGCUUUAACCUCCU |
| 6545 | 579 | UCAAACAUGGGAGAAACUACG |
| 6546 | 580 | UCCACAACUUGUAGGAGCUCC |
| 6547 | 581 | UGGUCAAGGCUUGACGAAGUU |
| 6548 | 582 | CUGUUCUACCAUCUCAUUGCA |
| 6549 | 583 | UGCUUUGCACUGCUGUAAUUU |
| 6550 | 584 | UGGUACACUGACUGAUAGAAG |
| 6551 | 585 | UGAUCCUCGCAUAGCCGCAAA |
| 6552 | 586 | CUCAGCAAUACAUGCUGCCUU |
| 6553 | 587 | AGAUCACAGAGUGACAGCUCG |
| 6554 | 588 | CCACUCUUCUGAUCUUUGCAG |
| 6555 | 589 | UUCAUACAUUUCCUCCAAUAG |
| 6556 | 590 | AGUGACUCCAUAUGUAUAGAU |
| 6557 | 591 | UCUACCAUCUCAUUGCAAAUU |
| 6558 | 592 | CAACAAGCUCUCUCUGCUGAU |
| 6559 | 593 | CAACAGCCUUAUAUUCUUCUG |
| 6560 | 594 | CAAAGUCUGCCUCUUGCGCUG |
| 6561 | 595 | UGGUCCUGUUUGAUUAAGAUG |
| 6562 | 596 | CACAGAGUGACAGCUCGCUGA |
| 6563 | 597 | UGGUGGUUGUUGGUUUGGUUG |
| 6564 | 598 | UUCCUUCAACCGUUCACCACU |
| 6565 | 599 | AUCCUUGAUGGUACCUUGAAU |
| 6566 | 600 | ACAACCCUGAUCUUCCUGUCG |
| 6567 | 601 | UCAUACAUUUCCUCCAAUAGU |
| 6568 | 602 | CUCAGAUGGAACCUGCUGCUU |
| 6569 | 603 | AGAAACUACGACAUCGUCAUC |
| 6570 | 604 | UCGAAGGAAUGGUUUCUUCCC |
| 6571 | 605 | AAUGUUUGCCGGGACAGGUAG |
| 6572 | 606 | UCAUCUCGGAGAUGCAUCUCC |
| 6573 | 607 | AUAGCAGGUUCUUGCGUACCA |
| 6574 | 608 | GAUGUAGACACUCCUCUUCAA |
| 6575 | 609 | UGGUUCUUACGACCCACUUUU |
| 6576 | 610 | UUCCUGAUAUAUGGUAAAGCA |
| 6577 | 611 | AUGCUGUGACUGCGGCUGGAG |
| 6578 | 612 | AACUUGCUGUCACGGAAGGGA |
| 6579 | 613 | UCCAUACUGUCCUCAGAUGGA |
| 6580 | 614 | AGUCCUUGGGUGCUUGUAGAA |
| 6581 | 615 | UGACGAAGGGCAGCAAUACAG |
| 6582 | 616 | AUGUUCACUGCACCACUGUUC |
| 6583 | 617 | ACUACGACAUCGUCAUCGGAC |
| 6584 | 618 | UGACUGCGGCUGGAGUUCUGG |
| 6585 | 619 | ACGGAAGGGAACCAGGUUCUG |
| 6586 | 620 | ACAUCAAUGGUGAAGGGCUUG |
| 6587 | 621 | GUAGAGUUUAGCUCUGCUUUG |

TABLE 9-continued

Results for KIF20A.
Score threshold: 70. Design: siRNA 21 nt.

| SEQ ID NO | siRNA_id | AS Sequence |
|---|---|---|
| 6588 | 622 | UUCAGACCCUGAUUGCUGAUG |
| 6589 | 623 | UCACCACUCUUCUGAUCUUUG |
| 6590 | 624 | UAGAGAGGUGUUAAUGUUUCC |
| 6591 | 625 | AGAGUUUCAUCAUAGGUAGAU |
| 6592 | 626 | CCAGGUUCUGCUUUGACCGGU |
| 6593 | 627 | AAGAGAGCUUCUAGCUCUUCA |
| 6594 | 628 | UCAGGUGUUGGAUGAAGUUGG |
| 6595 | 629 | UUCUACCAUCUCAUUGCAAAU |
| 6596 | 630 | UUCGCAGCCGCAGAGCACAAC |
| 6597 | 631 | CUGGUUGGUACCAAGGCGCUU |
| 6598 | 632 | AUCCCUCCAUCCUUGAUGGUA |
| 6599 | 633 | UGUGCAUAGAAAUCAUAUAAG |
| 6600 | 634 | ACUCCUUGAGGAUAUUUAGUU |
| 6601 | 635 | AGCAAUACAUGCUGCCUUCUU |
| 6602 | 636 | UUCUUCCGAAGGUCCAGUUUC |
| 6603 | 637 | GUUUCUGAAGCUCUGUCCGCA |
| 6604 | 638 | GAUCUGCUUGCUGUCUAGCCA |
| 6605 | 639 | GUCGUUCCAACUCUGAAGGUA |
| 6606 | 640 | AAGGAAUGGUUUCUUCCCUGG |
| 6607 | 641 | GAAGCUGGACUUUCGCAGCCG |
| 6608 | 642 | AAUUCAGACCCUGAUUGCUGA |
| 6609 | 643 | UCCAGGCCUCCUCAGCAUCUU |
| 6610 | 644 | CAGAGCAGUCUGAUAGCAGGU |
| 6611 | 645 | ACAUUUCCUCCAAUAGUUCCU |
| 6612 | 646 | AGCUGGACUUUCGCAGCCGCA |
| 6613 | 647 | AUUUCCUCCUGUCGGAUCUGC |
| 6614 | 648 | ACGGACACAACCCUGAUCUUC |
| 6615 | 649 | AUUGGAGAGCAAGGGCUUCAG |
| 6616 | 650 | UCCUUCAACCGUUCACCACUC |
| 6617 | 651 | UACUUUCACCUUCUCCAUACU |
| 6618 | 652 | UCACCAAGUUUCUGAAGCUCU |
| 6619 | 653 | AGUAGCUGACCCACCUCAGGG |
| 6620 | 654 | UCCUGAAGCUGCUGGGUGGAG |
| 6621 | 655 | UUGCAUCCUGGAUAUAAUUCC |
| 6622 | 656 | AGAGUUUAGCUCUGCUUUGCA |
| 6623 | 657 | CUUCAUUUCCUCCUGUCGGAU |
| 6624 | 658 | ACUGUCGAAGCUGGUGCUGGU |
| 6625 | 659 | AAGUAAAUUUCGAAGGAAUGG |
| 6626 | 660 | UCAGCAAUACAUGCUGCCUUC |
| 6627 | 661 | UUCCCUGGUGGUUGUUGGUUU |
| 6628 | 662 | CUGUCGAAGCUGGUGCUGGUA |
| 6629 | 663 | AGUAAAUUUCGAAGGAAUGGU |
| 6630 | 664 | CUGCAAGAGAGCUUCUAGCUC |
| 6631 | 665 | UCCUGGUUGGUACCAAGGCGC |
| 6632 | 666 | AAGGUCCAGUUUCACUAGCAC |
| 6633 | 667 | UUACAUAGGUGGUUUAUAAUAC |
| 6634 | 668 | AUAGGUAGAUGCACAGGGAUU |
| 6635 | 669 | CUUGAUGAACGAGUGCAGGGA |
| 6636 | 670 | CCAUAUGUAUAGAUGAGCCAG |
| 6637 | 671 | CUGCUGCUUGUCCUCUAGGGA |
| 6638 | 672 | UCUCCAUACUGUCCUCAGAUG |
| 6639 | 673 | CUGGUGCUGGUACCUAUCCGA |
| 6640 | 674 | UGCUCAGCAAUACAUGCUGCC |
| 6641 | 675 | ACAUGGGAGAAACUACGACAU |
| 6642 | 676 | CUACUGCUGGUACACUGACUG |
| 6643 | 677 | AGUGGUAGAGUUUAGCUCUGC |
| 6644 | 678 | UCCGAAGGUCCAGUUUCACUA |
| 6645 | 679 | UGUUCCCGCUGUUGCAUCUGU |
| 6646 | 680 | ACAGGGAUUCACAUUGACAAU |
| 6647 | 681 | UGAUGAACGAGUGCAGGGAUG |
| 6648 | 682 | AGGAAUGGUUUCUUCCCUGGU |
| 6649 | 683 | CUCUUCUGAUCUUUGCAGCGC |
| 6650 | 684 | ACACUCCUCUUCAAGGAAGUG |
| 6651 | 685 | UGUGCCCAUCGAUGACUUGUU |
| 6652 | 686 | UCUGUCCGCAACAGCCUUAUA |
| 6653 | 687 | AAUAGGUCAUAAAGCAGUUCG |
| 6654 | 688 | CUCCUCAGCAUCUUGCACAUG |
| 6655 | 689 | CUUAUGCAACUCUUCAGUGGU |
| 6656 | 690 | GUACACUGACUGAUAGAAGAG |
| 6657 | 691 | UGAAGACUAUGUUCCUUGAUG |
| 6658 | 692 | GAGGUAGAGACGACAGAGCAG |
| 6659 | 693 | CUUGUCCACAUCAAUGGUGAA |
| 6660 | 694 | UGAGUAUUGCAUCCUGGAUAU |

TABLE 9-continued

Results for KIF20A.
Score threshold: 70. Design: siRNA 21 nt.

| SEQ ID NO | siRNA_id | AS Sequence |
|---|---|---|
| 6661 | 695 | CUUCUGAUCUUUGCAGCGCUC |
| 6662 | 696 | UCUAGGGAGGUAGAGACGACA |
| 6663 | 697 | UCCCGCUCCUGAAUCUCUUCU |
| 6664 | 698 | UAGGUAGAUGCACAGGGAUUC |
| 6665 | 699 | CAUUUCCUCCAAUAGUUCCUU |
| 6666 | 700 | AGCAGGGACAGCUUCUUCAUU |
| 6667 | 701 | UCUGCUUUGCACUGCUGUAAU |
| 6668 | 702 | UGUAGAUCUCAAAGAAUGAGA |
| 6669 | 703 | GCUAGUGUCUGAGUAUUGCAU |
| 6670 | 704 | ACUGCACCACUGUUCCCGCUG |
| 6671 | 705 | AAUAAUAUCUUUAAUAUAACU |
| 6672 | 706 | AUCGGACAGCAAGCCCGCUGG |
| 6673 | 707 | UCCUGCUUCCUUCAACCGUUC |
| 6674 | 708 | UAUGUUCCUUGAUGAACGAGU |
| 6675 | 709 | AGGUUGAAGAAGGAUGCCUGU |
| 6676 | 710 | CAAUAUCAUCAUCAAGGCCUG |
| 6677 | 711 | AGACCUAUUUCUUCAGGAGAG |
| 6678 | 712 | GUUGUUCUGCAGUUCAGCCAG |
| 6679 | 713 | CUGCAGUCUGUUGAGCUUUGG |
| 6680 | 714 | AGUACAUCCUUUACCAUCUCC |
| 6681 | 715 | CAUGAAUCCAGUUGAGAUCUU |
| 6682 | 716 | CAUCGGACAGCAAGCCCGCUG |
| 6683 | 717 | CUCCUGUCGGAUCUGCUUGCU |
| 6684 | 718 | AUCUUUGCAGCGCUCUGAGCC |
| 6685 | 719 | AAGGGUCUCCACAUUCUCAAU |
| 6686 | 720 | AAUACGGACACAACCCUGAUC |
| 6687 | 721 | CAUUUCCUCCUGUCGGAUCUG |
| 6688 | 722 | UCACUGCACCACUGUUCCCGC |
| 6689 | 723 | AGUUAGUGACUCCAUAUGUAU |
| 6690 | 724 | AUCUUUCACAUAGGGAUUGCC |
| 6691 | 725 | AGAUGGAACCUGCUGCUUGUC |
| 6692 | 726 | AUAGAAAUCAUAUAAGUAAAU |
| 6693 | 727 | AGAGACCUAUUUCUUCAGGAG |
| 6694 | 728 | UGAGCGUAGGAUCCGGGCAUA |
| 6695 | 729 | UCGUUCCAACUCUGAAGGUAA |
| 6696 | 730 | CAAGGGUCUCCACAUUCUCAA |
| 6697 | 731 | GAACCUGCUGCUUGUCCUCUA |
| 6698 | 732 | AGGCUAUUGAAGAUCAGCGCC |
| 6699 | 733 | CUAGUCGCCGAAGCUGGACUU |
| 6700 | 734 | AUGGGAGAAACUACGACAUCG |
| 6701 | 735 | CUUCCUUCAACCGUUCACCAC |
| 6702 | 736 | AUGCUGCCUUCUUCCGAAGGU |
| 6703 | 737 | CUUCUAACUUCUUGUCCACAU |
| 6704 | 738 | AGAAGAUGCUGUGACUGCGGC |
| 6705 | 739 | UUCCCGCUGUUGCAUCUGUUC |
| 6706 | 740 | CAACCCUGAUCUUCCUGUCGU |
| 6707 | 741 | AAUUUCGAAGGAAUGGUUUCU |
| 6708 | 742 | AGAGAGGUGUUAAUGUUUCCU |
| 6709 | 743 | GAUGUCAUCACAAGUGGUCAA |
| 6710 | 744 | AAGGGCAGCAAUACAGCGGCC |
| 6711 | 745 | AUCAUGCAGGAACGGCUCGG |
| 6712 | 746 | GCAUCCUGGAUAUAAUUCCUG |
| 6713 | 747 | CAACUCUUCAGUGGUAGAGUU |
| 6714 | 748 | UCUGUUCUACCAUCUCAUUGC |
| 6715 | 749 | ACGCCGUGAGCUAGGAUCCG |
| 6716 | 750 | AAUGAGAUCCAGAUGGAGAAG |
| 6717 | 751 | ACAAGCUCUCUCUGCUGAUUG |
| 6718 | 752 | UCUCAAAGAAUGAGAUCCAGA |
| 6719 | 753 | UGGUUGGUACCAAGGCGCUUU |
| 6720 | 754 | AGUAUACUUUCACCUUCUCCA |
| 6721 | 755 | AAAUUUCAUCUCGGAGAUGCA |
| 6722 | 756 | UCUCGGAGAUGCAUCUCCAGC |
| 6723 | 757 | CUGAAGCUCUGUCCGCAACAG |
| 6724 | 758 | GUUAAUGUUUCCUGCUUCCUU |
| 6725 | 759 | UUCGAAGGAAUGGUUUCUUCC |
| 6726 | 760 | CUGAAGGUGUAGGAUCCUGAU |
| 6727 | 761 | AAUACAGCGGCCCAGGGUGUG |
| 6728 | 762 | GUAGGAGCUCCUCUUUGCCAU |
| 6729 | 763 | ACGAAGGGCAGCAAUACAGCG |
| 6730 | 764 | AGAAGCGAAUGUUUGCCGGGA |
| 6731 | 765 | CACUAGCACCAUGUUGUUCUG |
| 6732 | 766 | GAGAAGAUGCUGUGACUGCGG |
| 6733 | 767 | AGACUCACCAAGUUUCUGAAG |

TABLE 9-continued

Results for KIF20A.
Score threshold: 70. Design: siRNA 21 nt.

| SEQ ID NO | siRNA_id | AS Sequence |
|---|---|---|
| 6734 | 768 | AGUAUGAUACUGCUCAGCAAU |
| 6735 | 769 | CAGCCUAGGUCCGAAGACGUG |
| 6736 | 770 | CAUCAUAGGUAGAUGCACAGG |
| 6737 | 771 | CUGCUUGUCCUCUAGGGAGGU |
| 6738 | 772 | ACAGAGCAGUCUGAUAGCAGG |
| 6739 | 773 | UCCGACUUUCGAUGUAGACAC |
| 6740 | 774 | AGGGAGGUAGAGACGACAGAG |
| 6741 | 775 | AGAGCAAGGGCUUCAGAUCAG |
| 6742 | 776 | CAAACAUGGGAGAAACUACGA |
| 6743 | 777 | AUACUGCUCAGCAAUACAUGC |
| 6744 | 778 | ACUCUGAAGGUAACAAGGGCC |
| 6745 | 779 | ACACAACCCUGAUCUUCCUGU |
| 6746 | 780 | CAUCCUUGAUGGUACCUUGAA |
| 6747 | 781 | CACUGCACCACUGUUCCCGCU |
| 6748 | 782 | UGGAGAGCAAGGGCUUCAGAU |
| 6749 | 783 | GUAGACACUCCUCUUCAAGGA |
| 6750 | 784 | CUUGGGUGCUUGUAGAACAAG |
| 6751 | 785 | GUCGGAUCUGCUUGCUGUCUA |
| 6752 | 786 | UAGAAGAGAGCCCAGCAAUGC |
| 6753 | 787 | UCCUUCACAGUUAGGUUGAAG |
| 6754 | 788 | UCUUCCGAAGGUCCAGUUUCA |
| 6755 | 789 | CUCGCAUAGCCGCAAAGUCUG |
| 6756 | 790 | CUAAUAGGUCAUAAAGCAGUU |
| 6757 | 791 | ACUGCGGCUGGAGUUCUGGUU |
| 6758 | 792 | CAUCACAAGUGGUCAAGGCUU |
| 6759 | 793 | CCUCUUCUAACUUCUUGUCCA |
| 6760 | 794 | ACUCAAACAUGGGAGAAACUA |
| 6761 | 795 | AUGCAGGAACGGCCUCGGCCU |
| 6762 | 796 | GGCAACAAGCUCUCUCUGCUG |
| 6763 | 797 | GUCAUAAAGCAGUUCGUUGUA |
| 6764 | 798 | GUCCUCAGAUGGAACCUGCUG |
| 6765 | 799 | GAAGGAAUGGUUUCUUCCCUG |
| 6766 | 800 | CUUCUAGCUCUUCAAUCUUUU |
| 6767 | 801 | UCCUGGAUAUAAUUCCUGAUA |
| 6768 | 802 | UCCCGCGUUGCAUCUGUUCU |
| 6769 | 803 | CAAUACGGACACAACCCUGAU |
| 6770 | 804 | AGUCUGGUCCUGUUUGAUUAA |
| 6771 | 805 | UCACGGAAGGGAACCAGGUUC |
| 6772 | 806 | UGCCGGGACAGGUAGUGGGGC |
| 6773 | 807 | CACUGCUGUAAUUUAGCUUUA |
| 6774 | 808 | UGGAUAUAAUUCCUGAUAUAU |
| 6775 | 809 | AGGAUGCCUGUCCCACUUCUG |
| 6776 | 810 | UGAUAGCAGGUUCUUGCGUAC |
| 6777 | 811 | ACUUCGCAGCCGCAGAGCAC |
| 6778 | 812 | UUCAUUUCCUCCUGUCGGAUC |
| 6779 | 813 | GAAGGGAACCAGGUUCUGCUU |
| 6780 | 814 | UCCUCAGCAUCUUGCACAUGA |
| 6781 | 815 | GAGUACAUCCUUUACCAUCUC |
| 6782 | 816 | CAUCUCGGAGAUGCAUCUCCA |
| 6783 | 817 | GUGAACAAUAAUAUCUUUAAU |
| 6784 | 818 | CUGUCGGAUCUGCUUGCUGUC |
| 6785 | 819 | UCCUCUAGGGAGGUAGAGACG |
| 6786 | 820 | AGAAGGAUGCCUGUCCCACUU |
| 6787 | 821 | GAGUCAACUUGCUGUCACGGA |
| 6788 | 822 | UGUUGGUUUGGUUGCUGAUUU |
| 6789 | 823 | AGAUGCUGUGACUGCGGCUGG |
| 6790 | 824 | AGUGGACAGCUCCUCCUCUUG |
| 6791 | 825 | UGCUGCCUUCUUCCGAAGGUC |
| 6792 | 826 | CAAGGAAGUGGACAGCUCCUC |
| 6793 | 827 | GACAGAGCAGUCUGAUAGCAG |
| 6794 | 828 | CUGUGGACUCAAACAUGGGAG |
| 6795 | 829 | UGAAUCUCUUCUUGGUAAAAA |
| 6796 | 830 | ACCUCCUGAAGCUGCUGGGUG |
| 6797 | 831 | CUCAAGUAUACUUUCACCUUC |
| 6798 | 832 | GCUAUUGAAGAUCAGCGCCAG |
| 6799 | 833 | ACCGUUCACCACUCUUCUGAU |
| 6800 | 834 | UCCUCCUCUUGGAGGCCUCCA |
| 6801 | 835 | UCCUCAGAUGGAACCUGCUGC |
| 6802 | 836 | AUAGGUGGUUAUAAUACAAAA |
| 6803 | 837 | CACAUCAAUGGUGAAGGGCUU |
| 6804 | 838 | CAAGAGAGCUUCUAGCUCUUC |
| 6805 | 839 | GCUUCUAGCUCUUCAAUCUUU |
| 6806 | 840 | UCCGCAACAGCCUUAUAUUCU |

TABLE 9-continued

Results for KIF20A.
Score threshold: 70. Design: siRNA 21 nt.

| SEQ ID NO | siRNA_id | AS Sequence |
|---|---|---|
| 6807 | 841 | UCCCUGGUGGUUGUUGGUUUG |
| 6808 | 842 | CACUCGAGUCAACUUGCUGUC |
| 6809 | 843 | GACUGCUCUUCUCUUUCCCCA |
| 6810 | 844 | GAGAGACUCACCAAGUUUCUG |
| 6811 | 845 | GAGACGACAGAGCAGUCUGAU |
| 6812 | 846 | UUCUUCCCUGGUGGUUGUUGG |
| 6813 | 847 | UCAGUGACUCCUUGAGGAUAU |
| 6814 | 848 | AGGAGAGUAGCUGACCCACCU |
| 6815 | 849 | CUGACUGAUAGAAGAGAGCCC |
| 6816 | 850 | AUCCCGCUCCUGAAUCUCUUC |
| 6817 | 851 | GUAAAUUUCGAAGGAAUGGUU |
| 6818 | 852 | CUUUGCACUGCUGUAAUUUAG |
| 6819 | 853 | AACAAGGGCCUAACCCUCAAG |
| 6820 | 854 | CUCUGCUUUGCACUGCUGUAA |
| 6821 | 855 | CUUGUCAGUGACUCCUUGAGG |
| 6822 | 856 | AUGGAGAUGUCAGCUUCAUUU |
| 6823 | 857 | GAAACUACGACAUCGUCAUCG |
| 6824 | 858 | AGUCUGCCUCUUGCGCUGUUG |
| 6825 | 859 | GAGUUAGUGACUCCAUAUGUA |
| 6826 | 860 | ACAAUAAUAUCUUUAAUAUAA |
| 6827 | 861 | UCCUCUUCAAGGAAGUGGACA |
| 6828 | 862 | GUGUAGAGAGGUGUUAAUGUU |
| 6829 | 863 | CACCAAGUUUCUGAAGCUCUG |
| 6830 | 864 | ACUCACACCUAGUCGCCGAAG |
| 6831 | 865 | GUUCACCACUCUUCUGAUCUU |
| 6832 | 866 | ACCUAUUUCUUCAGGAGAGUA |
| 6833 | 867 | CGAGUCAACUUGCUGUCACGG |
| 6834 | 868 | AGAGACUCACCAAGUUUCUGA |
| 6835 | 869 | ACCUUGAAUCUGUGGGUUUU |
| 6836 | 870 | CACAGUUAGGUUGAAGAAGGA |
| 6837 | 871 | AGGUCAUAAAGCAGUUCGUUG |
| 6838 | 872 | UCCUCUUGGAGGCCUCCAUUU |
| 6839 | 873 | AACAUGGGAGAAACUACGACA |
| 6840 | 874 | GUCUGAGUAUUGCAUCCUGGA |
| 6841 | 875 | CUUCAACCGUUCACCACUCUU |
| 6842 | 876 | CAGUUUCACUAGCACCAUGUU |
| 6843 | 877 | CACCUUCUCCAUACUGUCCUC |
| 6844 | 878 | AACCUUUGUGACCGCCGUAGG |
| 6845 | 879 | CAUAGCCGCAAAGUCUGCCUC |
| 6846 | 880 | CUUUCACAUAGGGAUUGCCAU |
| 6847 | 881 | AACCCUCAAGUAUACUUUCAC |
| 6848 | 882 | CAUCUGUUCUACCAUCUCAUU |
| 6849 | 883 | GUCUGAUAGCAGGUUCUUGCG |
| 6850 | 884 | AUGGAGAAGCGAAUGUUUGCC |
| 6851 | 885 | GUCUCCACAUUCUCAAUACGG |
| 6852 | 886 | AUUACAUAGGUGGUUAUAAUA |
| 6853 | 887 | UGCGGCUGGAGUUCUGGUUGA |
| 6854 | 888 | CAAGUGGUCAAGGCUUGACGA |
| 6855 | 889 | UGAUCUUCCUGUCGUUCCAAC |
| 6856 | 890 | ACCUAGUCGCCGAAGCUGGAC |
| 6857 | 891 | CUCCUUCACAGUUAGGUUGAA |
| 6858 | 892 | AGGAUCCUGAUUGAGAAGAUG |
| 6859 | 893 | CGUCAUCGGACAGCAAGCCCG |
| 6860 | 894 | AUCUGCAGCUGUGGACUCAAA |
| 6861 | 895 | UCACUAGCACCAUGUUGUUCU |
| 6862 | 896 | UCAUCCCGCUCCUGAAUCUCU |
| 6863 | 897 | UCUGAAGCUCUGUCCGCAACA |
| 6864 | 898 | GCAUCUGUUCUACCAUCUCAU |
| 6865 | 899 | AGAUGCACAGGGAUUCACAUU |
| 6866 | 900 | AGCUCUCUCUGCUGAUUGGAG |
| 6867 | 901 | GUUUAGCUCUGCUUUGCACUG |
| 6868 | 902 | GAGUGACAGCUCGCUGAUCUU |
| 6869 | 903 | AGGUAACAAGGGCCUAACCCU |
| 6870 | 904 | GAAGAAACCUUGGAACACUCG |
| 6871 | 905 | AUAUAUGGUAAAGCAUAAAAG |
| 6872 | 906 | GAGAUCCAGAUGGAGAAGCGA |
| 6873 | 907 | CAUACAUUCCUCCAAUAGUU |
| 6874 | 908 | ACCACUGUUCCCGCUGUUGCA |
| 6875 | 909 | CUCACCAAGUUUCUGAAGCUC |
| 6876 | 910 | AUCUCAUUGCAAAUUUCAUCU |
| 6877 | 911 | CUGUUCCCGCUGUUGCAUCUG |
| 6878 | 912 | GAGAAACUACGACAUCGUCAU |
| 6879 | 913 | AGCACCAUGUUGUUCUGCAGU |

TABLE 9-continued

Results for KIF20A.
Score threshold: 70. Design: siRNA 21 nt.

| SEQ ID NO | siRNA_id | AS Sequence |
|---|---|---|
| 6880 | 914 | AUACGGACACAACCCUGAUCU |
| 6881 | 915 | AAGAGAGCCCAGCAAUGCCAC |
| 6882 | 916 | CUCGAGUCAACUUGCUGUCAC |
| 6883 | 917 | AAGGAUGCCUGUCCCACUUCU |
| 6884 | 918 | UUGCGACAUGACGGCAGGGGC |
| 6885 | 919 | GAGAGGUGUUAAUGUUUCCUG |
| 6886 | 920 | AAUCAUAUAAGUAAAUAAAAA |
| 6887 | 921 | CAAUCAUGCAGGAACGGCCUC |
| 6888 | 922 | GGGAUUCACAUUGACAAUCAU |
| 6889 | 923 | AGGUUCUUGCGUACCACAGAC |
| 6890 | 924 | UCAUUUCCUCCUGUCGGAUCU |
| 6891 | 925 | CAUCCCGCUCCUGAAUCUCUU |
| 6892 | 926 | GUUCUGCUUUGACCGGUUCUG |
| 6893 | 927 | UGCUACAUUUGGAAUUCAAUA |
| 6894 | 928 | CUUGUAGAACAAGGGUCUCCA |
| 6895 | 929 | AGGUAGAGACGACAGAGCAGU |
| 6896 | 930 | UGCUGUCACGGAAGGGAACCA |
| 6897 | 931 | CUUUGACCGGUUCUGCUGGUU |
| 6898 | 932 | GAAGAUGCUGUGACUGCGGCU |
| 6899 | 933 | CAAGUAUACUUUCACCUUCUC |
| 6900 | 934 | GGGUGCUUGUAGAACAAGGGU |
| 6901 | 935 | CACCUAGUCGCCGAAGCUGGA |
| 6902 | 936 | AGCCGCAAAGUCUGCCUCUUG |
| 6903 | 937 | GGUACCUAUCCGACUUUCGAU |
| 6904 | 938 | CGACUUUCGAUGUAGACACUC |
| 6905 | 939 | GAUGCUGUGACUGCGGCUGGA |
| 6906 | 940 | CAGACCCUGAUUGCUGAUGGG |
| 6907 | 941 | AUACUUUCACCUUCUCCAUAC |
| 6908 | 942 | AGGGCUUCAGAUCAGGUGUUG |
| 6909 | 943 | AGAUCCAGAUGGAGAAGCGAA |
| 6910 | 944 | ACUUGCUGUCACGGAAGGGAA |
| 6911 | 945 | AGAGGUGUUAAUGUUUCCUGC |
| 6912 | 946 | GAAACCUUGGAACACUCGAGU |
| 6913 | 947 | CAAAGCUCUGGUUCUUACGAC |
| 6914 | 948 | CUCAUUGGAGAGCAAGGGCUU |
| 6915 | 949 | CAUCUUGCACAUGAAUCCAGU |

TABLE 9-continued

Results for KIF20A.
Score threshold: 70. Design: siRNA 21 nt.

| SEQ ID NO | siRNA_id | AS Sequence |
|---|---|---|
| 6916 | 950 | UGAGUACAUCCUUUACCAUCU |
| 6917 | 951 | UGUGGACUCAAACAUGGGAGA |
| 6918 | 952 | CUGCUGAUUGGAGAGACUCAC |
| 6919 | 953 | ACGACAUCGUCAUCGGACAGC |
| 6920 | 954 | CAGUUCGUUGUAGAUCUCAAA |
| 6921 | 955 | CUCCUUGAGGAUAUUUAGUUU |
| 6922 | 956 | GAGAAGCGAAUGUUUGCCGGG |
| 6923 | 957 | AGAAAGGAUCCCUUGCGACAU |
| 6924 | 958 | CGACAGAGCAGUCUGAUAGCA |
| 6925 | 959 | UGUAGACACUCCUCUUCAAGG |
| 6926 | 960 | CGAAGGAAUGGUUUCUUCCCU |
| 6927 | 961 | UGGAGGCCUCCAUUUAGCAGG |
| 6928 | 962 | AUGUUUGCCGGGACAGGUAGU |
| 6929 | 963 | GAUCACAGAGUGACAGCUCGC |
| 6930 | 964 | CCGCUCCUGAAUCUCUUCUUG |
| 6931 | 965 | AGCAAUACAGCGGCCCAGGGU |
| 6932 | 966 | AAAGGAUCCCUUGCGACAUGA |
| 6933 | 967 | UCACAGUUAGGUUGAAGAAGG |
| 6934 | 968 | AGUUGAGAUCUUUCACAUAGG |
| 6935 | 969 | AUUGACAAUCAUGCAGGAACG |
| 6936 | 970 | CUGAUACUUAUGCAACUCUUC |
| 6937 | 971 | ACUCUUCAGUGGUAGAGUUUA |
| 6938 | 972 | CCUGAUUGAGAAGAUGCUGUG |
| 6939 | 973 | UGAAUCCAGUUGAGAUCUUUC |
| 6940 | 974 | GCAAGAGAGCUUCUAGCUCUU |
| 6941 | 975 | CCUCAAGUAUACUUUCACCUU |
| 6942 | 976 | AAGCUCUGGUUCUUACGACCC |
| 6943 | 977 | GACUGAUAGAAGAGAGCCCAG |
| 6944 | 978 | AAAUCUAUAAGUAAAUAAAA |
| 6945 | 979 | CUGGUUCUUACGACCCACUUU |
| 6946 | 980 | CGAAGGGCAGCAAUACAGCGG |
| 6947 | 981 | CUUCACAGUUAGGUUGAAGAA |
| 6948 | 982 | AGCAGUCUGAUAGCAGGUUCU |
| 6949 | 983 | GUAGAGACGACAGAGCAGUCU |
| 6950 | 984 | GGAGUUUCAACACAGUAUGAU |
| 6951 | 985 | UGCCCAUCGAUGACUUGUUUC |
| 6952 | 986 | UCCACAUUCUCAAUACGGACA |

TABLE 9-continued

Results for KIF20A.
Score threshold: 70. Design: siRNA 21 nt.

| SEQ ID NO | siRNA_id | AS Sequence |
|---|---|---|
| 6953 | 987 | ACCUGAAGACUAUGUUCCUUG |
| 6954 | 988 | UGUCAUCACAAGUGGUCAAGG |
| 6955 | 989 | CCUUGGAGUUUCAACACAGUA |
| 6956 | 990 | CUGAGUAUUGCAUCCUGGAUA |
| 6957 | 991 | CUUUGAGUACAUCCUUUACCA |
| 6958 | 992 | GUGAGCGUAGGAUCCGGCAU |
| 6959 | 993 | GUACAUCCUUUACCAUCUCCU |
| 6960 | 994 | CUUCUUCCGAAGGUCCAGUUU |
| 6961 | 995 | GGUACCUUGAAUCGUGUGGGU |
| 6962 | 996 | AUCCGGGCAUAAGGGCUGCAG |
| 6963 | 997 | CUUGGAGUUUCAACACAGUAU |
| 6964 | 998 | AAGGUAACAAGGGCCUAACCC |
| 6965 | 999 | GUGCUGGUACCUAUCCGACUU |
| 6966 | 1000 | UUACCUCAUUGGAGAGCAAGG |
| 6967 | 1001 | UGAGAUCCAGAUGGAGAAGCG |
| 6968 | 1002 | CUGGAGUUCUGGUUGAGGUGG |
| 6969 | 1003 | CAGCUGUGGACUCAAACAUGG |
| 6970 | 1004 | CUGAGUUAGUGACUCCAUAUG |
| 6971 | 1005 | ACCAUCUCCUUCACAGUUAGG |
| 6972 | 1006 | GACUCCAUAUGUAUAGAUGAG |
| 6973 | 1007 | GUUGUUGGUUUGGUUGCUGAU |
| 6974 | 1008 | GCAACAAGCUCUCUCUGCUGA |

TABLE 10

Results for LTB.
Score threshold: 70. Design: siRNA 21 nt.

| SEQ ID NO | siRNA_id | siRNA guide strand/ AS Sequence |
|---|---|---|
| 6975 | 1 | UUAUCGGCAGCACUGAAGCUU |
| 6976 | 2 | UGUUCCUUCGUCGUCUCCCAG |
| 6977 | 3 | UCAAUUUCCAAACAGUCUCCU |
| 6978 | 4 | UUUCCAAACAGUCUCCUACAU |
| 6979 | 5 | UUGACGUACACCCUCUCGCCC |
| 6980 | 6 | UUUAUCGGCAGCACUGAAGCU |
| 6981 | 7 | UUCUGAAACCCAGUCCUCCCU |
| 6982 | 8 | UAAUAGAGGCCGUCCUGCGGG |

TABLE 10-continued

Results for LTB.
Score threshold: 70. Design: siRNA 21 nt.

| SEQ ID NO | siRNA_id | siRNA guide strand/ AS Sequence |
|---|---|---|
| 6983 | 9 | UCGUGUACCAGAGAGGCCCGU |
| 6984 | 10 | UACAGAGAGCUGCGCAGCGUG |
| 6985 | 11 | UCCUUCGUCGUCUCCCAGCCU |
| 6986 | 12 | UCGAGCAGCAGCUCGGGAGUG |
| 6987 | 13 | UCUGAAACCCAGUCCUCCCUG |
| 6988 | 14 | UUCACGCACUCGCACCACGCA |
| 6989 | 15 | UUCCAAACAGUCUCCUACAUU |
| 6990 | 16 | AAGAAGGUCUUCCCUCUCGCG |
| 6991 | 17 | AUAUUCACGCACUCGCACCAC |
| 6992 | 18 | UCCAGCACUGGAGUCACCGUC |
| 6993 | 19 | ACUGAUGUUGACGUACACCCU |
| 6994 | 20 | UCGCGAAGUCCACCAUAUCGG |
| 6995 | 21 | UAGCCGACGAGACAGUAGAGG |
| 6996 | 22 | UCACGCACUCGCACCACGCAC |
| 6997 | 23 | AAGCUUUCCAUUCUUUAUUUU |
| 6998 | 24 | UAUCGGCAGCACUGAAGCUUU |
| 6999 | 25 | AUGUUGACGUACACCCUCUCG |
| 7000 | 26 | AGAAGGUCUUCCCUCUCGCGA |
| 7001 | 27 | AACAAGGUCACCAGAGAAGUG |
| 7002 | 28 | AACGCCUGUUCCUUCGUCGUC |
| 7003 | 29 | UCGUCUCCCAGCCUAGCCCCU |
| 7004 | 30 | UCGGCGUCCGAGAACUGCGUC |
| 7005 | 31 | AAUAUUCACGCACUCGCACCA |
| 7006 | 32 | UCGUCAGAAACGCCUGUUCCU |
| 7007 | 33 | UACCAGAGAGGCCCGUACCCU |
| 7008 | 34 | ACUGGAGUCACCGUCUCGGCG |
| 7009 | 35 | UAUGAGGUGGGCAGCUGGGAG |
| 7010 | 36 | UGAUGUUGACGUACACCCUCU |
| 7011 | 37 | AUCAAUUUCCAAACAGUCUCC |
| 7012 | 38 | UGACGUACACCCUCUCGCCCC |
| 7013 | 39 | AGUAGAGGUAAUAGAGGCCGU |
| 7014 | 40 | UGAAGCUUUCCAUUCUUUAUU |
| 7015 | 41 | CUGAUGUUGACGUACACCCUC |
| 7016 | 42 | UCCCGCUCGUCAGAAACGCCU |
| 7017 | 43 | AGCACUGGAGUCACCGUCUCG |
| 7018 | 44 | CAAUUUCCAAACAGUCUCCUA |
| 7019 | 45 | AAACGCCUGUUCCUUCGUCGU |

TABLE 10-continued

Results for LTB.
Score threshold: 70. Design: siRNA 21 nt.

| SEQ ID NO | siRNA_id | siRNA guide strand/ AS Sequence |
|---|---|---|
| 7020 | 46 | UAUUCACGCACUCGCACCACG |
| 7021 | 47 | AUAGAGGCCGUCCUGCGGGAG |
| 7022 | 48 | GACAGUGAUAGGCACCGCCAG |
| 7023 | 49 | AGCUUCUGAAACCCAGUCCUC |
| 7024 | 50 | AGCAACAAGGUCACCAGAGAA |
| 7025 | 51 | UUCCUUCGUCGUCUCCCAGCC |
| 7026 | 52 | UCCGAGAACUGCGUCCCGCUC |
| 7027 | 53 | AGAGCUGCGCAGCGUGACCGA |
| 7028 | 54 | CUGCGCAGCGUGACCGAGCGG |
| 7029 | 55 | AAUAGAGGCCGUCCUGCGGGA |
| 7030 | 56 | UGAAACCCAGUCCUCCCUGAU |
| 7031 | 57 | UGUUGACGUACACCCUCUCGC |
| 7032 | 58 | ACCCAGUCCUCCCUGAUCCUG |
| 7033 | 59 | ACAAGGUCACCAGAGAAGUGG |
| 7034 | 60 | UGGAGUCACCGUCUCGGCGCC |
| 7035 | 61 | AUCGGCAGCACUGAAGCUUUC |
| 7036 | 62 | AAUUUCCAAACAGUCUCCUAC |
| 7037 | 63 | AGAAACGCCUGUUCCUUCGUC |
| 7038 | 64 | UUCAGCGGAGCGCCUAUGAGG |
| 7039 | 65 | UCACCGUCUCGGCGCCCUCGA |
| 7040 | 66 | AACUGCGUCCCGCUCGUCAGA |
| 7041 | 67 | AUUCACGCACUCGCACCACGC |
| 7042 | 68 | AAAGAAGGUCUUCCCUCUCGC |
| 7043 | 69 | GUACAGAGAGCUGCGCAGCGU |
| 7044 | 70 | AGACAGUAGAGGUAAUAGAGG |
| 7045 | 71 | CAGUAGAGGUAAUAGAGGCCG |
| 7046 | 72 | UCCAAACAGUCUCCUACAUUU |
| 7047 | 73 | CAAACAGUCUCCUACAUUUUU |
| 7048 | 74 | GUAAUAGAGGCCGUCCUGCGG |
| 7049 | 75 | UUCGUCGUCUCCCAGCCUAGC |
| 7050 | 76 | AAGGUCUUCCCUCUCGCGAAG |
| 7051 | 77 | CUGUUCCUUCGUCGUCUCCCA |
| 7052 | 78 | CCUUCGUCGUCUCCCAGCCUA |
| 7053 | 79 | UGACUGAUGUUGACGUACACC |
| 7054 | 80 | UGCACCAGGCCGCCGAACCCC |
| 7055 | 81 | GAGGUAAUAGAGGCCGUCCUG |
| 7056 | 82 | UCUUCCCUCUCGCGAAGUCCA |
| 7057 | 83 | AGAGGUAAUAGAGGCCGUCCU |
| 7058 | 84 | AUUUCCAAACAGUCUCCUACA |
| 7059 | 85 | ACAGUAGAGGUAAUAGAGGCC |
| 7060 | 86 | CAGCUUCUGAAACCCAGUCCU |
| 7061 | 87 | AACCCAGUCCUCCCUGAUCCU |
| 7062 | 88 | UCCGGAGCUGCACCAGGCCGC |
| 7063 | 89 | UCAGAAACGCCUGUUCCUUCG |
| 7064 | 90 | UCGUCGUCUCCCAGCCUAGCC |
| 7065 | 91 | CAGCACUGGAGUCACCGUCUC |
| 7066 | 92 | CAGUCCUCCCUGAUCCUGGGG |
| 7067 | 93 | ACUGAAGCUUUCCAUUCUUUA |
| 7068 | 94 | UGCGCAGCGUGACCGAGCGGC |
| 7069 | 95 | UCAGCGGAGCGCCUAUGAGGU |
| 7070 | 96 | UCCCUCUCGCGAAGUCCACCA |
| 7071 | 97 | AGCACUGAAGCUUUCCAUUCU |
| 7072 | 98 | UAGAGGUAAUAGAGGCCGUCC |
| 7073 | 99 | ACUCGCACCACGCACUCAUAU |
| 7074 | 100 | CUCGGCGUCCGAGAACUGCGU |
| 7075 | 101 | AGGACAGUGAUAGGCACCGCC |
| 7076 | 102 | GCGAAGUCCACCAUAUCGGGG |
| 7077 | 103 | GAGCUGCGCAGCGUGACCGAG |
| 7078 | 104 | GAGAACUGCGUCCCGCUCGUC |
| 7079 | 105 | ACGCACUCGCACCACGCACUC |
| 7080 | 106 | GCACUGAAGCUUUCCAUUCUU |
| 7081 | 107 | ACAGCUAGCAGGAGGGAACCC |
| 7082 | 108 | ACGCCUGUUCCUUCGUCGUCU |
| 7083 | 109 | CACCACGCACUCAUAUUCCCU |
| 7084 | 110 | GUAGAGGUAAUAGAGGCCGUC |
| 7085 | 111 | ACAGAGAGCUGCGCAGCGUGA |
| 7086 | 112 | GAGACAGUAGAGGUAAUAGAG |
| 7087 | 113 | ACUGCGUCCCGCUCGUCAGAA |
| 7088 | 114 | CGCGAAGUCCACCAUAUCGGG |
| 7089 | 115 | GUAGCCGACGAGACAGUAGAG |
| 7090 | 116 | CACUGAAGCUUUCCAUUCUUU |
| 7091 | 117 | UCGGCAGCACUGAAGCUUUCC |

TABLE 11

GalNAC-siRNA conjugates.

| SEQ ID NO | siRNA_id | Passenger strand (sense) | SEQ ID NO | guide strand (antisense) |
|---|---|---|---|---|
| 7092 | Mfap4.1356 | GCUACUGCUCAACUCUGAA | 7141 | UUCAGAGUUGAGCAGUAGCCG |
| 7093 | Mfap4.760 | GCUUCUAUUACUCCCUCAA | 7142 | UUGAGGGAGUAAUAGAAGCCU |
| 7094 | Grhpr.361 | GACAGAUGCCACUGCAGAA | 7143 | UUCUGCAGUGGCAUCUGUCAG |
| 7095 | lftg1.698 | CGACAUUGACUGCCUCUAA | 7144 | UUAGAGGCAGUCAAUGUCGUG |
| 7096 | ltfg1.680 | CACUGAUUAUGGACUUCAA | 7145 | UUGAAGUCCAUAAUCAGUGGU |
| 7146 | Mfap4.1356 modified | 5'-cscsaGfcUfaCfuGfcUfcAfaCfuCfuGfaAfs(NHC6)(GalNAc3)-3' | 7151 | 5'-UfsUfscAfgAfgUfuGfaGfcAfgUfaGfcsdTsdT-3' |
| 7147 | Mfap4.760 modified | 5'-cscsaGfcUfuCfuAfuUfaCfuCfcCfuCfaAfs(NHC6)(GalNAc3)-3' | 7152 | 5'-UfsUfsgAfgGfgAfgUfaAfuAfgAfaGfcsdTsdT-3' |
| 7148 | Grhpr.361 modified | 5'-cscsaGfaCfaGfaUfgCfcAfcUfgCfaGfaAfs(NHC6)(GalNAc3)-3' | 7153 | 5'-UfsUfscUfgCfaGfuGfgCfaUfcUfgUfcsdTsdT-3' |
| 7149 | lftg1.698 modified | 5'-cscsaCfgAfcAfuUfgAfcUfgCfcUfcUfaAfs(NHC6)(GalNAc3)-3' | 7154 | 5'-UfsUfsaGfaGfgCfaGfuCfaAfuGfuCfgsdTsdT-3' |
| 7150 | ltfg1.680 modified | 5'-cscsaCfaCfuGfaUfuAfuGfgAfcUfuCfaAfs(NHC6)(GalNAc3)-3' | 7155 | 5'-UfsUfsgAfaGfuCfcAfuAfaUfcAfgUfgsdTsdT-3' | n: 2'-O-methyl residues
Nf: 2'-Fluoro residues
s: phosphorothioate backbone modification
dN: DNA residue
(NHC6): Aminohexyl linker
(GalNAc3): Trinatennary GalNAc cluster

TABLE 12

Human shRNAs sequences (sense-loop-antisense sequences)

| SEQ ID NO: | shRNA-id | Nucleic acid sequence |
|---|---|---|
| 7097 | huMfap4.1602 | TGCTGTTGACAGTGAGCGATAGGGACTGAAGGTCTCAATATAGTGAAGCCACAGATGTATATTGAGACCTTCAGTCCCTACTGCCTACTGCCTCGGA |
| 7098 | huMfap4.1603 | TGCTGTTGACAGTGAGCGCAGGGACTGAAGGTCTCAATAATAGTGAAGCCACAGATGTATTATTGAGACCTTCAGTCCCTATGCCTACTGCCTCGGA |
| 7099 | huMfap4.1642 | TGCTGTTGACAGTGAGCGAAACTGGCTTCATACACACAAATAGTGAAGCCACAGATGTATTTGTGTGTATGAAGCCAGTTCTGCCTACTGCCTCGGA |
| 7100 | huMfap4.1812 | TGCTGTTGACAGTGAGCGCCAGTGTAATAATAACATAATATAGTGAAGCCACAGATGTATATTATGTTATTATTACACTGTTGCCTACTGCCTCGGA |
| 7101 | huMfap4.318 | TGCTGTTGACAGTGAGCGACAGAAGAGATTCAATGGCTCATAGTGAAGCCACAGATGTATGAGCCATTGAATCTCTTCTGGTGCCTACTGCCTCGGA |
| 7102 | huMfap4.350 | TGCTGTTGACAGTGAGCGCCCGCGGCTGGAATGACTACAATAGTGAAGCCACAGATGTATTGTAGTCATTCCAGCCGCGGATGCCTACTGCCTCGGA |
| 7103 | huGrhpr.1125 | TGCTGTTGACAGTGAGCGAAAGGTGTGATTCTCTGAGGAATAGTGAAGCCACAGATGTATTCCTCAGAGAATCACACCTTCTGCCTACTGCCTCGGA |
| 7104 | huGrhpr.1172 | TGCTGTTGACAGTGAGCGCCACATTGGTGTTGGACACATTTAGTGAAGCCACAGATGTAAATGTGTCCAACACCAATGTGATGCCTACTGCCTCGGA |
| 7105 | huGrhpr.626 | TGCTGTTGACAGTGAGCGCTCCAGGCAGAGTTTGTGTCTATAGTGAAGCCACAGATGTATAGACACAAACTCTGCCTGGAATGCCTACTGCCTCGGA |
| 7106 | huGrhpr.750 | TGCTGTTGACAGTGAGCGCAACAGCTGTGTTCATCAACATTAGTGAAGCCACAGATGTAATGTTGATGAACACAGCTGTTTTGCCTACTGCCTCGGA |

TABLE 12-continued

Human shRNAs sequences
(sense-loop-antisense sequences)

| SEQ ID NO: | shRNA-id | Nucleic acid sequence |
|---|---|---|
| 7107 | huGrhpr.752 | TGCTGTTGACAGTGAGCGCCAGCTG<br>TGTTCATCAACATCATAGTGAAGCC<br>ACAGATGTATGATGTTGATGAACAC<br>AGCTGTTGCCTACTGCCTCGGA |
| 7108 | huGrhpr.954 | TGCTGTTGACAGTGAGCGACATGTC<br>CTTGTTGGCAGCTAATAGTGAAGCC<br>ACAGATGTATTAGCTGCCAACAAGG<br>ACATGGTGCCTACTGCCTCGGA |
| 7109 | huItfg1.1364 | TGCTGTTGACAGTGAGCGAAAGCAG<br>ATGCTTATTTTGTTATAGTGAAGCC<br>ACAGATGTATAACAAAATAAGCATC<br>TGCTTCTGCCTACTGCCTCGGA |
| 7110 | huItfg1.1683 | TGCTGTTGACAGTGAGCGACCAGCT<br>AATTGTCATTCCATATAGTGAAGCC<br>ACAGATGTATATGGAATGACAATTA<br>GCTGGGTGCCTACTGCCTCGGA |
| 7111 | huItfg1.2162 | TGCTGTTGACAGTGAGCGATCCAGT<br>GTTTGTGTATTTATATAGTGAAGCC<br>ACAGATGTATATAAATACACAAACA<br>CTGGAGTGCCTACTGCCTCGGA |
| 7112 | huItfg1.2163 | TGCTGTTGACAGTGAGCGACCCAGTG<br>TTTGTGTATTTATAATAGTGAAGCC<br>ACAGATGTATTATAAATACACAAAC<br>ACTGGATGCCTACTGCCTCGGA |
| 7113 | huItfg1.641 | TGCTGTTGACAGTGAGCGACAGCAT<br>TGACCACTACAAGTATAGTGAAGCC<br>ACAGATGTATACTTGTAGTGGTCAA<br>TGCTGGTGCCTACTGCCTCGGA |
| 7114 | huItfg1.971 | TGCTGTTGACAGTGAGCGATCCTAC<br>AAGATTTCAGCAATATAGTGAAGCC<br>ACAGATGTATATTGCTGAAATCTTG<br>TAGGACTGCCTACTGCCTCGGA |

TABLE 13

Mouse shRNA sequences
(sense-loop-antisense sequences)

| SEQ ID NO | shRNA_id | Nucleic acid sequence |
|---|---|---|
| 7115 | Mfap4.1073 | TGCTGTTGACAGTGAGCGAAAAGCC<br>AGAAGCTACCTTCTATAGTGAAGCC<br>ACAGATGTATAGAAGGTAGCTTCTG<br>GCTTTCTGCCTACTGCCTCGGA |
| 7116 | Mfap4.1118 | TGCTGTTGACAGTGAGCGCCAGCAG<br>TTTCCTTACTGCAGATAGTGAAGCC<br>ACAGATGTATCTGCAGTAAGGAAAC<br>TGCTGATGCCTACTGCCTCGGA |
| 7117 | Mfap4.1321 | TGCTGTTGACAGTGAGCGCTCCCTC<br>AAAATTCACCACCAATAGTGAAGCC<br>ACAGATGTATTGGTGGTGAATTTTG<br>AGGGATTGCCTACTGCCTCGGA |
| 7118 | Mfap4.1356 | TGCTGTTGACAGTGAGCGCCGGCTA<br>CTGCTCAACTCTGAATAGTGAAGCC<br>ACAGATGTATTCAGAGTTGAGCAGT<br>AGCCGTTGCCTACTGCCTCGGA |

TABLE 13-continued

Mouse shRNA sequences
(sense-loop-antisense sequences)

| SEQ ID NO | shRNA_id | Nucleic acid sequence |
|---|---|---|
| 7119 | Mfap4.274 | TGCTGTTGACAGTGAGCGACAAGTG<br>GACGGTTTTCCAGAATAGTGAAGCC<br>ACAGATGTATTCTGGAAAACCGTCC<br>ACTTGCTGCCTACTGCCTCGGA |
| 7120 | Mfap4.760 | TGCTGTTGACAGTGAGCGCAGGCTT<br>CTATTACTCCCTCAATAGTGAAGCC<br>ACAGATGTATTGAGGGAGTAATAGA<br>AGCCTTTGCCTACTGCCTCGGA |
| 7121 | Grhpr.1009 | TGCTGTTGACAGTGAGCGACCCAGC<br>GAACTCAAGCTGTAATAGTGAAGCC<br>ACAGATGTATTACAGCTTGAGTTCG<br>CTGGGCTGCCTACTGCCTCGGA |
| 7122 | Grhpr.1187 | TGCTGTTGACAGTGAGCGCTGCCAA<br>AAGCCTGTAATTCTATAGTGAAGCC<br>ACAGATGTATAGAATTACAGGCTTT<br>TGGCAATGCCTACTGCCTCGGA |
| 7123 | Grhpr.1193 | TGCTGTTGACAGTGAGCGCAAGCCT<br>GTAATTCTAGCATTATAGTGAAGCC<br>ACAGATGTATAATGCTAGAATTACA<br>GGCTTTTGCCTACTGCCTCGGA |
| 7124 | Grhpr.720 | TGCTGTTGACAGTGAGCGACAGCAA<br>GGATTTCTTCCAGAATAGTGAAGCC<br>ACAGATGTATTCTGGAAGAAATCCT<br>TGCTGCTGCCTACTGCCTCGGA |
| 7125 | Grhpr.361 | TGCTGTTGACAGTGAGCGACTGACA<br>GATGCCACTGCAGAATAGTGAAGCC<br>ACAGATGTATTCTGCAGTGGCATCT<br>GTCAGGTGCCTACTGCCTCGGA |
| 7126 | Grhpr.787 | TGCTGTTGACAGTGAGCGCCAGCAG<br>AGGAGATGTGGTAAATAGTGAAGCC<br>ACAGATGTATTTACCACATCTCCTC<br>TGCTGATGCCTACTGCCTCGGA |
| 7127 | Grhpr.736 | TGCTGTTGACAGTGAGCGACAGCAA<br>GGATTTCTTCCAGAATAGTGAAGCC<br>ACAGATGTATTCTGGAAGAAATCCT<br>TGCTGCTGCCTACTGCCTCGGA |
| 7128 | Grhpr.1024 | TGCTGTTGACAGTGAGCGCGCCCAG<br>CGAACTCAAGCTGTATAGTGAAGCC<br>ACAGATGTATACAGCTTGAGTTCGC<br>TGGGCATGCCTACTGCCTCGGA |
| 7129 | Grhpr.1025 | TGCTGTTGACAGTGAGCGACCCAGC<br>GAACTCAAGCTGTAATAGTGAAGCC<br>ACAGATGTATTACAGCTTGAGTTCG<br>CTGGGCTGCCTACTGCCTCGGA |
| 7130 | Iftg1.698 | TGCTGTTGACAGTGAGCGCCACGAC<br>ATTGACTGCCTCTAATAGTGAAGCC<br>ACAGATGTATTAGAGGCAGTCAATG<br>TCGTGATGCCTACTGCCTCGGA |
| 7131 | Itfg1.376 | TGCTGTTGACAGTGAGCGCGCCATC<br>CATACACTCAAAAATAGTGAAGCC<br>ACAGATGTATTTTTGAGTGTATGG<br>ATGGCATGCCTACTGCCTCGGA |
| 7132 | Itfg1.448 | TGCTGTTGACAGTGAGCGCGACGCC<br>ATAGTTGCCACCTTATAGTGAAGCC<br>ACAGATGTATAAGGTGGCAACTATG<br>GCGTCTTGCCTACTGCCTCGGA |

TABLE 13-continued

Mouse shRNA sequences
(sense-loop-antisense sequences)

| SEQ ID NO | shRNA_id | Nucleic acid sequence |
|---|---|---|
| 7133 | Itfg1.694 | TGCTGTTGACAGTGAGCGCGAGGCA GATGCTTACTTTGTATAGTGAAGCC ACAGATGTATACAAAGTAAGCATCT GCCTCATGCCTACTGCCTCGGA |
| 7134 | Itfg1.2450 | TGCTGTTGACAGTGAGCGACCAGAT AAAGTTATTCAAGTATAGTGAAGCC ACAGATGTATACTTGAATAACTTTA TCTGGCTGCCTACTGCCTCGGA |
| 7135 | Itfg1.2451 | TGCTGTTGACAGTGAGCGACAGATA AAGTTATTCAAGTAATAGTGAAGCC ACAGATGTATACTTGAATAACTTT ATCTGGTGCCTACTGCCTCGGA |
| 7136 | Itfg1.2802 | TGCTGTTGACAGTGAGCGCTGGATT GTCACCGAAGACATATAGTGAAGCC ACAGATGTATATGTCTTCGGTGACA ATCCATTGCCTACTGCCTCGGA |
| 7137 | Itfg1.2921 | TGCTGTTGACAGTGAGCGCAAGCTG GTATTTGAATACTAATAGTGAAGCC ACAGATGTATTAGTATTCAAATACC AGCTTTTGCCTACTGCCTCGGA |
| 7138 | Itfg1.680 | TGCTGTTGACAGTGAGCGCACCACT GATTATGGACTTCAATAGTGAAGCC ACAGATGTATTGAAGTCCATAATCA GTGGTTTGCCTACTGCCTCGGA |
| 7139 | Itfg1.875 | TGCTGTTGACAGTGAGCGCCACGAC ATTGACTGCCTCTAATAGTGAAGCC ACAGATGTATTAGAGGCAGTCAATG TCGTGATGCCTACTGCCTCGGA |
| 7140 | Itfg1.503 | TGCTGTTGACAGTGAGCGCACCACT GATTATGGACTTCAATAGTGAAGCC ACAGATGTATTGAAGTCCATAATCA GTGGTTTGCCTACTGCCTCGGA |

TABLE 14

Target sequences.

| SEQ ID NO: | Description | Sequence |
|---|---|---|
| 7156 | Human MFAP4 isoform 1 (UniProtKB: P55083-1, v2) | MKALLALPLLLLLSTPPCAPQVSGIRGDALERFCLQQPLDCDDIYAQGYQSDGVYLIYPSGPSVPVP VFCDMTTEGGKWTVFQKRFNGSVSFFRGWNDYKLGFGRADGEYWLGLQNMHLLTLKQKYELRVDLEDFE NNTAYAKYADFSISPNAVSAEEDGYTLFVAGFEDGGAGDSLSYHSGQKFSTFDRDQDLFVQNCAALSS GAFWFRSCHFANLNGFYLGGSHLSYANGINWAQWKGFYYSLKRTEMKIRRA |
| 7157 | Human MFAP4 isoform 2 (UniProtKB: P55083-2) | MGELSPLQRPLATEGTMKAQGVLLKLALLALPLLLLLSTPPCAPQVSGIRGDALERFCLQQPLDCDDI YAQGYQSDGVYLIYPSGPSVPVPVFCDMTTEGGKWTVFQKRFNGSVSFFRGWNDYKLGFGRADGEYWL GLQNMHLLTLKQKYELRVDLEDFENNTAYAKYADFSISPNAVSAEEDGYTLFVAGFEDGGAGDSLSYH SGQKFSTFDRDQDLFVQNCAALSSGAFWFRSCHFANLNGFYLGGSHLSYANGINWAQWKGFYYSLKRT EMKIRRA |
| 7158 | Human GRHPR isoform 1 (UniProtKB: Q9UBQ7-1, v1) | MRPVRLMKVFVTRRIPAEGRVALARAADCEVEQWDSDEPIPAKELERGVAGAHGLLCLLSDHVDKRIL DAAGANLKVISTMSVGIDHLALDEIKKRGIRVGYTPDVLTDTTAELAVSLLLTTCRRLPEAIEEVKNG GWTSWKPLWLCGYGLTQSTVGIIGLGRIGQAIARRLKPFGVQRPFLYTGRQPRPEEAAEFQAEFVSTPE LAAQSDFIVVACSLTPATEGLCNKDFFQKMKETAVFINISRGDVVNQDDLYQALASGKIAAAGLDVTS PEPLPTNHPLLTLKNCVILPHIGSATHRTRNTMSLLAANNLLAGLRGEPMPSELKL |
| 7159 | Human GRHPR isoform 2 (UniProtKB: Q9UBQ7-2) | MLGGVPTLCGTGNETWTLLALGQAIARRLKPFGVQRFLYTGRQPRPEEAAEFQAEFVSTPELAAQSDF IVVACSLTPATEGLCNKDFFQKMKETAVFINISRYPRATLPSKPGEEPSPLLPSGDFLPRGLLVRPQA ELAGFHKPNNQLRNSWEYTRPPYREEEPSEWAWPVCFSAVAPTRRGLAHSSVASGSVPREPLQAHYPP PQRAGLEDLKGPLEAASHTAEPGFVWLWFSDTLNLMLLGGQTLKLTWS |
| 7160 | Human ITFG1 (UniProtKB Q8TB96-1, v1) | MAAAGRLPSSWALFSPLLAGLALLGVGPVPARALHNVTAELFGAEAWGTLAAFGDLNSDKQTDLFVLR ERNDLIVFLADQNAPYFKPKVKVSFKNHSALITSVVPGDYDGDSQMDVLLTYLPKNYAKSELGAVIFW GQNQTLDPNNMTILNRTFQDEPLIMDFNGDLIPDIFGITNESNQPQILLGGNLSWHPALTTTSKMRIP HSHAFIDLTEDFTADLFLTTLNATTSTFQFEIWENLDGNFSVSTILEKPQNMMVVGQSAFADFDGDGH MDHLLPGCEDKNCQKSTIYLVRSGMKQWVPVLQDFSNKGTLWGFVPFVDEQQPTEIPIPITLHIGDYN MDGYPDALVILKNTSGSNQQAFLLENVPCNNASCEEARRMFKVYWELTDLNQIKDAMVATFFDIYEDG ILDIVVLSKGYTKNDFAIHTLKNNFEADAYFVKVIVLSGLCSNDCPRKITPFGVNQPGPYIMYTTVDA NGYLKNGSAGQLSQSAHLALQLPYNVLGLGRSANFLDHLYVGIPRPSGEKSIRKQEWTAIIPNSQLIV IPYPHNVPRSWSAKLYLTPSNIVLLTAIALIGVCVFILAIIGILHWQEKKADDREKRQEAHRFHFDAM |
| 7161 | Human ABCC4 isoform 1 (UniProtKB: O15439-1, v3) | MLPVYQEVKPNPLQDANLCSRVFFWWLNPLFKIGHKRRLEEDDMYSVLPEDRSQHLGEELQGFWDKEV LRAENDAQKPSLTRAIIKCYWKSYLVLGIFTLLIEESAKVIQPIFLGKIINYFENYDPMDSVALNTAYA YATVLTFCTLILAILHHLYFHVQCAGMRLRVAMCHMIYRKALRLSNMAMGKTTTGQIVNLLSNDVNK FDQVTVFLHFLWAGPLQAIAVTALLWMEIGISCLAGMAVLIILLPLQSCFGKLFSSLRSKTATFTDAR IRTMNEVITGIRIIKMYAWEKSFSNLITNLRKKEISKILRSSCLRGMNLASFFSASKIIVFVTPTTYV LLGSVITASRVFVAVTLYGAVRLTVTLFFPSAIERVSEAIVSIRRIQTFLLLDEISQRNRQLPSDGKK MVHVQDFTAFWDKASETPTLQGLFTVRPGELLAVVGPVGAGKSSLLSAVLGELAPSHGLVSVHGRIA YVSQQPWVFSGTLRSNILFGKKYEKERYEKVIKACALKKDLQLLEDGDLTVIGDRGTTLSGGQKARVN LARAVYQDADIYLLDDPLSAVDAEVSRHLFELCICQILHEKITILVTHQLQYLKAASQILILKDGKMV QKGTYTEFLKSGIDFGSLLKKDNEESEQPPVPGTPTLRNRTFSESSVWSQQSSRPSLKDGALESQDTE NVPVTLSEENRSEGKVGFQAYKNYFRAGAHWIVFIFLILLNTAAQVAYVLQDWWLSYWANKQSMLNVT VNGGGNVTEKLDLNWYLGIYSGLTVATVLFGIARSLLVFYVLVNSSQTLHNKMFESILKAPVLFFDRN PIGRILNRFSKDIGHLDDLLPLTFLDFIQTLLQVVGVVSVAVAVIPWIAIPLVPLGIIFIFLRRYFLE |

TABLE 14-continued

Target sequences.

| SEQ ID NO: | Description | Sequence |
|---|---|---|
| | | TSRDVKRLESTTRSPVFSHLSSSLQGLWTIRAYKAEERCQELFDAHQDLHSEAWFLFLTTSRWFAVRL<br>DAICAMFVIIVAFGSLILAKTLDAGQVGLALSYALTLMGMFQWCVRQSAEVENMMISVERVIEYTDLE<br>KEAPWEYQKRPPPAWPHEGVIIFDNVNFMYSPGGPLVLKHLTALIKSQEKVGIVGRTGAGKSSLISAL<br>FRLSEPEGKIWIDKILTTEIGLHDLRKKMSIIPQEPVLFTGTMRKNLDPFNEHTDEELWNALQEVQLK<br>ETIEDLPGKMDTELAESGSNFSVGQRQLVCLARAILRKNQILIIDEATANVDPRTDELIQKKIREKFA<br>HCTVLTIAHRLNTIIDSDKIMVLDSGRLKEYDEPYVLLQNKESLFYKMVQQLGKAEAAALTETAKQVY<br>FKRNYPHIGHTDHMVTNTSNGQPSTLTIFETAL |
| 7162 | Human ABCC4<br>isoform 2<br>(UniProtKB:<br>O15439-2) | MLPVYQEVKPNPLQDANLCSRVFFWWLNPLFKIGHKRRLEEDDMYSVLPEDRSQHLGEELQGFWDKEV<br>LRAENDAQKPSLTRAIIKCYWKSYLVLGIFTLIEESAKVIQPIFLGKIINYFENYDPMDSVALNTAYA<br>YATVLTFCTLILAILHHLYFYHVQCAGMRLRVAMCHMIYRKALRLSNMAMGKTTTGQIVNLLSNDVNK<br>FDQVTVFLHFLWAGPLQAIAVTALLWMEIGISCLAGMAVLIILLPLQSCFGKLFSSLRSKTATFTDAR<br>IRTMNEVITGIRIIKMYAWEKSFSNLITNLRKKEISKILRSSCLRGMNLASFFSASKIIVFVTFTTYV<br>LLGSVITASRVFVAVTLYGAVRLTVTLFFPSAIERVSEAIVSIRRIQTFLLLDEISQRNRQLPSDGKK<br>MVHVQDFTAFWDKASETPTLQGLSFTVRPGELLAVVGPVGAGKSSLLSAVLGELAPSHGLVSVHGRIA<br>YVSQQPWVFSGTLRSNILFGKKYEKERYEKVIKACALKKDLQLLEDGDLTVIGDRGTTLSGGQKARVN<br>LARAVYQDADIYLLDDPLSAVDAEVSRHLFELCICQILHEKITILVTHQLQYLKAASQILILKDGKMV<br>QKGTYTEFLKSGIDFGSLLKKDNEESEQPPVPGTPTLRNRTFSESSVW<br>SQQSSRPSLKDGALESQDVAYVLQDWWLSYWANKQSMLNVTVNGGGNVTEKLDLNWYLGIYSGLTVAT<br>VLFGIARSLLVFYVLVNSSQTLHNKMFESILKAPVLFFDRNPIGRILNRFSKDIGHLDDLLPLTFLDF<br>IQTLLQVVGVVSVAVAVIPWIAIPLVPLPLGIIFLRRYFLETSRDVKRLESTTRSPVFSHLSSSLQGL<br>WTIRAYKAEERCQELFDAHQDLHSEAWFLFLTTSRWFAVRLDAICAMFVIIVAFGSLILAKTLDAGQV<br>GLALSYALTLMGMFQWCVRQSAEVENMMISVERVIEYTDLEKEAPWEYQKRPPPAWPHEGVIIFDNVN<br>FMYSPGGPLVLKHLTALIKSQEKVGIVGRTGAGKSSLISALFRLSEPEGKIWIDKILTTEIGLHDLRK<br>KMSIIPQEPVLFTGTMRKNLDPFNEHTDEELWNALQEVQLKETIEDLPGKMDTELAESGSNFSVGQRQ<br>LVCLARAILRKNQILIIDEATANVDPRTDELIQKKIREKFAHCTVLTIAHRLNTIIDSDKIMVLDSGR<br>LKEYDEPYVLLQNKESLFYKMVQQLGKAEAAALTETAKQVYFKRNYPHIGHTDHMVTNTSNGQPSTLT<br>IFETAL |
| 7163 | Human ABCC4<br>isoform 3<br>(UniProtKB:<br>O15439-3) | MLPVYQEVKPNPLQDANLCSRVFFWWLNPLFKIGHKRRLEEDDMYSVLPEDRSQHLGEELQGFWDKEV<br>LRAENDAQKPSLTRAIIKCYWKSYLVLGIFTLIEESAKVIQPIFLGKIINYFENYDPMDSVALNTAYA<br>YATVLTFCTLILAILHHLYFYHVQCAGMRLRVAMCHMIYRKALRLSNMAMGKTTTGQIVNLLSNDVNK<br>FDQVTVFLHFLWAGPLQAIAVTALLWMEIGISCLAGMAVLIILLPLQSCFGKLFSSLRSKTATFTDAR<br>IRTMNEVITGIRIIKMYAWEKSFSNLITNLRKKEISKILRSSCLRGMNLASFFSASKIIVFVTFTTYV<br>LLGSVITASRVFVAVTLYGAVRLTVTLFFPSAIERVSEAIVSIRRIQTFLLLDEISQRNRQLPSDGKK<br>MVHVQDFTAFWDKASETPTLQGLSFTVRPGELLAVVGPVGAGKSSLLSAVLGELAPSHGLVSVHGRIA<br>YVSQQPWVFSGTLRSNILFGKKYEKERYEKVIKACALKKDLQLLEDGDLTVIGDRGTTLSGGQKARVN<br>LARAVYQDADIYLLDDPLSAVDAEVSRHLFELCICQILHEKITILVTHQLQYLKAASQILILKDGKMV<br>QKGTYTEFLKSGIDFGSLLKKDNEESEQPPVPGTPTLRNRTFSESSVWSQQSSRPSLKDGALESQDTE<br>NVPVTLSEENRSEGKVGFQAYKNYFRAGAHWIVFIFLILLNTAAQVAYVLQDWWLSYWANKQSMLNVT<br>VNGGGNVTEKLDLNWYLGIYSGLTVATVLFGIARSLLVFYVLVNSSQTLHNKMFESILKAPVLFFDRN<br>PIGRILNRFSKDIGHLDDLLPLTFLDFIQRWDLAVLSWLVSNS |
| 7164 | Human ABCC4<br>isoform 4<br>(UniProtKB:<br>O15439-4) | MLPVYQEVKPNPLQDANLCSRVFFWWLNPLFKIGHKRRLEEDDMYSVLPEDRSQHLGEELQGFWDKEV<br>LRAENDAQKPSLTRAIIKCYWKSYLVLGIFTLIEALRLSNMAMGKTTTGQIVNLLSNDVNKFDQVTVF<br>LHFLWAGPLQAIAVTALLWMEIGISCLAGMAVLIILLPLQSCFGKLFSSLRSKTATFTDARIRTMNEV<br>ITGIRIIKMYAWEKSFSNLITNLRKKEISKILRSSCLRGMNLASFFSASKIIVFVTFTTYVLLGSVIT<br>ASRVFVAVTLYGAVRLTVTLFFPSAIERVSEAIVSIRRIQTFLLLDEISQRNRQLPSDGKKMVHVQDF<br>TAFWDKASETPTLQGLSFTVRPGELLAVVGPVGAGKSSLLSAVLGELAPSHGLVSVHGRIAYVSQQPW<br>VFSGTLRSNILFGKKYEKERYEKVIKACALKKDLQLLEDGDLTVIGDRGTTLSGGQKARVNLARAVYQ<br>DADIYLLDDPLSAVDAEVSRHLFELCICQILHEKITILVTHQLQYLKAASQILILKDGKMVQKGTYTE<br>FLKSGIDFGSLLKKDNEESEQPPVPGTPTLRNRTFSESSVWSQQSSRPSLKDGALESQDTENVPVTLS<br>EENRSEGKVGFQAYKNYFRAGAHWIVFIFLILLNTAAQVAYVLQDWWLSYWANKQSMLNVTVNGGGNV<br>TEKLDLNWYLGIYSGLTVATVLFGIARSLLVFYVLVNSSQTLHNKMFESILKAPVLFFDRNPIGRILN<br>RFSKDIGHLDDLLPLTFLDFIQRWDLAVLSWLVSNS |
| 7165 | Human PAK3<br>isoform 1<br>(UniProtKB:<br>O75914-1, v2) | MSDGLDNEEKPPAPPLRMNSNNRDSSALNHSSKPLPMAPEEKNKKARLRSIFPGGGDKTNKKKEKERP<br>EISLPSDFEHTIHVGFDAVTGEFTPDLYGSQMCPGKLPEGIPEQWARLLQTSNITKLEQKKNPQAVLD<br>VLKFYDSKETVNNQKYMSFTSGDKSAHGYIAAHPSSTKTASEPPLAPPVSEEEDEEEEEEEDENEPPP<br>VIAPRPEHTKSIYTRSVVESIASPAVPNKEVTPPSAENANSSTLYRNTDRQRKKSKMTDEEILEKLRS<br>IVSVGDPKKKYTRFEKIGQGASGTVYTALDIATGQEVAIKQMNLQQQPKKELIINEILVMRENKNPNI<br>VNYLDSYLVGDELWVVMEYLAGGSLTDVVTETCMDEGQIAAVCRECLQALDFLHSNQVIHRDIKSDNI<br>LLGMDGSVKLTDFGFCAQITPEQSKRSTMVGTPYWMAPEVVTRKAYGPKVDIWSLGIMAIEMVEGEPP<br>YLNENPLRALYLIATNGTPELQNPERLSAVFRDFLNRCLEMDVDRRGSAKELLQHPFLKLAKPLSSLT<br>PLIIAAKEAIKNSSR |
| 7166 | Human PAK3<br>isoform 2<br>(UniProtKB:<br>O75914-2) | MSDGLDNEEKPPAPPLRMNSNNRDSSALNHSSKPLPMAPEEKNKKARLRSIFPGGGDKTNKKKEKERP<br>EISLPSDFEHTIHVGFDAVTGEFTGIPEQWARLLQTSNITKLEQKKNPQAVLDVLKFYDSKETVNNQK<br>YMSFTSGDKSAHGYIAAHPSSTKTASEPPLAPPVSEEEDEEEEEEEDENEPPPVIAPRPEHTKSIYTR<br>SVVESIASPAVPNKEVTPPSAENANSSTLYRNTDRQRKKSKMTDEEILEKLRSIVSVGDPKKKYTRFE<br>KIGQGASGTVYTALDIATGQEVAIKQMNLQQQPKKELIINEILVMRENKNPNIVNYLDSYLVGDELWV<br>VMEYLAGGSLTDVVTETCMDEGQIAAVCRECLQALDFLHSNQVIHRDIKSDNILLGMDGSVKLTDFGF<br>CAQITPEQSKRSTMVGTPYWMAPEVVTRKAYGPKVDIWSLGIMAIEMVEGEPPYLNENPLRALYLIAT<br>NGTPELQNPERLSAVFRDFLNRCLEMDVDRRGSAKELLQHPFLKLAKPLSSLTPLIIAAKEAIKNSSR |

TABLE 14-continued

Target sequences.

| SEQ ID NO: | Description | Sequence |
|---|---|---|
| 7167 | Human PAK3 isoform 3 (UniProtKB: O75914-3) | MSDGLDNEEKPPAPPLRMNSNNRDSSALNHSSKPLPMAPEEKNKKARLRSIFPGGGDKTNKKKEKERP EISLPSDFEHTIHVGFDAVTGEFTNSPFQTSRPVTVASSQSEGKMPDLYGSQMCPGKLPEGIPEQWAR LLQTSNITKLEQKKNPQAVLDVLKFYDSKETVNNQKYMSFTSGDKSAHGYIAAHPSSTKTASEPPLAP PVSEEEDEEEEEEEDENEPPPVIAPRPEHTKSIYTRSVVESIASPAVPNKEVTPPSAENANSSTLYRN TDRQRKKSKMTDEEILEKLRSIVSVGDPKKKYTRFEKIGQGASGTVYTALDIATGQEVAIKQMNLQQQ PKKELIINEILVMRENKNPNIVNYLDSYLVGDELWVVMEYLAGGSLTDVVTETCMDEGQIAAVCRECL QALDFLHSNQVIHRDIKSDNILLGMDGSVKLTDFGFCAQITPEQSKRSTMVGTPYWMAPEVVTRKAYG PKVDIWSLGIMAIEMVEGEPPYLNENPLRALYLIATNGTPELQNPERLSAVFRDFLNRCLEMDVDRRG SAKELLQHPFLKLAKPLSSLTPLIIAAKEAIKNSSR |
| 7168 | Human PAK3 isoform 4 (UniProtKB: O75914-4) | MSDGLDNEEKPPAPPLRMNSNNRDSSALNHSSKPLPMAPEEKNKKARLRSIFPGGGDKTNKKKEKERP EISLPSDFEHTIHVGFDAVTGEFTNSPFQTSRPVTVASSQSEGKMGIPEQWARLLQTSNITKLEQKKN PQAVLDVLKFYDSKETVNNQKYMSFTSGDKSAHGYIAAHPSSTKTASEPPLAPPVSEEEDEEEEEEED ENEPPPVIAPRPEHTKSIYTRSVVESIASPAVPNKEVTPPSAENANSSTLYRNTDRQRKKSKMTDEEI LEKLRSIVSVGDPKKKYTRFEKIGQGASGTVYTALDIATGQEVAIKQMNLQQQPKKELIINEILVMRE NKNPNIVNYLDSYLVGDELWVVMEYLAGGSLTDVVTETCMDEGQIAAVCRECLQALDFLHSNQVIHRD IKSDNILLGMDGSVKLTDFGFCAQITPEQSKRSTMVGTPYWMAPEVVTRKAYGPKVDIWSLGIMAIEM VEGEPPYLNENPLRALYLIATNGTPELQNPERLSAVFRDFLNRCLEMDVDRRGSAKELLQHPFLKLAK PLSSLTPLIIAAKEAIKNSSR |
| 7169 | Human TRNP1 (UniProtKB: Q6NT89-1, v2) | MPGCRISACGPGAQEGTAEQRSPPPPWDPMPSSQPPPPTPTLTPTPTGQSPPLPDAAGASAGAAEDQ ELQRWRQGASGIAGLAGPGGGSGAAAGAGGRALELAEARRRLLLEVEGRRRLVSELESRVLQLHRVFLA AELRLAHRAESLSRLSGGVAQAELYLAAHGSRLKKGPRRGRRGRPPALLASALGLGGCVPWGAGRLRR GHGPEPDSPFRRSPPRGPASPQR |
| 7170 | Human APLN (UniProtKB: Q9ULZ1-1, v1) | MNLRLCVQALLLLWLSLTAVCGGSLMPLPDGNGLEDGNVRHLVQPRGSRNGPGPWQGGRRKFRRQRPR LSHKGPMPF |
| 7171 | Apelin-36 (UniProtKB: Q9ULZ1-1, v1 positions 42-77) | LVQPRGSRNGPGPWQGGRRKFRRQRPRLSHKGPMPF |
| 7172 | Apelin-31 (UniProtKB: Q9ULZ1-1, v1 positions 47-77) | GSRNGPGPWQGGRRKFRRQRPRLSHKGPMPF |
| 7173 | Apelin-28 (UniProtKB: Q9ULZ1-1, v1 positions 50-77) | NGPGPWQGGRRKFRRQRPRLSHKGPMPF |
| 7174 | Apelin-13 (UniProtKB: Q9ULZ1-1, v1 positions 65-77) | QRPRLSHKGPMPF |
| 7175 | Human KIF20A isoform 1 (UniProtKB: O95235-1, v1) | MSQGILSPPAGLLSDDDVVVSPMFESTAADLGSVVRKNLLSDCSVVSTSLEDKQQVPSEDSMEKVKVY LRVRPLLPSELERQEDQGCVRIENVETLVLQAPKDSFALKSNERGIGQATHRFTFSQIFGPEVGQASF FNLTVKEMVKDVLKGQNWLIYTYGVTNSGKTHTIQGFTIKDGGILPRSLALIFNSLQGQLHPTPDLKPL LSNEVIWLDSKQIRQEEMKKLSLLNGGLQEEELSTSLKRSVYIESRIGTSTSFDSGIAGLSSISQCTS SSQLDETSHRWAQPDTAPLPVPANIRFSIWISFFEIYNELLYDLLEPPSQQRKRQTLRLCEDQNGNPY VKDLNWIHVQDAEEAWKLLKVGRKNQSFASTHLNQNSSRSHSIFSIRILHLQGEGDIVPKISELSLCD LAGSERCKDQKSGERLKEAGNINTLSLHTLGRCIAALRQNQQNRSKQNLVPFRDSKLTRVFQGFFTGRG RSCMIVNVNPCASTYDETLHVAKFSAIASQLVHAPPMQLGFPSLHSFIKEHSLQVSPSLEKGAKADTG LDDDIENEADISMYGKEELLQVVEAMKTLLLKERQEKLQLEMHLRDEICNEMVEQMQQREQWCSEHLD TQKELLEEMYEEKLNILKESLTSFYQEEIQERDEKIEELEALLQEARQQSVAHQQSGSELALRRSQRL AASASTQQLQEVKAKLQQCKAELNSTTEELHKYQKMLEPPPSAKPFTIDVDKKLEEGQKNIRLLRTEL QKLGESLQSAERACCHSTGAGKLRQALTTCDDILIKQDQTLAELQNNMVLVKLDLRKKAACIAEQYHT VLKLQGQVSAKKRLGTNQENQQPNQQPPGKKPFLRNLLPRTPTCQSSTDCSPYARILRSRRSPLLKSG PFGKKY |

TABLE 14-continued

Target sequences.

| SEQ ID NO: | Description | Sequence |
|---|---|---|
| 7176 | Human KIF20A isoform 2 (UniProtKB: O95235-2) | MSQGILSPPAGLLSDDDVVVSPMFESTAADLGSVVRKNLLSDCSVVSTSLEDKQQVPSEDSMEKEDQG CVRIENVETLVLQAPKDSFALKSNERGIGQATHRFTFSQIFGPEVGQASFFNLTVKEMVKDVLKGQNW LIYTYGVTNSGKTHTIQGTIKDGGILPRSLALIFNSLQGQLHPTPDLKPLLSNEVIWLDSKQIRQEEM KKLSLLNGGLQEEELSTSLKRSVYIESRIGTSTSFDSGIAGLSSISQCTSSSQLDETSHRWAQPDTAP LPVPANIRFSIWISFFEIYNELLYDLLEPPSQQRKRQTLRLCEDQNGRNPYVKDLNWIHVQDAEEAWKL LKVGRKNQSFASTHLNQNSSRSHSIFSIRILHLQGEGDIVPKISELSLCDLAGSERCKDQKSGERLKE AGNINTSLHTLGRCIAALRQNQQNRSKQNLVPFRDSKLTRVFQGFFTGRGRSCMIVNVNPCASTYDET LHVAKFSAIASQLVHAPPMQLGFPSLHSFIKEHSLQVSPSLEKGAKADTGLDDDIENEADISMYGKEE LLQVVEAMKTLLLLKERQEKLQLEMHLRDEICNEMVEQMQQREQWCSEHLDTQKELLEEMYEEKLNILK ESLTSFYQEEIQERDEKIEELEALLQEARQQSVAHQQSGSELALRRSQRLAASASTQQLQEVKAKLQQ CKAELNSTTEELHKYQKMLEPPPSAKPFTIDVDKKLEEGQKNIRLLRTELQKLGESLQSAERACCHST GAGKLRQALTTCDDILIKQDQTLAELQNNMVLVKLDLRKKAACIAEQYHTVLKLQGQVSAKKRLGTNQ ENQQPNQQPPGKKPFLRNLLPRTPTCQSSTDCSPYARILRSRRSPLLKSGPFGKKY |
| 7177 | Human LTB isoform 1 (UniProtKB: Q06643-1, v1) | MGALGLEGRGGRLQGRGSLLLAVAGATSLVTLLLAVPITVLAVLALVPQDQGGLVTETADPGAQAQQG LGFQKLPEEEPETDLSPGLPAAHLIGAPLKGQGLGWETTKEQAFLTSGTQFSDAEGLALPQDGLYYLY CLVGYRGRAPPGGGDPQGRSVTLRSSLYRAGGAYGPGTPELLLEGAETVTPVLDPARRQGYGPLWYTS VGFGGLVQLRRGERVYVNISHPDMVDFARGKTFFGAVMVG |
| 7178 | Human LTB isoform 2 (UniProtKB: Q06643-2) | MGALGLEGRGGRLQGRGSLLLAVAGATSLVTLLLAVPITVLAVLALVPQDQGGLGFRSCQRRSQKQIS APGSQLPTS |
| 7179 | Human MFAP4 transcript variant 1 mRNA NM_001198695.2 (GI: 1677501926 version 2) | GCAGACACCCAGCCACTCTGAGCAGAACTGACAGCATGAAGGTACGGGGCCCAGGGTCGGGGGACTCA TAGCATGGGGGAACTGAGCCCACTCCAGAGGCCCCTGGCCACAGAGGGCACTATGAAGGCACAAGGAG TTCTCTTGAAACTCGCACTCCTGGCCCTGCCGCTGCTGCTGCTTCTCTCCACGCCCCCGTGTGCCCCC CAGGTCTCCGGGATCCGAGGAGATGCTCTGGAGAGGTTTTGCCTTCAGCAACCCCTGGACTGTGACGA CATCTATGCCCAGGGCTACCAGTCAGACGGCGTGTACCTCATCTACCCCTCGGGCCCCAGTGTGCCTG TGCCCGTCTTCTGTGACATGACCACCGAGGGCGGGAAGTGGACGGTTTTCCAGAAGAGATTCAATGGC TCAGTAAGTTTCTTCCGCGGCTGGAATGACTACAAGCTGGGCTTCGGCCGTGCTGATGGAGAGTACTG GCTGGGGCTGCAGAACATGCACCTCCTGACACTGAAGCAGAAGTATGAGCTGCGAGTGGACTTGGAGG ACTTTGAGAACAACACGGCCTATGCCAAGTACGCTGACTTCTCCATCTCCCCGAACGCGGTCAGCGCA GAGGAGGATGGCTACACCCTCTTTGTGGCAGGCTTTGAGGATGGCGGGGCAGGTGACTCCTCGTCCTA CCACAGTGGCCAGAAGTTCTCTACCTTCGACCGGGACCAGGACCTCTTTGTGCAGAACTGCGCAGCTC TCTCCTCAGGAGCCTTCTGGTTCCGCAGCTGCCACTTTGCCAACCTCAATGGCTTCTACCTAGGTGGC TCCCACCTCTCTTATGCCAATGGCATCAACTGGGCCCAGTGGAAGGGCTTCTACTACTCCCTCAAACG CACTGAGATGAAAATCCGCCGGGCCTGAAGGGCTGGCCCCCTGAAGGGCTGGCCCCCTCAGGCACCTG GCTCCTCCTTGCTCCCCTGCTGATGGTGTCCTACCCCGAACTCCAAAAATTACACCTGGAGTCAGGTG CATGGTCTCCATGAGTGCTCCCTCTGCTGCCCCTGATGCATGCTTCTGCTGATTCCCGAGCACCAACT CCTTACAAGGGGGCCTTGTGGCTCTCAGCCATGCCACATCCCTGTCACACACCCAGGGCATCCATTCC TAAGCCAGACCCGGCTCCCCTACACCTGAAGTTACACTGCCAGCAGTTCCCCAGGCCTCTTCCGAGAG GCACATGGTTCTAGCCTGGACCTGGCTGGGCTCCATGAGAATGAGTTGCCTCCAACCTGTCCCAACAG CTGACAGCCAGGAGCCACTCTCCCAGCTGCAGGCCTTTGTGGTCCATCTTGTCCTGCTTCCTCACTGT GGACCCCTGTCTGGGCCACCCTAGTGTGCTAAGCTGAGCAGTGCAGTGTGAACAGGGCCCATGGTGTA TTCTAGGCCACAGCCCAGCACTCCTCTGGGCTGCTCTCAAACCATGTCCCATCTTCAGCATCCCTCCC ACCAACTTACTCCCCTGTGGTGAGTACCGTGGAACCCCAGCCCACCTCACTATCATACTCAGCTTCCC CTGATGGCCCATCCCAGCCCCTGAAGCTCTATGCCAAGAACACAGCTACCGCACACCACCCTGAAACA GCCACAGCCAAGGTAGGCATGCATATGAGGTCTTCCCCATACCCTCTGGGTGTTGAGAGGTTTAGCCA CATGAGGGAGCAGAGGACAATCTCTGCAGGGCTGGGAGTGGGTAGGGACTGAAGGTCTCAATAAACCT TCAGAACCTGAATGAACTGGCTTCATACACACAAACATATTTGTTTATCCCCAAATGTAGGCACCTG GCTCCTCCTTGCTCCCCTGCTGATGGTGTCCTACCCCGAACTCCAAAAATTACACCTGGAGTCAGGTG CAGAAGGGAACCTTGTATTTCACAGGCCTCATTTTGATGGCAAAAAGACAGTGTAATAATAACATAAT AATAATAAAAATATAATACTGAAAA |
| 7180 | Human MFAP4 transcript variant 2 mRNA NM_002404.3 (GI: 1677501522 version 3) | GCAGACACCCAGCCACTCTGAGCAGAACTGACAGCATGAAGGCACTCCTGGCCCTGCCGCTGCTGCTG CTTCTCTCCACGCCCCCGTGTGCCCCCCAGGTCTCCGGGATCCGAGGAGATGCTCTGGAGAGGTTTTG CCTTCAGCAACCCCTGGACTGTGACGACATCTATGCCCAGGGCTACCAGTCAGACGGCGTGTACCTCA TCTACCCCTCGGGCCCCAGTGTGCCTGTGCCCGTCTTCTGTGACATGACCACCGAGGGCGGGAAGTGG ACGGTTTTCCAGAAGAGATTCAATGGCTCAGTAAGTTTCTTCCGCGGCTGGAATGACTACAAGCTGGG CTTCGGCCGTGCTGATGGAGAGTACTGGCTGGGGCTGCAGAACATGCACCTCCTGACACTGAAGCAGA AGTATGAGCTGCGAGTGGACTTGGAGGACTTTGAGAACAACACGGCCTATGCCAAGTACGCTGACTTC TCCATCTCCCCGAACGCGGTCAGCGCAGAGGAGGATGGCTACACCCTCTTTGTGGCAGGCTTTGAGGA TGGCGGGGCAGGTGACTCCCTGTCCTACCACAGTGGCCAGAAGTTCTCTACCTTCGACCGGGACCAGG ACCTCTTTGTGCAGAACTGCGCAGCTCTCTCCTCAGGAGCCTTCTGGTTCCGCAGCTGCCACTTTGCC AACCTCAATGGCTTCTACCTAGGTGGCTCCCACCTCTCTTATGCCAATGGCATCAACTGGGCCCAGTG GAAGGGCTTCTACTACTCCCTCAAACGCACTGAGATGAAAATCCGCCGGGCCTGAAGGGCTGGCCCCC TCAGGCACCTTCCTCCCCTGGACACCCATGGTCTCCATGAGTGCTCCCTCTGCTGCCCCTGATGCAT GCTTCTGCTGATTCCCGAGCACCAACTCCTTACAAGGGGGCCTTGTGGCTCTCAGCCATGCCACATCC CTGTCACACACCCAGGGCATCCATTCCTAAGCCAGACCCGGCTCCCCTACACCTGAAGTTACACTGCC AGCAGTTCCCCAGGCCTCTTCCGAGAGGCACATGGTTCTAGCCTGGACCTGGCTGGGCTCCATGAGAA TGAGTTGCCTCCAACCTGTCCCAACAGCTGACAGCCAGGAGCCACTCTCCCAGCTGCAGGCCTTTGTG GTCCATCTTGTCCTGCTTCCTCACTGTGGACCCCTGTCTGGGCCACCCTAGTGTGCTAAGCTGAGCAG TGCAGTGTGAACAGGGCCCATGGTGTATTCTAGGCCACAGCCCAGCACTCCTCTGGGCTGCTCTCAAA CCATGTCCCATCTTCAGCATCCCTCCCACCAACTTACTCCCCTGTGGTGAGTACCGTGGAACCCCAGC CCACCTCACTATCATACTCAGCTTCCCCTGATGGCCCATCCCAGCCCCTGAAGCTCTATGCCAAGAAC ACAGCTACCGCACACCACCCTGAAACAGCCACAGCCAAGGTAGGCATGCATATGAGGTCTTCCCCATA |

TABLE 14-continued

Target sequences.

| SEQ ID NO: | Description | Sequence |
|---|---|---|
| | | CCCTCTGGGTGTTGAGAGGTTTAGCCACATGAGGGAGCAGAGGACAATCTCTGCAGGGCTGGGAGTGG<br>GTAGGGACTGAAGGTCTCAATAAACCTTCAGAACCTGAATGAACTGGCTTCATACACACAAACATATT<br>TGTTTATCCCCCAAATGTAGGCACCTGGCTCCTCCTTGCTCCCCTGCTGATGGTGTCCTACCCCGAAC<br>TCCAAAAATTACACCTGGAGTCAGGTGCAGAAGGGAACCTTGTATTTCACAGGCCTCATTTTGATGGC<br>AAAAAGACAGTGTAATAATAACATAATAATAATAAAAATATAATACTGAAAA |
| 7181 | Human GRHPR<br>transcript variant<br>1 mRNA<br>NM_012203.2<br>(GI: 1519473711<br>version 2) | ACATTCCCGGGCCAGCTTCTGTACTGCCAGGTCCGGGTCGGCGGCTGCACTGCGGATGAGACCGGTGC<br>GACTCATGAAGGTGTTCGTCACCCGCAGGATACCCGCCGAGGGTAGGGTCGCGCTCGCCCGGGCGGCA<br>GACTGTGAGGTGGAGCAGTGGGACTCGGATGAGCCCATCCCTGCCAAGGAGCTAGAGCGAGGTGTGGC<br>GGGGGCCCACGGCCTGCTCTGCCTCCTCTCCGACCACGTGGACAAGAGGATCCTGGATGCTGCAGGGG<br>CCAATCTCAAAGTCATCAGCACCATGTCTGTGGGCATCGACCACTTGGCTTTGGATGAAATCAAGAAG<br>CGTGGGATCCGAGTTGGCTACACCCCAGATGTCCTGACAGATACCACCGCCGAACTCGCAGTCTCCCT<br>GCTACTTACCACCTGCCGCCGGTTGCCGGGAGCCATCGAGGAAGTGAAGAATGGTGGCTGGACCTCGT<br>GGAAGCCCCTCTGGCTGTGTGGCTATGGACTCACGCAGAGCACTGTCGGCATCATCGGGCTGGGGCGC<br>ATAGGCCAGGCCATTGCTCGGCGTCTGAAACCATTCGGTGTCCAGAGATTTCTGTACACAGGGCGCCA<br>GCCCAGGCCTGAGGAAGCAGCAGAATTCCAGGCAGAGTTTGTGTCTACCCCTGAGCTGGCTGCCCAAT<br>CTGATTTCATCGTCGTGGCCTGCTCCTTAACACCTGCAACCGAGGGACTCTGCACAAGGACTTCTTC<br>CAGAAGATGAAGGAAACAGCTGTGTTCATCAACATCAGCAGGGGCGACGTCGTAAACCAGGACGACCT<br>GTACCAGGCCTTGGCCAGTGGTAAGATTGCAGCTGCTGGACTGGATGTGACGAGCCCAGAACCACTGC<br>CTACAAACCACCCTCTCCTGACCCTGAAGAACTGTGTGATTCTGCCCCACATTGGCAGTGCCACCCAC<br>AGAACCCGCAACACCATGTCCTTGTTGGCAGCTAACAACTTGGTCTGGCTGGCCTGAGAGGGGAGCCGT<br>GCCTAGTGAACTCAAGCTGTAGCCAAACAGTAGAGATGGAGGGCCGGAAGCAAACCGTGCCCTGGTA<br>TTGTCAGACACACCCAGGCTTGATTTGGATCCACAGGCAGAGCCAAGGGAAGGTGTGATTCTCTGAGG<br>AAAGAGTGATTCTGATATATGTACTTGTCACATTGGTGTTGGACACATTTGCGCCAAAAGTATGGTAA<br>TTCTATTATTAAATAATTCTCTGAGA |
| 7182 | Human ITFG1<br>transcript variant<br>1 mRNA<br>NM_030790.5<br>(GI: 1653961895<br>version 5) | GGGGGCTGAGGGGCTGCCATGGCGGCGGCGGGCCGGCTCCCGAGCTCCTGGGCCCTCTTCTCGCCGCT<br>CCTCGCAGGGCTTGCACTACTGGGAGTCGGGCCGGTCCCAGCGCGGGCGCTGCACAACGTCACGGCCG<br>AGCTCTTTGGGGCCGAGGCCTGGGGCACCCTTGCGGCTTTCGGGGACCTCAACTCCGACAAGCAGACG<br>GATCTCTTCGTGCTGCGGGAAAGAAATGACTTAATCGTCTTTTTGGCAGACAGAATGCACCCTATTT<br>TAAACCCAAAGTAAAGGTATCTTTCAAGAATCACAGTGCATTGATAACAAGTGTAGTCCCTGGGGATT<br>ATGATGGAGATTCTCAAATGGATGTCCTTCTGACATATCTTCCCAAAAATTATGCCAAGAGTGAATTA<br>GGAGCTGTTATCTTCTGGGGACAAAATCAAACATTAGATCCTAACAATATGACCATACTCAATAGGAC<br>TTTTCAAGATGAGCCACTAATTATGGATTTCAATGGTGATCTAATTCCTGATATTTTTGGTATCACAA<br>ATGAATCCAACCAGCCACAGATACTATTAGGAGGGAATTTATCATGGCATCCAGCATTGACCACTACA<br>AGTAAAATGCGAATTCCACATTCTCATGCATTTATTGATCTGACTGAAGATTTTACAGCAGATTTATT<br>CCTGACGACATTGAATGCCACCACTAGTACCTTCCAGTTTGAAATATGGGAAAATTTGGATGGAAACT<br>TCTCTGTCAGTACTATATTGGAAAAACCTCAAAATATGATGGTGGTTGGACAGTCAGCATTTGCAGAC<br>TTTGATGGAGATGGACACATGGATCATTTACTGCCAGGCTGTGAAGATAAAAATTGCCAAAAGAGTAC<br>CATCTACTTAGTGAGATCTGGGATGAAGCAGTGGGTTCCAGTCCTACAAGATTTCAGCAATAAGGGCA<br>CACTCTGGGGCTTTGTGCCATTTGTGGATGAACAGCAACCAACTGAAATACCAATTCCAATTACCCTT<br>CATATTGGAGACTACAATATGGATGGCTACCAGACGCTCTGGTCATACTAAAGACACATCTGGAAG<br>CAACCAGCAGGCCTTTTTACTGGAGAACGTCCCTTGTAATAATGCAAGCTGTGAAGAGGCGCGTCGAA<br>TGTTTAAAGTCTACTGGGAGCTGACAGACCTAAATCAAATTAAGGATGCCATGGTTGCCACCTTCTTT<br>GACATTTACGAAGATGGAATCTTGGACATTGTAGTGCTAAGTAAAGGATATACAAAGAATGATTTTGC<br>CATTCATACACTAAAAAATAACTTTGAAGCAGATGCTTTATTTTGTTAAAGTTATTGTTCTTAGTGGTC<br>TGTGTTCTAATGACTGTCCTCGTAAGATAACACCCTTTGGAGTGAATCAACCTGGACCTTATATCATG<br>TATACAACTGTAGATGCAAATGGGTATCTGAAAAATGGATCAGCTGGCCAACTCAGCCAATCCGCACA<br>TTTAGCTCTCCAACTACCATACAACGTGCTTGGTTTAGGTCGGAGCGCAAATTTTCTTGACCATCTCT<br>ACGTTGGTATTCCCCGTCCATCTGGAGAAAAATCTATACGAAAACAAGAGTGGACTGCAATCATTCCA<br>AATTCCCAGCTAATTGTCATTCCATACCCTCACAATGTCCCTCGAAGTTGGAGTGCCAAACTGTATCT<br>TACACCAAGTAATATTGTTCTGCTTACTGCTATAGCTCTCATCGGTGTCTGTGTTTTCATCTTGGCAA<br>TAATTGGCATTTTACATTGGCAGGAAAAGAAAGCAGATGATAGAGAAAAACGACAAGAAGCCCACCGG<br>TTTCATTTTGATGCTATGTGACTTGCCTTTAATATTACATAATGGAATGGCTGTTCACTTGATTAGTT<br>GAAACACAAATTCTGGCTTGAAAAAATAGGGGAGATTAAATATTATTTATAAATGATGTATCCCATGG<br>TAATTATTGGAAAGTATTCAAATAAATATGGTTTGAATATGTCACAAGGTCTTTTTTTTAAAGCACT<br>TTGTATATAAAAATTTGGGTTCTCTATTCTGTAGTGCTGTACATTTTTGTTCCTTTGTGGAATGTGTT<br>GCATGTACTCCAGTGTTTGTGTATTTATAATCTTATTTGCATCATGATGATGGAAAAGTTGTGTAAA<br>TAAAAATAATTAAATGAGCAGGAATTTTTGTGTCCACTTGACTTGGTCTTGCTTCTTTATTCTAATGAT<br>GCAAATTATACTTTTGTGAATATATCACGGAGTCATTAGGCATTCAGCTTCATCACAGCAGGTCAGGG<br>GTCTCACTGATGGCATACAATATAGTGATCGGGTACTCTGACTTGGTAGCACAGTAAGACAGACTTGC<br>CTTAAACTCCTAATTCAACACTTACAAAGTCATTGTTTGAACTTGGCTCTTGTTTAACCTCTGTAAA<br>CCTCAGTTTTCTTGTTTATTCAGTGGGGCTAATACTTGAGTTACTGTAAACATTAAATGGGATGATGT<br>ATGTGAAGTGCTTAGCTTGGTGCCTAGCACAGAGTAAGTGGTCAATATGTGGTAGTTGTCATTATTAA<br>TATTTTAGATGATCTTATTAGACTTATACATCTAATTATAGAAATACATAGACTTGATAGAATTTTAT<br>TTTCAGGCATGAAGAAATATTCTTTGGAAAAGCTAAATTTTTGGTGATTGACATAAAGATTTACTTGC<br>TCATATTAACTAAAAATTATAGTACTCTCCAAGAATTAATGTGCCCTAAAAATTTTCCTCCAAAAACT<br>TATCCTTATCATGTGATAATGAAGAACATTTGATTTCTTGAAAGGAAACTGCTGTAGGCAGCATCTGG<br>GAATGCAAATCTTCAATCACATTTCTATTCTCAAACACTTTGGAGAAGTCTATAATTTACATTCAGACT<br>TCAATGCAAATTTTGTATTGTGAACTTCACATTTCCAAAAAGTTACTTTAAAAAGACTTTAAGACTGA<br>AAAAAAAAGTTTATCAGTCGTAATAATTTTCTAGTATGCAAATGGACATGTGAGTGCCTATAAAACAC<br>AAAAATTTCTCTGAAAACAATTTTGTTCTTATTTTTTCTTTATAGTTCACTGAGATTGGCATGTGTT<br>TTTACTTTGTATCTAAGCATGTTAACATGTCTTCTTAATAAATATTCCTTATTGAAA |
| 7183 | Human ABCC4<br>transcript variant | GCTTCACAGGCTCCAGCCGAGCGGACAGGCGTGGCGGCCGGAGCCCCAGCATCCCTGCTTGAGGTCCA<br>GGAGCGGAGCCCGCGGCCACCGCCGCCTGATCAGCGCGACCCCGGCCCGCGCCCGCCCCGGCAA |

TABLE 14-continued

Target sequences.

| SEQ ID NO: | Description | Sequence |
| --- | --- | --- |
| | 1 mRNA<br>NM_005845.5<br>(GI: 1813751621<br>version 5) | GATGCTGCCCGTGTACCAGGAGGTGAAGCCCAACCCGCTGCAGGACGCGAACCTCTGCTCACGCGTGT<br>TCTTCTGGTGGCTCAATCCCTTGTTTAAAATTGGCCATAAACGGAGATTAGAGGAAGATGATATGTAT<br>TCAGTGCTGCCAGAAGACCGCTCACAGCACCTTGGAGAGGAGTTGCAAGGGTTCTGGGATAAAGAAGT<br>TTTAAGAGCTGAGAATGACGCACAGAAGCCTTCTTTAACAAGAGCAATCATAAAGTGTTACTGGAAAT<br>CTTATTTAGTTTTGGGAATTTTTACGTTAATTGAGGAAAGTGCCAAAGTAATCCAGCCCATATTTTTG<br>GGAAAAATTATTAATTATTTTGAAAATTATGATCCCATGGATTCTGTGGCTTTGAACACAGCGTACGC<br>CTATGCCACGGTGCTGACTTTTTGCACGCTCATTTTGGCTATACTGCATCACTTATATTTTTATCACG<br>TTCAGTGTGCTGGGATGAGGTTACGAGTAGCCATGTGCCATATGATTTATCGGAAGGCACTTCGTCTT<br>AGTAACATGGCCATGGGGAAGACAACCACAGGCCAGATAGTCAATCTGCTGTCCAATGATGTGAACAA<br>GTTTGATCAGGTGACAGTGTTCTTACACTTCCTGTGGGCAGGACCACTGCAGGCGATTGCAGTGACTG<br>CCCTACTCTGGATGGAGATAGGAATATCGTGCCTTGCTGGGATGGCAGTTCTAATCATTCTCCTGCCC<br>TTGCAAAGCTGTTTTGGGAAGTTGTTCTCATCACTGAGGAGTAAAACTGCAACTTTCACGGATGCCAG<br>GATCAGGACCCATGAATGAAGTTATAACTGGTATAAGGATAATAAAAATGTACGCCTGGGAAAAGTCAT<br>TTTCAAATCTTATTACCAATTTGAGAAAGAAGGAGATTTCCAAGATTCTGAGAAGTTCCTGCCTCAGA<br>GGGATGAATTTGGCTTCATTTTTCAGTCAAGCAAAATCATCGTGTTTGTGACCTTCACCACCTACGT<br>GCTCCTCGGCAGTGTGATCACAGCCAGCCGCGTGTTCGTGGCAGTGACGCTGTATGGGGCTGTGCGGC<br>TGACGGTTACCCTCTTCTTCCCCTCAGCCATTGAGAGGGTGTCAGAGGCAATCGTCAGCATCCGAAGA<br>ATCCAGACCTTTTTGCTACTTGATGAGATATCACAGCGCAACCGTCAGCTGCCGTCAGATGGTAAAAA<br>GATGGTGCATGTGCAGGATTTTACTGCTTTTTGGGATAAGGCATCAGAGACCCCAACTCTACAAGGCC<br>TTTCCTTTACTGTCAGACCTGGCGAATTGTTAGCTGTGGTCGGCCCCGTGGGAGCAGGGAAGTCATCA<br>CTGTTAAGTGCCGTGCTCGGGGAATTGGCCCCAAGTCACGGGCTGGTCAGCGTGCATGGAAGAATTGC<br>CTATGTGTCTCAGCAGCCCTGGGTGTTCTCGGGAACTCTGAGGAGTAATATTTTATTTGGGAAGAAAT<br>ACGAAAAGGAACGATATGAAAAAGTCATAAAGGCTTGTGCTCTGAAAAAGGATTTACAGCTGTTGGAG<br>GATGGTGATCTGACTGTGATAGGAGATCGGGGAACCACGCTGAGTGGAGGGCAGAAAGCACGGGTAAA<br>CCTTGCAAGAGCAGTGTATCAAGATGCTGACATCTATCTCCTGGACGATCCTCTCAGTGCAGTAGATG<br>CGGAAGTTAGCAGACACTTGTTCGAACTGTGTATTTGTCAAATTTTGCATGAGAAGATCACAATTTTA<br>GTGACTCATCAGTTGCAGTACCTCAAAGCTGCAAGTCAGATTCTGATATTGAAAGATGGTAAAATGGT<br>GCAGAAGGGGACTTACACTGAGTTCCTAAAATCTGGTATAGATTTTGGCTCCCTTTTAAAGAAGGATA<br>ATGAGGAAAGTGAACAACCTCCAGTTCCAGGAACTCCCACACTAAGGAATCGTACCTTCTCAGAGTCT<br>TCGGTTTGGTCTCAACAATCTTCTAGACCCTCCTTGAAAGATGGTGCTCTGGAGAGCCAAGATACAGA<br>GAATGTCCCAGTTACACTATCAGAGGAGAACCGTTCTGAAGGAAAAGTTGGTTTTCAGGCCTATAAGA<br>ATTACTTCAGAGCTGGTGCTCACTGGATTGTCTTCATTTTCCTTATTCTCCTAAACACTGCAGCTCAG<br>GTTGCCTATGTGCTTCAAGATTGGTGGCTTTCATACTGGGCAAACAAACAAAGTATGCTAAATGTCAC<br>TGTAAATGGAGGAGGAAATGTAACCGAGAAGCTAGATCTTAACTGGTACTTAGGAATTTATTCAGGTT<br>TAACTGTAGCTACCGTTCTTTTTGGCATAGCAAGATCTCTATTGGTATTCTACGTCCTTGTTAACTCT<br>TCACAAACTTTGCACAACAAAATGTTTGAGTCAATTCTGAAAGCTCCGGTATTATTCTTTGATAGAAA<br>TCCAATAGGAAGAATTTTAAATCGTTTCTCCAAAGACATTGGACACTTGGATGATTTGCTGCCGCTGA<br>CGTTTTTAGATTTCATCCAGCATTGCTACAAGTGGTTGGTGTGGTCTCTGTGGCTGTGGCCGTGATT<br>CCTTGGATCGCAATACCCTTGGTTCCCCTTGGAATCATTTTCATTTTTCTTCGGCGATATTTTTGGA<br>AACGTCAAGAGATGTGAAGCGCCTGGAATCTACAACTCGGAGTCCAGTGTTTTCCCACTTATCATCTT<br>CTCTCCAGGGGCTCTGGACCATCCGGGCATACAAAGCAGAAGAGAGGTGTCAGGAACTGTTTGATGCA<br>CACCAGGATTTACATTCAGAGGCTTGGTTCTTGTTTTTGACAACGTCCCGCTGGTTTGCCGTCCGTCT<br>GGATGCCATCTGTGCCATGTTTGTCATCATCGTTGCCTTTGGGTCCCTGATTCTGGCAAAAACTCTGG<br>ATGCCGGGCAGGTTGGTTTGGCACTGTCCTATGCCCTCACGCTCATGGGGATGTTTCAGTGGTGTGTT<br>CGACAAAGTGCTGAAGTTGAGAATATGATGATCTCAGTAGAAAGGGTCATTGAATACACAGACCTTGA<br>AAAAGAAGCACCTTGGGAATATCAGAAACGCCCACCACCAGCCTGGCCCCATGAAGGAGTGATAATCT<br>TTGACAATGTGAACTTCATGTACAGTCCAGGTGGGCCTCTGGTACTGAAGCATCTGACAGCACTCATT<br>AAATCACAAGAAAGGTTGGCATTGTGGGAAGAACCGGAGCTGGAAAAAGTTCCCTCATCTCAGCCCTT<br>TTTTAGATTGTCAGAACCCGAAGGTAAAATTTGGATTGATAAGATCTTGACAACTGAAATTGGACTTC<br>ACGATTTAAGGAAGAAGATGTCAATCATACCTCAGGAACCTGTTTTGTTCACTGGAACAATGAGGAAA<br>AACCTGGATCCCTTTAATGAGCACACACGGATGAGGAACTGTGGAATGCCTTACAAGAGGTACAACTTAA<br>AGAAACCATTGAAGATCTTCCTGGTAAAATGGATACTGAATTAGCAGAATCAGGATCCAATTTTAGTG<br>TTGGACAAAGACAACTGGTGTGCCTTGCCAGGGCAATTCTCAGGAAAAATCAGATATTGATTATTGAT<br>GAAGCGACGGCAAATGTGGATCCAAGAACTGATGAGTTAATACAAAAAAAAAATCCGGGAGAAATTTGC<br>CCACTGCACCGTGCTAACCATTGCACACAGATTGAACACCATTATTGACAGCGACAAGATAATGGTTT<br>TAGATTCAGGAAGACTGAAGAATATGATGAGCCGTATGTTTGCTGCAAAATAAAGAGAGCCTATTT<br>TACAAGATGGTGCAACAACTGGGCAAGGCAGAAGCCGCTGCCCTCACTGAAACAGCAAAACAGGTATA<br>CTTCAAAAGAAATTATCCACATATTGGTCACACTGACCACATGTTACAAACACTTCCAATGGACAGC<br>CCTCGACCTTAACTATTTTCGAGACAGCACTGTGAATCCAACCAAAAATGTCAAGTCCGTTCCGAAGGC<br>ATTTTCCACTAGTTTTTGGACTATGTAAACCACATTGTACTTTTTTTTACTTTGGCAACAAATATTTA<br>TACATACAAGATGCTAGTTCATTTGAATATTTCTCCCAACTTATCCAAGGATCTCCAGCTCTAACAAA<br>ATGGTTTATTTTTATTTAAATGTCAATAGTTGTTTTTAAAATCCAAATCAGAGGTGCAGGCCACCAG<br>TTAAATGCCGTCTATCAGGTTTTGTGCCTTAAGAGACTACAGAGTCAAAGCTCATTTTAAAGGAGTA<br>GGACAAAGTTGTCACAGGTTTTTGTTGTTGTTTTATTGCCCCCAAAATTACATGTTAATTTCCATTT<br>ATATCAGGGATTCTATTTACTTGAAGACTGTGAAGTTGCCATTTTGTCTCATTGTTTTCTTTGACATA<br>ACTAGGATCCATTATTTCCCCTGAAGGCTTCTTGTTAGAAAATAGTACAGTTACAACCAATAGG<br>AACAACAAAAAGAAAAGTTTGTGACATTGTAGTAGGGAGTGTGTACCCCTTACTCCTCCCATCAAAAA<br>AAAAATGGATACATGGTTAAAGGATAGAAGGGCAATATTTTATCATATGTTCTAAAAGAAGGAAGA<br>GAAAATACTACTTTCTCAAAATGGAAGCCCTTAAAGGTGCTTTGATACTGAAGGACACAAATGTGACC<br>GTCCATCCTCCTTTAGAGTTGCATGACTTGGACACGGTAACTGTTCAGTTTTAGACTCAGCATTGTG<br>ACACTTCCCAAGAAGGCCAAACCTCTAACCGACATTCCTGAAATACGTGGCATTATTCTTTTTTGGAT<br>TTCTCATTTATGGAAGGCTAACCCTCTGTTGACTGTAAGCCTTTTGGTTTGGGCTGTATTGAAATCCT<br>TTCTAAATTGCATGAATAGGCTCTGCTAACGTGATGAGACAAACTGAAAATTATTGCAAGCATTGACT<br>ATAATTATGCAGTACGTTCTCAGGATGCATCCAGGGGTTCATTTTCATGAGCCTGTCCAGGTTAGTTT<br>ACTCCTGACCACTAATAGCATTGTCATTTGGGCTTTCTGTTGAATGAATCAACAAACCACAATACTTC<br>CTGGGACCTTTTGTACTTTATTTGAACTATGAGTCTTTAATTTTTCCTGATGATGGTGGCTGTAATAT |

TABLE 14-continued

Target sequences.

| SEQ ID NO: | Description | Sequence |
|---|---|---|
| | | GTTGAGTTCAGTTTACTAAAGGTTTTACTATTATGGTTTGAAGTGGAGTCTCATGACCTCTCAGAATA<br>AGGTGTCACCTCCCTGAAATTGCATATATGTATATAGACATGCACACGTGTGCATTTGTTTGTATACA<br>TATATTTGTCCTTCGTATAGCAAGTTTTTTGCTCATCAGCAGAGAGCAACAGATGTTTTATTGAGTGA<br>AGCCTTAAAAAGCACACACCACACACAGCTAACTGCCAAAATACATTGACCGTAGTAGCTGTTCAACT<br>CCTAGTACTTAGAAATACACGTATGGTTAATGTTCAGTCCAACAAACCACACACAGTAAATGTTTATT<br>AATAGTCATGGTTCGTATTTTAGGTGACTGAAATTGCATCAGTGATCATAATGAGGTTTGTTAAAACG<br>ATAGCTATATTCAAAATGTCTATATGTTTATTTGGACTTTTGAGGTTAAAGACAGTCATATAAACGTC<br>CTGTTTCTGTTTTAATGTTATCATAGAATTTTTTAATGAAACTAAATTCAATTGAAATAAATGATAGT<br>TTTCATCTCCA |
| 7184 | Human ABCC4<br>transcript variant<br>2 mRNA<br>NM_001105515.3<br>(GI: 1677498821<br>version 3) | GCTTCACAGGCTCCAGCCGAGCGGACAGGCGTGGCGGCCGGAGCCCCAGCATCCCTGCTTGAGGTCCA<br>GGAGCGGAGCCCGCGGCCACCGCCGCCTGATCAGCGCGACCCCGGCCCGCGCCCGCCCCGCCCGGCAA<br>GATGCTGCCCGTGTACCAGGAGGTGAAGCCCAACCCGCTGCAGGACGCGAACCTCTGCTCACGCGTGT<br>TCTTCTGGTGGCTCAATCCCTTGTTTAAAATTGGCCATAAACGGAGATTAGAGGAAGATGATATGTAT<br>TCAGTGCTGCCAGAAGACCGCTCACAGCACCTTGGAGAGGAGTTGCAAGGGTTCTGGGATAAAGAAGT<br>TTTAAGAGCTGAGAATGACGCACAGAAGCCTTCTTTAACAAGAGCAATCATAAAGTGTTACTGGAAAT<br>CTTATTTAGTTTTGGGAATTTTTACGTTAATTGAGGAAAGTGCCAAAGTAATCCAGCCCATATTTTTG<br>GGAAAAATTATTAATTATTTTGAAAATTATGATCCCATGGATTCTGTGGCTTTGAACACAGCGTACGC<br>CTATGCCACGGTGCTGACTTTTTGCACGCTCATTTTGGCTATACTGCATCACTTATATTTTTATCACG<br>TTCAGTGTGCTGGGATGAGGTTACGAGTAGCCATGTGCCATATGATTTATCGGAAGGCACTTCGTCTT<br>AGTAACATGGCCATGGGGAAGACAACCACAGGCCAGATAGTCAATCTGCTGTCCAATGATGTGAACAA<br>GTTTGATCAGGTGACAGTGTTCTTACACTTCCTGTGGGCAGGACCACTGCAGGCGATTGCAGTGACTG<br>CCCTACTCTGGATGGAGATAGGAATATCGTGCCTTGCTGGGATGGCAGTTCTAATCATTCTCCTGCCC<br>TTGCAAAGCTGTTTTGGGAAGTTGTTCTCATCACTGAGGAGTAAAACTGCAACTTTCACGGATGCCAG<br>GATCAGGACCATGAATGAAGTTATAACTGGTATAAGGATAATAAAAATGTACGCCTGGGAAAAGTCAT<br>TTTCAAATCTTATTACCAATTTGAGAAAGAAGGAGATTTCCAAGATTCTGAGAAGTTCCTGCCTCAGA<br>GGGATGAATTTGGCTTCATTTTTCAGTGCAAGCAAAATCATCGTGTTTGTGACCTTCACCACCTACGT<br>GCTCCTCGGCAGTGTGATCACAGCCAGCCGCGTGTTCGTGGCAGTGACGCTGTATGGGGCTGTGCGGC<br>TGACGGTTACCCTCTTCTTCCCCTCAGCCATTGAGAGGGTGTCAGAGGCAATCGTCAGCATCCGAAGA<br>ATCCAGACCTTTTTGCTACTTGATGAGATATCACAGCGCAACCGTCAGCTGCCGTCAGATGGTAAAAA<br>GATGGTGCATGTGCAGGATTTTACTGCTTTTTGGGATAAGGCATCAGAGACCCCAACTCTACAAGGCC<br>TTTCCTTTACTGTCAGACCTGGCGAATTGTTAGCTGTGGTCGGCCCCGTGGGAGCAGGGAAGTCATCA<br>CTGTTAAGTGCCGTGCTCGGGGAATTGGCCCCAAGTCACGGGCTGGTCAGCGTGCATGGAAGAATTGC<br>CTATGTGTCTCAGCAGCCCTGGGTGTTCTCGGGAACTCTGAGGAGTAATATTTTATTTGGGAAGAAAT<br>ACGAAAAGGAACGATATGAAAAAGTCATAAAGGCTTGTGCTCTGAAAAAGGATTTACAGCTGTTGGAG<br>GATGGTGATCTGACTGTGATAGGAGATCGGGGAACCACGCTGAGTGGAGGGCAGAAAGCACGGGTAAA<br>CCTTGCAAGAGCAGTGTATCAAGATGCTGACATCTATCTCCTGGACGATCCTCTCAGTGCAGTAGATG<br>CGGAGTTAGCAGACACTTGTTCGAACTGTGTATTTGTCAAATTTTGCATGAGAAGATCACAATTTTA<br>GTGACTCATCAGTTGCAGTACCTCAAAGCTGCAAGTCAGATTCTGATATTGAAAGATGGTAAAATGGT<br>GCAGAAGGGGACTTACACTGAGTTCCTAAAATCTGGTATAGATTTTGGCTCCCTTTTAAAGAAGGATA<br>ATGAGGAAAGTGAACAACCTCCAGTTCCAGGAACTCCCACACTAAGGAATCGTACCTTCTCAGAGTCT<br>TCGGTTTGGTCTCAACAATCTTCTAGAACTTCCTTGAAAGATGGTGCTCTGGAGAGCCAAGATACAGA<br>GAATGTCCCAGTTACACTATCAGAGGAGAACCGTTCTGAAGGAAAAGTTGGTTTTCAGGCCTATAAGA<br>ATTACTTCAGAGCTGGTGCTCACTGGATTGTCTTCATTTTCCTTATTCTCCTAAACACTGCAGCTC<br>AGGTTGCCTATGTGCTTCAAGATTGGTGGCTTTCATACTGGGCAAACAAACAAAGTATGCTAAATGTC<br>ACTGTAAATGGAGGAGGAAATGTAACCGAGAAGCTAGATCTTAACTGGTACTTAGGAATTTATTCAGG<br>TTTAACTGTAGCTACCGTTCTTTTTGGCATAGCAAGATCTCTATTGGTATTCTACGTCCTTGTTAACT<br>CTTCACAAACTTTGCACAACAAAATGTTTGAGTCAATTCTGAAAGCTCCGGTATTATTCTTTGATAGA<br>AATCCAATAGGAAGAATTTTAAATCGTTTCTCCAAAGACATTGGACACTTGGATGATTTGCTGCCGCT<br>GACGTTTTTAGATTTCATCCAGAGATGGATCTCGCTGTGTTGTCCTGGCTGGTCTCAACCTCCTAGG<br>CTCAAGCAATCCTCCTCCCTCCTCAAGCAAACCTCAGTGCTGGGATTATAGGCATGAGCCACTGTACC<br>TGGCTAAATGTTGTTTTTTTGATATTCAATTTTTGTTTATAGAATTTTCATTTGTTTTGCTCTTATAC<br>TTTTCATCTTTTTATGTTTATTGACCAATTAAATATCATTTGGGTAAGCACCTATTTAAGTGTCTTAA<br>CAATTTTTCTATTGAGTACTCTGGGTTTTTGTTTTGTTTTTCTTACTGATTTGTAGAATTCTTTATGT<br>ATTCTGAATTGCAGATACCTTCCTTCTGTACTAATGCTTATCTTTTTAGCCCTGTAATATTGTGTTTT<br>CATAAACATACTTATCAATCTTT |
| 7185 | Human ABCC4<br>transcript variant<br>3 mRNA<br>NM_001301829.2<br>(GI: 1677530022<br>version 2) | GCTTCACAGGCTCCAGCCGAGCGGACAGGCGTGGCGGCCGGAGCCCCAGCATCCCTGCTTGAGGTCCA<br>GGAGCGGAGCCCGCGGCCACCGCCGCCTGATCAGCGCGACCCCGGCCCGCGCCCGCCCCGCCCGGCAA<br>GATGCTGCCCGTGTACCAGGAGGTGAAGCCCAACCCGCTGCAGGACGCGAACCTCTGCTCACGCGTGT<br>TCTTCTGGTGGCTCAATCCCTTGTTTAAAATTGGCCATAAACGGAGATTAGAGGAAGATGATATGTAT<br>TCAGTGCTGCCAGAAGACCGCTCACAGCACCTTGGAGAGGAGTTGCAAGGGTTCTGGGATAAAGAAGT<br>TTTAAGAGCTGAGAATGACGCACAGAAGCCTTCTTTAACAAGAGCAATCATAAAGTGTTACTGGAAAT<br>CTTATTTAGTTTTGGGAATTTTTACGTTAATTGAGGAAAGTGCCAAAGTAATCCAGCCCATATTTTTG<br>GGAAAAATTATTAATTATTTTGAAAATTATGATCCCATGGATTCTGTGGCTTTGAACACAGCGTACGC<br>CTATGCCACGGTGCTGACTTTTTGCACGCTCATTTTGGCTATACTGCATCACTTATATTTTTATCACG<br>TTCAGTGTGCTGGGATGAGGTTACGAGTAGCCATGTGCCATATGATTTATCGGAAGGCACTTCGTCTT<br>AGTAACATGGCCATGGGGAAGACAACCACAGGCCAGATAGTCAATCTGCTGTCCAATGATGTGAACAA<br>GTTTGATCAGGTGACAGTGTTCTTACACTTCCTGTGGGCAGGACCACTGCAGGCGATTGCAGTGACTG<br>CCCTACTCTGGATGGAGATAGGAATATCGTGCCTTGCTGGGATGGCAGTTCTAATCATTCTCCTGCCC<br>TTGCAAAGCTGTTTTGGGAAGTTGTTCTCATCACTGAGGAGTAAAACTGCAACTTTCACGGATGCCAG<br>GATCAGGACCATGAATGAAGTTATAACTGGTATAAGGATAATAAAAATGTACGCCTGGGAAAAGTCAT<br>TTTCAAATCTTATTACCAATTTGAGAAAGAAGGAGATTTCCAAGATTCTGAGAAGTTCCTGCCTCAGA<br>GGGATGAATTTGGCTTCATTTTTCAGTGCAAGCAAAATCATCGTGTTTGTGACCTTCACCACCTACGT<br>GCTCCTCGGCAGTGTGATCACAGCCAGCCGCGTGTTCGTGGCAGTGACGCTGTATGGGGCTGTGCGGC<br>TGACGGTTACCCTCTTCTTCCCCTCAGCCATTGAGAGGGTGTCAGAGGCAATCGTCAGCATCCGAAGA |

TABLE 14-continued

Target sequences.

| SEQ ID NO: | Description | Sequence |
|---|---|---|
| | | ATCCAGACCTTTTTGCTACTTGATGAGATATCACAGCGCAACCGTCAGCTGCCGTCAGATGGTAAAAA<br>GATGGTGCATGTGCAGGATTTTACTGCTTTTTGGGATAAGGCATCAGAGACCCCAACTCTACAAGGCC<br>TTTCCTTTACTGTCAGACCTGGCGAATTGTTAGCTGTGGTCGGCCCCGTGGGAGCAGGGAAGTCATCA<br>CTGTTAAGTGCCGTGCTCGGGGAATTGGCCCCAAGTCACGGGCTGGTCAGCGTGCATGGGAAGAATTGC<br>CTATGTGTCTCAGCAGCCCTGGGTGTTCTCGGGAACTCTGAGGAGTAATATTTTATTTGGGAAGAAAT<br>ACGAAAAGGAACGATATGAAAAAGTCATAAAGGCTTGTGCTCTGAAAAAGGATTTACAGCTGTTGGAG<br>GATGGTGATCGACTGTGATAGGAGATCGGGGAACCACGCTGAGTGGAGGGCAGAAAGCACGGGTAAA<br>CCTTGCAAGAGCAGTGTATCAAGATGCTGACATCTATCTCCTGGACGATCCTCTCAGTGCAGTAGATG<br>CGGAAGTTAGCAGACACTTGTTCGAACTGTGTATTTGTCAAATTTTGCATGAGAAGATCACAATTTTA<br>GTGACTCATCAGTTGCAGTACCTCAAAGCTGCAAGTCAGATTCTGATATTGAAAGATGGTAAAATGGT<br>GCAGAAGGGGACTTACACTGAGTTCCTAAAATCTGGTATAGATTTTGGCTCCCTTTTAAAGAAGGATA<br>ATGAGGAAAGTGAACAACCTCCAGTTCCAGGAACTCCCACACTAAGGAATCGTACCTTCTCAGAGTCT<br>TCGGTTTGGTCTCAACAATCTTCTAGACCCTCCTTGAAAGATGGTGCTCTGGAGAGCCAAGATGTTGC<br>CTATGTGCTTCAAGATTGGTGGCTTTCATACTGGGCAAACAAACAAAGTATGCTAAATGTCACTGTAA<br>ATGGAGGAGGAAATGTAACCGAGAAGCTAGATCTTAACTGGTACTTAGGAATTTATTCAGGTTTAACT<br>GTAGCTACCGTTCTTTTTGGCATAGCAAGATCTCTATTGGTATTCTACGTCCTTGTTAACTCTTCACA<br>AACTTTGCACAACAAAATGTTTGAGTCAATTCTGAAAGCTCCGGTATTATTCTTTGATAGAAATCCAA<br>TAGGAAGAATTTTAAATCGTTTCTCCAAAGACATTGGACACTTGGATGATTTGCTGCCGCTGACGTTT<br>TTAGATTTCATCCAGACATTGCTACAAGTGGTTGGTGTGGTCTCTGTGGCTGTGGCCGTGATTCCTTG<br>GATCGCAATACCCTTGGTTCCCCTTGGAATCATTTTCATTTTTCTTCGGCGATATTTTTGGAAACGT<br>CAAGAGATGTGAAGCGCTCGGAATCTACAACTCGGAGTCCAGTGTTTTCCCACTTATCATCTTCTCTC<br>CAGGGGCTCTGGACCATCCGGGCATACAAAGCAGAAGAGAGGTGTCAGGAACTGTTTGATGCACACCA<br>GGATTTACATTCAGAGGCTTGGTTCTTGTTTTTGACAACGTCCCGCTGGTTTGCCGTCCGTCTGGATG<br>CCATCTGTGCCATGTTTGTCATCATCGTTGCCTTTGGGTCCCTGATTCTGGCAAAAACTCTGGATGCC<br>GGGCAGGTTGGTTTGGCACTGTCCTATGCCCTCACGCTCATGGGGATGTTTCAGTGGTGTGTTCGACA<br>AAGTGCTGAAGTTGAGAATATGATGATCTCAGTAGAAAGGGTCATTGAATACACAGACCTTGAAAAAG<br>AAGCACCTTGGGAATATCAGAAACGCCCACCACCAGCCTGGCCCCATGAAGGAGTGATAATCTTTGAC<br>AATGTGAACTTCATGTACAGTCCAGGTGGGCCTCTGGTACTGAAGCATCTGACAGCACTCATTAAATC<br>ACAAGAAAAGGTTGGCATTGTGGGAAGAACCGGAGCTGGAAAAAGTTCCCTCATCTCAGCCCTTTTTA<br>GATTGTCAGAACCCGAAGGTAAAATTTGGATTGATAAGATCTTGACAACTGAAATTGGACTTCACGAT<br>TTAAGGAAGAAGATGTCAATCATACCTCAGGAACCTGTTTTGTTCACTGGAACAATGAGGAAAAACCT<br>GGATCCCTTTAATGAGCACACGGATGAGGAACTGTGGAATGCCTTACAAGAGGTACAACTTAAAGAAA<br>CCATTGAAGATCTTCCTGGTAAAATGGATACTGAATTAGCAGAATCAGGATCCAATTTTAGTGTTGGA<br>CAAAGACAACTGGTGTGCCTTGCCAGGGCAATTCTCAGGAAAAATCAGATATTGATTATTGATGAAGC<br>GACGGCAAATGTGGATCCAAGAACTGATGAGTTAATACAAAAAAAAAATCCGGGAGAAATTTGCCCACT<br>GCACCGTGCTAACCATTGCACACAGATTGAACACCATTATTGACAGCGACAAGATAATGGTTTTAGAT<br>TCAGGAAGACTGAAAGAATATGATGAGCCGTATGTTTTGCTGCAAAATAAAGAGAGCCTATTTTACAA<br>GATGGTGCAACAACTGGGCAAGGCAGAAGCCGCTGCCCTCACTGAAACAGCAAAACAGGTATACTTCA<br>AAAGAAATTATCCACATATTGGTCACACTGACCACATGGTTACAAACACTTCCAATGGACAGCCCTCG<br>ACCTTAACTATTTTCGAGACAGCACTGTGAATCAACCAAAATGTCAAGTCCGTTCCGAAGGCATTTT<br>CCACTAGTTTTTGGACTATGTAAACCACATTGTACTTTTTTTACTTTGGCAACAAATATTTATACAT<br>ACAAGATGCTAGTTCATTTGAATATTTCTCCCAACTTATCCAAGGATCTCCAGCTCTAACAAAATGGT<br>TTATTTTTATTTAAATGTCAATAGTTGTTTTTTAAAATCCAAATCAGAGGTGCAGGCCACCAGTTAAA<br>TGCCGTCTATCAGGTTTTGTGCCTTAAGAGACTACAGAGTCAAAGCTCATTTTTAAGGAGTAGGACA<br>AAGTTGTCACAGGTTTTTGTTGTTGTTTTATTGCCCCCAAAATTACATGTTAATTTCCATTTATATC<br>AGGGATTCTATTTACTTGAAGACTGTGAAGTTGCCATTTTGTCTCATTGTTTTCTTTGACATAACTAG<br>GATCCATTATTTCCCCTGAAAGGCTTCTTGTTAGAAAATAGTACAGTTACAACCAATAGGAACAACAAA<br>AAGAAAAGTTTGTGACATTGTAGTAGGGAGTGTGTACCCCTTACTCCCCATCAAAAAAAAAAATGGA<br>TACATGGTTAAAGGATAGAAGGGCAATATTTTATCATATGTTCTAAAAGAGAAGGAAGAGAAAATACT<br>ACTTTCTCAAAATGGAAGCCCTTAAAGGTGCTTTGATACTGAAGGACACAAATGTGACCGTCCATCCT<br>CCTTTAGAGTTGCATGACTTGGACACGGTAACTGTTGCAGTTTTAGACTCAGCATTGTGACACTTCCC<br>AAGAAGGCCAAACCTCTAACCGACATTCCTGAAATACGTGGCATTATTCTTTTTTGGATTTCTCATTT<br>ATGGAAGGCTAACCCTCTGTTGACTGTAAGCCTTTTGGTTTGGGCTGTATTGAAATCCTTTCTAAATT<br>GCATGAATAGGCTCTGCTAACGTGATGAGACAAACTGAAAATTATTGCAAGCATTGACTATAATTATG<br>CAGTACGTTCTCAGGATGCATCCAGGGGTTCATTTTCATGAGCCTGTCCAGGTTAGTTTACTCCTGAC<br>CACTAATAGCATTGTCATTTGGGCTTTCTGTTGAATGAATCAACAAACCACAATACTTCCTGGGACCT<br>TTTGTACTTTATTTGAACTATGAGTCTTTAATTTTTCCTGATGATGGTGGCTGTAATATGTTGAGTTC<br>AGTTTACTAAAGGTTTTACTATTATGGTTTGAAGTGGAGTCTCATGACCTCTCAGAATAAGGTGTCAC<br>CTCCCTGAAATTGCATATATGTATATAGACATGCACACGTGTGCATTTGTTTGTATACATATATTTGT<br>CCTTCGTATAGCAAGTTTTTTGCTCATCAGCAGAGAGCAACAGATGTTTATTGAGTGAAGCCTTAAA<br>AAGCACACACCACACACAGCTAACTGCCAAAATACATTGACCGTAGTAGCTGTTCAACTCCTAGTACT<br>TAGAAATACACGTATGGTTAATGTTCAGTCCAACAAACCACACACAGTAAATGTTTATTAATAGTCAT<br>GGTTCGTATTTTAGGTGACTGAAATTGCATCAGTGATCATAATGGGTTTGTTAAAACGATAGCTATA<br>TTCAAAATGTCTATATGTTATTTGGACTTTTGAGGTTAAAGACAGTCATATAAACGTCCTGTTTCTG<br>TTTTAATGTTATCATAGAATTTTTAATGAAACTAAATTCAATTGAAATAAATGATAGTTTTCATCTC<br>CA |
| 7186 | Human ABCC4<br>transcript variant<br>4 mRNA<br>NM_001301830.2<br>(GI: 1677498275<br>version 2) | GCTTCACAGGCTCCAGCCGAGCGGACAGGCGTGGCGGCCGGAGCCCCAGCATCCCTGCTTGAGGTCCA<br>GGAGCGGAGCCCGCGGCCACCGCCGCCTGATCAGCGCGACCCCGGCCCGCGCCCGCCCGGCAA<br>GATGCTGCCCGTGTACCAGGAGGTGAAGCCCAACCCGCTGCAGGACGCGAACCTCTGCTCACGCGTGT<br>TCTTCTGGTGGCTCAATCCCTTCTTGTTTAAAATTGGCCATAAACGGAGATTAGAGGAAGATGATATT<br>TCAGTGCTGCCAGAAGACCGCTCACAGCACCTTGGAGAGGAGTTGCAAGGGTTCTGGGATAAAGAAGT<br>TTTAAGAGCTGAGAATGACCACAGAAGCCTTCTTTAACAAGAGCAATCATAAAGTGTTACTGGAAAT<br>CTTATTTAGTTTTGGGAATTTTTACGTTAATTGAGGCACTTCGTCTTAGTAACATGGCCATGGGGAAG<br>ACAACCACAGGCCAGATAGTCAATCTGCTGTCCAATGATGTGAACAAGTTTGATCAGGTGACAGTGTT<br>CTTACACTTCCTGTGGGCAGGACCACTGCAGGCGATTGCAGTGACTGCCCTACTCTGGATGGAGATAG |

TABLE 14-continued

Target sequences.

| SEQ ID NO: | Description | Sequence |
|---|---|---|
| | | GAATATCGTGCCTTGCTGGGATGGCAGTTCTAATCATTCTCCTGCCCTTGCAAAGCTGTTTTGGGAAG<br>TTGTTCTCATCACTGAGGAGTAAAACTGCAACTTTCACGGATGCCAGGATCAGGACCATGAATGAAGT<br>TATAACTGGTATAAGGATAATAAAAATGTACGCCTGGGAAAAGTCATTTTCAAATCTTATTACCAATT<br>TGAGAAGAAGGAGATTTCCAAGATTCTGAGAAGTTCCTGCCTCAGAGGGATGAATTTGGCTTCATTT<br>TTCAGTGCAAGCAAAATCATCGTGTTTGTGACCTTCACCACCTACGTGCTCCTCGGCAGTGTGATCAC<br>AGCCAGCCGCGTGTTCGTGGCAGTGACGCTGTATGGGGCGTGTCGGCTGACGGTTACCCTCTTCTTCC<br>CCTCAGCCATTGAGAGGGTGTCAGAGGCAATCGTCAGCATCCGAAGAATCCAGACCTTTTTGCTACTT<br>GATGAGATATCACAGCGCAACCGTCAGCTGCCGTCAGATGGTAAAAAGATGGTGCATGTGCAGGATTT<br>TACTGCTTTTTGGGATAAGGCATCAGAGACCCCAACTCTACAAGGCCTTTCCTTTACTGTCAGACCTG<br>GCGAATTGTTAGCTGTGGTCGGCCCCGTGGGAGCAGGGAAGTCATCACTGTTAAGTGCCGTGCTCGGG<br>GAATTGGCCCCAAGTCACGGGCTGGTCAGCGTGCATGGAAGAATTGCCTATGTGTCTCAGCAGCCCTG<br>GGTGTTCTCGGGAACTCTGAGGAGTAATATTTTATTTGGGAAGAAATACGAAAAGGAACGATATGAAA<br>AAGTCATAAAGGCTTGTGCTCTGAAAAAGGATTTACAGCTGTTGGAGGATGGTGATCTGACTGTGATA<br>GGAGATCGGGGAACCACGCTGAGTGGAGGGCAGAAAGCACGGGTAAACCTTGCAAGAGCAGTGTATCA<br>AGATGCTGACATCTATCTCCTGGACGATCCTCTCAGTCAGTAGATGCGGAAGTTAGCAGACACTTGT<br>TCGAACTGTGTATTTGTCAAATTTTGCATGAGAAGATCACAATTTTAGTGACTCATCAGTTGCAGTAC<br>CTCAAAGCTGCAAGTCAGATTCTGATATTGAAAGATGGTAAAATGGTGCAGAAGGGGACTTACACTGA<br>GTTCCTAAAATCTGGTATAGATTTTGGCTCCCTTTTAAAGAAGGATAATGAGGAAAGTGAACAACCTC<br>CAGTTCCAGGAACTCCCACACTAAGGAATCGTACCTTCTCAGAGTCTTCGGTTTGGTCTCAACAATCT<br>TCTAGACCCTCCTTGAAAGATGGTGCTCTGGAGAGCCAAGATACAGAGAATGTCCCAGTTACACTATC<br>AGAGGGAGAACCGTTCTGAAGGAAAAGTTGGTTTTCAGGCCTATAAGAATTACTTTGGGTCTGGTGCTC<br>ACTGGATTGTCTTCATTTTCCTTATTCTCCTAAACACTGCAGCTCAGGTTGCCTATGTGCTTCAAGAT<br>TGGTGGCTTTCATACTGGGCAAACAAACAAAGTATGCTAAATGTCACTGTAAATGGAGGAGGAAATGT<br>AACCGAGAAGCTAGATCTTAACTGGTACTTAGGAATTTATTCAGGTTTAACTGTAGCTACCGTTCTTT<br>TTGGCATAGCAAGATCTCTATTGGTATTCTACGTCCTTGTTAACTCTTCACAAACTTTGCACAACAAA<br>ATGTTTGAGTCAATTCTGAAAGCTCCGGTATTATTCTTTGATAGAAATCCAATAGGAAGAATTTTAAA<br>TCGTTTCTCCAAAGACATTGGACACTTGGATGATTTGCTGCCGCTGACGTTTTTAGATTTCATCCAGA<br>GATGGGATCTCGCTGTGTTGTCCTGGCTGGTCTCAAACTCCTAGGCTCAAGCAATCCTCCTCCCTCCT<br>CAAGCAAACCTCAGTGCTGGGATTATAGGCATGAGCCACTGTACCTGGCTAAATGTTGTTTTTTGAT<br>ATTCAATTTTTGTTTATAGAATTTTCATTTGTTTTGCTCTTATACTTTTCATCTTTTTATGTTTATTG<br>ACCAATTAAATATCATTTGGGTAAGCACCTATTTAAGTGTCTTAACAATTTTTCTATTGAGTACTCTG<br>GGTTTTTGTTTTGTTTTTCTTACTGATTTGTAGAATTCTTTATGTATTCTGAATTGCAGATACCTTCC<br>TTCTGTACTAATGCTTATCTTTTAGCCCTGTAATATTGTGTTTTCATAAACATACTTATCAATCTTT |
| 7187 | Human PAK3<br>transcript variant<br>1 mRNA<br>NM_001128166.3<br>(GI: 1889680926<br>version 3) | AGAGCATCCTCAGCAGCTGCCACCGAAGCAGCCTCCTCCTTCTCTCTTCCTCCTCCTCCTACCACGGC<br>CGCCGCCACCACCGCTGCGGCTGTGATCTCCTATCCCCTCTGGTCCTCCTTCCTCCCCCAGTTCCTGC<br>TCCTCCTCCCATCCCCTGCTCCTCCTGCCCAGCAGCGAAGGGCAGAACCCTCGGCTGCCGCCCTCCTT<br>CGCTCTGACCAAGAAGCAGCTGGAACAGAATAACATACAGAGGACAGCTTTCTTCTTCTGAGGAGTCAG<br>AAGTTCAGTTCGCCCAACATGGAATGACTTGAGGAGCTGTGAAATTAGTTGTAACTGAAAATGTCTGA<br>CGGTCTGGATAATGAAGAGAAACCCCCGGCTCCTCCACTGAGGATGAATAGTAACAACCGGGATTCTT<br>CAGCACTCAACCACAGCTCCAAACCACTTCCCATGGCCCCTGAAGAGAAGAATAAGAAAGCCAGGCTT<br>CGCTCTATCTTCCCAGGAGGAGGGGATAAAACAATAAGAAGGAGAAGGAGAAAGAGCGCCCAGAGATCTC<br>TCTTCCTTCAGACTTTGAGCATACGATTCATGTGGGGTTTGATGCAGTCACCGGGGAATTCACTGGAA<br>TTCCAGAGCAATGGGCACGATTACTCCAAACTTCCAACATAACAAAATTGGAACAGAAGAAGAACCCA<br>CAAGCTGTTCTAGATGTTCTCAAATTCTATGATTCCAAAGAAACAGTCAACAACCAGAAATACATGAG<br>CTTTACATCAGGAGATAAAAGTGCACATGGATACATAGCAGCCCATCCTTCGAGTACAAAAACAGCAT<br>CTGAGCCTCCATTGGCCCCTCCTGTGTCTGAAGAAGAAGATGAAGAGGAAGAAGAAGAAGAAGATGAA<br>AATGAGCCACCACCAGTTATCGCACCAAGACCAGAGCATACAAAATCAATCTATACTCGTTCTGTGGT<br>TGAATCCATTGCTTCACCAGCAGTACCAAATAAAGAGGTCACACCACCCTCTGCTGAAAATGCCAATT<br>CCAGTACTTTGTACAGGAACACAGATCGGCAAAGAAAAAATCCAAGATGACAGATGAGGAGATCTTA<br>GAGAAGCTAAGAAGCATTGTGAGTGTTGGGGACCCAAAGAAAAAATACACAAGATTTGAAAAAATTGG<br>TCAAGGGGCATCAGGTACTGTTTATACAGCACTAGACATTGCAACAGGACAAGAGGTGGCCATAAAGC<br>AGATGAACTTCAACAGCAACCCAAGAAGGAATTAATTATTAATGAAATTCTGGTCATGAGGGAAAAT<br>AAGAACCCTAATATTGTTAATTATTTAGATAGCTACCTTGGTGGGTGATGAACTATGGGTAGTCATGGA<br>ATACTTGGCTGGTGGCTCTCTGACTGATGTGGTCACAGAGACCTGTATGGATGAAGGACAGATAGCAG<br>CTGTCTGCAGAGAGTGCCTGCAAGCTTTGGATTTCCTGCACTCAAACCAGGTGATCCATAGAGATATA<br>AAGAGTGACAATATTCTTCTCGGGATGGATGGCTCTGTTAAATTGACTGACTTTGGGTTCTGTGCCCA<br>GATCACTCCTGAGCAAAGTAAACGAAGCACTATGGTGGGAACCCCATATTGGATGGCACCTGAGGTGG<br>TGACTCGAAAAGCTTATGGTCCGAAAGTTGATATCTGGTCTCTTGGAATTATGGCAATTGAAATGGTG<br>GAAGGTGAACCCCCTTACCTTAATGAAAATCCACTCAGGGCATTGTATCTGATAGCCACTAATGGAAC<br>TCCAGAGCTCCAGAATCCTGAGAGACTGTCAGCTGTATTCCGTGACTTTTTAAATCGCTGTCTTGAGA<br>TGGATGTGGATAGGCGAGGATCTGCCAAGGAGCTTTTGCAGCATCCATTTTTAAAATTAGCCAAGCCT<br>CTCTCCAGCCTGACTCCTCTGATTATCGCTGCAAAGGAAGCAATTAAGAACAGCAGCCGCTAAGCCTG<br>CAAGCCTTACACCTCACCATCTCCCTCATGAGTAAGACTGAAATAAAACTCTGCTGCAGGAAAGATGG<br>AAGAAAAGACAGTCAAATGGGTGGGGTTCTTTACCTTTCAAATGAATAGAAACTTCTTATAAGCCT<br>TTTTCCTACTCCCTCAGATTATGTAATTTATTTGTAAGCCTGAATCGCAGCCCAAACAGGGCAGCAAT<br>GTTGAGTGACCATAAAGTGGTCACTTCCACCGTGAAGCGAAAGAGCCAGTAGTGAATCCCCTCATTT<br>TGTGCATTCACTTTGAAGAAAAAGGTTTCTCAAAGATGCACACTCCCTCTTCATAGTGTTGTGTTTGT<br>TTTTAAGTTAGAGAGTAGTCCCTCTTGCATTCAAACCTCCTTCAAAACTCCTTACCCAATGTGATGTT<br>TTTCACTTGCATTGTCATTAGATGTCCAGAAAAAAAAAGATGTCAAAATGTTTTTCTAAAAAAGAA<br>AGCAAAAAAGCAAGGCAAAAAAAACAAACAAACAAACAAACAAAACAAACAAGCAA<br>ACAAAAATACCAGAGCAAGTACTGTGTGAACATGTGGAAGTCCATGCCCTAATAGAGTTGCAATTTT<br>TTATTCTTCTTCTATAGTGGTGGCTTGGTTTGTGTACCTATTTTCTGCATTTGTATTGGAAAGGTT<br>TCTTTTAAGACATTTTCCAAAGTGGAGAGGAATATGTGTGTTCAGGAAGGGCTTTCAAAAAACTGTA<br>TATCTAAATAAAGCTCAAACGGTGAAATCCTGTCACATTTTCACAATGATGCTTAAAAGATAATTGAG<br>TAAACCAGGTTGTTAATCTCCTTAATACCTGAAAGAGGACACACTGAAACTGAAACTGTGACATCCTG |

TABLE 14-continued

Target sequences.

| SEQ ID NO: | Description | Sequence |
|---|---|---|
| | | CTAGGTGAGTTCAGGTTCTGAACCTAGGAAATCCTCATAGGAGAAACCACATTTAAACAAAGATGGGA
CTTTCTCTGAGAGCCAAAACCAGATAAATGTAGAATACTGAAATCCTTGTTGGACATTAAGTAAACAA
AGATAATGATACCTAAATTAATCCTCTCTTGTGCTTATGAAACATATGCACTGTAAAATAGGCATACC
AGGAGGAAATAGATACATTAATCATCATTTACTTATGATACAAATTATTTATTTTGACAATTTATAAC
GTTTAAAAAAGTTTTTTAAAGATCTAGAGAAAGGTGATATAGTAAACATTCAACTCTGTAAGAAATGG
GAGGTCAGTGAAGGCTACATCCCAATCAATATTTGGCTCTAAGTACCTCTTCCCATTTTTCCTATGTA
TCACCTATTTCTGTTTCGGAATATGGTGTGTTCATGCTTAGTTCTTTGGGCTTTTGAATATCAAAAGC
ATATTCATAAATGTCTTGAAATTCTCTCCAGTGGAAAATAATTTTAACTTACAATCATATCCCAAGAA
ATGTCAGTCCGACAGAATTCCTTATATGACTTGGGGAAAATAACAAAATTTGACTACTATTTCACCAT
ATATCTATTTATTAAAAAATTCAACAGTTGGCACTTCCTGAATCTTCTGAGAGTAGAAAAATATCTGC
GGAGTGTCTGTGTAGAAAAGGATATGCCTCTCTTTTGAGTGTATTGACAATTTTGTAAATTACAGAAA
GTTGTTTCTCTAAGCCTTTGAAAAACTAACAATTTGTGTTATAGAAGGCTTCTTAATTTGCAGTATAA
AAGAATCTAAACAGAACTTATGTACATTCAGCCAGAAGGGGAAAAGAGATCAGTTACATAGGCCTCTCT
CCTTCTTTGCCAAGGTACATCCATCCATCTAACCATCCATATATCCACATCTTAAAATGAAAGCACTT
TCTTTAGAGTTTCAGCAAACTATATAGTGTACGTGTTTATGTTCAGGAGATGACCCCACTGGTGTATT
TCCTATTTTCCCTATTGTTTTCTTTGACTGTAAAAGTTGGGAGAGGCTTGACCTCCTCCCCTTGAAAA
TGTCCACAGTGGGATAAAACAACAAATGTGAAAAGAAAATGAAACGGTAATATTAATTTGAAGCATAC
TATGTTATACTTTGCAAAAACGAATCTGGGCCTGTAATTTTTAATGCCACACTGCTCTAATGAGAGAG
AGAGGCCTTAATTTTGATTTCATTTAAAAATAAGTACTTTAAAAAATTTTTCACTCATAGTGCCGGGA
AATTCAATGAAATCCTGGGATGCAAATAAAAATCAGTACATTAGTGACTGTGTCCTGCCAGTGGAGAG
AGCCCAATACCTGGTTAGGAAGCCCTATTCATTAGTTAGCATCCCTTACATGTTGAGGAAGGCCTTTT
TTTGTTGTTATTTTGGAGACCTTGGAGCAGTGACCCTTCAGATCACTGTAGGCAGAGAAATGGCTTCT
CTCTTATGCTTTCAGTTCAGCATATTAACAATGAGGAGCCAGGTACTTCTTTACTACCACTTTGTACC
AAGATTTGATAATAATATATCCCAGGAGGCATTACTTTTATAAATTTGTATTCATGTAAATTTTCAAA
TGAGAACAGCTTCTAAAGCCCCTTCCCTGTATTGGAGAGTTATGTATATTTCTAATAAGTATTAGAAA
GAAGCTGTTTCTCATGCCACAGTGATGCTGAAGGATTCACATTTGGTACAATCGAGTAACTTGAACGC
CAGATTGTTAACAGTTTATTCTCTTTCCCTGGATTTTTAAGCTCATCTTGACACAGGTGAGTCTATCC
AAATCTTTGATGTTGCTAGTGTGCCCTGAGATAACGAGGGCACATCTTTCAATGTTGATTCCAAATG
TCCTGAGTTAGGAATAGGGCAGTGGGAAAGTCAGGGAAGGGTGAGAAGCACAGTAGAGATTATTTATT
TAAAAAAGGAAAGAACGTTAATGTTGTTAGCAAGGATCCAGTGCGTTGTCATAATCCCATGAGGATTT
TCAGATGACACAATCCCCTCAAATCAGTCACCATGTTGGGTAATGACTTCGTTCTTGCTGATCTCGTG
TGTGTGTCATTGTAAATATTTGTGTGTCCATGTTCCATTTTGGCTACTGGATGGCCAAGCCATGTAAG
AAGATTTAACTCAAGTATTTATTCTTTATGTTATTCAGATTTCTTTCAGGCTTGTGAACTGCACCCCA
ATGTTTGAGTTTAACCACCTGATCCTTACATCTATCCCTCCCCGGTGAAGCACATTCCATTGCTAAAA
GAAAAGAAACACGAAATTGCTTCCTGTTGTCTGTATAACTGTTTTGATAGTTTGAGATATTTGTCTA
TAAATGATATTTCTCAGCTCAAAGATCGTGTAAATAATTATATTCCTTTGCTCAATGGGTTTATTTCT
AATGAGGCTGCCAGTTCTGAGAGATTCTATAATATCACTTTTAAATAACATAAACAGGGATTACAACT
ATGTAAAAAGAAATGCATATGGACAAAGACTGGGAACACAGATAATTGAAATCAGTTGTGTTAGGGTG
GTGGAATTATGTGAATTTTTTTTCTTTTTAAAATTTTATTTGATATTGTTATAATATTGCTTTACAA
TAAATAAACAGCAGAAAGGGAACTATAGACACATAGAAAAGATGCCAGAAGCAGATGCCTTCTGGCCA
GAGCGCAGAGCATGCAGGGCAGAGATATTTGCTAGTTACAATTATTCCATAGGCTTTATGCTTGCCTG
GGTGCTGAGGTTGGCACACGCTCGGGTATGGCACACGCTTTCTTAGGAGACTATTATCTATAAGTTAA
AGCTAGGGAGATGTCACTATTAGAACTCCAAACACACTCTTCTGCTTTAAAACAGGTTGTCTGCCCTC
TGCTTTGGTATGGCATTCGGGTGTCTGTTTTGTGGTTGCTTTAGATTGGAGGGGTGACCATTTTATTA
GCCCCCTTGATAACATCTGTTGCAGATATTGCCTTTCTGGAACGTTTTAACAGACTCTCAGGTTGAAT
TTTGGAGGACTAGAAGGATAAAATCCCCAGCTCCCACCATTTTCTTGTCCAACAGGATATTACTGTAT
ATCATTCAGGTAGGATTCTTCTTTTAATAACCAATAGGGCAAGTCCCACTAATTTCAATAGAAGTTAT
GACTTGCAATTAAAAGCTGACTTTGAAATCATTAAACAAATATGTAGGACTGTCTCTGCCTGTTGGCA
TTCAGTTATAGTTCTGTTAATTTTGGCTTGGGATGGTCTCCATGTGCTTTTTTCTGCCTATTTATAGG
TTGTTTGCAGTAGTTGTGATTTTTAAAGAGCAAGGGAGACCATCTAACCAAAGGATAACTTCCTTCTA
ACTCACCAAAGAAATTTTAGGTGAGAACTTTAATAATGAGGTAGTCACCTCAGATATGCTGCTTAGTT
TCACTAAAAGCAGACCCTATACCTAGAGAAGTCACTGGCTTTTTATTGGTCATTCTCAATACAGAAAT
ACTTAGGGGAGTCTTAACCCTGCCATCCCCGGTTGAATCTCTTGGTCTTTATCTAAGCTACTTGCAGT
TAATATTCAGTTAAGCAAAGGTATGGCCAGTAGTGCAAGTATCTCCCAGTCTCTGAGCTCTGAACAAG
AGGACTGAAATTCAGCATTTGTAAACTGACAGTTTGATGGGCTCTGGGATTTGAAGTGAACTCAGCACA
CAATTCTGAACGTGTATTTGCATGTGGACTGGGAAGGAAATAAATGGGAACTTGGAAATAATGGAATA
TTTCTCCTATGAAAGAATTTTTCGTAGAAGATTTGTTTTTGATATAATCTTTCTGTTGGTTAGCTTTT
AGTGTTTTCATTCCTTTTCTGATCCACACTCCTTTAAGTGACCAAATGAATATAACCCAACATGCATT
GGGAATGTGTTTAATATTAAACAATGTCTAACTGAATCTGCAAATGCGGGAACTGAGATATCACCTCC
ATGTGCACACCTGTGTGTACGAGTATTCTATACAACTTGTAGCATTTACTGCCACTTAATTG
GGTTGAACTTGCAAGATAAACTTTTGGAAACTGCTTAGTGCCATCGGAGTCTCCTTTAGAAGCTGCCA
TCAGGCAAATGCTATCCCATAATACCAGCAGTAAGCCTGGCAACATGTTCAACAGATTTAGTACCCAA
GAGGAAATCAACAGCGATAGTAGAGAATGAGTCAGATGTAGTGGGATAAATACTAGCCTAGGAAGAAG
GAGCCCCGGAGTCTAATATGAGCTTTATTACTAAATTGCTATGTGACGCTAGGCAAGTCACTTAACCT
CTCCATGGCTGTTTCCTCATCTGTAAAATAAGTGTATTGGACTAGATGATCCTTAGGGTCTTTCCAAA
AGTCTAACATTCTATGGCATTATAGGTTGCCTTGCAAATTCAGCCTGCTATAGTGATGGCAAATATCA
CGTTTAAGCCTGAGTCTCTTATGTTGCAGTTAAATAAAAGAACTATTGTAAGATGATTTTTAAAATTCA
AGCAAATGGGCCGGGTGCGGTGGCTCATACCTGTAATCCCAGCACTTTGGGAGGCCAAGGCAGGCGGA
TCACCTGAGGTCAGGAGTTCGAGACCAGCCTGACCAACATAGAGAAACCCCATCTCTACTAAAAATAC
AAAATTAGCCGGGTGTGGTGGCGGGCGCCTGTAATCCCAGCTACTTGGGAGGCTGAGGTGGGAGAATC
GCTTGAACCCAGGAGGCGGAGGTTGTGGTGAGCTGAGATCATGCCATTGCAGTCCAGCCTCGGCACA
AGAGTGAAACTTCGTCTCCAAAAAAAAAAACTCAAGCAAATGAAGTTCATAATAATAGGGGATGTTGA
TAAAACTTGTGGCAGCCTTCCAATTCATTTACAGTTGTTTCGTTTTGTTTTGTTTTAATGTCCATTT
TCTGTTGACTGTTCCCAGTTTTCATTTTCCATACAGTCTGTATGTAAAGTCTGGTTTTCATTAAGCTG
TGGCCAGTATTTGCCACTACAACAGAAACACACTGTCACACTTGCTAGAATATAACTGTACTTGAGCT
TCTCCTTTCCTGTGAAGTAGTGCTGGGCTTTCTAGAGTTTAATTCTCAAGTGGCACAAGATAGCAGAG |

TABLE 14-continued

Target sequences.

| SEQ ID NO: | Description | Sequence |
|---|---|---|
| | | CCCATGCATTTTAATGGCTGAGACTGCTAAGAGTGAACCTAAACACTTACAAGTTGCAGAGAGAAATG
AAAAAGTAATTACATGCTATTAGCATTGAGAAATGTTGACAAATTAATTTGTTGGGAACCAAAGATAG
CATTTCTGATGACAACTCCCACAGTGATTGGCCAGTTGTATGATGAGTACACTGCTGGAAAGAGGGTA
AACTGGGAGTTAGTGGATGGTCCCAATGCCCTGCCTACAGCAGAGTGCCAACCAGCCCTGAGTGCAAA
ATTCAAGTTCAATGTGTGTGCTTGTGTGTGGTGTGCTTTATGGACCCGCAAATACCATATTCATTATT
GATGATAAGATCTTCACAGAATCCTGTAGCTACTAATGCATTGAGTTTTTAATCTCAGTACATCAGCC
AGGAGGAGCCAGATCACAGGGTAGTGATGTCTACTGGGATTATACTCATAACATCTACACAAAACAAG
TTGAGAAGGATCCACGTTTTCATTGTTTATCAGAATTGTATCTCATTTGGCTGAGCATTACTTTTGTC
AGAATGTGTTATCTGTAAACCATGTGTAGTGAAATTCTTCTGTAACTTTGGATTAAAGGTATTTATGG
TCTTTTTGTTTGTTTGATTTTTAAGTAAGTTATTTCTTTTGTAGACCTGCTGATGGTATGGTTCCATC
CTTCTGACCTCAGCATCCAATCTTTTTAAGGATTTTTGTTTTCAATATTGTTATTTTAAATTGTGGTT
GAAGCAATAGAAAATTGAAATATGGATTGTGCATGACTGTGTCTTGAGTGTAAAAATATTGCAGTTTG
AAACTTGGACCTAAAGTATTGCAAATAAAAATGACAAACATCAATGA |
| 7188 | Human PAK3
transcript variant
2 mRNA
NM_002578.5
(GI: 1519316149
version 5) | ACCGCGGGCGGGCAGCTGTGCCAGCTAACCGTCTGGGATCTCGCACTGGGGGCTGCAGCTTTTCCCCG
CCTCGAGCCAGTGTGCGGGGGCGGGAGAAGAGCCAGGGGGAGCGGGCTGGGCCCGGGGCTGCGGCTGC
GGCCGCGGGGCTGCGGCTCCCCAGCCCCGCCAGCTGGAGCGCTCGGAGGTAGAGGAAAGGTCTTGACG
GGGTGGCTGGATCCGTGGCAGAATCCAGTTCCAGATTCTAGACTTGAGGGTTCTGGGCTGTTGGTCTG
TAGAAGCGAAGGAGAGAAGGACTCAAATCCAGGCCAAGTGTATGGCTGTCTGAGGTATTGGAACAGAA
GGAGGTCCATTCCTGTTGGTGACAACACCGTGGCCCTGTTCTGGGATGAGCAAGGTGTAAAGGTTTCC
CCCAAGAAAGAGCAGCTGAGTCCTTGCATCTTGTGGCAGCTGGTGTGCCCAGCACTGAGTCTGTAGGA
GCTGAAGCCAGCCCGGACCCTTCTCATGGGCAGTGCCCACCTGTGCTGAAGTCCTGCAGCGGTGGCGG
TGTGAGGAGCTGTGAATTAGTTGTAACTGAAAATGTCTGACGGTCTGGATAATGAAGAGAAACCCCC
GGCTCCTCCACTGAGGATGAATAGTAACAACCGGGATTCTTCAGCACTCAACCACAGCTCCAAACCAC
TTCCCATGGCCCCTGAAGAGAAGAATAAGAAAGCCAGGCTTCGCTCTATCTTCCCAGGAGGAGGGGAT
AAAACCAATAAGAAGAAGGAGAAAGAGCGCCCAGAGATCTCTCTTCCTTCAGACTTTGAGCATACGAT
TCATGTGGGGTTTGATGCAGTCACCGGGGAATTCACTGGAATTCCAGAGCAATGGGCACGATTACTCC
AAACTTCCAACATAACAAAATTGGAACAGAAGAAGAACCCACAAGCTGTTCTAGATGTTCTCAAATTC
TATGATTCCAAAGAAACAGTCAACAACCAGAAATACATGAGCTTTCATCAGGAGATAAAAGTGCACA
TGGATACATAGCAGCCCATCCTTCGAGTACAAAAACAGCATCTGAGCCTCCATTGGCCCCTCCTGTGT
CTGAAGAAGAAGATGAAGAGGAAGAAGAAGAAGATGAAAATGAGCCACCACCAGTTATCGCACCA
AGACCAGAGCATACAAAATCAATCTATACTCGTTCTGTGGTTAATCCATTGCTTCACCAGCAGTACC
AAATAAAGAGGTCACACCACCCTCTGCTGAAAATGCCAATTCCAGTACTTTGTACAGGAACACAGATC
GGCAAGAAAAAAATCCAAGATGACAGATGAGGAGATCTTAGAGAAGCTAAGAAGCATTGTGAGTGTT
GGGGACCCAAAGAAAAAATACACAAGATTTGAAAAAATTGGTCAAGGGGCATCAGGTACTGTTTATAC
AGCACTAGACATTGCAACAGGACAAGAGGTGGCCATAAAGCAGATGAACCTTCAACAGCAACCCAAGA
AGGAATTAATTATTAATGAAATTCTGGTCATGAGGGAAAATAAGAACCCTAATATTGTTAATTATTTA
GATAGCTACTTGGTGGGTGATGAACTATGGGTAGTCATGGAATACTTGGCTGGTGGCTCTCTGACTGA
TGTGGTCACAGAGACCTGTATGGATGAAGGACAGATAGCAGCTGTCTGCAGAGAGTGCCTGCAAGCTT
TGGATTTCCTGCACTCAAACCAGGTGATCCATAGAGATATAAAGAGTGACAATATTCTTCTCGGGATG
GATGGCTCTGTTAAATTGACTGACTTTGGGTTCTGTGCCCAGATCACTCCTGAGCAAAGTAAACGAAG
CACTATGGTGGGAACCCCATATTGGATGCCAGAGGTGGTGACTCGAAAAGCTTATGGTCCGAAAG
TTGATATCTGGTCTCTTGGAATTATGGCAATTGAAATGGTGGAAGGTGAACCCCCTTACCTTAATGAA
AATCCACTCAGGGCATTGTATCTGATAGCCACTAATGGAACTCCAGAGCTCCAGAATCCTGAGAGACT
GTCAGCTGTATTCCGTGACTTTTTAAATCGCTGTCTTGAGATGGATGTGGATAGGCGAGGATCTGCCA
AGGAGCTTTTGCAGCATCCATTTTTAAAATTAGCCAAGCCTCTCTCCAGCCTGACTCCTCTGATTATC
GCTGCAAAGGAAGCAATTAAGAACAGCAGCCGCTAAGACTGCAAGCCTTACACCTCACCATCTCCCTC
ATGAGTAAGACTGAAATAAAACTCTGCTGCAGGAAAGATGGAAGAAAGACAGTCAAATGGGGTGG
GGGTTCTTTACCTTTCAAATGAATAGAAACTTCTTATAAGCCTTTTTCCTACTCCCTCAGATTATGTA
ATTTATTTGTAAGCCTGAATCGCAGCCCAAACAGGGCAGCAATGTTGAAGTGACCATAAAGTGGTCAC
TTCCACCGTGAAGCGAAAGAGCCAGTAGTGAATCCCCTCATTTTGTGCATTCACTTTGAAGAAAAAGG
TTTCTCAAAGATGCACACTCCCTCTTCATAGTGTTGTGTTTGTTTTTAAGTTAGAGAGTAGTCCCTCT
TGCATTCAAACCTCCTTCAAAACTCCTTACCCAATGTGATGTTTTTCACTTGCATTGTCATTAGATGT
CCAGAAAAAAAAAGATGTCAAATGTTTTTCTAAAAAAAAGAAAGCAAAAAAGCAAGGCAAAAAAAA
AAAAAAAAACAAACAAAAACAAAACAAAACAAACAAGCAAACAAAAATACCAGAGCAAGTACTG
TGTGAACATGTGGAAGTCCATGCCCTAATAGAGTTGCAATTTTTATTCTTCTTCTATAGTGGTGGCT
TGGTTTGTGTACCTATTTTTCTGCATTTGTATTGGAAAAGGTTTCTTTTAAGCATTTTCCAAAAGTG
GAGAGGAAATATGTGTTCAGGAAGGGCTTTCAAAAAACTGTATATCTAAATAAAGCTCAAACGGTA
AATCCTGTCACATTTTCACAATGATGCTTAAAAGATAATTGAGTAAACCAGGTTGTTAATCTCCTTAA
TACCTGAAAGAGGACACACTGAAACTGAAACTGTGACATCCTGCTAGGTGAGTTCAGGTTCTGAACCT
AGGAAATCCTCATAGGAGAAACCACATTTAAACAAAGATGGGACTTTCTCTGAGAGCCAAAACCAGAT
AAATGTAGAATACTGAAATCCTTGTTGGACATTAAGTAAACAAAGATAATGATACCTAAATTAATCCT
CTCTTGTGCTTATGAAACATATGCACTGTAAAATAGGCATACCAGGAGGAAATAGATACATTAATCAT
CATTTACTTATGATACAAATTATTTATTTTGACAATTTATAACGTTTAAAAAAGTTTTTTAAAGATCT
AGAGAAAGGTGATATAGTAAACATTCAACTCTGTAAGAAATGGGAGGTCAGTGAAGGCTACATCCCAA
TCAATATTTGGCTCTAAGTACCTCTTCCCATTTTTCCTATGTATCACCTATTTCTGTTTCGGAATATG
GTGTGTTCATGCTTAGTTCTTTGGGCTTTTGAATATCAAAAGCATATTCATAAATGTCTTGAAATTCT
CTCCAGTGGAAATAATTTTAACTTACAATCATATCCCAAGAAATGTCAGTCCGACAGAATTCCTTAT
ATGACTTGGGGAAAATAACAAATTTGACTACTATTTCACCCATATATCTATTTATTAAAAAATTCAAC
AGTTGGCACTTCCTGAATCTTCTGAGAGTAGAAAAATATCTGCGGAGTGTCTGTGTAGAAAAGGATAT
GCCTCTCTTTGAGTGTATTGACAATTTGTAAATTACAGAAAGTTGTTTCTCTAAGCCTTTGAAAAA
CTAACAATTTGTGTTATAGAAGGCTTCTTAATTTGCAGTATAAAAGAATCTAAACAGAACTTATGTAC
ATTCAGCCAGAAGGGAAAGAGATCAGTTACATAGGCCTCTCTCCTTCTTTGCCAAGGTACATCCATC
CATCTAACCATCCATATATCCACATCTTAAAATGAAAGCACTTTCTTTAGAGTTTCAGCAAACTATAT
AGTGTACGTGTTTATGTTCAGGAGATGACCCCACTGGTGTATTTCCTATTTTCCCTATTGTTTTCTTT
GACTGTAAAAGTTGGGAGAGGCTTGACCTCCTCCCCCTTGAAAATGTCCACAGTGGGATAAAACAACAA |

TABLE 14-continued

Target sequences.

| SEQ ID NO: | Description | Sequence |
|---|---|---|
| | | ATGTGAAAAGAAAATGAAACGGTAATATTAATTTGAAGCATACTATGTTATACTTTGCAAAAACGAAT<br>CTGGGCCTGTAATTTTTAATGCCACACTGCTCTAATGAGAGAGAGAGGCCTTAATTTTGATTTCATTT<br>AAAAATAAGTACTTTAAAAAATTTTTCACTCATAGTGCCGGGAAATTCAATGAAATCCTGGGATGCAA<br>ATAAAAATCAGTACATTAGTGACTGTGTCCTGCCAGTGGAGAGAGCCCAATACCTGGTTAGGAAGCCC<br>TATTCATTAGTTAGCATCCCTTACATGTTGAGAAGGCCTTTTTTTTGTTGTTATTTTGGAGACCTTGG<br>AGCAGTGACCCTTCAGATCACTGTAGGCAGAGAAATGGCTTCTCTCTTATGCTTTCAGTTCAGCATAT<br>TAACAATGAGGAGCCAGGTACTTCTTTACTACCACTTTGTACCAAGATTTGATAATAATATATCCCAG<br>GAGGCATTACTTTTATAAATTTGTATTCATGTAAATTTTCAAATGAGAACAGCTTCTAAAGCCCCTTC<br>CCTGTATTGGAGAGTTATGTATATTTCTAATAAGTATTAGAAAGAAGCTGTTTCTCATGCCACAGTGA<br>TGCTGAAGGATTCACATTTGGTACAATCGAGTAACTTGAACGCCAGATTGTTAACAGTTTATTCTCTT<br>TCCCTGGATTTTTAAGCTCATCTTGACACAGGTGAGTCTATCCAAATCTTTGATGTTGCTAGTGTGCC<br>CTGAGATAACGAGGGCACATCTTTCAATGTTGATTCCAAAATGTCCTGAGTTAGGAATAGGGCAGTGG<br>GAAAGTCAGGGAAGGGTGAGAAGCACAGTAGAGATTATTTATTTAAAAAAGGAAAGAACGTTAATGTT<br>GTTAGCAAGGATCCAGTGCGTTGTCATAATCCCATGAGGATTTTCAGATGACACAATCCCCTCAAATC<br>AGTCACCATGTTGGGTAATGACTTCGTTCTTGCTGATCTCGTGTGTGTGTCATTGTAAATATTTGTGT<br>GTCCATGTTCCATTTTGGCTACTGGATGGCCAAGCCATGTAAGAAGATTTAACTCAAGTATTTATTCT<br>TTATGTTATTCAGATTTCTTTCAGGCTTGTGAACTGCACCCCAATGTTTGAGTTTAACCACCTGATCC<br>TTACATCTATCCCTCCCCGGTGAAGCACATTCCATTGCTAAAAGAAAAAGAAACACGAAATTGCTTCC<br>TGTTGTCTGTATAACTGTTTTGATAGTTTGAGATATTTGTCTATAAATGATATTTCTCAGCTCAAAGA<br>TCGTGTAAATAATTATATTCCTTTGCTCAATGGGTTTATTTCTAATGAGGCTGCCAGTTCTGAGAGAT<br>TCTATAATATCACTTTTAAATAACATAAACAGGGATTACAACTATGTAAAAAGAAATGCATATGGACA<br>AAGACTGGGAACACAGATAATTGAAATCAGTTGTGTTAGGGTGGTGGAATTATGTGAATTTTTTTTTC<br>TTTTTAAAATTTTATTTGATATTGTTATAATATTGCTTTACAATAAATAAACAGCAGAAAGGGAACTA<br>TAGACACATAGAAAAGATGCCAGAAGCAGATGCCTTCTGGCCAGAGCGCAGAGCATGCAGGGCAGAGA<br>TATTTGCTAGTTACAATTATTCCATAGGCTTTATGCTTGCCTGGGTGCTGAGGTTGGCACACGCTCGG<br>GTATGGCACACGCTTTCTTAGGGAGACTATTATCTATAAGTTAAAGCTAGGGAGATGTCACTATTAGAA<br>CTCCAAACACACTCTTCTGCTTTAAAACAGGTTGTCTGCCCTCTGCTTTGGTATGGCATTCGGGTGTC<br>TGTTTTGTGGTTGCTTTAGATTGGAGGGGTGACCATTTTATTAGCCCCCTTGATAACATCTGTTGCAG<br>ATATTGCCTTTCTGGAACGTTTTAACAGACTCTCAGGTTGAATTTTGGAGGACTAGAAGGATAAAATC<br>CCCAGCTCCCACCATTTTCTTGTCCAACAGGATATTACTGTATATCATTCAGGTAGGATTCTTCTTTT<br>AATAACCAATAGGGCAAGTCCCACTAATTTCAATAGAAGTTATGACTTGCAATTAAAAGCTGACTTTG<br>AAATCATTAAACAAATATGTAGGACTGTCTCTGCCTGTTGGCATTCAGTTATAGTTCTGTTAATTTTG<br>GCTTGGGATGGTCTCCATGTGCTTTTTTCTGCCTATTTATAGGTTGTTTGCAGTAGTTGTGATTTTTA<br>AAGAGCAAGGGAGACCATCTAACCAAAGGATAACTTCCTTCTAACTCACCAAAGAAATTTTAGGTGAG<br>AACTTTAATAATGAGGTAGTCACCTCAGATATGCTGCTTAGTTTCACTAAAAGCAGACCCTATACCTA<br>GAGAAGTCACTGGCTTTTTATTGGTCATTCTCAATACAGAAATACTTAGGGGAGTCTTAACCCTGCCA<br>TCCCCGGTTGAATCTCTTGGTCTTTATCTAAGCTACTTGCAGTTAATATTCAGTTAAGCAAAGGTATG<br>GCCAGTAGTGCAAGTATCTCCCAGTCTCTGAGCTCTGAACAAGAGGACTGAAATTCAGCATTTGTAAA<br>CTGACAGTTTGATGGGCCTGGGATTTGAAGTGAACTCAGCACACAATTCTGAACGTGTATTTGCATGT<br>GGACTGGGAAGGAAATAAATGGGAACTTGGAAATAATGGAATATTTCTCCTATGAAGAATTTTTCGT<br>AGAAGATTTGTTTTTGATATAATCTTTCTGTTGGTTAGCTTTTAGTGTTTTCATTCCTTTTCTGATCC<br>ACACTCCTTTAAGTGACCAAATGAATATAACCCAACATGCATTGGGAATGTGTTTAATATTAAACAAT<br>GTCTAACTGAATCTGCAAATGCGGGAACTGAGATATCACCTCCATGTGCACACCTGTGTGTACGAGTA<br>TTCTATACAACTTGTAGCATTTACTGCCACTTAATTGGGTTGAACTTGCAAGATAAACTTTTGGAAAC<br>TGCTTAGTGCCATCGGAGTCTCCTTTAGAAGCTGCCATCAGGCAAATGCTATCCCATAATACCAGCAG<br>TAAGCCTGGCAACATGTTCAACAGATTTAGTACCCAAGAGGAAATCAACAGCGATAGTAGAGAATGAG<br>TCAGATGTAGTGGGATAAATACTAGCGTAGGAAGAAGGAGCCCCGGAGTCTAATATGAGCTTTATTAC<br>TAAATTGCTATGTGACGCTAGGCAAGTCACTTAACCTCTCCATGGCTGTTTCCTCATCTGTAAAATAA<br>GTGTATTGGACTAGATGATCCTTAGGGTCTTTCCAAAAGTCTAACATTCTATGGCATTATAGGTTGCC<br>TTGCAAATTCAGCCTGCTATAGTGATGGCAAATATCACGTTTAAGCCTGAGTCTCTTATGTTGCAGTT<br>AAATAAAAGAACTATGTAAGATGATTTTTAAAATTCAAGCAAATGGGCCGGGTGCGGTGGCTCATACC<br>TGTAATCCCAGCACTTTGGGAGGCCAAGGCAGGCGGATCACCTGAGGTCAGGAGTTCGAGACCAGCCT<br>GACCAACATAGAGAAACCCCATCTCTACTAAAAATACAAAATTAGCCGGGTGTGGTGGCGGGCGCCTG<br>TAATCCCAGCTACTTGGGAGGCTGAGGTGGGAGAATCGCTTGAACCCAGGAGGCGGAGGTTGTGGTGA<br>GCTGAGATCATGCCATTGCACTCCAGCCTCGGCAACAAGAGTGAAACTTCGTCTCCAAAAAAAAAAAC<br>TCAAGCAAATGAAGTTCATAATAATAGGGGATGTTGATAAAACTTGTGGCAGCCTTCCAATTCATTTA<br>CAGTTGTTTCGTTTTGTTTTTGTTTAATGTCCATTTTCTGTTGACTGTTCCCAGTTTTCATTTTCCA<br>TACAGTCTGTATGTAAAGTCTGGTTTTCATTAAGCTGTGGCCAGTATTTGCCACTACAACAGAAACAC<br>ACTGTCACACTTGCTAGAATATAACTGTACTTGAGCTTCTCCTTTCCTGTGAAGTAGTGCTGGGCTTT<br>CTAGAGTTTAATTCTCAAGTGGCACAAGATAGCAGAGCCCATGCATTTTAATGGCTGAGACTGCTAAG<br>AGTGAACCTAAACACTTACAAGTTGCAGAGAGAAATGAAAAGTAATTACATGCTATTAGCATTGAGA<br>AATGTTGACAAATTAATTTGTTGGGAACCAAAGATAGCATTTCTGATGACAACTCCCACAGTGATTGG<br>CCAGTTGTATGATGAGTACACTGCTGGAAAGAGGGTAAACTGGGAGTTAGTGGATGGTCCCAATGCCC<br>TGCCTACAGCAGAGTGCCAACCAGCCCTGAGTGCAAAATTCAAGTTCAATGTGTGTGCTTGTGTGTGG<br>TGTGCTTTATGGACCCGCAAATACCCATATTCATTATTGATGATAAGATCTTCACAGAATCCTGTAGCT<br>ACTAATGCATTGAGTTTTTAATCTCAGTACATCAGCCAGGAGGAGCCAGATCACAGGGTAGTGATGTC<br>TACTGGGATTATACTCATAACATCTACACAAAACAAGTTGAGAAGGATCCACGTTTTCATTGTTTATC<br>AGAATTGTATCTCATTTGGCTGAGCATTACTTTTGTCAGAATGTGTTATCTGTAAACCATGTGTAGTG<br>AAATTCTTCTGTAACTTTGGATTAAAGGTATTTATGGTCTTTTTGTTTGTTTGATTTTTAAGTAAGTT<br>ATTTCTTTTGTAGACCTGCTGATGGTATGGTTCCATCCTTCTGACCTCAGCATCCAATCTTTTTAAGG<br>ATTTTTGTTTCAATATTGTTATTTTAAATTGTGGTTGAAGCAATAGAAAATTGAAATATGGATTGTG<br>CATGACTGTGTCTTGAGTGTAAAAATATTGCAGTTTGAAACTTGGACCTAAAGTATTGCAAATAAAAA<br>TGACAAACATCAATGA |

TABLE 14-continued

Target sequences.

| SEQ ID NO: | Description | Sequence |
|---|---|---|
| 7189 | Human PAK3 transcript variant 3 mRNA NM_001128167.3 (GI: 1890283404 version 3) | AGAGCATCCTCAGCAGCTGCCACCGAAGCAGCCTCCTCCTTCTCTCTTCCTCCTCCTCCTACCACGGC<br>CGCCGCCACCACCGCTGCGGCTGTGATCTCCTATCCCCTCTGGTCCTCCTTCCTCCCCCAGTTCCTGC<br>TCCTCCTCCCATCCCCTGCTCCTCCTGCCCAGCAGCGAAGGGCAGAACCCTCGGCTGCCGCCCTCCTT<br>CGCTCTGACCAAGAAGAGGCTGGAACAGGAGCTGTGAAATTAGTTGTAACTGAAAATGTCTGACGGTC<br>TGGATAATGAAGAGAAACCCCGGCTCCTCCACTGAGGATGAATAGTAACAACCGGGATTCTTCAGCA<br>CTCAACCACAGCTCCAAACCACTTCCCATGGCCCCTGAAGAGAAGAATAAGAAAGCCAGGCTTCGCTC<br>TATCTTCCCAGGAGGAGGGGATAAAACCAATAAGAAGAAGGAGAAAGAGCGCCCAGAGATCTCTCTTC<br>CTTCAGACTTTGAGCATACGATTCATGTGGGGTTTGATGCAGTCACCGGGGAATTCACTGGAATTCCA<br>GAGCAATGGGCACGATTACTCCAAACTTCCAACATAACAAAATTGGAACAGAAGAAGAACCCACAAGC<br>TGTTCTAGATGTTCTCAAATTCTATGATTCCAAAGAAACAGTCAACAACCAGAAATACATGAGCTTTA<br>CATCAGGAGATAAAGTGCACATGGATACATAGCAGCCCATCCTTCGAGTACAAAACAGCATCTGAG<br>CCTCCATTGGCCCCTCCTGTGTCTGAAGAAGAAGATGAAGAGGAAGAAGAAGAAGAAGATGAAAATGA<br>GCCACCACCAGTTATCGCACCAAGACCAGAGCATACAAAATCAATCTATACTCGTTCTGTGGTTGAAT<br>CCATTGCTTCACCAGCAGTACCAAATAAAGAGGTCACACCACCCTCTGCTGAAAATGCCAATTCCAGT<br>ACTTTGTACAGGAACACAGATCGGCAAAGAAAAAATCCAAGATGACAGATGAGGAGATCTTAGAGAA<br>GCTAAGAAGCATTGTGAGTGTTGGGGACCCAAAGAAAAAATACACAAGATTTGAAAAATTGGTCAAG<br>GGGCATCAGGTACTGTTTATACAGCACTAGACATTGCAACAGGACAAGAGGTGGCCATAAAGCAGATG<br>AACCTTCAACAGCAACCCAAGAAGGAATTAATTATTAATGAAATTCTGGTCATGAGGGAAAATAAGAA<br>CCCTAATATTGTTAATTATTTAGATAGCTACTTGGTGGGTGATGAACTATGGGTAGTCATGGAATACT<br>TGGCTGGTGGCTCTCTGACTGATGTGGTCACAGAGACCTGTATGGATGAAGGACAGATAGCAGCTGTC<br>TGCAGAGAGTGCCTGCAAGCTTTGGATTTCCTGCACTCAAACCAGGTGATCCATAGAGATATAAAGAG<br>TGACAATATTCTTCTCGGGATGGATGGCTCTGTTAAATTGACTGACTTTGGGTTCTGTGCCCAGATCA<br>CTCCTGAGCAAAGTAAACGAAGCACTATGGTGGGAACCCCATATTGGATGGCACCTGAGGTGGTGACT<br>CGAAAAGCTTATGGTCCGAAAGTTGATATCTGGTCTCTTGGAATTATGGCAATTGAAATGGTGGAAGG<br>TGAACCCCCTTACCTTAATGAAAATCCACTCAGGGCATTGTATCTGATAGCCACTAATGAACTCCAG<br>AGCTCCAGAATCCTGAGAGACTGTCAGCTGTATTCCGTGACTTTTTAAATCGCTGTCTTGAGATGGAT<br>GTGGATAGGCGAGGATCTGCCAAGGAGCTTTTGCAGCATCCATTTTTAAAATTAGCCAAGCCTCTCTC<br>CAGCCTGACTCCTCTGATTATCGCTGCAAAGGAAGCAATTAAGAACAGCAGCCGCTAAGACTGCAAGC<br>CTTACACCTCCACCATCTCCCTCATGAGTAAGACTGAAATAAAACTCTGCTGCAGGAAAGATGGAAGAA<br>AAGACAGTCAAATGGGGTGGGGGTTCTTTACCTTTCAAATGAATAGAAACTTCTTATAAGCCTTTTTC<br>CTACTCCCTCAGATTATGTAATTTATTTGTAAGCCTGAATCGCAGCCCAAACAGGGCAGCAATGTTGA<br>AGTGACCATAAAGTGGTCACTTCCACCGTGAAGCGAAAGAGCCAGTAGTGAATCCCCTCATTTGTGC<br>ATTCACTTTGAAGAAAAAGGTTTCTCAAAGATGCACACTCCCTCTTCATAGTGTTGTGTTTGTTTTTA<br>AGTTAGAGAGTAGTCCCTCTTGCATTCAAACCTCCTTCAAAACTCCTTACCCAATGTGATGTTTTTCA<br>CTTGCATTGTCATTAGATGTCCAGAAAAAAAAAGATGTCAAATGTTTTTCTAAAAAAAGAAAGCAA<br>AAAAAGCAAGGCAAAAAAAAAAAAAAAACAAACAAAAACAAAAACAAAACAAAAACAAGCAAACAAA<br>AAATACCAGAGCAAGTACTGTGTGAACATGTGGAAGTCCATGCCCTAATAGAGTTGCAATTTTTTATT<br>CTTCTTCTATAGTGGTGGCTTGGTTTGTGTACCTATTTTTCTGCATTTGTATTGGAAAAGGTTTCTTT<br>TAAGACATTTTCCAAAAGTGGAGAGGAATATGTGTGTTCAGGAAGGGCTTTCAAAAAACTGTATATCT<br>AAATAAAGCTCAAACGGTGAAATCCTGTCACATTTTCACAATGATGCTTAAAAGATAATTGAGTAAAC<br>CAGGTTGTTAATCTCCTTAATACCTGAAAGAGGACACACTGAAACTGAAACTGTGACATCCTGCTAGG<br>TGAGTTCAGGTTCTGAACCTAGGAAATCCTCATAGGAGAAACCACATTTAAACAAAGATGGGACTTTC<br>TCTGAGAGCCAAAACCAGATAAATGTAGAATACTGAAATCCTTGTTGGACATTAAGTAAACAAAGATA<br>ATGATACCTAAATTAATCCTCTCTTGTGCTTATGAAACATATGCACTGTAAATAGGCATACCAGGAG<br>GAAATAGATACATTAATCATCATTTACTTATGATACAAATTATTTATTTTGACAATTTATAACGTTTA<br>AAAAAGTTTTTTAAAGATCTAGAGAAAGTGATATAGTAAACATTCAACTCTGTAAGAAATGGGAGGT<br>CAGTGAAGGCTACATCCCAATCAATATTTGGCTCTAAGTACCTCTTCCCATTTTTCCTATGTATCACC<br>TATTTCTGTTTCGGAATATGGTGTGTTCATGCTTAGTTCTTTGGGCTTTTGAATATCAAAAGCATATT<br>CATAAATGTCTTGAAATTCTCTCCAGTGGAAAATAATTTTAACTTACAATCATATCCCAAGAAATGTC<br>AGTCCGACAGAATTCCTTATATGACTTGGGGAAAATAACAAAATTTGACTACTATTTCACCATATATC<br>TATTTATTAAAAAATTCAACAGTTGGCACTTCCTGAATCTTCTGAGAGTAGAAAAATATCTGCGGAGT<br>GTCTGTGTAGAAAAGGATATGCCTCTCTTTTGAGTGTATTGACAATTTTGTAAATTACAGAAAGTTGT<br>TTCTCTAAGCCTTTGAAAAACTAAACAATTTGTGTTATAGAAGGCTTCTTAATTTGCAGTATAAAAGAA<br>TCTAAACAGAACTTATGTACATTCAGCCAGAAGGGGAAAGAGATCAGTTACATAGGCCTCTCTCCTTC<br>TTTGCCAAGGTACATCCATCCATCTAACCATCCATATATCCACATCTTAAAATGAAAGCACTTTCTTT<br>AGAGTTTCAGCAAACTATATAGTGTACGTGTTTATGTTCAGGAGATGACCCCACTGGTGTATTTCCTA<br>TTTTCCCTATTGTTTCTTTGACTGTAAAAGTTGGGAGAGGCTTGACCTCCTCCCCTTGAAAATGTCC<br>ACAGTGGGATAAAACAACAAATGTGAAAAGAAAATGAAACGGTAATATTAATTTGAAGCATACTATGT<br>TATACTTTGCAAAAACGAATCTGGGCCTGTAATTTTTAATGCCACACTGCTCTAATGAGAGAGAGAGG<br>CCTTAATTTTGATTTCATTTAAAAATAAGTACTTTAAAAAATTTTTCACTCATAGTGCCGGGAAATTC<br>AATGAAATCCTGGGATGCAAATAAAAATCAGTACATTAGTGACTGTGTCCTGCCAGTGGAGAGAGCCC<br>AATACCTGGTTAGGAAGCCCTATTCATTAGTTAGCATCCCTTACATGTTGAGAAGGCCTTTTTTTGT<br>TGTTATTTTGGAGACCTTGGAGCAGTGACCCTTCAGATCACTGTAGGCAGAGAAATGGCTTCTCTCTT<br>ATGCTTTCAGTTCAGCATATTAACAATGAGGAGCCAGGTACTTCTTTACTACCACTTTGTACCAAGAT<br>TTGATAATAATATATCCCAGGAGGCATTACTTTTATAAATTTGTATTCATGTAAATTTTCAAATGAGA<br>ACAGCTTCTAAAGCCCCTTCCCTGTATTGGAGAGTTATGTATATTTCTAATAAGTATTAGAAAGAAGC<br>TGTTTCTCATGCCACAGTGATGCTGAAGGATTCACATTTGGTACAATCGAGTAACTTGAACGCCAGAT<br>TGTTAACAGTTTATTCTCTTTCCCTGGATTTTTAAGCTCATCTTGACACAGGTGAGTCTATCCAAATC<br>TTTGATGTTGCTAGTGTGCCCTGAGATAACGAGGGCACATCTTTCAATGTTGATTCCAAAATGTCCTG<br>AGTTAGGAATAGGGCAGTGGGAAAGTCAGGGAAGGGTGAGAAGCACAGTAGAGATTATTTATTTAAAA<br>AAGGAAAGAACGTTAATGTTGTTACAAGGATCCAGTGCGTTGTCATAATCCCATGAAGATTTTCAGA<br>TGACACAATCCCCTCAAATCAGTCACCATGTTGGGTAATGACTTCGTTCTTGCTGATCTCGTGTGTGT<br>GTCATTGTAAATATTTGTGTGTCCATGTTCCATTTTGGCTACTGGATGGCCAAGCCATGTAAGAAGAT<br>TTAACTCAAGTATTTATTCTTTATGTTATTCAGATTTCTTTCAGGCTTGTGAACTGCACCCCAATGTT<br>TGAGTTTAACCACCTGATCCTTACATCTATCCCTCCCCGGTGAAGCACATTCCATTGCTAAAAGAAAA<br>AGAAACACGAAATTGCTTCCTGTTGTCTGTATAACTGTTTTGATAGTTTGAGATATTTGTCTATAAAT |

TABLE 14-continued

Target sequences.

| SEQ ID NO: | Description | Sequence |
|---|---|---|
| | | GATATTTCTCAGCTCAAAGATCGTGTAAATAATTATATTCCTTTGCTCAATGGGTTTATTTCTAATGA<br>GGCTGCCAGTTCTGAGAGATTCTATAATATCACTTTTAAATAACATAAACAGGGATTACAACTATGTA<br>AAAAGAAATGCATATGGACAAAGACTGGGAACACAGATAATTGAAATCAGTTGTGTTAGGGTGGTGGA<br>ATTATGTGAATTTTTTTTCTTTTTAAAATTTTATTTGATATTGTTATAATATTGCTTTACAATAAAT<br>AAACAGCAGAAAGGGAACTATAGACACATAGAAAAGATGCCAGAAGCAGATGCCTTCTGGCCAGAGCG<br>CAGAGCATGCAGGGCAGAGATATTTGCTAGTTACAATTATTCCATAGGCTTTATGCTTGCCTGGGTGC<br>TGAGGTTGGCACACGCTCGGGTATGGCACACGCTTTCTTAGGGACTATTATCTATAAGTTAAAGCTA<br>GGGAGATGTCACTATTAGAACTCCAAACACACTCTTCTGCTTTAAAACAGGTTGTCTGCCCTCTGCTT<br>TGGTATGGCATTCGGGTGTCTGTTTTGTGGTTGCTTTAGATTGGAGGGGTGACCATTTTATTAGCCCC<br>CTTGATAACATCTGTTGCAGATATTGCCTTTCTGGAACGTTTTAACAGACTCTCAGGTTGAATTTTGG<br>AGGACTAGAAGGATAAAATCCCCAGCTCCCACCATTTTCTTGTCCAACAGGATATTACTGTATATCAT<br>TCAGGTAGGATTCTTCTTTTAATAACCAATAGGGCAAGTCCCACTAATTTCAATAGAAGTTATGACTT<br>GCAATTAAAAGCTGACTTTGAAATCATTAAACAAATATGTAGGACTGTCTCTGCCTGTTGGCATTCAG<br>TTATAGTTCTGTTAATTTTGGCTTGGGATGGTCTCCATGTGCTTTTTCTGCCTATTTATAGGTTGTT<br>TGCAGTAGTTGTGATTTTAAAGAGCAAGGGAGACCATCTAACCAAAGGATAACTTCCTTCTAACTCA<br>CCAAAGAAATTTTAGGTGAGAACTTTAATAATGAGGTAGTCACCTCAGATATGCTGCTTAGTTTCACT<br>AAAAGCAGACCCTATACCTAGAGAAGTCACTGGCTTTTTATTGGTCATTCTCAATACAGAAATACTTA<br>GGGGAGTCTTAACCCTGCCATCCCCGGTTGAATCTCTTGGTCTTTATCTAAGCTACTTGCAGTTAATA<br>TTCAGTTAAGCAAAGGTATGGCCAGTAGTGCAAGTATCTCCCAGTCTCTGAGCTCTGAACAAGAGGAC<br>TGAAATTCAGCATTTGTAAACTGACAGTTTGATGGGCCTGGGATTTGAAGTGAACTCAGCACACAATT<br>CTGAACGTGTATTTGCATGTGGACTGGGAAGGAAATAAATGGGAACTTGGAAATAATGGAATATTTCT<br>CCTATGAAAGAATTTTTCGTAGAAGATTTGTTTTTGATATAATCTTTCTGTTGGTTAGCTTTTAGTGT<br>TTTCATTCCTTTTCTGATCCACACTCCTTTAAGTGACCAAATGAATATAACCCAACATGCATTGGGAA<br>TGTGTTTAATATTAAACAATGTCTAACTGAATCTGCAAATGCGGGAACTGAGATATCACCTCCATGTG<br>CACACCTGTGTGTACAGTATTCTATACAACTTGTAGCATTTACTGCCACTTAATTGGGTTGAACTTG<br>CAAGATAAACTTTTGGAAACTGCTTAGTGCCATCGGAGTCTCCTTTAGAAGCTGCCATCAGGCAAATG<br>CTATCCCATAATACCAGCAGTAAGCCTGGCAACATGTTCAACAGATTTAGTACCCAAGAGGAAATCAA<br>CAGCGATAGTAGAGAATGAGTCAGATGTAGTGGGATAAATACTAGCCTAGGAAGAAGGAGCCCCGGAG<br>TCTAATATGAGCTTTATTACTAAATTGCTATGTGACGCTAGGCAAGTCACTTAACCTCTCCATGCTG<br>TTTCCTCATCTGTAAAATAAGTGTATTGGACTAGATGATCCTTAGGGTCTTTCCAAAAGTCTAACATT<br>CTATGGCATTATAGGTTGCCTTGCAAATTCAGCCTGCTATAGTGATGGCAAATATCACGTTTAAGCCT<br>GAGTCTCTTATGTTGCAGTTAAATAAAAGAACTATGTAAGATGATTTTTAAAATTCAAGCAAATGGGC<br>CGGGTGCGGTGGCTCATACCTGTAATCCCAGCACTTTGGGAGGCCAAGGCAGGCGGATCACCTGAGGT<br>CAGGAGTTCGAGACCAGCCTGACCAACATAGAGAAACCCCATCTCTACTAAAAATACAAAATTAGCCG<br>GGTGTGGTGGCGGGCGCCTGTAATCCCAGCTACTTGGGAGGCTGAGGTGGGAGAATCGCTTGAACCCA<br>GGAGGCGGAGGTTGTGGTGAGCTGAGATCATGCCATTGCACTCCAGCCTCGGCAACAAGAGTGAAACT<br>TCGTCTCCAAAAAAAAAAACTCAAGCAAATGAAGTTCATAATAATAGGGATGTTGATAAAACTTGTG<br>GCAGCCTTCCAATTCATTTACAGTTGTTTCGTTTTGTTTTTGTTTTAATGTCCATTTTCTGTTGACTG<br>TTCCCAGTTTTCATTTTCCATACAGTCTGTATGTAAAGTCTGGTTTTCATTAAGCTGTGGCCAGTATT<br>TGCCACTACAACAGAAACACACTGTCACACTTGCTAGAATATAACTGTACTTGAGCTTCTCCTTTCCT<br>GTGAAGTAGTGCTGGGCTTTCTAGAGTTTAATTCTCAAGTGGCACAAGATAGCAGAGCCCATGCATTT<br>TAATGGCTGAGACTGCTAAGAGTGAACCTAAACACTTACAAGTTGCAGAGAGAAATGAAAAGTAATT<br>ACATGCTATTAGCATTGAGAAATGTTGACAAATTAATTTGTTGGGAACCAAAGATAGCATTTCTGATG<br>ACAACTCCCACAGTGATTGGCCAGTTGTATGATGAGTACACTGCTGGAAAGAGGGTAAACTGGGAGTT<br>AGTGGATGGTCCCAATGCCCTGCCTACAGCAGAGTGCCAACCAGCCCTGAGTGCAAAATTCAAGTTCA<br>ATGTGTGTGCTTGTGTGGTGTGCTTTATGGACCCGCAAATACCATATTCATTATTGATGATAAGAT<br>CTTCACAGAATCCTGTAGCTACTAATGCATTGAGTTTTTAATCTCAGTACATCAGCCAGGAGGAGCCA<br>GATCACAGGGTAGTGATGTCTACTGGGATTATACTCATAACATCTACACAAAACAAGTTGAGAAGGAT<br>CCACGTTTTCATTGTTTATCAGAATTGTATCTCATTTGGCTGAGCATTACTTTTGTCAGAATGTGTTA<br>TCTGTAAACCATGTGTAGTGAAATTCTTCTGTAACTTTGGATTAAAGGTATTTATGATTCATTTTGTT<br>GTTTGATTTTAAGTAAGTTATTTCTTTTGTAGACCTGCTGATGGTATGGTTCCATCCTTCTGACCTC<br>AGCATCCAATCTTTTTAAGGATTTTTGTTTTCAATATTGTTATTTTAAATTGTGGTTGAAGCAATAGA<br>AAATTGAAATATGGATTGTGCATGACTGTGTCTTGAGTGTAAAAATATTGCAGTTTGAAACTTGGACC<br>TAAAGTATTGCAAATAAAAATGACAAACATCAATGA |
| 7190 | Human PAK3<br>transcript variant<br>4 mRNA<br>NM_001128168.3<br>(GI: 1676441496<br>version 3) | ACCGCGGGCGGGCAGCTGTGCCAGCTAACCGTCTGGGATCTCGCACTGGGGGCTGCAGCTTTTCCCCG<br>CCTCGAGCCAGTGTGCGGGGCGGGAGAAGAGCCAGGGGGAGCGGGCTGGGCCCGGGGCTGCGGCTGC<br>GGCCGCGGGGCTGCGGCTCCCCAGCCCCGCCAGCTGGAGCGCTCGGAGGTAGAGGAAAGGTCTTGACG<br>GGGTGGCTGGATCCGTGGCAGAATCCAGTTCCAGATTCTAGACTTGAGGGTTCTGGGCTGTTGGTCTG<br>TAGAGTCGAAGGAGAGAAGGACTCAAATCCAGGCCAAGTGTATGGCTGTCTGAGGTATTGGAACAGAA<br>GGAGGTCCATTCCTGTTGGTGACAACACCGTGGCCCTGTTCTGGGATGAGCAAGGTGTAAAGCAGGTT<br>TCCCCCAAGAAAGAGCAGCTGAGTCCTTGCATCTTGTGGCAGCTGGTGTGCCCAGCACTGAGTCTGTA<br>GGAGCTGAAGCCAGCCCGGACCCTTCTCATGGGCAGTGCCCACCTGTGCTGAAGTCCTGCAGCGGTGG<br>CGGTGTGAGGAGCTGTGAAATTAGTTGTAACTGAAAATGTCTGACGGTCTGGATAATGAAGAGAAACC<br>CCCGGCTCCTCCACTGAGGATGAATAGTAACAACCGGGATTCTTCAGCACTCAACCACAGCTCCAAAC<br>CACTTCCCATGGCCCCTGAAGAGAAGAATAAGAAAGCCAGGCTTCGCTCTATCTTCCCAGGAGGAGGG<br>GATAAAACCAATAAGAAGAAGGAAGAAAAGAGCGCCCAGAGATCTCTCTTCCTTCAGACTTTGAGCATAC<br>GATTCATGTGGGGTTTGATGCAGTCACCGGGGAATTCACTAACTCCCCTTTCCAGACCTCTAGACCTG<br>TGACGGTCGCTTCAAGTCAATCAGAGGGAAAAATGCCAGATCTCTATGGCTCACAGATGTGCCCAGGG<br>AAGCTCCCAGAGGGAATTCCAGAGCAATGGGCACGATTACTCCAAACTTCCAACATAACAAAATTGGA<br>ACAGAAGAAGAACCCACAAGCTGTTCTAGATGTTCTCAAATTCTACAGCTTCTTTCTATGATTCCAAAACAGTCAACA<br>ACCAGAAATACATGAGCTTTACATCAGGAGATAAAAGTGCACATGGATACATAGCAGCCCATCCTTCG<br>AGTACAAAAACAGCATCTGAGCCTCCATTGGCCCCTCCTGTGTCTGAAGAAGAAGATGAAGAGGAAGA<br>AGAAGAAGAAGATGAAAATGAGCCACCACCAGTTATCGCACCAAGACCAGAGCATACAAAATCAATCT<br>ATACTCGTTCTGTGGTTGAATCCATTGCTTCACCAGCAGTACCAAATAAAGAGGTCACACCACCCTCT<br>GCTGAAAATGCCAATTCCAGTACTTTGTACAGGAACACAGATCGGCAAAGAAAAAAATCCAAGATGAC |

TABLE 14-continued

Target sequences.

| SEQ ID NO: | Description | Sequence |
|---|---|---|
| | | AGATGAGGAGATCTTAGAGAAGCTAAGAAGCATTGTGAGTGTTGGGGACCCAAAGAAAAAATACACAA |
| | | GATTTGAAAAAATTGGTCAAGGGGCATCAGGTACTGTTTATACAGCACTAGACATTGCAACAGGACAA |
| | | GAGGTGGCCATAAAGCAGATGAACCTTCAACAGCAACCCAAGAAGGAATTAATTATTAATGAAATTCT |
| | | GGTCATGAGGGAAAATAAGAACCCTAATATTGTTAATTATTTAGATAGCTACTTGGTGGGTGATGAAC |
| | | TATGGGTAGTCATGGAATACTTGGCTGGTGGCTCTCTGACTGATGTGGTCACAGAGACCTGTATGGAT |
| | | GAAGGACAGATAGCAGCTGTCTGCAGAGAGTGCCTGCAAGCTTTGGATTTCCTGCACTCAAACCAGGT |
| | | GATCCATAGAGATATAAAGAGTGACAATATTCTTCTCGGGATGGATGGCTCTGTTAAATTGACTGACT |
| | | TTGGGTTCTGTGCCCAGATCACTCCTGAGCAAAGTAAACGAAGCACTATGGTGGGAACCCACATATTGG |
| | | ATGGCACCTGAGGTGGTGACTCGAAAAGCTTATGGTCCGAAAGTTGATATCTGGTCTCTTGGAATTAT |
| | | GGCAATTGAAATGGTGGAAGGTGAACCCCCTTACCTTAATGAAAATCCACTCAGGGCATTGTATCTGA |
| | | TAGCCACTAATGGAACTCCAGAGCTCCAGAATCCTGAGAGACTGTCAGCTGTATTCCGTGACTTTTTA |
| | | AATCGCTGTCTTGAGATGGATGTGGATAGGCGAGGATCTGCCAAGGAGCTTTTGCAGCATCCATTTTT |
| | | AAAATTAGCCAAGCCTCTCTCCAGCCTGACTCCTCTGATTATCGCTGCAAGGAAGCAATTAAGAACA |
| | | GCAGCCGCTAAGACTGCAAGCCTTACACCTCACCATCTCCCTCATGAGTAAGACTGAAATAAAACTCT |
| | | GCTGCAGGAAAGATGGAAGAAAAGACAGTCAAATGGGGTGGGGGTTCTTTACCTTTCAAATGAATAGA |
| | | AACTTCTTATAAGCCTTTTTCCTACTCCCTCAGATTATGTAATTTATTTGTAAGCCTGAATCGCAGCC |
| | | CAAACAGGGCAGCAATGTTGAAGTGACCATAAAGTGGTCACTTCCACCGTGAAGCGAAAGAGCCAGTA |
| | | GTGAATCCCCTCATTTTGTGCATTCACTTTGAAGAAAAAGGTTTCTCAAAGATGCACACTCCCTCTTC |
| | | ATAGTGTTGTGTTTGTTTTTAAGTTAGAGAGTAGTCCCTCTTGCATTCAAACCTCCTTCAAAACTCCT |
| | | TACCCAATGTGATGTTTTTCACTTGCATTGTCATTAGATGTCCAGAAAAAAAAAAGATGTCAAAATGT |
| | | TTTTCTAAAAAAAGAAAGCAAAAAAAGCAAGGCAAAAAAAAAAAAAAAAACAAACAAAAACAAAAACA |
| | | AAACAAAAACAAGCAAACAAAAAAATACCAGAGCAAGTACTGTGTGAACATGTGGAAGTCCATGCCCTA |
| | | ATAGAGTTGCAATTTTTTATTCTTCTTCTATAGTGGTGGCTTGGTTTGTGTACCTATTTTTCTGCATT |
| | | TGTATTGGAAAAGGTTTCTTTTAAGACATTTTCCAAAGTGGAGAGGAATATGTGTGTTCAGGAAGGG |
| | | CTTTCAAAAAACTGTATATCTAAATAAAGCTCAAACGGTGAAATCCTGTCACATTTTCACAATGATGC |
| | | TTAAAAGATAATTGAGTAAACCAGGTTGTTAATCTCCTTAATACCTGAAAGAGGACACACTGAAACTG |
| | | AAACTGTGACATCCTGCTAGGTGAGTTCAGGTTCTGAACCTAGGAAATCCTCATAGGAGAAACCACAT |
| | | TTAAACAAAGATGGGACTTTCTCTGAGAGCCAAAACCAGATAAATGTAGAATACTGAAATCCTTGTTG |
| | | GACATTAAGTAAACAAAGATAATGATACCTAAATTAATCCTCTCTTGTGCTTATGAAACATATGCACT |
| | | GTAAAATAGGCATACCAGGAGGAAATAGATACATTAATCATCATTTACTTATGATACAAATTATTTAT |
| | | TTTGACAATTTATAACGTTTAAAAAAGTTTTTTAAAGATCTAGAGAAAGGTGATATAGTAAACATTCA |
| | | ACTCTGTAAGAAATGGGAGGTCAGTGAAGGCTACATCCCAATCAATATTTGGCTCTAAGTACCTCTTC |
| | | CCATTTTTCCTATGTATCACCTATTTCTGTTTCGGAATATGGTGTGTTCATGCTTAGTTCTTTGGGCT |
| | | TTTGAATATCAAAAGCATATTCATAAATGTCTTGAAATTCTCTCCAGTGGAAAATAAATTTTAACTTAC |
| | | AATCATATCCCAAGAAATGTCAGTCCGACAGAATTCCTTATATGACTTGGGGAAAATAACAAAATTTG |
| | | ACTACTATTTCACCATATATCTATTTATTAAAAAATTCAACAGTTGGCACTTCCTGAATCTTCTGAGA |
| | | GTAGAAAAATATCTGCGGAGTGTCTGTGTAGAAAAGGATATGCCTCTCTTTTGAGTGTATTGACAATT |
| | | TTGTAAATTACAGAAAGTTGTTTCTCTAAGCCTTTGAAAAACTAACAATTTGTGTTATAGAAGGCTTC |
| | | TTAATTTGCAGTATAAAAGAATCTAAACAGAACTTATGTACATTCAGCCAGAAGGGGAAAGAGATCAG |
| | | TTACATAGGCCTCTCTCCTTCTTTGCCAAGGTACATCCATCCATCTAACCATCCATATATCCACATCT |
| | | TAAAATGAAAGCACTTTCTTTAGAGTTTCAGCAAACTATATAGTGTACGTGTTTATGTTCAGGAGATG |
| | | ACCCCACTGGTGTATTTCCTATTTTCCCTATTGTTTTCTTTGACTGTAAAAGTTGGGAGAGGCTTGAC |
| | | CTCCTCCCCTTGAAAATGTCCACAGTGGGATAAAACAACAAATGTGAAAAGAAAATGAAACGGTAATA |
| | | TTAATTTGAAGCATACTATGTTATACTTTGCAAAAACGAATCTGGGCCTGTAATTTTTAATGCCACAC |
| | | TGCTCTAATGAGAGAGAGAGGCCTTAATTTTGATTTCATTTAAAAATAAGTACTTTAAAAAATTTTTC |
| | | ACTCATAGTGCCGGGAAATTCAATGAAATCCTGGGATGCAAATAAAAATCAGTACATTAGTGACTGTG |
| | | TCCTGCCAGTGGAGAGAGCCCAATACCTGGTTAGGAAGCCCTATTCATTAGTTAGCATCCCTTACATG |
| | | TTGAGAAGGCCTTTTTTTTGTTGTTATTTTGGAGACCTTGGAGCAGTGACCCTTCAGATCACTGTAGG |
| | | CAGAGAAATGGCTTCTCTCTTATGCTTTCAGTTCAGCATATTAACAATGAGGAGCCAGGTACTTCTTT |
| | | ACTACCACTTTGTACCAAGATTTGATAATAATATATCCCAGGAGGCATTACTTTTTAAAATTTGTATT |
| | | CATGTAAATTTTCAAATGAGAACAGCTTCTAAAGCCCCTTCCCTGTATTGGAGAGTTATGTATATTTC |
| | | TAATAAGTATTAGAAAGAAGCTGTTTCTCATGCCACAGTGATGCTGAAGGATTCACATTTGGTACAAT |
| | | CGAGTAACTTGAACGCCAGATTGTTAACAGTTTATTCTCTTTCCCTGGATTTTTAAGCTCATCTTGAC |
| | | ACAGGTGAGTCTATCCAAATCTTTGATGTTGCTAGTGTGCCCTGAGATAACGAGGGCACATCTTTCAA |
| | | TGTTGATTCCAAAATGTCCTGAGTTAGGAATAGGGCAGTGGGAAAGTCAGGGAAGGGTGAGAAGCACA |
| | | GTAGAGATTATTTATTTAAAAAAGGAAAGAACGTTAATGTTGTTAGCAAGGATCCAGTGCGTTGTCAT |
| | | AATCCCATGAGGATTTTCAGATGACACAATCCCCTCAAATCAGTCACCATGTTGGGTAATGACTTCGT |
| | | TCTTGCTGATCTCGTGTGTGTGTCATTGTAAATATTTGTGTGTCCATGTTCCATTTTGGCTACTGGAT |
| | | GGCCAAGCCATGTAAGAAGATTTAACTCAAGTATTTATTCTTTATGTTATTCAGATTTCTTTCAGGCT |
| | | TGTGAACTGCACCCCAATGTTTGAGTTTAACCACCTGATCCTTACATCTATCCCTCCCCGGTGAAGCA |
| | | CATTCCATTGCTAAAAGAAAAAGAAACACGAATTGCTTCCTGTTGTCTGTATAACTGTTTTGATAGT |
| | | TTGAGATATTTGTCTATAAATGATATTTCTCAGCTCAAAGATCGTGTAAATAATTATATTCCTTTGCT |
| | | CAATGGGTTTATTTCTAATGAGGCTGCCAGTTCTGAGAGATTCTATAATATCACTTTTAAATAACATA |
| | | AACAGGGATTACAACTATGTAAAAGAAATGCATATGGACAAAGACTGGGAACACAGATAATTGAAAT |
| | | CAGTTGTGTTAGGGTGGTGGAATTATGTGAATTTTTTTTCTTTTTAAAATTTATTTGATATTGTTA |
| | | TAATATTGCTTTACAATAAATAAACAGCAGAAAGGGAACTATAGACACATAGAAAAGATGCCAGAAGC |
| | | AGATGCCTTCTGGCCAGAGCGCAGAGCATGCAGGGCAGAGATATTTGCTAGTTACAATTATTCCATAG |
| | | GCTTTATGCTTGCCTGGGTGCTGAGGTTGGCACACGCTCGGGTATGGCACACGCTTTCTTAGGAGACT |
| | | ATTATCTATAAGTTAAAGCTAGGGAGATGTCACTATTAGAACTCCAAACACACTCTTCTGCTTTAAAA |
| | | CAGGTTGTCTGCCCTCTGCTTTGGTATGGCATTCGGGTGTCTGTTTTGTGGTTGCTTTAGATTGGAGG |
| | | GGTGACATTTTATTAGCCCCTTGATAACATCTGTTGCAGATATTGCCTTTCTGGAACGTTTTAACA |
| | | GACTCTCAGGTTGAATTTTGGAGGACTAGAAGGATAAAATCCCCAGCTCCCACCATTTTCTTGTCCAA |
| | | CAGGATATTACTGTATATCATTCAGGTAGGATTCTTCTTTTAATAACCAATAGGGCAAGTCCCACTAA |
| | | TTTCAATAGAAGTTATGACTTGCAATTAAAAGCTGACTTTGAAATCATTAAACAAATATGTAGGACTG |
| | | TCTCTGCCTGTTGGCATTCAGTTATAGTTCTGTTAATTTTGGCTTGGGATGGTCTCCATGTGCTTTTT |
| | | TCTGCCTATTTATAGGTTGTTTGCAGTAGTTGTGATTTTTAAAGAGCAAGGGAGACCATCTAACCAAA |

TABLE 14-continued

Target sequences.

| SEQ ID NO: | Description | Sequence |
|---|---|---|
| | | GGATAACTTCCTTCTAACTCACCAAAGAAATTTTAGGTGAGAACTTTAATAATGAGGTAGTCACCTCA
GATATGCTGCTTAGTTTCACTAAAAGCAGACCCTATACCTAGAGAAGTCACTGGCTTTTTATTGGTCA
TTCTCAATACAGAAATACTTAGGGGAGTCTTAACCCTGCCATCCCCGGTTGAATCTCTTGGTCTTTAT
CTAAGCTACTTGCAGTTAATATTCAGTTAAGCAAAGGTATGGCCAGTAGTGCAAGTATCTCCCAGTCT
CTGAGCTCTGAACAAGAGGACTGAAATTCAGCATTTGTAAACTGACAGTTTGATGGGCCTGGGATTTG
AAGTGAACTCAGCACACAATTCTGAACGTGTATTTGCATGTGGACTGGGAAGGAAATAAATGGGAACT
TGGAAATAATGGAATATTTCTCCTATGAAAGAATTTTTCGTAGAAGATTTGTTTTTGATATAATCTTT
CTGTTGGTTAGCTTTTAGTGTTTTCATTCCTTTTCTGATCCACACTCCTTTAAGTGACCAAATGAATA
TAACCCAACATGCATTGGGAATGTGTTTAATATTAAACAATGTCTAACTGAATCTGCAAATGCGGGAA
CTGAGATATCACCTCCATGTGCACACCTGTGTGTACGAGTATTCTATACAACTTGTAGCATTTACTGC
CACTTAATTGGGTTGAACTTGCAAGATAAACTTTTGGAAACTGCTTAGTGCCATCGGAGTCTCCTTTA
GAAGCTGCCATCAGGCAAATGCTATCCCATAATACCAGCAGTAAGCCTGGCAACATGTTCAACAGATT
TAGTACCCAAGAGGAAATCAACAGCGATAGTAGAGAATGAGTCAGATGTAGTGGGATAAATACTAGCC
TAGGAAGAAGGAGCCCCGGAGTCTAATATGAGCTTTATTACTAAATTGCTATGTGACGCTAGGCAAGT
CACTTAACCTCTCCATGGCTGTTTCCTCATCTGTAAAATAAGTGTATTGGACTAGATGATCCTTAGGG
TCTTTCCAAAAGTCTAACATTCTATGGCATTATAGGTTGCCTTGCAAATTCAGCCTGCTATAGTGATG
GCAAATATCACGTTTAAGCCTGAGTCTCTTATGTTGCAGTTAAATAAAAGAACTATGTAAGATGATTT
TTAAAATTCAAGCAAATGGGCCGGGTGCGGTGGCTCATACCTGTAATCCCAGCACTTTGGGAGGCCAA
GGCAGGCGGATCACCTGAGGTCAGGAGTTCGAGACCAGCCTGACCAACATAGAGAAACCCCATCTCTA
CTAAAAATACAAAATTAGCCGGGTGTGGTGGCGGGCGCCTGTAATCCCAGCTACTTGGGAGGCTGAGG
TGGGAGAATCGCTTGAACCCAGGAGGCGGAGGTTGTGGTGAGCTGAGATCATGCCATTGCACTCCAGC
CTCGGCAACAAGAGTGAAACTTCGTCTCCAAAAAAAAAAACTCAAGCAAATGAAGTTCATAATAATAG
GGGATGTTGATAAAACTTGTGGCAGCCTTCCAATTCATTTACAGTTGTTTCGTTTTGTTTTTGTTTTA
ATGTCCATTTTCTGTTGACTGTTCCCAGTTTTCATTTTCCATACAGTCTGTATGTAAAGTCTGGTTTT
CATTAAGCTGTGGCCAGTATTTGCCACTACAACAGAAACACACTGTCACACTTGCTAGAATATAACTG
TACTTGAGCTTCTCCTTTCCTGTGAAGTAGTGCTGGGCTTTCTAGAGTTTAATTCTCAAGTGGCACAA
GATAGCAGAGCCCATGCATTTTAATGGCTGAGACTGCTAAGAGTGAACCTAAACACTTACAAGTTGCA
GAGAGAAATGAAAAGTAATTACATGCTATTAGCATTGAGAAATGTTGACAAATTAATTTGTTGGGAA
CCAAAGATAGACATTTCTGATGACAACTCCCACAGTGATTGGCCAGTTGTATGATGAGTACACTGCTGG
AAAGAGGGTAAACTGGGAGTTAGTGGATGGTCCCAATGCCCTGCCTACAGCAGAGTGCCAACCAGCCC
TGAGTGCAAAATTCAAGTTCAATGTGTGTGCTTGTGTGGTGTGCTTTATGGACCCGCAAATACCAT
ATTCATTATTGATGATAAGATCTTCACAGAATCCTGTAGCTACTAATGCATTGAGTTTTTAATCTCAG
TACATCAGCCAGGAGGAGCCAGATCACAGGGTAGTGATGTCTACTGGGATTATACTCATAACATCTAC
ACAAAACAAGTTGAGAAGGATCCACGTTTTCATTGTTTATCAGAATTGTATCTCATTTGGCTGAGCAT
TACTTTTGTCAGAATGTGTTATCTGTAAACCATGTGTAGTGAAATTCTTCTGTAACTTTGGATTAAAG
GTATTTATGGTCTTTTTGTTTGTTTGATTTTTAAGTAAGTTATTCTTTTGTAGACCTGCTGATGGTA
TGGTTCCATCCTTCTGACCTCAGCATCCAATCTTTTTAAGGATTTTTGTTTTCAATATTGTTATTTTA
AATTGTGGTTGAAGCAATAGAAAATTGAAATATGGATTGTGCATGACTGTGTCTTGAGTGTAAAAATA
TTGCAGTTTGAAACTTGGACCTAAAGTATTGCAAATAAAAATGACAAACATCAATGA |
| 7191 | Human TRNP1 mRNA NM_001013642.3 (GI: 1519242294 version 3) | GGGGTGGGGGCTGTGGCCGTGTCTAGCTGTTCGGGTGTGCTGTGGTCATCCTCCCTGCGCACCTACAG
CCGCAGAACCGCCGGTGGGGGGCGGGGATGCCGGGCTGCCGCATCAGCGCCTGCGGCCCGGGGGCCCA
GGAGGGGACGGCAGAGCAGAGGTCGCCGCCGCCGCCCTGGGATCCCATGCCGTCCTCTCAGCCCCCGC
CCCCAACTCCGACCTTGACTCCTACCCCGACCCCGGGTCAGTCCCCGCCGCTGCCGGACGCAGCTGGG
GCTTCAGCAGGCGCGGCCGAGGACCAGGAGCTGCAGCGCTGGCGCCAGGGCGCTAGCGGGATCGCGGG
GCTCGCCGGCCCCGGAGGGGGCTCTGGCGCGGCTGCGGGGGCGGGGGCTCGCGCGCTGGAGCTGGCCG
AAGCACGGCGGCGGCTGCTGGAGGTGGAGGGCCGCCGGCGCCTGGTGTCGGAGCTGGAGAGCCGCGTG
CTGCAGCTGCACCGCGTTTTCTTGGCGGCCGAGCTGCGCCTGGCGCACCGCGCGGAGAGCCTGAGCCG
CCTGAGCGGCGGCGTGGCGCAGGCCGAGCTCTACCTGGCGGCTCACGGGTCGCGCCTCAAGAAGGGCC
CGCGCCGCGGCCGCCGCGCGGCGACCCCCCGCGCTGCTGGCCTCGGCGCTGGGCTGGGCGGCTGCGTG
CCCTGGGGTGCCGGGCGACTGCGGCGCGGCCACGGCCCCGAGCCCGACTCGCCCTTCCGCCGCAGCCC
GCCCCGCGGCCCCGCCTCCCCGCAGCGCTGACCTCCACGCCCGGACCCCTGGCCACCCCGACAAGCTT
CGCCGAGGTGCCGACCGACCGACTGATCGCGGACGCCGGCTGGAAGGACTACGGATCCGCAGGAAGAG
GCAGTTGGGGGCCAGGGGCCCAGTAGAGGGCTGAGCTCCTTCCAACTCCTCAGAACCTTCCACTCTA
TGGATCTGGACCTCTGGATTCGGCTTTCTCCCTGGGCACTGCCTTCAGGAAGACGTTGAGAATTGACC
TTACACAATCCCAGCGCCCTCCTCACAGGAGCCTTTCACTTTACAGTGGCAAGGGCTGGTTCTGGAG
AACTGGCTGATGCTCTGAATTTCTTCATATACCCCACATTTGACTTTGGCTTACACTGTACAATTGGA
GATGTTGCTACAGGTCCCTGGAGATGCAATCAGATTAAGCGTAGCAAGCATTGCCAATGGGAAAGTCAA
AATAATTTATTTTTTCCCTTTCCCCCTACCCCATCCCCAGCCAAGAATTTCTTTTCAAGATATCGT
CATCATTCTTAAACAACATTCTTAACCCCCAGCTGGGGTCCCCATTTTAATAGATGTCATTGCTTCAA
GTCTAACGGCGCCGGGAGGCCTGTTTGAGGGAAAACATTAGTTTGAAAAATCCCCGTTCCCTTCATCC
ACTGCCCTTGTTCTCCACGTGGGAGTGTGCTTGTGGCCCCTCAGAAAGATAGTCTGCTGGCTCCTAGG
GGTTGGGTGGGGGACACACCTTTTTCTCAGGAAGAGGTGATGGCAATGTAAAACATCTAAGCAAAGT
TTTAAATGAAAAAAGGAAACACATTTAAACATCCTGATAATGGAGGGAAGGGGGCACATTTACACA
TAGCCCAGAACTTGTAGAATTCTGCATAGTGAATGTATATTGAATTAGTCTCCTGCCTTATACATTCA
GGAGGAATAAATTTCCATAATGTAAGGCAAATGCATGGGGTTCTGAGGTTCACTTTGCAAGTGCCCTT
GCTGCCTTTCCTCTGTGTCTATTATGGCTCTTTAAGTTGACGGTTCCTGGAGCAGCTTGTATTTAGTT
TCGTTTGGCAGTCTGGCCCTGTTGACTTTGATTTGCAGACCAATTCTCCCTTGACCTGACTCACAGCC
GCCTGCTCTTACCCCCCTCCTCAGGAAGTCTTCCTCATTAAAGGATGTGATGACGGA |
| 7192 | Human APLN mRNA NM_017413.5 (GI: 1519315208 version 5) | GAGCATTCTCTCTGGCAGCCGGGTCACGGGCAGTTGCAGCCGCGGCCGAGCAGCCAGCCGCTAAGAA
AGAGCTCGCCGCTGCCGCTCCCGGAGCCGCCGAGGCCAGCTTCGCGGCGCTGCCCCGCGGCGGGAGAG
GAGGCTGCAGAAGAGCGGAGGCGGCCAGCGGGAGCGGCGGGGCTCAGCGCGCACACTCAGCGGCCGGG
GAGCCTCCCGAGCTCTGCGCCCGCACGCGCCAGCCGCGGCTCGCGCCTTTCTTGGCCTCCGGGCGCCC
GACCTCTCCTCCCCGCGCCGGCTCGCCGGGGCCGCGGCGGCCCAAGGAGCAGCATGAATCTGCGGCT
CTGCGTGCAGGCGCTCCTGCTGCTCTGGCTCTCCTTGACCGCGGTGTGTGGAGGGTCCCTGATGCCGC |

TABLE 14-continued

Target sequences.

| SEQ ID NO: | Description | Sequence |
|---|---|---|
| | | TTCCCGATGGGAATGGGCTGGAAGACGGCAATGTCCGCCACCTGGTGCAGCCCAGAGGGTCAAGGAAT<br>GGGCCAGGGCCCTGGCAGGGAGGTCGGAGGAAATTCCGCCGCCAGCGGCCCCGCCTCTCCCATAAGGG<br>ACCCATGCCTTTCTGAAGCAGGACTGAAGGGGCCCCCAAGTGCCCACCCCCGGCGGTTATGTCTCCTC<br>CATAGATTGGTCTGCTTCTCTGGAGGCCTCACGTCCATTCAGCTCTCACCTCGCACCTGCTGTAGCCA<br>CCAGTGGGCCCAGCTCTTCTCACCTGCCTGCTTCCCCCAGTGGCGTGCTCCTGGCTGTAGTTTGGATG<br>ATTCCCGTTCTCTCACAAGAATCCGTCCAGTCCATCTTCCTGGCCCCTCCCTGGACTGACTTTGGAGA<br>CCTAGCCCCAGAAAGCCTCCCTTCTTCTCCAGGTCCCCTCCGCCCAGTCCCTGCCTGTCTCATCTAA<br>CGCCCCAAACCTTCATTTGGGCCTTCCTTCCTCATGTCTGCCCTGAGCGCGGGGTGGAAGTGCTCCCT<br>TCTGTGGGCTCCAGCAGATCCCTTGTTTTCCTGTCAGTTGGACCCCTCACCTGGCCTCCAGGGAAGAA<br>TGCAGAGAAAAGCAAGGAGAGACTCTAGTTAAGAGGTGCTGGCTGCGGGGATCCAGACAGGGCACATT<br>GGGGGCATGGAAGTGCCAGGGTGGTTTTCAGGGAGCTCTGGTGAAGTGGGTGGAGCATCAGCGTTTGCT<br>CAGTTAAGGGAGAGGTAGAGAGGGGCCCGTGAAGTCCTTTGTCACTTCTCTTGCCTTAGTGTGCCTCC<br>CAATACTCCCTTCTTCCTGCCCCCACACCCCATCCCCAGCTAGCCCAAGCTCCAGGTCAGGAGGGGAG<br>GGTGCTGGGCCTGACATGGCTATATACCCTCCCAGGAGTAAAAGCCAAGCAAGAGGTTGTTTTTGCCA<br>AGAATCACAGAATGTTAGAGCTGACAGGACCCTTGAAGGTCACTTAGCCTTCTTAGGCAAACGCCTGC<br>AAAACAGAAGCCTGGAGAGGGGAGTGACCTGCTCAGAGTCATTGCAGAGCCGGGATGGGGACCAGGTC<br>TCCCATCTCCTACTTTATGACGCCCTCTTCCCTCTTGATGATGTCTTTTCAAAGCAAATGAAGTGCCT<br>TTTCCCGAGGCTGGGGCTGGGGGTGGCTGGGAGGGGAAGGGAAGGGAGAGGCAAGCTGGCTGTGAACT<br>GTCCTGTTGTGGGGCTGGAGCTGCTCCCACCTCCCTGACCTACCCCTGCTGCACCATTCCCCCAGCTG<br>GGCTGGAAGGTTCCATAACTGGCCAGCTGCCCCCATAACTGGCAGCATTCCCAGACCCAGGGTACTCT<br>AATAGGGGCGGCTCAGGCACTGAGACTACCGCTCAACCCCAGGGTGGTTTTCAGGAGTCCGAGGTAGC<br>CTTCAATCACTGGACTCCATGGCCTTCCCTTCGTGTTGACCGGACCTTCCTTCCAGGGCTTTTCCTTT<br>GGGGGAGGCGGAGAGGGAGAAGAAGGAAGGGAAGGGCAGAAGGAAGGAGGGAAGAAAAGAAAGCAAA<br>GGAACAGAAGGAAGGAAAGAAAGATGGGAGGAAGTGCAGCAGGAATAGCACCCTCTCCCCGGGAGGCC<br>CTAGCTTCCGTGAGGGGCCATCACCAGCCATTCCTTGGAGGGGGCTTTCTCCCCTTTTGCTTGAGCAG<br>GGTTCCCAGGAGGGGAGAAAGAGAAGACAAGAGCCTGATGCCCAACTTTGTGTGTGGGGACGGGGGA<br>GTCAGGGCCCCCAAGTCCCACAATAGCCCCAATGTTTGCCTATCCACCTCCCCCAAGCCCCTTTACC<br>TATGCTGCTGCTAACGCTGCTGCTGCTGCTGCTGCTTAAAGGCTCATGCTTGGAGTGGGGACT<br>GGTCGGTGCCCAGAAAGTCTCTTCTGCCACTGACGCCCCCATCAGGGATTGGGCTTCTTTCCCCCTT<br>CCTTTCTGTGTCTCCTGCCTCATCGGCCTGCCATGACCTGCAGCCAAGCCCAGCCCCGTGGGGAAGGG<br>GAGAAAGTGGGGATGCTAAGAAAGCTGGGAGATAGGGAACAGAAGAGGGTAGTGGGTGGGCTAGGG<br>GGGCTGCCTTATTTAAAGTGGTTGTTTATGATTCTTATACTAATTTATACAAAGATATTAAGGCCCTG<br>TTCATTAAGAAATTGTTCCCTTCCCCTGTGTTCAATGTTTGTAAAGATTGTTCTGTGTAAATATGTCT<br>TTATAATAAACAGTTAAAAGCTGACAGTTCGCCCTTACTCTTGGAGGTCATGTTCAGGAGGGGCATTC<br>CTTTCCCCTGGGGGTCATGGGTGTCCCCATGCCCACATATTGCACGTGCAGGGAGGTAAGTGCCTGCA<br>TCCCAAATCGGTTCTAGGTCAACTGGCCTCAAACTGATTTGCCATGAGCTCACAAAATGAATCCCTAT<br>GCTTAATGACCAGGTCACATAAAATCCAGCCCACTTACAGGTTTTCTGGCATCTGTTTGGGTGTCCTA<br>ATTTTTTTGGCAGTGTCATTTGAAGAATTTTTTTAAAGCAGTTTATTTAAGAACATACTGATTAAATG<br>CAGGATGCGCTACTAAAAATTGTTTTGTATCCTTGGTGGGTGTCTTCTGCTATTTTATCTACTTTTGAA<br>CACTTTCAGGACTTTTTAGCCAGTTTGCCTTTCTTGAAAAATGTTATGTTTTCAGCAATAAATACATT<br>TGATAATGACTTTGTTTGTATCATTTTATGTTTCACAAAGTAGAGTTGCTTGATGAATGAGATAGCCT<br>GAAAAATAAAATGCAAAGAGTTCAATATAA |
| 7193 | Human KIF20A<br>transcript variant<br>1 mRNA<br>NM_005733.3<br>(GI: 1519313609<br>version 3) | GGAGTTGTGCTCTGCGGCTGCGAAAGTCCAGCTTCGGCGACTAGGTGTGAGTAAGCCAGTATCCCAGG<br>AGGAGCAAGTGGCACGTCTTCGGACCTAGGCTGCCCCTGCCGTCATGTCGCAAGGGATCCTTTCTCCG<br>CCAGCGGGCTTGCTGTCCGATGACGATGTCGTAGTTTCTCCCATGTTTGAGTCCACAGCTGCAGATTT<br>GGGGTCTGTGGTACGCAAGAACCTGCTATCAGACTGCTCTGTCGTCTCTACCTCCCTAGAGGACAAGC<br>AGCAGGTTCCATCTGAGGACAGTATGGAGAAGGTGAAAGTATACTTGAGGGTTAGGCCCTTGTTACCT<br>TCAGAGTTGGAACGACAGGAAGATCAGGGTTGTGTCCGTATTGAGAATGTGGAGACCCTTGTTCTACA<br>AGCACCCAAGGACTCTTTTGCCCTGAAGACAATGAACGGGGAATTGGCCAAGCCACACACAGGTTCA<br>CCTTTTCCCAGATCTTTGGGCCAGAAGTGGGACAGGCATCCTTCTTCAACCTAACTGTGAAGGAGATG<br>GTAAAGGATGTACTCAAAGGGCAGAACTGGCTCATCTATACATATGGAGTCACTAACTCAGGGAAAAC<br>CCACACGATTCAAGGTACCATCAAGGATGGAGGGATTCTCCCCGGTCCCTGGCGCTGATCTTCAATA<br>GCCTCCAAGGCCAACTTCATCCAACACCTGATCTGAAGCCCTTGCTCTCCAATGAGGTAATCTGGCTA<br>GACAGCAAGCAGATCCGACAGGAGGAAATGAAGAAGCTGTCCCTGCTAAATGGAGGCCTCCAAGAGGA<br>GGAGCTGTCCACTTCCTTGAAGAGGAGTGTCTACATCGAAAGTCGGATAGGTACCAGCACCAGCTTCG<br>ACAGTGGCATTGCTGGGCTCTCTTCTATCAGTCAGTGTACCAGCAGTAGCCAGCTGGATGAAACAAGT<br>CATCGATGGGCACAGCCAGACACTGCCCCACTACCTGTCCCGGCAAACATTCGCTTCTCCATCTGGAT<br>CTCATTCTTTGAGATCTACAACGAACTGCTTTATGACCTATTAGAACCGCCTAGCCAACAGCGCAAGA<br>GGCAGACTTTGCGGCTATGCGAGGATCAAAATGGCAATCCCTATGTGAAAGATCTCAACTGGATTCAT<br>GTGCAAGATGCTGAGGAGGCCTGGAAGCTCCTAAAAGTGGGTCGTAAGAACCAGAGCTTTGCCAGCAC<br>CCACCTCAACCAGAACTCCAGCCGCAGTCACAGCATCTTCTCAATCAGGATCCTACACCTTCAGGGGG<br>AAGGAGATATAGTCCCCAAGATCAGCGAGCTGTCACTCTGTGATCTGGCTGGCTCAGAGCGCTGCAAA<br>GATCAGAAGAGTGGTGAACGGTTGAAGGAAGCAGGAAACATTAACACCTCTCTACACACCCTGGGCCG<br>CTGTATTGCTGCCCTTCGTCAAAACCAGCAGAACCGGTCAAAGCAGAACCTGGTTCCCTTCCGTGACA<br>GCAAGTTGACTCGAGTGTTCCAAGGTTTCTTCACAGGCCGAGGCCGTTCCTGCATGATTGTCAATGTG<br>AATCCCTGTGCATCTACCTATGATGAAACTCTCATGTGGCCAAGTTCTCAGCCATTGCTAGCCAGCT<br>TGTGCATGCCCCACCTATGCAACTGGGATTCCCATCCCTGCACTCGTTCATCAAGGAACATAGTCTTC<br>AGGTATCCCCAGCTTAGAGAAAGGGCTAAGGCAGACACAGGCCTTGATGATGATATTGAAAATGAA<br>GCTGACATCTCCATGTATGGCAAAGAGGAGCTCCTACAAGTTGTGGAAGCCATGAAGACACTGCTTTT<br>GAAGGAACGACAGGAAAAGCTACAGCTGGAGATGCATCTCCGAGATGAAATTTGCAATGAGATGGTAG<br>AACAGATGCAACAGCGGGAACAGTGGTGCAGTGAACATTTGGACACCCAAAAGGAACTATTGGAGGAA<br>ATGTATGAAGAAAACTAAATATCCTCAAGGAGTCACTGACAAGTTTTTACCAAGAAGAGATTCAGGA<br>GCGGGATGAAAAGATTGAAGAGCTAGAAGCTCTCTTGCAGGAAGCCAGACAACAGTCAGTGGCCCATC<br>AGCAATCAGGGTCTGAATTGGCCCTACGGCGGTCACAAAGGTTGGCAGCTTCTGCCTCCACCCAGCAG<br>CTTCAGGAGGTTAAAGCTAAATTACAGCAGTGCAAAGCAGAGCTAAACTCTACCACTGAAGAGTTGCA |

TABLE 14-continued

Target sequences.

| SEQ ID NO: | Description | Sequence |
|---|---|---|
| | | TAAGTATCAGAAAATGTTAGAACCACCACCCTCAGCCAAGCCCTTCACCATTGATGTGGACAAGAAGT
TAGAAGAGGGCCAGAAGAATATAAGGCTGTTGCGGACAGAGCTTCAGAAACTTGGTGAGTCTCTCCAA
TCAGCAGAGAGAGCTTGTTGCCACAGCACTGGGGCAGGAAAACTTCGTCAAGCCTTGACCACTTGTGA
TGACATCTTAATCAAACAGGACCAGACTCTGGCTGAACTGCAGAACAACATGGTGCTAGTGAAACTGG
ACCTTCGGAAGAAGGCAGCATGTATTGCTGAGCAGTATCATACTGTGTTGAAACTCCAAGGCCAGGTT
TCTGCCAAAAAGCGCCTTGGTACCAACCAGGAAAATCAGCAACCAAACCAACAACCACCAGGGAAGAA
ACCATTCCTTCGAAATTTACTTCCCCGAACACCAACCTGCCAAAGCTCAACAGACTGCAGCCCTTATG
CCCGGATCCTACGCTCACGGCGTTCCCCTTTACTCAAATCTGGGCCTTTTGGCAAAAGTACTAAGGC
TGTGGGGAAAGAGAAGAGCAGTCATGGCCCTGAGGTGGGTCAGCTACTCTCCTGAAGAAATAGGTCTC
TTTTATGCTTTACCATATATCAGGAATTATATCCAGGATGCAATACTCAGACACTAGCTTTTTTCTCA
CTTTTGTATTATAACCACCTATGTAATCTCATGTTGTTGTTTTTTTTTATTTACTTATATGATTTCTA
TGCACACAAAAACAGTTATATTAAAGATATTATTGTTCACATTTTTTATTGAATTCCAAATGTAGCAA
AATCATTAAAACAAATTATAAAAGGGACAGAAAAA |
| 7194 | Human LTB transcript variant 1 mRNA NM_002341.2 (GI: 1720810086 version 2) | AGTCTCAATGGGGGCACTGGGGCTGGAGGGCAGGGGTGGGAGGCTCCAGGGGAGGGGTTCCCTCCTGC
TAGCTGTGGCAGGAGCCACTTCTCTGGTGACCTTGTTGCTGGCGGTGCCTATCACTGTCCTGGCTGTG
CTGGCCTTTAGTGCCCCAGGATCAGGGAGGACTGGTAACGGAGACGGCCGACCCCGGGGCACAGGCCCA
GCAAGGACTGGGGTTTCAGAAGCTGCCAGAGGAGGAGCCAGAAACAGATCTCAGCCCCGGGCTCCCAG
CTGCCCACCTCATAGGCGCTCCGCTGAAGGGGCAGGGGCTAGGCTGGGAGACGACGAAGGAACAGGCG
TTTCTGACGAGCGGGACGCAGTTCTCGGACGCCGAGGGGCTGGCGCTCCCGCAGGACGGCCTCTATTA
CCTCTACTGTCTCGTCGGCTACCGGGGCCGGGCGCCCCCTGGCGGCGGGGACCCCCAGGGCCGCTCGG
TCACGCTGCGCAGCTCTCTGTACCGGGCGGGGGCGCCTACGGGCCGGGCACTCCCGAGCTGCTGCTC
GAGGGCGCCGAGACGGTGACTCCAGTGCTGGACCCGGCCAGGAGACAAGGGTACGGGCCTCTCTGGTA
CACGAGCGTGGGGTTCGGCGGCCTGGTGCAGCTCCGGAGGGGCGAGAGGGTGTACGTCAACATCAGTC
ACCCCGATATGGTGGACTTCGCGAGAGGGAAGACCTTCTTTGGGGCCGTGATGGTGGGGTGAGGGAAT
ATGAGTGCGTGGTGCGAGTGCGTGAATATTGGGGGCCCGGACGCCCAGGACCCCATGGCAGTGGGAAA
AATGTAGGAGACTGTTTGGAAATTGATTTTGAACCTGATGAAAATAAAGAATGGAAAGCTTCAGTGCT
GCCGATAAA |
| 7195 | Human LTB transcript variant 2 mRNA NM_009588.1 (GI: 6996015, version 1) | CAGTCTCAATGGGGGCACTGGGGCTGGAGGGCAGGGGTGGGAGGCTCCAGGGGAGGGGTTCCCTCCTG
CTAGCTGTGGCAGGAGCCACTTCTCTGGTGACCTTGTTGCTGGCGGTGCCTATCACTGTCCTGGCTGT
GCTGGCCTTAGTGCCCCAGGATCAGGGAGGACTGGGTTTCAGAAGCTGCCAGAGGAGGAGCCAGAAAC
AGATCTCAGCCCCGGGCTCCCAGCTGCCCACCTCATAGGCGCTCCGCTGAAGGGGCAGGGGCTAGGCT
GGGAGACGACGAAGGAACAGGCGTTTCTGACGAGCGGGACGCAGTTCTCGGACGCCGAGGGGCTGGCG
CTCCCGCAGGACGGCCTCTATTACCTCTACTGTCTCGTCGGCTACCGGGGCCGGGCGCCCCCTGGCGG
CGGGGACCCCCAGGGCCGCTCGGTCACGCTGCGCAGCTCTCTGTACCGGGCGGGGGCGCCTACGGGC
CGGGCACTCCCGAGCTGCTGCTCGAGGGCGCCGAGACGGTGACTCCAGTGCTGGACCCGGCCAGGAGA
CAAGGGTACGGGCCTCTCTGGTACACGAGCGTGGGGTTCGGCGGCCTGGTGCAGCTCCGGAGGGGCGA
GAGGGTGTACGTCAACATCAGTCACCCCGATATGGTGGACTTCGCGAGAGGGAAGACCTTCTTTGGGG
CCGTGATGGTGGGGTGAGGGAATATGAGTGCGTGGTGCGAGTGCGTGAATATTGGGGCCCGGACGCC
CAGGACCCCATGGCAGTGGGAAAAATGTAGGAGACTGTTTGGAAATTGATTTTGAACCTGATGAAAAT
AAAGAATGGAAAGCTTCAGTGCTGCCGATAAA |

SEQUENCE LISTING

The patent contains a lengthy sequence listing. A copy of the sequence listing is available in electronic form from the USPTO web site (https://seqdata.uspto.gov/?pageRequest=docDetail&DocID=US12421515B2). An electronic copy of the sequence listing will also be available from the USPTO upon request and payment of the fee set forth in 37 CFR 1.19(b)(3).

The invention claimed is:

1. A method of treating fibrosis in a disease characterised by fibrosis, comprising administering a therapeutically-effective amount of an inhibitory nucleic acid comprising or encoding antisense nucleic acid for inhibiting T-cell immunomodulatory protein (ITFG1) gene expression to a subject having the disease characterised by fibrosis, wherein the inhibitory nucleic acid is an siRNA, dsiRNA, shRNA or antisense oligonucleotide.

2. The method according to claim 1, wherein the disease characterised by fibrosis is a disease characterised by fibrosis of the liver.

3. The method according to claim 2, wherein the disease characterised by fibrosis of the liver is selected from: acute liver disease, chronic liver disease, metabolic liver disease, steatosis, liver fibrosis, primary sclerosing cholangitis (PSC), cirrhosis, mild liver fibrosis, advanced liver fibrosis, non-alcoholic fatty liver disease (NAFLD), non-alcoholic steatohepatitis (NASH), alcoholic fatty liver disease (ALFD), alcohol-related liver disease (ARLD), hepatic ischemia reperfusion injury, primary biliary cirrhosis (PBC), hepatitis, liver damage, liver injury, liver failure, metabolic syndrome, obesity, diabetes mellitus, end-stage liver disease, inflammation of the liver, lobular inflammation, and hepatocellular carcinoma (HCC).

4. The method according to claim 3, wherein the disease characterised by fibrosis of the liver is selected from: acute liver disease, chronic liver disease, metabolic liver disease, steatosis, liver fibrosis, primary sclerosing cholangitis (PSC), cirrhosis, non-alcoholic fatty liver disease (NAFLD), non-alcoholic steatohepatitis (NASH), hepatic ischemia reperfusion injury, primary biliary cirrhosis (PBC) hepatitis and liver damage.

5. The method according to claim 1, wherein the inhibitory nucleic acid comprises one or more modified nucleotides selected from: 2'-O-methyluridine-3'-phosphate, 2'-O-methyladenosine-3'-phosphate, 2'-O-methylguanosine-3'-phosphate, 2'-O-methylcytidine-3'-phosphate, 2'-O-methyluridine-3'-phosphorothioate, 2'-O-methyladenosine-3'-phosphorothioate, 2'-O-methylguanosine-3'-phosphorothioate, 2'-O-methylcytidine-3'-phosphorothioate, 2'-fluorouridine-3'-phosphate, 2'-fluoroadenosine-3'-phosphate, 2'-fluoroguanosine-3'-phosphate, 2'-fluorocytidine-3'-phosphate, 2'-fluorocytidine-3'-phosphorothioate, 2'-fluoroguanosine-3'-phosphorothioate, 2'-fluoroadenosine-3'-phosphorothioate, and 2'-fluorouridine-3'-phosphorothioate.

6. The method according to claim 1, wherein the antisense nucleic acid for inhibiting the expression of ITFG1 comprises or consists of a nucleotide sequence having at least 75% sequence identity to any one of SEQ ID NOs: 457 to 1482.

7. The method according to claim 1, wherein the inhibitory nucleic acid comprises a moiety facilitating delivery to and/or uptake by a hepatocyte and/or hepatic tissue.

8. The method according to claim 1, wherein the inhibitory nucleic acid comprises one or more GalNAc moieties.

9. A method of inhibiting fibrosis of the liver in a subject, comprising administering to a subject in need thereof an inhibitory nucleic acid comprising or encoding antisense nucleic acid for inhibiting T-cell immunomodulatory protein (ITFG1) gene expression, wherein the inhibitory nucleic acid is an siRNA, dsiRNA, shRNA or antisense oligonucleotide.

10. The method according to claim 9, wherein the subject has a disease characterised by fibrosis of the liver.

11. The method according to claim 10, wherein the disease characterised by fibrosis of the liver is selected from: acute liver disease, chronic liver disease, metabolic liver disease, steatosis, liver fibrosis, primary sclerosing cholangitis (PSC), cirrhosis, mild liver fibrosis, advanced liver fibrosis, non-alcoholic fatty liver disease (NAFLD), non-alcoholic steatohepatitis (NASH), alcoholic fatty liver disease (ALFD), alcohol-related liver disease (ARLD), hepatic ischemia reperfusion injury, primary biliary cirrhosis (PBC), hepatitis, liver damage, liver injury, liver failure, metabolic syndrome, obesity, diabetes mellitus, end-stage liver disease, inflammation of the liver, lobular inflammation, and hepatocellular carcinoma (HCC).

12. The method according to claim 11, wherein the disease characterised by fibrosis of the liver is selected from: acute liver disease, chronic liver disease, metabolic liver disease, steatosis, liver fibrosis, primary sclerosing cholangitis (PSC), cirrhosis, non-alcoholic fatty liver disease (NAFLD), non-alcoholic steatohepatitis (NASH), hepatic ischemia reperfusion injury, primary biliary cirrhosis (PBC) hepatitis and liver damage.

13. The method according to claim 9, wherein the inhibitory nucleic acid comprises one or more modified nucleotides selected from: 2'-O-methyluridine-3'-phosphate, 2'-O-methyladenosine-3'-phosphate, 2'-O-methylguanosine-3'-phosphate, 2'-O-methylcytidine-3'-phosphate, 2'-O-methyluridine-3'-phosphorothioate, 2'-O-methyladenosine-3'-phosphorothioate, 2'-O-methylguanosine-3'-phosphorothioate, 2'-O-methylcytidine-3'-phosphorothioate, 2'-fluorouridine-3'-phosphate, 2'-fluoroadenosine-3'-phosphate, 2'-fluoroguanosine-3'-phosphate, 2'-fluorocytidine-3'-phosphate, 2'-fluorocytidine-3'-phosphorothioate, 2'-fluoroguanosine-3'-phosphorothioate, 2'-fluoroadenosine-3'-phosphorothioate, and 2'-fluorouridine-3'-phosphorothioate.

14. The method according to claim 9, wherein the antisense nucleic acid for inhibiting the expression of ITFG1 comprises or consists of a nucleotide sequence having at least 75% sequence identity to any one of SEQ ID NOs: 457 to 1482.

15. The method according to claim 9, wherein the inhibitory nucleic acid comprises a moiety facilitating delivery to and/or uptake by a hepatocyte and/or hepatic tissue.

16. The method according to claim 9, wherein the inhibitory nucleic acid comprises one or more GalNAc moieties.

* * * * *